United States Patent
Baska et al.

(10) Patent No.: US 11,298,363 B2
(45) Date of Patent: Apr. 12, 2022

(54) TRIAZOLOBENZAZEPINES AS VASOPRESSIN V1A RECEPTOR ANTAGONISTS

(71) Applicant: RICHTER GEDEON NYRT., Budapest (HU)

(72) Inventors: Ferenc Baska, Budapest (HU); Éva Bozó, Budapest (HU); Imre Bata, Budapest (HU); Krisztina Szondiné Kordás, Budapest (HU); Krisztina Vukics, Budapest (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 16/954,085

(22) PCT Filed: Dec. 14, 2018

(86) PCT No.: PCT/IB2018/060077
§ 371 (c)(1),
(2) Date: Jun. 15, 2020

(87) PCT Pub. No.: WO2019/116324
PCT Pub. Date: Jun. 20, 2019

(65) Prior Publication Data
US 2021/0260072 A1   Aug. 26, 2021

(30) Foreign Application Priority Data
Dec. 15, 2017  (HU) .................................. P1700521

(51) Int. Cl.
*C07D 487/04* (2006.01)
*C07D 491/20* (2006.01)
*C07D 519/00* (2006.01)
*A61K 31/55* (2006.01)

(52) U.S. Cl.
CPC ............ *A61K 31/55* (2013.01); *C07D 487/04* (2013.01); *C07D 491/20* (2013.01); *C07D 519/00* (2013.01)

(58) Field of Classification Search
CPC ... C07D 487/04; C07D 491/20; C07D 519/00
See application file for complete search history.

(56) References Cited

FOREIGN PATENT DOCUMENTS

| | | |
|---|---|---|
| CN | 106349241 A | 1/2017 |
| EP | 0382185 A2 | 8/1990 |
| EP | 1582521 A1 | 10/2005 |
| WO | WO-9303013 A1 | 2/1993 |
| WO | WO-9503305 A1 | 2/1995 |
| WO | WO-9534540 A1 | 12/1995 |
| WO | WO-9715556 A1 | 5/1997 |
| WO | WO-0187855 A1 | 11/2001 |
| WO | WO-0202531 A1 | 1/2002 |
| WO | WO-0244179 A1 | 6/2002 |
| WO | WO-03031407 A2 | 4/2003 |
| WO | WO-2004074291 A1 | 9/2004 |
| WO | WO-2005039565 A1 * | 5/2005 ........... A61K 31/404 |
| WO | WO-2005063754 A1 | 7/2005 |
| WO | WO-2005068466 A1 | 7/2005 |
| WO | WO-2006021213 A2 | 3/2006 |
| WO | WO-2006021882 A1 | 3/2006 |
| WO | WO-2006072458 A2 | 7/2006 |
| WO | WO-2006100082 A2 | 9/2006 |

(Continued)

OTHER PUBLICATIONS

AdisInsight: OPC 21268 Latest Information Update: Oct. 6, 2006 http://adisinsight.springer.com/drugs/800000284.
AdisInsight: Relcovaptan Latest Information Update: Oct. 3, 2006 http://adisinsight.springer.com/drugs/800004942.
AdisInsight: RG 7314 Latest Information Update: Sep. 10, 2017 http://adisinsight.springer.com/drugs/800035102.
AdisInsight: RG 7713—Latest Information Update: Nov. 5, 2015 http://adisinsight.springer.com/drugs/800043668.

(Continued)

*Primary Examiner* — Matthew P Coughlin
(74) *Attorney, Agent, or Firm* — Sterne, Kessler, Goldstein & Fox P.L.L.C.

(57) ABSTRACT

The present invention relates to 5,6-dihydro-4H-[1,2,4]triazolo[4,3-a][1]benzazepine derivatives of general formula (I) and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof which are centrally and/or peripherally acting V1a receptor modulators, particularly V1a receptor antagonists. Additional subject of the present invention is the process for the preparation of the compounds and the intermediates of the preparation process as well. The invention also relates to the pharmaceutical compositions containing the compounds or together with one or more other active substances, as well as to the use in the treatment and/or prophylaxis of a disease or condition associated with V1a receptor function.

21 Claims, No Drawings

(56) References Cited

FOREIGN PATENT DOCUMENTS

| WO | WO-2006124748 A2 | 11/2006 |
| WO | WO-2007006688 A1 | 1/2007 |
| WO | WO-2007009906 A1 | 1/2007 |
| WO | WO-2007014851 A2 | 2/2007 |
| WO | WO-2008052628 A1 | 5/2008 |
| WO | WO-2008092887 A1 | 8/2008 |
| WO | WO-2009001968 A1 | 12/2008 |
| WO | WO-2010060836 A1 | 6/2010 |
| WO | WO-2010097576 A1 | 9/2010 |
| WO | WO-2010108052 A2 | 9/2010 |
| WO | WO-2011052519 A1 | 5/2011 |
| WO | WO-2011114109 A1 | 9/2011 |
| WO | WO-2011128265 A1 | 10/2011 |
| WO | WO-2011131596 A1 | 10/2011 |
| WO | WO-2011141396 A1 | 11/2011 |
| WO | WO-2011143150 A1 | 11/2011 |
| WO | WO-2014048945 A1 | 4/2014 |
| WO | WO-2014127350 A1 | 8/2014 |
| WO | WO-2016091776 A1 | 6/2016 |
| WO | WO-2016138532 A1 | 9/2016 |
| WO | WO-2017007756 A1 | 1/2017 |
| WO | WO-2017191102 A1 | 11/2017 |
| WO | WO-2017191107 A1 | 11/2017 |
| WO | WO-2017191114 A1 | 11/2017 |

OTHER PUBLICATIONS

AdisInsight: SRX 246—Latest Information Update: Feb. 16, 2017 http://adisinsight.springer.com/drugs/800023656.

AdisInsight: SRX 251—Latest Information Update: Nov. 4, 2017 http://adisinsight.springer.com/drugs/800025117.

AdisInsight: VA 111913—Latest Information Update: Aug. 25, 2015 http://adisinsight.springer.com/drugs/800028777.

Arndt, F., and Eistert, B., "Ein Verfahren zur Überführung von Carbonsäuren in ihre höheren Homologen bzw. deren Derivate," Berichte der deutschen chemischen Gesellschaft (A and B Series) 68(1):200-208 Wiley-Blackwell, France (Jan. 1935).

Bambini-Junior, V., et al., "Animal Model of Autism Induced by Prenatal Exposure to Valproate: Behavioral Changes and Liver Parameters," Brain Research 1408:8-16 Elsevier, Netherlands (Aug. 2011).

Beal, D.M., et al., "Preparation of Triazolobenzodiazepine Derivatives as Vasopressin V1a Antagonists," Tetrahedron Letters 52(45):5913-5917 Elsevier, Netherlands (Nov. 2011).

Bielsky, I.F., et al., "Sexual Dimorphism in the Vasopressin System: Lack of an Altered Behavioral Phenotype in Female V1a Receptor Knockout Mice," Behavioural Brain Research 164(1):132-136 Elsevier, Netherlands (Oct. 2005).

Bielsky, I.F., et al., "Profound Impairment in Social Recognition and Reduction in Anxiety-Like Behavior in Vasopressin V1a Receptor Knockout Mice," Neuropsychopharmacology 29(3):483-493 Nature Publishing Group, England (Mar. 2004).

Bleickardt, C.J., et al., "Characterization of the V1a Antagonist, JNJ-17308616, in Rodent Models of Anxiety-Like Behavior," Psychopharmacology 202(4):711-718 Springer-Verlag, Germany (Mar. 2009).

Brouard, R., et al., "Effect of SR49059, An Orally Active V1a Vasopressin Receptor Antagonist, in the Prevention of Dysmenorrhoea," BJOG 107(5):614-619 Wiley-Blackwell, England (May 2000).

Christensen, J., et al., "Prenatal Valproate Exposure and Risk of Autism Spectrum Disorders and Childhood Autism," JAMA 309(16):1696-1703 American Medical Association (Apr. 2013).

De-Vries, G.J., and Miller, M.A., "Anatomy and Function of Extrahypothalamic Vasopressin Systems in the Brain," Progress in Brain Research 119:3-20 Elsevier, Netherlands (1998).

Ebner, K., et al., "Forced Swimming Triggers Vasopressin Release Within the Amygdala to Modulate Stress-Coping Strategies in Rats," The European Journal of Neuroscience 15(2):384-388 Wiley-Blackwell, France (Jan. 2002).

Egashira, N., et al., "Impaired Social Interaction and Reduced Anxiety-Related Behavior in Vasopressin V1a Receptor Knockout Mice," Behavioural Brain Research 178(1):123-127 Elsevier/North-Holland Biomedical Press, Netherlands (Mar. 2007).

Egashira, N., et al., "New Topics in Vasopressin Receptors and Approach to Novel Drugs: Role of the Vasopressin Receptor in Psychological and Cognitive Functions," Journal of Pharmacological Sciences 109(1):44-49 Japanese Pharmacological Society, Japan (Jan. 2009).

Fabio, K.M., et al., "Pharmacokinetics and Metabolism of SRX246: A Potent and Selective Vasopressin 1a Antagonist," Journal of Pharmaceutical Sciences 102(6):2033-2043 Elsevier, United States (Jun. 2013).

Ferris, C.F., et al., "Imaging the Neural Circuitry and Chemical Control of Aggressive Motivation," BMC Neuroscience 9:111 BioMed Central, England (Nov. 2008).

Foley, A.G., et al., "Pentyl-4-yn-VPA, A Histone Deacetylase Inhibitor, Ameliorates Deficits in Social Behavior and Cognition in a Rodent Model of Autism Spectrum Disorders," European Journal of Pharmacology 727:80-86 Elsevier Science, Netherlands (Mar. 2014).

Frank, E., and Landgraf, R., "The Vasopressin System—from Antidiuresis to Psychopathology," European Journal of Pharmacology 583(2-3):226-242 Elsevier Science, Netherlands (Apr. 2008).

Freedman, T.B., et al., "Absolute Configuration Determination of Chiral Molecules in the Solution State Using Vibrational Circular Dichroism," Chirality 15(9):743-758 Wiley, United States (Nov. 2003).

Freeman, S.M., et al., "Selective Localization of Oxytocin Receptors and Vasopressin 1a Receptors in the Human Brainstem," Social Neuroscience 12(2):113-123 Routledge, England (Apr. 2017).

Gizowski, C., et al., "Clock-Driven Vasopressin Neurotransmission Mediates Anticipatory Thirst Prior to Sleep," Nature 537(7622):685-688 Nature Publishing Group, England (Sep. 2016).

Glickman, G., "Circadian Rhythms and Sleep in Children with Autism," Neuroscience and Biobehavioral Reviews 34(5):755-768 Pergamon Press, United States (Apr. 2010).

Gouzenes, L., "V1a- and V2-type Vasopressin Receptors Mediate Vasopressin-Induced Ca2+ Responses in Isolated Rat Supraoptic Neurones," The Journal of physiology 517 (Pt 3) 771-779 Cambridge University Press, England (Jun. 1999).

Grundschober et al., Poster Presented at 53rd Annual Meeting of the American College of Neuropsychopharmacology, Poster 36.2 A New Vasopressin V1a Antagonist Restores Normal Social Behavior and Reveals a Specific Brain Network in the Rat Valproate Model of Autism, pp. S62-S63, Phoenix, USA (Dec. 2014).

Guillon, C.D., et al., "Azetidinones as Vasopressin V1a Antagonists", Bioorganic & Medicinal Chemistry 15(5):2054-2080 Elsevier Science England (Mar. 2007).

International Search Report and Written Opinion for International Application No. PCT/IB2018/060077, European Patent Office, Netherlands, dated Feb. 15, 2019, 11 Pages.

Jarvis, M.F., et al., [3H]A-317491, A Novel High-Affinity Non-Nucleotide Antagonist That Specifically Labels Human P2X2/3 and P2X3 Receptors,The Journal of Pharmacology and Experimental Therapeutics 310(1):407-416 American Society for Pharmacology and Experimental Therapeutics. United States (Jul. 2004).

Johnson, P.S., et al "Discovery of PF-184563, S Potent and Selective V1a Antagonist for the Treatment of Dysmenorrhoea. The Influence of Compound Flexibility on Microsomal Stability?," Bioorganic & Medicinal Chemistry Letters 21(19):5684-5687 Elsevier Science Ltd, England (Oct. 2011).

Kendler, K.S., et al "Life Event Dimensions of Loss, Humiliation, Entrapment, and Danger in the Prediction of Onsets of Major Depression and Generalized Anxiety," Archives of General Psychiatry 60(8):789-796 American Medical , United States (Aug. 2003).

Kim, S.J., et al "Transmission Disequilibrium Testing of Arginine Vasopressin Receptor 1A (AVPR1A) Polymorphisms in Autism," Molecular Psychiatry 7(5):503-507 Nature Publishing Group, (Jun. 2002).

Klin, A., et al., "Two-year-olds with Autism Orient to Non-Social Contingencies Rather Than Biological Motion," Nature Nature 459(7244):257-261 Publishing Group, England (May 2009).

(56) References Cited

OTHER PUBLICATIONS

Latypov, S.K., et al., "Assignment of the Absolute Configuration of β-Chiral Primary Alcohols by NMR: Scope and Limitations," Journal of the American Chemical Society 120(19):4741-4751 American Chemical Society (May 1998).

Lowry, O.H., et al., "Protein Measurement With the Folin Phenol Reagent," The Journal of Biological Chemistry 193(1):265-275 Elsevier, United States (Nov. 1951).

Meanwell, N.A., et al "1,3-Dihydro-2H-Imidazo[4,5-b]Quinolin-2-Ones—Inhibitors of Blood Platelet cAMP Phosphodiesterase and Induced Aggregation" Journal of Medicinal Chemistry 34(9) 2906-2916 American Chemical Society, United States (Sep. 1991).

Meyer-Lindenberg, A., et al., "Genetic Variants in AVPR1A Linked to Autism Predict Amygdala Activation and Personality Traits in Healthy Humans," Molecular Psychiatry 14(10):968-975 Nature Publishing Group Specialist Journals, England (Oct. 2009).

Nadler, J.J., et al "Automated Apparatus for Quantitation of Social Approach Behaviors in Mice," Genes, Brain, and Behavior 3(5):303-14 Munksgaard, England (Oct. 2004).

Neumann, I.D., "Brain Oxytocin: a Key Regulator of Emotional and Social Behaviours in Both Females and Males," Journal of Neuroendocrinology 20(6):858-865 Wiley & Sons, United States (Jun. 2008).

Peter, G.M., Wuts: Greene's Protective Groups in Organic Synthesis: Fifth Edition, Chapter 2 Protection for the Hydroxyl Group, Including 1,2- and 1 ,3-Diols, pp. 17-471 Wiley & Sons, United States (2014).

Peter, G.M., Wuts: Greene's Protective Groups inOrganic Synthesis: Fifth Edition, Chapter 7. Protection for the Amino Group, pp. 895-1193 Wiley & Sons, United States (2014).

Quinn, L.P., et al., LABORAS: Initial Pharmacological Validation of a System Allowing Continuous Monitoring of Laboratory Rodent Behaviour,Journal of Neuroscience Methods 130(1):83-92 Elsevier/North-Holland Biomedical Press, Netherlands (Nov. 2003).

Rautio, J., et al., "Prodrugs: Design and Clinical Applications," Nature Reviews. Drug Discovery 7(3):255-270, Nature Publishing Group, England (Mar. 2008).

Robben, J.H., et al., "Functional Rescue of Vasopressin V2 Receptor Mutants in MDCK Cells by Pharmacochaperones: Relevance to Therapy of Nephrogenic Diabetes Insipidus," American Journal of Physiology. Renal Physiology 292(1):F253-F260 American Physiological Society, United States (Jan. 2007).

Roullet, F., et al., "In Utero Exposure to Valproic Acid and Autism—A Current Review of Clinical and Animal Studies," Neurotoxicology and Teratology 36:47-56 Pergamon Press, United States (Mar.-Apr. 2013).

Royer, D., et al., "Diastereodivergence and Appendage Diversity in the Multicomponent Synthesis of Aryl-Pyrrolo-Tetrahydrocarbazoles," Tetrahedron 66(40):9607-9618 Elsevier, United States (Sep. 2008).

Russell, R., et al., "In Vitro and in Vivo Pharmacological Characterisation of the Potent and Selective Vasopressin V(1a) Receptor Antagonist 4-[4-(4-chloro-phenyl)-5-[1,2,3]triazol-2-ylmethyl-4h-[1,2,4]triazol-3-yl]-piperidin-1-yl-(3,5-difluoro-phenyl) Methanone (Pf-00738245)," European Journal of Pharmacology 670(2-3):347-355 Elsevier Science, Netherlands (Nov. 2011).

Seco, J.M., et al., "A Practical Guide for the Assignment of the Absolute Configuration of Alcohols, Amines and Carboxylic Acids by NMR," Tetrahedron: Asymmetry 12(21):2915-2925 (Nov. 2001).

Seco, J.M., et al., "Boc-Phenylglycine: The Reagent of Choice for the Assignment of the Absolute Configuration of α-Chiral Primary Amines by 1H NMR Spectroscopy," The Journal of Organic Chemistry 4669-4675 ACS Publications, Spain (Jun. 1999).

Serradeil-Le Gal, C., et al., "Biochemical And Pharmacological Properties Of SR 49059, A New, Potent, Nonpeptide Antagonist Of Rat And Human Vasopressin V1a Receptors," The Journal Of Clinical Investigation 92(1):224-231 American Society for Clinical Investigation, United States (Jul. 1993).

Serradeil-Le Gal, C., et al., "Nonpeptide Vasopressin Receptor Antagonists: Development Of Selective And Orally Active V1a, V2 and V1b Receptor Ligands," Progress in Brain Research 139:197-210 Elsevier, Netherlands (2002).

Simion, F., et al., "A Predisposition for Biological Motion in the Newborn Baby," Proceedings of the National Academy of Sciences of the United States of America 105(2):809-813 National Academy of Sciences, United States (Jan. 2008).

Simon, N.G., et al., "Vasopressin Antagonists As Anxiolytics and Antidepressants: Recent Developments," Recent Patents on CNS Drug Discovery 3(2):77-93 Bentham Science Publishers, United Arab Emirates (Jun. 2008).

Stephens, P.J., et al., "The Determination of the Absolute Configurations of Chiral Molecules Using Vibrational Circular Dichroism (VCD) Spectroscopy," Chirality 20(5):643-663 Wiley, United States (May 2008 ).

Szot, P., et al., "Distribution of Messenger RNA for the Vasopressin V1a Receptor in the CNS of Male and Female Rats," Brain Research Molecular Brain Research 24(1-4):1-10 Elsevier, Netherlands (Jul. 1994).

Tahara, A., et al., "AVP-Induced Mitogenic Responses of Chinese Hamster Ovary Cells Expressing Human V1A or V1B Receptors," Pflugers Archiv : European Journal of Physiology 437(2):219-226 Springer, Germany (Jan. 1999).

Tahara, A., et al., "Pharmacologic Characterization of the Oxytocin Receptor in Human Uterine Smooth Muscle Cells," British Journal of Pharmacology 129(1):131-139 Wiley, England (Jan. 2000).

Umbricht, D., et al., "A Single Dose, Randomized, Controlled Proof-Of-Mechanism Study of a Novel Vasopressin 1a Receptor Antagonist (RG7713) in High-Functioning Adults with Autism Spectrum Disorder," Neuropsychopharmacology 42(9):1914-1923 Nature Publishing Group, England (Aug. 2017).

Yamamura, Y., et al., "OPC-21268, An Orally Effective, Nonpeptide Vasopressin V1 Receptor Antagonist," Science 252(5005):572-574 American Association for the Advancement of Science, Japan (Apr. 1991).

Yang, S.Y., et al., "Association Study Between Single Nucleotide Polymorphisms in Promoter Region of AVPR1A and Korean Autism Spectrum Disorders," Neuroscience Letters 479(3):197-200 Elsevier Scientific, Ireland (Aug. 2010).

Yang, S.Y., et al., "Family-Based Association Study of Microsatellites in the 5' Flanking Region of AVPR1A with Autism Spectrum Disorder in the Korean Population," Psychiatry Research 178(1):199-201 Elsevier/North-Holland Biomedical Press, Ireland (Jun. 2010).

Yirmiya, N., et al., "Association Between the Arginine Vasopressin 1a Receptor (AVPR1a) Gene and Autism in a Family-Based Study: Mediation by Socialization Skills," Molecular Psychiatry 11(5):488-494 Nature Publishing Group Specialist Journals, England (May 2006).

* cited by examiner

TRIAZOLOBENZAZEPINES AS VASOPRESSIN V1A RECEPTOR ANTAGONISTS

THE FIELD OF THE INVENTION

The present invention relates to 5,6-dihydro-4H-[1,2,4] triazolo[4,3-a][1]benzazepine derivatives of general formula (I) and/or salts thereof and/or geometric isomers thereof and/or stereoisomers thereof and/or enantiomers thereof and/or racemates thereof and/or diastereomers thereof and/ or biologically active metabolites thereof and/or prodrugs thereof and/or solvates thereof and/or hydrates thereof and/ or polymorphs thereof which are centrally and/or peripherally acting V1a receptor modulators, particularly V1a receptor antagonists. Additional subject of the present invention is the process for the preparation of the compounds and intermediates of the preparation process as well. The invention also relates to pharmaceutical compositions containing the compounds and to the use thereof in the treatment and/or prophylaxis of a disease or condition associated with V1a receptor function.

THE BACKGROUND OF THE INVENTION

The vasopressin (antidiuretic hormone, ADH, CYIQNCPRG) is a 9-amino acid peptide hormone produced by the magnocellular neurons of the paraventricular (PVN) and supraoptic (SON) nuclei of the hypothalamus and secreted directly into the posterior lobe of the pituitary gland where the hormone is stored until entering into the bloodstream. In the periphery, the major role of vasopressin is in the contraction of blood vessels, as well as in glucose metabolism and in the regulation of excretion.

For this reason, the conditions due to inappropriate secretion of vasopressin thus the lack of vasopressin may lead to pathological changes in the body, such as the central form of diabetes insipidus or abnormally low blood pressure (hypotension), while in the case of elevated levels of vasopressin or exogenous administration various forms of strengthening of the aggressive behaviour can be observed (Ferris et al., BMC Neuroscience 2008, 9:111).

Oxytocin (OXT, CYIQNCPLG) is a vasopressin-related peptide hormone, differing from that in one amino acid and its receptor is also related to vasopressin receptors. The effects of compounds on the oxytocin receptor show species-specific differences, but the oxytocin hormone itself is identical in the different mammalian species. Similarly, the vasopressin peptide is the same in all mammals (except marsupials and pigs) and the effects exerted through its receptors may also show species-specific differences. The anxiolytic effect of oxytocin exerted in the central nervous system is well-known (Neumann I D. *J Neuroendocrinol* 2008, 20(6): 858-65), therefore the inhibition of the oxytocin receptor in the central nervous system can trigger anxiety as undesirable side effect.

Three vasopressin receptors are distinguished, all of them are G-protein coupled receptors. The V1a receptor (V1aR) is expressed centrally in the cerebral cortex, hippocampus and pituitary gland, furthermore peripherally in the liver, vascular smooth muscle, lung, uterus and testes (Frank et al., *Eur J Pharmacol* 2008, 583:226-42). The V1b receptors (V1bR) are also can be found in the cortex, hippocampus and pituitary gland, and in the periphery they play an important role in the regulation of the pancreas and the adrenal glands. In contrast to this, the V2 receptor (V2R) is mainly localised on the periphery, in the kidneys where it increases water reabsorption, thereby exerting the antidiuretic effect of vasopressin (Robben et al., *Am J Physiol Renal Physiol* 2007, 292(1): F253-60). Thus, due to changes in the regulation of water balance the effect on the V2 receptor may cause undesirable side effect.

The secondary signalling pathway of V1a and V1b receptors include the change of intracellular $Ca^{2+}$ concentration through phosphatidylinositol, whereas the V2 receptors activate adenylate cyclase enzyme and influence cAMP levels (Gouzenes et al, *J Physiol* 1999, 517(Pt3):771-9; Tahara et al., *Pflugers Arch* 1999, 437(2):219-26).

An important role is attached to the V1a receptors in the regulation of the circadian rhythm. One-third of the neurons in the suprachiasmatic nucleus (SCN) express vasopressin and the mRNA of V1a receptors exhibit daily fluctuations in this brain region of which the highest values can be observed during night hours (de Vries and Miller, *Prog Brain Res* 1998, 119:3-20). Vasopressin shows sexual dimorphism in inducing behavioural effects, despite the fact that distribution and amount of the V1aR mRNAs do not differ in men and women (Szot et al., *Brain Res Mol Brain Res* 1994, 24(1-4):1-10). Experiments in mice have shown that the increased water absorption prior to their sleep period was triggered by their internal clock and not their physiological necessities (Gizowski et al., *Nature* 2016, 537(7622):685-8). Sleep disorder is a major accompanying symptom of autism (Glickman, *Neurosci Biobehav Rev* 2010, 34(5):755-68).

Vasopressin acts as a neuromodulator in the brain, its elevated level can be detected in the amygdala under stress (Ebner et al., *Eur J Neurosci* 2002, 15(2):384-8). Such stressful life situations are well known to increase the likelihood of developing depression and anxiety (Kendler et al., *Arch Gen Psychiatry* 2003, 60(8):789-96: Simon et al., *Recent Pat CNS Drug Discov,* 2008, 3(2):77-93; Egashira et al., *J Pharmacol Sci* 2009, 109(1):44-9; Bielsky et al., *Neuropsychopharmacology* 2004, 29(3):483-93). The expression of V1aR is high in the brain, especially in certain parts of the limbic system, such as the amygdala, the lateral septum and the hippocampus which play an important role in the development of anxiety. Male V1aR gene knocked out mice exhibited reduced anxiety in the elevated plus maze, the open field and the light-dark box tests, but these differences could not be detected in females (Bielsky et al., *Behav Brain Res* 2005, 164(1):132-6).

The male V1aR knockout mice did not show any phenotypic difference in motor performances. In normal light-dark-cycle experiments, V1aR KO mice showed no difference compared to their wild-type littermates, however, in the experiments carried out in continuous darkness the diurnal rhythm of V1a knockout mice was shifted significantly (Egashira et al., *Behav Brain Res* 2007, 178(1):123-7).

The V1aR KO mice showed modified activity in the prepulse inhibition test, in the test which is accepted as animal model of sensory motor deficiency observed in most schizophrenic patients. Egashira et al. have shown decreased function in the social interaction test, which is suitable to measure socio-cognitive behaviour of the V1aR KO mice in both sexes, but it was not observed after the treatment with antagonist (Bleickard et al., *Psychopharmacology (Berl),* 2009, 202:711-18).

Two microsatellite polymorphisms associated with autism could be determined in the case of variants of the AVPR1A gene encoding the V1a receptor (Kim et al., *Mol Psychiatry* 2002, 7:503-7; Yirmiya et al., *Mol Psychiatry* 2006, 11:488-94; Yang et al., *Psychiatry Res,* 2010, 178(1):199-201; Yang et al., *Neurosci Lett* 2010, 479(3):197-200). It also refers to a genetic connection that altered activation of amygdala could be detected in patients carrying two risk alleles in the V1aR gene. These modified receptors have been shown to be able to alter the activation threshold of amygdala during emotional facial recognition process (Meyer-Lindenberg et al., *Mol Psychiatry* 2009, 14:968-75).

Preclinical data also support the efficacy of V1aR antagonists in autism. A widely used and accepted animal model of autism is to study the behaviour of rats exposed to valproate (VPA) treatment in utero. The reduced social behaviour of VPA-treated animals could be reversed by the V1aR antagonist compound to the normal level. In a functional magnetic resonance imaging study it was also found that decreased perfusion values were restored by the V1aR antagonist in different brain regions of prenatally VPA-treated animals. The decreased function of the cortex, the inferior colliculus, the hippocampus and the hypothalamus was increased by treatment with the V1aR antagonist, whereas in the ventral tegmentum, the striatum and the colliculus superior, the augmented perfusion was normalised by the V1aR antagonist (Grundschober et al., Poster presented at *Annual Meeting of the American College of Neuropsychopharmacology*, 2014, Phoenix, USA). For this reason, V1aR antagonist compounds showing favourable blood-brain barrier penetration are expected to be advantageous.

Influencing V1aR with small molecule antagonists is a promising strategy for the treatment of various pathological conditions of the female sex organs (such as, but not limited to, dysmenorrhea, sexual dysfunction), long-lasting pathological conditions in blood pressure control (such as, but not limited to, hypertension and/or chronic heart failure), conditions resulting from inappropriate secretion of vasopressin (such as, but not limited to, diabetes insipidus, renal failure, nephrotic syndrome and cirrhosis). It can be considered another promising strategy in the treatment of anxiety, depression, aggression, and disorders of the central nervous system where one of the symptoms and/or syndromes of the disease may be related to the latter three diseases or show comorbidity with them. These include, but not limited to, autistic spectrum disorder (well-functioning autism, Asperger's syndrome, Pervasive Developmental Disorder-Not Otherwise Specified (PDD-NOS), autism spectrum disorder (ASD) and its various syndromic forms: fragile X syndrome, Prader-Willi syndrome, Rett syndrome, tuberous sclerosis), obsessive compulsive disorder (OCD), various forms of Down syndrome and post-traumatic stress disorder (PTSD). V1aR antagonists are also suitable for the treatment of aggressive behavioural disorders and/or irritability (such as, but not limited to, patients with ASD, or suffering from Huntington's disease (HD) or various forms of schizophrenia), behavioural hyperactivity disorders (such as, but not limited to, attention deficit hyperactivity disorder (ADHD)), cognitive disorders (such as, but not limited to, dementia, mild cognitive disorders (MCI), cognitive impairment associated with schizophrenia (CIAS), and Alzheimer's disease), and other neuropsychiatric disorders (such as, but not limited to, schizophrenia and associated diseases).

Many patent applications deal with V1a receptor antagonists, for example, Otsuka discloses benzoheterocyclic derivatives (WO 95/034540 A1, WO 2009/001968 A1, WO 2011/052519 A1), Astellas Pharma (Yamanouchi) discloses condensed benzodiazepine and triazole derivatives (WO 95/03305 A1, WO 01/87855 A1, WO 02/44179 A1), AbbVie discloses oxindole derivatives (WO 2006/072458 A2, WO 2006/100082 A2), Bayer Pharma discloses aryl- or heteroaryltriazole derivatives (WO 2017/191102 A1, WO 2017/191107 A1, WO 2017/191114 A1). Various benzoazulene core containing derivatives (WO 2005/068466 A1, WO 2006/021213 A2, WO 2006/021882 A1, WO 2011/114109 A1, WO 2011/128265 A1, WO 2011/141396 A1, WO 2014/127350 A1), spirindolinone and indolylcarbonyl derivatives (WO 97/15556 A1, WO 2007/009906 A1, WO 2007/014851 A2) are also described as V1a receptor antagonists.

The first clinical developments considered the V1a receptor as peripheral target, the poor brain penetration was therefore beneficial in the development of compounds. Such was Sanofi's indoline core compound, relcovaptan (SR-49059, WO 93/03013 A1), which was developed until the Phase 2 clinical trial. Among the indications studied were premature birth, pelvic pain observed during the menstruation, dysmenorrhea (Brouard et al., *Br J Obstetr Gynaecol* 2000, 107:614-9), heart failure, hypertension, and coronary spasm, but it was also tested as an antineoplastic agent in small-cell lung carcinoma until the last clinical trial was stopped in 2003 (Serradeil-Le Gal et al., *Prog Brain Res* 2002, 139:197-210; Adisnsight: Relcovaptan—Latest Information Update: 3 Oct. 2006 http://adisinsight.springer.com/drugs/800004942). Relcovaptan has been in clinical development since 1993 and it is the most frequently used in vitro tool in the V1aR research (Tahara et al., *Br J Pharmacol* 2000, 129:131-9).

Pfizer studied its triazole derivative PF 00738245 (WO 2005/063754 A1) and compound PF-184563 of triazolobenzodiazepine core (WO 2004/074291 A1) in preclinical development for dysmenorrhea, based on measured data these are efficient V1aR antagonists (Russell et al., *Eur. J Pharmacol*, 2011, 670(2): 347-355; Johnson et al., *Bioorg Med Chem Lett* 2011, 21:5684-7) but their development was terminated.

By the examination of effects exerted on the central nervous system, the treatment of depression and anxiety has also been raised as a novel therapeutic area. Johnson & Johnson's compound JNJ-17308616 of spirobenzazepine core was one of the first central nervous system acting V1aR antagonist compound (Bleickard et al., *Psychopharmacology (Berl.)*, 2009, 202:711-18: WO 02/02531 A1) which demonstrated efficacy in a variety of different animal models used for anxiety research: significantly reduced anxiety behaviour in the elevated plus maze test, marble burying test, and in the separation-induced ultrasonic vocalisation of rat pups. Although it proved to be effective in influencing the elevated 0-labyrinth and the conditioned lick response, due to its poor metabolic stability measured in rodents, its efficacy was not good and was measurable only at high doses and therefore it was difficult to test.

Azevan's V1aR antagonist azetidone derivatives, SRX246 and SRX251 (also known as AP1246 or AP1251, WO 03/031407 A2) also reached the clinical trial phase. Clinical trials of SRX246 are also currently ongoing for the treatment of aggression, and intermittent explosive disorder and irritability in Huntington's Disease and post-traumatic stress disorder, as well as in the human behavioural models of anxiety and fear (Adisinsight: SRX 246—Latest Information Update: 16 Feb. 2017 http://adisinsight.springer.com/drugs/800023656). Clinical trial was conducted with SRX251 to treat dysmenorrhea but both Phase 1 studies were discontinued in 2016 and similarly to SRX246 it was also investigated for aggression in the preclinical development (AdisInsight: SRX 251—Latest Information Update: 4 Nov. 2017 http://adisinsight.springer.com/drugs/800025117). SRX-246 and SRX-251 are active on the human V1a receptor and in rats both compounds were detectable in the brain at approximately 100-fold of the effective concentrations detected in the binding assay (Guillon et al., *Bioorg Med Chem* 2007, 15:2054-80; Fabio et al., *J Pharm Sci* 2013, 102(6):2033-43).

Vantia's V1aR antagonist compound, VA 111913 of pyrazolobenzodiazepine core (WO 2010/097576 A1; Adisinsight: VA 111913—Latest Information Update: 25 Aug. 2015 http://adisinsight.springer.com/drugs/800028777) was tested in Phase 2 clinical trial for the treatment of dysmenorrhea but there is no information about its development since 2015.

Otsuka's V1aR antagonist, the quinolinone derivative OPC 21268 (EP0382185A2; Adisinsight: OPC 21268—Latest Information Update: 6 Oct. 2006 http://adisinsight.springer.com/drugs/800000284) was tested for the indication of gastric mucosal damage indication in the preclinical phase, whereas in Phase 2 clinical trials it was studied for heart failure and hypertension but there is no information on its development since 2015 (Yamamura et al., *Science* 1991, 252:572; Serradeil-Le Gal et al., *J Clin Invest* 1993, 92(1): 224).

When examining the brainstem in postmortem human samples selective localisation of V1a receptors unrelated to oxytocin receptors could be detected in the nucleus prepositus, which plays a role in eye gaze stabilisation (Freeman et al., *Soc Neurosci* 2017, 12(2):113-123). A fundamental skill required for human social behaviour is the recognition and eye-tracking of biologically relevant information (Klin et al., *Nature* 2009, 459:257-63, Simion et al., *PNAS* 2008, 105(2):809-13). The most active V1aR researcher Hoffmann-La Roche reached Phase 1 study with their indole derivative RO5028442 (RG-7713; WO 2007/006688 A1), where positive effect on the orientation of eye-gaze pattern could be detected in humans (Umbricht et al., *Neuropsychopharmacology* 2017, 42 (9):1914-1923; Adisinsight: RG 7713—Latest Information Update: 5 Nov. 2015 http://adisinsight.springer.com/drugs/800043668). Phase 2 clinical trials for the treatment of autism are currently ongoing with balovaptan of the triazolobenzodiazepine core (RG-7314, RO5285119; WO 2010/060836 A1; Adisinsight: RG 7314—Latest Information Update: 10 Sep. 2017 http://adisinsight.springer.com/drugs/800035102).

Despite the numerous V1aR antagonist compounds and clinical studies, unmet medical need still persists to develop a V1aR antagonist that is suitable for the treatment and/or prophylaxis of various pathological conditions of the female sex organs, long-standing conditions in blood pressure control, conditions resulting from inappropriate secretion of vasopressin, anxiety, depression, aggression, disorders of the central nervous system where one of the symptoms and/or syndromes of the disease may be related to anxiety, depression, aggression or show comorbidity with them (autistic spectrum disorder, obsessive compulsive disorder, various forms of Down syndrome, post-traumatic stress disorder), aggressive behavioural disorders and/or irritability, behavioural hyperactivity disorders, cognitive disorders or other neuropsychiatric disorders.

SUMMARY OF THE INVENTION

Our aim was to synthetize novel structured V1a receptor antagonists whose physical-chemical (e.g. kinetic or thermodynamic solubility, ionisation, lipophilicity or permeability) or pharmaceutical properties (e.g. metabolic stability, CYP-450 enzyme inhibition) provide the favourable bioavailability, ADME (absorption, distribution, metabolism, excretion), membrane penetration or blood-brain barrier penetration.

Surprisingly, such novel 5,6-dihydro-4H-[1,2,4]triazolo[4,3-a][1]benzazepine derivatives of general formula (I) have been prepared which show V1a receptor antagonistic activity profile.

The present invention relates to compounds of general formula (I)

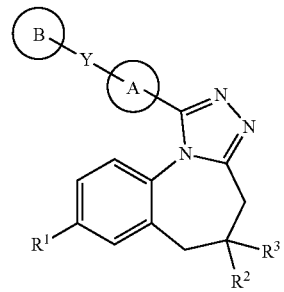

wherein
ring A is a cycloalkyl or heterocyclyl group;
Y is —O—, —C(O)—, —CH$_2$—, —NH—, —C$_{1-4}$alkyl-N(R$^{18}$)— or bond if ring B is present; or —N(C$_{1-4}$alkyl)$_2$, C(O)OC$_{1-4}$alkyl, C$_{1-4}$alkyl optionally substituted with halogen, C$_{1-4}$alkoxy group or halogen if ring B is not present;
ring B is an optionally substituted heteroaryl, aryl or heterocyclyl group;
or B—Y-A- jointly represents 3H-spiro[2-benzofuran-1,4'-piperidin-1'-yl]; or

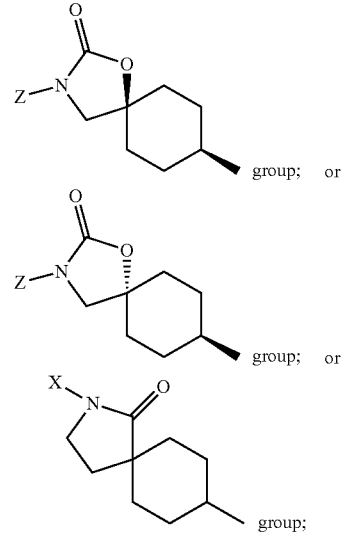

group; or group; or group;

R$^1$ is a hydrogen, halogen, C$_{1-4}$alkyl, C$_{1-4}$alkoxy, CF$_3$ or CN;
R$^2$ is a hydrogen or C$_{1-4}$alkyl group;
R$^1$ is a NR$^4$R$^5$, OR$^6$ group or halogen;
or R$^2$ and R$^3$ jointly represent —O—(CH$_2$)$_m$—O—, oxo or =N—OH group;
R$^4$ and R$^5$ is independently a hydrogen; C$_{1-4}$alkyl optionally substituted with OH, halogen, cycloalkyl, optionally substituted aryl or NR$^8$R$^9$ group; Cy$^1$; C(O)R$^7$; S(O$_2$)R$^{10}$ or C$_{2-4}$alkynyl group;
or R$^4$ and R$^5$ taken together with the N to which they are attached form a heterocycle;
R$^5$ is a hydrogen; C$_{1-4}$alkyl optionally substituted with OH, halogen, Cy$^2$, C$_{1-4}$alkoxy, C$_{1-4}$alkoxy-S(O)$_2$ or NR$^{11}$R$^{12}$ group; C(O)R$^{13}$; Si(CH$_3$)$_2$-t-butyl or C$_{2-4}$alkynyl group;

$R^7$ is a $C_{1-4}$alkyl optionally substituted with OH, CN, halogen, $Cy^3$ or $NR^{11}R^{12}$ group; $C_{1-4}$alkoxy, $C_{2-4}$alkenyl, $Cy^3$ or $N(C_{1-4}alkyl)_2$ group;

$R^8$ and $R^9$ is independently a hydrogen, $C_{1-4}$alkyl or $C(O)OR^{21}$ group;

$R^{10}$ is a $C_{1-4}$alkyl, OH or $NR^{14}R^{15}$ group;

$R^{11}$ and $R^{12}$ is independently a hydrogen or $C_{1-4}$alkyl group; or $R^{11}$ and $R^{12}$ taken together with the N to which they are attached form an optionally substituted heterocycle;

$R^{13}$ is a $C_{1-4}$alkyl optionally substituted with CN or $NR^{19}R^{20}$ group; $Cy^3$ or $NR^{16}R^{17}$ group;

$R^{14}$ and $R^{15}$ is independently a hydrogen or $C_{1-4}$alkyl group;

$R^{16}$ and $R^{17}$ is independently a hydrogen, $C_{1-4}$alkyl, or optionally substituted aryl group;

or $R^{16}$ and $R^{17}$ taken together with the N to which they are attached form a heterocycle;

$R^{18}$ and $R^{21}$ is a hydrogen or $C_{1-4}$alkyl group;

$R^{19}$ and $R^{20}$ is independently a hydrogen or $C_{1-4}$alkyl group;

$Cy^1$ is an optionally substituted cycloalkyl, heterocyclyl or heteroaryl group;

$Cy^2$ is an optionally substituted aryl or cycloalkyl group;

$Cy^3$ is an optionally substituted aryl, cycloalkyl, heterocyclyl or heteroaryl group;

X is a $C_{1-4}$alkyl, aryl or heteroaryl group;

Z is a $C_{1-4}$alkyl group;

m is 2, 3, 4 or 5 and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

The present invention also relates to pharmaceutical compositions containing the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof as active substances.

In addition, the present invention also relates to the preparation of the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof, to the intermediates of the preparation process and to the chemical and pharmaceutical preparation of pharmaceutical compositions containing the compounds.

The invention also relates to a method for treating a mammal, including humans, suffering from a central and/or peripheral disease, where modulation, preferably antagonism of the V1a receptor may have therapeutic benefits wherein the compound of formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof or a therapeutically effective amount thereof in a composition is administered.

The invention also relates to the use of the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof for the manufacture of a medicament for the treatment and/or prophylaxis of a disease or condition associated with V1a receptor function.

DETAILED DESCRIPTION OF THE INVENTION

The present invention relates to V1a receptor modulators, in particular V1a receptor antagonists. It is a further objective of the invention to provide selective V1a receptor inhibitor compounds since selectivity is less likely to cause undesirable side effects. Another aspect of the invention is to provide compounds with favourable physicochemical properties as favourable physical-chemical properties are expected to result in beneficial bioavailability, ADME (absorption, distribution, metabolism, excretion), membrane penetration or blood-brain barrier penetration of the compounds.

The compounds of general formula (I) of the present invention are thus V1a receptor antagonists which are centrally and/or peripherally acting therapeutic agents in the treatment and/or prophylaxis of various pathological conditions of the female sex organs, long-standing conditions in blood pressure control, conditions resulting from inappropriate secretion of vasopressin, anxiety, depression, aggression, disorders of the central nervous system where one of the symptoms and/or syndromes of the disease may be related to anxiety, depression, aggression or show comorbidity with them (autistic spectrum disorder, obsessive compulsive disorder, various forms of Down syndrome, post-traumatic stress disorder), aggressive behavioural disorders and/or irritability, behavioural hyperactivity disorders, cognitive disorders or other neuropsychiatric disorders.

The present invention relates to compounds of general formula (I)

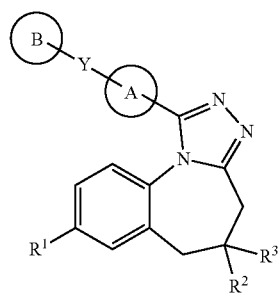

wherein
ring A is a cycloalkyl or heterocyclyl group;
Y is —O—, —C(O)—, —CH$_2$—, —NH—, —C$_{1-4}$alkyl-N(R$^{18}$)— or bond if ring B is present; or —N(C$_{1-4}$alkyl)$_2$, C(O)OC$_{1-4}$alkyl, C$_{1-4}$alkyl optionally substituted with halogen, C$_{1-4}$alkoxy group or halogen if ring B is not present;
ring B is an optionally substituted heteroaryl, aryl or heterocyclyl group;
or B—Y-A- jointly represents 3H-spiro[2-benzofuran-1,4'-piperidin-1'-yl]; or

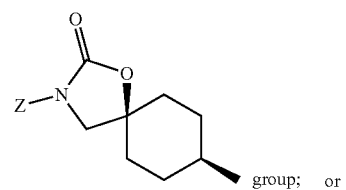

group; or

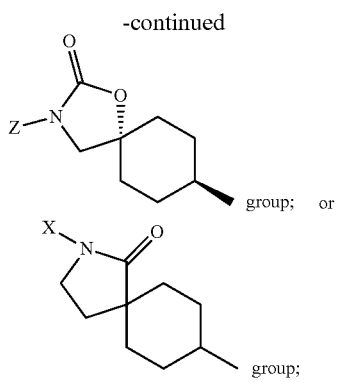
group; or group;

$R^1$ is a hydrogen, halogen, $C_{1-4}$alkyl, $C_{1-4}$alkoxy, $CF_3$ or CN;
$R^2$ is a hydrogen or $C_{1-4}$alkyl group;
$R^3$ is a $NR^4R^5$, $OR^6$ group or halogen;
or $R^2$ and $R^3$ jointly represent —O—$(CH_2)_m$—O—, oxo or =N—OH group;
$R^4$ and $R^5$ is independently a hydrogen; $C_{1-4}$alkyl optionally substituted with OH, halogen, cycloalkyl, optionally substituted aryl or $NR^8R^9$ group; $Cy^1$; $C(O)R^7$; $S(O_2)R^{10}$ or $C_{2-4}$alkynyl group;
or $R^4$ and $R^5$ taken together with the N to which they are attached form a heterocycle;
$R^6$ is a hydrogen; $C_{1-4}$alkyl optionally substituted with OH, halogen, $Cy^2$, $C_{1-4}$alkoxy, $C_{1-4}$alkoxy-$S(O)_2$ or $NR^{11}R^{12}$ group; $C(O)R^{13}$; $Si(CH_3)_2$-t-butyl or $C_{2-4}$alkynyl group;
$R^7$ is a $C_{1-4}$alkyl optionally substituted with OH, CN, halogen, $Cy^3$ or $NR^{11}R^{12}$ group; $C_{1-4}$alkoxy, $C_{2-4}$alkenyl, $Cy^3$ or $N(C_{1-4}$alkyl$)_2$ group;
$R^8$ and $R^9$ is independently a hydrogen, $C_{1-4}$alkyl or $C(O)OR^{21}$ group;
$R^{10}$ is a $C_{1-4}$alkyl, OH or $NR^{14}R^{15}$ group;
$R^{11}$ and $R^{12}$ is independently a hydrogen or $C_{1-4}$alkyl group;
or $R^{11}$ and $R^{12}$ taken together with the N to which they are attached form an optionally substituted heterocycle;
$R^{13}$ is a $C_{1-4}$alkyl optionally substituted with CN or $NR^{19}R^{20}$ group; $Cy^3$ or $NR^{16}R^{17}$ group;
$R^{14}$ and $R^{15}$ is independently a hydrogen or $C_{1-4}$alkyl group;
$R^{16}$ and $R^{17}$ is independently a hydrogen, $C_{1-4}$alkyl, or optionally substituted aryl group;
or $R^{16}$ and $R^{17}$ taken together with the N to which they are attached form a heterocycle;
$R^{18}$ and $R^{21}$ is a hydrogen or $C_{1-4}$alkyl group;
$R^{19}$ and $R^{20}$ is independently a hydrogen or $C_{1-4}$alkyl group;
$Cy^1$ is an optionally substituted cycloalkyl, heterocyclyl or heteroaryl group;
$Cy^2$ is an optionally substituted aryl or cycloalkyl group;
$Cy^3$ is an optionally substituted aryl, cycloalkyl, heterocyclyl or heteroaryl group;
X is a $C_{1-4}$alkyl, aryl or heteroaryl group;
Z is a $C_{1-4}$alkyl group;
m is 2, 3, 4 or 5
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

Definition of the general terms used herein, whether or not the terms in question are presented individually or in combination with other groups are described below.

The term "cycloalkyl group" refers alone or in combination with other groups to 3- to 8-membered, preferably 3- to 6-membered, saturated or unsaturated, preferably saturated carbocyclic groups. Examples include cyclopropyl, cyclobutyl, cyclopentyl or cyclohexyl. In ring A, the term "cycloalkyl group" refers preferably to a 4- to 6-membered, saturated or unsaturated, preferably saturated carbocyclic group. Examples include cyclobutyl, cyclopentyl or cyclohexyl, more preferably cyclobutyl or cyclohexyl. Particularly preferred is the cyclohexyl group. The term "substituted cycloalkyl group" refers preferably to a cycloalkyl group having geminal halogen substitution.

The term "aryl group" refers alone or in combination with other groups to a 6- to 14-membered, preferably 6- to 10-membered aromatic carbocyclic moiety comprising at least one aromatic ring or a condensed ring systems containing at least one aromatic ring. Examples include, but are not limited to, phenyl, benzyl, naphthyl, biphenyl, anthryl, azulenyl or indanyl. Particularly preferred is the phenyl group.

The term "heterocyclyl group" refers alone or in combination with other groups to 3- to 8-membered, preferably 4- to 7-membered, saturated or unsaturated, preferably saturated, monocyclic, bicyclic, condensed and/or bridged ring cycle containing 1, 2 or 3 heteroatoms selected from O, S or N. Examples include, but are not limited to, oxirane, oxetane, tetrahydrofuran, tetrahydropyran, piperidine, pyrrolidine, morpholine, piperazine, 1,3-oxazolidine, 1,3-thiazolidine, thiomorpholine 1,1-dioxide, azepane, 1-azabicyclo[2.2.2]octane and the like. Preferably pyrrolidinyl, piperidinyl, piperazinyl or 1-azabicyclo[2.2.2]oct-3-yl. More preferably, piperidinyl or piperazinyl.

When ring A is heterocyclyl, then heterocyclyl refers preferably to a 4- to 7-membered saturated heterocyclyl group containing 1 or 2 N, wherein ring A is attached via a ring nitrogen to Y or to the triazole ring of the 5,6-dihydro-4H-[1,2,4]triazolo[4,3-a][1]benzazepine core. Examples include, but are not limited to, azetidinyl, 1,3-diazetidinyl, pyrrolidinyl, pyrazolidinyl, imidazolidinyl, piperidinyl, piperazinyl, azepanyl, 1,3- or 1,4-diazepanyl. Preferably azetidinyl, pyrrolidinyl, piperidinyl or piperazinyl. Particularly preferred is piperidinyl.

In the case of $Cy^1$ or $Cy^1$, the heterocycle refers preferably to a 4- to 7-membered saturated heterocyclyl group containing 1 O, more preferably oxetane or tetrahydropyran.

When "$R^4$ and $R^5$ taken together with the N to which they are attached form a heterocycle", the heterocycle refers preferably to a 4- to 7-membered saturated ring containing 1, 2 or 3 heteroatoms selected from O, S or N, more preferably pyrrolidine, 3-oxazolidine, 1,3-thiazolidine, piperidine, piperazine, morpholinyl or thiomorpholine-1,1-dioxide.

When "$R^{11}$ and $R^{12}$", or "$R^{16}$ and $R^{17}$ taken together with the N to which they are attached form a heterocycle", the heterocycle is preferably selected from the group comprising morpholin-4-yl, 4-methylpiperazin-1-yl, pyrrolidinyl, piperidinyl, piperazinyl, 1,3-oxazolidine, 1,3-thiazolidine or thiomorpholine-1,1-dioxide.

The term "heteroaryl group" refers alone or in combination with other groups to a cyclic aromatic group containing a single 5- to 6-membered ring containing 1, 2 or 3 heteroatoms in which group at least one heterocyclic ring is aromatic. The "6-membered mono-heteroaryl" refers to a monocyclic aromatic group which is a single 6-membered ring containing 1, 2, or 3 heteroatoms selected from O, S or N. Examples include, but are not limited to, pyridinyl, pyrimidinyl, pyrazinyl, pyridazinyl, thiazinyl, oxazinyl and the like. Preferred single 6-membered mono-heteroaryl groups contain 1 or 2 N. A preferred 6-membered ring is pyridinyl, more preferably pyridin-2-yl and pyridin-3-yl. Particularly preferred is pyridin-2-yl. The term "5-membered mono-heteroaryl" refers to a monocyclic aromatic group which is a single 5-membered ring containing 1, 2 or 3 heteroatoms selected from O, S or N. Preferred 5-membered mono-heteroaryl groups contain 2 N and 1 O, 2 N and 1 S, 2 N, 1 N or 1 S or 1 N and 1 O. Examples include, but are not limited to, thiophenyl, furanyl, pyrrolyl, imidazolyl, thiazolyl, isoxazolyl, isothiazolyl, oxadiazolyl, thiadiazolyl, 1H-pyrazolyl, triazolyl and the like. A preferred 5-membered ring is isoxazol-3-yl and 1,3,4-oxadiazol-5-yl.

In the case of $Cy^1$, the heteroaryl refers preferably to a 6-membered mono-heteroaryl group containing 1 or 2 N, more preferably pyridine, pyrimidine or pyrazine.

When ring B is an optionally substituted heteroaryl group, the heteroaryl group is preferably 3-chloropyridin-2-yl, 3-methylpyridin-2-yl or 5-methylisoxazol-3-yl.

The term "bond" refers to a single bond, in which one pair of electrons is shared between two atoms.

The term "$C_{1-4}$alkyl group" refers alone or in combination with other groups to a straight or branched, single or multiple branched, hydrocarbon radical and consists of 1 to 4 carbon atoms. Examples include, but are not limited to, methyl, ethyl, propyl, i-propyl (isopropyl), n-butyl, 2-butyl (sec-butyl) or t-butyl (tert-butyl) group. Preferred alkyl groups are those consisting of 1 to 3 carbon atoms. More preferred are methyl, ethyl and isopropyl groups. Particularly preferred is the methyl group.

The term "$C_{2-4}$alkenyl group" refers alone or in combination with other groups to a straight or branched, single or multiple branched, hydrocarbon radical having one double bond and consists of 2 to 4 carbon atoms. Examples include, but are not limited to, vinyl, propen-1-yl, propen-2-yl, butene-1-yl or butene-3-yl. Preferred alkenyl groups are those consisting of 2 to 3 carbon atoms. Particularly preferred is the vinyl group.

The term "$C_{2-4}$alkynyl group" refers alone or in combination with other groups to a hydrocarbon radical having one triple bond and consist of 2 to 4 carbon atoms. Examples include, but are not limited to, ethynyl, propynyl, propargyl, 1-butynyl, 2-butynyl and the like. Preferred alkynyl groups are those consisting of three carbon atoms. More preferred is the propargyl group.

The term "$C_{1-4}$alkoxy group" refers alone or in combination with other groups to —O—$C_{1-4}$alkyl group, wherein the $C_{1-4}$alkyl group is as defined above. Examples include, but are not limited to, methoxy, ethoxy, propoxy, t-butoxy. Preferred alkoxy groups are methoxy, propoxy or t-butoxy. Particularly preferred are the methoxy and t-butoxy groups.

The term "Boc" refers alone or in combination with other groups to t-butoxycarbonyl group.

The term "halogen" refers alone or in combination with other groups to fluorine, chlorine, bromine or iodine, preferably fluorine, chlorine or bromine, more preferably chlorine or bromine. Particularly preferred is chlorine.

The term "optionally substituted" on any atom of the relevant group refers to the substitution by one or more $C_{1-4}$alkyl, $C_{1-4}$alkoxy groups, oxo groups or halogens. Here, "one or more" means from one to the highest possible number of substitution, that is, from replacing one hydrogen to replacing all hydrogens. One, two or three substituents on a given atom are preferred. Even more preferred are one or two, or one substitution. Particularly preferred is one substitution for a substituted aryl or heteroaryl group. The expression "$C_{1-4}$alkyl optionally substituted with halogen" refers preferably to a $C_{1-4}$alkyl group having one, two or three halogen substituents on any atom of the $C_{1-4}$alkyl group, more preferably to a methyl group having three halogen substituents. Particularly preferred is CF group.

The term "salt" refers to pharmaceutically acceptable and/or pharmaceutically non-acceptable salts. The pharmaceutically acceptable salt refers to a conventional acid addition and base addition salts which preserve the biological efficacy and properties of the compounds of general formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide. These salts often exhibit more favourable solubility properties than the compounds used for their preparation and are therefore more suitable for use in the preparation for example of liquid or emulsion formulations. The pharmaceutically non-acceptable salts may be preferred for the purification and isolation of the compounds of general formula (I) and therefore also fall within the scope of the invention.

The term "prodrug" refers to derivatives of compounds of general formula (I) according to the invention which themselves have no therapeutic effect but containing such groups which, after in vivo chemical or metabolic degradation (biotransformation) become "biologically active metabolites" which are responsible for the therapeutic effect. Such decomposing groups associated with the compounds of general formula (I) of the present invention, in particular those suitable for prodrugs, are known in the art and may also be applied for the compounds of the present invention (Rautio et al., *Nat Rev Drug Discov* 2008, 7:255-270).

The compounds of general formula (I) may exist in various geometric isomeric forms. In addition, certain compounds of general formula (I) may contain one or more asymmetric centers, thus exist in the form of stereoisomers and diastereomers. All of these compounds, such as cis isomers, trans isomers, diastereomeric mixtures, racemates, non-racemic mixtures of enantiomers, substantially pure and pure enantiomers also fall within the scope of the invention. The substantially pure enantiomers contain up to 5 wt %, preferably 2 wt %, most preferably 1 wt %, of the corresponding opposite enantiomer.

Optical isomers can be prepared by resolving the racemic mixtures by known methods, for example, by using an optically active acid or base to form diastereoisomeric salts or by forming covalent diastereomers. Suitable acids include, for example, tartaric acid, diacetyltartaric acid, dibenzoyltartaric acid, ditoluoyltartaric acid and camphorsulfonic acid. Diastereoisomeric mixtures can be separated into individual diastereomers based on their physical and/or chemical differences, by methods known to those skilled in the art, such as chromatography or fractional crystallization. Subsequently, the optically active bases or acids are liberated from the separated diastereoisomeric salts. Various methods of separating optical isomers include chiral chromatography (e.g., chiral HPLC columns) optionally used by derivatization with the aim to maximize the separation of enantiomers. Appropriate chiral HPLC columns are Diacel columns, such as CHIRALPAK or CHIRALCEL columns, which can be routinely chosen as desired. Where applicable, enzymatic separations carried out by derivatization may also be used. The optically active compounds of general formula (I) can also be prepared using optically active starting materials using chiral synthesis without racemization reaction conditions.

The absolute configuration of the chiral compounds was determined by VCD (vibrational circular dichroism spectroscopy) method described in the literature (Freedman et al., *Chirality* 2003, 15(9):743-58; Stephens et al., *Chirality* 2008, 20:643-663) and/or by $^1$H NMR spectroscopic assays of the diastereomeric pair of compounds synthesized from chiral compounds (Seco et al., *J Org Chem* 1999, 64:4669-4675; Seco et al., *Tetrahedron Asymmetry* 2001, 12:2915-2925; Latypov et al., *J. Am. Chem. Soc.* 1998, 120, 4741-4751).

The compounds of general formula (I) may exist in various polymorphic forms. As is known in the art, polymorphism is the ability of a compound to crystallize in more than one crystalline form, i.e. in polymorphic form. Polymorphic forms of a particular compound can be defined by identical chemical formula or composition and differ in their chemical structure like the crystalline structures of two different chemical compounds.

The compounds of general formula (I) and salts thereof may also be present as solvates or hydrates, which also fall within the scope of the invention. The term "solvate" refers to non-covalent combinations of solvent and solute. The term "hydrate" refers to non-covalent combinations of water and solute.

The present invention further relates to pharmaceutical compositions containing the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof.

The present invention also relates to the chemical and pharmaceutical preparation of pharmaceutical compositions containing the compound of general formula (I) and/or salt thereof and/or geometric isomer thereof and/or stereoisomer thereof and/or enantiomer thereof and/or racemate thereof and/or diastereomer thereof and/or solvate thereof and/or hydrate thereof and/or polymorph thereof.

The pharmaceutical compositions of the present invention may be formulated in various pharmaceutical formulations, such as, but not limited to, solid oral dosage forms such as tablets (e.g. buccal, sublingual, effervescent, chewable, orally dispersible), capsules, pills, pilulas, orally dispersible films, granules, powders: liquid formulations such as solutions, emulsions, suspensions, syrups, elixirs, drops; parenteral dosage forms such as intravenous injections, intramuscular injections, subcutaneous injections; other forms of medicine such as eye drops, semi-solid ophthalmic preparations, semi-solid dermal preparations (such as ointments, creams, pastes), transdermal therapeutic systems, suppositories, rectal capsules, rectal solutions, emulsions and suspensions, etc.

One embodiment of the invention relates to pharmaceutical compositions for paediatric use, such as, but not limited to, solutions, syrups, elixirs, suspensions, powders for the preparation of suspensions, dispersible or effervescent tablets, chewable tablets, orodispersible tablets, tablets or coated tablets, orally sparkling powders or granules, capsules.

The pharmaceutical compositions of the present invention may be prepared by methods known per se, such as conventional mixing, dissolution, emulsification, suspending, microencapsulation, lyophilisation, extrusion and spheronisation, lamination, film coating, granulation, encapsulation, drageeing or pressing.

The pharmaceutical compositions of the present invention may be formulated in the usual way using one or more physiologically acceptable excipients, including binders, which promote the incorporation of the active substance into pharmaceutically acceptable pharmaceutical forms. The proper formulation depends on the mode of administration chosen. Any of the techniques and excipients well known in the art can be used.

The excipients applicable in the preparation may be selected from the following categories, such as, but not limited to, fillers of tablets and capsules, binders of tablets and capsules, modified drug release agents, disintegrants, glidants, lubricants, sweeteners, taste-masking agents, flavourants, coating materials, surfactants, stabilisers, preservatives or antioxidants, buffering agents, complexing agents, wetting or emulsifying agents, salts for adjusting the osmotic pressure, lyophilisation excipients, microencapsulating agents, ointment materials, penetration enhancers, solubilisers, solvents, suppository materials, suspending agents. Suitable pharmaceutical excipients can be for example: starch, microcrystalline cellulose, talc, glucose, lactose, gelatin, silica, talc, magnesium stearate, sodium stearate, glycerol monostearate, cellulose derivatives, sodium chloride, glycerol, propylene glycol, water, ethanol and the like.

Another embodiment of the present invention relates to the use of special binders that can improve the solubility, dissolution, penetration, absorption or bioavailability of the active substance(s), such as, but not limited to, hydrophilic polymers, hot melting extruding excipients, surfactants, buffering agents, complexing agents, emulsifying agents, lyophilization excipients, disintegrants, microencapsulating agents, penetration promoters, solubilisers, cosolvents, suspending agents.

The excipients described above and the various methods of preparation are only representative examples. Other materials and process techniques known in the art may also be used.

The terms "disease or condition associated with V1a receptor function" or "disease or condition associated with the central and/or peripheral modulation, preferably antagonisation of the V1a receptor" refer to a disease or condition selected from the group consisting of various pathological conditions of the female sex organs, long-standing conditions in blood pressure control, conditions resulting from inappropriate secretion of vasopressin, anxiety, depression, aggression, disorders of the central nervous system where one of the symptoms and/or syndromes of the disease may be related to anxiety, depression, aggression or show comorbidity with them (autistic spectrum disorder, obsessive compulsive disorder, various forms of Down syndrome, post-traumatic stress disorder), aggressive behavioural disorders and/or irritability, behavioural hyperactivity disorders, cognitive disorders or other neuropsychiatric disorders.

The various pathological conditions of the female sex organs include, but not limited to, dysmenorrhea (primary and/or secondary) or sexual dysfunction.

The long-standing conditions in blood pressure control include, but not limited to, hypertension and/or chronic heart failure.

The conditions resulting from inappropriate secretion of vasopressin include, but not limited to, diabetes insipidus, renal failure, nephrotic syndrome or cirrhosis.

The disorders of the central nervous system where one of the symptoms and/or syndromes of the disease may be related to anxiety, depression, aggression or show comorbidity with them include, but not limited to, autistic spectrum disorder (well-functioning autism, Asperger's syndrome, Pervasive Developmental Disorder-Not Otherwise Specified (PDD-NOS), autism spectrum disorder (ASD) and its various syndrome forms: fragile X syndrome, Prader-Willi syndrome, Rett syndrome, tuberous sclerosis), obsessive compulsive disorder (OCD), various forms of Down syndrome and post-traumatic stress disorder (PTSD).

The aggressive behavioural disorders and/or irritability include, but not limited to, ASD, Huntington's disease or different forms of schizophrenia.

The behavioural hyperactivity disorders include, but not limited to, attention deficit hyperactivity disorder.

The cognitive disorders include, but not limited to, dementia, mild cognitive disorders, cognitive impairment associated with schizophrenia or Alzheimer's disease.

The other neuropsychiatric disorders include, but not limited to, schizophrenia and associated diseases.

In one embodiment, the disease or condition associated with V1a receptor function or disease or condition associated with the central and/or peripheral modulation, preferably antagonisation of V1a receptor refers to autistic spectrum disorder.

The present invention relates to a method for treating and/or preventing a disease or condition associated with V1a receptor function, comprising the administration to a subject in need of treatment and/or prophylaxis, preferably a mammal, more preferably a human being, of a therapeutically effective amount of a compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof alone or with at least one pharmaceutically acceptable excipient in the form of a pharmaceutical formulation.

The present invention relates to a method for the treatment of a subject, preferably a mammal, more preferably a human being, suffering from a disease or condition selected from the group consisting of various pathological conditions of the female sex organs, long-standing conditions in blood pressure control, conditions resulting from inappropriate secretion of vasopressin, anxiety, depression, aggression, disorders of the central nervous system where one of the symptoms and/or syndromes of the disease may be related to anxiety, depression, aggression or show comorbidity with them (autistic spectrum disorder, obsessive compulsive disorder, various forms of Down syndrome, post-traumatic stress disorder), aggressive behavioural disorders and/or irritability, behavioural hyperactivity disorders, cognitive disorders or other neuropsychiatric disorders, or combination of the these diseases. This method of treatment comprises the administration to a subject in need of such treatment, preferably a mammal, more preferably a human being, the therapeutically effective amount of the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof. The method of treatment may include the administration to a subject in need of such treatment, preferably a mammal, more preferably a human being, of a therapeutically effective amount of a pharmaceutical composition comprising the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof.

The present invention relates to the use of the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof for the manufacture of a medicament for the treatment and/or prophylaxis of a disease or condition associated with V1a receptor function.

The term "treatment" refers to the alleviation of a specific pathological condition, the elimination or reduction of one or more of the symptoms of the condition, the slowing or elimination of the progression of the disease state, and the prevention or delay of recurrence of the pathological condition of a patient or subject already suffering from or diagnosed with the disease. "Prevention" (or prophylaxis or delay of occurrence of the disease) is typically performed by administering the drug in the same or similar way as if it were given to a patient with a disease or condition already developed.

The term "therapeutically effective amount" refers to the amount of active substance resulting in the treatment, cure, prevention or improvement of the disease or pathological condition or side effect, and reduces the progression of the disease or pathological condition in comparison with the corresponding subject who did not receive such amount. The term also includes effective amounts to enhance normal physiological functioning. For use in therapy the compound of general formula (I) and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof as well as any pharmaceutically acceptable salt thereof may be administered in a therapeutically effective amount as a raw chemical. In addition, the active substance can be made available as a pharmaceutical formulation. The exact therapeutically effective amount of the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof depends on a number of factors including, but not limited to, the age and body weight of the subject (patient) treated, the precise type of disease requiring treatment and its seriousness, the nature of the medicinal product and the route of administration.

The term "mammal" refers to any member of the "Mammalia" class, including, but not limited to, humans.

The present invention also relates to pharmaceutical compositions comprising the compound of general formula (I) and/or salt thereof and/or geometric isomer thereof and/or stereoisomer thereof and/or enantiomer thereof and/or racemate thereof and/or diastereomer thereof and/or prodrug thereof and/or solvate thereof and/or hydrate thereof and/or polymorph thereof suitable for the treatment of a disease or condition associated with the central and/or peripheral modulation, preferably antagonisation of the V1a receptor.

The compound of the invention may also be used in combination with one or more of the compounds of the invention or with one or more other active substance (e.g., psycholeptics, psychoanaleptics, antihypertensives, spasmolytics, antiepileptics or other agents) in a mammal, including, but not limited to, humans, suffering from a central and/or peripheral disease, where the central and/or peripheral modulation, preferably antagonisation of V1a receptor has therapeutic benefits.

Psycholeptics include, but not limited to, antipsychotics, anxiolytics, and sedatohipnotics or narcotics.

Antipsychotics include, but not limited to, typical and atypical antipsychotics, such as phenothiazines with aliphatic side chains (chlorpromazine, promazine, levomepromazine, acepromazine, trifluproazine, ciamemazine, chlorproethazine, protipendyl), piperazine-derived phenothiazines (dixyrazine, flufenazine, perazine, perfenazine, prochlorperazine, thiopropazate, trifluoperazine, acetophenazine, thioproperazine, butaperazine, perazine), piperidine-derived phenothiazines (periciazine, thioridazine, mesoridazine, pipothiazine), thioxanthenes (chlorprothixene, clopenthixole, flupentixol, thiothixene, zuclopenthixol), butyrophenone derivatives (haloperidol, triflupidol, melperone, moperone, pipamperone, bromperidol, benperidol, droperidol, timiperone, fluanisone), diphenylbutylpiperidine derivatives (fluspirilene, penfluridol, pimozide), diazepine-, oxazepine- or thiazepine derivatives (clozapine, olanzapine, clotiapine, quetiapine, loxapine, azenapine), indole derivatives (sertindole, ziprasidone, lurazidone, molindone, oxipertine), benzamide derivatives (sulpiride, sultropride, tiapride, remoxipride, amisulpride, veralipride, nemonapride, verasulpiride) or other agents (risperidone, aripiprazole, cariprazine, brexpiprazole, metoclopramide, mosapramine, iloperidone, paliperidone, amoxapine, amperoside, perospirone, carpipramine, clocapramine, tetrabenazine, lithium).

Anxiolytics include, but not limited to, benzodiazepines (diazepam, chlorodiazepoxide, medazepam, oxazepam, potassium chlorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, coxazolam, tophizopam), diphenylmethane derivatives (hydroxyzine, captodiame), carbamates (meprobamate, emilcamate, mebutamate), dibenzobicyclooctadiene derivatives (benzoquinone), azaspirode-diones (buspirone), other agents (mefenoxalone, gedocarnil, etifoxine, fabomotizole, trimethosine), derivatives acting by increasing $GABA_A$-mediated inhibition or compounds acting on a serotonin receptor, and other GABAergic agents (such as $GABA_A$ α5 NAMs, e.g. basmisanil, $GABA_A$ α5 PAMs, e.g. RG7816).

Sedative hypnotics or narcotics include, but not limited to, barbiturates (pentobarbital, amobarbital, butobarbital, barbital, aprobarbital, secobarbital, talbutal, vinylbital, vinbarbital, cyclobarbital, heptabarbital, reposal, methohexitol, hexobarbital, thiopental, ethallobarbital, allobarbitol, proxibarbital), aldehydes (chloral hydrate, chloralodol, acetylglycinamide chloral hydrate, dichloralphenazone, paraldehyde), benzodiazepines (flurazepam, nitrazepam, flunitrazepam, estazolam, triazolam, lormetazepam, temazepam, midazolam, brotizolam, quazepam, loprazolam, doxefazepam, cinolazepam), piperidindione derivatives (glutethimide, methyprylon, pyrithyldione), cyclopyrrolone benzodiazepine derivatives (zopiclone, zolpidem, zaleplon, eszopiclone), melatonin receptor agonists (melatonin, ramelteon) or other hypnotics and sedatives (methaqualone, clmethiazole, bromisoval, carbromal, scopolamine, propiomazine, triclofos, ethchlorvynol, *Valerianae* Radix, hexapropymate, bromides, apronal, valnoctamide, methylpentynol, niaprazine, dexmedetomidine).

Psychoanaleptics include, but not limited to, psychostimulants or antidepressants.

Psychostimulants include, but not limited to, centrally acting sympathomimetics (amphetamine, dexamphetamine, methamphetamine, methylphenidate, pemoline, fencamfamine, modafinil, phenozolone, atomoxetine, phenetilline, dexmethylphenidate, lysdexamfetamine), nootropics or other psychostimulants (caffeine, propentofylline, meclofenoxate, pyritinol, piracetam, deanol, fipexide, citocoline, oxiracetam, pirisudanol, linopirdine, nizofenone, aniracetam, acetylcarnitine, idebenone, prolintane, pipradrol, pramiracetam, adrafinil, vinpocetine, tacrine, donepezil, rivastigmine, galantamine, ipidachrine, memantine, mebicar, phenibut).

Antidepressants include, but not limited to, non-selective monoamine reuptake inhibitors (desipramine, imipramine, imipramine oxide, clomipramine, opipramol, trimipramine, lofepramine, dibenzepine, amitriptyline, nortriptyline, protriptyline, doxepin, iprindole, melitracene, butriptyline, dosulepin, amoxapine, dimetacrine, amineptin, maprotiline, quinupramine), serotonin modulator and stimulators (vilazodone, vortioxetine), selective serotonin reuptake inhibitors (zimeldine, fluoxetine, paroxetine, sertraline, alaproclate, fluvoxamine, etoperidone, citalopram, escitalopram), non-selective hydrazide-derived monoamine oxidase inhibitors (isocarboxazide, nialamide, phenelzine, tranylcypromine, iproniazid, iprocloside), non-hydrazide monoamine oxidase inhibitors (moclobemide, toloxatone) or other agents (oxitriptan, tryptophan, mianserin, nomifensin, trazodone, nefazodone, minaprine, bifemelane, viloxazine, oxaflozane, mirtazapine, medifoxamine, tianeptine, pivagabine, venlafaxine, milnacipran, reboxetine, pyrazidol, duloxetine, agomelatine, desvenlafaxine, bupropion, gepirone, Hyperici herba extractum).

Antihypertensives include, but not limited to, P receptor blockers, thiazide diuretics, angiotensin-converting-enzyme inhibitors, calcium antagonists, angiotensin receptor antagonists (losartan), Rauwolfia alkaloids (rescinnamine, reserpine, deserpidine, methoserpidine, bietaserpine), methyldopa, imidazoline receptor agonists (clonidine, guanfacine, tolonidine, moxonidine, rilmenidine), ganglion blocking antiadrenergic agents (sulfonium derivative trimetaphan, secondary and tertiary amine mecamylamine), peripherally acting antiadrenergic agents, alpha-adrenoreceptor blockers (prazosin, indoramin, trimazosin, doxazosin, urapidil), guanidine derivatives (betanidine, guanethidine, guanoxane, debrisoquine, guanoclor, guanazodine, guanoxabenz), agents acting on arteriolar smooth muscle, the thiazide derivative diazoxide, hydrazinophthalazine derivatives (dihydralazine, hydralazine, endralazine, cadralazine), the pyrimidine derivative minoxidil, the nitroferricyanide derivative nitroprusside, the guanidine derivative pinacidil, the non-Rauwolfia alkaloid veratrum, the tyrosine hydroxylase inhibitory metyrosine, the MAO inhibitor pargyline, the serotonin antagonist ketanserin, or other antihypertensives (bosentan, ampbrisentan, sitaxentan, macitentan, riociguat) and a combination of these substances with a diuretic.

Spasmolytics or antispasmodics include, but not limited to, peripheral muscle relaxants, curare alkaloids, choline derivatives, other quaternary ammonium muscle relaxants (pancuronium, gallamine, vecuronium, atracurium, hexafluronium, pipecuronium bromide, doxacurium chloride, fazadinium bromide, rocuronium bromide, mivacurium bromide, cisatracurium, botulinum toxin), central nervous system muscle relaxants, carbamic acid esters (phenprobamate, carisoprodol, metocarbamol, styranate, febarbamate), oxazole-, thiazine- and triazine derivatives (chlormezanone, chlorzoxazone), ethers related to antihistamines (orphenadrine, guaifenesin) and other histaminergic agents (such as histamine $H_3$ receptor antagonists/inverse agonists e.g. ciproxifan, thioperamide, pitolisant, clobenpropit, ABT-239, conessine, A-349,821, betahistine), other centrally acting agents (baclofen, arbaclofen, tizanidine, pridinol, tolperisone, thiocolchicoside, mephenesin, tertazepam, cyclobenzaprine, phenyramidl), the directly acting muscle relaxant dantrolene and its derivatives, compounds acting by increasing GABAamediated inhibition or decreasing conduction of Na (phenytoin, carbamazepine, lamotrigine, VPA), gamma-aminobutyric acid derivatives (vigabatrin, gabapentin), other GABAergic agents (such as $GABA_B$ PAMs, e.g. ADX71441), esters with a tertiary amino group (xyphencyclimine, camylofin, mebeverine, trimebutine, rociverine, dicycloverine, dihexyverine, difemerine, piperidolate), quaternary ammonium compounds (benzilone, glycopyrronium, oxyphenonium, penthienate, propantheline, otilonium bromide, methantheline, tridihexethyl, isopropamide, hexocyclium, poldine, mepenzolate, bevonium, pipenzolate, diphemanil, emetonium iodide, tiemonium iodide, prifinium bromide, timepidium bromide and fenpiverinium), amides with tertiary amines (astra 1397, nicofetamide, tiropramide), papaverine and its derivatives (drotaverine, moxaverine, etaverine), agents acting on serotonin receptors (alosetron, tegaserod, cilansteron, prucalopride), other agents of functional gastrointestinal disorders (fenpiprane, diisopromine, chlorbenzoxamine, pinaverium, fenoverine, idanpramine, proxazole, alverine, trepibutone, isometheptene, caroverine, phloroglucinol, silicones, trimethyldiphenylpropylamine), succinimide derivative (ethosuximide, phensuximide, mesuximide) or *Belladonna* alkaloids and their derivatives (atropine, hyoscyamine, butylscopolamine, methylatropine, methylscopolamine, fentonium, cimetropium bromide).

Antiepileptics include, but not limited to, barbiturates and their derivatives (methylphenobarbital, phenobarbital, primidone, barbexaclone, metharbital), hydantoin derivatives (ethotion, phenytoin, amino(diphenylhydantoin) valeric acid, mephenytoin, fosphenytoin), oxazolidine derivatives (paramethadione, trimethadione, ethadion), succinimide derivatives (ethosuximide, phensuximide, mesuximide), benzodiazepine derivative clonazepam, carboxamide derivatives (carbamazepine, oxcarbazepine, rufinamide), fatty acid derivatives (valproic acid, valpromide, aminobutyric acid, vigabatrin, progabide, tiagabine) and other antiepileptics (sultiame, phenacemide, lamotrigine, felbamate, topiramate, gabapentin, pheneturide, levetiracetam, zonisamide, pregabalin, stiripentl, lacosamide, carisbamate, retigabine, brivaracetam, beclamide).

Other agents include, but not limited to, medicinal products (probiotics, digestive aids/digestives, herbal extracts), vitamins (both water soluble and fat soluble, such as, but not limited to, vitamin A, D3, E, K, B1, B5, B6, B12, C or their derivatives) and nutritional supplements (coenzymes e.g. Q10, flavonoids e.g. resveratrol, lecithin, unsaturated fatty acids, including fatty acids ω-3 and ω-6).

The compounds of the invention may also be used in combination with phosphodiesterase 5 isoenzyme inhibitors (PDE5), nitric oxide donors, cyclooxygenase inhibitors, other V1a receptor antagonists (such as balovaptan) or L-arginine for the treatment and/or prophylaxis of a disease or condition associated with V1a receptor function.

The combinational composition may comprise the compound of the invention together with another active substance in a single dosage form or separately. The combinational composition may be administered simultaneously, separately or sequentially.

Suitable dosage forms include oral, rectal, mucous, transdermal or intestinal administration; parenteral administration including intramuscular, subcutaneous, intravenous, intramedullary injections as well as intraarticular, intrathecal, direct intraventricular, intraperitoneal, intranasal or intraocular injections and eye drops.

Alternatively, the compounds may be administered locally and not systemically, for example by direct injection of the compound to the kidney or the heart, often in a modified release formulation. In addition, the drug may be administered in a targeted carrier system, for example in a tissue-specific antibody encapsulated liposome. The liposomes transfer the active substance selectively to the target organ, which absorbs it.

The pharmaceutical composition may be administered in various ways and in pharmaceutical forms. The compound of the invention may be administered alone or in combination with pharmaceutically acceptable excipients, in single or multiple doses. The dose required to achieve the appropriate therapeutic effect may vary widely and must always be adapted to individual needs with regard to the stage of disease, the condition and weight of the patient to be treated, and the sensitivity to the active substance, the way of dosage regimen, and the numbers of daily treatments.

For simple administration, it is preferred that the pharmaceutical compositions consist of dosage units that contain the amount of drug to be administered once, or a small number of its multiple, or half, one third, one quarter. Such dosage units are, for example, tablets that can be provided with a half or quarter groove to facilitate halving or quarter-splitting of the tablet in order to measure the required amount of drug.

Pharmaceutical compositions containing the active substance according to the invention generally contain from 0.01 to 500 mg of active substance per dosage unit. It is of course also possible that the amount of active substance in each formulation exceeds the above limit either up or down.

Further preferred groups of compounds of general formula (I) are those wherein each embodiments of ring A, ring B, X, Y, Z, $R^1$-$R^{21}$, $Cy^1$-$Cy^3$ and m described below are optionally combined. Any combination of the preferred, more preferred or most preferred embodiments of ring A, ring B, X, Y, Z, $R^1$-$R^{21}$, $Cy^1$-$Cy^3$ or m as defined below are also preferred, more preferred and most preferred groups of compounds of formula (I).

In certain embodiments of the invention, ring A in the compounds of general formula (I) is a 4 to 6-membered saturated carbocycle.

In certain preferred embodiments of the invention, ring A in the compounds of general formula (I) is cyclobutyl or cyclohexyl.

In certain more preferred embodiments of the invention, ring A in the compounds of general formula (I) is cyclohexyl.

In certain embodiments of the invention, ring A in the compounds of general formula (I) is a 4- to 7-membered saturated heterocyclyl group containing 1 or 2 N, wherein ring A is attached via a ring nitrogen to Y.

In certain embodiments of the invention, ring A in the compounds of general formula (I) is a 4- to 7-membered saturated heterocyclyl group containing 1 or 2 N, wherein ring A is attached via a ring nitrogen to the triazole ring of the 5,6-dihydro-4H-[1,2,4]triazolo[4,3-a][1]benzazepine core.

In certain embodiments of the invention, ring A in the compounds of general formula (I) is azetidinyl, 1,3-diazetidinyl, pyrrolidinyl, pyrazolidinyl, imidazolidinyl, piperidinyl, piperazinyl, azepanyl, 1,3- or 1,4-diazepanyl, wherein ring A is attached via a ring nitrogen to Y.

In certain embodiments of the invention, ring A in the compounds of general formula (I) is azetidinyl, 1,3-diazetidinyl, pyrrolidinyl, pyrazolidinyl, imidazolidinyl, piperidinyl, piperazinyl, azepanyl, 1,3- or 1,4-diazepanyl, wherein ring A is attached via a ring nitrogen to the triazole ring of the 5,6-dihydro-4H-[1,2,4]triazolo[4,3-a][1]benzazepine core.

In certain preferred embodiments of the invention, ring A in compounds of general formula (is azetidin-1,3-diyl, piperidin-1,4-diyl or piperazine-1,4-diyl, wherein ring A is attached via a ring nitrogen to Y or to the triazole ring of the 5,6-dihydro-4H-[1,2,4]triazolo[4,3-a][1]benzazepine core.

In certain embodiments of the invention, ring B in the compounds of general formula (I) is optionally substituted aryl group.

In certain preferred embodiments of the invention, ring B in the compounds of general formula (I) is optionally substituted phenyl.

In certain embodiments of the invention, ring B in the compounds of general formula (I) is optionally substituted heterocyclyl group.

In certain preferred embodiments of the invention, ring B in the compounds of general formula (I) is optionally substituted tetrahydrofuranyl, tetrahydropyranyl, pyrrolidinyl, piperidinyl, piperazinyl, morpholinyl or azabicyclo[2.2.2]octyl.

In certain more preferred embodiments of the invention, ring B in the compounds of general formula (I) is tetrahydrofuran-3-yl, tetrahydropyran-4-yl, pyrrolidin-1-yl, pyrrolidin-1-yl-2-one, piperidin-1-yl, 4-methyl-piperazin-1-yl, morpholin-4-yl or 1-azabicyclo[2.2.2]oct-3-yl.

In certain embodiments of the invention, ring B in the compounds of general formula (I) is optionally substituted heteroaryl group.

In certain embodiments of the invention, ring B in the compounds of general formula (I) is optionally substituted single 6- or 5-membered mono heteroaryl group.

In certain preferred embodiments of the invention, ring B in the compounds of general formula (I) is optionally substituted pyridinyl, pyrimidinyl or isoxazolyl.

In certain more preferred embodiments of the invention, ring B in the compounds of general formula (I) is pyridin-2-yl, pyridin-3-yl, 3-chloropyridin-2-yl, 3-methyl-pyridin-2-yl, pyrimidin-2-yl or 5-methyl-isoxazol-3-yl.

In certain most preferred embodiments of the invention, ring B in the compounds of general formula (I) is pyridin-2-yl.

In certain embodiments of the invention, Y in the compounds of general formula (I) is —O—, if ring B is present.

In certain embodiments of the invention, Y in the compounds of general formula (I) is —C(O)—, if ring B is present.

In certain embodiments of the invention, Y in the compounds of general formula (I) is —CH$_2$—, if ring B is present.

In certain embodiments of the invention, Y in the compounds of general formula (I) is —NH—, if ring B is present.

In certain embodiments of the invention, Y in the compounds of general formula (I) is —C$_{1-4}$alkyl-N(R$^{18}$)—, if ring B is present.

In certain preferred embodiments of the invention, Y in the compounds of general formula (I) is a single bond, if ring B is present.

In certain embodiments of the invention, Y in the compounds of general formula (I) is —N(C$_{1-4}$alkyl)$_2$, C(O)OC$_{1-4}$alkyl, C$_{1-4}$alkyl optionally substituted with halogen, C$_{1-4}$alkoxy group or halogen, if ring B is not present.

In certain embodiments of the invention, Y in the compounds of general formula (I) is C$_{1-4}$alkyl optionally substituted with halogen or C$_{1-4}$alkoxy group, if ring B is not present.

In certain preferred embodiments of the invention, Y in the compounds of general formula (I) is C$_{1-3}$ alkyl group, if ring B is not present.

In certain more preferred embodiments of the invention, Y in the compounds of general formula (I) is methyl, ethyl, or propyl group, if ring B is not present.

In certain preferred embodiments of the invention, Y in the compounds of general formula (I) is C$_{1-3}$ alkoxy group, if ring B is not present.

In certain more preferred embodiments of the invention, Y in the compounds of general formula (I) is methoxy or ethoxy group, if ring B is not present.

In certain preferred embodiments of the invention, Y in the compounds of general formula (I) is CF$_3$ group, if ring B is not present.

In certain embodiments of the invention, Y in the compounds of general formula (I), if ring B is not present, refers to one group selected from the group consisting of —N(C$_{1-4}$alkyl)$_2$, C(O)OC$_{1-4}$alkyl, C$_{1-4}$alkyl optionally substituted with halogen, C$_{1-4}$alkoxy group and halogen.

In certain preferred embodiments of the invention, Y in the compounds of general formula (I), if ring B is not present, refers to one group selected from the group consisting of dimethylamine, C(O)OC$_{1-4}$alkyl and CF$_3$ group.

In certain embodiments of the invention, Y in the compounds of general formula (I), if ring B is not present, refers to two groups selected from the group consisting of C$_{1-4}$alkyl optionally substituted with halogen, C$_{1-4}$alkoxy group and halogen.

In certain preferred embodiments of the invention, Y in the compounds of general formula (I), if ring B is not present, refers to two groups selected from the group consisting of C$_{1-3}$alkyl, C$_{1-3}$alkoxy, CF$_3$ group and fluorine.

In certain more preferred embodiments of the invention, Y in the compounds of general formula (I), if ring B is not present, refers to two groups selected from the group consisting of methyl, ethyl, propyl, methoxy, ethoxy, CF$_3$ group and fluorine.

In certain even more preferred embodiments of the invention, Y in the compounds of general formula (I), if ring B is not present, refers to two groups selected from the group consisting of methyl, ethyl, propyl, methoxy and ethoxy group.

In certain preferred embodiments of the invention, in the compounds of general formula (I), ring A is cyclobutyl or cyclohexyl, Y refers to one group selected from the group consisting of —N(C$_{1-4}$alkyl)$_2$, —C(O)OC$_{1-4}$alkyl, CF$_3$ and halogen and ring B is not present.

In certain preferred embodiments of the invention, in the compounds of general formula (I), ring A is cyclobutyl or cyclohexyl, Y refers to two groups selected from the group consisting of C$_{1-4}$alkyl optionally substituted with halogen, C$_{1-4}$alkoxy group and halogen and ring B is not present.

In certain preferred embodiments of the invention, in the compounds of general formula (I), ring A is cyclobutyl or cyclohexyl, Y is —O— or bond and ring B is optionally substituted phenyl, piperidin-1-yl, morpholin-4-yl, 1-azabicyclo[2.2.2]oct-3-yl, pyridin-2-yl, pyridin-3-yl, 3-chloro-pyridin-2-yl, 3-methylpyridin-2-yl, pyrimidin-2-yl or 5-methylisoxazol-3-yl.

In certain more preferred embodiments of the invention, in the compounds of general formula (I), ring A is cyclohexyl, Y is —O— and ring B is pyridin-2-yl, pyridin-3-yl, 3-chloro-pyridin-2-yl, 3-methylpyridin-2-yl, pyrimidin-2-yl or 5-methylisoxazol-3-yl.

In certain most preferred embodiments of the invention, in the compounds of general formula (I), ring A is cyclohexyl, Y is —O— and ring B is pyridin-2-yl.

In certain preferred embodiments of the invention, in the compounds of general formula (I), ring A is azetidin-1,3-diyl, piperidin-1,4-diyl or piperazine-1,4-diyl, wherein ring A is attached via a ring nitrogen to Y or to the triazole ring of the 5,6-dihydro-4H-[1,2,4]triazolo[4,3-a][1]benzazepine core, Y is —O— or bond and ring B is optionally substituted phenyl, piperidin-1-yl, morpholin-4-yl, 1-azabicyclo[2.2.2]oct-3-yl, pyridin-2-yl, pyridin-3-yl, 3-chloro-pyridin-2-yl, 3-methylpyridin-2-yl, pyrimidin-2-yl or 5-methylisoxazol-3-yl.

In certain more preferred embodiments of the invention, in the compounds of general formula (I), ring A is piperidin-1,4-diyl or piperazine-1,4-diyl, wherein ring A is attached via a ring nitrogen to Y or to the triazole ring of the 5,6-dihydro-4H-[1,2,4]triazolo[4,3-a][1]benzazepine core, Y is —O— or bond and ring B is pyridin-2-yl or pyridin-3-yl.

In certain embodiments of the invention, in the compounds of general formula (I), ring A is cyclobutyl, cyclohexyl or pyrrolidinyl, Y is —C(O)— and ring B is pyrrolidin-1-yl, piperidin-1-yl, morpholin-4-yl, 4-methyl-piperazinyl or pyridine-3-yl.

In certain embodiments of the invention, B—Y-A- in the compounds of general formula (I) jointly represents 3H-spiro[2-benzofuran-1,4'-piperidin-1'-yl], 1-oxa-3-azaspiro[4.5]decan-2-on-8-yl substituted at 3-position by $C_{1-4}$alkyl or 2-azaspiro[4.5]decan-1-on-8-yl substituted at 2-position by $C_{1-4}$alkyl, aryl or heteroaryl.

In certain preferred embodiments of the invention, B—Y-A- in the compounds of general formula (I) jointly represents 3H-spiro[2-benzofuran-1,4'-piperidin-1'-yl], (5S,8S)-3-methyl-1-oxa-3-azaspiro[4.5]decan-2-on-8-yl, (5R,8R)-3-methy-1-oxa-3-azaspiro[4.5]decan-2-on-8-yl, (5R,8R)-2-(propan-2-yl)-2-azaspiro[4.5]decan-1-one or (5S,8S)-2-(propan-2-yl)-2-azaspiro[4.5]decan-1-one.

In certain embodiments of the invention, $R^1$ in the compounds of general formula (I) is hydrogen.

In certain embodiments of the invention, $R^1$ in the compounds of general formula (I) is halogen.

In certain preferred embodiments of the invention, $R^1$ in the compounds of general formula (I) is chlorine, bromine or fluorine.

In certain more preferred embodiments of the invention, $R^1$ in the compounds of general formula (I) is chlorine.

In certain embodiments of the invention, $R^1$ in the compounds of formula (I) is $C_{1-4}$alkyl.

In certain preferred embodiments of the invention, $R^1$ in the compounds of general formula (I) is methyl.

In certain embodiments of the invention, $R^1$ in the compounds of general formula (I) is $C_{1-4}$alkoxy.

In certain preferred embodiments of the invention, $R^1$ in the compounds of general formula (I) is methoxy.

In certain embodiments of the invention, $R^1$ in the compounds of general formula (I) is $CF_3$.

In certain embodiments of the invention, $R^1$ in the compounds of general formula (I) is CN.

In certain embodiments of the invention, in the compounds of general formula (I), $R^2$ is hydrogen or $C_{1-4}$alkyl, $R^3$ is $NR^4R^5$, $OR^6$ group or halogen.

In certain embodiments of the invention, in the compounds of general formula (I), $R^2$ is $C_{1-4}$alkyl, $R^3$ is $NR^4R^5$, $OR^6$ group or halogen.

In certain embodiments of the invention, in the compounds of general formula (I), $R^2$ is hydrogen, $R^3$ is $NR^4R^5$, $OR^6$ group or halogen.

In certain preferred embodiments of the invention, in the compounds of general formula (I), $R^2$ is hydrogen, $R^3$ is $NR^4R^5$ or $OR^6$ group and the absolute configuration of the carbon at position 5 in the 5,6-dihydro-4H-[1,2,4]triazolo[4,3-a][1]benzazepine core is (R).

In certain embodiments of the invention, in the compounds of general formula (I), $R^2$ is hydrogen, $R^3$ is $NR^4R^5$ or $OR^6$ group and the absolute configuration of the carbon at position 5 in the 5,6-dihydro-4H-[1,2,4]triazolo[4,3-a][1]benzazepine core is (S).

In certain embodiments of the invention, in the compounds of general formula (I), $R^2$ is hydrogen, $R^3$ is $NR^4R^5$ or $OR^6$ group.

In certain embodiments of the invention, in the compounds of general formula (I), $R^2$ is hydrogen, $R^3$ is $NR^4R^5$ group.

In certain embodiments of the invention, in the compounds of general formula (I), $R^2$ is hydrogen or $C_{1-4}$alkyl group, $R^3$ is $NR^4R^5$ group, wherein $R^4$ and $R^5$ are hydrogen.

In certain embodiments of the invention, in the compounds of general formula (I), $R^2$ is hydrogen, $R^3$ is $NR^4R^5$ group, wherein $R^4$ is hydrogen, $R^5$ is $C_{1-4}$alkyl group.

In certain preferred embodiments of the invention, in the compounds of general formula (I), $R^2$ is hydrogen, $R^3$ is $NR^4R^5$ group, wherein $R^4$ is hydrogen $R^5$ is isopropyl group.

In certain embodiments of the invention, in the compounds of general formula (I), $R^2$ is hydrogen, $R^3$ is $NR^4R^5$ group, wherein $R^4$ and $R^5$ are $C_{1-4}$alkyl groups.

In certain preferred embodiments of the invention, in the compounds of general formula (I), $R^2$ is hydrogen, $R^3$ is $NR^4R^5$ group, wherein $R^4$ and $R^5$ is independently methyl, ethyl or isopropyl group.

In certain more preferred embodiments of the invention, in the compounds of general formula (I), $R^2$ is hydrogen, $R^3$ is $NR^4R^5$ group, wherein $R^4$ and $R^5$ are methyl groups.

In certain embodiments of the invention, in the compounds of general formula (I), $R^2$ is hydrogen, $R^3$ is $NR^4R^5$ group, wherein $R^4$ is hydrogen, $R^5$ is OH-substituted $C_{1-4}$alkyl group.

In certain preferred embodiments of the invention, in the compounds of general formula (I), $R^2$ is hydrogen, $R^3$ is $NR^4R^5$ group, wherein $R^4$ is hydrogen, $R^5$ is hydroxymethyl or hydroxyethyl-group.

In certain embodiments of the invention, in the compounds of general formula (I), $R^2$ is hydrogen, $R^3$ is $NR^4R^5$ group, wherein $R^4$ is hydrogen, $R^5$ is halo-substituted $C_{1-4}$alkyl group.

In certain preferred embodiments of the invention, in the compounds of general formula (I), $R^2$ is hydrogen, $R^3$ is $NR^4R^5$ group, wherein $R^4$ is hydrogen, $R^5$ is trifluoro-substituted $C_{1-2}$alkyl group.

In certain preferred embodiments of the invention, in the compounds of general formula (I), $R^2$ is hydrogen, $R^3$ is $NR^4R^5$ group, wherein $R^4$ is hydrogen, $R^5$ is methyl-cyclopropyl group.

In certain embodiments of the invention, in the compounds of general formula (I), $R^2$ is hydrogen, $R^3$ is $NR^4R^5$ group, wherein $R^4$ is hydrogen, $R^5$ is 4-fluorophenyl-substituted methyl or ethyl group.

In certain embodiments of the invention, in the compounds of general formula (I), $R^2$ is hydrogen, $R^3$ is $NR^4R^5$ group, wherein $R^4$ is hydrogen, $R^5$ is $C_{1-4}$alky substituted with $NR^8R^9$ group, wherein $R^8$ and $R^9$ are independently hydrogen, $C_{1-4}$alkyl group or $C(O)OR^2$ group.

In certain preferred embodiments of the invention, in the compounds of general formula (I), $R^2$ is hydrogen, $R^3$ is $NR^4R^5$ group, wherein $R^4$ is hydrogen, $R^5$ is $C_{1-4}$alky substituted with $NR^8R^9$ group, wherein $R^3$ is hydrogen, $R^9$ is $C(O)OR^{21}$ group.

In certain embodiments of the invention, in the compounds of general formula (I), $R^2$ is hydrogen, $R^3$ is $NR^4R^5$ group, wherein $R^4$ is hydrogen, $R^1$ is $C_{1-4}$alky substituted with $NR^8R^9$ group, wherein $R^8$ and $R^9$ are independently hydrogen or $C_{1-4}$alkyl group.

In certain preferred embodiments of the invention, in the compounds of general formula (I), $R^2$ is hydrogen, $R^3$ is $NR^4R^5$ group, wherein $R^4$ is hydrogen, $R^5$ is aminomethyl or -ethyl group.

In certain preferred embodiments of the invention, in the compounds of general formula (I), $R^2$ is hydrogen, $R^3$ is $NR^4R^5$ group, wherein $R^4$ is hydrogen, $R^5$ is dimethylaminomethyl or -ethyl group.

In certain embodiments of the invention, in the compounds of general formula (I), $R^2$ is hydrogen, $R^3$ is $NR^4R^5$ group, wherein $R^4$ is hydrogen, $R^5$ is $Cy^1$.

In certain preferred embodiments of the invention, in the compounds of general formula (I), $R^2$ is hydrogen, $R^3$ is $NR^4R^5$ group, wherein $R^4$ is hydrogen, $R^5$ is cyclobutyl, cyclopentyl, cyclohexyl, 4,4-difluoro-cyclohexyl, oxetan-2-yl or tetrahydropyranyl.

In certain preferred embodiments of the invention, in the compounds of general formula (I), $R^2$ is hydrogen, $R^3$ is $NR^4R^5$ group, wherein $R^4$ is hydrogen, $R^5$ is pyridin-2-yl, pyrimidin-2-yl or pyrazin-2-yl.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is methyl, ethyl or isopropyl group.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is $C_{1-4}$alkyl substituted with OH, CN, halogen, $Cy^3$ or $NR^{11}R^{12}$ group.

In certain preferred embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is methyl, ethyl or isopropyl group substituted with OH, CN or trifluoro.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is methyl or ethyl substituted with $NR^{11}R^{12}$ group, wherein $R^{11}$ and $R^{12}$ are independently hydrogen or methyl or $R^{11}$ and $R^{12}$ taken together with the N to which they are attached form morpholin-4-yl or 4-methyl-piperazin-1-yl.

In certain preferred embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is aminomethyl group.

In certain preferred embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is dimethylaminomethyl group.

In certain preferred embodiments of the invention, in the compounds of general formula (I), $R^2$ is hydrogen, $R^3$ is $NR^4R^5$ group, wherein $R^4$ is hydrogen, $R^5$ is C(O)R group, wherein $R^7$ is phenyl and/or $NH_2$-substituted methyl.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is t-butoxy group.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is vinyl group.

In certain embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is $Cy^3$ group.

In certain preferred embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is 4-fluorophenyl, cyclopropyl, cyclobutyl, dihalo-cyclobutyl or cyclohexyl, oxetanyl, tetrahydropyran-4yl, 4-methyl-piperidinyl, or 5-methyl-1,3,4-oxadiazol-2-yl.

In certain preferred embodiments of the invention, in the compounds of general formula (I), $R^2$ is hydrogen, $R^3$ is $NR^4R^5$ group, wherein $R^4$ is hydrogen, $R^5$ is $C(O)R^7$ group, wherein $R^7$ is dimethylamino group.

In certain preferred embodiments of the invention, in the compounds of general formula (I), $R^2$ is hydrogen, $R^3$ is $NR^4R^5$ group, wherein $R^4$ is hydrogen or methyl, $R^5$ is $S(O_2)R^{10}$, wherein $R^{10}$ is methyl, OH, $NH_2$, NH-t-butyl or dimethylamino group.

In certain embodiments of the invention, in the compounds of general formula (I), $R^2$ is hydrogen, $R^3$ is $NR^4R^5$ group, wherein $R^4$ is hydrogen or $C_{1-4}$alkyl group, $R^5$ is $C_{2-4}$alkynyl group.

In certain preferred embodiments of the invention, in the compounds of general formula (I), $R^2$ is hydrogen, $R^3$ is $NR^4R^5$ group, wherein $R^4$ is methyl group, $R^5$ is propargyl group.

In certain embodiments of the invention, in the compounds of general formula (I), $R^2$ is hydrogen, $R^3$ is $NR^4R^5$ group, wherein $R^4$ and $R^5$ taken together with the N to which they are attached form a 4- to 7-membered heterocycle containing optionally one or more heteroatoms selected from O, S or N.

In certain preferred embodiments of the invention, in the compounds of general formula (I), $R^2$ is hydrogen, $R^3$ is $NR^4R^5$, wherein $R^4$ and $R^5$ taken together with the N to which they are attached form pyrrolidine, piperidine, piperazine, morpholine, 1,3-oxazolidine, 1,3-thiazolidine or thiomorpholine-1,1-oxide.

In certain preferred embodiments of the invention, in the compounds of general formula (I), $R^2$ is hydrogen, $R^3$ is $OR^6$ group, wherein $R^6$ is hydrogen.

In certain preferred embodiments of the invention, in the compounds of general formula (I), $R^2$ is hydrogen, $R^3$ is $OR^6$ group, wherein $R^6$ is methyl, ethyl or isopropyl group.

In certain more preferred embodiments of the invention, in the compounds of general formula (I), $R^2$ is hydrogen, $R^3$ is $OR^6$ group, wherein $R^6$ is methyl group.

In certain embodiments of the invention, in the compounds of general formula (I), $R^2$ is hydrogen, $R^3$ is $OR^6$ group, wherein $R^6$ is OH— or halogen substituted $C_{1-4}$alkyl group.

In certain preferred embodiments of the invention, in the compounds of general formula (I), $R^2$ is hydrogen, $R^3$ is $OR^6$ group, wherein $R^6$ is chloro- or fluoro-substituted methyl or ethyl group.

In certain embodiments of the invention, in the compounds of general formula (I), $R^2$ is hydrogen, $R^3$ is $OR^6$ group, wherein $R^6$ is cyclopropyl-methyl group.

In certain embodiments of the invention, in the compounds of general formula (I), $R^2$ is hydrogen, $R^3$ is $OR^6$ group, wherein $R^6$ is $C_{1-4}$alkyl substituted with $C_{1-4}$alkoxy group.

In certain preferred embodiments of the invention, in the compounds of general formula (I), $R^2$ is hydrogen, $R^3$ is $OR^6$ group, wherein $R^6$ is methoxy-ethyl group.

In certain embodiments of the invention, in the compounds of general formula (I), $R^2$ is hydrogen, $R^3$ is $OR^6$ group, wherein $R^6$ is $C_{1-4}$alkyl substituted with $C_{1-4}$alkyl-S(O)$_2$ group.

In certain preferred embodiments of the invention, in the compounds of general formula (I), $R^2$ is hydrogen, $R^3$ is $OR^6$ group, wherein $R^6$ is methylsulfonyl-ethyl group.

In certain embodiments of the invention, in the compounds of general formula (I), $R^2$ is hydrogen, $R^3$ is $OR^6$ group, wherein $R^6$ is methyl or ethyl substituted with $NR^{11}R^{12}$ group, wherein $R^{11}$ and $R^{12}$ are independently hydrogen or methyl.

In certain embodiments of the invention, in the compounds of general formula (I), $R^2$ is hydrogen, $R^3$ is $OR^6$ group, wherein $R^6$ is methyl or ethyl substituted with $NR^{11}R^{12}$ wherein $R^{11}$ and $R^{12}$ taken together with the N to which they are attached form a morpholin-4-yl.

In certain preferred embodiments of the invention, in the compounds of general formula (I), $R^2$ is hydrogen, $R^3$ is OR, group, wherein $R^6$ is dimethylamino-ethyl-group.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $C_{1-4}$alkyl group.

In certain embodiments of the invention, in the compounds of general formula (I), $R^2$ is hydrogen, $R^3$ is $OR^6$ group, wherein $R^6$ is $C(O)R^{13}$, wherein $R^{13}$ is methyl, ethyl or t-butyl.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $C_{1-4}$alkyl group substituted with CN.

In certain preferred embodiments of the invention, in the compounds of general formula (I), $R^2$ is hydrogen, $R^3$ is $OR^6$ group, wherein $R^6$ is $C(O)R^{13}$, wherein $R^{13}$ is cyanomethyl group.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $C_{1-4}$alkyl group substituted with $NR^{19}R^{20}$ group.

In certain preferred embodiments of the invention, in the compounds of general formula (I), $R^2$ is hydrogen, $R^3$ is $OR^6$ group, wherein $R^6$ is $C(O)R^{13}$, wherein $R^{13}$ is dimethyl-amino-methyl group.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $Cy^3$ group.

In certain preferred embodiments of the invention, in the compounds of general formula (I), $R^2$ is hydrogen, $R^3$ is $OR^6$ group, wherein $R^6$ is $C(O)R^{13}$, wherein $R^{13}$ is dihalo-substituted cycloalkyl group.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $NR^{16}R^{17}$, wherein $R^{16}$ and $R^{17}$ are independently hydrogen, $C_{1-4}$alkyl or optionally substituted aryl.

In certain embodiments of the invention, in the compounds of general formula (I), $R^2$ is hydrogen, $R^3$ is $OR^6$ group, wherein $R^6$ is $C(O)R^{13}$, wherein $R^{13}$ is $NR^{16}R^{17}$, wherein $R^{16}$ and $R^{17}$ taken together with the N to which they are attached form a piperidine or pyrrolidine.

In certain embodiments of the invention, in the compounds of general formula (I), $R^2$ is hydrogen, $R^3$ is $OR^6$ group, wherein $R^6$ is $Si(CH_3)_2$-t-butyl.

In certain embodiments of the invention, in the compounds of general formula (I), $R^2$ is hydrogen, $R^3$ is $OR^6$ group, wherein $R^6$ is $C_{2-4}$alkynyl group.

In certain preferred embodiments of the invention, in the compounds of general formula (I), $R^2$ is hydrogen, $R^3$ is $OR^6$ group, wherein $R^6$ is propargyl group.

In certain embodiments of the invention, in the compounds of general formula (I), $R^2$ is $C_{1-4}$alkyl, $R^3$ is $NR^4R^5$ or $OR^6$ group.

In certain embodiments of the invention, in the compounds of general formula (I), $R^2$ is $C_{1-4}$alkyl, $R^3$ is $OR^6$ group.

In certain embodiments of the invention, in the compounds of general formula (I), one of $R^2$ and $R^3$ is methyl or isopropyl other is OR, wherein $R^6$ is hydrogen.

In certain embodiments of the invention, in the compounds of general formula (I), $R^2$ is hydrogen and $R^3$ is halogen.

In certain preferred embodiments of the invention, in the compounds of general formula (I), $R^2$ is hydrogen and $R^3$ is fluorine.

In certain embodiments of the invention, in the compounds of general formula (I), $R^2$ is $C_{1-4}$alkyl group and $R^3$ is halogen.

In certain preferred embodiments of the invention, in the compounds of general formula (I), $R^2$ and $R^3$ jointly represent —O—$(CH_2)_m$—O— and m=2, 3 or 4.

In certain more preferred embodiments of the invention, in the compounds of general formula (I), $R^2$ and $R^3$ jointly represent —O—$(CH_2)_m$—O— and m=2.

In certain preferred embodiments of the invention, in the compounds of general formula (I), $R^2$ and $R^3$ jointly represent an oxo-group.

In certain embodiments of the invention, in the compounds of general formula (I), $R^2$ and $R^3$ jointly represent a =N—OH group.

While the invention has been described in connection with certain embodiments, certain preferred, more preferred or most preferred embodiments, it is not intended to limit the scope of the invention to the particular form set forth, but on the contrary, it is intended to cover such alternatives, modifications, and equivalents as may be included within the spirit and scope of the invention as defined by the statements of invention. Examples of alternative claims directed to the compounds of the present invention may include:

(1) The compounds of general formula (I) as described above, or in any other embodiment.

(2) The compound as described in (1), or in any other embodiment, wherein $R^1$ is a hydrogen, fluorine, chlorine, bromine, methyl, methoxy, $CF_3$ or CN group.

(3) The compound as described in any of (1) to (2), or in any other embodiment, wherein ring A is a 3- to 6-membered saturated carbocyclic or a 4- to 7-membered saturated heterocycle containing 1 or 2 N;

ring B is an optionally substituted 5- or 6-membered mono-heteroaryl group, 6- to 10-membered aromatic carbocycle, or 4- to 7-membered saturated, monocyclic, bicyclic, condensed and/or bridged heterocycle containing 1, 2 or 3 heteroatoms selected from O, S or N;
or B—Y-A- jointly represent a 3H-spiro[2-benzofuran-1,4'-piperidin-1'-yl]; or

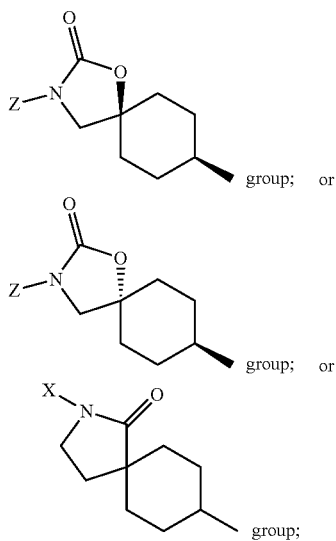

group; or group; or group;

X is isopropyl group;
Z is methyl group.

(4) The compound as described in any of (1) to (3), or in any other embodiment, wherein ring B is an optionally substituted 6-membered mono-heteroaryl group, phenyl, or 5- to 6-membered saturated, monocyclic heterocycle containing 1 or 2 heteroatoms selected from O, S or N.

(5) The compound as described in any of (1) to (4), or in any other embodiment, wherein Y is —O—, —C(O)—, —CH$_2$—, —NH—, —C$_{1-4}$alkyl-N(R$^{18}$)— or a single bond if ring B is present and R$^{18}$ is a hydrogen or methyl group.

(6) The compound as described in any of (1) to (5), or in any other embodiment, wherein ring A is a 4- to 6-membered saturated carbocyclic group or a 4- to 7-membered saturated heterocycle containing 1 or 2 N attached via a ring nitrogen to Y or to the triazole ring of the 5,6-dihydro-4H-[1,2,4]triazolo[4,3-a][1]benzazepine core.

(7) The compound as described in any of (1) to (6), or in any other embodiment, wherein ring A is a cyclohexyl group, Y is —O—, ring B is a pyridin-2-yl and R$^1$ is chlorine.

(8) The compound as described in any of (1) to (6), or in any other embodiment, wherein ring A is a piperidine, piperazine, or pyrrolidine, Y is —O—, —C(O)—, —CH$_2$—, or a single bond, ring B is a pyridine, piperidine, tetrahydrofuran, or tetrahydropyran and R$^1$ is chlorine.

(9) The compound as described in any of (1) to (3), or in any other embodiment, wherein Y is —N(C$_{1-4}$alkyl)$_2$, C(O)OC$_{1-4}$alkyl, C$_{1-4}$alkyl optionally substituted with halogen, C$_{1-4}$alkoxy group or halogen and ring B is not present.

(10) The compound as described in (9), or in any other embodiment, wherein ring A is a 4- to 6-membered saturated carbocyclic group.

(11) The compound as described in (10), or in any other embodiment, wherein Y is one group selected from the group consisting of —N(C$_{1-4}$alkyl)$_2$, C(O)OC$_{1-4}$alkyl, C$_{1-4}$alkyl optionally substituted with halogen, C$_{1-4}$alkoxy group and halogen.

(12) The compound as described in (10), or in any other embodiment, wherein Y is two groups selected from the group consisting of C$_{1-4}$alkyl optionally substituted with halogen, C$_{1-4}$alkoxy group and halogen.

(13) The compound as described in any of (1) to (12), or in any other embodiment, wherein R$^2$ is a hydrogen or C$_{1-4}$alkyl group and R$^3$ is a NR$^4$R$^5$ group.

(14) The compound as described in (13), or in any other embodiment, wherein R$^2$ is a hydrogen.

(15) The compound as described in (14), or in any other embodiment, wherein R$^4$ and R$^5$ is independently a hydrogen; C(O)R$^7$; C$_{1-4}$alkyl optionally substituted with OH, halogen, cycloalkyl, optionally substituted aryl or NR$^8$R$^9$ group.

(16) The compound as described in (15), or in any other embodiment, wherein R$^4$ and R$^5$ are hydrogens.

(17) The compound as described in (15), or in any other embodiment, wherein R$^4$ is a hydrogen, R$^5$ is a C$_{1-4}$alkyl group.

(18) The compound as described in (15), or in any other embodiment, wherein R$^4$ and R$^5$ are C$_{1-4}$alkyl groups.

(19) The compound as described in (15), or in any other embodiment, wherein R$^4$ is a hydrogen, R$^5$ is a C(O)R$^1$ group.

(20) The compound as described in (14), or in any other embodiment, wherein R$^4$ is a hydrogen, R$^5$ is Cy$^1$.

(21) The compound as described in (14), or in any other embodiment, wherein R$^4$ is a hydrogen or C$_{1-4}$alkyl, R$^5$ is a S(O$_2$)R$^{10}$ group.

(22) The compound as described in (14), or in any other embodiment, wherein R$^4$ and R$^5$ taken together with the N to which they are attached form a 4- to 7-membered heterocycle containing optionally 1, 2 or 3 heteroatoms selected from O, S or N.

(23) The compound as described in any of (1) to (12), or in any other embodiment, wherein R$^2$ is a hydrogen or C$_{1-4}$alkyl group; R$^3$ is an OR$^6$ group.

(24) The compound as described in (23), or in any other embodiment, wherein R$^2$ is a hydrogen.

(25) The compound as described in (24), or in any other embodiment, wherein R$^6$ is a hydrogen.

(26) The compound as described in (24), or in any other embodiment, wherein R$^6$ is a C$_{1-4}$alkyl group.

(27) The compound as described in (24), or in any other embodiment, wherein R$^6$ is a C(O)R$^{13}$ group.

(28) The compound as described in any of (13) to (27), or in any other embodiment, wherein the absolute configuration of the carbon at position 5 in the 5,6-dihydro-4H-[1,2,4]triazolo[4,3-a][1]benzazepine core is (R).

(29) The compound as described in any of (13) to (27), or in any other embodiment, wherein the absolute configuration of the carbon at position 5 in the 5,6-dihydro-4H-[1,2,4]triazolo[4,3-a][1]benzazepine core is (S).

(30) The compound as described in any of (1) to (12), or in any other embodiment, wherein R$^2$ and R$^3$ jointly represent —O—(CH$_2$)$_m$—O—, oxo or =N—OH group, m is 2, 3, 4 or 5.

(31) The compound as described in (30), or in any other embodiment, wherein R$^2$ and R$^3$ jointly represent —O—(CH$_2$)$_m$—O— group and m is 2.

A preferred group of compounds of general formula (i) of the present invention are, for example, the following compounds and/or salts and/or solvates and/or hydrates and/or polymorphs and/or biologically active metabolites and/or prodrugs thereof:

1. tert-butyl [8-chloro-1-[1-(pyridin-2-yl)piperidin-4-yl]-5,6-dihydro-4H-[1,2,4]triazolo[4,3-a][1]benzazepin-5-yl]carbamate,
2. 8-chloro-1-[1-(pyridin-2-yl)piperidin-4-yl]-5,6-dihydro-4H-[1,2,4]triazolo[4,3-a][1]benzazepine-5-amine,
3. N-[8-chloro-1-(pyridin-2-yl)piperidin-4-yl]-5,6-dihydro-4H-[1,2,4]triazolo[4,3-a][1]benzazepin-5-yl]acetamide,
4. N-(8-chloro-[1-(pyridin-2-yl)piperidin-4-yl]-5,6-dihydro-4H-[1,2,4]triazolo[4,3-a][1]benzazepin-5-yl)-2-methylpropanamide,
5. tert-butyl {8-chloro-1-[trans-4-(pyridin-2-yloxy)cyclohexyl]-5,6-dihydro-4H-[1,2,4]triazolo[4,3-a][1]benzazepine-5-yl}carbamate,
6. 8-chloro-1-[trans-4-(pyridin-2-yloxy)cyclohexyl]-5,6-dihydro-4H-[1,2,4]triazolo[4,3-a][1]benzazepine-5-amine,
7. (5S)-8-chloro-1-[trans-4-(pyridin-2-yloxy)cyclohexyl]-5,6-dihydro-4H-[1,2,4]triazolo[4,3-a][1]benzazepine-5-amine,
8. (5R)-8-chloro-1-[trans-4-(pyridin-2-yloxy)cyclohexyl]-5,6-dihydro-4H-[1,2,4]triazolo[4,3-a][1]benzazepine-5-amine,
9. N-{8-chloro-1-[trans-4-(pyridin-2-yloxy)cyclohexyl]-5,6-dihydro-4H-[1,2,4]triazolo[4,3-a][1]benzazepin-5-yl}acetamide,
10. N-{8-chloro-1-[trans-4-(pyridin-2-yloxy)cyclohexyl]-5,6-dihydro-4H-[1,2,4]triazolo[4,3-a][1]benzazepin-5-yl}glycinamide,
11. N-{(5S)-8-chloro-1-[trans-4-(pyridin-2-yloxy)cyclohexyl]-5,6-dihydro-4H-[1,2,4]triazolo[4,3-a][1]benzazepin-5-yl}glycinamide,
12. N-{(5R)-8-chloro-1-[trans-4-(pyridin-2-yloxy)cyclohexyl]-5,6-dihydro-4H-[1,2,4]triazolo[4,3-a][1]benzazepin-5-yl}glycinamide,
13. (2S)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide,
14. (2R)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide,
15. N-{8-chloro-1-[trans-4-(pyridin-2-yloxy)cyclohexyl]-5,6-dihydro-4H-[1,2,4]triazolo[4,3-a][1]benzazepin-5-yl}-2-hydroxyacetamide,
16. 3-{8-chloro-1-[trans-4-(pyridin-2-yloxy)cyclohexyl]-5,6-dihydro-4H-[1,2,4]triazolo[4,3-a][1]benzazepin-5-yl}-1,1-dimethylurea,
17. N-{8-chloro-1-[trans-4-(pyridin-2-yloxy)cyclohexyl]-5,6-dihydro-4H-[1,2,4]triazolo[4,3-a][1]benzazepin-5-yl}-$N^2,N^2$-dimethylglycinamide,
18. N-{8-chloro-1-[trans-4-(pyridin-2-yloxy)cyclohexyl]-5,6-dihydro-4H-[1,2,4]triazolo[4,3-a][1]benzazepin-5-yl}methanesulfonamide,
19. N-{8-chloro-1-[trans-4-(pyridin-2-yloxy)cyclohexyl]-5,6-dihydro-4H-[1,2,4]triazolo[4,3-a][1]benzazepin-5-yl}-N-methylmethanesulfonamide,
20. N'-{8-chloro-1-[trans-4-(pyridin-2-yloxy)cyclohexyl]-5,6-dihydro-4H-[1,2,4]triazolo[4,3-a][1]benzazepin-5-yl}-N,N-dimethylsulfamide,
21. 8-chloro-N-methyl-1-[trans-4-(pyridin-2-yloxy)cyclohexyl]-5,6-dihydro-4H-[1,2,4]triazolo[4,3-a][1]benzazepine-5-amine,
22. 8-chloro-N,N-dimethyl-1-[trans-4-(pyridin-2-yloxy)cyclohexyl]-5,6-dihydro-4H-[1,2,4]triazolo[4,3-a][1]benzazepine-5-amine,
23. 8-chloro-N-ethyl-1-[trans-4-(pyridin-2-yloxy)cyclohexyl]-5,6-dihydro-4H-[1,2,4]triazolo[4,3-a][1]benzazepine-5-amine,
24. 8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine,
25. (5S)-8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine,
26. (5R)-8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine,
27. 8-chloro-N-cyclobutyl-1-[trans-4-(pyridin-2-yloxy)cyclohexyl]-5,6-dihydro-4H-[1,2,4]triazolo[4,3-a][1]benzazepine-5-amine,
28. 8-chloro-N-(oxetan-3-yl)-1-[trans-4-(pyridin-2-yloxy)cyclohexyl]-5,6-dihydro-4H-[1,2,4]triazolo[4,3-a][1]benzazepine-5-amine,
29. 8-chloro-1-[trans-4-(pyridin-2-yloxy)cyclohexyl]-N-(tetrahydro-2H-pyran-4-yl)-5,6-dihydro-4H-[1,2,4]triazolo[4,3-a][1]benzazepine-5-amine,
30. 8-chloro-N-(4,4-difluorocyclohexyl)-1-[trans-4-(pyridin-2-yloxy)cyclohexyl]-5,6-dihydro-4H-[1,2,4]triazolo[4,3-a][1]benzazepine-5-amine,
31. 8-methoxy-1-[trans-4-(pyridin-2-yloxy)cyclohexyl]-5,6-dihydro-4H-[1,2,4]triazolo[4,3-a][1]benzazepine-5-amine hydrochloride,
32. 8-methoxy-N-(propan-2-yl)-1-[trans-4-(pyridin-2-yloxy)cyclohexyl]-5,6-dihydro-4H-[1,2,4]triazolo[4,3-a][1]benzazepine-5-amine,
33. tert-butyl {1-[trans-4-(pyridin-2-yloxy)cyclohexyl]-8-(trifluoromethyl)-5,6-dihydro-4H-[1,2,4]triazolo[4,3-a][1]benzazepin-5-yl}carbamate,
34. 1-[trans-4-(pyridin-2-yloxy)cyclohexyl]-8-(trifluoromethyl)-5,6-dihydro-4H-[1,2,4]triazolo[4,3-a][1]benzazepine-5-amine hydrochloride,
35. N,N-dimethyl-1-[trans-4-(pyridin-2-yloxy)cyclohexyl]-8-(trifluoromethyl)-5,6-dihydro-4H-[1,2,4]triazolo[4,3-a][1]benzazepine-5-amine,
36. N-(propan-2-yl)-1-[trans-4-(pyridin-2-yloxy)cyclohexyl]-8-(trifluoromethyl)-5,6-dihydro-4H-[1,2,4]triazolo[4,3-a][1]benzazepine-5-amine,
37. 8-methyl-1-[trans-4-(pyridin-2-yloxy)cyclohexyl]-5,6-dihydro-4H-[1,2,4]triazolo[4,3-a][1]benzazepine-5-amine,
38. 8-methyl-N-(propan-2-yl)-1-[trans-4-(pyridin-2-yloxy)cyclohexyl]-5,6-dihydro-4H-[1,2,4]triazolo[4,3-a][1]benzazepine-5-amine,
39. 8-bromo-1-[trans-4-(pyridin-2-yloxy)cyclohexyl]-5,6-dihydro-4H-[1,2,4]triazolo[4,3-a][1]benzazepine-5-amine,
40. 8-bromo-N-(propan-2-yl)-1-[trans-4-(pyridin-2-yloxy)cyclohexyl]-5,6-dihydro-4H-[1,2,4]triazolo[4,3-a][1]benzazepine-5-amine,
41. 8-chloro-1-(3,3-difluorocyclobutyl)-N-(propan-2-yl)-5,6-dihydro-4H-[1,2,4]triazolo[4,3-a][1]benzazepine-5-amine,
42. 8-chloro-1-(4,4-difluorocyclohexyl)-N-(propan-2-yl)-5,6-dihydro-4H-[1,2,4]triazolo[4,3-a][1]benzazepine-5-amine,
43. 8-chloro-1-[trans-4-(trifluoromethyl)cyclohexyl]-5,6-dihydro-4H-[1,2,4]triazolo[4,3-a][1]benzazepine-5-amine,
44. 8-chloro-N-(propan-2-yl)-1-[trans-4-(trifluoromethyl)cyclohexyl]-5,6-dihydro-4H-[1,2,4]triazolo[4,3-a][1]benzazepine-5-amine,
45. 8-bromo-1-[trans-4-(trifluoromethyl)cyclohexyl]-5,6-dihydro-4H-[1,2,4]triazolo[4,3-a][1]benzazepine-5-amine, 46. 8-bromo-N-(propan-2-yl)-1-[trans-4-(trifluoromethyl)cyclohexyl]-5,6-dihydro-4H-[1,2,4]triazolo[4,3-a][1]benzazepine-5-amine,
47. 1'-[trans-4-(pyridin-2-yloxy)cyclohexyl]-8'-(trifluoromethyl)-4'H,6'H-spiro[1,3-dioxolane-2,5'-[1,2,4]triazolo[4,3-a][1]benzazepine],
48. 1-[trans-4-(pyridin-2-yloxy)cyclohexyl]-8-(trifluoromethyl)-4H-[1,2,4]triazolo[4,3-a][1]benzazepin-5(6H)-one,
49. 1-[trans-4-(pyridin-2-yloxy)cyclohexyl]-8-(trifluoromethyl)-5,6-dihydro-4H-[1,2,4]triazolo[4,3-a][1]benzazepin-5-ol,
50. 5-methoxy-1-[trans-4-(pyridin-2-yloxy)cyclohexyl]-8-(trifluoromethyl)-5,6-dihydro-4H-[1,2,4]triazolo[4,3-a][1]benzazepine,
51. 5-(cyclopropylmethoxy)-1-[trans-4-(pyridin-2-yloxy)cyclohexyl]-8-(trifluoromethyl)-5,6-dihydro-4H-[1,2,4]triazolo[4,3-a][1]benzazepine,
52. 5-{[tert-butyl(dimethyl)silyl]oxy}-8-chloro-1-[trans-4-(pyridin-2-yloxy)cyclohexyl]-5,6-dihydro-4H-[1,2,4]triazolo[4,3-a][1]benzazepine,
53. 8'-chloro-1'-[trans-4-(pyridin-2-yloxy)cyclohexyl]-4'H,6'H-spiro[1,3-dioxolane-2,5'-[1,2,4]triazolo[4,3-a][1]benzazepine],
54. 8-chloro-1-[trans-4-(pyridin-2-yloxy)cyclohexyl]-4H-[1,2,4]triazolo[4,3-a][1]benzazepin-5(6H)-one,
55. 8-chloro-1-[trans-4-(pyridin-2-yloxy)cyclohexyl]-5,6-dihydro-4H-[1,2,4]triazolo[4,3-a][1]benzazepin-5-ol,
56. (5S)-8-chloro-1-[trans-4-(pyridin-2-yloxy)cyclohexyl]-5,6-dihydro-4H-[1,2,4]triazolo[4,3-a][1]benzazepin-5-ol,
57. (5R)-8-chloro-1-[trans-4-(pyridin-2-yloxy)cyclohexyl]-5,6-dihydro-4H-[1,2,4]triazolo[4,3-a][1]benzazepin-5-ol,
58. 8-chloro-5-methoxy-1-[trans-4-(pyridin-2-yloxy)cyclohexyl]-5,6-dihydro-4H-[1,2,4]triazolo[4,3-a][1]benzazepine,
59. 5-(cyclopropylmethoxy)-8-chloro-1-[trans-4-(pyridin-2-yloxy)cyclohexyl]-5,6-dihydro-4H-[1,2,4]triazolo[4,3-a][1]benzazepine,
60. 2-({8-chloro-1-[trans-4-(pyridin-2-yloxy)cyclohexyl]-5,6-dihydro-4H-[1,2,4]triazolo[4,3-a][1]benzazepin-5-yl}oxy)-N,N-dimethylethanamine,
61. 8'-chloro-1'-[trans-4-(trifluoromethyl)cyclohexyl]-4'H,6'H-spiro[1,3-dioxolane-2,5'-[1,2,4]triazolo[4,3-a][1]benzazepine],
62. 8'-bromo-1'-[trans-4-(pyridin-2-yloxy)cyclohexyl]-4'H,6'H-spiro[1,3-dioxolane-2,5'-[1,2,4]triazolo[4,3-a][1]benzazepine],
63. 1'-[trans-4-(pyridin-2-yloxy)cyclohexyl]-4'H,6'H-spiro[1,3-dioxolane-2,5'-[1,2,4]triazolo[4,3-a][1]benzazepine],
64. 8-bromo-1-[trans-4-(pyridin-2-yloxy)cyclohexyl]-4H-[1,2,4]triazolo[4,3-a][1]benzazepin-5(6H)-one,
65. 8-bromo-1-[trans-4-(pyridin-2-yloxy)cyclohexyl]-5,6-dihydro-4H-[1,2,4]triazolo[4,3-a][1]benzazepin-5-ol,
66. 1'-[trans-4-(pyridin-2-yloxy)cyclohexyl]-4'H,6'H-spiro[1,3-dioxolane-2,5-[1,2,4]triazolo[4,3-a][1]benzazepin]-8'-carbonitrile,
67. (5S)-8-chloro-N,N-dimethyl-1-[trans-4-(pyridin-2-yloxy)cyclohexyl]-5,6-dihydro-4H-[1,2,4]triazolo[4,3-a][1]benzazepine-5-amine,
68. (5S)—N-{8-chloro-1-[trans-4-(pyridin-2-yloxy)cyclohexyl]-5,6-dihydro-4H-[1,2,4]triazolo[4,3-a][1]benzazepin-5-yl}acetamide,
69. 8'-chloro-1'-[trans-4-(pyridin-2-ylmethyl)cyclohexyl]-4'H,6'H-spiro[1,3-dioxolane-2,5'-[1,2,4]triazolo[4,3-a][1]benzazepine],
70. [trans-4-(8'-chloro-4'H,6'H-spiro[1,3-dioxolane-2,5'-[1,2,4]triazolo[4,3-a][1]benzazepine]-1'-yl)cyclohexyl](pyrrolidin-1-yl)methanone,
71. 8-chloro-1-[trans-4-(trifluoromethyl)cyclohexyl]-4H-[1,2,4]triazolo[4,3-a][1]benzazepin-5(6H)-one,
72. 8-chloro-1-[trans-4-(trifluoromethyl)cyclohexyl]-5,6-dihydro-4H-[1,2,4]triazolo[4,3-a][1]benzazepine-5-ol,
73. (cis)-8-(8'-chloro-4'H,6'H-spiro[1,3-dioxolane-2,5'-[1,2,4]triazolo[4,3-a][1]benzazepin]-1'-yl)-3-methyl-1-oxa-3-azaspiro[4.5]decan-2-one,
74. 8-chloro-5-methoxy-1-[trans-4-(trifluoromethyl)cyclohexyl]-5,6-dihydro-4H-[1,2,4]triazolo[4,3-a][1]benzazepine,
75. (trans)-8-(8'-chloro-4'H,6'H-spiro[1,3-dioxolane-2,5'-[1,2,4]triazolo[4,3-a][1]benzazepin]-1'-yl)-3-methyl-1-oxa-3-azaspiro[4.5]decan-2-one,
76. N-{(5S)-8-chloro-1-[trans-4-(pyridin-2-yloxy)cyclohexyl]-5,6-dihydro-4H-[1,2,4]triazolo[4,3-a][1]benzazepin-5-yl}-N-methylmethanesulfonamide,
77. (5S)-8-chloro-N-ethyl-1-[trans-4-(pyridin-2-yloxy)cyclohexyl]-5,6-dihydro-4H-[1,2,4]triazolo[4,3-a][1]benzazepine-5-amine,
78. (5S)-8-chloro-N-methyl-1-[trans-4-(pyridin-2-yloxy)cyclohexyl]-5,6-dihydro-4H-[1,2,4]triazolo[4,3-a][1]benzazepine-5-amine,
79. 8'-chloro-1'-[1-(pyrimidin-2-yl)azetidin-3-yl]-4'H,6'H-spiro[1,3-dioxolane-2,5'-[1,2,4]triazolo[4,3-a][1]benzazepine],
80. N-{(5S)-8-chloro-1-[trans-4-(pyridin-2-yloxy)cyclohexyl]-5,6-dihydro-4H-[1,2,4]triazolo[4,3-a][1]benzazepin-5-yl}-4-fluorobenzamide,
81. 8'-bromo-1'-[trans-4-(trifluoromethyl)cyclohexyl]-4'H,6'H-spiro[1,3-dioxolane-2,5'-[1,2,4]triazolo[4,3-a][1]benzazepine],
82. 5-(propan-2-ylamino)-1-[trans-4-(pyridin-2-yloxy)cyclohexyl]-5,6-dihydro-4H-[1,2,4]triazolo[4,3-a][1]benzazepin-8-carbonitrile trifluoroacetate,
83. (5S)-8-chloro-N-(4-fluorobenzyl)-1-[trans-4-(pyridin-2-yloxy)cyclohexyl]-5,6-dihydro-4H-[1,2,4]triazolo[4,3-a][1]benzazepine-5-amine,
84. 1'-[trans-4-(trifluoromethyl)cyclohexyl]-4'H,6'H-spiro[1,3-dioxolane-2,5'-[1,2,4]triazolo[4,3-a][1]benzazepine]-8'-carbonitrile,
85. [trans-4-(8'-bromo-4'H,6'H-spiro[1,3-dioxolane-2,5'-[1,2,4]triazolo[4,3-a][1]benzazepin]-1'-yl)cyclohexyl](piperidin-1-yl)methanone,
86. methyl trans-4-(8-bromo-5-oxo-5,6-dihydro-4H-[1,2,4]triazolo[4,3-a][1]benzazepin-1-yl)cyclohexanecarboxylate,
87. 8-bromo-1-[trans-4-(piperidin-1-ylcarbonyl)cyclohexyl]-4H-[1,2,4]triazolo[4,3-a][1]benzazepin-5(6H)-one,
88. 8'-chloro-1'-[trans-4-(trifluoromethyl)cyclohexyl]-4'H,6'H-spiro[1,3-dioxane-2,5'-[1,2,4]triazolo[4,3-a][1]benzazepine],
89. 1'-[trans-4-(piperidin-1-ylcarbonyl)cyclohexyl]-4'H,6'H-spiro[1,3-dioxolane-2,5'-[1,2,4]triazolo[4,3-a][1]benzazepin]-8'-carbonitrile,
90. 8'-chloro-1'-[trans-4-(pyridin-2-yloxy)cyclohexyl]-4'H,6'H-spiro[1,3-dioxane-2,5'-[1,2,4]triazolo[4,3-a][1]benzazepine],
91. 8-bromo-1-[trans-4-(trifluoromethyl)cyclohexyl]-4H-[1,2,4]triazolo[4,3-a][1]benzazepin-5(6H)-one,
92. [trans-4-(8-bromo-5-hydroxy-5,6-dihydro-4H-[1,2,4]triazolo[4,3-a][1]benzazepin-1-yl)cyclohexyl](piperidin-1-yl)methanone, 93. 8-bromo-1-[trans-4-(trifluoromethyl)cyclohexyl]-5,6-dihydro-4H-[1,2,4]triazolo[4,3-a][1]benzazepin-5-ol,
94. 1-(1,4'-bipiperidin-1'-yl)-8'-chloro-4'H,6'H-spiro[1,3-dioxolane-2,5'-[1,2,4]triazolo[4,3-a][1]benzazepine],
95. tert-butyl [1-(1,4'-bipiperidin-1'-yl)-8-chloro-5,6-dihydro-4H-[1,2,4]triazolo[4,3-a][1]benzazepin-5-yl]carbamate,
96. 8'-fluoro-1'-[trans-4-(pyridin-2-yloxy)cyclohexyl]-4'H,6'H-spiro[1,3-dioxolane-2,5'-[1,2,4]triazolo[4,3-a][1]benzazepine],
97. (5S)-8-chloro-N-(4-fluorobenzyl)-N-methyl-1-[trans-4-(pyridin-2-yloxy)cyclohexyl]-5,6-dihydro-4H-[1,2,4]triazolo[4,3-a][1]benzazepin-5-amine,
98. N-{(5S)-8-chloro-1-[trans-4-(pyridin-2-yloxy)cyclohexyl]-5,6-dihydro-4H-[1,2,4]triazolo[4,3-a][1]benzazepin-5-yl}prop-2-enamide,
99. (5R)-8-chloro-N-ethyl-1-[trans-4-(pyridin-2-yloxy)cyclohexyl]-5,6-dihydro-4H-[1,2,4]triazolo[4,3-a][1]benzazepin-5-amine,
100. (5R)-8-chloro-N-methyl-1-[trans-4-(pyridin-2-yloxy)cyclohexyl]-5,6-dihydro-4H-[1,2,4]triazolo[4,3-a][1]benzazepin-5-amine,
101. (5R)-8-chloro-N,N-dimethyl-1-[trans-4-(pyridin-2-yloxy)cyclohexyl]-5,6-dihydro-4H-[1,2,4]triazolo[4,3-a][1]benzazepin-5-amine,
102. 1-[trans-4-(pyridin-2-yloxy)cyclohexyl]-4H-[1,2,4]triazolo[4,3-a][1]benzazepin-5(6H)-one,
103. (5S)-8-chloro-5-methoxy-1-[trans-4-(pyridin-2-yloxy)cyclohexyl]-5,6-dihydro-4H-[1,2,4]triazolo[4,3-a][1]benzazepine,
104. (5R)-8-chloro-5-methoxy-1-[trans-4-(pyridin-2-yloxy)cyclohexyl]-5,6-dihydro-4H-[1,2,4]triazolo[4,3-a][1]benzazepine,
105. 8-chloro-5-(propan-2-yloxy)-1-[trans-4-(pyridin-2-yloxy)cyclohexyl]-5,6-dihydro-4H-[1,2,4]triazolo[4,3-a][1]benzazepine,
106. 8'-chloro-1'-[trans-4-(pyridin-2-yloxy)cyclohexyl]-4'H,6'H-spiro[1,3-dioxepane-2,5'-[1,2,4]triazolo[4,3-a][1]benzazepine],
107. 1-[trans-4-(pyridin-2-yloxy)cyclohexyl]-5,6-dihydro-4H-[1,2,4]triazolo[4,3-a][1]benzazepin-5-ol,
108. [trans-4-(8'-chloro-4'H,6'H-spiro[1,3-dioxolane-2,5'-[1,2,4]triazolo[4,3-a][1]benzazepin]-1'-yl)cyclohexyl](morpholin-4-yl)methanone
109. 5-methoxy-1-[trans-4-(pyridin-2-yloxy)cyclohexyl]-5,6-dihydro-4H-[1,2,4]triazolo[4,3-a][1]benzazepine,
110. 8-fluoro-1-[trans-4-(pyridin-2-yloxy)cyclohexyl]-4H-[1,2,4]triazolo[4,3-a][1]benzazepin-5(6H)-one,
111. 8-fluoro-1-[trans-4-(pyridin-2-yloxy)cyclohexyl]-5,6-dihydro-4H-[1,2,4]triazolo[4,3-a][1]benzazepin-5-ol,
112. tert-butyl {8-chloro-1-[trans-4-(morpholin-4-yl)cyclohexyl]-5,6-dihydro-4H-[1,2,4]triazolo[4,3-a][1]benzazepin-5-yl}carbamate,
113. 8-chloro-1-[trans-4-(morpholin-4-yl)cyclohexyl]-5,6-dihydro-4H-[1,2,4]triazolo[4,3-a][1]benzazepin-5-amine,
114. 8-chloro-1-[trans-4-(morpholin-4-yl)cyclohexyl]-N-(propan-2-yl)-5,6-dihydro-4H-[1,2,4]triazolo[4,3-a][1]benzazepin-5-amine,
115. (5r,8r)-8-(8'-chloro-4'H,6'H-spiro[1,3-dioxolane-2,5'-[1,2,4]triazolo[4,3-a][1]benzazepin]-1'-yl)-2-(propan-2-yl)-2-azaspiro[4.5]decan-1-one,
116. (5r,8r)-8-(8-chloro-5-hydroxy-5,6-dihydro-4H-[1,2,4]triazolo[4,3-a][1]benzazepin-1-yl)-2-(propan-2-yl)-2-azaspiro[4.5]decan-1-one,
117. (5S)-8-chloro-1-[trans-4-(pyridin-2-yloxy)cyclohexyl]-5-(pyrrolidin-1-yl)-5,6-dihydro-4H-[1,2,4]triazolo[4,3-a][1]benzazepine,
118. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylpropanamide,
119. N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide,
120. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide,
121. N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide,
122. (5S)-8-chlor-5-(morpholin-4-yl)-1-[trans-4-(pyridin-2-yloxy)cyclohexyl]-5,6-dihydro-4H-[1,2,4]triazolo[4,3-a][1]benzazepine,
123. N-{(5R)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylpropanamide,
124. N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide,
125. N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide,
126. N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide,
127. (5S)-8-chloro-5-(piperidin-1-yl)-1-[trans-4-(pyridin-2-yloxy)cyclohexyl]-5,6-dihydro-4H-[1,2,4]triazolo[4,3-a][1]benzazepine,
128. (5S)—N-(butan-2-yl)-8-chloro-1-[trans-4-(pyridin-2-yloxy)cyclohexyl]-5,6-dihydro-4H-[1,2,4]triazolo[4,3-a][1]benzazepin-5-amine,
129. (5s,8s)-8-(8'-chloro-4'H,6'H-spiro[1,3-dioxolane-2,5'-[1,2,4]triazolo[4,3-a][1]benzazepin]-1'-yl)-2-(propan-2-yl)-2-azaspiro[4.5]decan-1-one,
130. 8-chloro-5-methoxy-1-[trans-4-(morpholin-4-yl)cyclohexyl]-5,6-dihydro-4H-[1,2,4]triazolo[4,3-a][1]benzazepine,
131. 8-chloro-5-ethoxy-1-[trans-4-(pyridin-2-yloxy)cyclohexyl]-5,6-dihydro-4H-[1,2,4]triazolo[4,3-a][1]benzazepine,
132. (5R)-8-chloro-5-methoxy-1-[trans-4-(trifluoromethyl)cyclohexyl]-5,6-dihydro-4H-[1,2,4]triazolo[4,3-a][1]benzazepine,
133. (5S)-8-chloro-5-methoxy-1-[trans-4-(trifluoromethyl)cyclohexyl]-5,6-dihydro-4H-[1,2,4]triazolo[4,3-a][1]benzazepine,
134. 8-fluoro-5-methoxy-1-[trans-4-(pyridin-2-yloxy)cyclohexyl]-5,6-dihydro-4H-[1,2,4]triazolo[4,3-a][1]benzazepine,
135. 8-chloro-N-(propan-2-yl)-1-[1-(pyridin-2-yl)piperidin-4-yl]-5,6-dihydro-4H-[1,2,4]triazolo[4,3-a][1]benzazepin-5-amine,
136. 2-({8-chloro-1-[trans-4-(pyridin-2-yloxy)cyclohexyl]-5,6-dihydro-4H-[1,2,4]triazolo[4,3-a][1]benzazepin-5-yl}oxy)ethanol,
137. (5S)-8-chloro-N,N-diethyl-1-[trans-4-(pyridin-2-yloxy)cyclohexyl]-5,6-dihydro-4H-[1,2,4]triazolo[4,3-a][1]benzazepin-5-amine,
138. 8-chloro-N-methyl-N-(propan-2-yl)-1-[trans-4-(pyridin-2-yloxy)cyclohexyl]-5,6-dihydro-4H-[1,2,4]triazolo[4,3-a][1]benzazepin-5-amine,
139. tert-butyl {8-chloro-1-[4-(3-chloropyridin-2-yl)piperazin-1-yl]-5,6-dihydro-4H-[1,2,4]triazolo[4,3-a][1]benzazepin-5-yl}carbamate, 140. tert-butyl 4-(8-chloro-5-methoxy-5,6-dihydro-4H-[1,2,4]triazolo[4,3-a][1]benzazepin-1-yl)piperidine-1-carboxylate,
141. N-{(5R)-8-chloro-1-[trans-4-(pyridin-2-yloxy)cyclohexyl]-5,6-dihydro-4H-[1,2,4]triazolo[4,3-a][1]benzazepin-5-yl}-D-valinamide,
142. tert-butyl {1-[trans-4-(pyridin-2-yloxy)cyclohexyl]-5,6-dihydro-4H-[1,2,4]triazolo[4,3-a][1]benzazepin-5-yl}carbamate,
143. tert-butyl {8-fluoro-1-[trans-4-(pyridin-2-yloxy)cyclohexyl]-5,6-dihydro-4H-[1,2,4]triazolo[4,3-a][1]benzazepin-5-yl}carbamate,
144. 1-[trans-4-(pyridin-2-yloxy)cyclohexyl]-5,6-dihydro-4H-[1,2,4]triazolo[4,3-a][1]benzazepin-5-amine,
145. 8-fluoro-1-[trans-4-(pyridin-2-yloxy)cyclohexyl]-5,6-dihydro-4H-[1,2,4]triazolo[4,3-a][1]benzazepin-5-amine,
146. 8-fluoro-N-(propan-2-yl)-1-[trans-4-(pyridin-2-yloxy)cyclohexyl]-5,6-dihydro-4H-[1,2,4]triazolo[4,3-a][1]benzazepin-5-amine,
147. 8-fluoro-N,N-dimethyl-1-[trans-4-(pyridin-2-yloxy)cyclohexyl]-5,6-dihydro-4H-[1,2,4]triazolo[4,3-a][1]benzazepin-5-amine,
148. N,N-dimethyl-1-[trans-4-(pyridin-2-yloxy)cyclohexyl]-5,6-dihydro-4H-[1,2,4]triazolo[4,3-a][1]benzazepin-5-amine,
149. 8'-fluoro-1'-[trans-4-(trifluoromethyl)cyclohexyl]-4'H,6'H-spiro[1,3-dioxolane-2,5'-[1,2,4]triazolo[4,3-a][1]benzazepine],
150. N-(propan-2-yl)-1-[trans-4-(pyridin-2-yloxy)cyclohexyl]-5,6-dihydro-4H-[1,2,4]triazolo[4,3-a][1]benzazepin-5-amine,
151. N-{(5S)-8-chloro-1-[trans-4-(pyridin-2-yloxy)cyclohexyl]-5,6-dihydro-4H-[1,2,4]triazolo[4,3-a][1]benzazepin-5-yl}tetrahydro-2H-pyran-4-carboxamide,
152. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-methylbutanamide,
153. N-{(5S)-8-chloro-1-[trans-4-(pyridin-2-yloxy)cyclohexyl]-5,6-dihydro-4H-[1,2,4]triazolo[4,3-a][1]benzazepin-5-yl}-N$^3$,N$^3$-dimethyl-β-alaninamide,
154. (5S)-8-chloro-N-cyclopentyl-1-[trans-4-(pyridin-2-yloxy)cyclohexyl]-5,6-dihydro-4H-[1,2,4]triazolo[4,3-a][1]benzazepin-5-amine,
155. 8'-chloro-1'-(1'H,3H-spiro[2-benzofuran-1,4'-piperidin]-1'-yl)-4'H,6'H-spiro[1,3-dioxolane-2,5'-[1,2,4]triazolo[4,3-a][1]benzazepine],
156. 8-chloro-1-(1'H,3H-spiro[2-benzofuran-1,4'-piperidin]-1'-yl)-4H-[1,2,4]triazolo[4,3-a][1]benzazepin-5(6H)-one,
157. 8'-chloro-1'-[4-(pyridin-2-yloxy)piperidin-1-yl]-4'H,6'H-spiro[1,3-dioxolane-2,5'-[1,2,4]triazolo[4,3-a][1]benzazepine],
158. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylbutanamide,
159. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-hydroxy-2-methylpropanamide,
160. (5S)-8-chloro-N-ethyl-N-methyl-1-[trans-4-(pyridin-2-yloxy)cyclohexyl]-5,6-dihydro-4H-[1,2,4]triazolo[4,3-a][1]benzazepin-5-amine,
161. (5S)-8-chloro-N-(2-methylpropyl)-1-[trans-4-(pyridin-2-yloxy)cyclohexyl]-5,6-dihydro-4H-[1,2,4]triazolo[4,3-a][1]benzazepin-5-amine,
162. 8'-chloro-1'-[trans-4-(morpholin-4-yl)cyclohexyl]-4'H,6'H-spiro[1,3-dioxolane-2,5'-[1,2,4]triazolo[4,3-a][1]benzazepine] hydrochloride,
163. 8-chloro-N,N-dimethyl-1-(1'H,3H-spiro[2-benzofuran-1,4'-piperidin]-1'-yl)-5,6-dihydro-4H-[1,2,4]triazolo[4,3-a][1]benzazepin-5-amine,
164. 8'-chloro-1'-[4-(3-chloropyridin-2-yl)piperazin-1-yl]-4'H,6'H-spiro[1,3-dioxolane-2,5'-[1,2,4]triazolo[4,3-a][1]benzazepine],
165. (5S)-8-chloro-N-(2,2-dimethylpropyl)-1-[trans-4-(pyridin-2-yloxy)cyclohexyl]-5,6-dihydro-4H-[1,2,4]triazolo[4,3-a][1]benzazepin-5-amine,
166. [trans-4-(8-chloro-5-methoxy-5,6-dihydro-4H-[1,2,4]triazolo[4,3-a][1]benzazepin-1-yl)cyclohexyl](4-methylpiperazin-1-yl)methanone,
167. (5R)-8-chloro-5-(morpholin-4-yl)-1-[trans-4-(pyridin-2-yloxy)cyclohexyl]-5,6-dihydro-4H-[1,2,4]triazolo[4,3-a][1]benzazepine,
168. N-{(5R)-8-chloro-1-[trans-4-(pyridin-2-yloxy)cyclohexyl]-5,6-dihydro-4H-[1,2,4]triazolo[4,3-a][1]benzazepin-5-yl}acetamide,
169. N-{(5R)-8-chloro-1-[trans-4-(pyridin-2-yloxy)cyclohexyl]-5,6-dihydro-4H-[1,2,4]triazolo[4,3-][1]benzazepin-5-yl}-2-hydroxy-2-methylpropanamide,
170. 8-chloro-5-methoxy-1-[1-(tetrahydro-2H-pyran-4-yl)piperidin-4-yl]-5,6-dihydro-4H-[1,2,4]triazolo[4,3-a][1]benzazepine,
171. 8'-chloro-1'-[4-(pyridin-2-yl)piperazin-1-yl]-4'H,6'H-spiro[1,3-dioxolane-2,5'-[1,2,4]triazolo[4,3-a][1]benzazepine],
172. 8-chloro-1-(1'H,3H-spiro[2-benzofuran-1,4'-piperidin]-1'-yl)-5,6-dihydro-4H-[1,2,4]triazolo[4,3-a][1]benzazepin-5-ol,
173. 8-chloro-1-[4-(3-chloropyridin-2-yl)piperidin-1-yl]-5,6-dihydro-4H-[1,2,4]triazolo[4,3-a][1]benzazepin-5-ol,
174. (5R)-8-chloro-1-[trans-4-(pyridin-2-yloxy)cyclohexyl]-5-(pyrrolidin-1-yl)-5,6-dihydro-4H-[1,2,4]triazolo[4,3-a][1]benzazepine,
175. 8-chloro-5-methoxy-1-{1-[(3S)-tetrahydrofuran-3-yl]piperidin-4-yl}-5,6-dihydro-4H-[1,2,4]triazolo[4,3-a][1]benzazepine,
176. (5R)-8-fluoro-5-methoxy-1-[trans-4-(pyridin-2-yloxy)cyclohexyl]-5,6-dihydro-4H-[1,2,4]triazolo[4,3-a][1]benzazepine,
177. (5S)-8-fluoro-5-methoxy-1-[trans-4-(pyridin-2-yloxy)cyclohexyl]-5,6-dihydro-4H-[1,2,4]triazolo[4,3-a][1]benzazepine,
178. 8-chloro-5-methoxy-1-{1-[(3R)-tetrahydrofuran-3-yl]piperidin-4-yl}-5,6-dihydro-4H-[1,2,4]triazolo[4,3-a][1]benzazepine,
179. N-{(5R)-8-chloro-1-[trans-4-(pyridin-2-yloxy)cyclohexyl]-5,6-dihydro-4H-[1,2,4]triazolo[4,3-a][1]benzazepin-5-yl}-N$^3$,N$^3$-dimethyl-β-alaninamide,
180. N-{(5R)-8-chloro-1-[trans-4-(pyridin-2-yloxy)cyclohexyl]-5,6-dihydro-4H-[1,2,4]triazolo[4,3-a][1]benzazepin-5-yl}tetrahydro-2H-pyran-4-carboxamide,
181. 8-chloro-1-[4-(pyridin-2-yloxy)piperidin-1-yl]-5,6-dihydro-4H-[1,2,4]triazolo[4,3-a][1]benzazepin-5-ol,
182. 8-chloro-5-methoxy-1-[trans-4-(4-methylpiperazin-1-yl)cyclohexyl]-5,6-dihydro-4H-[1,2,4]triazolo[4,3-a][1]benzazepine,
183. 8-chloro-5-methoxy-1-[cis-4-(4-methylpiperazin-1-yl)cyclohexyl]-5,6-dihydro-4H-[1,2,4]triazolo[4,3-a][1]benzazepine,
184. 8-chloro-5-methoxy-1-[1-(pyridin-3-ylmethyl)pyrrolidin-3-yl]-5,6-dihydro-4H-[1,2,4]triazolo[4,3-a][1]benzazepine,
185. 8-chloro-5-methoxy-1-[1-(pyridin-2-ylmethyl)pyrrolidin-3-yl]-5,6-dihydro-4H-[1,2,4]triazolo[4,3-a][1]benzazepine, 186. N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-cyanoacetamide,
187. [3-(8-chloro-5-methoxy-5,6-dihydro-4H-[1,2,4]triazolo[4,3-a][1]benzazepin-1-yl)pyrrolidin-1-yl](pyridin-3-yl)methanone,
188. 8'-chloro-1'-{1-[(3R)-tetrahydrofuran-3-yl]piperidin-4-yl}-4'H,6'H-spiro[1,3-dioxolane-2,5'-[1,2,4]triazolo[4,3-a][1]benzazepine],
189. [3-(8-chloro-5-methoxy-5,6-dihydro-4H-[1,2,4]triazolo[4,3-a][1]benzazepin-1-yl)pyrrolidin-1-yl](pyridin-2-yl)methanone,
190. trans-4-(8'-chloro-4'H,6'H-spiro[1,3-dioxolane-2,5'-[1,2,4]triazolo[4,3-a][1]benzazepin]-1'-yl)-N,N-dimethylcyclohexanamine,
191. 8-chloro-5-methoxy-1-(1'H,3H-spiro[2-benzofuran-1,4'-piperidin]-1'-yl)-5,6-dihydro-4H-[1,2,4]triazolo[4,3-a][1]benzazepine,
192. 8-chloro-1-[4-(3-chloropyridin-2-yl)piperazin-1-yl]-5-methoxy-5,6-dihydro-4H-[1,2,4]triazolo[4,3-a][1]benzazepine,
193. N-[trans-4-(8'-chloro-4'H,6'H-spiro[1,3-dioxolane-2,5'-[1,2,4]triazolo[4,3-a][1]benzazepin]-1'-yl)cyclohexyl]pyridin-2-amine,
194. N'-{(5R)-8-chloro-1-[trans-4-(pyridin-2-yloxy)cyclohexyl]-5,6-dihydro-4H-[1,2,4]triazolo[4,3-a][1]benzazepin-5-yl}-N,N-dimethylethane-1,2-diamine,
195. 8-chloro-1-[trans-4-(pyridin-2-yloxy)cyclohexyl]-5,6-dihydro-4H-[1,2,4]triazolo[4,3-a][1]benzazepin-5-yl acetate,
196. 2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethanol,
197. 8-chloro-5-methoxy-1-[4-(pyridin-2-yloxy)piperidin-1-yl]-5,6-dihydro-4H-[1,2,4]triazolo[4,3-a][1]benzazepine,
198. 8'-chloro-1'-(trans-4-methoxy-4-methylcyclohexyl)-4'H,6'H-spiro[1,3-dioxolane-2,5'-[1,2,4]triazolo[4,3-a][1]benzazepine],
199. (5S)-8-chloro-N-(cyclopropylmethyl)-1-[trans-4-(pyridin-2-yloxy)cyclohexyl]-5,6-dihydro-4H-[1,2,4]triazolo[4,3-a][1]benzazepin-5-amine,
200. N-{(5S)-8-chloro-1-[trans-4-(pyridin-2-yloxy)cyclohexyl]-5,6-dihydro-4H-[1,2,4]triazolo[4,3-a][1]benzazepin-5-yl}-1-methylpiperidine-4-carboxamide,
201. N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2,2-trifluoroacetamide,
202. 8-chloro-5-(2-methoxyethoxy)-1-[trans-4-(pyridin-2-yloxy)cyclohexyl]-5,6-dihydro-4H-[1,2,4]triazolo[4,3-a][1]benzazepine,
203. 8-chloro-1-(4-methoxy-4-methylcyclohexyl)-N-(propan-2-yl)-5,6-dihydro-4H-[1,2,4]triazolo[4,3-a][1]benzazepin-5-amine,
204. 8'-chloro-1'-(trans-4-methoxy-4-methylcyclohexyl)-4'H,6'H-spiro[1,3-dioxane-2,5-[1,2,4]triazolo[4,3-a][1]benzazepine],
205. 8'-chloro-1'-(cis-4-methoxy-4-methylcyclohexyl)-4'H,6'H-spiro[1,3-dioxane-2,5'-[1,2,4]triazolo[4,3-a][1]benzazepine],
206. 8-chloro-5-fluoro-1-[trans-4-(pyridin-2-yloxy)cyclohexyl]-5,6-dihydro-4H-[1,2,4]triazolo[4,3-a][1]benzazepine,
207. 8-chloro-5-[2-(methylsulfonyl)ethoxy]-1-[trans-4-(pyridin-2-yloxy)cyclohexyl]-5,6-dihydro-4H-[1,2,4]triazolo[4,3-a][1]benzazepine,
208. 8-chloro-N-hydroxy-1-[trans-4-(pyridin-2-yloxy)cyclohexyl]-4H-[1,2,4]triazolo[4,3-a][1]benzazepin-5(6H)-imine,
209. (5S)-8-chloro-N-methyl-N-(prop-2-yn-1-yl)-1-[trans-4-(pyridin-2-yloxy)cyclohexyl]-5,6-dihydro-4H-[1,2,4]triazolo[4,3-a][1]benzazepin-5-amine,
210. N-{(5S)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide,
211. 8-chloro-5-(prop-2-yn-1-yloxy)-1-[trans-4-(pyridin-2-yloxy)cyclohexyl]-5,6-dihydro-4H-[1,2,4]triazolo[4,3-a][1]benzazepine,
212. 8-chloro-1-[trans-4-(pyridin-2-yloxy)cyclohexyl]-5,6-dihydro-4H-[1,2,4]triazolo[4,3-a][1]benzazepin-5-yl 4,4-difluorocyclohexanecarboxylate,
213. 8-chloro-1-[trans-4-(pyridin-2-yloxy)cyclohexyl]-5,6-dihydro-4H-[1,2,4]triazolo[4,3-a][1]benzazepin-5-yl 3,3-difluorocyclobutanecarboxylate,
214. N-{(5S)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide,
215. 8-chloro-1-[trans-4-(pyridin-2-yloxy)cyclohexyl]-5,6-dihydro-4H-[1,2,4]triazolo[4,3-a][1]benzazepin-5-yl cyanoacetate,
216. 8-chloro-1-[trans-4-(pyridin-2-yloxy)cyclohexyl]-5,6-dihydro-4H-[1,2,4]triazolo[4,3-a][1]benzazepin-5-yl N,N-dimethylglycinate,
217. N-{(5R)-8-chloro-1-[trans-4-(pyridin-2-yloxy)cyclohexyl]-5,6-dihydro-4H-[1,2,4]triazolo[4,3-a][1]benzazepin-5-yl}-2,2,2-trifluoroacetamide,
218. 1-[cis-4-(8-chloro-5-methoxy-5,6-dihydro-4H-[1,2,4]triazolo[4,3-a][1]benzazepin-1-yl)cyclohexyl]pyrrolidin-2-one,
219. 1-[trans-4-(8-chloro-5-methoxy-5,6-dihydro-4H-[1,2,4]triazolo[4,3-a][1]benzazepin-1-yl)cyclohexyl]pyrrolidin-2-one,
220. N-{(5R)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide,
221. N-{(5R)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide,
222. 8-chloro-5-methoxy-1-[cis-4-methoxy-4-(trifluoromethyl)cyclohexyl]-5,6-dihydro-4H-[1,2,4]triazolo[4,3-a][1]benzazepine,
223. 8-chloro-5-methoxy-1-[trans-4-methoxy-4-(trifluoromethyl)cyclohexyl]-5,6-dihydro-4H-[1,2,4]triazolo[4,3-a][1]benzazepine,
224. (5S)-8-chloro-1-[trans-4-(pyridin-2-yloxy)cyclohexyl]-N-(2,2,2-trifluoroethyl)-5,6-dihydro-4H-[1,2,4]triazolo[4,3-a][1]benzazepin-5-amine,
225. N-{(5S)-8-chloro-1-[trans-4-(pyridin-2-yloxy)cyclohexyl]-5,6-dihydro-4H-[1,2,4]triazolo[4,3-a][1]benzazepin-5-yl}-3-methyloxetane-3-carboxamide,
226. N-{(5R)-8-chloro-1-[trans-4-(pyridin-2-yloxy)cyclohexyl]-5,6-dihydro-4H-[1,2,4]triazolo[4,3-a][1]benzazepin-5-yl}-3-methyloxetane-3-carboxamide,
227. trans-4-(8'-chloro-4'H,6'H-spiro[1,3-dioxolane-2,5'-[1,2,4]triazolo[4,3-a][1]benzazepin]-1'-yl)-N-(4-methoxybenzyl)cyclohexanamine,
228. tert-butyl [2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethyl]carbamate,
229. 8'-chloro-1'-(trans-4-ethoxy-4-ethylcyclohexyl)-4'H,6'H-spiro[1,3-dioxolane-2,5'-[1,2,4]triazolo[4,3-a][1]benzazepine], 230. trans-4-(8'-chloro-4'H,6'H-spiro[1,3-dioxolane-2,5'-[1,2,4]triazolo[4,3-a][1]benzazepin]-1'-yl)-N-(4-methoxybenzyl)-N-methylcyclohexanamine,
231. 8'-chloro-1'-[1-(pyridin-3-ylmethyl)pyrrolidin-3-yl]-4'H,6'H-spiro[1,3-dioxolane-2,5'-[1,2,4]triazolo[4,3-a][1]benzazepine],
232. 8-chloro-5-methoxy-1-[4-(pyridin-2-yl)piperazin-1-yl]-5,6-dihydro-4H-[1,2,4]triazolo[4,3-a][1]benzazepine,
233. 8-chloro-1-(trans-4-ethyl-4-methoxycyclohexyl)-N,N-dimethyl-5,6-dihydro-4H-[1,2,4]triazolo[4,3-a][1]benzazepin-5-amine,
234. 8-chloro-1-(trans-4-ethoxy-4-methylcyclohexyl)-N,N-dimethyl-5,6-dihydro-4H-[1,2,4]triazolo[4,3-a][1]benzazepin-5-amine,
235. 8'-chloro-1'-[trans-4-methoxy-4-(trifluoromethyl)cyclohexyl]-4'H,6'H-spiro[1,3-dioxolane-2,5'-[1,2,4]triazolo[4,3-a][1]benzazepine],
236. 8'-chloro-1'-[cis-4-methoxy-4-(trifluoromethyl)cyclohexyl]-4'H,6'H-spiro[1,3-dioxolane-2,5'-[1,2,4]triazolo[4,3-a][1]benzazepine],
237. 8'-chloro-1'-(trans-4-ethoxy-4-methylcyclohexyl)-4'H,6'H-spiro[1,3-dioxolane-2,5'-[1,2,4]triazolo[4,3-a][1]benzazepine],
238. 8'-chloro-1'-(trans-4-ethoxy-4-propylcyclohexyl)-4'H,6'H-spiro[1,3-dioxolane-2,5' [1,2,4]triazolo[4,3-a][1]benzazepine],
239. 8'-chloro-1'-[1-(pyridin-2-ylmethyl)pyrrolidin-3-yl]-4'H,6'H-spiro[1,3-dioxolane-2,5'-[1,2,4]triazolo[4,3-a][1]benzazepine],
240. 8'-chloro-1'-(cis-4-ethyl-4-methoxycyclohexyl)-4'H,6'H-spiro[1,3-dioxolane-2,5'-[1,2,4]triazolo[4,3-a][1]benzazepine],
241. 8'-chloro-1'-(trans-4-ethyl-4-methoxycyclohexyl)-4'H,6'H-spiro[1,3-dioxolane-2,5'-[1,2,4]triazolo[4,3-a][1]benzazepine],
242. 8'-chloro-1'-(trans-4-methoxy-4-propylcyclohexyl)-4'H,6'H-spiro[1,3-dioxolane-2,5'-[1,2,4]triazolo[4,3-a][1]benzazepine],
243. 8'-chloro-1'-(cis-4-methoxy-4-propylcyclohexyl)-4'H,6'H-spiro[1,3-dioxolane-2,5'-[1,2,4]triazolo[4,3-a][1]benzazepine],
244. 8-chloro-1-(trans-4-ethoxy-4-ethylcyclohexyl)-N-(propan-2-yl)-5,6-dihydro-4H-[1,2,4]triazolo[4,3-a][1]benzazepin-5-amine,
245. 8-chloro-1-(trans-4-ethoxy-4-ethylcyclohexyl)-N,N-dimethyl-5,6-dihydro-4H-[1,2,4]triazolo[4,3-a][1]benzazepin-5-amine,
246. 8'-chloro-1'-[(3R)-1-(pyridin-2-ylmethyl)pyrrolidin-3-yl]-4'H,6'H-spiro[1,3-dioxolane-2,5'-[1,2,4]triazolo[4,3-a][1]benzazepine],
247. 8-chloro-5-methoxy-1-[(3R)-1-(pyridin-3-ylmethyl)pyrrolidin-3-yl]-5,6-dihydro-4H-[1,2,4]triazolo[4,3-a][1]benzazepine,
248. 8-chloro-5-methoxy-1-[(3R)-1-(pyridin-2-ylmethyl)pyrrolidin-3-yl]-5,6-dihydro-4H-[1,2,4]triazolo[4,3-a][1]benzazepine,
249. 8'-chloro-1'-[(3S)-1-(pyridin-3-ylmethyl)pyrrolidin-3-yl]-4'H,6'H-spiro[1,3-dioxolane-2,5'-[1,2,4]triazolo[4,3-a][1]benzazepine],
250. 8'-chloro-1'-[(3R)-1-(pyridin-3-ylmethyl)pyrrolidin-3-yl]-4'H,6'H-spiro[1,3-dioxolane-2,5'-[1,2,4]triazolo[4,3-a][1]benzazepine],
251. 8-chloro-5-methoxy-1-[(3S)-1-(pyridin-3-ylmethyl)pyrrolidin-3-yl]-5,6-dihydro-4H-[1,2,4]triazolo[4,3-a][1]benzazepine,
252. 8'-chloro-1'-[(3S)-1-(pyridin-2-ylmethyl)pyrrolidin-3-yl]-4'H,6'H-spiro[1,3-dioxolane-2,5'-[1,2,4]triazolo[4,3-a][1]benzazepine] and
253. 8-chloro-5-methoxy-1-[(3S)-1-(pyridin-2-ylmethyl)pyrrolidin-3-yl]-5,6-dihydro-4H-[1,2,4]triazolo[4,3-a][1]benzazepine.

The present invention also relates to the synthesis of compounds of general formula (I). Accordingly, the compounds of formula (I) of the present invention can be prepared by one of the following methods:

In so far as, in the compound of formula (I), $R^2$ is hydrogen, $R^3$ is —NHBoc or —OSi(CH$_3$)$_2$-t-butyl group and ring A is a cycloalkyl or a 4- to 7-membered saturated heterocycle containing 1 N, wherein ring A is attached via the ring nitrogen to Y, the compounds of general formula (I) of the present invention are prepared by reacting compounds of general formula (II)

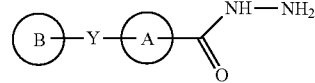

wherein ring B and Y are as defined above for general formula (I) and ring A is a cycloalkyl or a 4- to 7-membered saturated heterocycle containing 1 N, wherein ring A is attached via the ring nitrogen to Y—and compounds of general formula III

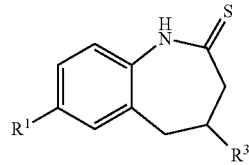

wherein $R^1$ is as defined above for general formula (I), $R^3$ is hydrogen, $R^3$ is —NHBoc or —OSi(CH$_3$)$_2$-t-butyl group—or the compounds of general formula (IV)

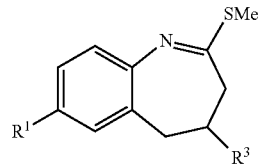

wherein $R^1$ is as defined above for formula (I), $R^2$ is hydrogen, $R^3$ is —NHBoc or —OSi(CH$_3$)$_2$-t-butyl group.

The procedure is shown in detail in Scheme 1:

Scheme 1

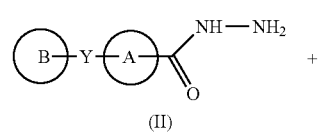

-continued

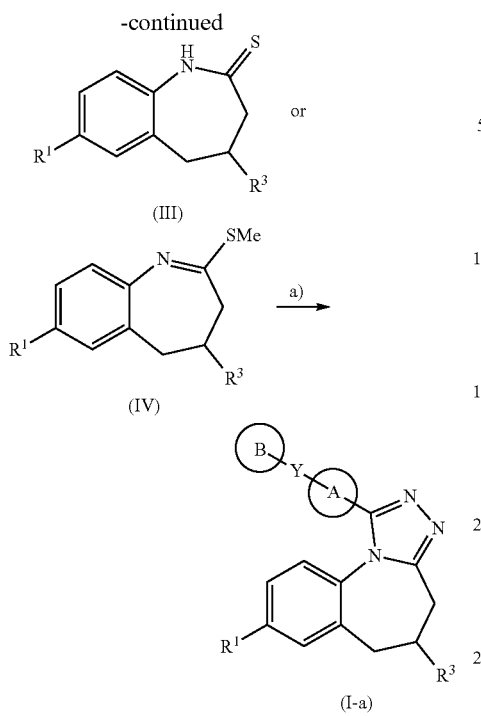

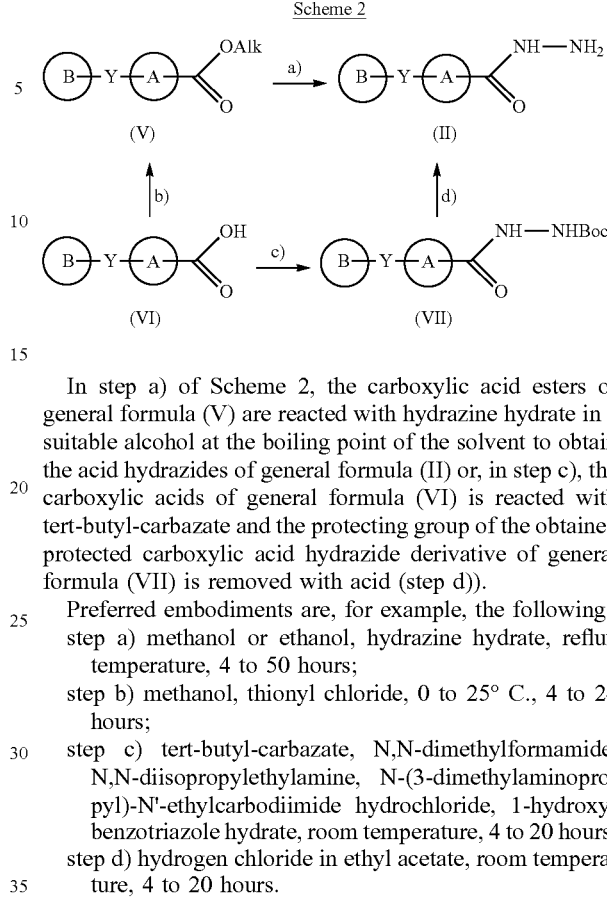

In step a) of Scheme 1 the acid hydrazide of general formula (II) is reacted with the benzazepine-thione of general formula (III) or the methylsulfanyl-benzazepine derivatives of general formula (IV). The reaction is preferably carried out in a suitable solvent, at the boiling point of the solvent, with a reaction time required of 4 to 150 hours. Suitable solvents include xylene, n-butanol, 1,4-dioxane.

Preferred embodiments are, for example, the following:
i) reaction of (II) and (III) in xylene at 140° C. for 20 to 150 hours, or
ii) reaction of (II) and (III) in n-butanol at 110° C. for 20 to 50 hours, or
iii) reaction of (II) and (III) in 1,4-dioxane at 110° C. for 4 to 20 hours, or
iv) reaction of (II) and (IV) in xylene in the presence of catalytic hydrogen chloride at 140° C. for 4 to 20 hours, or
v) reaction of (II) and (IV) in 1,4-dioxane in the presence of catalytic hydrogen chloride at 110° C. for 4 to 20 hours.

Synthesis of the acid hydrazides of general formula (II) can be carried out in various ways (Scheme 2):

In step a) of Scheme 2, the carboxylic acid esters of general formula (V) are reacted with hydrazine hydrate in a suitable alcohol at the boiling point of the solvent to obtain the acid hydrazides of general formula (II) or, in step c), the carboxylic acids of general formula (VI) is reacted with tert-butyl-carbazate and the protecting group of the obtained protected carboxylic acid hydrazide derivative of general formula (VII) is removed with acid (step d)).

Preferred embodiments are, for example, the following:
step a) methanol or ethanol, hydrazine hydrate, reflux temperature, 4 to 50 hours;
step b) methanol, thionyl chloride, 0 to 25° C., 4 to 24 hours;
step c) tert-butyl-carbazate, N,N-dimethylformamide, N,N-diisopropylethylamine, N-(3-dimethylaminopropyl)-N'-ethylcarbodiimide hydrochloride, 1-hydroxybenzotriazole hydrate, room temperature, 4 to 20 hours;
step d) hydrogen chloride in ethyl acetate, room temperature, 4 to 20 hours.

The carboxylic acid esters of general formula (V) and the carboxylic acids of general formula (VI) are either commercially available or can be prepared according to the methods described in the Examples.

In so far as, in the compounds of general formula (I), $R^1$ is as defined above for general formula (I), $R^2$ is hydrogen, $R^3$ is —NHBoc, the benzazepine-thione derivatives of general formula (III) and methylsulfanyl benzazepine derivatives of general formula (IV) can be prepared according to the following procedures:

The key intermediate benzazepine derivative of general formula (XIII) can be prepared according to the following Method A (Scheme 3) and Method B (Scheme 4):

Method A:

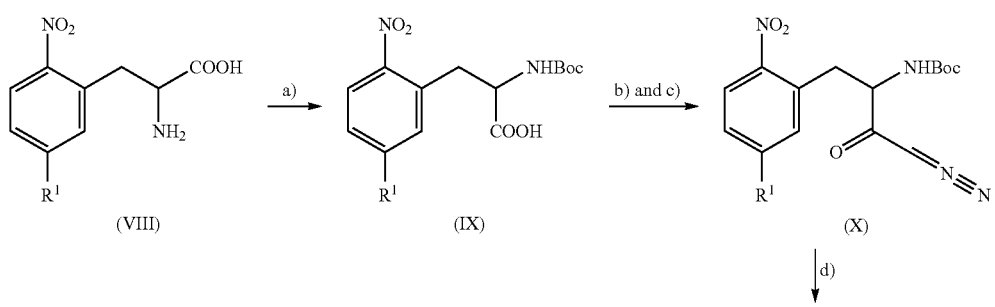

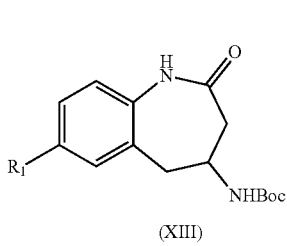

In step a) of Scheme 3, amino group of the amino acid derivative of general formula (VIII), which is commercially available or can be prepared according to the methods described in the Examples,—wherein $R^1$ is as defined above for general formula (I)—is protected by a tert-butoxycarbonyl protecting group, then with the thus obtained protected amino acid derivative (IX)—wherein $R^1$ is as defined above for general formula (I)—the Arndt-Eistert reaction (Arndt, F., Eistert, B. *Chem Ber* 1935, 68(1):200-208) is carried out in two steps: first, the acid chloride prepared in situ from the compound of general formula (IX) is reacted with diazomethane (steps b) and c)) to give the diazo compound of general formula (X)—wherein $R^1$ is as defined above for general formula (I)—which in step d) is converted to the amino acid derivative of general formula (XI) in the presence of a silver salt—wherein $R^1$ is as defined above for general formula (I). The nitro group of the latter is reduced (step e)) to obtain the amine of general formula (XII)—wherein $R^1$ is as defined above for general formula (I)—, which is ring-closed by means of a reagent capable of forming an amide bond (step f)) to obtain the benzazepine derivative of general formula (XIII)—wherein $R^1$ is as defined above for general formula (I).

Preferred embodiments are, for example, the following:
step a) di-tert-butyl dicarbonate, 1,4-dioxane, aqueous sodium hydroxide solution, room temperature, 4 to 20 hours;
step b) isobutyl chloroformate, triethylamine, diethyl ether, −30° C., 15 to 45 minutes;
step c) diazomethane solution in ether, −30° C. to 0° C., 1 to 3 hours;
step d) silver benzoate, 1,4-dioxane, water, room temperature, 4 to 20 hours;
step e) i) sodium borohydride, methanol, nickel chloride, room temperature, 4 to 20 hours, or
 ii) hydrogenation in the presence Pt/C catalyst, toluene, room temperature, 4 to 20 hours;
step f) N,N-dimethylformamide, N,N-diisopropylethylamine, N-(3-dimethylaminopropyl)-N'-ethylcarbodiimide hydrochloride, 1-hydroxybenzotriazole hydrate, room temperature, 4 to 20 hours.

Method B:

Scheme 4

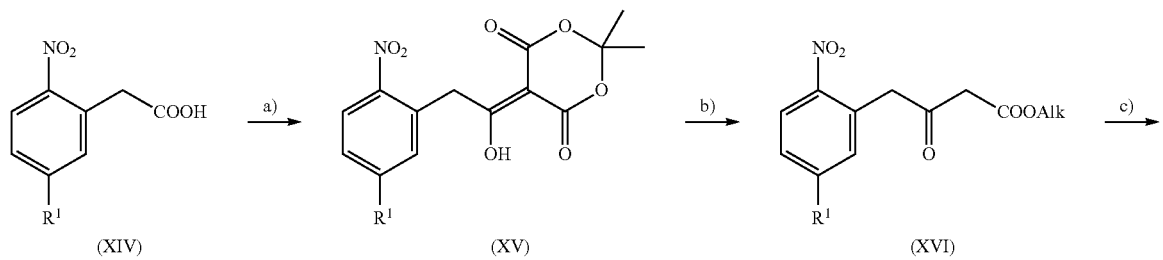

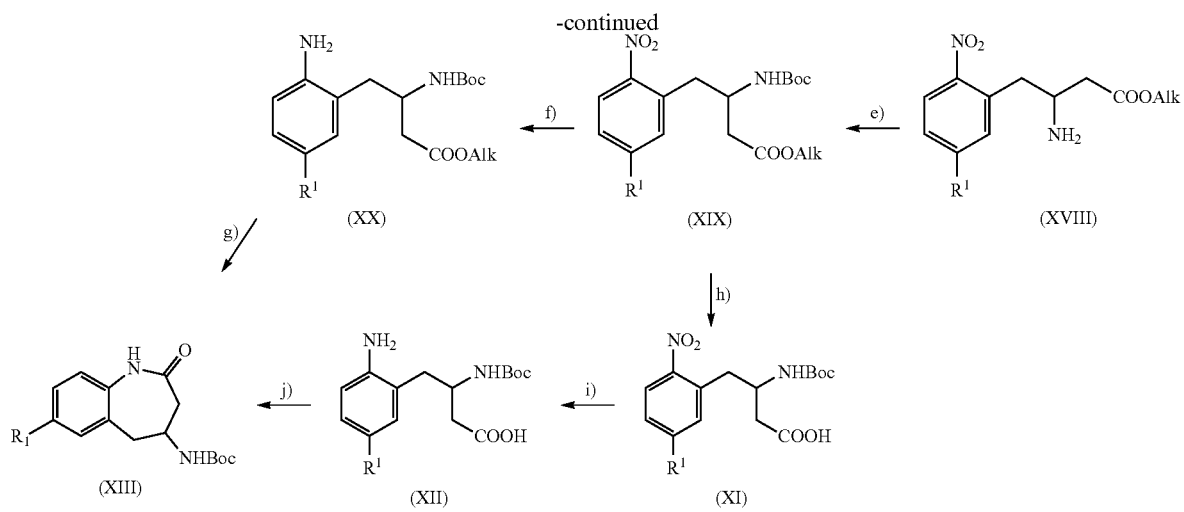

In step a) of Scheme 4, the phenylacetic acid derivative of general formula (XIV), which is commercially available or can be prepared according to the methods described in the Examples—wherein $R^1$ is as defined above for general formula (I)—is reacted with Meldrum's acid to obtain the compound of general formula (XV)—wherein $R^1$ is as defined above for general formula (I)—, which is reacted with a suitable alcohol (step b)) to obtain the keto ester derivative of general formula (XVI)—wherein $R^1$ is as defined above for general formula (I) and Alk is $C_{1-4}$alkyl group—, the latter is converted to the compound of general formula (XVII) by the addition of ammonium acetate (step c))—wherein $R^1$ is as defined above for general formula (I) and Alk is $C_{1-4}$alkyl group—, which is reduced in step d) and the resulting amino compound of general formula (XVIII) is obtained—wherein $R^1$ is as defined above for general formula (I) and Alk is $C_{1-4}$alkyl group—of which amino group is protected with tert-butoxycarbonyl group (step e)) to obtain the compound of general formula (XIX)—wherein $R^1$ is as defined above for general formula (I) and Alk is $C_{1-4}$alkyl group. The nitro group of the latter is reduced in step f) and the thus obtained compound of general formula (XX)—wherein $R^1$ is as defined above for general formula (I) and Alk is $C_{1-4}$alkyl group—is ring-closed in the presence of a suitable base (step g)) to obtain the compound of formula (XIII)—wherein $R^1$ is as defined above for general formula (I).

The compound of formula (XIII) can also be prepared by hydrolysing the compound of general formula (XIX)—wherein $R^1$ is as defined above for general formula (I) and Alk is $C_{1-4}$alkyl group—in the presence of a suitable base (step h)) and the resulting compound of formula (XI)—wherein $R^1$ is as defined above for general formula (I)—is converted to the compound of general formula (XIII) via the steps shown in Method A (step i) of Method B is identical to step e) of Method A and step j) of Method B is identical to step f) of Method A).

Preferred embodiments are, for example, the following:
step a) Meldrum's acid, acetonitrile, N,N-diisopropylethylamine, pivaloyl chloride, 4-dimethylaminopyridine, 20 to 50° C., 4 to 6 hours;
step b) methanol, toluene, 110 to 120° C., 1 to 6 hours;
step c) ammonium acetate, methanol, room temperature, 20 to 75 hours or 60° C. for 5 to 20 hours;
step d) sodium triacetoxyborohydride, acetic acid, room temperature, 2 to 48 hours;
step e) sodium bicarbonate, methanol, di-tert-butyl dicarbonate, 5 to 25° C.; 1 to 20 hours;
step f) i) hydrogenation in the presence of Pt/C catalyst, toluene, room temperature, 4 to 20 hours, or
  ii) hydrogenation in the presence of Pd/C catalyst, methanol, room temperature, 4 to 20 hours;
step g) i) methanol, sodium methoxide, room temperature, 2 to 20 hours, or
  ii) tetrahydrofuran, potassium tert-butoxide, 0 to 25° C., 2 to 20 hours;
step h) lithium hydroxide, methanol, water, tetrahydrofuran, room temperature, 4 to 20 hours.

The benzazepine-thione derivatives of general formula (III) and the methylsulfanylbenzazepine derivatives of general formula (IV) are prepared (Scheme 5) by reacting a compound of general formula (XIII) obtained by Method A or B Scheme 5

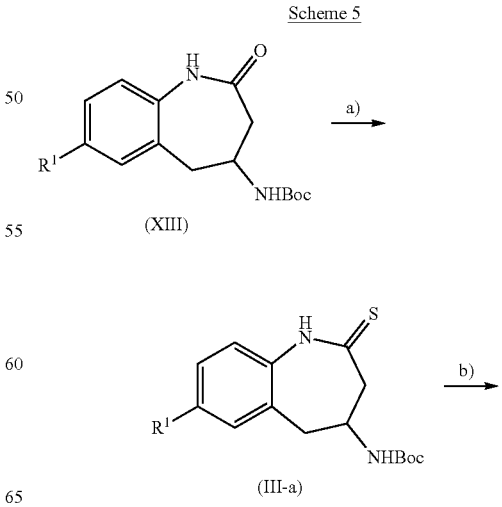

-continued

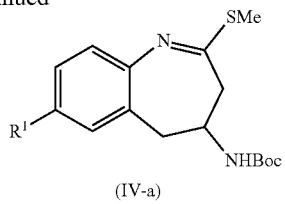

(IV-a)

wherein $R^1$ is as defined above for general formula (I)—with Lawesson reagent (step a)), then the thus obtained benzazepine-thione of general formula (III-a)—wherein $R^1$ is as defined above for general formula (I)—is methylated (step b)) to give the methylsulfanyl-benzazepine derivative of general formula (IV-a)—wherein $R^1$ is as defined above for general formula (I).

Preferred embodiments are, for example, the following:
step a) i) Lawesson reagent, pyridine, 90 to 120° C., 4 to 20 hours, or
ii) Lawesson reagent, tetrahydrofuran, room temperature, 4 to 20 hours;
step b) iodomethane, potassium carbonate, acetone, room temperature, 4 to 24 hours.

The compounds of general formula (I-b) are prepared by reacting a compound of general formula (III-a) or a compound of general formula (IV-a) with a compound of general formula (II) (Scheme 6)

Scheme 6

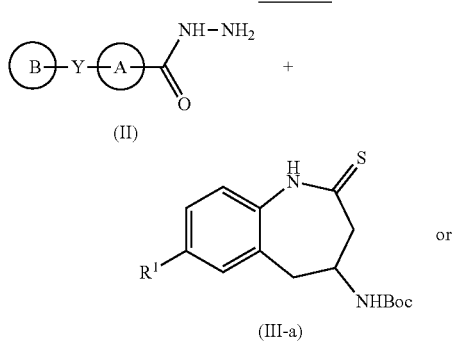

-continued

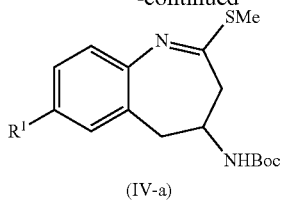

(IV-a)

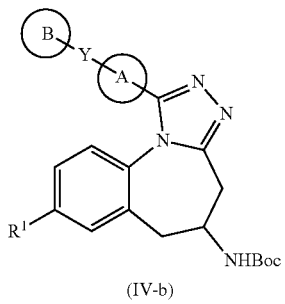

(IV-b)

wherein ring B, Y, $R^1$ is as defined above for general formula (I), ring A is a cycloalkyl or a 4- to 7-membered saturated heterocycle containing 1 N, wherein ring A is attached via the ring nitrogen to Y.

Preferred embodiments of step a) of Scheme 6 are, for example, the following:
i) reaction of (II) and (III-a) in xylene at 140° C. for 20 to 150 hours, or
ii) reaction of (II) and (III-a) in n-butanol at 110° C. for 20 to 50 hours, or
i) reaction of (II) and (III-a) in 1,4-dioxane at 110° C. for 4 to 20 hours, or
iv) reaction of (II) and (IV-a) in xylene in the presence of catalytic hydrogen chloride at 140° C. for 4 to 20 hours, or
v) reaction of (II) and (IV-a) in 1,4-dioxane in the presence of catalytic hydrogen chloride at 110° C. for 4 to 20 hours.

The thus obtained compounds of general formula (I-b) if desired can also be converted to another compound of the general formula (I) by known methods with the introduction of new substituents and/or with the modification, removal of the existing substituents and/or with salt-formation and/or with releasing the base from salts and/or with the preparation of the enantiomers from the racemic mixtures. This is illustrated in detail in Scheme 7:

Scheme 7

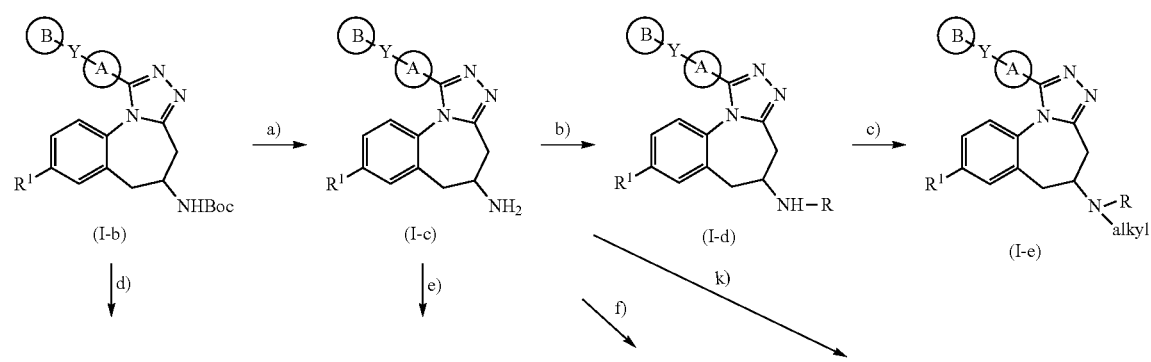

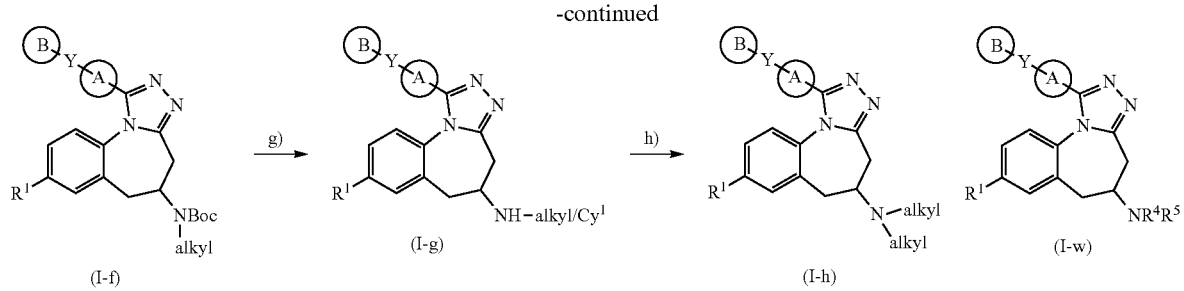

The protecting group of compound of general formula (I-b) can be removed in a suitable acidic medium (step a)), the thus obtained compounds of general formula (I-c)—wherein ring B, Y, $R^1$ are as defined above for general formula (I), ring A is a cycloalkyl or a 4- to 7-membered saturated heterocycle containing 1 N, wherein ring A is attached via the ring nitrogen to Y—can be sulfonylated or acylated (step b)) and the compounds of general formula (I-d)—wherein R is $C(O)R^7$ or $S(O_2)R^1$ as defined in general formula (I) in the meaning of $R^4$ or $R^5$—, may optionally be alkylated (step c)) thus, the compounds of general formula (I-e) are obtained. After the alkylation (step d)) of the compounds of general formula (I-b) followed by deprotection (step g)) gives the mono-alkyl derivatives of general formula (I-g) which can be converted with further alkylation (step h)) to di-alkyl derivatives of general formula (I-h). The two alkyl groups can be different and/or identical. The monoalkyl or $Cy^1$ derivatives of general formula (I-g) can also be prepared by reductive amination (step e)) from the amine derivative of general formula (I-c). The dialkyl derivatives of general formula (I-h) can also be prepared from the amine derivatives of general formula (I-c) by reductive amination (step f)) if the two alkyl groups are identical. The compounds of general formula (I-w)—wherein $R^4$ and $R^5$ taken together with the N to which they are attached form a heterocycle—can also be obtained from the compounds of general formula (I-c) (step k)) using a suitable dihalogen compound in the presence of a base. Pure enantiomers can be obtained by chiral HPLC or resolution from compounds of general formula (I-c) from which acyl and/or alkyl derivatives can also be prepared. When the compound of general formula (I-c) is a pure enantiomer, the chiral compound of general formula (I-b) is prepared to produce further chiral monoalkyl derivatives. In the general formulae (I-e), (I-f), (I-g) and (I-h), the term "alkyl" is optionally substituted $C_{1-4}$alkyl as defined in general formula (I) in the meaning of $R^4$ or $R^5$ and in the general formula (I-g) $Cy^1$ is as defined for formula (I).

Preferred embodiments are, for example, the following:
step a) and g) hydrogen chloride in ethyl acetate, room temperature, 1 to 20 hours
step b) i) sulfonyl chloride, pyridine, room temperature, 4 to 20 hours, or
ii) sulfonyl chloride, dichloromethane, triethylamine or N,N-diisopropylethylamine, room temperature, 4 to 20 hours, or
iii) acyl chloride, pyridine, at room temperature for 4 to 20 hours, or
iv) acyl chloride, dichloromethane, triethylamine or N,N-diisopropylethylamine, room temperature, 4 to 20 hours, or
v) acid anhydride, pyridine, room temperature, 4 to 20 hours, or
vi) acid, N,N,N',N'-tetramethyl-O-(1H-benzotriazol-1-yl)uronium hexafluorophosphate, N,N-dimethylformamide, N,N-diisopropylethylamine or triethylamine, room temperature, 4 to 20 hours, or
vii) acid, N-(3-dimethylaminopropyl)-N'-ethylcarbodiimide hydrochloride, N,N-diisopropylethylamine, N,N-dimethylformamide, 1-hydroxybenzotriazole hydrate, room temperature, 4 to 20 hours;
step c) d) and h) alkyl halide, sodium hydride, tetrahydrofuran or N,N-dimethylformamide, room temperature, 4 to 20 hours;
step e) aldehyde or ketone, 1,2-dichloroethane, acetic acid, sodium triacetoxy borohydride, room temperature, 4 to 20 hours;
step f) aldehyde or ketone, methanol, acetic acid, sodium triacetoxy borohydride, room temperature, 4 to 20 hours;
step k) dihalogen derivative, N,N-dimethylformamide, cesium carbonate, 20-60° C., 10-30 hours.

In so far as, in the compound of general formula (I), $R^2$ is hydrogen, $R^3$ is —$OSi(CH_3)_2$-t-butyl group, the benzazepine-thione derivatives of general formula (III) can be prepared by the procedure of Scheme 8:

Scheme 8

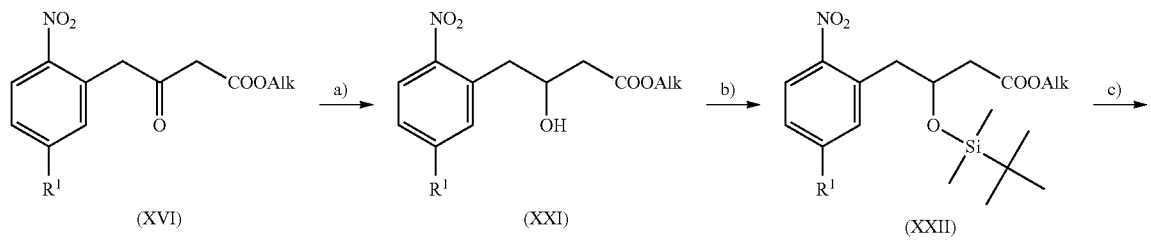

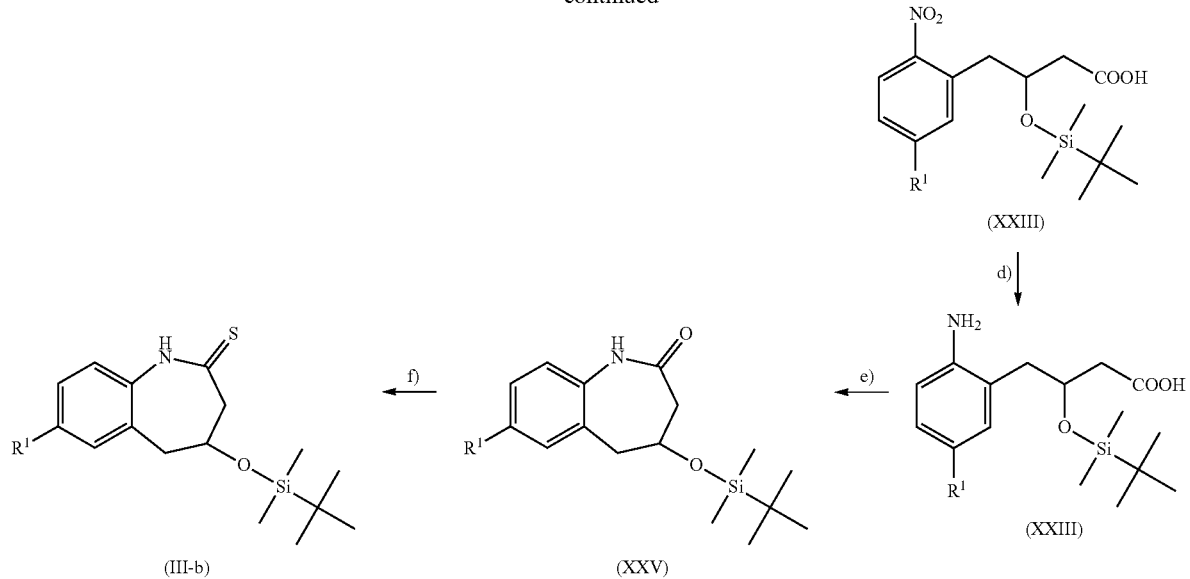

The keto group of the keto ester of general formula (XVI)—wherein $R^1$ is as defined above for general formula (I) and Alk is $C_{1-4}$alkyl group—is reduced (step a)) and then the hydroxy group of the compound of general formula (XX)—wherein $R^1$ is as defined above for general formula (I) and Alk is $C_{1-4}$alkyl group—is protected by a silyl protecting group (step b)) to obtain the compound of general formula (XXII)—wherein $R^1$ is as defined above for formula (I) and Alk is $C_{1-4}$alkyl group. The ester group of the latter is hydrolysed (step c)), then the nitro group of the thus obtained compound of general formula (XXII)—wherein $R^1$ is as defined above for general formula (I)—is reduced (step d)) to give the amine derivative of general formula (XXIV)—wherein $R^1$ is as defined above for general formula (I)—which is ring-closed by means of a reagent capable of forming an amide bond (step e)) to obtain the benzazepine of general formula (XV)—wherein is as defined above for general formula (I)—which is reacted with Lawesson reagent (step f)) to give the benzazepine-thione derivative of general formula (III-b)—wherein $R^1$ is as defined above for general formula (I).

Preferred embodiments are, for example, the following:

step a) sodium borohydride, methanol, room temperature, 4 to 20 hours;

step b) 1H-imidazole, tert-butyl-dimethylchlorosilane, N,N-dimethylformamide, room temperature, 4 to 20 hours;

step c) lithium hydroxide, methanol, water, tetrahydrofuran, room temperature, 4 to 20 hours;

step d) hydrogenation in the presence of a Pt/C catalyst, toluene, room temperature, 4 to 20 hours;

step e) N-(3-dimethylaminopropyl)-N-ethylcarbodiimide hydrochloride, N,N-diisopropylethylamine, N,N-dimethylformamide, 1-hydroxybenzotriazole hydrate, room temperature, 4 to 20 hours;

step f) Lawesson reagent, pyridine, 120° C., 4 to 20 hours.

The compounds of general formula (I-i) can be prepared by reacting compounds of general formula (III-b) and compounds of general formula (II) (Scheme 9):

Scheme 9

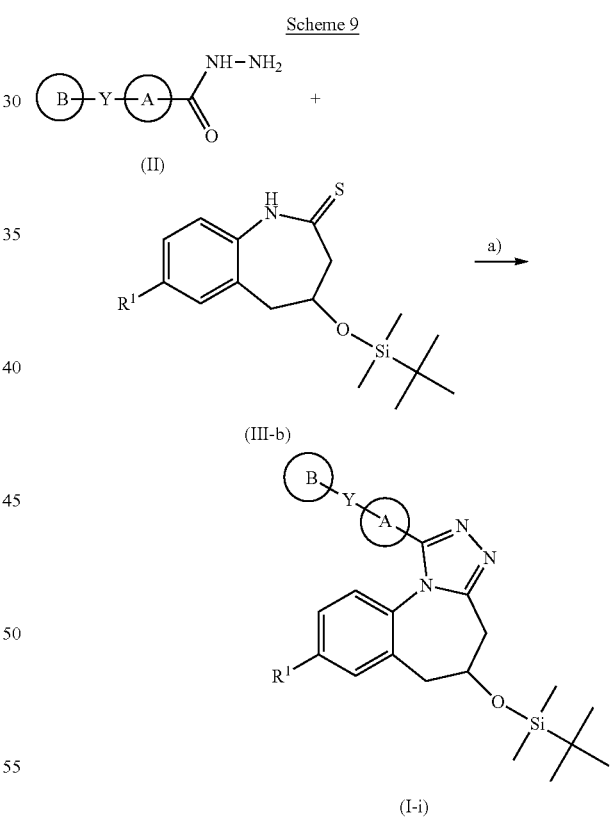

wherein ring B, Y, $R^1$ are as defined above for general formula (I), ring A is a cycloalkyl or a 4- to 7-membered saturated heterocycle containing 1 N, wherein ring A is attached via the ring nitrogen to Y.

A preferred embodiment is, for example, the following:
step a) xylene at 140° C. for 20 to 120 hours.

The silyl protecting group of the compounds of general formula (I-i) is removed (Scheme 10) to obtain the hydroxy derivatives of general formula (I-j), Scheme 10

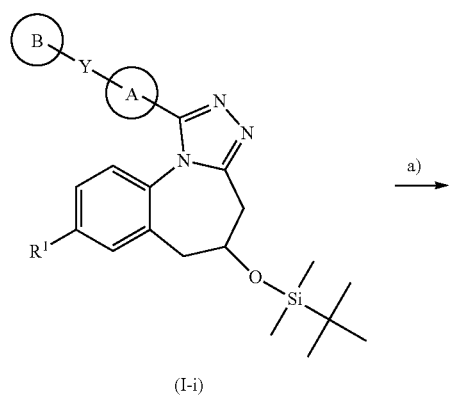

(I-i)

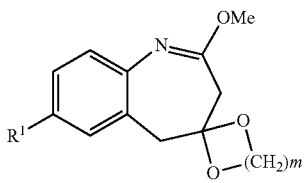

(XXVI)

wherein R and m are as defined above for general formula (I).

The procedure is illustrated in detail in Scheme 11:

Scheme 11

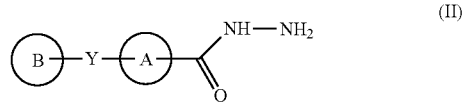

(II)

+

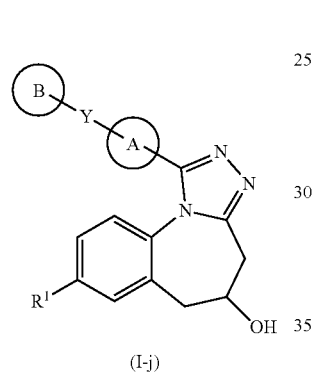

(I-j)

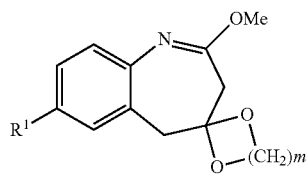

(XXVI)

wherein ring B, Y, $R^1$ are as defined above for general formula (I), ring A is a cycloalkyl or a 4- to 7-membered saturated heterocycle containing 1 N, wherein ring A is attached via the ring nitrogen to Y.

A preferred embodiment is, for example, the following:

step a) tetrabutylammonium fluoride, tetrahydrofuran, room temperature, 3 to 10 hours.

In so far as, in the compound of formula (I), $R^2$ and $R^3$ jointly represent —O—$(CH_2)_m$—O— group and ring A is a cycloalkyl or a 4- to 7-membered saturated heterocycle containing 1 N, wherein ring A is attached via the ring nitrogen to Y, the compounds of general formula (I) of the present invention are prepared by reacting compounds of formula (II)

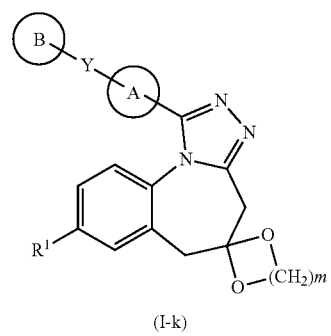

(I-k)

A preferred embodiment is, for example, the following:

step a) dichloromethane, trifluoroacetic acid, trimethyl-oxonium tetrafluoroborate, 40° C., 20 to 40 hours.

The methoxybenzazepine derivative of general formula (XXVI) can be prepared according to the procedure of Scheme 12:

(II)

wherein ring B and Y are as defined above for general formula (I) and ring A is a cycloalkyl or a 4- to 7-membered saturated heterocycle containing 1 N, wherein ring A is attached via the ring nitrogen to Y—with the in situ prepared compound of general formula (XXVI), Scheme 12

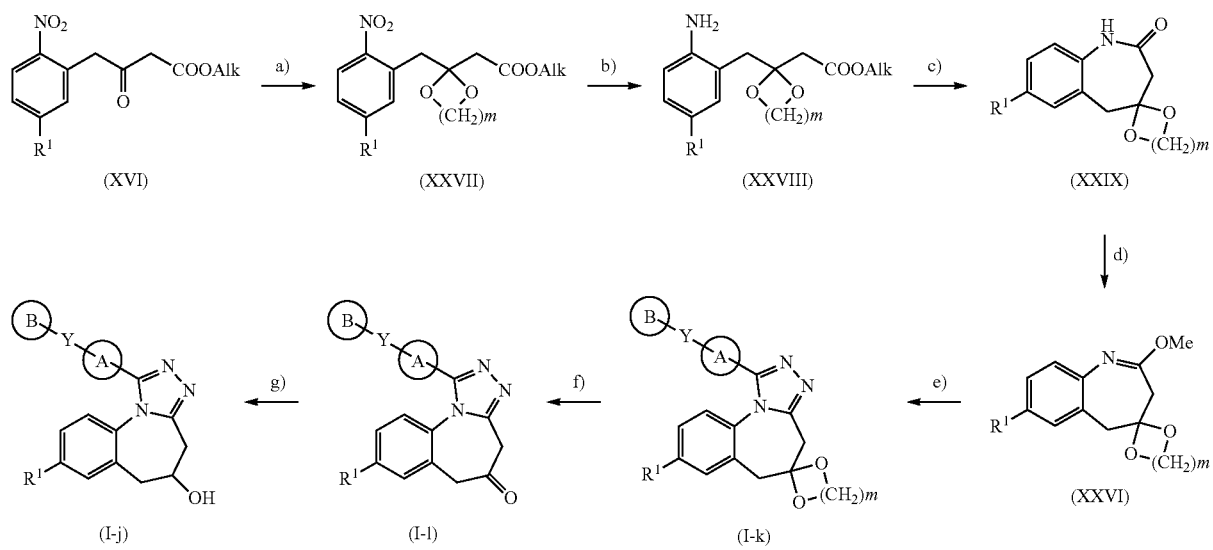

The keto group of the keto ester of general formula (XVI) is protected by a suitable α,ω-$C_{2-5}$diol (step a)) followed by reduction of the nitro group of the compound of general formula (XXVII)—wherein $R^1$ and m are as defined above for general formula (I) and Alk is $C_{1-4}$alkyl group—to give the compound of general formula (XXVIII) (step b))—wherein $R^1$ and m are as defined above for general formula (I) and Alk is $C_{1-4}$alkyl group—the latter is ring-closed in the presence of a suitable base (step c)) to obtain the benzazepine of general formula (XXIX)—wherein $R^1$ and m are as defined above for general formula (I) and Alk is $C_{1-4}$alkyl group—from which the methoxybenzazepine derivative of general formula (XXVI)—wherein $R^1$ and m are as defined above for general formula (I) and Alk is $C_{1-4}$alkyl group—is prepared by methylation (step d)), and the latter without isolation is reacted with an acid hydrazide of general formula (II) (step e))—wherein ring B and Y are as defined above for general formula (I), ring A is a cycloalkyl or a 4- to 7-membered saturated heterocycle containing 1 N, wherein ring A is attached via the ring nitrogen to Y—to obtain the compound of general formula (I-k)—wherein ring B, Y, $R^1$ and m are as defined above for general formula (I) and ring A is a cycloalkyl or a 4- to 7-membered saturated heterocycle containing 1 N, wherein ring A is attached via the ring nitrogen to Y—after removing the ketal protecting group (step f)) to give the oxo compound of general formula (I-l)—wherein ring B, Y, $R^1$ and m are as defined above for general formula (I) and ring A is a cycloalkyl or a 4- to 7-membered saturated heterocycle containing 1 N, wherein ring A is attached via the ring nitrogen to Y—then the latter is reduced (step g)) to obtain the hydroxy derivative of general formula (I-j)—wherein ring B, Y, $R^1$ and m are as defined above for general formula (I) and ring A is a cycloalkyl or a 4- to 7-membered saturated heterocycle containing 1 N, wherein ring A is attached via the ring nitrogen to Y.

Preferred embodiments are, for example, the following:
step a) trimethyl orthoformate, methanol, ethylene glycol, p-toluenesulfonic acid, 50° C., 50 to 100 hours;
step b) hydrogenation in the presence of a Pt/C catalyst, toluene, room temperature, 4 to 20 hours;
step c) tetrahydrofuran, potassium tert-butoxide, room temperature, 2 to 20 hours;
step d) dichloromethane, trifluoroacetic acid, trimethyl-oxonium tetrafluoroborate, room temperature, 20 to 25 hours;
step e) acid hydrazide of formula (II), dichloromethane, 50° C., 6 to 20 hours;
step f) methanol, cc. hydrochloric acid, 70° C., 2 to 6 hours;
step g) methanol, sodium borohydride, 0 to 25° C., 2 to 4 hours.

The compounds of formula (I-k) if desired can also be converted to another compound of the general formula (I) by known methods with the introduction of new substituents and/or with the modification, removal of the existing substituents.

The hydroxy derivatives of general formula (I-j) prepared from the compound of general formula (I-i) or the compound of general formula (I-l) if desired can also be converted to another compound of general formula (I) by known methods with the introduction of new substituents and/or with the modification, removal of the existing substituents and/or with salt-formation and/or with releasing the base from salts and/or with the preparation of the enantiomers from the racemic mixtures. This is illustrated in detail in Scheme 13:

Scheme 13

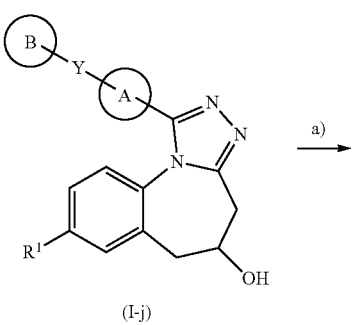

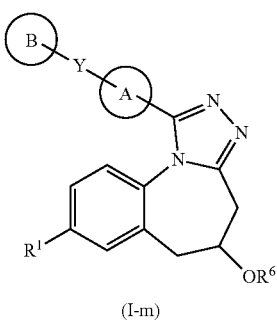

(I-m)

Preferred embodiments of step a) of Scheme 13 are, for example, the following:

i) alkyl halide, sodium hydride, tetrahydrofuran or N,N-dimethylformamide, room temperature, 4 to 20 hours, or ii) acyl chloride, dichloromethane, triethylamine or N,N-diisopropylethylamine, room temperature, 4 to 20 hours, or iii) acyl chloride, pyridine, room temperature, 4 to 20 hours.

Pure enantiomers can be obtained by chiral HPLC from compounds of general formula (I-j) from which acyl and/or alkyl derivatives can also be prepared.

In so far as, in the compound of general formula (I), $R^2$ is hydrogen, $R^3$ is —NHBoc or $R^2$ and $R^3$ jointly represent —O—$(CH_2)_m$—O— group and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1]benzazepine core, the compounds of general formula (I) of the present invention are prepared by reacting compounds of general formula (XXX)

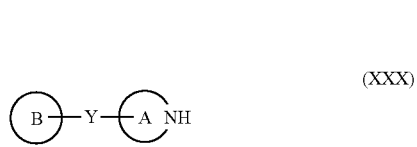

(XXX)

wherein ring B and Y are as defined above for general formula (I) and ring A is a 4- to 7-membered saturated heterocycle containing 1 or 2 N—and compounds of general formula

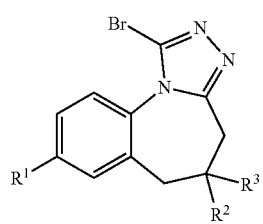

(XXXI)

wherein $R^1$ is as defined above for general formula (I), $R^2$ is hydrogen, $R^3$ is —NHBoc or $R^2$ and $R^3$ jointly represent —O—$(CH_2)_m$—O— group and m is as defined above for general formula (I).

The procedure is illustrated in detail in Scheme 14:

Scheme 14

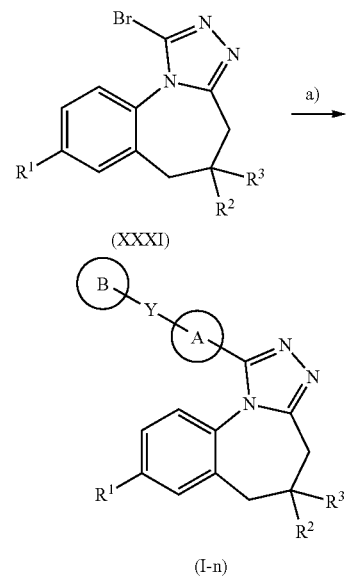

(I-n)

Preferred embodiment of step a) of Scheme 14 is for example, the following:

i) melt (without solvent) at 120-150° C. for 3 to 72 hours.

The amine derivatives of general formula (XXX) are either commercially available or can be prepared according to the methods described in the Examples.

In so far as $R^2$ is hydrogen, $R^3$ is —NHBoc, the triazolo-benzazepine derivatives of general formula (XXXI) can be prepared according to the procedure of Scheme 15:

Scheme 15

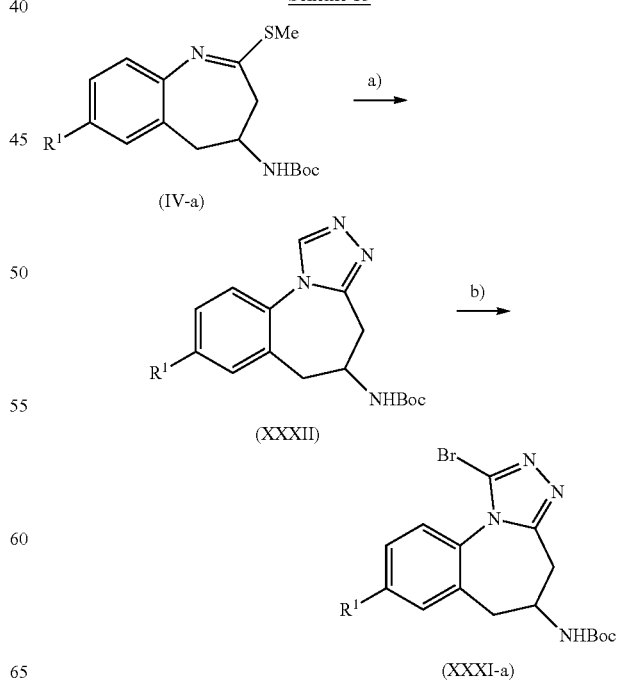

(XXXI-a)

The compounds of general formula (IV-a) are reacted with formylhydrazine (step a)) and the resulting compound of general formula (XXXII)—wherein $R^1$ is as defined for general formula (I)—is brominated (step b)), thus the bromo derivative of general formula (XXXI-a) is obtained—wherein $R^1$ is as defined above for general formula (I).

Preferred embodiments are, for example, the following:
step a) formylhydrazine, 1,4-dioxane, 90° C., 3 to 10 hours;
step b) N-bromosuccinimide, tetrahydrofuran, 70° C., 10 to 60 minutes.

As shown in Scheme 16, the compounds of general formula (XXXI-a) are reacted with the compound of general formula (XXX) (step a))—wherein ring B and Y are as defined above for general formula (I) and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1]benzazepine core—, removing the protecting group from the resulting compound of general formula (I-o) (step b)), then the thus obtained amine derivatives of general formula (I-p)—wherein ring B, Y and $R^1$ are as defined above for general formula (I) and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1]benzazepine core—can be sulfonylated, acylated or alkylated (step c)) to obtain the compounds of general formula (I-q)—wherein ring B, Y and $R^1$ are as defined above for general formula (I) and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1]benzazepine core and $R^1$ is optionally substituted $C_{1-4}$alkyl. C(O)R or $S(O_2)R^1$ as defined under the meaning of $R^4$ or $R^5$ in general formula (I).

Scheme 16

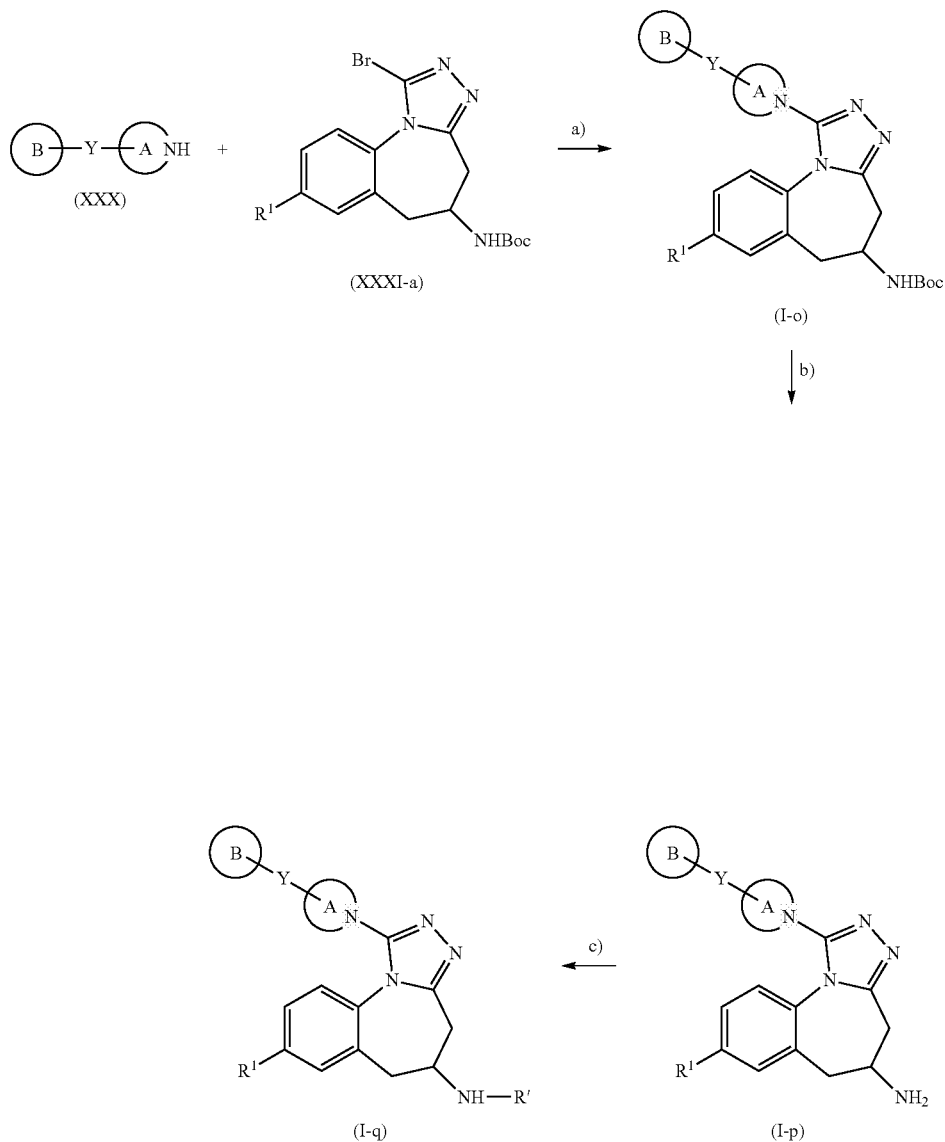

Preferred embodiments are, for example, the following:

step a) melt (without solvent), 120-150° C., 3 to 72 hours;

step b) hydrogen chloride in ethyl acetate, room temperature, 4 to 20 hours;

step c) i) sulfonyl chloride, pyridine, room temperature, 4 to 20 hours, or ii) sulfonyl chloride, dichloromethane, triethylamine or N,N-diisopropylethylamine, room temperature, 4 to 20 hours, or iii) acyl chloride, pyridine, room temperature, 4 to 20 hours, or iv) acyl chloride, dichloromethane, triethylamine or N,N-diisopropylethylamine, room temperature, 4 to 20 hours, or v) acid anhydride, pyridine, room temperature, 4 to 20 hours, or vi) acid, N,N,N',N'-tetramethyl-O-(1H-benzotriazol-1-yl)uronium hexafluorophosphate, N,N-dimethylformamide, N,N-diisopropylethylamine, room temperature, 4 to 20 hours, or vii) acid, N-(3-dimethylaminopropyl)-N'-ethylcarbodiimide hydrochloride, N,N-diisopropylethylamine, N,N-dimethylformamide, 1-hydroxybenzotriazole hydrate, room temperature, 4 to 20 hours, or viii) alkyl halide, sodium hydride, tetrahydrofuran or N,N-dimethylformamide, room temperature, 4 to 20 hours, or ix) aldehyde or ketone, 1,2-dichloroethane, acetic acid, sodium triacetoxy borohydride, room temperature, 4 to 20 hours.

When $R^2$ and $R^3$ jointly represent —O—$(CH_2)_m$—O— group, the triazolo-benzazepine derivatives of general formula (XXXI) can be prepared according to the procedure of Scheme 17:

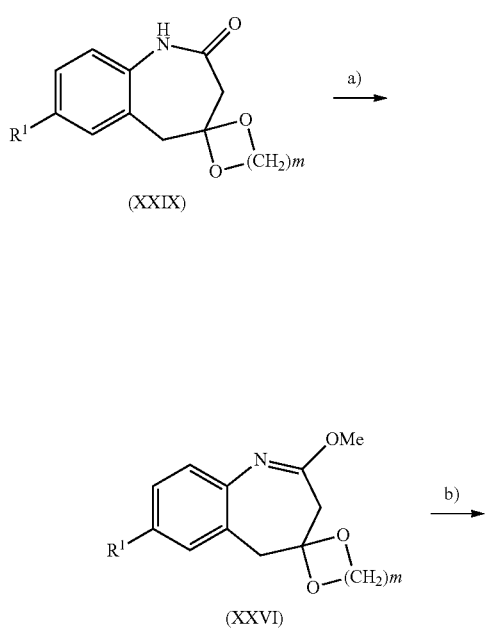

Scheme 17

(XXIX)

(XXVI)

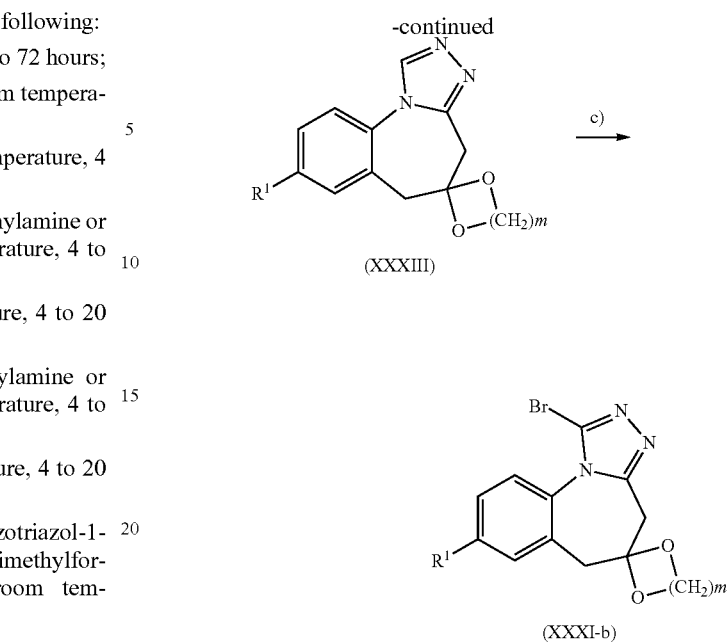

(XXXIII)

(XXXI-b)

The methoxybenzazepine derivative of general formula (XXVI) obtained in situ from compound of general formula (XXIX) is reacted with formylhydrazine (steps a) and b)) and the resulting compounds of general formula (XXXIII)—wherein $R^1$ and m are as defined above for general formula (I)—are brominated (step c)), thus the bromo compounds of general formula (XXXI-b) are obtained—wherein $R^1$ and m are as defined above for general formula (I).

Preferred embodiments are, for example, the following:

step a) dichloromethane, trifluoroacetic acid, trimethyloxonium tetrafluoroborate, room temperature, 20 to 25 hours;

step b) formyl hydrazine, dichloromethane, 40° C., optionally change of solvent to dioxane, 90° C., 15 to 40 hours;

step c) N-bromosuccinimide, tetrahydrofuran, 70° C., 10 to 60 minutes.

According to Scheme 18, the compounds of general formula (XXXI-b) are reacted with the compounds of general formula (XXX) (step a))—wherein ring B and Y are as defined above for general formula (I) and ring A is a 4- to 7-membered saturated heterocycle containing 1 or 2 N—, the protecting group from the resulting compounds of general formula (I-r) is removed (step b)), and the resulting keto derivatives of general formula (I-s) are reduced (step c))—wherein ring B, Y, m and $R^1$ are as defined above for general formula (I) and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1]benzazepine core—to obtain the hydroxy derivatives of general formula (I-t) which may be acylated or alkylated (step d)), thus the compounds of general formula (I-u) are obtained—wherein ring B, Y, $R^1$ and $R^6$ are as defined above for general formula (I) and ring A is a 4- to 7-membered saturated heterocycle containing 1 or 2 N, wherein ring A is attached via a ring nitrogen to the triazole ring of the 5,6-dihydro-4H-[1,2,4]triazolo[4,3-a][1] benzazepine core.

Scheme 18

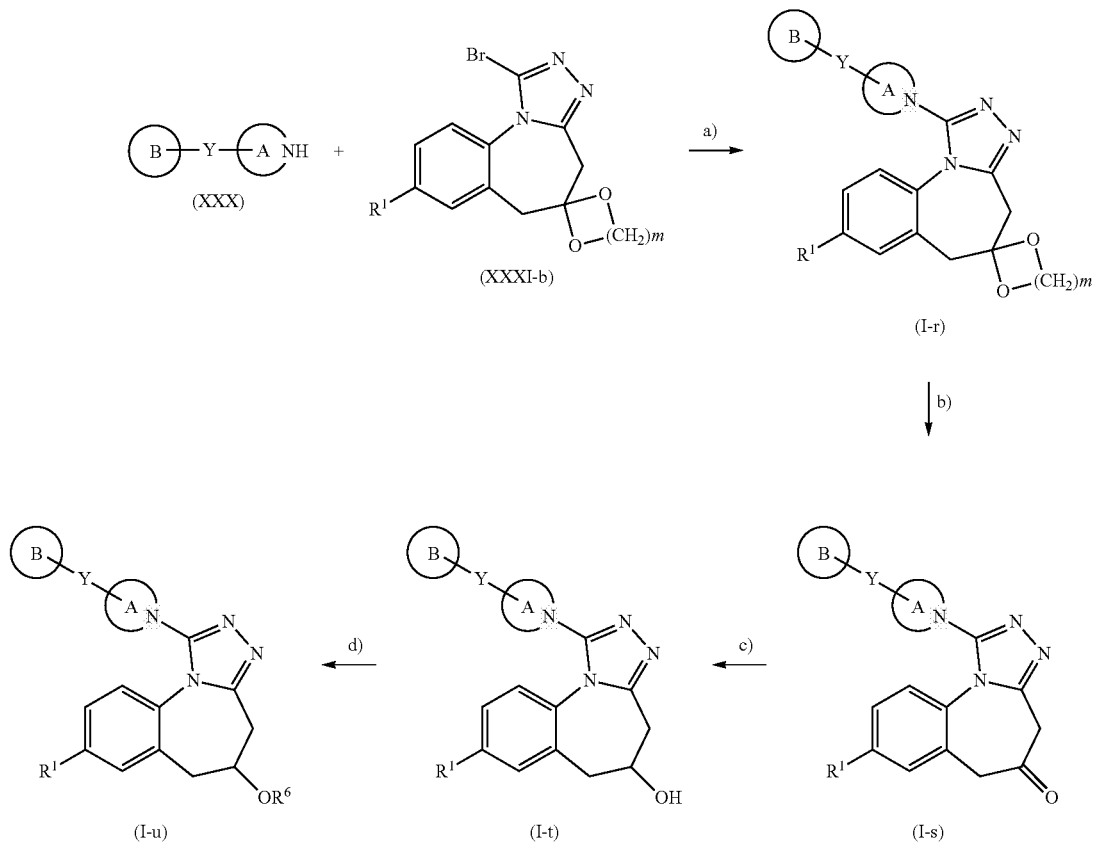

Preferred embodiments are, for example, the following:

step a) melt (without solvent), 130 to 140° C., 3 to 72 hours;

step b) methanol, cc. hydrochloric acid, 70° C., 2 to 6 hours;

step c) methanol, sodium borohydride, 0 to 25° C., 2 to 4 hours;

step d) i) acyl chloride, pyridine, room temperature, 4 to 20 hours, or
  ii) acyl chloride, dichloromethane, triethylamine or N,N-diisopropylethylamine, room temperature, 4 to 20 hours, or
  iii) alkyl halide, sodium hydride, tetrahydrofuran or N,N-dimethylformamide, room temperature, 4 to 20 hours.

The hydroxy derivatives of general formula (I-t) if desired can also be converted to another compound of general formula (I) by known methods with the introduction of new substituents and/or with the modification, removal of the existing substituents and/or with salt-formation and/or with releasing the base from salts and/or with the preparation of the enantiomers from the racemic mixtures.

In so far as, in the compound of general formula (I), $R^2$ is hydrogen, $R^3$ is $NR^4R^5$ and $R^4$ and $R^5$ taken together with the N to which they are attached form a heterocycle, the compounds of general formula (I) of the present invention are prepared according to the procedure of Scheme 19 in a way that:

Scheme 19

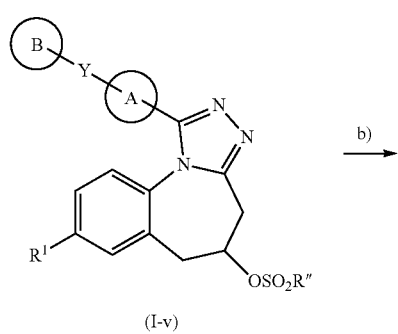

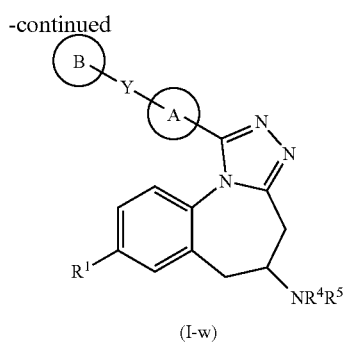

(I-w)

the compounds of general formulae (I-j) or (I-t) are sulfonylated (step a)) and the resulting compounds of general formula (I-v) are reacted—wherein ring B, Y, ring A and $R^1$ are as defined above for general formula (I) and R" is methyl, trifluoromethyl or 4-methylphenyl group—with an amine of formula $NHR^4R^5$ (step b))—wherein $R^4$ and $R^5$ taken together with the N to which they are attached form a heterocycle—to obtain the compounds of general formula (I-w). Amines of formula $NHR^4R^5$ are commercially available or can be synthesized by known methods.

Preferred embodiments are, for example, the following:
step a) i) sulfonyl chloride, pyridine, room temperature, 4 to 20 hours, or
ii) sulfonyl chloride, dichloromethane, triethylamine or N,N-diisopropylethylamine, room temperature, 4 to 20 hours;
step b) $NHR^4R^5$, N,N-dimethylformamide, 60 to 120° C., 4 to 24 hours.

In so far as, in the compounds of general formula (I), $R^2$ is $C_{1-4}$alkyl, $R^3$ is $OR^6$ group, the compounds of general formula (I) of the present invention are prepared according to Schemes 20 and 21 in a way that:

(step b)), and the obtained oxo derivative of general formula (XXXV) which is reacted with a suitable alkyl lithium or Grignard reagent (step c)) to obtain the compound of formula general (XXXVI)—wherein $R^1$ is as defined above for general formula (I) and $PG^1$ is a protecting group, preferably 4-methoxybenzyl protecting group and $R^2$ is $C_{1-4}$alkyl group. By protecting the hydroxy group of compounds of general formula (XXXVI) (step d)), protected hydroxy derivatives of general formula (XXXVII)—wherein $R^1$ is as defined above for general formula (I), PG is a protecting group, preferably 4-methoxybenzyl protecting group, $R^2$ is $C_{1-4}$alkyl group and $PG^2$ is a protecting group (Peter G. M. Wuts: Greene's Protective Groups in Organic Synthesis: Fifth Edition, Chapter 2 Protection for the Hydroxyl Group, Including 1,2- and 1,3-Diols, pages 17-471), preferably silyl protecting group—are obtained. After deprotection (step e)) of the compounds of general formula (XXXVII), then from the thus obtained compounds of general formula (XXXVIII) the benzazepine-thione derivatives of general formula (XXXX) are prepared with Lawesson reagent (step f)), followed by methylation (step g)) to obtain the compounds of general formula (XL).

Preferred embodiments are, for example, the following:
step a) 4-methoxybenzylchloride, sodium hydride, N,N-dimethylformamide, 0 to 25° C., 3 to 6 hours;
step b) acetic acid, reflux, 6 to 20 hours;
step c) i) alkyl lithium, tetrahydrofuran, (−78)° C., 1 to 4 hours, or
ii) $R^2$MgCl×LiCl, tetrahydrofuran, (−20° C.) to (−15° C.), 1 to 6 hours, or
iii) $R^2$MgCl, tetrahydrofuran, $CeCl_3$, (−78) to 0° C., 12 to 70 hours;
step d) 1H-imidazole, silyl chloride, N,N-dimethylformamide, room temperature, 4 to 20 hours;
step e) i) ammonium cerium nitrate, water, acetonitrile, to 25° C., 6 to 18 hours, or Scheme 20

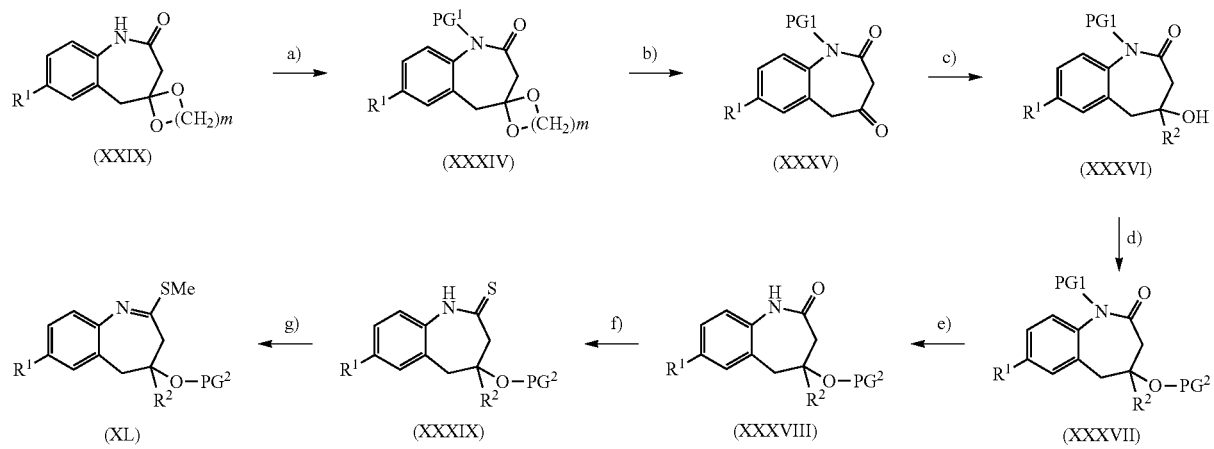

the compounds of general formula (XXXIV) is protected (step a)) to obtain the compounds of general formula (XXXIV)—wherein $R^1$ and m are as defined above for general formula (I) and $PG^1$ is a protecting group (Peter G. M. Wuts: Greene's Protective Groups in Organic Synthesis: Fifth Edition, Chapter 7. Protection for the Amino Group, pages 895-1193), preferably 4-methoxybenzyl protecting group—and then the ketal is removed with a suitable acid ii) trifluoroacetic acid, dichloromethane, room temperature, 12 to 24 hours, or
iii) trifluoromethanesulfonic acid, dichloromethane, room temperature, 2 to 12 hours;
step f) Lawesson reagent, pyridine, reflux, 4 to 5 hours;
step g) iodomethane, potassium carbonate, acetone, room temperature, 4 to 24 hours.

The compounds of general formulae (XXXIX) or (XL) are reacted with the compounds of general formula (II) (step a) of Scheme 21), to give the compounds of general formula (I-x)—wherein ring B, Y, ring A and R¹ are as defined above for general formula (I), PG² is a protecting group (Peter G. M. Wuts: Greene's Protective Groups in Organic Synthesis: Fifth Edition, Chapter 2 Protection for the Hydroxyl Group, Including 1,2- and 1,3-Diols, pages 17-471), preferably silyl protecting group, and R² is $C_{1-4}$alkyl group. The protecting group is removed (step b)) from the resulting compounds of general formula (I-x) to obtain the compounds of general formula (I-y).

iii) reaction of (II) and (XXXIX) in 1,4-dioxane at 110° C. for 4 to 20 hours, or iv) reaction of (II) and (XL) in xylene in the presence of catalytic hydrogen chloride at 140° C. for 4 to 20 hours, or v) reaction of (II) and (XL) in 1,4-dioxane in the presence of catalytic hydrogen chloride at 110° C. for 4 to 20 hours;

step b) tetrabutylammonium fluoride, tetrahydrofuran, room temperature, 3 to 10 hours;

Scheme 21

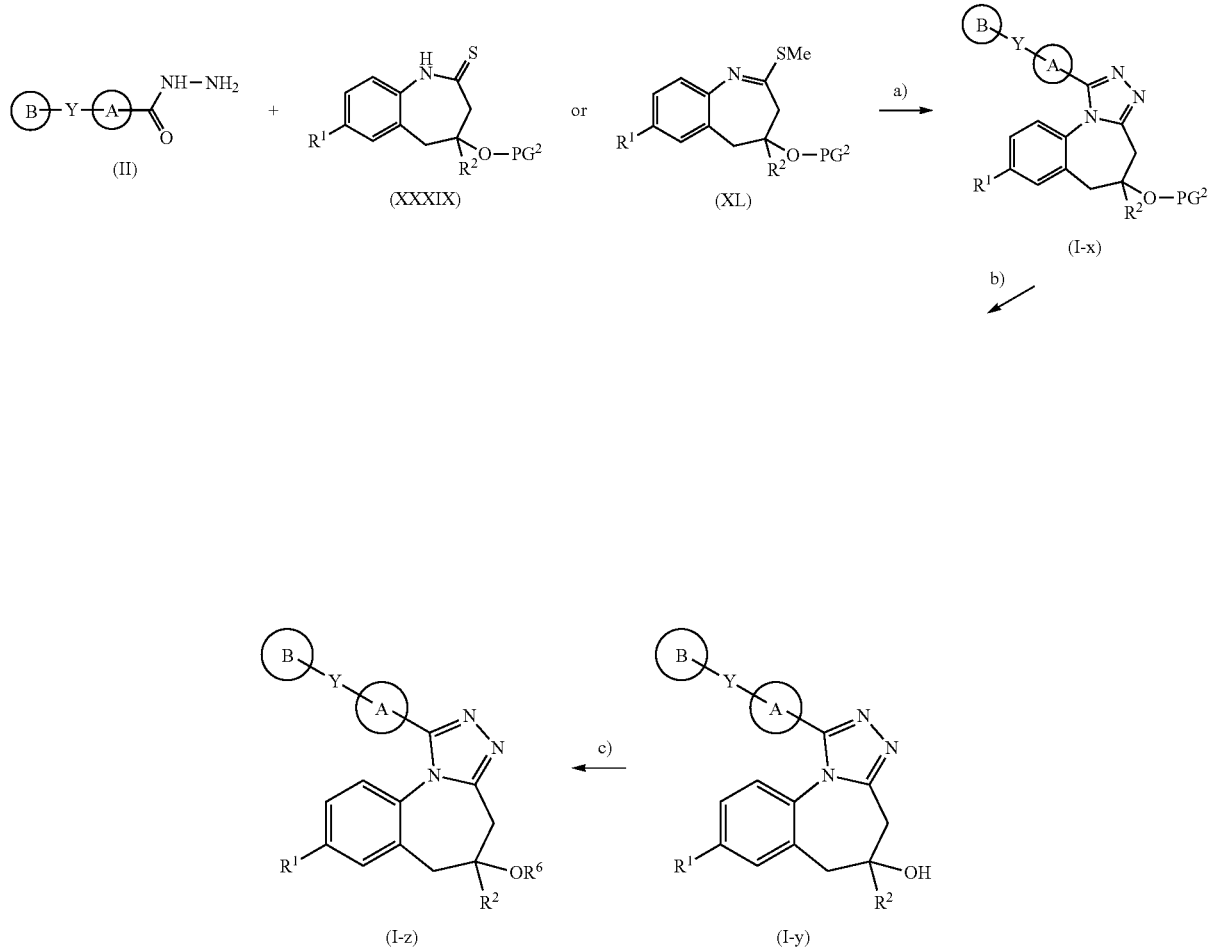

The hydroxy derivatives of general formula (I-y) if desired can also be converted to another compound of the general formula (I) by known methods with the introduction of new substituents and/or with the modification, removal of the existing substituents and/or with salt-formation and/or with releasing the base from salts and/or with the preparation of the enantiomers from the racemic mixtures, for example using the methods described in step c).

Preferred embodiments are, for example, the following:

step a) i) reaction of (II) and (XXXIX) in xylene at 140° C. for 20 to 150 hours, or ii) reaction of (II) and (XXXIX) in n-butanol at 110° C. for 20 to 50 hours, or step c) i) alkyl halide, sodium hydride, tetrahydrofuran or N,N-dimethylformamide, room temperature, 4 to 20 hours, or ii) acyl chloride, dichloromethane, triethylamine or N,N-diisopropylethylamine, room temperature, 4 to 20 hours, or iii) acyl chloride, pyridine, room temperature, 4 to 20 hours.

In so far as, in the compound of general formula (I), R² is hydrogen, R³ is —OCH₃ group, the benzazepine-thione derivatives of general formula (III) can be prepared by the procedure of Scheme 22:

Scheme 22

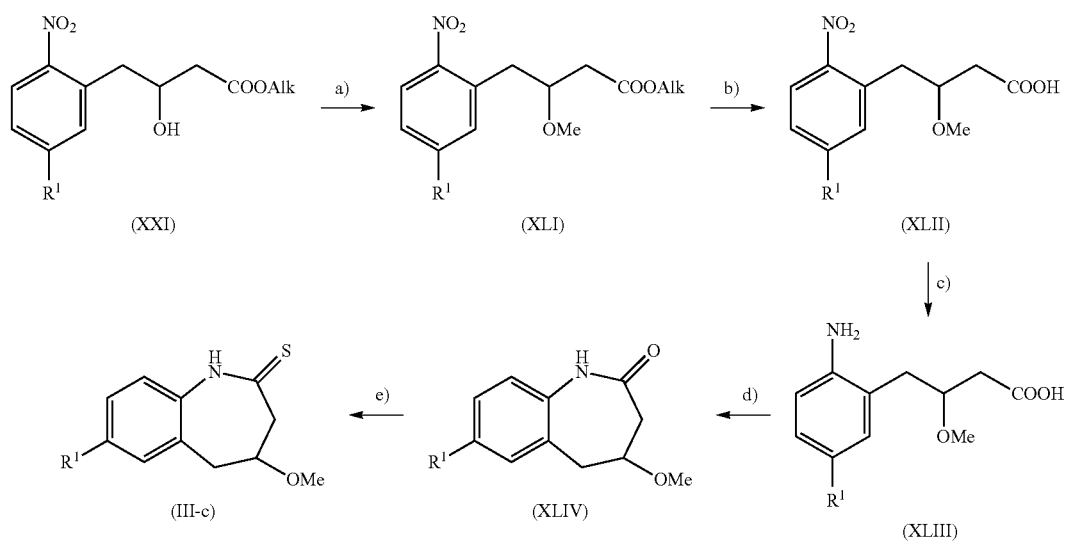

The hydroxy group of the compound of general formula (XXI)—wherein $R^1$ is as defined above for general formula (I) and Alk is $C_{1-4}$alkyl group—is methylated (step a)) to obtain the compound of general formula (XLI)—wherein $R^1$ is as defined above for general formula (I) and Alk is $C_{1-4}$alkyl group. The ester group of the latter is hydrolysed (step b)), then the nitro group of the thus obtained compound of general formula (XLII)—wherein $R^1$ is as defined above for general formula (I)—is reduced (step c)) to give the amine derivative of general formula (XLIII)—wherein $R^1$ is as defined above for general formula (I)—which is ring-closed by means of a reagent capable of forming an amide bond (step d)) to obtain the benzazepine of general formula (XLIV)—wherein $R^1$ is as defined above for general formula (I)—which is reacted with Lawesson reagent (step e)) to obtain the benzazepine-thione derivative of general formula (III-c)—wherein $R^1$ is as defined above for general formula (I).

Preferred embodiments are, for example, the following:

step a) dichloromethane, 1,8-bis(dimethylamino)naphthalene, trimethyloxonium tetrafluoroborate, room temperature, 20 to 25 hours;

step b) sodium hydroxide, methanol, water, room temperature, 4 to 20 hours;

step c) hydrogenation in the presence of a Pt/C catalyst, toluene, room temperature, 4 to 20 hours;

step d) N-(3-dimethylaminopropyl)-N'-ethylcarbodiimide hydrochloride, N,N-diisopropylethylamine, N,N-dimethylformamide, 1-hydroxybenzotriazole hydrate, room temperature, 4 to 20 hours;

step e) Lawesson reagent, tetrahydrofuran, room temperature, 2 to 20 hours;

The compounds of general formula (I-aa) can be prepared by reacting compounds of general formula (III-c) and compounds of general formula (II) (Scheme 23):

Scheme 23

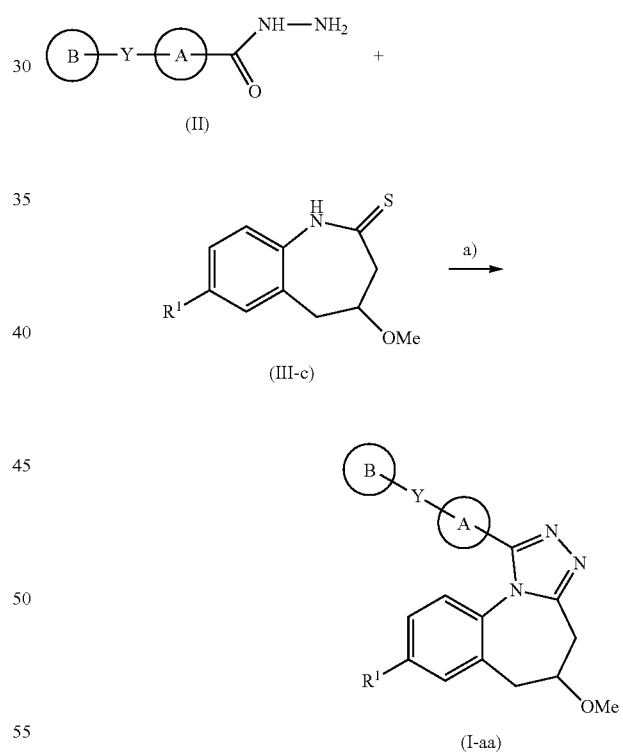

wherein ring B, Y, $R^1$ are as defined above for general formula (I), ring A is a cycloalkyl or a 4- to 7-membered saturated heterocycle containing 1 N, wherein ring A is attached via the ring nitrogen to Y.

A preferred embodiment is, for example, the following:

step a) butanol at 140° C. for 20 to 120 hours.

The compound of general formula (I-aa) can also be synthesized from compound of general formula (XLIV) according to the method depicted on Scheme 24.

Scheme 24

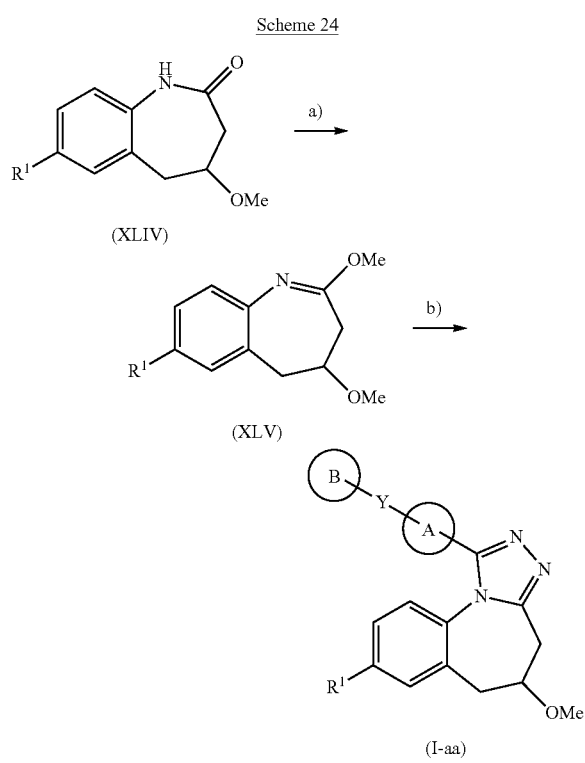

The compound of general formula (XLIV) is methylated with trimethyloxonium tetrafluoroborate (step a)) and the so obtained compound of general formula (XLV) is reacted in situ with compound of general formula (II)—wherein ring B, Y, $R^1$ are as defined above for general formula (I), ring A is a cycloalkyl or a 4- to 7-membered saturated heterocycle containing 1 N, wherein ring A is attached via the ring nitrogen to Y—(step b)) to obtain compounds of general formula (I-aa).

A preferred embodiment is, for example, the following:
step a) dichloromethane, trifluoroacetic acid, trimethyloxonium tetrafluoroborate, room temperature, 20 to 40 hours;
step b) i) compound of formula (II), dichloromethane, 40° C., 2 to 20 hours
ii) compound of formula (II), acetonitrile, reflux temperature, 1 to 10 hours.

The "reagent capable of forming an amide bond" used for the preparation of compounds of general formulae (XIII), (XXV) and (XLIV) may be, for example, hydroxybenzotriazole (HOBt) and N-(3-dimethylaminopropyl)-N'-ethylcarbodiimide hydrochloride (EDC) or O-(benzotriazol-1-yl)-N,N,N',N'-tetramethyluronium hexafluorophosphate (HBTU). The reaction is preferably carried out in the presence of a base—such as triethylamine or N,N-diisopropylethylamine (DIPEA)—in a suitable solvent—such as N,N-dimethylformamide, acetonitrile, hydrocarbons or chlorinated hydrocarbons or mixtures thereof—at between room temperature and 0° C. The reaction is followed by thin layer chromatography. The required reaction time is 4 to 20 hours.

The reagents and detailed process steps required for the above reactions are set forth in the Examples.

An aspect of the present invention is novel intermediates represented by the general formulae (III-a), (III-b), (III-c), (IV-a), (XIII), (XXV), (XXIX) and (XLIV) synthesised in the process for preparing the compound of general formula (I) wherein $R^1$ is as defined above for general formula (I), especially tert-butyl (7-chloro-2-oxo-2,3,4,5-tetrahydro-1H-1-benzazepin-4-yl)carbamate (Intermediate 3), tert-butyl (7-chloro-2-thioxo-2,3,4,5-tetrahydro-1H-1-benzazepin-4-yl)carbamate (Intermediate 4), tert-butyl [7-chloro-2-(methylsulfanyl)-4,5-dihydro-3H-1-benzazepin-4-yl]carbamate (Intermediate 5), tert-butyl-(7-bromo-2-oxo-2,3,4,5-tetrahydro-1H-1-benzazepin-4-yl)carbamate (Intermediate 32), tert-butyl-(7-bromo-2-thioxo-2,3,4,5-tetrahydro-1H-1-benzazepin-4-yl)carbamate (Intermediate 33), 7-bromo-1,5-dihydrospiro[1-benzazepine-4,2'-[1,3]dioxolane]-2(3H)-one (Intermediate 36), 7-chloro-1,5-dihydrospiro[1-benzazepine-4,2'-[1,3]dioxolane]-2(3H)-one (Intermediate 53), 4-{[tert-butyl(dimethyl)silyl]oxy}-7-chloro-1,3,4,5-tetrahydro-2H-1-benzazepin-2-one (Intermediate 62), 4-{[tert-butyl(dimethyl)silyl]oxy}-7-chloro-1,3,4,5-tetrahydro-2H-1-benzazepin-2-thione (Intermediate 63), 7-chloro-4-methoxy-1,3,4,5-tetrahydro-2H-1-benzazepin-2-one (step d) of Intermediate 103) or 7-chloro-4-methoxy-1,3,4,5-tetrahydro-2H-1-benzazepine-2-thione (Intermediate 103).

The activity data of each of the compounds of general formula (I) of the present invention are determined in vitro and in vivo by the methods described below.

Human Vasopressin V1a Receptor Binding Assay
Cells and Radioligand

The immortalized 1321N1 cell line (Perkin Elmer, ES-361-M400-UA) constitutively and stably expressing human vasopressin V1a receptor and vasopressin (8-L-Arginine), [Phenylalanyl-3,4,5-$^3$H(N)] labelled compound (Perkin Elmer Life and Analytical Sciences) as radioligand were used to determine the affinity of the prepared compounds.

Method

Membrane-preparation: Membrane preparation of immortalized 1321N1 cells expressing the propagated human Vasopressin V1a receptor was made according to Jarvis's method (Jarvis et al., *J Pharmacol Exp Ther* 2004, 310:407-16). Cells were suspended in preparative buffer (50 mM Tris, 1 mM EDTA, 0.1 mM PMSF) and homogenized with glass homogenizing potter. To separate the raw membrane fraction two consecutive centrifugation procedures (40,000 g for 20 minutes at 4° C.) were executed, then the membrane was taken into the preparatory buffer during a final washing step, it was divided into aliquots which were stored at −80° C. until the time of measurement.

The protein content of the prepared membrane was determined according to Lowry's method using standard dilution line of bovine serum albumin (BSA) (Lowry et al., *J Biol Chem* 1951, 193:265-75).

Receptor binding test: In the receptor binding assay, the substances with unknown affinity were used at a minimum of 8 different concentrations, with 3 parallels at each concentration. To determine the final affinity value, the results of at least two independent experiments were taken into account. The assay mixture included the incubation buffer (50 mM Tris-HCl, pH 7.4+3% BSA), membrane preparation of 1321N1 cells expressing the human Vasopressin V1a receptor (167 µg/ml) and Vasopressin (8-L-Arginine), [Phenylalanyl-3,4,5-$^3$H(N)] as radioligand (1 nM).

Non-specific binding values were determined in the presence of unlabeled 1.2×10$^{-6}$ M (Arg$^8$)-vasopressin. Samples were incubated in a total volume of 0.33 ml for 60 minutes at 27° C. Membrane-bound and free ligands were separated by filtration through a 0.5% polyethyleneimine-impregnated UniFilter® GF/B™. After drying the filter plates, 40 µl Microscint-20 (Packard) scintillation cocktail was added to the samples. Finally, radioactivity was measured using MicroBeta² Microplate Counter (Perkin Elmer).

The $IC_{50}$ data (i.e. the concentration of the unknown substance which displaces 50% of specific bound radioligand) is calculated from the concentration-displacement curve using the sigmoid fitting mathematical method $y=(A1-A2)/(1+(x/x_0)p)+A2$ with Origin 7.5. software (OriginLab Corporation, Northampton, USA). During fitting, the asymptotes are not fixed. The K values (inhibition constant) are given with Cheng-Prusoff equation $K_i=IC_{50}/[1+(L/K_D)]$ wherein [L] is the radioligand concentration used in the experiment and $[K_D]$ is the affinity of the radioactively labelled ligand for the given receptor. The $K_D$ is determined beforehand using the Scatchard curve.

Functional Assay to Test Compounds on Human Vasopressin V1a Receptor Expressing Cell Line Cells The immortalized 1321N1 cell line (Perkin Elmer, ES-361-M400-UA) constitutively and stably expressing human vasopressin V1a receptor were used to measure the prepared compounds. The ordinary secondary messenger pathway of the measured GPCR receptor was used, the endogenous $G_q$-associated system.

Method

Using 30,000 cells/plate, compounds were measured on 96-well plates. The buffer composition of the measurements was the following (expressed in mM): 140 NaCl, 5 KCl, 2 $CaCl_2$), 2 $MgCl_2$, 10 glucose, 10 HEPES (4-(2-hydroxyethyl)-1-piperazine-ethanesulfonic acid), 2 probenecid, pH=7.4. FLIPR Calcium 5 kit (Molecular Devices) was used as fluorescent dye, the medium was not removed prior to filling with the dye and the cells were not washed out either before or after. The incubation was performed at room temperature, the final concentration of DMSO was 1%. The materials to be measured were administered in 15 to 20 minutes pretreatment, at least two parallels of each compound in each concentration was measured.

Fluorescence signal was used to determine the intracellular $Ca^{2+}$ level, the reader was FlexStation II96. Cytoplasmic $Ca^{2+}$ concentrations were measured by fluorometry using the FlexStation II96 plate reader (excitation: 485 nm, emission: 525 nm). The fluorescence signal was logged in every 1.4 seconds for 1 minute. The reference compounds used were the following: (Arg⁸)-vasopressin as agonist at concentration of $EC_{80}$, determined for each plate, and relcovaptan as antagonist at 1 µM. The % of inhibition at each concentration and the $IC_{50}$ value of the compounds were determined where a concentration line was also measured.

The total AVP concentration-response curve was recorded on each plate. The effect of compounds measured was expressed by percentage of relative inhibition compared to control response. For the graphic representation of the data, nonlinear four parameter alignments were applied using SoftMaxPro software according to the following formula: $y=A-D/(1+(x/C)^B)+D$, wherein: A=0 and D=100–lower/upper fixed asymptotes, y=percentage of inhibition, x=logarithm of concentrations of the tested compound, B=steepness of curve and C–$IC_{50}$ (the concentration belonging to the 50% inhibition of the control response). The average $IC_{50}$ values were calculated from at least three independent measurements in all cases.

TABLE 1

The effectiveness of the compounds of the present invention measured in human vasopressin V1a receptor binding assay and functional assay

| Example No. | $K_i$ (nM) on hV1a cell line | $IC_{50}$ (nM) on hV1a cell line |
|---|---|---|
| 1 | 6 | 95 |
| 2 | 7 | 170 |
| 3 | 2.1 | 16 |
| 4 | 70 | 825 |
| 5 | 3.8 | 17 |
| 6 | 2 | 9 |
| 7 | 2.1 | 20 |
| 8 | 1.3 | 6.8 |
| 9 | 0.8 | 3 |
| 10 | 1.8 | 12 |
| 11 | 32 | 480 |
| 12 | 0.8 | 9 |
| 13 | 5 | 45 |
| 14 | 1.1 | 10 |
| 15 | 0.4 | 3.7 |
| 16 | 3 | 10 |
| 17 | 2.1 | 35 |
| 18 | 0.5 | 1.6 |
| 19 | 0.4 | 1.8 |
| 20 | 0.7 | 1 |
| 21 | 0.7 | 4 |
| 22 | 0.5 | 2.8 |
| 23 | 1 | 6.4 |
| 24 | 1 | 7 |
| 25 | 2.3 | 23 |
| 26 | 0.7 | 4.5 |
| 27 | 1.1 | 7 |
| 28 | 0.7 | 5.4 |
| 29 | 0.6 | 5.4 |
| 30 | 1.4 | 15 |
| 31 | 17 | 260 |
| 32 | 6 | 85 |
| 33 | 111 | 480 |
| 34 | 52 | 700 |
| 35 | 9.7 | 160 |
| 36 | 36 | 610 |
| 37 | 7 | 100 |
| 38 | 2 | 30 |
| 39 | 1.4 | 8.3 |
| 40 | 0.9 | 8.4 |
| 41 | 600 | N.D. |
| 42 | 42% at 1 µM | N.D. |
| 43 | 88 | 210 |
| 44 | 26 | 480 |
| 45 | 38 | 870 |
| 46 | 23 | 410 |
| 47 | 0.8 | 2.3 |
| 48 | 18 | 340 |
| 49 | 7.5 | 140 |
| 50 | 2.7 | 20 |
| 51 | 7.6 | 55 |
| 52 | 11 | 60 |
| 53 | 0.3 | 0.9 |
| 54 | 0.6 | 1.2 |
| 55 | 0.3 | 1.1 |
| 56 | 0.3 | 1.2 |
| 57 | 0.3 | 1.8 |
| 58 | 0.3 | 1.4 |
| 59 | 0.8 | 2.5 |
| 60 | 2.0 | 45 |
| 61 | 0.4 | 2.5 |
| 62 | 0.2 | 1.1 |
| 63 | 0.3 | 1.4 |
| 64 | 0.5 | 1.1 |
| 65 | 0.5 | 1.0 |
| 66 | 0.8 | 2.2 |
| 67 | 0.6 | 2.3 |
| 68 | 9.4 | 33 |
| 69 | 10 | 139 |
| 70 | 0.4 | 1.2 |
| 71 | 14 | 22 |
| 72 | 7.5 | 21 |
| 73 | 1.6 | 3.3 |

TABLE 1-continued

The effectiveness of the compounds of the present invention measured in human vasopressin V1a receptor binding assay and functional assay

| Example No. | $K_i$ (nM) on hV1a cell line | $IC_{50}$ (nM) on hV1a cell line |
|---|---|---|
| 74 | 4 | 2.6 |
| 75 | 3.7 | 10.4 |
| 76 | 1.1 | 2.2 |
| 77 | 1.9 | 18 |
| 78 | 1.7 | 12 |
| 79 | 71 | 1855 |
| 80 | 58 | 520 |
| 81 | 0.2 | 1.4 |
| 82 | 29 | 445 |
| 83 | 4.4 | 44 |
| 84 | 11.4 | 72 |
| 85 | 0.4 | 1.8 |
| 86 | 2.2 | 12 |
| 87 | 2.5 | 57 |
| 88 | 0.3 | 0.9 |
| 89 | 0.4 | 1.9 |
| 90 | 10.2 | 152 |
| 91 | 9.1 | 45 |
| 92 | 1.9 | 16 |
| 93 | 3.2 | 16 |
| 94 | 2.0 | 23 |
| 95 | 547 | 22% at 1 μM |
| 96 | 0.2 | 0.8 |
| 97 | 122 | 34% at 1 μM |
| 98 | 2.1 | 39 |
| 99 | 0.3 | 2.5 |
| 100 | 0.2 | 1.5 |
| 101 | 0.2 | 1.3 |
| 102 | 5.9 | 23 |
| 103 | 0.2 | 0.7 |
| 104 | 0.2 | 0.6 |
| 105 | 0.3 | 1.4 |
| 106 | 0.1 | 1.8 |
| 107 | 1.0 | 12 |
| 108 | 0.2 | 4.9 |
| 109 | 0.4 | 2.7 |
| 110 | 2.1 | 8.3 |
| 111 | 0.3 | 2.4 |
| 112 | 45.4 | 213 |
| 113 | 21 | 305 |
| 114 | 26.5 | 205 |
| 115 | 0.5 | 0.8 |
| 116 | 0.7 | 2.1 |
| 117 | 0.9 | 4.3 |
| 118 | 66 | 251 |
| 119 | 27 | 111 |
| 120 | 52 | 465 |
| 121 | 79 | 442 |
| 122 | 3 | 14 |
| 123 | 2.1 | 6.3 |
| 124 | 1.7 | 5.1 |
| 125 | 0.8 | 2.3 |
| 126 | 0.6 | 1.8 |
| 127 | 2.8 | 17 |
| 128 | 2 | 14 |
| 129 | 0.5 | 20 |
| 130 | 2.4 | 6.1 |
| 131 | 0.3 | 0.7 |
| 132 | 0.3 | 2.5 |
| 133 | 0.4 | 6.5 |
| 134 | 0.2 | 1.5 |
| 135 | 2.9 | 54 |
| 136 | 0.2 | 1.6 |
| 137 | 0.7 | 9.2 |
| 138 | 0.2 | 5 |
| 139 | 9.3 | 130 |
| 140 | 2.4 | 57 |
| 141 | 0.7 | 8.9 |
| 142 | 14.3 | 225 |
| 143 | 5.0 | 156 |
| 144 | 34 | 168 |
| 145 | 12.7 | 47 |
| 146 | 3.2 | 78 |
| 147 | 1.0 | 9.4 |
| 148 | 1.2 | 26 |
| 149 | 0.8 | 15 |
| 150 | 5.0 | 94 |
| 151 | 30 | 209 |
| 152 | 67 | 737 |
| 153 | 20.5 | 307 |
| 154 | 0.8 | 21 |
| 155 | 0.04 | 0.7 |
| 156 | 0.5 | 9.5 |
| 157 | 0.1 | 0.5 |
| 158 | 62 | 1510 |
| 159 | 8 | 216 |
| 160 | 0.4 | 4.9 |
| 161 | 1.8 | 34 |
| 162 | 0.5 | 2.9 |
| 163 | 1.0 | 6.2 |
| 164 | 0.3 | 0.9 |
| 165 | 1.5 | 21 |
| 166 | 6.2 | 169 |
| 167 | 0.4 | 2.6 |
| 168 | 0.4 | 0.8 |
| 169 | 0.9 | 2.3 |
| 170 | 15.3 | 38 |
| 171 | 0.6 | 1.2 |
| 172 | 0.7 | 5.6 |
| 173 | 1.6 | 11 |
| 174 | 0.7 | 3 |
| 175 | 50.5 | 323 |
| 176 | 0.4 | 1.1 |
| 177 | 0.3 | 0.9 |
| 178 | 3.9 | 19 |
| 179 | 0.2 | 1.4 |
| 180 | 1.1 | 4.1 |
| 181 | 0.5 | 1.8 |
| 182 | 19 | 416 |
| 183 | 102 | 2120 |
| 184 | 0.6 | 25 |
| 185 | 4.1 | 19 |
| 186 | 0.4 | 1.2 |
| 187 | 86 | 4750 |
| 188 | 0.5 | 5.3 |
| 189 | 10 | 229 |
| 190 | 5.3 | 105 |
| 191 | 0.3 | 2.9 |
| 192 | 0.8 | 6.3 |
| 193 | 0.1 | 0.9 |
| 194 | 1.1 | 22 |
| 195 | 0.3 | 1.6 |
| 196 | 0.5 | 2.7 |
| 197 | 0.3 | 4.1 |
| 198 | 0.2 | 0.9 |
| 199 | 2.2 | 23 |
| 200 | 114 | 1187 |
| 201 | 3.9 | 19 |
| 202 | 0.4 | 1.0 |
| 203 | 10.1 | 210 |
| 204 | 0.2 | 2.7 |
| 205 | 0.2 | 2.7 |
| 206 | 0.2 | 0.9 |
| 207 | 0.3 | 4.2 |
| 208 | 0.1 | 2.2 |
| 209 | 0.2 | 1.6 |
| 210 | 56 | 292 |
| 211 | 0.7 | 1.3 |
| 212 | 2.8 | 34 |
| 213 | 0.6 | 5.5 |
| 214 | 66 | 672 |
| 215 | 0.2 | 3.7 |
| 216 | 0.7 | 1.5 |
| 217 | 0.3 | 1.4 |
| 218 | 97 | 1253 |
| 219 | 0.2 | 22 |

TABLE 1-continued

The effectiveness of the compounds of the present invention measured in human vasopressin V1a receptor binding assay and functional assay

| Example No. | $K_i$ (nM) on hV1a cell line | $IC_{50}$ (nM) on hV1a cell line |
|---|---|---|
| 220 | 0.4 | 2.6 |
| 221 | 0.9 | 9.8 |
| 222 | 5.8 | 40 |
| 223 | 1.6 | 8.1 |
| 224 | 0.7 | 3.6 |
| 225 | 48 | 854 |
| 226 | 0.5 | 4.2 |
| 227 | 1.0 | 51 |
| 228 | 0.8 | 6.1 |
| 229 | 0.4 | 2.1 |
| 230 | 0.7 | 12 |
| 231 | 1.1 | 5.9 |
| 232 | 1.3 | 9.2 |
| 233 | 6.9 | 53 |
| 234 | 3.8 | 57 |
| 235 | 0.3 | 22 |
| 236 | 0.9 | 4.2 |
| 237 | 0.2 | 1.5 |
| 238 | 0.7 | 8.2 |
| 239 | 1.2 | 5.6 |
| 240 | 0.5 | 3.1 |
| 241 | 0.4 | 2.6 |
| 242 | 0.5 | 1.8 |
| 243 | 0.4 | 2.8 |
| 244 | 25 | 263 |
| 245 | 7 | 130 |
| 246 | 0.5 | 3.4 |
| 247 | 5 | 30 |
| 248 | 2.3 | 22 |
| 249 | 0.8 | 7 |
| 250 | 2.9 | 27 |
| 251 | 18.5 | 152 |
| 252 | 0.7 | 8.2 |
| 253 | 5 | 66 |

Mouse Vasopressin V1a Receptor Binding Assay
Cells and Radioligand

The immortalized 1321N1 cell line (B9/1321N1 clone) constitutively and stably expressing Mouse vasopressin V1a receptor vasopressin (8-L-Arginine), [Phenylalanyl-3,4,5-$^3$H(N)] labelled compound (Perkin Elmer Life and Analytical Sciences) as radioligand were used to determine the affinity of the prepared compounds.

Method

Membrane-preparation: Membrane preparation of immortalized 1321N1 cells expressing the propagated mouse Vasopressin V1a receptor was made according to Jarvis's method (Jarvis et al., *J Pharmacol Exp Ther* 204, 310:407-16). Cells were suspended in preparative buffer (50 mM Tris, 1 mM EDTA, 0.1 mM PMSF) and homogenized with glass homogenizing potter. To separate the raw membrane fraction two consecutive centrifugation procedures (40,000 g for 25 minutes at 4° C.) were executed, then the membrane was taken into the preparatory buffer during a final washing step, it was divided into aliquots which were stored at −80° C. until the time of measurement.

The protein content of the prepared membrane was determined according to Lowry's method using standard dilution line of bovine serum albumin (BSA) (Lowry et al., *J Biol Chem* 1951, 193:265-75).

Receptor binding test: In the receptor binding assay, the substances with unknown affinity were used at a minimum of 8 different concentrations, with 3 parallels at each concentration. To determine the final affinity value, the results of at least two independent experiments were taken into account. The assay mixture included the incubation buffer (50 mM Tris-HCl, pH 7.4+3% BSA), membrane preparation of 1321N1 cells expressing the mouse vasopressin V1a receptor (152 μg/ml) and vasopressin (8-L-Arginine), [Phenylalanyl-3,4,5-$^3$H(N)] as radioligand (~35-50% concentration of $K_D$).

Non-specific binding values were determined in the presence of an unlabeled $1.2 \times 10^{-6}$ M (Arg$^8$)-vasopressin. Samples were incubated in a total volume of 0.33 ml for 60 minutes at 27° C. Membrane-bound and free ligands were separated by filtration through a 0.5% polyethyleneimine-impregnated UniFilter® GF/B™ After drying the filter plates, 40 μl Microscint-20 (Packard) scintillation cocktail was added to the samples. Finally, radioactivity was measured using MicroBeta$^2$ Microplate Counter (Perkin Elmer).

The radioligand clamping ability of a substance is determined in at least two independent experiments. Specific radioligand binding can be defined as the difference between total and non-specific binding in the presence of a saturation amount of the unlabeled ligand or different concentrations of the substance to be tested. The results are given as a percentage of inhibition of the specific binding achieved in the presence of the substance to be tested.

The $IC_{50}$ data (i.e. the concentration of the unknown substance which displaces 50% of specific bound radioligand) is calculated from the concentration-displacement curve using the sigmoid fitting mathematical method $y=(A1-A2)/(1+(x/x_0)p)+A2$ with Origin 7.5. software (OriginLab Corporation, Northampton, USA). During fitting, the asymptotes are not fixed. The $K_i$ values (inhibition constant) are given with Cheng-Prusoff equation $K_i=IC_{50}/[1+(L/K_D)]$ wherein [L] is the radioligand concentration used in the experiment and [$K_D$] is the affinity of the radioactively labelled ligand for the given receptor. The $K_D$ is determined beforehand using the Scatchard curve.

TABLE 2

The binding affinity of certain compounds of the present invention measured in mouse vasopressin V1a receptor binding assay

| Example No. | $K_i$ (nM) on mV1a cell line |
|---|---|
| 8 | 161 |
| 9 | 31 |
| 24 | 25 |
| 25 | 353 |
| 26 | 15 |
| 53 | 1.1 |
| 54 | 43 |
| 55 | 21 |
| 57 | 12 |
| 62 | 0.6 |
| 63 | 13 |

Human Vasopressin V2 Receptor Binding Assay
Cells and Radioligand

The immortalized 1321N1 cell line (Perkin Elmer, ES-363-M400UA) (Lot No:1765208) stably and constitutively expressing human vasopressin V2 receptor, CHO-K1 cell membrane expressing human Vasopressin V2 receptor (Perkin Elmer, 6110541400UA) and vasopressin (8-L-Arginine), [Phenylalanyl-3,4,5-$^3$H(N)] labelled compound (Perkin Elmer Life and Analytical Sciences) as radioligand were used to determine the affinity of the prepared compounds.

Method

Receptor binding test: In the receptor binding assay, the substances with unknown affinity were used at a minimum of 8 different concentrations, with 3 parallels at each concentration. To determine the final affinity value, the results of at least two independent experiments were taken into account. The assay mixture included the incubation buffer (50 mM Tris-HCl, pH 7.4+3% BSA), membrane preparation of 1321N1 cells expressing the human vasopressin V2 receptor (1.82 µg/ml) and Vasopressin (8-L-Arginine), [Phenylalanyl-3,4,5-$^3$H(N)] as radioligand (~concentration of $K_D$).

Non-specific binding values were determined in the presence of an unlabeled $1.2\times10^{-6}$ M $(Arg^8)$-vasopressin. Samples were incubated in a total volume of 0.55 ml for 90 minutes at 27° C. Membrane-bound and free ligands were separated by filtration through a 0.5% polyethyleneimine-impregnated UniFilter® GF/B™. After drying the filter plates, 40 µl Microscint-20 (Packard) scintillation cocktail was added to the samples. Finally, radioactivity was measured using MicroBeta$^2$ Microplate Counter (Perkin Elmer).

The radioligand displacement ability of a substance is determined in at least two independent experiments. Specific radioligand binding can be defined as the difference between total and non-specific binding in the presence of a saturation amount of the unlabeled ligand or different concentrations of the substance to be tested. The results are given as a percentage of inhibition of the specific binding achieved in the presence of the substance to be tested.

The $IC_{50}$ data (i.e. the concentration of the unknown substance which displaces 50% of specific bound radioligand) is calculated from the concentration-displacement curve using the sigmoid fitting mathematical method $y=(A1-A2)/(1+(x/x_0)p)+A2$ with Origin 7.5. software (OriginLab Corporation, Northampton, USA). During fitting, the asymptotes are not fixed. The $K_i$ values (inhibition constant) are given with Cheng-Prusoff equation $K_i=IC_{50}/[1+(L/K_D)]$ wherein [L] is the radioligand concentration used in the experiment and $[K_D]$ is the affinity of the radioactively labelled ligand for the given receptor. The $K_D$ is determined beforehand using the Scatchard curve.

TABLE 3

The binding affinity of certain compounds of the present invention measured in human vasopressin V2 receptor binding assay on 1321N1 cell line

| Example No. | $K_i$ or inhibition % at 1 µM on hV2 1321N1 cell line |
| --- | --- |
| 1 | 4% |
| 6 | 3% |
| 8 | 3050 nM |
| 9 | 1190 nM |
| 18 | 255 nM |
| 19 | 610 nM |
| 20 | 365 nM |
| 21 | 35% |
| 24 | 2190 nM |
| 25 | 6% |
| 26 | 36% |
| 47 | 366 nM |
| 53 | 40 nM |
| 54 | 662 nM |
| 55 | 469 nM |
| 57 | 446 nM |
| 62 | 53 nM |
| 63 | 575 nM |

Method

Receptor binding assays were performed in at least 8 concentrations, with two or rather three parallel samples in each concentration, in at least two independent experiments using an incubation buffer (50 mM Tris-HCl, 5 mM $MgCl_2$, pH 7.4+0.1% BSA), membrane preparation of CHO-K1 cells (Perkin Elmer, 6110541400UA) expressing the human vasopressin V2 receptor (7 µg/µl) and Vasopressin (8-L-Arginine), [Phenylalanyl-3,4,5-$^3$H(N)] as radioligand (~concentration of $K_D$).

Non-specific binding values can be determined in the presence of an unlabeled $1.2\times10^{-6}$ M $(Arg^8)$-vasopressin. Samples incubated in a total volume of 0.55 mL for 90 minutes at 27° C. Membrane-bound and free ligands were separated by filtration through a polyethyleneimine-impregnated UniFilter® GF/B™. The filter plates were washed three times with 0.5 mL of ice-cold washing buffer (50 mM Tris-HCl, pH 7.4). After drying the filter plates, 40 µl of Microscint20 (Packard) scintillation cocktail was added to each well. Finally, radioactivity was measured using Tri-Carb 2900TR liquid scintillation analyzer (Perkin Elmer).

The radioligand displacement ability of a substance is determined in at least two independent experiments. Specific radioligand binding can be defined as the difference between total and non-specific binding in the presence of a saturation amount of the unlabeled ligand or different concentrations of the substance to be tested. The results are given as a percentage of inhibition of the specific binding achieved in the presence of the substance to be tested.

The $IC_{50}$ data (i.e. the concentration of the unknown substance which displaces 50% of specific bound radioligand) is calculated from the concentration-displacement curve using the sigmoid fitting mathematical method $y=(A1-A2)/(1+(x/x_0)p)+A2$ with Origin 7.5. software (OriginLab Corporation, Northampton, USA). During fitting, the asymptotes are not fixed. The $K_i$ values (inhibition constant) are given with Cheng-Prusoff equation K: $=IC_{50}/[1+(L/K_D)]$ wherein [L] is the radioligand concentration used in the experiment and $[K_D]$ is the affinity of the radioactively labelled ligand for the given receptor. The $K_D$ is determined beforehand using the Scatchard curve.

Affinity data (K) measured on the 1321N1 cell line expressing human vasopressin V2 receptor are in very close correlation with $K_i$ results generated with CHO-K1 cell line expressing human vasopressin V2 receptor.

Functional V1a In Vivo Test

Animals

Male mice (NMRI, ToxiCoop) weighing 18-40 g were used. Animals were kept at least 5 days after delivery, during housing and measurements they were fed and drink ad libitum. The experiments were permitted by the Local Animal Protection Committee and carried out in accordance with the European Animal Protection Directives (EU Directive 2010/63/EU).

Method

Animal behaviour was measured by an automated behavioral analysis system (LABORAS™). The sensors located below platforms detect the mechanical vibration generated by the movement of animal, and transform into an electrical signal (Quinn et al., *J Neurosci Methods* 2003, 130:83-92). After analyzing signals, the system analyzes the time spent with the following behavioral parameters: locomotion, immobility, climbing, grooming. The grooming algorithm by definition is able to measure the scratching behavioral response. During the experiment, mice were pretreated with the test substance or vehicle, and after the pretreatment period scratching-inducing compound (s.c. 0.3 mg/kg oxytocin) was administered, and then the animals were individually placed into measuring cages. Their behaviour was observed for 1 hour. To reduce the exploratory activity, the animals were measured after a 1-hour habituation to the cage. The behavioural parameters were compared to the parallel measured parameters of the control animals.

The behavioural inhibitory effect of the substances was calculated with average values of parallel measured vehicle treated groups and presented as the percentage of inhibition: 0% was expressed as average value of scratching behaviour of vehicle pretreated animals (and phys. saline s.c. pretreated with vehicle), while 100% was expressed as average value of scratching of vehicle pretreated animals that received oxytocin subcutaneously. For statistical analysis one-way analysis of variance (ANOVA) with Tukey post hoc test were used.

Surprisingly, it has been found that certain compounds of the present invention produced significant effect on the mouse V1a receptor in vivo functional test.

TABLE 4

The efficacy of certain compounds of the present invention in the mouse in vivo V1a functional test: the inhibition of oxytocin-induced scratching behaviour response after 10 mg/kg p.o. pretreatment in mice.

| Example No. | inhibition (%) |
| --- | --- |
| 8 | 64 |
| 9 | 106* |
| 12 | 34 |
| 23 | 75 |
| 24 | 94* |
| 25 | 42* |
| 26 | 71 |
| 29 | 89 |
| 53 | 118 |
| 54 | 70 |
| 55 | 91 |
| 56 | 92 |
| 57 | 84 |
| 58 | 96 |
| 60 | 40 |
| 61 | 41 |
| 62 | 99 |
| 63 | 49 |
| 66 | 76 |
| 74 | 30 |
| 88 | 79 |
| 89 | 50 |
| 96 | 49 |
| 99 | 60 |
| 100 | 96 |
| 101 | 105 |
| 103 | 71 |
| 104 | 67 |
| 126 | 43 |
| 157 | 108 |
| 198 | 41 |
| 204 | 65 |
| 205 | 66 |

*after i.p. treatment

The Prenatal Valproate Model of Autism Spectrum Disorder (ASD) in Rats

The prenatal valproate model has excellent construct and face validity, thus it is a widely accepted animal model of ASD (Christensen et al, *JAMA* 2013, 309:1696-1703; Roullet et al, *Neurotoxicol Teratol.* 2013, 36:45-56). In this model, time-mated female Wistar rats (Harlan, UK) were treated with single-dose of valproic acid (VPA, i.p. 600 mg/kg) on 12.5 days of pregnancy. After birth and separation, the examined male offsprings were kept under standard laboratory conditions until completion of the studies. Four animals were kept together in standard cages at 22-24° C. external temperature and in 12-12 hour light-dark cycle (07.30 a.m.-07.30 p.m.). Food and water were available ad libitum. After once daily treatment with the test substance for 7 days and pretreatment on the day of measurement, the behaviour of the rats was assessed in the social preference test on the $59^{th}$ or $60^{th}$ postnatal day. The social preference test is a largely accepted test method for determining the autistic behaviour of rodents (Nadler et al, *Genes Brain Behav* 2004, 3:303-314; Bambini-Junior et al, *Brain Res* 2011, 1408:8-16). The test consists of two paradigms, the first is the social approach avoidance test. In this paradigm the social behaviour of examined animals can be determined with a special three-chamber apparatus. In the apparatus, the contact behaviour of the conspecific and empty separated area surrounded with a perforated wall can be examined and compared. Prenatally valproate-treated rats produce autistic behaviour and spend significantly less time with seeking response toward conspecific than the in utero vehicle-treated control animals. One day later, on the $60^{th}$ postnatal day, rats were tested in the social memory and recognition paradigm. In this, the contact behaviour with a new, previously unknown conspecific can be measured compared to a familiar conspecific.

In the social approach avoidance paradigm valproate treated rats (VPA/VEH) showed significant decrease of active time spent with social behaviour compared to the in utero vehicle-treated control animals (VEH/VEH). Certain 5,6-dihydro-4H-[1,2,4]triazolo[4,3-a][1]benzazepine compounds of the present invention substituted at position 5 were unexpectedly effective in this assay and the treatment statistically significantly reversed the value of VPA/VEH to the value of VEH/VEH treated animals.

Rats treated with SAHA (suberoil anilide or vorinostat) used as positive control also showed statistically significant increase in time spent with social seeking response (Foley et al, *Eur J Pharmacol* 2014, 727:80-86).

In the social memory recognition paradigm valproate treated rats showed significant decrease of the active time spent with seeking new, non-familiar animal compared to the in utero vehicle-treated control animals. Certain 5,6-dihydro-4H-[1,2,4]triazolo[4,3-a][1]benzazepine compounds of the present invention substituted at position 5 made the behaviour of animals more socialized and were capable to significantly increase the active time spent with seeking response from the new animals. Unexpectedly, the treatment reversed the value of VPA/VEH to the value of VEH/VEH treated animals. Rats treated with SAHA used as positive control also showed statistically significant increase in the time spent with seeking response.

Certain compounds of the present invention therefore exhibited significant behavioral benefits in the present animal model that implies the clinical symptoms of ASD, thus providing a therapeutic opportunity for the treatment of human ASD symptoms.

TABLE 5

The effects on active contact time in the paradigms of social approach avoidance and social memory recognition of certain compounds of the present invention

| | social approach avoidance | | social memory recognition | |
| --- | --- | --- | --- | --- |
| | active contact time [sec] | % effect | active novelty contact time [sec] | % effect |
| Example 26 | | | | |
| VEH/VEH | 147.1 ± 13.8 | | 136.6 ± 7.6 | |
| VPA/VEH | 41.1 ± 8.2 | | 18.0 ± 6.2 | |

TABLE 5-continued

The effects on active contact time in the paradigms of social approach avoidance and social memory recognition of certain compounds of the present invention

| | social approach avoidance | | social memory recognition | |
|---|---|---|---|---|
| | active contact time [sec] | % effect | active novelty contact time [sec] | % effect |
| VPA/SAHA | | | | |
| 5 mg/kg i.p. | 156.0 ± 6.7 | 115 | 155.5 ± 5.8 | 137 |
| VPA/Example 26 | | | | |
| 1.5 mg/kg i.p. | 71.2 ± 15.9 | 30 | 83.7 ± 11.8 | 66 |
| 5 mg/kg i.p. | 116.4 ± 22.5 | 75 | 133.5 ± 10.0 | 115 |
| 15 mg/kg i.p. | 148.7 ± 8.3 | 107 | 141.9 ± 9.1 | 124 |

Data presented in the table are given as mean ± standard error of mean(S.E.M.) and rounded up to one decimal form. The percentages were calculated from the raw data and rounded up to integer values (wherein VEH/VEH = 100%, VPA/VEH = 0%).

The present invention will be further illustrated by the following embodiments without limiting the scope of the present invention to them. From the above description part and from the examples, the person skilled in the art may ascertain the essential features of the invention and without departing from its essence and scope, may make certain changes and modifications in order to adapt the invention to various applications and conditions. As a result, the invention is not limited to the following illustrative examples, but rather to the scope determined by the appended claims.

In general, the compounds of general formula (I) can be prepared according to the common general knowledge of the person skilled in the art and/or the methods described for the working examples and/or intermediates. Solvents, temperatures, pressures and other reaction conditions can be easily selected by the person skilled in the art. Starting materials are commercially available and/or can be easily prepared by the person skilled in the art. During the preparation of compounds combinatorial techniques can be used, for example, where the present intermediate groups are suitable for the use of these methods.

In describing the synthesises, the following terms and abbreviations have been used: dry=anhydrous
Boc=tert-butoxycarbonyl
DIPEA=N,N-diisopropyl-ethylamine
DMAP=4-dimethylamino-pyridine
DMF=N,N-dimethylformamide
EDC=N-(3-dimethylaminopropyl)-N'-ethylcarbodiimide hydrochloride
HOBt=1-hydroxybenzotriazole hydrate
HBTU=N,N,N',N'-tetramethyl-O-(1H-benzotriazol-1-yl) uronium hexafluorophosphate
$K_2CO_3$=potassium carbonate
Lawesson reagent=2,4-bis(4-methoxyphenyl)-1,3,2,4-dithiadiphosphethane-2,4-disulfide
Meldrum's acid=2,2-dimethyl-1,3-dioxane-4,6-dione
$MgSO_4$=magnesium sulfate
$NaBH_4$=sodium borohydride
$NaBH(OAc)_3$=sodium triacetoxy borohydride
$NaHCO_3$=sodium bicarbonate
NaCl=sodium chloride
$Na_2CO_3$=sodium carbonate
NaOH=sodium hydroxide
$Na_2SO_4$=sodium sulfate
Pd/C=palladium on carbon
Phg=phenylglycine
Pt/C=platinum on carbon
THF=tetrahydrofuran Intermediate 1

3-[(tert-butoxycarbonyl)amino]-4-(5-chloro-2-nitrophenyl)butanoic acid

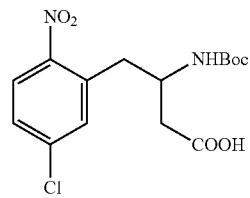 [SMILES: CC(C)(C)OC(=O)NC(CC(=O)O)Cc1cc(Cl)ccc1[N+](=O)[O-]]

Method A)

a) 2-[(tert-butoxycarbonyl)amino]-3-(5-chloro-2-nitrophenyl)propanoic acid

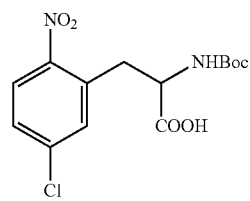 [SMILES: CC(C)(C)OC(=O)NC(Cc1cc(Cl)ccc1[N+](=O)[O-])C(=O)O]

To a cooled and stirred mixture of 3.03 g (12.4 mmol) of 2-amino-3-(5-chloro-2-nitrophenyl)propanic acid (N. A. Meanwell et al., *J Med Chem* 1991, 34:2906-2916), 55 mL of 1,4-dioxane, 12 mL of water and 12.4 mL of 10% NaOH solution, 3.35 g of di-tert-butyl dicarbonate (15.4 mmol) was added and the mixture was stirred at room temperature overnight. After completion of the reaction, the pH of the mixture was adjusted to 7 with 10% hydrochloric acid solution, and it was concentrated. Dichloromethane was added to the residue and stirred at room temperature for 1 hour. The precipitated solid was filtered, washed with dichloromethane, the filtrate was concentrated and the residue was purified by column chromatography using dichloromethane:methanl=9:1 as eluent. Thus 383 g (90%) of the title product was obtained. MS (ESI) m/z 367.1 (M+Na)$^+$.

b) Tert-butyl N-[1-(5-chloro-2-nitrophenyl)-4-diazo-3-oxobutan-2-yl]carbamate

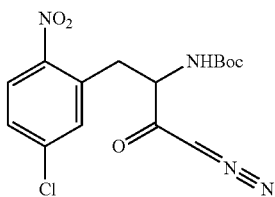 [SMILES: CC(C)(C)OC(=O)NC(Cc1cc(Cl)ccc1[N+](=O)[O-])C(=O)C=[N+]=[N-]]

A mixture of 2.55 g (7.4 mmol) of 2-[(tert-butoxycarbonyl)amino]-3-(5-chloro-2-nitrophenyl)propanic acid, 40 mL of diethyl ether and 1.25 mL (9.0 mmol) of triethylamine was cooled to −30° C. and 1.15 mL (8.9 mmol) of isobutyl chloroformate was added dropwise with stirring. The mixture was stirred at −30° C. for 15 minutes, then a solution of 0.7 M diazomethane in 50 mL of diethyl ether was added dropwise to keep the temperature between −25° C. and −30° C. The mixture was allowed to warm to 0° C. and stirred at this temperature for 1 hour, then the excess diazomethane was decomposed with acetic acid. The reaction mixture was diluted with ethyl acetate, the pH was adjusted to 7 with saturated NaHCO₃ solution, the phases were separated and the organic phase was washed with saturated NaCl solution, dried over anhydrous Na₂SO₄, filtered and concentrated. The residue was purified by column chromatography using dichloromethane:methanol=95:5 as eluent. Thus, 1.72 g (63%) of the title product was obtained. MS (ESI) m/z 391.1 (M+Na)⁺.

c) 3-[(tert-butoxycarbonyl)amino]-4-(5-chloro-2-nitrophenyl)butanoic acid

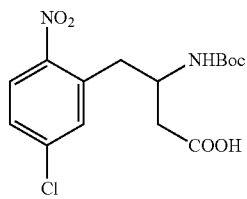 [SMILES: CC(C)(C)OC(=O)NC(CC(=O)O)Cc1cc(Cl)ccc1[N+](=O)[O-]]

A mixture of 8.26 g (22.4 mmol) of tert-butyl N-[1-(5-chloro-2-nitrophenyl)-4-diazo-3-oxobutan-2-yl]carbamate, 300 mL of 1,4-dioxane, 60 mL of water and 0.49 g (2.1 mmol) of silver benzoate was stirred at room temperature for 20 hours, then diluted with 300 mL of ethyl acetate, 300 mL of 5% hydrochloric acid was added and the phases were separated.

The organic phase was washed with saturated NaCl, dried over anhydrous Na₂SO₄, filtered and concentrated. The residue was purified by column chromatography using dichloromethane:methanol=9:1 as eluent. Thus, 5.28 g (66%) of the title product was obtained. MS (ESI) m/z 381.1 (M+Na)⁺.

Method B)

a) 5-[2-(5-chlor-2-nitrophenyl)-1-hydroxyethylidene]-2,2-dimethyl-1,3-dioxane-4,6-dione

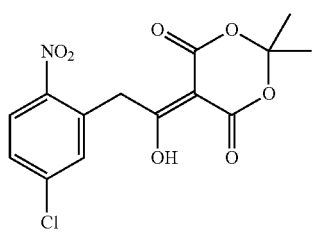 [SMILES: CC1(C)OC(=O)C(=C(O)Cc2cc(Cl)ccc2[N+](=O)[O-])C(=O)O1]

4.925 g (22.84 mmol) of (5-chloro-2-nitrophenyl) acetic acid (Enamine Ltd.) was dissolved in 250 mL of acetonitrile and 8.95 mL (51.4 mmol) of DIPEA, 279 mg (2.3 mmol) of DMAP and 3.72 g (25.1 mmol) of Meldrum's acid were added while stirring. After cooling, 3.1 mL (25.1 mmol) of pivaloyl chloride was slowly added dropwise to keep the temperature below 30° C. The reaction mixture was stirred for 4 hours at 45° C., then the solution was cooled to 0° C.

and 90 mL of 1N hydrochloric acid and 90 mL of water were added. The precipitated material was filtered, washed with water, and dried. Thus, 6.62 g (85%) of the title product was obtained as white powder which was used without further purification in the next step.

b) Methyl 4-(5-chloro-2-nitrophenyl)-3-oxobutanoate

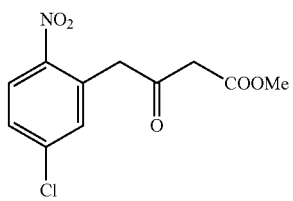

A mixture of 6.62 g (19.4 mmol) of 5-[2-(5-chloro-2-nitrophenyl)-1-hydroxyethylidene]-2,2-dimethyl-1,3-dioxane-4,6-dine, 70 mL of methanol and 280 mL of toluene was refluxed for 3 hours. The mixture was cooled to room temperature, 130 mL of saturated NaCl and 100 mL of ethyl acetate were added, the phases were separated, the organic phase was dried over anhydrous MgSO₄, filtered and concentrated. Thus, 5.21 g (99%) of the title product was obtained as a cream-coloured oil, which was crystallized on standing within a few days. MS (ESI) m/z 272.1 (M+H)⁺.

c) Methyl 3-amino-4-(5-chloro-2-nitrophenyl)but-2-enoate

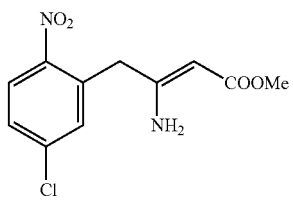 [SMILES: COC(=O)/C=C(\N)Cc1cc(Cl)ccc1[N+](=O)[O-]]

A mixture of 5.40 g (20 mmol) of methyl 4-(5-chloro-2-nitrophenyl)-3-oxobutanoate, 60 mL of methanol and 7.8 g (101 mmol) of ammonium acetate was heated at reflux for 5 hours then concentrated. Saturated NaHCO₃ solution was added to the residue and extracted with dichloromethane. The organic phase was dried over anhydrous MgSO₄, filtered and concentrated. Thus, 4.85 g (90%) of the title product was obtained as yellow solid. MS (ESI) m/z 271.7 (M+H)⁺.

d) Methyl 3-amino-4-(5-chloro-2-nitrophenyl)butanoate

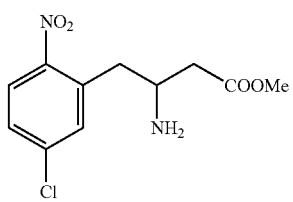 [SMILES: COC(=O)CC(N)Cc1cc(Cl)ccc1[N+](=O)[O-]]

11.23 g (41.5 mmol) of methyl 3-amino-4-(5-chlor-2-nitrophenyl)but-2-enoate was dissolved in 120 mL of acetic acid and 6.27 g (29.6 mmol) of NaBH(OAc)$_3$ was added during cooling and stirring. The mixture was stirred at room temperature for 2 hours and further 6.27 g (29.6 mmol) of NaBH(OAc)$_3$ was added. The reaction mixture was stirred at room temperature for 20 hours and poured into ice-cold water. The pH of the mixture was adjusted to 8 with solid K$_2$CO$_3$ and extracted with ethyl acetate, the organic phase was dried over anhydrous MgSO$_4$, filtered and concentrated. Thus, 11.32 g (100%) of the title product was obtained as yellow oil. MS (ESI) m/z 273.7 (M+H)$^+$.

e) Methyl 3-[(tert-butoxycarbonyl)amino]-4-(5-chloro-2-nitrophenyl)butanoate

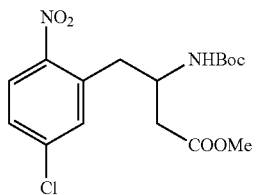 [SMILES: COC(=O)CC(Cc1cc(Cl)ccc1[N+](=O)[O-])NC(=O)OC(C)(C)C]

To a mixture of 11.32 g (41.5 mmol) of methyl 3-amino-4-(5-chloro-2-nitrophenyl)butanoate, 330 mL of methanol and 6.82 g (82.4 mmol) of NaHCO$_3$ 11.32 g (51.9 mmol) of di-tert-butyl dicarbonate was added during cooling and stirring and the mixture was stirred at room temperature for 20 hours. The reaction mixture was concentrated, 500 mL of water was added to the residue, the precipitated product was filtered, washed with water, and dried. Thus, 13.83 g (89%) of the title product was obtained as yellow powder. MS (ESI) m/z 395.0 (M+Na)$^+$.

f) 3-[(tert-butoxycarbonyl)amino]-4-(5-chloro-2-nitrophenyl)butanoic acid

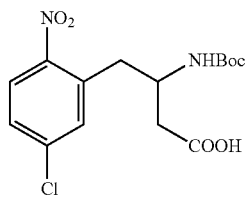 [SMILES: CC(C)(C)OC(=O)NC(CC(=O)O)Cc1cc(Cl)ccc1[N+](=O)[O-]]

To a stirred mixture of 13.83 g (37.1 mmol) of methyl 3-[(tert-butoxycarbonyl)amino]-4-(5-chloro-2-nitrophenyl) butanoate, 260 mL of THF, 130 mL of methanol and 130 mL of water, 8 g (190 mmol) of lithium hydroxide monohydrate was added while stirred. The reaction mixture was stirred at room temperature for 20 hours, and then concentrated. 300 mL of water was added to the residue, the pH of the mixture was adjusted to 5 with 10% hydrochloric acid and the mixture was stirred at room temperature for 1 hour. The precipitated product was filtered, washed with water, and dried. Thus, 13.2 g (99%) of the title product was obtained. MS (ESI) m/z 381.1 (M+Na)$^+$.

Intermediate 2

4-(2-amino-5-chlorophenyl)-3-[(tert-butoxycarbonyl)amino]butanoic acid

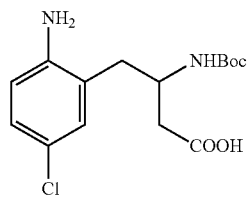 [SMILES: CC(C)(C)OC(=O)NC(CC(=O)O)Cc1cc(Cl)ccc1N]

Method A)

To a mixture of 5.28 g (14.7 mmol) of 3-[(tert-butoxycarbonyl)amino]-4-(5-chloro-2-nitrophenyl)butanoic acid (Intermediate 1), 140 mL of methanol and 350 mg (1.47 mmol) of nickel chloride hexahydrate, 1.35 g (35.7 mmol) of NaBH$_4$ was added under ice-cooling, then the reaction mixture was stirred at room temperature for 20 hours. The pH of the reaction mixture was adjusted to 6 with 10% hydrochloric acid, the mixture was filtered through Celite, the filtrate was concentrated and the residue was purified by column chromatography using dichloromethane:methanol=9:1 as eluent. Thus, 2.11 g (44%) of the title product was obtained. MS (ESI) m/z 351.2 (M+Na)$^+$.

Method B)

To a mixture of 3.0 g (8.34 mmol) of 3-[(tert-butoxycarbonyl)amino]-4-(5-chloro-2-nitrophenyl)butanoic acid (Intermediate 1) and 400 mL of toluene, 300 mg of 5% Pt/C catalyst was added under argon, then the reaction mixture was stirred at room temperature in hydrogen atmosphere. After completion of the reaction, the catalyst was filtered through Celite, washed with methanol, and the filtrate was concentrated. Thus, 2.64 g (96%) of the title product was obtained.

Intermediate 3

Tert-butyl (7-chloro-2-oxo-2,3,4,5-tetrahydro-1H-1-benzazepin-4-yl)carbamate

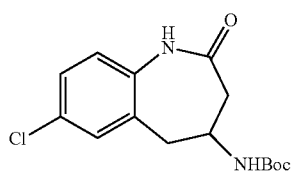 [SMILES: CC(C)(C)OC(=O)NC1CC(=O)Nc2ccc(Cl)cc2C1]

A mixture of 5.52 g (16.79 mmol) of 4-(2-amino-5-chlorophenyl)-3-[(tert-butoxycarbonyl)amino]butanoic acid (Intermediate 2), 60 mL of DMF, 3.9 g (20.34 mmol) of EDC, 7 mL (40.2 mmol) of DIPEA and 3.08 g (20.1 mmol) of HOBt was stirred at room temperature for 20 hours, then the reaction mixture was concentrated. 100 mL of saturated NaHCO$_3$ solution was added to the residue, and the mixture was stirred at room temperature for 1 hour. The crystalline product was filtered off, washed with water, and dried. Thus, 4.71 g (90%) of the title product was obtained. MS (ESI) m/z 333.1 (M+Na)$^+$.

Intermediate 4

Tert-butyl (7-chloro-2-thioxo-2,3,4,5-tetrahydro-1H-1-benzazepin-4-yl)carbamate

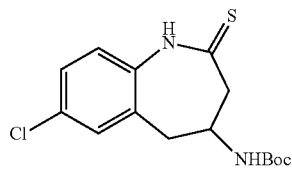 [SMILES: CC(C)(C)OC(=O)NC1CC(=S)Nc2ccc(Cl)cc2C1]

A mixture of 2.35 g (7.56 mmol) of tert-butyl (7-chloro-2-oxo-2,3,4,5-tetrahydro-1H-1-benzazepin-4-yl)carbamate (Intermediate 3), 65 mL of pyridine and 3.98 g (9.84 mmol) of Lawesson reagent was stirred at 120° C. for 4 hours, then the reaction mixture was concentrated. 100 mL of saturated NaHCO$_3$ solution was added to the residue and the mixture was stirred at room temperature for 1 hour. The crystalline product was filtered off, washed with water, and dried. Thus, 2.32 g (94%) of the title product was obtained. MS (ESI) m/z 327.2 (M+H)$^+$.

Intermediate 5

Tert-butyl [7-chloro-2-(methylsulfanyl)-4,5-dihydro-3H-1-benzazepin-4-yl]carbamate

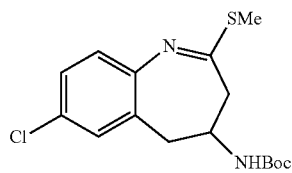 [SMILES: CSC1=Nc2ccc(Cl)cc2CC(NC(=O)OC(C)(C)C)C1]

A mixture of 2.32 g (7.1 mmol) of tert-butyl (7-chloro-2-thioxo-2,3,4,5-tetrahydro-1H-1-benzazepin-4-yl)carbamate (Intermediate 4), 140 mL of acetone, 1.96 g (14.2 mmol) of K$_2$CO$_3$ and 1.33 mL (21.4 mmol) of iodomethane was stirred at room temperature for 20 hours. The reaction mixture was concentrated, water was added to the residue and extracted with ethyl acetate, the organic phase was dried over anhydrous Na$_2$SO$_4$, filtered, and concentrated. Thus, 2.04 g (84%) of the title product was obtained. MS (ESI) m/z 341.2 (M+H)$^+$.

Intermediate 6

Ethyl (5-methoxy-2-nitrophenyl)acetate

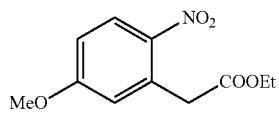 [SMILES: CCOC(=O)Cc1cc(OC)ccc1[N+](=O)[O-]]

To a mixture of 10.18 g (90.7 mmol) of potassium-tert-butoxide and 90 mL of dry DMF a mixture of 3.86 mL (36.3 mmol) of ethyl chloroacetate, 5.56 g (36.3 mmol) of 4-nitroanisole (Merck) and 40 mL of dry DMF was added dropwise at 0° C. under nitrogen. The resulting dark purple reaction mixture was stirred at 0° C. for 2.5 hours, then 35 mL of 3N hydrochloric acid was added dropwise and diluted with water. The mixture was extracted twice with ethyl acetate, the combined organic phases were washed with aqueous NaCl, dried over anhydrous Na$_2$SO$_4$, filtered and concentrated. Thus, 7.33 g (84%) of the title product was obtained as brown oil. MS (ESI) m/z 240.2 (M+H)$^+$.

Intermediate 7

(5-methoxy-2-nitrophenyl)acetic acid

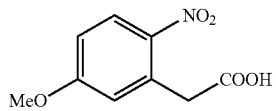

A mixture of 7.33 g (30.6 mmol) of ethyl (5-methoxy-2-nitrophenyl)acetate (Intermediate 6), 1.54 g (36.8 mmol) of lithium hydroxide monohydrate, 90 mL of THF and 45 mL of water was stirred at room temperature for 16 hours. The organic solvent was evaporated and the residue was extracted with ethyl acetate. 40 mL of 1N hydrochloric acid was added to the aqueous phase, extracted twice with ethyl acetate, the combined organic phases were dried over anhydrous Na$_2$SO$_4$, filtered and concentrated. Thus, 2.27 g (35%) of the title product was obtained. MS (ESI) m/z 229.1 (M+NH$_4$)$^+$.

Intermediate 8

5-[1-hydroxy-2-(5-methoxy-2-nitrophenyl)ethylidene]-2,2-dimethyl-1,3-dioxane-4,6-dione

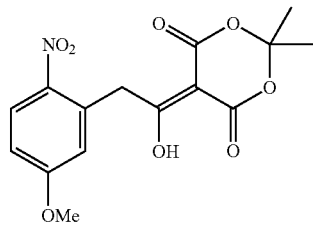 [SMILES: COc1ccc([N+](=O)[O-])c(CC(O)=C2C(=O)OC(C)(C)OC2=O)c1]

To a mixture of 2.27 g (10.7 mmol) of (5-methoxy-2-nitrophenyl) acetic acid (Intermediate 7), 40 mL of dry acetonitrile, 1.70 g (11.8 mmol) of Meldrum's acid, 131 mg (1.07 mmol) of DMAP and 4.21 mL (24.2 mmol) of DIPEA, 1.46 mL (11.8 mmol) trimethylacetyl chloride was added dropwise and the reaction mixture was stirred at 40° C. for 4 hours. The mixture was cooled to 0° C., 26 mL of 1N hydrochloric acid was added dropwise and diluted with 60 mL of water. The precipitated product was filtered off, washed with water and dried over phosphorus pentoxide in a vacuum desiccator. Thus, 2.45 g (68%) of the title product was obtained which was used without further purification.

Intermediate 9 methyl 4-(5-methoxy-2-nitrophenyl)-3-oxobutanoate

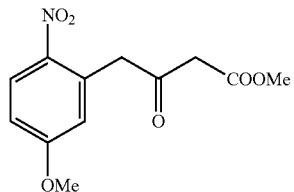 [SMILES: COC(=O)CC(=O)Cc1cc(OC)ccc1[N+](=O)[O-]]

A mixture of 2.45 g (7.26 mmol) of 5-[1-hydroxy-2-(5-methoxy-2-nitrophenyl)ethylidene]-2,2-dimethyl-1,3-dioxane-4,6-dione (Intermediate 8), 10 mL of methanol and 30 mL of toluene was stirred at 115° C. for 1.5 hours. The mixture was cooled to room temperature, ethyl acetate and aqueous NaCl were added. The phases were separated, the organic phase was dried over anhydrous $Na_2SO_4$, filtered and concentrated. Cyclohexane was added to the residue, stirred for 1 hour and the product was filtered off. Thus 1.85 g (95%) of the title product was obtained. MS (ESI) m/z 268.2 $(M+H)^+$.

Intermediate 10 methyl 3-amino-4-(5-methoxy-2-nitrophenyl)but-2-enoate

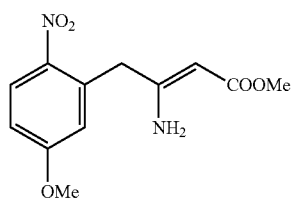 [SMILES: COC(=O)/C=C(\N)Cc1cc(OC)ccc1[N+](=O)[O-]]

A mixture of 1.07 g (4 mmol) of methyl 4-(5-methoxy-2-nitrophenyl)-3-oxobutanoate (Intermediate 9), 20 mL of methanol and 6.17 g (80 mmol) of ammonium acetate was stirred at room temperature for 16 hours. The mixture was diluted with water, stirred for 1 hour, and the product was filtered off. Thus, 0.92 g (86%) of the title product was obtained which was used without further purification.

Intermediate 11 methyl 3-amino-4-(5-methoxy-2-nitrophenyl)butanoate

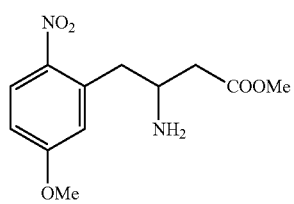 [SMILES: COC(=O)CC(N)Cc1cc(OC)ccc1[N+](=O)[O-]]

To 9 mL of acetic acid, 0.67 g (17.8 mmol) of $NaBH_4$ was added over 45 minutes while keeping the temperature around 10° C. 0.79 g (3 mmol) of methyl-3-amino-4-(5-methoxy-2-nitrophenyl)but-2-enoate (Intermediate 10) was added to the resulting mixture and stirred at room temperature for 1.5 hours. The mixture was diluted with water during cooling, then basified with solid $K_2CO_3$ and extracted twice with ethyl acetate. The combined organic phases were washed with aqueous $K_2CO_3$ solution and then with aqueous NaCl solution, dried over anhydrous $Na_2SO_4$, filtered and concentrated. Thus, 0.69 g (87%) of the title product was obtained. MS (ESI) m/z 269.2 $(M+H)^+$.

Intermediate 12 methyl 3-(tert-butoxycarbonyl)amino-4-(5-methoxy-2-nitrophenyl)butanoate

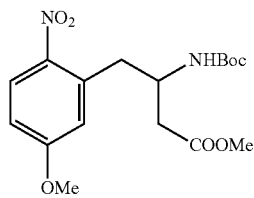 [SMILES: COC(=O)CC(Cc1cc(OC)ccc1[N+](=O)[O-])NC(=O)OC(C)(C)C]

To a mixture of 0.69 g (2.6 mmol) of methyl 3-amino-4-(5-methoxy-2-nitrophenyl)butanoate (Intermediate 11), 20 mL of methanol and 0.7 g (3.22 mmol) di-tert-butyl-dicarbonate, 0.43 g (5.14 mmol) of $NaHCO_3$ was added at 10° C. The reaction mixture was stirred at room temperature for 1.5 hours, diluted with water, and the precipitated product was filtered. Thus 0.72 g (76%) of the title product was obtained. MS (ESI) m/z 391.1 $(M+Na)^+$.

Intermediate 13 methyl 4-(2-amino-5-methoxyphenyl)-3-[(tert-butoxycarbonyl)amino]butanoate

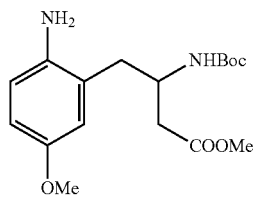 [SMILES: COC(=O)CC(Cc1cc(OC)ccc1N)NC(=O)OC(C)(C)C]

Methyl 0.72 g (2 mmol) of 3-[(tert-butoxycarbonyl)amino]-4-(5-methoxy-2-nitrophenyl)butanoate (Intermediate 12) in 50 mL of methanol was hydrogenated in the presence of 80 mg of 10% Pd/C at room temperature under atmospheric pressure. After filtration of the catalyst, the filtrate was concentrated to yield 0.62 g (94%) of the title product. MS (ESI) m/z 339.3 $(M+H)^+$.

Intermediate 14

Tert-butyl (7-methoxy-2-oxo-2,3,4,5-tetrahydro-1H-1-benzazepin-4-yl)carbamate

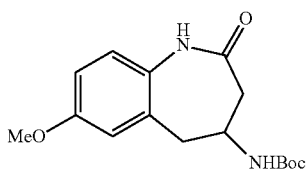 [SMILES: COc1ccc2c(c1)CC(NC(=O)OC(C)(C)C)CC(=O)N2]

0.56 g (1.7 mmol) of methyl 4-(2-amino-5-methoxyphenyl)-3-[(tert-butoxycarbonyl)amino]-butanoate (Intermediate 13) was dissolved in 12 mL of methanol and 0.26 mL of 30% methanolic sodium methoxide solution was added, and the mixture was stirred at room temperature for 20 hours. 1.7 mL of 1N hydrochloric acid was added to the mixture during cooling, diluted with water, and the resulting precipitate was filtered, washed with water and dried over phosphorus pentoxide in a vacuum desiccator. Thus, 0.4 g (80%) of the title product was obtained. MS (ESI) m/z 329.2 (M+Na)$^+$.

Intermediate 15

Tert-butyl (7-methoxy-2-thioxo-2,3,4,5-tetrahydro-1H-1-benzazepin-4-yl)carbamate

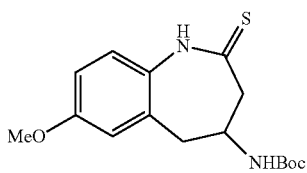

A mixture of 044 g (1.4 mmol) of tert-butyl (7-methoxy-2-oxo-2,3,4,5-tetrahydro-1H-1-benzazepin-4-yl)carbamate (Intermediate 14), 20 mL of pyridine and 1.34 g (3.3 mmol) of Lawesson reagent was stirred at 120° C. for 4.5 hours. The reaction mixture was cooled to room temperature, diluted with ethyl acetate, and washed twice with 5% NaHCO$_3$ solution. The organic phase was dried over anhydrous Na$_2$SO$_4$, filtered and concentrated. Diethyl ether was added to the residue and the precipitated solid was filtered off after 1 hour of stirring. The crude product was recrystallized from 7 mL of ethanol to yield 0.15 g (32%) of the title product. MS (ESI) m/z 345.2 (M+Na)$^+$.

Intermediate 16

5-[1-hydroxy-2-(5-methyl-2-nitrophenyl)ethylidene]-2,2-dimethyl-1,3-dioxane-4,6-dione

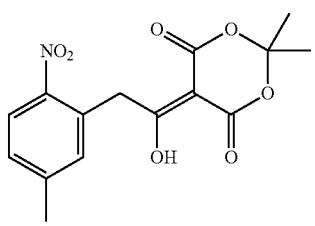 [SMILES: Cc1ccc([N+](=O)[O-])c(CC(O)=C2C(=O)OC(C)(C)OC2=O)c1]

The title product was prepared from 2-(5-methyl-2-nitrophenyl) acetic acid (Astatech Inc.) according to the method described for Intermediate 8, and was used without further purification.

Intermediate 17 methyl 4-(5-methyl-2-nitrophenyl)-3-oxobutanoate

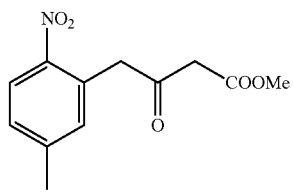 [SMILES: COC(=O)CC(=O)Cc1cc(C)ccc1[N+](=O)[O-]]

The title product was prepared from 5-[1-hydroxy-2-(5-methyl-2-nitrophenyl)ethylidene]-2,2-dimethyl-1,3-dioxane-4,6-dione (Intermediate 1) according to the method described for Intermediate 9, and was used without further purification.

Intermediate 18 methyl 3-amino-4-(5-methyl-2-nitrophenyl)but-2-enoate

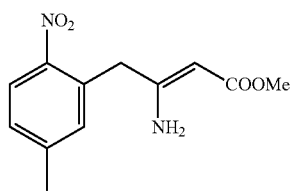 [SMILES: COC(=O)/C=C(\N)Cc1cc(C)ccc1[N+](=O)[O-]]

The title product was prepared from methyl 4-(5-methyl-2-nitrophenyl)-3-oxobutanoate (Intermediate 17) according to the method described for Intermediate 10, and was used without further purification.

Intermediate 19 methyl 3-amino-4-(5-methyl-2-nitrophenyl)butanoate

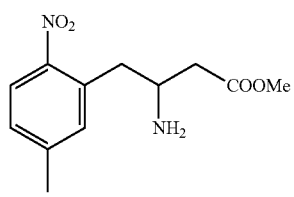 [SMILES: COC(=O)CC(N)Cc1cc(C)ccc1[N+](=O)[O-]]

The title product was prepared from methyl-3-amino-4-(5-methyl-2-nitrophenyl)but-2-enoate (Intermediate 18) according to the method described for Intermediate 11, and was used without further purification.

Intermediate 20 methyl 3-[(tert-butoxycarbonyl)amino]-4-(5-methyl-2-nitrophenyl)butanoate

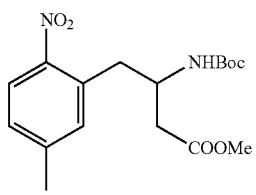 [SMILES: COC(=O)CC(Cc1cc(C)ccc1[N+](=O)[O-])NC(=O)OC(C)(C)C]

The title product was prepared from methyl-3-amino-4-(5-methyl-2-nitrophenyl)butanoate (Intermediate 19) according to the method described for Intermediate 12, and was used without further purification.

Intermediate 21 methyl 4-(2-amino-5-methyl-phenyl)-3-[(tert-butoxycarbonyl)amino]butanoate

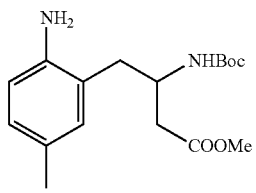 [SMILES: COC(=O)CC(Cc1cc(C)ccc1N)NC(=O)OC(C)(C)C]

The title product was prepared from ethyl-3-[(tert-butoxycarbonyl)amino]-4-(5-methyl-2-nitrophenyl)butanoate (Intermediate 20) according to the method described for Intermediate 13, and was used without further purification.

Intermediate 22

Tert-butyl (7-methyl-2-oxo-2,3,4,5-tetrahydro-1H-1-benzazepin-4-yl)carbamate

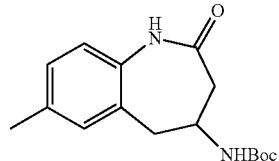 [SMILES: Cc1ccc2c(c1)CC(NC(=O)OC(C)(C)C)CC(=O)N2]

The title product was prepared from methyl 4-(2-amino-5-methyl-phenyl)-3-[(tert-butoxycarbonyl)amino]butanoate (Intermediate 21) according to the method described for Intermediate 14. MS (ESI) m/z 313.1 (M+Na)$^+$.

Intermediate 23

Tert-butyl (7-methyl-2-thioxo-2,3,4,5-tetrahydro-1H-1-benzazepin-4-yl)carbamate

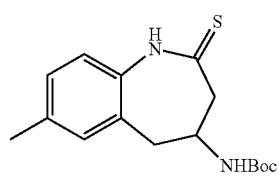 [SMILES: Cc1ccc2c(c1)CC(NC(=O)OC(C)(C)C)CC(=S)N2]

A mixture of 0.71 g (2.4 mmol) of tert-butyl (7-methyl-2-oxo-2,3,4,5-tetrahydro-1H-1-benzazepin-4-yl)carbamate (Intermediate 22), 25 mL of dry THF and 0.59 g (1.47 mmol) of Lawesson reagent was stirred at room temperature for 16 hours. The solvent was evaporated and the residue was purified by column chromatography using cyclohexane: ethyl acetate=80:20 as eluent to yield 0.42 g (56%) of the title product. MS (ESI) m/z 307 (M+H)$^+$.

Intermediate 24

Ethyl (5-bromo-2-nitrophenyl)acetate

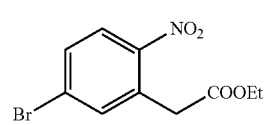

The title product was prepared from 4-nitro-bromobenzene (Combi-Blocks Inc.) according to the method described for Intermediate 6. MS (ESI) m/z 305.1 (M+NH$_4$)$^+$.

Intermediate 25

(5-bromo-2-nitrophenyl) acetic acid

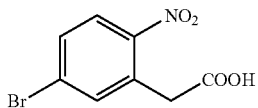

The title product was prepared from ethyl-(5-bromo-2-nitrophenyl)acetate (Intermediate 24) according to the method described for Intermediate 7, and was used without further purification.

Intermediate 26

5-[1-hydroxy-2-(5-bromo-2-nitrophenyl)ethylidene]-2,2-dimethyl-1,3-dioxane-4,6-dione

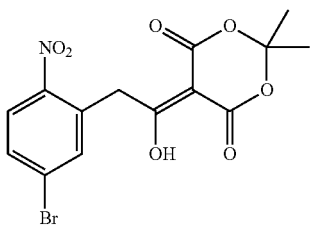

The title product was prepared from (5-bromo-2-nitrophenyl) acetic acid (Intermediate 25) according to the method described for Intermediate 8, and was used without further purification.

Intermediate 27 methyl 4-(5-bromo-2-nitrophenyl)-3-oxobutanoate

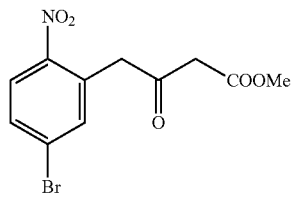 [SMILES: COC(=O)CC(=O)Cc1cc(Br)ccc1[N+](=O)[O-]]

The title product was prepared from 5-[1-hydroxy-2-(5-bromo-2-nitrophenyl)ethylidene]-2,2-dimethyl-1,3-dioxane-4,6-dione (Intermediate 26) according to the method described for Intermediate 9. MS (ESI) m/z 335.0 (M+NH$_4$)$^+$.

Intermediate 28 methyl 3-amino-4-(5-bromo-2-nitrophenyl)but-2-enoate

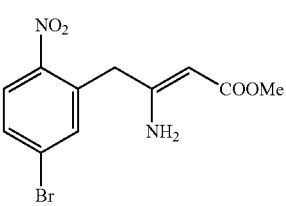 [SMILES: COC(=O)/C=C(\N)Cc1cc(Br)ccc1[N+](=O)[O-]]

The title product was prepared from methyl 4-(5-bromo-2-nitrophenyl)-3-oxobutanoate (Intermediate 27) according to the method described for Intermediate 10, and was used without further purification.

Intermediate 29 methyl 3-amino-4(5-bromo-2-nitrophenyl)butanoate

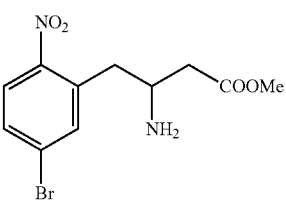

The title product was prepared from methyl-3-amino-4-(5-bromo-2-nitrophenyl)but-2-enoate (Intermediate 28) according to the method described for Intermediate 11. MS (ESI) m/z 319.0 (M+H)$^+$.

Intermediate 30 methyl 3-(tert-butoxycarbonyl)amino-4-(5-bromo-2-nitrophenyl)butanoate

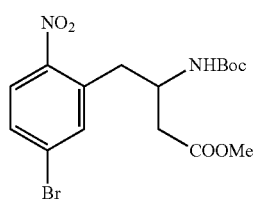 [SMILES: COC(=O)CC(Cc1cc(Br)ccc1[N+](=O)[O-])NC(=O)OC(C)(C)C]

The title product was prepared from methyl-3-amino-4-(5-bromo-2-nitrophenyl)butanoate (Intermediate 29) according to the method described for Intermediate 12. MS (ESI) m/z 439.1 (M+Na)$^+$.

Intermediate 31 methyl 4-(2-amino-5-bromo-phenyl)-3-[(tert-butoxycarbonyl)amino]butanoate

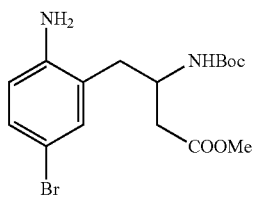 [SMILES: COC(=O)CC(Cc1cc(Br)ccc1N)NC(=O)OC(C)(C)C]

2.45 g (5.87 mmol) of methyl 3-[(tert-butoxycarbonyl)amino]-4-(5-bromo-2-nitrophenyl)butanoate (Intermediate 30) in 200 mL of toluene was hydrogenated at room temperature under atmospheric pressure in the presence of 0.25 g of 5% Pt/C catalyst. After filtration of the catalyst, the filtrate was concentrated to yield 2.15 g (94%) of the title product. MS (ESI) m/z 409.1 (M+Na)$^+$.

Intermediate 32

Tert-butyl 7-bromo-2-oxo-2,3,4,5-tetrahydro-1H-1-benzazepin-4-yl)carbamate

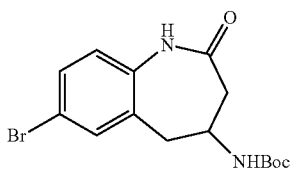

To a mixture of 2.15 g (5.55 mmol) of methyl 4-(2-amino-5-bromo-phenyl)-3-[(tert-butoxycarbonyl)amino]butanoate (Intermediate 31) and 60 mL of dry THF 0.69 g (6.11 mmol) potassium tert-butoxide was added under nitrogen at 0° C. over 30 minutes and the reaction mixture was stirred at room temperature for 3 hours. Dry ice was then added, and then the mixture was diluted with ethyl acetate and water. The phases were separated, the aqueous phase was extracted with ethyl acetate, the combined organic phases were washed with aqueous NaCl solution, dried over anhydrous Na$_2$SO$_4$, filtered and concentrated. Diethyl ether was added to the crude product, stirred for 1 hour at room temperature, filtered and washed with diethyl ether. Thus, 0.83 g (42%) of the title product was obtained. MS (ESI) m/z 409.1 (M+Na)$^+$.

Intermediate 33

Tert-butyl (7-bromo-2-thioxo-2,3,4,5-tetrahydro-1H-1-benzazepin-4-yl)carbamate

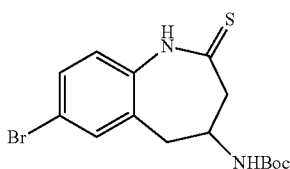

A mixture of 0.83 g (2.3 mmol) of tert-butyl (7-bromo-2-oxo-2,3,4,5-tetrahydro-1H-1-benzazepin-4-yl)carbamate (Intermediate 32), 28 mL of dry THF and 0.57 g (1.4 mmol) of Lawesson reagent was stirred at room temperature for 16 hours. The solvent was evaporated, diethyl ether was added to the residue and the precipitated solid was filtered off after 1 hour of stirring. Thus, 0.79 g (91%) of the title product was obtained. MS (ESI) m/z 371 (M+H)$^+$.

Intermediate 34 methyl[2-(5-bromo-2-nitrobenzyl)-1,3-dioxolan-2-yl]acetate

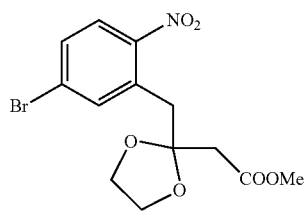 [SMILES: COC(=O)CC1(Cc2cc(Br)ccc2N)OCCO1]

A mixture of 3.28 g (10.4 mmol) of methyl 4-(5-bromo-2-nitrophenyl)-3-oxobutanoate (Intermediate 27), 1.7 mL of methanol, 118 mg (0.6 mmol) of p-toluene-sulfonic acid monohydrate, 5.68 mL (52 mmol) of trimethyl orthoformate and 11.6 mL (207 mmol) ethylene glycol was stirred at 50° C. for 96 hours. Aqueous K$_2$CO$_3$ solution was added to the reaction mixture, then extracted twice with ethyl acetate. The organic phases were dried over anhydrous Na$_2$SO$_4$, filtered and concentrated. The residue was purified by column chromatography using cyclohexane:ethyl acetate=80:20 as eluent. Thus, 2.29 g (61%) of the title product was obtained. MS (ESI) m/z 379.1 (M+NH$_4$).

Intermediate 35 methyl [2-(2-amino-5-bromobenzyl)-1,3-dioxolan-2-yl]acetate

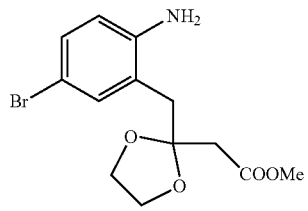

2.29 g (6.4 mmol) of methyl-[2-(5-bromo-2-nitrobenzyl)-1,3-dioxolan-2-yl]acetate (Intermediate 34) in 200 mL of toluene was hydrogenated at room temperature under atmospheric pressure in the presence of 0.56 g 5% Pt/C catalyst. After filtration of the catalyst, the filtrate was concentrated to yield 2.1 g (100%) of the title product. MS (ESI) m/z 330.0 (M+H)$^+$.

Intermediate 36

7-bromo-1,5-dihydrospiro[1-benzazepine-4,2'-[1,3]dioxolane]-2(3H)-one

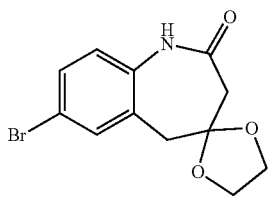 [SMILES: O=C1CC2(Cc3cc(Br)ccc3N1)OCCO2]

The title product was prepared from methyl [2-(2-amino-5-bromobenzyl)-1,3-dioxolan-2-yl]acetate (Intermediate 35) according to the method described for Intermediate 32. MS (ESI) m/z 300.0 (M+H)+.

Intermediate 37

Ethyl [2-nitro-5-trifluoromethyl)phenyl]acetate

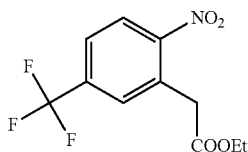 [SMILES: CCOC(=O)Cc1cc(C(F)(F)F)ccc1[N+](=O)[O-]]

7.45 g (66.55 mmol) potassium tert-butoxide was added to 75 mL of DMF under stirring and argon. The mixture was cooled to 0° C. and a solution of 5.00 g (26.16 mmol) of 1-nitro-4-(trifluoromethyl)benzene (Apollo Scientific Ltd.) and 2.98 mL (28.00 mmol) of chloroacetic acid ethyl ester in 25 mL of DMF was added dropwise. A dark purple reaction mixture was obtained which was stirred at 0° C. for 1.5 hours. Under ice-water cooling, 5% hydrochloric acid was added to the reaction mixture until the pH of the solution was about 3. As a result of acidification, the colour of the solution became yellow. The reaction mixture was extracted with 3×50 mL of ethyl acetate and the combined organic phases were washed with saturated NaHCO$_3$ solution and saturated NaCl solution. The solution was dried over MgSO$_4$, filtered and concentrated. Thus, 6.86 g (95%) of the title product was obtained as orange oil. MS (ESI) m/z 278.2 (M+H)+.

Intermediate 38

[2-nitro-5-(trifluormethyl)phenyl]acetic acid

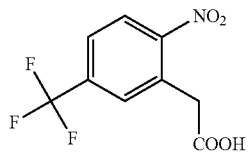 [SMILES: O=C(O)Cc1cc(C(F)(F)F)ccc1[N+](=O)[O-]]

6.85 g (24.71 mmol) of ethyl [2-nitro-5-(trifluoromethyl)phenyl]acetate (Intermediate 37) was dissolved in the mixture of 100 mL of THF, 50 mL of methanol and 50 mL of water. 5.18 g (123.45 mmol) of lithium hydroxide monohydrate was added to the orange solution and the reaction mixture was stirred at room temperature for 12 hours. The reaction mixture was concentrated and after dilution with water the pH was adjusted to about 4-5 with 1N hydrochloric acid. Orange precipitate appeared which was filtered off (the starting material of the previous step, 1-nitro-4-(trifluoromethyl)benzene). Further acidification (pH=2) resulted in further precipitation (expected product), thus the suspension was cooled in an ice-water bath, the yellow crystalline material was filtered off and washed with a little water. The acidic aqueous phase was extracted twice with 30 mL of ethyl acetate, the combined organic phases were washed with saturated NaCl solution, dried over MgSO$_4$, filtered and concentrated. The yellow product was dried in a drying oven. Thus, 4.88 g (79%) of the title product was obtained as yellow powder. MS (ESI) m/z does not ionize.

Intermediate 39

5-{1-hydroxy-2-[2-nitro-5-(trifluoromethyl)phenyl]ethyliden}-2,2-dimethyl-1,3-dioxane-4,6-dione

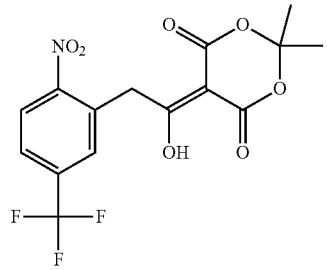 [SMILES: CC1(C)OC(=O)C(=C(O)Cc2cc(C(F)(F)F)ccc2[N+](=O)[O-])C(=O)O1]

4.79 g (19.23 mmol) of [2-nitro-5-(trifluoromethyl)phenyl]acetic acid (Intermediate 38) was dissolved in 250 mL of acetonitrile. 7.54 mL (43.30 mmol) of DIPEA, 3.05 g (21.20 mmol) of Meldrum's acid and 0.24 g (1.92 mmol) of DMAP was added to the solution. With moderate stirring and measuring the temperature of the solution, 2.61 mL (21.20 mmol) of trimethylacetyl chloride was added dropwise in a way that the temperature of the mixture did not exceed 30° C. The reaction mixture was then stirred at 40° C. for 4 hours. The solution was cooled in an ice-water bath and the pH was adjusted to acidic by the addition of 90 mL of 1N hydrochloric acid. After addition of further 90 mL of water, large precipitation occurred which was filtered off, washed with mother liquor and then with water. The product was dried in vacuo using phosphorus pentoxide at room temperature. Thus, 6.02 g (83%) of the title product was obtained as white powder. MS (ESI) m/z decomposes.

Intermediate 40 methyl 4-[2-nitro-5-(trifluoromethyl)phenyl]-3-oxobutanoate

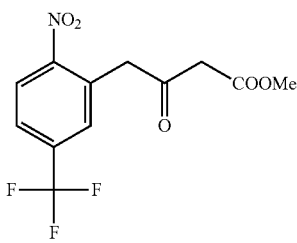 [SMILES: COC(=O)CC(=O)Cc1cc(C(F)(F)F)ccc1[N+](=O)[O-]]

5.11 g (13.60 mmol) of 5-{1-hydroxy-2-[2-nitro-5-(trifluoromethyl)phenyl]ethylidene}-2,2-dimethyl-1,3-dioxane-4,6-dione (Intermediate 39) was dissolved in a mixture of 68 mL of methanol and 264 mL of toluene, and the reaction mixture was stirred at 110° C. for 3 hours. After cooling to room temperature, 130 mL of saturated NaCl solution and 100 mL of ethyl acetate were poured into the solution. The phases were separated and the organic phase was dried over MgSO$_4$, filtered and concentrated. Thus, 4.09 g (98%) of the title product was obtained as yellow, waxy material. MS (ESI) m/z 306.1 (M+H)+; 323.1 (M+NH$_4$)+.

Intermediate 41 methy{2-[2-nitro-5-(trifluoromethyl)benzyl]-1,3-dioxolan-2-yl}acetate

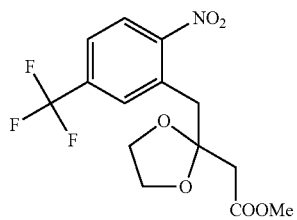 [SMILES: COC(=O)CC1(Cc2cc(C(F)(F)F)ccc2[N+](=O)[O-])OCCO1]

To a mixture of 4.87 g (15.95 mmol) of methyl 4-[2-nitro-5-(trifluoromethyl)phenyl]-3-oxobutanoate (Intermediate 40), 2.46 mL (60.80 mmol) of methanol, 15.00 mL (268.00 mmol) of ethylene glycol, and 7.49 mL (68.50 mmol) of trimethyl orthoformate, 0.18 g (0.94 mmol) p-toluenesulfonic acid monohydrate was added. The reaction mixture was stirred at 50° C. for 72 hours, then cooled and 70 mL of saturated Na$_2$CO$_3$ solution and 70 mL of water were added, which resulted in a highly precipitated mixture. The mixture was extracted twice with 100 mL of ethyl acetate and the combined organic phases were washed with saturated NaCl solution. After drying over MgSO$_4$, it was filtered and concentrated. The residue was purified by column chromatography using cyclohexane:ethyl acetate=4:1 as eluent. Thus, 2.75 g (49%) of the title product was obtained as light yellow oil. MS (ESI) m/z 316.1 (M+H)+; 367.1 (M+NH$_4$)+.

Intermediate 42 methyl{2-[2-amino-5-(trifluoromethyl)benzyl]-1,3-dioxolan-2-yl}acetate

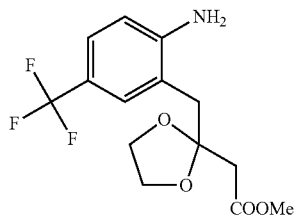 [SMILES: COC(=O)CC1(Cc2cc(C(F)(F)F)ccc2N)OCCO1]

2.19 g (6.27 mmol) of methyl{2-[2-nitro-5-(trifluoromethyl)benzyl]-1,3-dioxolan-2-yl}acetate (Intermediate 41) in 50 mL of toluene was hydrogenated at room temperature under atmospheric pressure in the presence of 0.219 g 5% Pt/C catalyst. After filtration of the catalyst, the filtrate was concentrated to yield 2.00 g (100%) of the title product as light orange oil. MS (ESI) m/z 320.2 (M+H)+.

Intermediate 43

7-trifluoromethyl-1,5-dihydrospiro[1-benzazepine-4,2'-[1,3]dioxolane]-2(3H)-one

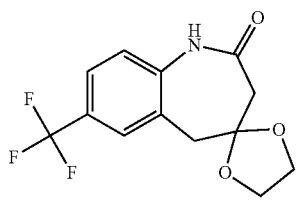 [SMILES: O=C1CC2(Cc3cc(C(F)(F)F)ccc3N1)OCCO2]

2.00 g (6.3 mmol) of methyl{2-[2-amino-5-(trifluoromethyl)benzyl]-1,3-dioxolan-2-yl}acetate (Intermediate 42) was dissolved in 70 mL of dry THF, then under argon the solution was cooled to 0° C. and 0.78 g (6.91 mmol) of potassium tert-butoxide was added. The dark coloured solution was stirred at room temperature for 4 hours, then dry ice was added to the reaction mixture. The solution was concentrated and the residue was purified by column chromatography using dichloromethane:methanol=95:5 as eluent. Thus, 1.05 g (58%) of the title product was obtained as white powder. MS (ESI) m/z 288.1 (M+H)+.

Intermediate 44 methyl 3-amino-4-[2-nitro-5-trifluoromethyl)phenyl] butanoate hydrochloride

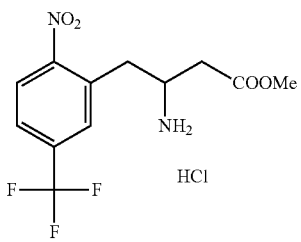 [SMILES: COC(=O)CC(N)Cc1cc(C(F)(F)F)ccc1[N+](=O)[O-] ; Cl]

a) Methyl 3-amino-4-[2-nitro-5-(trifluoromethyl)phenyl]but-2-enoate

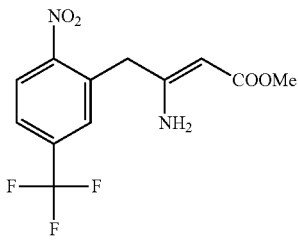 [SMILES: COC(=O)/C=C(\N)Cc1cc(C(F)(F)F)ccc1[N+](=O)[O-]]

1.00 g (3.3 mmol) of methyl 4-[2-nitro-5-(trifluoromethyl)phenyl]-3-oxobutanoate (Intermediate 40) was dissolved in 30 mL of methanol and 2.78 g (36.0 mmol) of ammonium-acetate was added. The reaction mixture was stirred at room temperature for 72 hours. 150 mL of water was added to the light brown solution and extracted twice with 70 mL of ethyl acetate. The combined organic phases were washed with saturated NaCl solution, dried over MgSO$_4$, filtered and concentrated, then dried over phosphorus pentoxide in desiccator. Thus 0.96 g (96%) of the title product was obtained.

b) Methyl 3-amino-4-[2-nitro-5-(trifluoromethyl)phenyl]butanoate hydrochloride 2.00 g (9.4 mmol) of NaBH(OAc)$_3$ was added to 15 mL of glacial acetic acid at 10° C. under aqueous cooling. A mixture of 0.96 g (3.2 mmol) of methyl 3-amino-4-[2-nitro-5-(trifluoromethyl)phenyl]but-2-enoate in 5 mL of glacial acetic acid was added dropwise to the above obtained solution, and the reaction mixture was stirred at room temperature for 2 hours. Then, under cooling with ice-water, 50 mL of water and 50 mL of 30% NaOH solution were added to the reaction mixture. The pH was adjusted to approximately 8 with saturated NaHCO$_3$ solution and extracted twice with 70 mL of ethyl acetate. The combined organic phases were washed with saturated NaCl solution, dried over MgSO$_4$ and filtered. Calculated amount of 2.5M hydrogen chloride solution in ethyl acetate solution was added to the filtered ethyl acetate solution, and the mixture was concentrated. The residue was crystallized by trituration with diisopropyl ether. Thus, 0.78 g (72%) of the title product was obtained as white powder. MS (ESI) m/z 307.1 (M+H)$^+$.

Intermediate 45 methyl 3-[(tert-butoxycarbonyl)amino]-4-[2-nitro-5-(trifluoromethyl)phenyl]butanoate

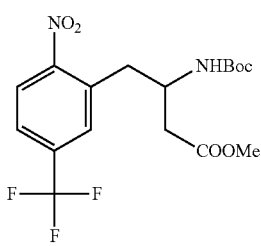 [SMILES: COC(=O)CC(Cc1cc(C(F)(F)F)ccc1[N+](=O)[O-])NC(=O)OC(C)(C)C]

0.78 g (2.3 mmol) of methyl 3-amino-4-[2-nitro-5-(trifluoromethyl)phenyl]butanoate hydrochloride (Intermediate 44) was dissolved in 20 mL of methanol. 0.77 g (9.10 mmol) of NaHCO$_3$ was added to the so obtained solution and 0.62 g (2.85 mmol) of di-tert-butyl dicarbonate was added to the suspension under ice-cooling and stirring, then the reaction mixture was allowed to warm to room temperature and stirred for 16 hours. During the work-up, 100 mL of water was poured into the mixture, then the precipitated material was filtered, washed with water, and dried. Thus 0.88 g (72%) of the title product was obtained as white powder. MS (ESI) m/z 429.2 (M+Na)$^+$.

Intermediate 46

3-[(tert-butoxycarbonyl)amino]-4-[2-nitro-5-(trifluoromethyl)phenyl]butanoic acid

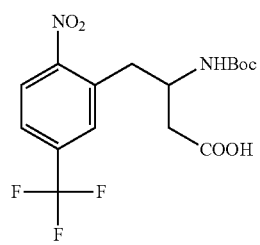

The title product was prepared from methyl 3-[(tert-butoxycarbonyl)amino]-4-[2-nitro-5-(trifluoromethyl)phenyl]butanoate (Intermediate 45) according to the method described in step f) of Method B) of Intermediate 1. MS (ESI) m/z 415.1 (M+Na)$^+$.

Intermediate 47

4-[2-amino-5-(trifluoromethyl)phenyl]-3-[(tert-butoxycarbonyl)amino]butanoic acid

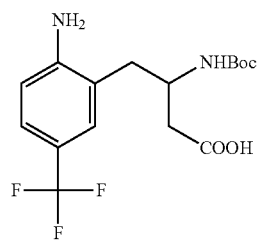

The title product was prepared from 3-[(tert-butoxycarbonyl)amino]-4-[2-nitro-5-(trifluoromethyl)phenyl]butanoic acid (Intermediate 46) according to the method described for Intermediate 42. MS (ESI) m/z 385.2 (M+Na)$^+$.

Intermediate 48

Tert-buty [2-oxo-7-(trifluoromethyl)-2,3,4,5-tetra-hydro-1H-1-benzazepin-4-yl]carbamate

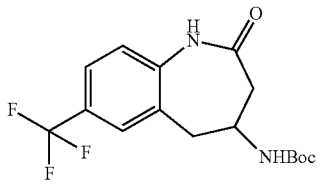

A mixture of 0.60 g (1.7 mmol) of 4-[2-amino-5-(trifluoromethyl)phenyl]-3-[(tert-butoxycarbonyl)amino]butanoic acid (Intermediate 47), 20 mL of DMF, 0.60 mL (3.39 mmol) of DIPEA, 0.30 g (1.99 mmol) of HOBt and 0.38 g (1.99 mmol) of EDC was stirred at room temperature for 16 hours and then concentrated. 30 mL of saturated NaHCO$_3$ solution was poured to the residue and after a short stirring the precipitated material was filtered, washed with water, and dried. Thus, 0.49 g (87%) of the title product was obtained as brown powder. MS (ESI) m/z 367.1 (M+H)$^+$.

Intermediate 49

Tert-butyl [2-thioxo-7-(trifluoromethyl)-2,3,4,5-tetrahydro-1H-1-benzazepin-4-yl]carbamate

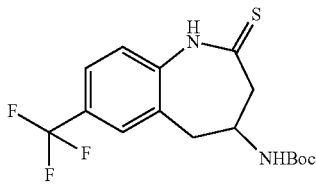 [SMILES: CC(C)(C)OC(=O)NC1CC(=O)Nc2ccc(C(F)(F)F)cc2C1]

A mixture of 0.46 g (1.3 m ol) of tert-butyl [2-oxo-7-(trifluoromethyl)-2,3,4,5-tetrahydro-1H-1-benzazepin-4-yl]carbamate (Intermediate 48), 10 mL of pyridine and 0.70 g (1.7 mmol) of Lawesson reagent was stirred at 120° C. for 3 hours. The reaction mixture was concentrated and stirred at room temperature for 12 hours after addition of 10 mL of water and 20 mL of saturated NaHCO$_3$ solution. The precipitated material was filtered, washed with water, and dried. Thus, 0.44 g (92%) of the title product was obtained as brown powder which was used without further purification.

Intermediate 50

Tert-butyl [2-(m ethylsulfanyl)-7-(trifluoromethyl)-4,5-dihydro-3H-1-benzazepin-4-yl]carbamate

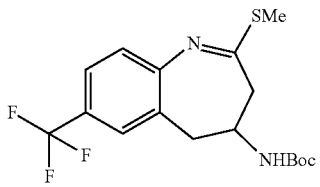 [SMILES: CSC1=Nc2ccc(C(F)(F)F)cc2CC(NC(=O)OC(C)(C)C)C1]

0.44 g (1.2 mmol) of tert-butyl [2-thioxo-7-(trifluoromethyl)-2,3,4,5-tetrahydro-1H-1-benzazepin-4-yl]carbamate (Intermediate 49) was dissolved in 30 mL of acetone, and 0.34 g (2.44 mmol) of K$_2$CO$_3$ was added. 0.23 mL (3.7 mmol) of iodomethane was added dropwise to the reaction mixture and it was stirred at room temperature for 24 hours. 20 mL of ethyl acetate was poured to the reaction mixture and the organic phase was first washed with water, then with saturated NaCl solution, dried over MgSO$_4$, filtered and concentrated. Thus, 0.46 g (100%) of the title product was obtained as orange powder. MS (ES) m/z 375.1 (M+H)$^+$.

Intermediate 51 methyl [2-(5-chloro-2-nitrobenzyl)-1,3-dioxolan-2-yl]acetate

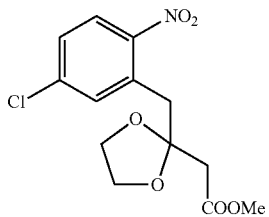 [SMILES: COC(=O)CC1(Cc2cc(Cl)ccc2[N+](=O)[O-])OCCO1]

The title product was prepared from methyl 4-(5-chloro-2-nitrophenyl)-3-oxobutanoate (step b) of Method B) of Intermediate 1) according to the method described for Intermediate 41. MS (ESI) m/z 316.1 (M+H)+; 333.1 (M+NH$_4$)$^+$.

Intermediate 52 methyl [2-(2-amino-5-chlorobenzyl)-1,3-dioxolan-2-yl]acetate

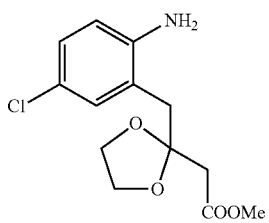 [SMILES: COC(=O)CC1(Cc2cc(Cl)ccc2N)OCCO1]

The title product was prepared from methyl [2-(5-chloro-2-nitrobenzyl)-1,3-dioxolan-2-yl]acetate (Intermediate 51) according to the method described for Intermediate 42. MS (ESI) m/z 286.1 (M+H)$^+$.

Intermediate 53

7-chloro-1,5-dihydrospiro[1-benzazepine-42'-[1,3]dioxolane]-2(3H)-one

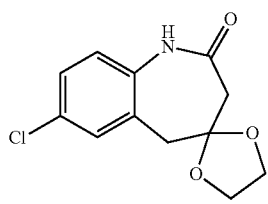 [SMILES: O=C1CC2(Cc3cc(Cl)ccc3N1)OCCO2]

The title product was prepared from methyl [2-(2-amino-5-chlorobenzyl)-1,3-dioxolan-2-yl]acetate (Intermediate 52) according to the method described for Intermediate 43. MS (ESI) m/z 254.1 (M+H)$^+$.

Intermediate 54

Tert-butyl 2-{[trans-4-trifluoromethyl)cyclohexyl]carbonyl}hydrazine carboxylate

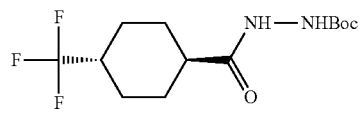

2.13 g (10.9 mmol) of trans-4-(trifluoromethyl)cyclohexan carboxylic acid (Manchester Organics Ltd.) was dissolved in 50 mL of DMF. 1.44 g (10.9 mmol) of tert-butylhydrazine carboxylate, 4.75 mL (27.3 mmol) of DIPEA, 2.00 g (13.10 mmol) of HOBt and 2.51 g (13.1 mmol) of EDC was added to the solution. The reaction mixture was stirred at room temperature for 36 hours, then concentrated. 40 mL of saturated NaHCO$_3$ solution was added to the residue and after a short stirring the precipitate was filtered, washed with water and dried in a vacuum oven over phosphorus pentoxide. Thus, 3.35 g (99%) of the title product was obtained as white powder. GC-MS (EI) m/z 310.1.

Intermediate 55

Trans-4-(trifluoromethyl)cyclohexanecarboxylic acid hydrazide

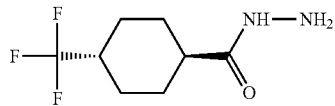 [SMILES: NNC(=O)[C@H]1CC[C@H](C(F)(F)F)CC1]

3.35 g (10.8 mmol) of tert-butyl 2-{[trans-4-(trifluoromethyl)cyclohexyl]carbonyl}hydrazine carboxylate (Intermediate 54) was dissolved in a mixture of 50 mL of ethyl acetate and 20 mL of ethanol, then 30 mL of 2.5 M hydrogen chloride solution in ethyl acetate was added. The reaction mixture was stirred at room temperature for 16 hours, then 150 mL of diethyl ether was added and it was cooled in an ice-water bath. The precipitated product was filtered and washed with diethyl ether. The filtered material was stirred with 100 mL of saturated NaHCO$_3$ solution (pH ~8), filtered, washed with water, and dried in a vacuum oven over phosphorous pentoxide. Thus, 177 g (78%) of the title product was obtained as white powder. GC-MS (EI) m/z 210.1

Intermediate 56

Tert-butyl 2-[(3,3-difluorocyclobutyl)carbonyl]hydrazine carboxylate

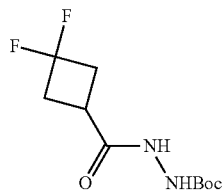 [SMILES: CC(C)(C)OC(=O)NNC(=O)C1CC(F)(F)C1]

The title product was prepared from 3,3-difluoro-cyclobutane carboxylic acid (Combi-Blocks Inc.) according to the method described for Intermediate 54. GC-MS (EI) m/z 250.1.

Intermediate 57

3,3-difluorocyclobutane carboxylic acid hydrazide

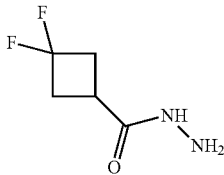

The title product was prepared from tert-butyl 2-[(3,3-difluorocyclobutyl)carbonyl]hydrazine carboxylate (Intermediate 56) according to the method described for Intermediate 55. GC-MS (EI) m/z 150.1.

Intermediate 58 methyl 4-(5-chloro-2-nitrophenyl)-3-hydroxybutanoate

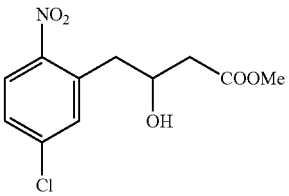 [SMILES: COC(=O)CC(O)Cc1cc(Cl)ccc1[N+](=O)[O-]]

3.13 g (11.5 mmol) of methyl 4-(5-chloro-2-nitrophenyl)-3-oxobutanoate (step b) of Method B) of Intermediate 1) was dissolved in 100 mL of methanol, the solution was cooled to 0° C., and 0.48 g (12.6 mmol) of NaBH$_4$ was added to the reaction mixture. The resulting mixture was stirred at room temperature for 16 hours. The reaction mixture was concentrated and 100 mL of water was added to the residue, the pH of the solution was adjusted to about 7 with 5% hydrochloric acid. The aqueous phase was extracted with diethyl ether, the organic phase was dried over MgSO₄, filtered and concentrated. Thus, 2.85 g (90%) of the title product was obtained which was used without further purification in the next step.

Intermediate 59 methyl 3-{[tert-butyl(dimethyl)silyl]oxy}-4-(5-chloro-2-nitrophenyl)butanoate

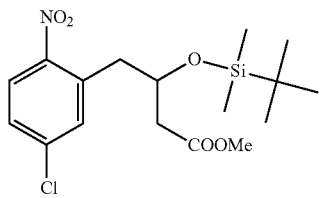 [SMILES: COC(=O)CC(Cc1cc(Cl)ccc1[N+](=O)[O-])O[Si](C)(C)C(C)(C)C]

1.36 g (5.0 mmol) of methyl 4-(5-chloro-2-nitrophenyl)-3-hydroxybutanoate (Intermediate 58) was dissolved in 15 mL of DMF, then 0.85 g (12.4 mmol) of 1H-imidazole and 0.90 g (6.0 mmol) of tert-butyl dimethylchlorosilane was added. The solution was stirred at room temperature for 24 hours. The reaction mixture was poured into water and the product was extracted twice with 50 mL of ethyl acetate. The combined organic phases were washed with saturated NaCl solution, dried over MgSO₄, filtered and concentrated. The residue was purified by column chromatography using n-hexane:ethyl acetate=4:1 as eluent. Fractions containing the expected product were concentrated to yield 1.70 g (88%) of the title product. MS (ESI) m/z 388.2 (M+H)⁺.

Intermediate 60

3-{[tert-butyl(dimethyl)silyl]oxy}-4-(5-chlor-2-nitrophenyl)butanoic acid

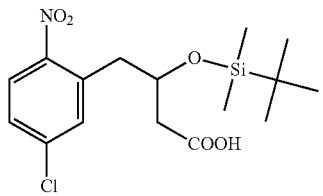 [SMILES: CC(C)(C)[Si](C)(C)OC(CC(=O)O)Cc1cc(Cl)ccc1[N+](=O)[O-]]

The title product was prepared from methyl 3-{[tert-butyl(dimethyl)silyl]oxy}-4-(5-chloro-2-nitrophenyl)butanoate (Intermediate 59) according to the method described for Intermediate 38. MS (ESI) m/z 374.2 (M+H)⁺.

Intermediate 61

4-(2-amino-5-chlorophenyl)-3-{[tert-butyl(dimethyl)silyl]oxy}butanoic acid

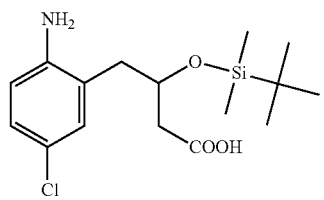 [SMILES: CC(C)(C)[Si](C)(C)OC(CC(=O)O)Cc1cc(Cl)ccc1N]

The title product was prepared from 3-{[tert-butyl(dimethyl)silyl]oxy}-4-(5-chloro-2-nitrophenyl)butanoic acid (Intermediate 60) according to the method described for Intermediate 42. MS (ESI) m/z 344.2 (M+H)⁺.

Intermediate 62

4-{[tert-butyl(dimethyl)silyl]oxy}-7-chloro-1,3,4,5-tetrahydro-2H-1-benzazepine-2-one

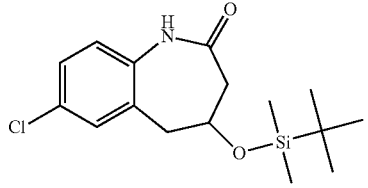 [SMILES: CC(C)(C)[Si](C)(C)OC1CC(=O)Nc2ccc(Cl)cc2C1]

The title product was prepared from 4-(2-amino-5-chlorophenyl)-3-{[tert-butyl(dimethyl)silyl]oxy}butanoic acid (Intermediate 61) according to the method described for Intermediate 48. MS (ESI) m/z 326.2 (M+H)⁺.

Intermediate 63

4-{[tert-butyl(dimethyl)silyl]oxy}-7-chloro-1,3,4,5-tetrahydro-2H-1-benzazepine-2-thione

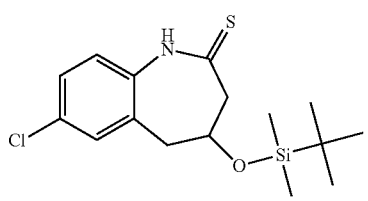 [SMILES: CC(C)(C)[Si](C)(C)OC1CC(=S)Nc2ccc(Cl)cc2C1]

The title product was prepared from 4-{[tert-butyl(dimethyl)silyl]oxy}-7-chloro-1,3,4,5-tetrahydro-2H-1-benzazepine-2-one (Intermediate 62) according to the method described for Intermediate 49. MS (ESI) m/z 342.1 (M+H)⁺.

Intermediate 64 methyl trans-4-(piperidin-1-ylmethyl)cyclohexane carboxylate

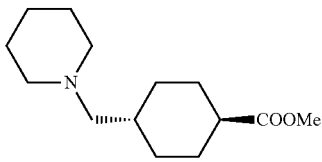 [SMILES: COC(=O)[C@H]1CC[C@H](CN2CCCCC2)CC1]

0.30 g (1.8 mmol) of methyl trans-4-formylcyclohexane carboxylate (Synthonix) was dissolved in 10 mL of 1,2-dichloroethane, and 0.52 mL (5.3 mmol) piperidine and 0.19 mL (3.4 mmol) acetic acid were added to the solution. The resulting mixture was cooled to 0° C. and 1.16 g (5.5 mmol) of NaBH(OAc)$_3$ was added, and the mixture was stirred at room temperature for 16 hours. Then, 30 mL of water was added to the reaction mixture and the pH of the mixture was adjusted to about 9 with Na$_2$CO$_3$ solution. The mixture was extracted twice with 20 mL of dichloromethane, the combined organic phases were dried over anhydrous MgSO$_4$, filtered and concentrated. Thus, 0.40 g (95%) of the title product was obtained which was used without further purification.

Intermediate 65

Trans-4-(piperidin-1-ylmethyl)cyclohexane carboxylic acid hydrazide

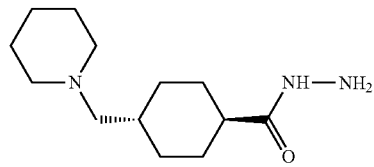 [SMILES: NNC(=O)[C@H]1CC[C@H](CN2CCCCC2)CC1]

0.40 g (1.7 mmol) of methyl trans-4-(piperidin-1-ylmethyl)cyclohexane carboxylate (Intermediate 64) was dissolved in 5 mL of methanol, and the solution was poured into a pressure-resistant glass reactor. 5 ml (100 mmol) of hydrazine hydrate was added and the reaction mixture was stirred at 75° C. for 16 hours. The reaction mixture was concentrated and cyclohexane and anhydrous toluene were evaporated off the residue. Thus, 039 g (97%) of the title product was obtained as white powder. GC-MS (EI) m/z 239.2.

Intermediate 66

Tert-butyl 2-[(4,4-difluorocyclohexyl)carbonyl]hydrazine carboxylate

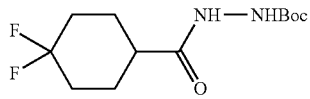 [SMILES: CC(C)(C)OC(=O)NNC(=O)C1CCC(F)(F)CC1]

The title product was prepared from 4,4-difluorocyclohexane carboxylic acid (Combi-Blocks Inc.) according to the method described for Intermediate 54. MS (ESI) m/z 301.2 (M+Na)$^+$.

Intermediate 67

4,4-difluorocyclohexane carboxylic acid hydrazide

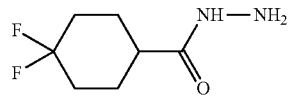

3.39 g (12.2 mmol) of tert-butyl 2-[(4,4-difluorocyclohexyl)carbonyl]hydrazine carboxylate (Intermediate 66) was dissolved in 50 mL of ethyl acetate, then 50 mL of 2.5M hydrogen chloride solution in ethyl acetate was added to the solution. The reaction mixture was stirred at room temperature for 16 hours and then concentrated. 15 mL of dichloromethane and 15 mL of distilled water was added to the residue, and the pH of the aqueous phase was basified with saturated NaHCO$_3$ solution, then the mixture was concentrated. The obtained residue was suspended in ethyl acetate, the insoluble solid was filtered off, the filtrate was dried over MgSO$_4$, filtered and concentrated. Thus, 2.08 g (93%) of the title product was obtained as white powder. MS (ESI) m/z 179.2 (M+H)$^+$.

Intermediate 68

Ethyl [2-(2-nitrobenzyl)-1,3-dioxolan-2-yl]acetate

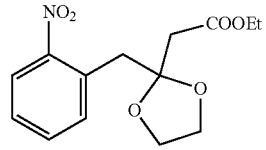 [SMILES: CCOC(=O)CC1(Cc2ccccc2[N+](=O)[O-])OCCO1]

2.00 g (8.0 mmol) of ethyl 4-(2-nitrophenyl)-3-oxobutanoate (D. Royer et al., *Tetrahedron* 2008, 64:9607-9618) was dissolved in 25 mL of toluene, then 4.45 mL (79.6 mmol) of ethylene glycol and 0.23 g (1.19 mmol) p-toluenesulfonic acid monohydrate were added to the resulting solution. Dean-Stark head was applied to the flask and the reaction mixture was boiled for 6 hours and then stirred at 50° C. for 48 hours. The resulting mixture was concentrated, the residue was mixed with water and extracted with diethyl ether. The organic phase was dried over MgSO$_4$, filtered and concentrated. The resulting crude product was purified by column chromatography using cyclohexane:ethyl acetate=4:1 as eluent. Thus, 0.68 g (29%) of the title product was obtained as pale yellow oil. MS (ESI) m/z 296.2 (M+H)$^+$.

Intermediate 69

Ethyl [2-(2-aminobenzyl)-1,3-dioxolan-2-yl]acetate

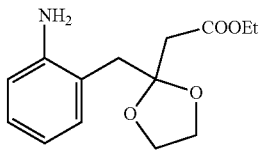 [SMILES: CCOC(=O)CC1(Cc2ccccc2N)OCCO1]

The title product was prepared from ethyl [2-(2-nitrobenzyl)-1,3-dioxolan-2-yl]acetate (Intermediate 68) according to the method described for Intermediate 42. MS (ESI) m/z 266.2 (M+H)⁺.

Intermediate 70

1,5-dihydrospiro[1-benzazepine-4,2'-[1,3]dioxolane]-2(3H)-one

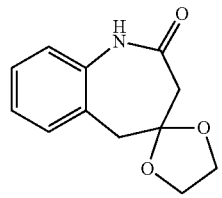 [SMILES: O=C1CC2(Cc3ccccc3N1)OCCO2]

The title product was prepared from ethyl [2-(2-aminobenzyl)-1,3-dioxolan-2-yl]acetate (Intermediate 69) according to the method described for Intermediate 43. MS (ESI) m/z 220.2 (M+H)⁺.

Intermediate 71

Ethyl 3-amino-4-(2-nitrophenyl)but-2-enoate

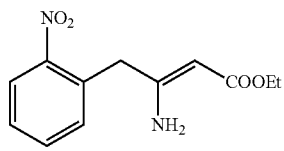 [SMILES: CCOC(=O)/C=C(\N)Cc1ccccc1[N+](=O)[O-]]

The title product was prepared from ethyl 4-(2-nitrophenyl)-3-oxobutanoate (D. Royer et al., *Tetrahedron* 2008, 64:9607-9618) according to the method described in step c) of Method B) of Intermediate 1. MS (ESI) m/z 252.1 (M+H)⁺.

Intermediate 72

Ethyl 3-amino-4-(2-nitrophenyl)butanoate

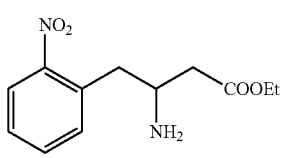 [SMILES: CCOC(=O)CC(N)Cc1ccccc1[N+](=O)[O-]]

1.29 g (6.1 mmol) of NaBH(OAc)₃ was dissolved in 10 mL of acetic acid and a solution of 0.51 g (2.03 mmol) of ethyl 3-amino-4-(2-nitrophenyl)but-2-enoate (Intermediate 71) in 5 mL of acetic acid was slowly added dropwise to the previous solution. The resulting mixture was stirred at room temperature for 48 hours. Then, the pH was adjusted to 8 with saturated NaHCO₃ solution and extracted with dichloromethane, and then the organic phase was dried over anhydrous MgSO₄, filtered and concentrated. Thus, 0.19 g (37%) of the title product was obtained as yellow oil. MS (ESI) m/z 253.2 (M+H)⁺.

Intermediate 73

Ethyl 3-tert-butoxycarbonyl)amino-4-(2-nitrophenyl)butanoate

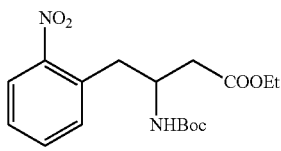 [SMILES: CCOC(=O)CC(Cc1ccccc1[N+](=O)[O-])NC(=O)OC(C)(C)C]

The title product was prepared from ethyl 3-amino-4-(2-nitrophenyl)butanoate (Intermediate 72) according to the method described in step e) of Method B) of Intermediate 1. MS (ESI) m/z 375.1 (M+Na)⁺.

Intermediate 74

3-[tert-butoxycarbonyl)amino]-4-(2-nitrophenyl)butanoic acid

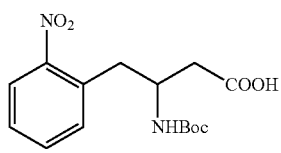 [SMILES: CC(C)(C)OC(=O)NC(CC(=O)O)Cc1ccccc1[N+](=O)[O-]]

The title product was prepared from ethyl 3-[tert-butoxycarbonyl)amino]-4-(2-nitrophenyl)butanoate (Intermediate 73) according to the method described in step f) of Method B) of Intermediate 1. MS (ESI) m/z 347.1 (M+Na)⁺.

Intermediate 75

4-(2-aminophenyl)-3-[(tert-butoxycarbonyl)amino]butanoic acid

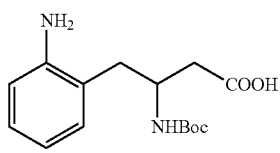 [SMILES: CC(C)(C)OC(=O)NC(CC(=O)O)Cc1ccccc1N]

The title product was prepared from 3-[tert-butoxycarbonyl)amino]4(2-nitrophenyl)butanoic acid (Intermediate 74) according to the method described in Method B) of Intermediate 2. MS (ESI) m/z 295.1 (M+H)⁺.

Intermediate 76

Tert-butyl (2-oxo-2,3,4,5-tetrahydro-1H-1-benzazepin-4-yl)carbamate

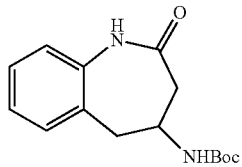 [SMILES: CC(C)(C)OC(=O)NC1CC(=O)Nc2ccccc2C1]

The title product was prepared from 4-(2-aminophenyl)-3-[(tert-butoxycarbonyl)amino]butanoic acid (Intermediate 75) according to the method described for Intermediate 3. MS (ESI) m/z 299.0 (M+Na)⁺.

Intermediate 77

Tert-butyl (2-thioxo-2,3,4,5-terrahydro-1H-1-benzazepin-4-yl)carbamate

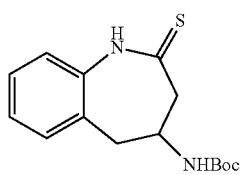 [SMILES: CC(C)(C)OC(=O)NC1CC(=S)Nc2ccccc2C1]

The title product was prepared from tert-butyl (2-oxo-2,3,4,5-tetrahydro-1H-1-benzazepin-4-yl)carbamate (Intermediate 76) according to the method described for Intermediate 4, which was used without further purification.

Intermediate 78

Trans-4-(pyrrolidin-1-ylcarbonyl)cyclohexane carboxylic acid hydrazide

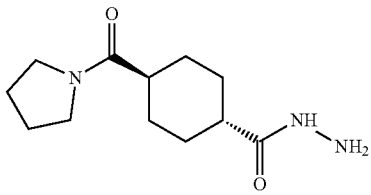 [SMILES: NNC(=O)[C@H]1CC[C@H](C(=O)N2CCCC2)CC1]

a) Methyl trans-4-(pyrrolidin-1-ylcarbonyl cyclohexane carboxylate

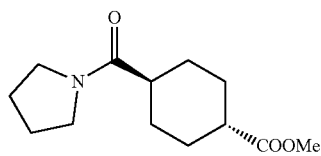 [SMILES: COC(=O)[C@H]1CC[C@H](C(=O)N2CCCC2)CC1]

A mixture of 186 mg (1 mmol) of trans-4-(methoxycarbonyl)cyclohexane carboxylic acid (Combi-Blocks Inc.), 83.5 μL (1 mmol) of pyrrolidine, 5 mL of dry DMF, 348 μL (2 mmol) of DIPEA, 230 mg (1.2 mmol) of EDC, and 162 mg (1.2 mmol) of HOBt was stirred at room temperature for 24 hours. Ethyl acetate and aqueous NaHCO₃ solution were added to the reaction mixture. The phases were separated and the aqueous phase was extracted once with ethyl acetate. The combined organic phases were washed with 1N hydrochloric acid and water, dried over anhydrous Na₂SO₄, filtered and concentrated. Thus, 180 mg (75%) of the title product was obtained. GC-MS (EI) m/z 239.

b) Trans-4-(pyrrolidin-1-ylcarbonyl)cyclohexane carboxylic acid hydrazide 180 mg (0.75 mmol) of methyl trans-4-(pyrrolidin-1-ylcarbonyl)cyclohexane carboxylate, 1.1 mL of methanol and 1.1 mL of hydrazine-hydrate were stirred in a pressure-resistant glass reactor at 75° C. for 24 hours. The reaction mixture was concentrated and cyclohexane was added, then evaporated off. Thus, 183 mg (76%) of the title product was obtained. GC-MS (EI) m/z 239.

Intermediate 79

Trans-4-(morpholin-1-ylcarbonyl)cyclohexane carboxylic acid hydrazide

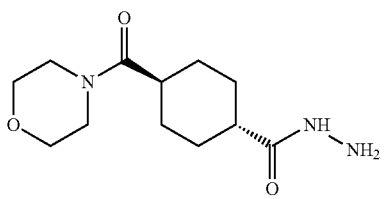 [SMILES: NNC(=O)[C@H]1CC[C@H](C(=O)N2CCOCC2)CC1]

a) Methyl trans-4-(morpholin-4-ylcarbonyl)cyclohexane carboxylate

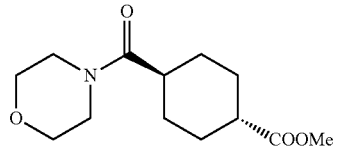 [SMILES: COC(=O)[C@H]1CC[C@H](C(=O)N2CCOCC2)CC1]

The title product was prepared from trans-4-(methoxycarbonyl)cyclohexane carboxylic acid (Combi-Blocks Inc.) and morpholine according to the method described in step a) of Intermediate 78. GC-MS (EI) m/z 255.

b) Trans-4-(Morpholin-1-ylcarbonyl)cyclohexanecarboxylic acid hydrazide

The title product was prepared from methyl trans-4-(morpholin-4-ylcarbonyl)cyclohexane carboxylate according to the method described in step b) of Intermediate 78. GC-MS (EI) m/z 255.

Intermediate 80

Trans-4-(dimethylamino)cyclohexane carboxylic acid hydrazide

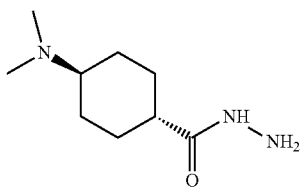

The title product was prepared from methyl trans-4-(dimethylamino)cyclohexane carboxylate (EP 1 582 521 A1 (5 Oct. 2005) TANABE SEIYAKU CO.) according to the method described for Intermediate 65. MS (ESI) m/z 186.3 (M+H)$^+$.

Intermediate 81

Trans-4-(morpholin-4-yl)cyclohexane carboxylic acid hydrazide

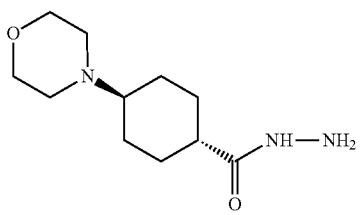 [SMILES: NNC(=O)[C@H]1CC[C@H](N2CCOCC2)CC1]

The title product was prepared from methyl trans-4-(morpholin-4-yl)cyclohexane carboxylate (EP 1 582 521 A1 (5 Oct. 2005) TANABE SEIYAKU CO.) according to the method described for Intermediate 65. GC-MS (EI) m/z 227

Intermediate 82

1-(pyrimidin-2-yl)azetidine-3-carboxylic acid hydrazide

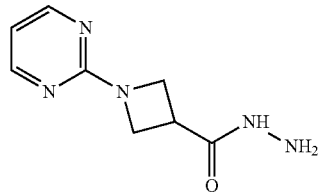 [SMILES: NNC(=O)C1CN(c2ncccn2)C1]

The title product was prepared from methyl 1-(pyrimidin-2-yl)azetidine-3-carboxylate (WO 2006/124748 A2 (23 Nov. 2006) LEXICON GENETICS INCORP.) according to the method described for Intermediate 65. MS (ESI) m/z 194.2 (M+H)$^+$.

Intermediate 83

1-(pyridin-2-yl)azetidine-3-carboxylic acid hydrazide

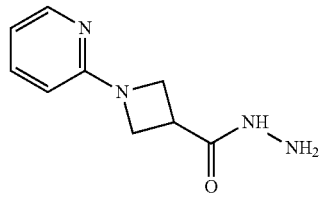 [SMILES: NNC(=O)C1CN(c2ccccn2)C1]

The title product was prepared from methyl 1-(pyridin-2-yl)azetidine-3-carboxylate (WO 2017/007756 A1 (12 Jan. 2017) RODIN THERAPEUTICS INC.) according to the method described for Intermediate 65. GC-MS (EI) m/z 192

Intermediate 84

Ethyl (trans)-3-methyl-2-oxo-1-oxa-3-azaspiro[4.5]decane-8-carboxylate

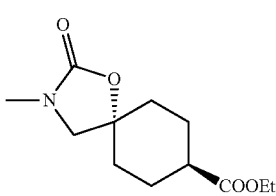 [SMILES: CCOC(=O)[C@H]1CC[C@]2(CC1)CN(C)C(=O)O2]

and

Intermediate 85

Ethyl (cis)-3-methyl-2-oxo-1-oxa-3-azaspiro[4.5]decane-8-carboxylate

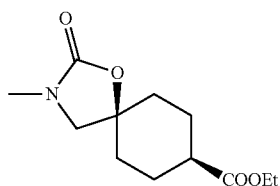 [SMILES: CCOC(=O)[C@H]1CC[C@@]2(CC1)CN(C)C(=O)O2]

1.8 g (45.0 mmol) of 60% sodium hydride dispersion in oil was suspended in 60 mL of dry DMF, cooled to 0-5° C., then 6.00 g (26.4 mmol) of a 1:1 mixture of ethyl (cis)-2-oxo-1-oxa-3-azaspiro[4.5]decane-8-carboxylate and ethyl (trans)-2-oxo-1-oxa-3-azaspiro[4.5]decane-8-carboxylate (WO 2008/092887 A1, (7 Aug. 2008) GLAXO GROUP LTD.) dissolved in 60 mL of DMF was added dropwise in such a way that the temperature of the mixture remained between 0 and 5° C. The reaction mixture was stirred for 20 minutes at this temperature, then 2.46 mL (39.5 mmol) of iodomethane was added dropwise over 20 minutes. The mixture was stirred for a further hour at 0-5° C., then allowed to warm to room temperature and stirred for 3 hours at this temperature. Then, 1.8 mL (31 mmol) of acetic acid was added dropwise over 10 minutes, after stirring for 15 minutes, the reaction mixture was concentrated and 90 mL of n-heptane was evaporated off the residue twice. 180 ml of ethyl acetate, 90 mL of saturated NaHCO$_3$ solution and 90 mL of water were added to the residue, the phases were separated, the organic phase was washed with 90 mL of NaCl, dried over Na$_2$SO$_4$, filtered and concentrated. The residue was purified by column chromatography using toluene:isopropanol=93:7 as eluent. The appropriate fractions were concentrated and the residues were crystallized with diisopropyl ether. Thus, 1.38 g (22%) of ethyl (trans)-3-methyl-2-oxo-1-oxa-3-azaspiro[4.5]decane-8-carboxylate (Intermediate 84) and 2.45 g (39%) of ethyl (cis)-3-methyl-2-oxo-1-oxa-3-azaspiro[4.5]decane-8-carboxylate (Intermediate 85) were obtained as white powder. GC-MS (E) m/z 241.

Intermediate 86

Trans)-3-methyl-2-oxo-1-oxa-3-azaspiro[4.5]decane-8-carboxylic acid hydrazide

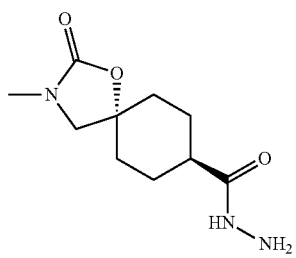 [SMILES: CN1C[C@]2(CC[C@@H](C(=O)NN)CC2)OC1=O]

The title product was prepared from ethyl (trans)-3-methyl-2-oxo-1-oxa-3-azaspiro[4.5]decane-8-carboxylate (Intermediate 84) according to the method described for Intermediate 65. GC-MS (EI) m/z 227.

Intermediate 87

(cis)-3-methyl-2-oxo-1-oxa-3-azaspiro[4.5]decane-8-carboxylic acid hydrazide

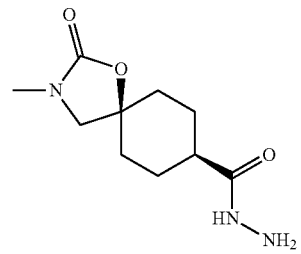 [SMILES: CN1C[C@]2(CC[C@H](C(=O)NN)CC2)OC1=O]

The title product was prepared from ethyl (cis)-3-methyl-2-oxo-1-oxa-3-azaspiro[4.5]decane-8-carboxylate (Intermediate 85) according to the method described for Intermediate 65. GC-MS (EI) m/z 227.

Intermediate 88

5-[2-(5-fluoro-2-nitrophenyl)-1-hydroxyethylidene]-2,2-dimethyl-1,3-dioxane-4,6-dione

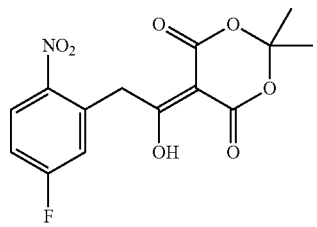 [SMILES: CC1(C)OC(=O)C(=C(O)Cc2cc(F)ccc2[N+](=O)[O-])C(=O)O1]

The title product was prepared from (5-fluoro-2-nitrophenyl)acetic acid (Combi-Blocks Inc.) according to the method described for Intermediate 39. MS (ESI) m/z 348.0 (M+Na)$^+$.

Intermediate 89 methyl 4-(5-fluoro-2-nitrophenyl)-3-oxobutanoate

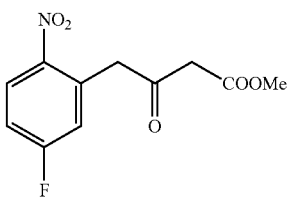 [SMILES: COC(=O)CC(=O)Cc1cc(F)ccc1[N+](=O)[O-]]

The title product was prepared from 5-[2-(5-fluoro-2-nitrophenyl)-1-hydroxyethylidene]-2,2-dimethyl-1,3-dioxane-4,6-dine (Intermediate 88) according to the method described for Intermediate 40. MS (ESI) m/z 273.1 (M+NH$_4$)$^+$.

Intermediate 90 methyl [2-(5-fluoro-2-nitrobenzyl-1,3-dioxolan-2-yl]acetate

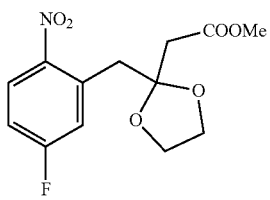 [SMILES: COC(=O)CC1(Cc2cc(F)ccc2[N+](=O)[O-])OCCO1]

The title product was prepared from methyl 4-(5-fluoro-2-nitrophenyl)-3-oxobutanoate (Intermediate 89) according to the method described for Intermediate 41. MS (ESI) m/z 317.2 $(M+NH_4)^+$.

Intermediate 91 methyl [2-(2-amino-5-fluorobenzyl)-1,3-dioxolan-2-yl]acetate

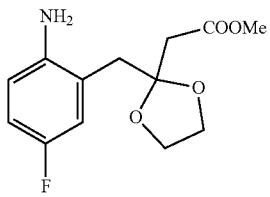 [SMILES: COC(=O)CC1(Cc2cc(F)ccc2N)OCCO1]

The title product was prepared from methyl [2-(5-fluoro-2-nitrobenzyl)-1,3-dioxolan-2-yl]acetate (Intermediate 90) according to the method described for Intermediate 42. MS (ESI) m/z 270.2 $(M+H)^+$.

Intermediate 92

7-fluoro-1,5-dihydrospiro[1-benzazepine-4,2'-[1,3]dioxolane]-2(3H)-one

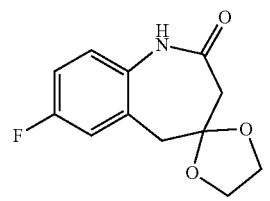 [SMILES: O=C1CC2(Cc3cc(F)ccc3N1)OCCO2]

The title product was prepared from methyl [2-(2-amino-5-fluorobenzyl)-1,3-dioxolan-2-yl]acetate (Intermediate 91) according to the method described for Intermediate 43. MS (ESI) m/z 238.2 $(M+H)^+$.

Intermediate 93

Tert-butyl (8-chloro-5,6-dihydro-4H-[1,2,4]triazolo[4,3-a][1]benzazepine-5-ylcarbamate

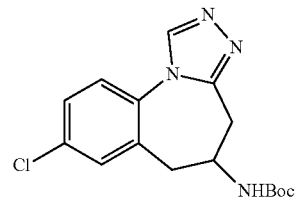 [SMILES: CC(C)(C)OC(=O)NC1Cc2cc(Cl)ccc2-n2cnnc2C1]

164 mg (0.48 mmol) of tert-butil [7-chloro-2-(methylsulfanyl)-4,5-dihydro-3H-1-benzazepin-4-yl]carbamate (Intermediate 5) was dissolved in 3 mL of 1,4-dioxane and the resulting solution was heated to 90° C. 145 mg (2.41 mmol) of formyl hydrazide was added over 4 hours under argon. The reaction mixture was then stirred at 90° C. for another 8 hours and after cooling to room temperature, the solvent was evaporated in vacuo. The residue was purified by column chromatography using dichloromethane:methanol=95:5 as eluent. Thus, 145 mg (95%) of the title product was obtained as white solid. MS (ESI) m/z 335.1 $(M+H)^+$.

Intermediate 94

Tert-butyl (1-bromo-8-chloro-5,6-dihydro-4H-[1,2,4]triazolo[4,3-a][1]benzazepin-5-yl)carbamate

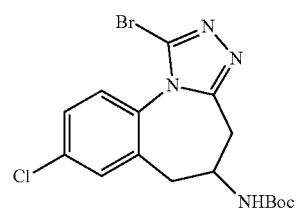 [SMILES: CC(C)(C)OC(=O)NC1Cc2cc(Cl)ccc2-n2c(Br)nnc2C1]

528 mg (1.58 mmol) of tert-butyl (8-chloro-5,6-dihydro-4H-[1,2,4]triazolo[4,3-a][1]benzazepin-5-yl)carbamate (Intermediate 93) was dissolved in 35 mL of THF. 622 mg (3.5 mmol) of N-bromosuccinimide was added and the resulting pale yellow solution was stirred at reflux for 60 minutes with illumination by an RH-500 type halogen lamp (Tracon Electric). At this time, the colour of the solution initially darkened and then gradually became discoloured. After cooling to room temperature, the solvent was evaporated in vacuo. The residue was purified by column chromatography using dichloromethane:methanol=97:3 as eluent. Thus, 592 mg (90%) of the title product was obtained as white solid. MS (ESI) m/z 415.1 $(M+H)^+$.

Intermediate 95

8'-chloro-4'H,6'H-spiro[1,3-dioxolane-2,5'-[1,2,4]triazolo[4,3-a][1]benzazepine]

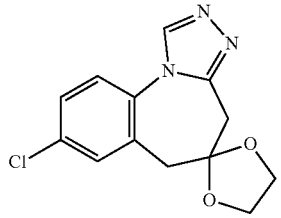 [SMILES: Clc1ccc2c(c1)CC1(Cc3nncn3-2)OCCO1]

356.5 mg (1.405 mmol) of 7-chloro-1,5-dihydrospiro[1-benzazepine-4,2'-[1,3]dioxolane]-2(3H)-one (Intermediate 53) was dissolved in 22 mL of dichloromethane and 11 μL (0.144 mmol) of trifluoroacetic acid was added. Under argon, 249.4 mg (1.686 mmol) of trimethyloxonium tetrafluoroborate was added and the reaction mixture was stirred at room temperature for 24 hours. At this time, 422.0 mg (7.027 mmol) of formyl hydrazide was added in 5 portions at reflux temperature over 4 hours, then the reaction mixture was stirred at reflux temperature for 15 hours. The reaction mixture was concentrated and the residue was dissolved in 22 mL of dioxane and the mixture was stirred at 80° C. for 2.5 hours. After cooling to room temperature, the solvent was evaporated in vacuo. The residue was purified by column chromatography using dichloromethane:methanl=95:5 as eluent. Thus, 248 mg (64%) of the title product was obtained. MS (ESI) m/z 335.1 (M+H)$^+$.

Intermediate 96

1'-bromo-8'-chloro-4'H,6'H-spiro[3-dioxolane-2,5'-[1,2,4]triazolo[4,3-a][1]benzazepine]

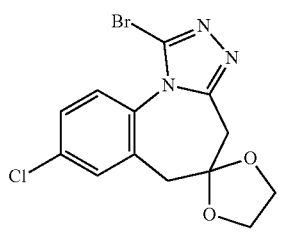 [SMILES: Clc1ccc2c(c1)CC1(Cc3nnc(Br)n3-2)OCCO1]

The title product was prepared from 8'-chloro-4'H,6'H-spiro[1,3-dioxolane-2,5'-[1,2,4]triazolo[4,3-a][1]benzazepine] (Intermediate 95) according to the method described for Intermediate 94. MS (ESI) m/z 358.0 (M+H)$^+$.

Intermediate 97

Trans-4-(piperidin-1-ylcarbonyl)cyclohexane carboxylic acid hydrazide

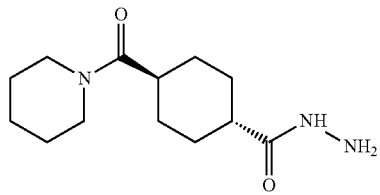 [SMILES: NNC(=O)[C@H]1CC[C@H](C(=O)N2CCCCC2)CC1]

a) Methyl trans-4-(piperidin-1-ylcarbonyl)cyclohexane carboxylate

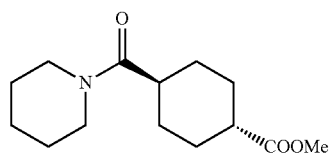 [SMILES: COC(=O)[C@H]1CC[C@H](C(=O)N2CCCCC2)CC1]

The title product was prepared from trans-4-(methoxycarbonyl)cyclohexane carboxylic acid (Combi-Blocks Inc.) and piperidine according to the method described in step a) of Intermediate 78. GC-MS (E) m/z 253.

b) Trans-4-(piperidin-1-ylcarbonyl)cyclohexane carboxylic acid hydrazide

The title product was prepared from methyl trans-4-(piperidin-1-ylcarbonyl)cyclohexane carboxylate according to the method described in step b) of Intermediate 78. GC-MS (EI) m/z 253.

Intermediate 98

7-chloro-1,5-dihydrospiro[1-benzazepine-4,2'-[1,3]dioxane]-2(3H)-one

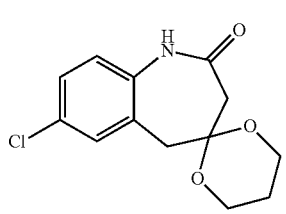 [SMILES: O=C1CC2(Cc3cc(Cl)ccc3N1)OCCCO2]

a) Methyl 2-(5-chloro-2-nitrobenzyl)-1,3-dioxan-2-yl acetate

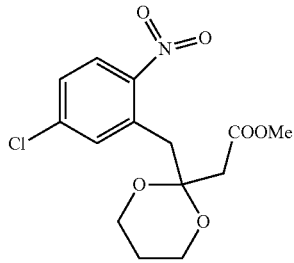 [SMILES: COC(=O)CC1(Cc2cc(Cl)ccc2[N+](=O)[O-])OCCCO1]

The title product was prepared from methyl 4-(5-chloro-2-nitrophenyl)-3-oxobutanoate (step b) of Method B) of Intermediate 1) and 1,3-propanediol according to the method described for Intermediate 41. MS (ESI) m/z 330.2 (M+H)⁺.

b) Methyl [2-(2-amino-5-chlorobenzyl)-1,3-dioxan-2-yl]acetate

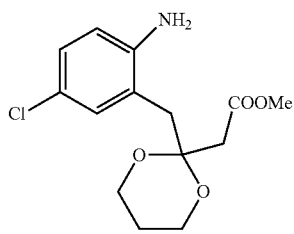 [SMILES: COC(=O)CC1(Cc2cc(Cl)ccc2N)OCCCO1]

The title product was prepared from methyl [2-(5-chloro-2-nitrobenzyl)-1,3-dioxan-2-yl]acetate (step a) of Intermediate 98) according to the method described for Intermediate 42. MS (ESI) m/z 322.2 (M+Na)⁺.

c) 7-chloro-1,5-dihydrospiro[1-benzazepine-4,2'-[1,3]dioxane]-2(3H)-one

The title product was prepared from methyl [2-(2-amino-5-chlorobenzyl)-1,3-dioxan-2-yl]acetate (step b) of Intermediate 98) according to the method described for Intermediate 43. MS (ESI) m/z 268.1 (M+H)⁺.

Intermediate 99 methyl (5s,8s)-1-oxo-2-(propan-2-yl)-2-azaspiro[4.5]decane-8-carboxylate

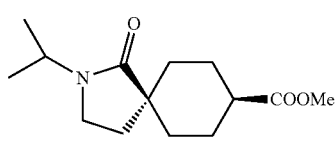 [SMILES: COC(=O)[C@H]1CC[C@]2(CCN(C(C)C)C2=O)CC1]

And

Intermediate 100 methyl (5r,8r)-1-oxo-2-(propan-2-yl)-2-azaspiro[4.5]decane-8-carboxylate

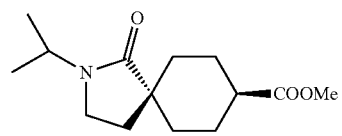 [SMILES: COC(=O)[C@H]1CC[C@@]2(CCN(C(C)C)C2=O)CC1]

A mixture of 0.9 g (4.0 mmol) of dimethyl trans-1-(2-oxoethyl)cyclohexane-1,4-dicarboxylate (WO 2011/143150 A1, (05.10. 2011) SANOFI), 40 mL of 1,2-dichloroethane, 316 μL (3.71 mmol) of isopropylamine and 637 μL (11.1 mmol) of acetic acid was cooled to 5° C. and 2.36 g (11.1 mmol) of sodium triacetoxyborohydride was added to the reaction mixture at such a rate to keep the internal temperature below 5° C. After completion of the addition the reaction mixture was stirred at room temperature for 2 h, then diluted with water. The pH of the mixture was adjusted to 8 by addition of 10% K₂CO₃ solution, the phases were separated and the water phase was extracted with dichloromethane. The combined organic phases were successively washed with 10% K₂CO₃ solution, water and brine, dried over Na₂SO₄, filtered and concentrated. The residue was dissolved in 40 mL of dry THF and 330 mg (2.94 mmol) of potassium tert-butoxide was added. The reaction mixture was stirred at room temperature for 3 h, then neutralized by addition of solid CO₂. After addition of water the THF was evaporated and the water phase was extracted with ethyl acetate. The organic phase was dried over Na₂SO₄, filtered and concentrated. The residue was purified by flash column chromatography using cyclohexane: ethyl acetate=45:55 mixture as eluent to yield 56 mg (6%) of methyl (5s,8s)-1-ox-2-(propan-2-yl)-2-azaspiro[4.5]decane-8-carboxylate (Intermediate 99) as the first fraction and 172 mg (19%) of methyl (5r,8r)-1-oxo-2-(propan-2-yl)-2-azaspiro[4.5]decane-8-carboxylate (Intermediate 100) as the second fraction. GC-MS (E) m/z 253.

Intermediate 101

(5s,8s)-1-oxo-2-(propan-2-yl)-2-azaspiro[4.5]decane-8-carbohydrazide

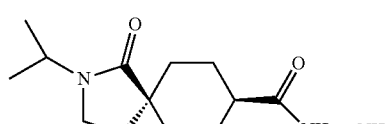

The title compound was prepared methyl (5s,8s)-1-oxo-2-(propan-2-yl)-2-azaspiro[4.5]decane-8-carboxylate (Intermediate 99) according to the method described for Intermediate 65. GC-MS (EI) m/z 253.

Intermediate 102

(5r,8r)-1-oxo-2-(propan-2-yl-2-azaspiro[4.5]decane-8-carbohydrazide

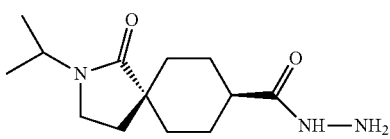

The title compound was prepared from methyl (5r,8r)-1-oxo-2-(propan-2-yl)-2-azaspiro[4.5]decane-8-carboxylate (Intermediate 100) according to the method described for Intermediate 65. GC-MS (EI) m/z 253.

Intermediate 103

7-chloro-4-methoxy-1,3,4,5-tetrahydro-2H-1-benzazepine-2-thione

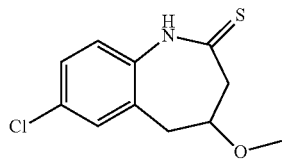

a) Methyl 4-(5-chloro-2-nitrophenyl)-3-methoxybutanoate

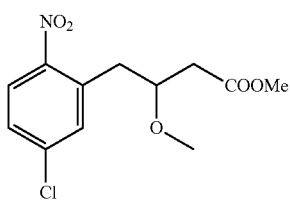

A mixture of 1.37 g (5 mmol) of methyl 4-(5-chloro-2-nitrophenyl)-3-hydroxybutanoate (Intermediate 58), 90 mL of dichloromethane, 1.4 g of 4 Å molecular sieves, 3.21 g (15 mmol) of 1,8-bis(dimethylamino)naphthalene and 2.22 g (15 mmol) of trimethyloxonium tetrafluoroborate was stirred at room temperature for 20 h, then filtered and the solid material was washed with dichloromethane. The filtrate was washed with 3M HCl solution and water, dried over $Na_2SO_4$, filtered and concentrated. The residue was purified by flash column chromatography using cyclohexane: ethyl acetate=65:35 as eluent to yield 1097 g (76%) of the title compound. MS (ESI) m/z 310.1 (M+Na)$^+$.

b) 4-(5-chloro-2-nitrophenyl)-3-methoxybutanoic acid

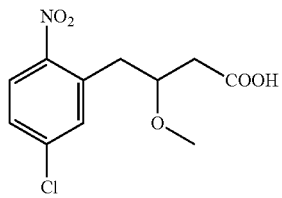 [SMILES: COC(CC(=O)O)Cc1cc(Cl)ccc1[N+](=O)[O-]]

A mixture of 0.52 g (1.8 mmol) of methyl 4-(5-chloro-2-nitrophenyl)-3-methoxybutanoate (Step a) of Intermediate 103), 5 mL methanol, 0.9 mL of 4M NaOH and 1.6 mL of water was stirred at room temperature for 20 h, then the reaction mixture was acidified with 1M HCl solution. The precipitated product was filtered off, washed with water and dried to yield 386 mg (78%) of the title compound. MS (ESI) m/z 296.1 (M+Na)$^+$.

c) 4-(2-amino-5-chlorophenyl)-3-methoxybutanoic acid

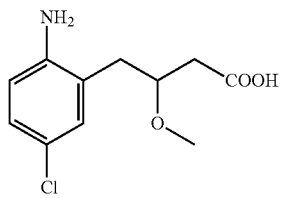

The title compound was prepared from 4-(5-chloro-2-nitrophenyl)-3-methoxybutanoic acid (Step b) of Intermediate 103) according to the method described in Method B of Intermediate 2. MS (ESI) m/z 244.1 (M+H)$^+$.

d) 7-chloro-4-methoxy-1,3,4,5-tetrahydro-2H-1-benzazepin-2-one

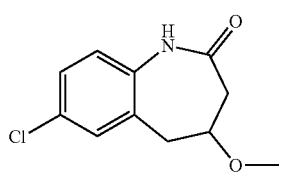

The title compound was prepared from 4-(2-amino-5-chlorophenyl)-3-methoxybutanic acid (Step c) of Intermediate 103) according to the method described for Intermediate 3. MS (ESI) m/z 226.1 (M+H)$^+$.

e) 7-chloro-4-methoxy-1,3,4,5-tetrahydro-2H-1-benzazepine-2-thione

The title compound was prepared from 7-chloro-4-methoxy-1,3,4,5-tetrahydr-2H-1-benzazepin-2-ne (Step d) of Intermediate 103) according to the method described for Intermediate 23. MS (ESI) m/z 242.1 (M+H)$^+$.

Intermediate 104

7-chloro-1,5-dihydrospiro[1-benzazepine-4,2'-[1,3]dioxepan]-2(3H)-one

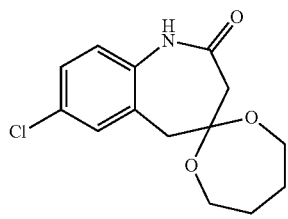 [SMILES: O=C1CC2(Cc3cc(Cl)ccc3N1)OCCCCO2]

a) Methyl [2-(5-chloro-2-nitrobenzyl)-1,3-dioxepan-2-yl]acetate

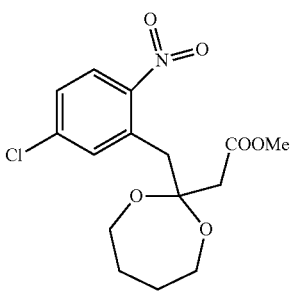 [SMILES: COC(=O)CC1(Cc2cc(Cl)ccc2[N+](=O)[O-])OCCCCO1]

The title compound was prepared from methyl 4-(5-chloro-2-nitrophenyl)-3-oxobutanoate (Step b) of Method B of Intermediate 1) and 1,4-butanediol according to the method described for Intermediate 41. MS (ESI) m/z 366.1 (M+Na)$^+$.

b) Methyl [2-(2-amino-5-chlorobenzyl)-1,3-dioxepan-2-yl]acetate

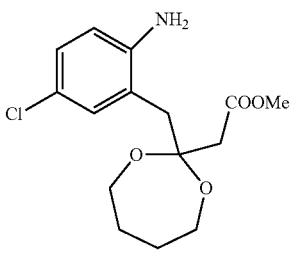 [SMILES: COC(=O)CC1(Cc2cc(Cl)ccc2N)OCCCCO1]

The title compound was prepared from methyl [2-(5-chloro-2-nitrobenzyl)-1,3-dioxepan-2-yl]acetate (Step a) of Intermediate 104) according to the method described for Intermediate 42 and it was used without further purification in the next step.

c) 7-chloro-1,5-dihydrospiro[1-benzazepine-4,2'-[1,3]dioxepan]-2(3H)-one

The title compound was prepared from methyl [2-(2-amino-5-chlorobenzyl)-1,3-dioxepan-2-yl]acetate (Step b) of Intermediate 104) according to the method described for Intermediate 43. MS (ESI) m/z 282.1 (M+H)$^+$.

Intermediate 105

Tert-butyl [2-(methylsulfanyl)-4,5-dihydro-3H-1-benzazepin-4-yl]carbamate

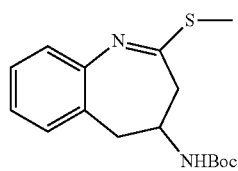 [SMILES: CSC1=Nc2ccccc2CC(NC(=O)OC(C)(C)C)C1]

The title compound was prepared from tert-butyl (2-thioxo-2,3,4,5-tetrahydro-1H-1-benzazepin-4-yl)carbamate (Intermediate 77) according to the method described for Intermediate 5 and it was used without further purification in the next step.

Intermediate 106

Tert-buty [7-fluoro-2-(methylsulfanyl)-4,5-dihydro-3H-1-benzazepin-4-yl]carbamate

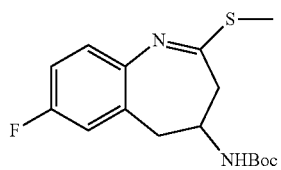 [SMILES: CSC1=Nc2ccc(F)cc2CC(NC(=O)OC(C)(C)C)C1]

a) Methyl 3-amino-4-(5-fluoro-2-nitrophenyl)but-2-enoate

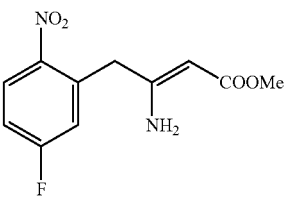

The title compound was prepared from methyl 4-(5-fluoro-2-nitrophenyl)-3-oxobutanoate (Intermediate 89) according to the method described in Step c) of Method B of Intermediate 1 and it was used without further purification in the next step.

b) Methyl 3-amino-4-(5-fluoro-2-nitrophenyl)butanoate

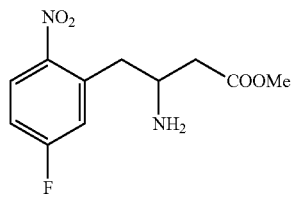

The title compound was prepared from methyl 3-amino-4-(5-fluoro-2-nitrophenyl)but-2-enoate (Step a) of Intermediate 106) according to the method described in Step d) of Method B of Intermediate 1 and it was used without further purification in the next step.

c) Methyl 3-[(tert-butoxycarbonyl)amino]-4-(5-fluoro-2-nitrophenyl)butanoate

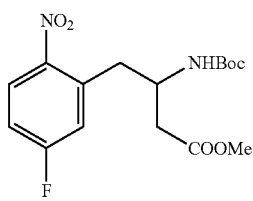

The title compound was prepared from methyl 3-amino-4-(5-fluoro-2-nitrophenyl)butanoate (Step b) of Intermediate 106) according to the method described in Step e) of Method B of Intermediate 1. MS (ESI) m/z 379.1 (M+Na)$^+$.

d) Methyl 4-(2-amino-5-fluorophenyl)-3-[(tert-butoxycarbonyl)amino]butanoate

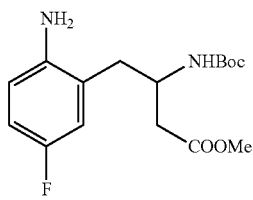

The title compound was prepared from methyl 3-[(tert-butoxycarbonyl)amino]-4-(5-fluoro-2-nitrophenyl)butanoate (Step c) of Intermediate 106) according to the method described for Intermediate 31 and it was used without further purification in the next step.

e) Tert-butyl (7-fluoro-2-oxo-2,3,4,5-tetrahydro-1H-1-benzazepin-4-yl)carbamate

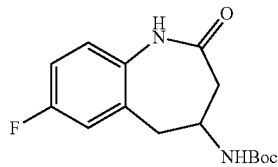 [SMILES: CC(C)(C)OC(=O)NC1CC(=O)Nc2ccc(F)cc2C1]

The title compound was prepared from methyl 4-(2-amino-5-fluorophenyl)-3-[(tert-butoxycarbonyl)amino]butanoate (Step d) of Intermediate 106) according to the method described for Intermediate 32. MS (ESI) m/z 317.1 (M+Na)$^+$.

f) Tert-butyl (7-fluoro-2-thioxo-2,3,4,5-tetrahydro-1H-1-benzazepin-4-yl)carbamate

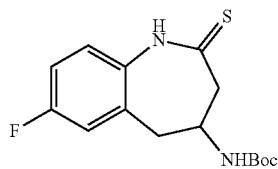 [SMILES: CC(C)(C)OC(=O)NC1CC(=S)Nc2ccc(F)cc2C1]

The title compound was prepared from tert-butyl (7-fluoro-2-oxo-2,3,4,5-tetrahydro-1H-1-benzazepin-4-yl)carbamate (Step e) of Intermediate 106) according to the method described for Intermediate 33 and it was used without further purification in the next step.

g) Tert-butyl [7-fluoro-2-(methylsulfanyl)-4,5-dihydro-3H-1-benzazepin-4-yl]carbamate The title compound was prepared from tert-butyl (7-fluoro-2-thioxo-2,3,4,5-tetrahydro-1H-1-benzazepin-4-yl)carbamate (Step f) of Intermediate 106) according to the method described for Intermediate 5 and it was used without further purification in the next step.

Intermediate 107

Trans-4-[(4-methylpiperazin-1-yl)carbonyl]cyclohexanecarbohydrazide

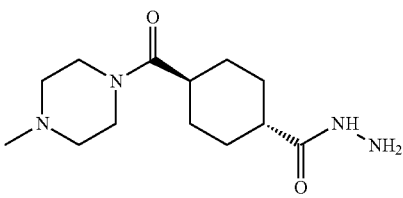 [SMILES: CN1CCN(C(=O)[C@H]2CC[C@H](C(=O)NN)CC2)CC1]

a) Methyl trans-4-[(4-methylpiperazin-1-yl)carbonyl]cyclohexanecarboxylate

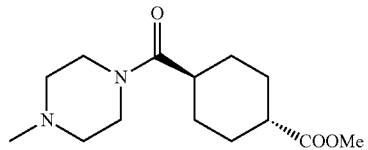 [SMILES: COC(=O)[C@H]1CC[C@H](C(=O)N2CCN(C)CC2)CC1]

The title compound was prepared from trans-4-(methoxycarbonyl)cyclohexane carboxylic acid and 1-methylpiperazine according to the method described in Step a) of Intermediate 78 and it was used without further purification in the next step.

b) Trans-4-[(4-methylpiperazin-1-yl)carbonyl]cyclohexanecarbohydrazide

The title compound was prepared from methyl trans-4-[(4-methylpiperazin-1-yl)carbonyl]cyclohexanecarboxylate (Step a) of Intermediate 107) according to the method described in Step b) of Intermediate 78 and it was used without further purification in the next step.

Intermediate 108

1-(tetrahydro-2H-pyran-4-yl)piperidine-4-carbohydrazide

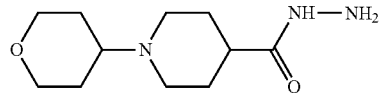

The title compound was prepared from ethyl 1-(tetrahydro-2H-pyran-4-yl)piperidine-4-carboxylate (WO 2016/138532 A1 (1 Sep. 2016) VERSION CORPORATION) according to the method described in Step b) of Intermediate 78 and it was used without further purification in the next step.

Intermediate 109

1-[(3S)-tetrahydrofuran-3-yl]piperidine-4-carbohydrazide

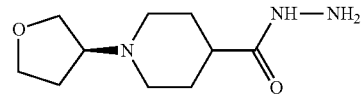 [SMILES: NNC(=O)C1CCN([C@H]2CCOC2)CC1]

a) Ethyl 1-[(3S)-tetrahydrofuran-3-yl]piperidine-4-carboxylate

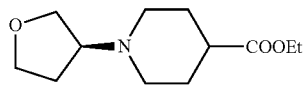 [SMILES: CCOC(=O)C1CCN([C@H]2CCOC2)CC1]

A mixture of 1.93 g (7.97 mmol) of (3R)-tetrahydrofuran-3-yl 4-methylbenzenesulfonate (WO 2016/91776 A1 (16 Jun. 2016) EVOTEC AG), 2.46 mL (15.9 mmol) of ethyl piperidine-4-carboxylate, 39 mL of acetonitrile and 4.4 g (31.9 mmol) of $K_2CO_3$ was stirred at 70° C. for 24 h, then cooled to room temperature and diluted with ethyl acetate. The so obtained mixture was washed with water and this water phase was discarded. The organic layer was washed with 1M HCl solution and this acidic water phase was alkalified with 10% $K_2CO_3$ solution, extracted with ethyl acetate, the combined organic layers were dried over $Na_2SO_4$, filtered and concentrated. The residue was purified by flash column chromatography using dichloromethane:methanol=91:9 as eluent to yield 603 mg (27%) of the title compound. GC-MS (EI) m/z 227.

b) 1-[(3S)-tetrahydrofuran-3-yl]piperidine-4-carbohydrazide

The title compound was prepared from ethyl 1-[(3S)-tetrahydrofuran-3-yl]piperidine-4-carboxylate (Step a) of Intermediate 109) according to the method described in Step b) of Intermediate 78 and it was used without further purification in the next step.

Intermediate 110

1-[(3R)-tetrahydrofuran-3-yl]piperidine-4-carbohydrazide

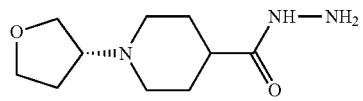 [SMILES: NNC(=O)C1CCN([C@@H]2CCOC2)CC1]

a) Ethyl 1-[(3R)-tetrahydrofuran-3-yl]piperidine-4-carboxylate

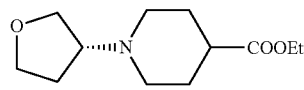 [SMILES: CCOC(=O)C1CCN([C@@H]2CCOC2)CC1]

The title compound was prepared from (3S)-tetrahydrofuran-3-yl 4-methylbenzenesulfonate (WO 2016/91776 A1 (16 Jun. 2016) EVOTEC AG) according to the method described in Step a) of Intermediate 109. GC-MS (EI) m/z 227.

b) 1-[(3R)-tetrahydrofuran-3-yl]piperidine-4-carbohydrazide

The title compound was prepared from ethyl 1-[(3R)-tetrahydrofuran-3-yl]piperidine-4-carboxylate (Step a) of Intermediate 110) according to the method described in Step b) of Intermediate 78 and it was used without further purification in the next step.

Intermediate 111

Ethyl cis-4-(4-methylpiperazin-1-yl)cyclohexanecarboxylate

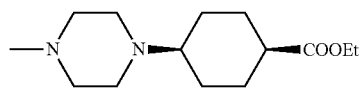 [SMILES: CCOC(=O)[C@H]1CC[C@@H](N2CCN(C)CC2)CC1]

And

Intermediate 112

Ethyl trans-4-(4-methylpiperazin-1-yl)cyclohexanecarboxylate

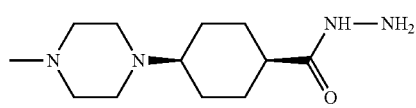

A mixture of 1.27 mL (8 mmol) of ethyl 4-oxocyclohexanecarboxylate, 887 µL (8 mmol) of 1-methylpiperazine, 4 mL of methanol and 20 mL of dichloromethane was cooled to 5° C. and 3.39 g (16 mmol) of sodium triacetoxyborohydride was added to the reaction mixture at such a rate to keep the internal temperature below 5° C. After completion of the addition the reaction mixture was stirred at room temperature for 24 h, then concentrated. The residue was dissolved in 1M HCl solution and extracted with dichloromethane. The acidic water phase was alkalified with 10% $K_2CO_3$ solution, extracted with ethyl acetate, the combined organic layers were dried over $Na_2SO_4$, filtered and concentrated to yield 640 mg (30%) of the title compounds as a mixture. GC-MS (EI) m/z 254.

Intermediate 113

Cis-4-(4-methylpiperazin-1-yl)cyclohexanecarbohydrazide

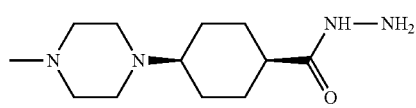

And

Intermediate 114

Trans-4-(4-methylpiperazin-1-yl)cyclohexanecarbohydrazide

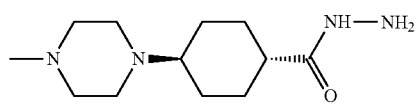

The title compounds were prepared from a mixture of ethyl cis-4-(4-methylpiperazin-1-yl)cyclohexanecarboxylate (Intermediate 111) and ethyl trans-4-(4-methylpiperazin-1-yl)cyclohexanecarboxylate (Intermediate 112) according to the method described in Step b) of Intermediate 78. GC-MS (EI) m/z 240.

Intermediate 115

1-(pyridin-3-yl)methylpyrrolidine-3-carbohydrazide

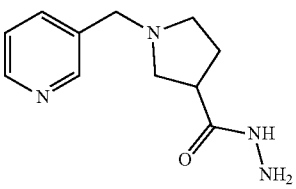

a) Methyl 1-(pyridin-3-ylmethyl)pyrrolidine-3-carboxylate

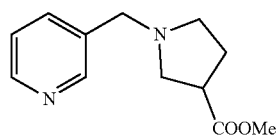 [SMILES: COC(=O)C1CCN(Cc2cccnc2)C1]

The title compound was prepared from methyl pyrrolidine-3-carboxylate and pyridine-3-carbaldehyde according to the method described for Intermediate 111 and 112 and it was used without further purification in the next step.

b) 1-(pyridin-3-ylmethyl)pyrrolidine-3-carbohydrazide

The title compound was prepared from methyl 1-(pyridin-3-ylmethyl)pyrrolidine-3-carboxylate (Step a) of Intermediate 115) according to the method described in Step b) of Intermediate 78. GC-MS (EI) m/z 220.

Intermediate 116

1-(pyridin-2-ylmethyl)pyrrolidine-3-carbohydrazide

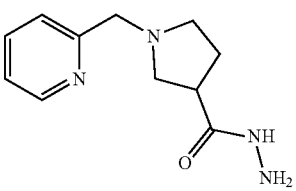

a) Methyl 1-(pyridin-2-ylmethyl)pyridine-3-carboxylate

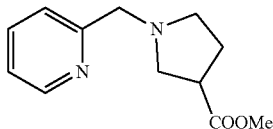 [SMILES: COC(=O)C1CCN(Cc2ccccn2)C1]

The title compound was prepared from methyl pyrrolidine-3-carboxylate and pyridine-2-carbaldehyde according to the method described for Intermediate 111 and 112. MS (ESI) m/z 221.2 (M+H)$^+$.

b) 1-(pyridin-2-ylmethyl)pyrrolidine-3-carbohydrazide

The title compound was prepared from methyl 1-(pyridin-2-ylmethyl)pyrrolidine-3-carboxylate (Step a) of Intermediate 116) according to the method described in Step b) of Intermediate 78 and it was used without further purification in the next step.

Intermediate 117

1-(pyridin-3-ylcarbonyl)pyrrolidine-3-carbohydrazide

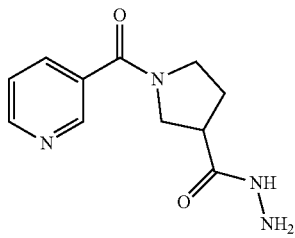 [SMILES: NNC(=O)C1CCN(C(=O)c2cccnc2)C1]

a) Methyl 1-(pyridin-3-ylcarbonyl)pyrrolidine-3-carboxylate

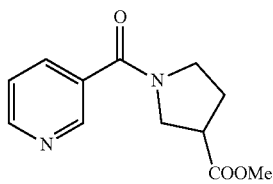 [SMILES: COC(=O)C1CCN(C(=O)c2cccnc2)C1]

The title compound was prepared from pyridine-3-carboxylic acid and methyl pyrrolidine-3-carboxylate according to the method described in Step a) of Intermediate 78. MS (ESI) m/z 235.1 (M+H)$^+$.

b) 1-(pyridin-3-ylcarbonyl)pyrrolidine-3-carbohydrazide

The title compound was prepared from methyl 1-(pyridin-3-ylcarbonyl)pyrrolidine-3-carboxylate (Step a) of Intermediate 117) according to the method described in Step b) of Intermediate 78. GC-MS (EI) m/z 234.

Intermediate 118

1-(pyridin-2-ylcarbonyl)pyrrolidine-3-carbohydrazide

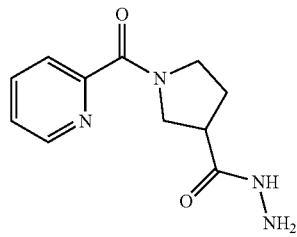 [SMILES: NNC(=O)C1CCN(C(=O)c2ccccn2)C1]

a) Methyl 1-(pyridin-2-ylcarbonyl)pyrrolidine-3-carboxylate

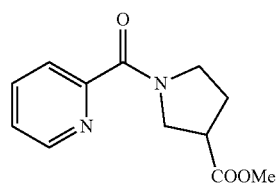 [SMILES: COC(=O)C1CCN(C(=O)c2ccccn2)C1]

The title compound was prepared from pyridine-2-carboxylic acid and methyl pyrrolidine-3-carboxylate according to the method described in Step a) of Intermediate 78. MS (ESI) m/z 235.2 (M+H)$^+$.

b) 1-(pyridin-2-ylcarbonyl)pyrrolidine-3-carboxylic acid

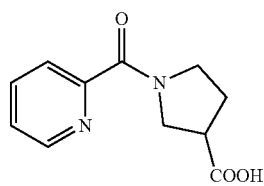 [SMILES: O=C(O)C1CCN(C(=O)c2ccccn2)C1]

The title compound was prepared from methyl 1-(pyridin-2-ylcarbonyl)pyrrolidine-3-carboxylate (Step a) of Intermediate 118) according to the method described for Intermediate 7. MS (ESI) m/z 221.1 (M+H)$^+$.

c) Tert-butyl 2-{[1-(pyridin-2-ylcarbonyl)pyrrolidin-3-yl]carbonyl}hydrazinecarboxylate

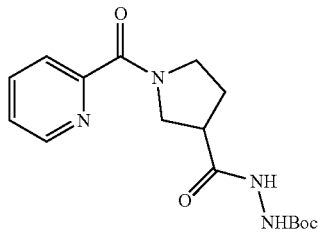 [SMILES: CC(C)(C)OC(=O)NNC(=O)C1CCN(C(=O)c2ccccn2)C1]

The title compound was prepared from 1-(pyridin-2-ylcarbonyl)pyrrolidine-3-carboxylic acid (Step b) of Intermediate 118) according to the method described for Intermediate 54. MS (ESI) m/z 335.2 (M+H)$^+$.

d) 1-(pyridin-2-ylcarbonyl)pyrrolidine-3-carbohydrazide

The title compound was prepared from tert-butyl 2-{[1-(pyridin-2-ylcarbonyl)pyrrolidin-3-yl]carbonyl}hydrazinecarboxylate (Step c) of Intermediate 118) according to the method described for Intermediate 55 and it was used without further purification in the next step.

Intermediate 119

4-methoxy-4-methylcyclohexanecarbohydrazide

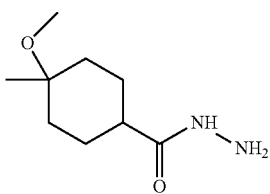

a) Ethyl 4-hydroxy-4-methylcyclohexanecarboxylate

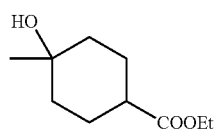

Under argon to a stirred solution of 100 mL (220 mmol) of 2M trimethylaluminum in toluene a solution of 8.7 mL (55 mmol) of ethyl 4-oxocyclohexanecarboxylate in 50 mL of toluene was added over 2.5 h at −60° C. After completion of the addition the mixture was stirred at −60° C. for 0.5 h, then allowed to warm to −20° C. over 2 h. The reaction mixture was transferred over 25-30 min via a cannula to an ice-cold mixture of 180 mL of ethyl acetate, 425 mL of water, 75 mL of concentrated hydrochloric acid and 100 g of crushed ice while keeping the internal temperature below 10° C. The phases were separated, the organic phase was successively washed with 400 mL of water and 400 mL of brine, dried over Na$_2$SO$_4$, filtered and concentrated to yield 5.44 g (53%) of title compound. According to. $^1$HNMR spectroscopy it was a 28:72 mixture of cis- and trans-isomers. This mixture was used in the next step without further purification.

b) Ethyl 4-methoxy-4-methyl cyclohexanecarboxylate

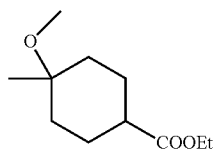

Under argon to a stirred mixture of 2.16 g (54 mmol) of 60% sodium hydride in mineral oil, 34 mL of dry THF, 200 mg (0.54 mmol) of tetrabutylammonium iodide, 49 mg (0.72 mmol) of imidazole and 3.36 mL (54 mmol) of iodomethane a solution of 3.36 g (18 mmol) of ethyl 4-hydroxy-4-methylcyclohexanecarboxylate (Step a) of Intermediate 119) in 21 mL of dry THF was added over 30-40 min at 20-25° C. The reaction mixture was stirred at room temperature for 3 h, then cooled to 0-5° C. and 2.28 mL (40 mmol) of acetic acid was added over 10 min. The mixture was stirred for 15 min, then poured into a mixture of 280 mL of diethyl ether and 120 mL of saturated NaHCO$_3$ solution. The phases were separated, the organic phase was washed with brine, dried over Na$_2$SO$_4$, filtered and concentrated. The residue was purified by column chromatography using n-hexane: ethyl acetate=85:15 as eluent to yield 2.3 g (64%) of the title compound. According to $^1$HNMR spectroscopy it was a 21:79 mixture of cis- and trans-isomers.

c) 4-methoxy-4-methylcyclohexanecarbohydrazide

The title compound was prepared from ethyl 4-methoxy-4-methylcyclohexanecarboxylate (Step b) of Intermediate 119) according to the method described for Intermediate 65. According to $^1$HNMR spectroscopy it was a 21:79 mixture of cis- and trans-isomers.

Intermediate 120

4-(2-oxopyrrolidin-1-yl)cyclohexanecarbohydrazide

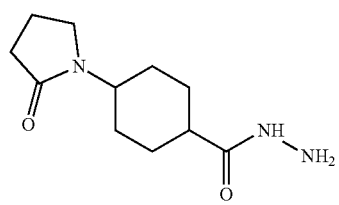 [SMILES: NNC(=O)C1CCC(N2CCCC2=O)CC1]

The title compound was prepared from ethyl 4-(2-oxopyrrolidin-1-yl)cyclohexanecarboxylate (WO2010/108052 A2 (20 Mar. 2009) H. LUNDBECK A/S) according to the method described for Intermediate 65 and it was used without further purification in the next step.

Intermediate 121 methyl trans-4-methoxy-4-(trifluoromethyl)cyclohexanecarboxylate

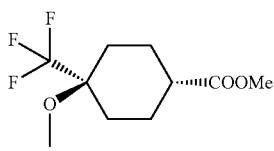 [SMILES: COC(=O)[C@H]1CC[C@@](OC)(C(F)(F)F)CC1]

And

Intermediate 122 methy cis-4-methoxy-4-(trifluoromethyl)cyclohexanecarboxylate

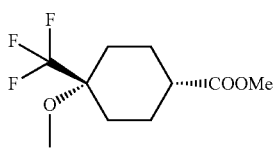 [SMILES: COC(=O)[C@H]1CC[C@](OC)(C(F)(F)F)CC1]

Under argon to a stirred mixture of 573 mg (2.7 mmol) of 4-hydroxy-4-(trifluoromethyl)cyclohexanecarboxylic acid, 5 mL of dry DMF and 5 mL of dry THF 324 mg (8.1 mmol) of 60% sodium hydride in mineral oil was added at 0° C. The reaction mixture was stirred at this temperature for 0.5 h, then 1.18 mL (18.9 mmol) of iodomethane was added and the reaction mixture was allowed to warm to room temperature. After 3 h stirring at room temperature 0.59 mL (9.45 mmol) of iodomethane was added and stirring was continued for 5 h. The reaction was quenched by addition of 9 mL of 1M hydrochloric acid solution, then diluted with dichloromethane and the phases were separated. The organic phase was washed with saturated NaHCO₃ solution, dried over Na₂SO₄, filtered and concentrated. The residue was purified by column chromatography using cyclohexane:dichloromethane=1:1 as eluent to yield 242 mg (37%) of methyl trans-4-methoxy-4-(trifluoromethyl)cyclohexanecarboxylate (Intermediate 121) as the first fraction and 277 mg (43%) of methyl cis-4-methoxy-4-(trifluoromethyl)cyclohexanecarboxylate (Intermediate 122) as the second fraction.

Intermediate 123

Cis-4-methoxy-4-(trifluoromethyl)cyclohexanecarbohydrazide

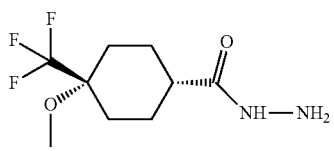 [SMILES: CO[C@]1(C(F)(F)F)CC[C@H](C(=O)NN)CC1]

The title compound was prepared from methyl cis-4-methoxy-4-(trifluoromethyl)cyclohexanecarboxylate (Intermediate 122) according to the method described for Intermediate 65. GC-MS (EI) m/z 240.

Intermediate 124

Trans-4-methoxy-4-(trifluoromethyl)cyclohexanecarbohydrazide

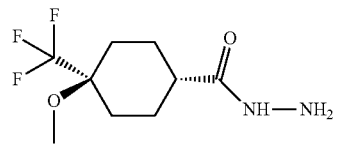 [SMILES: CO[C@]1(C(F)(F)F)CC[C@@H](C(=O)NN)CC1]

The title compound was prepared from methyl trans-4-methoxy-4-(trifluoromethyl)cyclohexanecarboxylate (Intermediate 121) according to the method described for Intermediate 65. GC-MS (EI) m/z 240.

Intermediate 125

Trans-4-[(4-methoxybenzyl)amino]cyclohexanecarbohydrazide

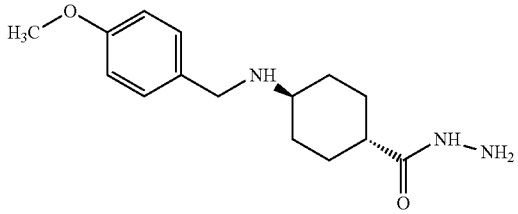 [SMILES: COc1ccc(CN[C@H]2CC[C@H](C(=O)NN)CC2)cc1]

a) Methyl trans-4-[(4-methoxybenzyl)amino]cyclohexanecarboxylate

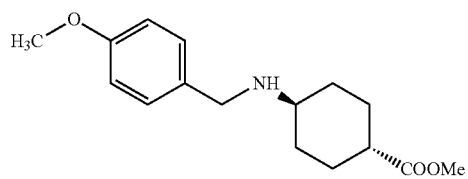 [SMILES: COc1ccc(CN[C@H]2CC[C@H](C(=O)OC)CC2)cc1]

A mixture of 2.0 g (10.3 mol) of methyl trans-4-aminocyclohexanecarboxylate hydrochloride (Combi-Blocks), 20 mL of 1,2-dichloroethane, 1.38 mL (11.4 mmol) of 4-methoxybenzaldehyde and 1.12 mL (19.6 mmol) of acetic acid was cooled to 5° C. and 6.78 g (32.0 mmol) of sodium triacetoxyborohydride was added to the reaction mixture at such a rate to keep the internal temperature below 5° C. After completion of the addition the reaction mixture was stirred at room temperature for 20 h, then diluted with water. The pH of the mixture was adjusted to 8 by addition of 10% Na₂CO₃ solution, the phases were separated and the water phase was extracted with dichloromethane. The combined organic phases were dried over MgSO$_4$, filtered and concentrated to yield 1.48 g (52%) of the title compound. MS (ESI) m/z 278.2 (M+H)$^+$.

b) Trans-4-[(4-methoxybenzyl)amino]cyclohexanecarbohydrazide

The title compound was prepared from methyl trans-4-[(4-methoxybenzyl)amino]cyclohexanecarboxylate (Step a) of Intermediate 125) according to the method described for Intermediate 65 and it was used without further purification in the next step.

Intermediate 126

Trans-4-ethoxy-4-ethylcyclohexanecarbohydrazide

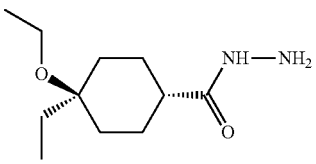

a) Ethyl 4-ethyl-4-hydroxycyclohexanecarboxylate

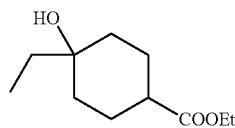

The title compound was prepared from ethyl 4-oxocyclohexanecarboxylate and 25% triethylaluminum solution in toluene according to the method described in Step a) of Intermediate 119. According to $^1$HNMR spectroscopy it was a 27:73 mixture of cis- and trans-isomers. This mixture was used in the next step without further purification.

b) Ethyl trans-4-ethoxy-4-ethylcyclohexanecarboxylate

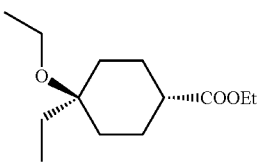 [SMILES: CCOC(=O)[C@H]1CC[C@](CC)(OCC)CC1]

Under argon to a stirred mixture of 1.32 g (33 mmol) of 60% sodium hydride in mineral oil, 22 mL of dry toluene, 406 mg (11 mmol) of tetrabutylammonium iodide and 2.85 mL (22 mmol) of ethyl trifluoromethanesulfonate a solution of 2.2 g (11 mmol) of ethyl 4-ethyl-4-hydroxycyclohexanecarboxylate (Step a) of Intermediate 126) in 11 mL of dry toluene was added over 30-40 min at 20-25° C. The reaction mixture was stirred at room temperature for 20 h, then cooled to 0-5° C. and it was poured into an ice-cold mixture of 220 mL of ethyl acetate, 110 mL of saturated NaHCO$_3$ solution and 30 mL of water. The mixture was stirred at 5° C. for 0.5 h, then at room temperature for 20 h. The phases were separated, the organic phase was washed with brine, dried over Na$_2$SO$_4$, filtered and concentrated. The residue was purified by column chromatography using n-hexane:ethyl acetate=94:6 as eluent to yield 1.77 g (71%) of the title compound. According to $^1$HNMR spectroscopy it was a 3:97 mixture of cis- and trans-isomers.

c) Trans-4-ethoxy-4-ethylcyclohexanecarbohydrazide

The title compound was prepared from ethyl 4-ethoxy-4-ethylcyclohexanecarboxylate (Step b) of Intermediate 126) according to the method described for Intermediate 65. According to $^1$HNMR spectroscopy it was a 3:97 mixture of cis- and trans-isomers. This mixture was used in the next step without further purification.

Intermediate 127

4-ethyl-4-methoxycyclohexane-carbohydrazide

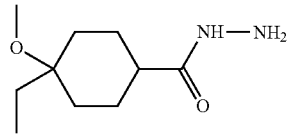

a) Ethyl 4-methoxy-4-ethylcyclohexanecarboxylate

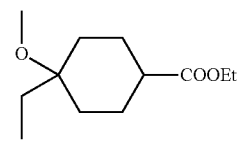

The title compound was prepared from ethyl 4-ethyl-4-hydroxycyclohexanecarboxylate (Step a) of Intermediate 126) and methyl trifluoromethanesulfonate according to the method described in Step b) of Intermediate 126. According to $^1$HNMR spectroscopy it was a 19:81 mixture of cis- and trans-isomers.

b) 4-ethyl-4-methoxycyclohexane-carbohydrazide

The title compound was prepared from ethyl 4-methoxy-4-ethylcyclohexanecarboxylate (Step a) of Intermediate 127) according to the method described for Intermediate 65. According to $^1$HNMR spectroscopy it was a 20:80 mixture of cis- and trans-isomers. This mixture was used in the next step without further purification.

Intermediate 128

Trans-4-ethoxy-4-methylcyclohexanecarbohydrazide

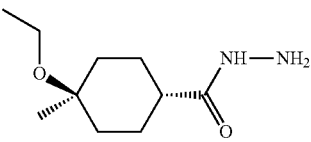

a) Ethyl trans-4-ethoxy-4-methylcyclohexanecarboxylate

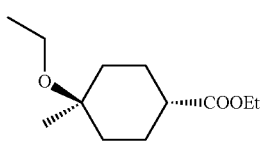

The title compound was prepared from ethyl 4-hydroxy-4-methylcyclohexanecarboxylate (Step a) of Intermediate 119) and ethyl trifluoromethanesulfonate according to the method described in Step b) of Intermediate 126. According to ¹HNMR spectroscopy it was a 4:96 mixture of cis- and trans-isomers.

b) Trans-4-ethoxy-4-methylcyclohexanecarbohydrazide

The title compound was prepared from ethyl 4-methoxy-4-ethylcyclohexanecarboxylate (Step a) of Intermediate 128) according to the method described for Intermediate 65. According to ¹HNMR spectroscopy it was a 7:93 mixture of cis- and trans-isomers. This mixture was used in the next step without further purification.

Intermediate 129

4-ethoxy-4-proplycyclohexanecarbohydrazide

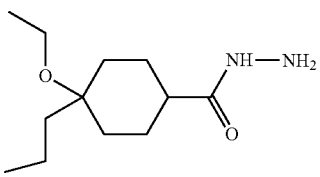 [SMILES: CCCC1(OCC)CCC(C(=O)NN)CC1]

a) Ethyl 4-hydroxy-4-(prop-2-en-1-yl)cyclohexanecarboxylate

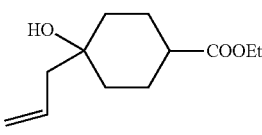

To a solution of 11.9 mL (12.76 g, 75.0 mmol) of ethyl 4-oxoyclohexanearboxylate in 225 mL of THF 188 mL of 25% ammonium chloride solution and 9.81 g (150 mmol) of zinc powder were added. The mixture was stirred at room temperature for 5 min, then 9.7 mL (13.56 g, 112.0 mmol) of allyl bromide was added dropwise over 20 min. At the end of the addition the temperature of the reaction mixture rose to 42-43° C. The mixture was stirred at ambient temperature for 4 h, then poured into a mixture of 180 mL of water and 750 mL of ethyl acetate. After addition of 30 mL of 1.0 M hydrochloric acid solution the phases were separated, the organic phase was washed with 2×375 mL of brine, dried over Na₂SO₄, filtered and concentrated to yield 15.39 g (96%) of the title compound. According to ¹HNMR spectroscopy it was a 60:40 mixture of cis- and trans-isomers.

b) Ethyl 4-hydroxy-4-propylcyclohexanecarboxylate

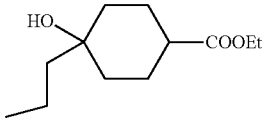

A mixture of 14.86 g (70 mmol) of ethyl 4-hydroxy-4-(prop-2-en-1-yl)cyclohexanecarboxylate (Step a) of Intermediate 129), 250 mL of THF and 1.49 g 10% Pd on carbon was hydrogenated. After completion of the reaction the mixture was filtered through Celite and washed with 3×25 mL of THF. The filtrate was concentrated and 3×100 mL of dichloromethane was evaporated off the residue to yield 14.89 g (99%) of the title compound, which was used without further purification.

c) Ethyl 4-ethoxy-4-propylcyclohexanecarboxylate

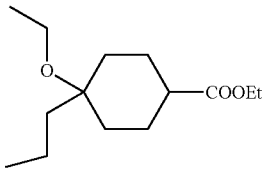 [SMILES: CCCC1(OCC)CCC(C(=O)OCC)CC1]

The title compound was prepared from ethyl 4-hydroxy-4-propylcyclohexanecarboxylate (Step b) of Intermediate 129) and ethyl trifluoromethanesulfonate according to the method described in Step b) of Intermediate 126. According to ¹HNMR spectroscopy it was a 16:84 mixture of cis- and trans-isomers.

d) 4-ethoxy-4-propylcyclohexanecarbohydrazide

The title compound was prepared from ethyl 4-ethoxy-4-propylcyclohexanecarboxylate (Step c) of Intermediate 129) according to the method described for Intermediate 65. According to ¹HNMR spectroscopy it was a 16:84 mixture of cis- and trans-isomers. This mixture was used in the next step without further purification.

Intermediate 130

4-methoxy-4-propylcyclohexanecarbohydrazide

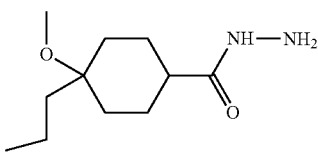

a) Ethyl 4-methoxy-4-propylcyclohexanecarboxylate

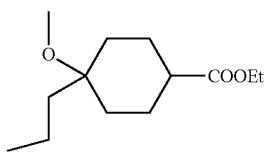 [SMILES: CCCC1(OC)CCC(C(=O)OCC)CC1]

The title compound was prepared from ethyl 4-hydroxy-4-propylcyclohexanecarboxylate (Step b) of Intermediate 129) and methyl trifluoromethanesulfonate according to the method described in Step b) of Intermediate 126. According to $^1$HNMR spectroscopy it was a 57:43 mixture of cis- and trans-isomers.

b) 4-methoxy-4-propylcyclohexanecarbohydrazide

The title compound was prepared from ethyl 4-methoxy-4-propylcyclohexanecarboxylate (Step a) of Intermediate 130) according to the method described for Intermediate 65. According to $^1$H-NMR spectroscopy it was a 57:43 mixture of cis- and trans-isomers. This mixture was used in the next step without further purification.

Intermediate 131

(3R)-1-(pyridin-2-ylmethyl)pyrrolidine-3-carbohydrazide

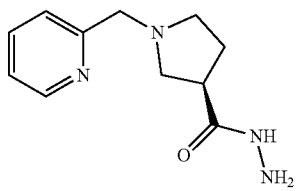 [SMILES: NNC(=O)[C@@H]1CCN(Cc2ccccn2)C1]

a) Methyl (3R-1-(pyridin-2-ylmethyl)pyrrolidine-3-carboxylate

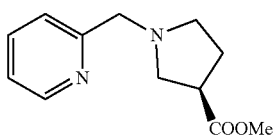 [SMILES: COC(=O)[C@@H]1CCN(Cc2ccccn2)C1]

The title compound was prepared from methyl (3R)-pyrrolidine-3-carboxylate and pyridine-2-carbaldehyde according to the method described for Intermediate 111 and 112. MS (ESI) m/z 221.1 (M+H)$^+$.

b) (3R)-1-pyridin-2-ylmethyl)pyrrolidine-3-carbohydrazide

The title compound was prepared from methyl (3R)-1-(pyridin-2-ylmethyl)pyrrolidine-3-carboxylate (Step a) of Intermediate 131) according to the method described in Step b) of Intermediate 78 and it was used without further purification in the next step.

Intermediate 132

(3S)-1-(pyridin-2-ylmethyl)pyrrolidine-3-carbohydrazide

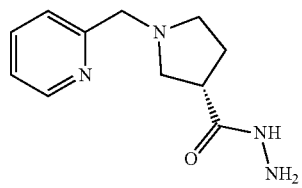 [SMILES: NNC(=O)[C@H]1CCN(Cc2ccccn2)C1]

a) Methyl (3S)-1-(pyridin-2-ylmethyl)pyrrolidine-3-carboxylate

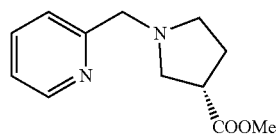

The title compound was prepared from methyl (3S)-pyrrolidine-3-carboxylate and pyridine-2-carbaldehyde according to the method described for Intermediate 111 and 112. MS (ESI) m/z 221.1 (M+H)$^+$.

b) (3S)-1-(pyridin-2-ylmethyl)pyrrolidine-3-carbohydrazide

The title compound was prepared from methyl (3S)-1-(pyridin-2-ylmethyl)pyrrolidine-3-carboxylate (Step a) of Intermediate 132) according to the method described in Step b) of Intermediate 78 and it was used without further purification in the next step.

Intermediate 133

(3R)-1-(pyridin-3-ylmethyl)pyrrolidine-3-carbohydrazide

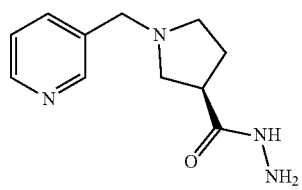 [SMILES: NNC(=O)[C@@H]1CCN(Cc2cccnc2)C1]

a) Methyl (3R)-1-(pyridin-2-3-ylmethyl)pyrrolidine-3-carboxylate

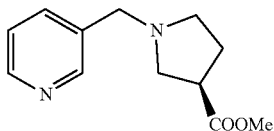 [SMILES: COC(=O)[C@@H]1CCN(Cc2cccnc2)C1]

The title compound was prepared from methyl (3R)-pyrrolidine-3-carboxylate and pyridine-3-carbaldehyde according to the method described for Intermediate 111 and 112. MS (ESI) m/z 221.1 (M+H)+.

b) (3R)-1-pyridin-3-ylmethyl)pyrrolidine-3-carbohydrazide

The title compound was prepared from methyl (3R)-1-(pyridin-3-ylmethyl)pyrrolidine-3-carboxylate (Step a) of Intermediate 133) according to the method described in Step b) of Intermediate 78 and it was used without further purification in the next step.

Intermediate 134

3S-1-(pyridin-3-ylmethyl)pyrrolidine-3-carbohydrazide

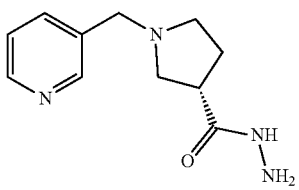 [SMILES: NNC(=O)[C@H]1CCN(Cc2cccnc2)C1]

a) Methyl (3S)-1-(pyridin-2-3-ylmethyl)pyrrolidine-3-carboxylate

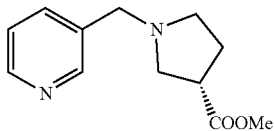

The title compound was prepared from methyl (3S)-pyrrolidine-3-carboxylate and pyridine-3-carbaldehyde according to the method described for Intermediate 111 and 112. MS (ESI) m/z 221.1 (M+H)+.

b) (3S)-1-(pyridin-3-ylmethyl)pyrrolidine-3-carbohydrazide

The title compound was prepared from methyl (3S)-1-(pyridin-3-ylmethyl)pyrrolidine-3-carboxylate (Step a) of Intermediate 134) according to the method described in Step b) of Intermediate 78 and it was used without further purification in the next step.

Intermediate 135

Trans-4-(pyridin-2-ylamino)cyclohexanecarbohydrazide

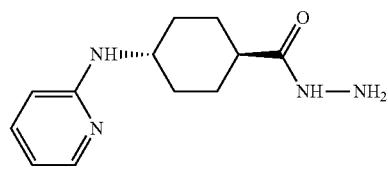 [SMILES: NNC(=O)[C@H]1CC[C@H](Nc2ccccn2)CC1]

a) Methyl trans-4-(pyridin-2-ylamino)cyclohexanecarboxylate

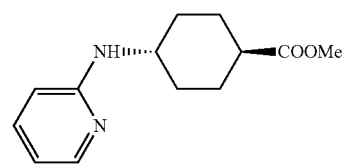 [SMILES: COC(=O)[C@H]1CC[C@H](Nc2ccccn2)CC1]

A mixture of 1.5 g (7.745 mmol) of methyl trans-4-aminocyclohexanecarboxylate hydrochloride, 4 mL (46.5 mmol) of 2-fluoropyridine and 1.35 mL (7.75 mmol) of DIPEA was stirred at 125° C. in a pressure-resistant glass reactor for 20 hours, then cooled to room temperature. The reaction mixture was diluted with 20 mL of ethyl acetate, washed with 2×30 mL of water and saturated NaCl solution, the organic phase was dried over anhydrous $Na_2SO_4$, filtered and concentrated to yield 325 mg (18%) of the title compound. MS (ESI) m/z 235.1 (M+H)+.

b) Trans-4-(pyridin-2-ylamino)cyclohexanecarbohydrazide

The title compound was prepared from methyl trans-4-(pyridin-2-ylamino)cyclohexanecarboxylate (Step a) of Intermediate 135) according to the method described in Step b) of Intermediate 78 and it was used without further purification in the next step.

Example 1

Tert-butyl [8-chloro-1-[1-(pyridin-2-yl)piperidin-4-yl]-5,6-dihydro-4H-[1,2,4]triazolo[4,3-a][1]benzazepin-5-yl]carbamate

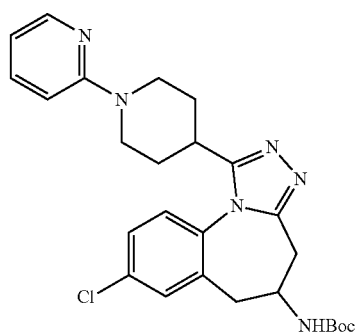 [SMILES: CC(C)(C)OC(=O)NC1Cc2cc(Cl)ccc2-n2c(nnc2C2CCN(c3ccccn3)CC2)C1]

A mixture of 236 mg (0.72 mmol) of tert-butyl (7-chloro-2-thioxo-2,3,4,5-tetrahydro-1H-1-benzazepin-4-yl)carbamate (Intermediate 4), 15 mL of xylene and 190 mg (0.86 mmol) of 1-(pyridin-2-yl)piperidine-4-carbohydrazide (D. M. Beal et al., *Tetrahedron Lett* 2011, 52:5913-5917) was stirred under argon for 24 hours, then the reaction mixture was concentrated and the residue was purified by column chromatography using dichloromethane:methanol=9:1 as eluent. Thus, 200 mg (56%) of the title product was obtained. MS (ESI) m/z 495.3 (M+H)$^+$.

Example 2

8-chloro-1-[1-(pyridin-2-yl)piperidin-4-yl]-5,6-dihydro-4H-[1,2,4]triazolo[4,3-a][1]benzazepine-5-amine

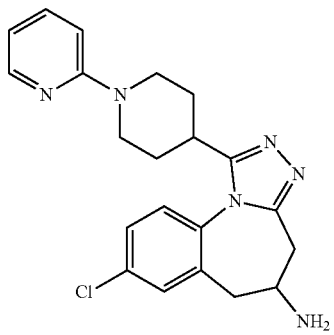 [SMILES: NC1Cc2cc(Cl)ccc2-n2c(nnc2C2CCN(c3ccccn3)CC2)C1]

To a solution of 200 mg (0.4 mmol) of tert-butyl [8-chloro-1-[1-(pyridin-2-yl)piperidin-4-yl]-5,6-dihydro-4H-[1,2,4]triazolo[4,3-a][1]benzazepin-5-yl]carbamate (Example 1) in 10 mL of ethyl acetate 5 mL of 2.5M hydrogen chloride solution in ethyl acetate was added and the reaction mixture was stirred at room temperature for 5 hours. Diethyl ether was added and the mixture was stirred at room temperature for 30 minutes. The precipitated product was filtered, washed with diethyl ether and dried. The product was dissolved in a mixture of dichloromethane and saturated NaHCO$_3$, after one hour of stirring the phases were separated and the aqueous phase was extracted with dichloromethane, the combined organic phases were dried over anhydrous Na$_2$SO$_4$, filtered and concentrated. The residue was purified by column chromatography using dichloromethane:methanol=4:1 as eluent. Thus 96 mg (61%) of the title product was obtained. MS (ESI) m/z 395.3 (M+H)$^+$.

Example 3

N-[8-chloro-[1-(pyridin-2-yl)piperidin-4-yl]-5,6-dihydro-4H-[1,2,4]triazolo[4,3-a][1]benzazepin-5-yl]acetamide

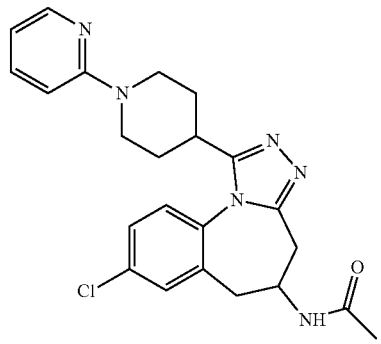 [SMILES: CC(=O)NC1Cc2cc(Cl)ccc2-n2c(nnc2C2CCN(c3ccccn3)CC2)C1]

A mixture of 43 mg (0.1 mmol) of 8-chloro-1-[1-(pyridin-2-yl)piperidin-4-yl]-5,6-dihydro-4H-[1,2,4]triazolo[4,3-a][1]benzazepine-5-amine (Example 2), 1 mL of pyridine and 82 µL (0.9 mmol) of acetic anhydride was stirred at room temperature for 20 hours, then 5 mL of water was added to the reaction mixture and extracted three times with 20 mL of dichloromethane. The combined organic phases were dried over anhydrous Na$_2$SO$_4$, filtered and concentrated. Thus, 23 mg (48%) of the title product was obtained. MS (ESI) m/z 437.2 (M+H)$^+$.

Example 4

N-(8-chloro-[1-pyridin-2-yl)piperidin-4-yl]-5,6-dihydro-4H-[1,2,4]triazolo[4,3-a][1]benzazepin-5-yl)-2-methylpropanamide

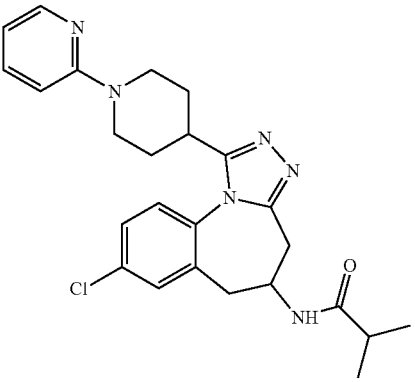 [SMILES: CC(C)C(=O)NC1Cc2cc(Cl)ccc2-n2c(nnc2C2CCN(c3ccccn3)CC2)C1]

To a mixture of 62 mg (0.157 mmol) of 8-chloro-1-[1-(pyridin-2-yl)piperidin-4-yl]-5,6-dihydro-4H-[1,2,4]triazolo[4,3-a][1]benzazepine-5-amine (Example 2), 10 mL of dichloromethane and 40 µl (0.23 mmol) of DIPEA, 24 µl (0.23 mmol) of isobutyryl chloride was added and the reaction mixture was stirred at room temperature for 20 hours. The reaction mixture was diluted with dichloromethane, washed with water, the organic phase was dried over anhydrous Na$_2$SO$_4$, filtered and concentrated. The residue

Example 5

Tert-butyl {8-chloro-1-[trans-4-(pyridin-2-yloxy)cyclohexyl]-5,6-dihydro-4H-[1,2,4]triazolo[4,3-a][1]benzazepine-5-yl}carbamate

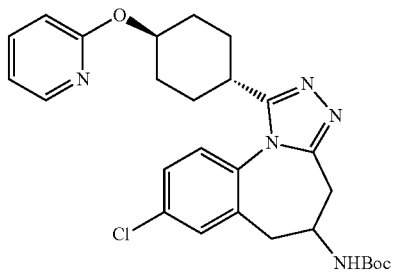 [SMILES: CC(C)(C)OC(=O)NC1Cc2cc(Cl)ccc2-n2c(nnc2[C@H]2CC[C@H](Oc3ccccn3)CC2)C1]

Method A)

A mixture of 2.26 g (6.9 mmol) of tert-butyl (7-chloro-2-thioxo-2,3,4,5-tetrahydro-1H-1-benzazepin-4-yl)carbamate (Intermediate 4), 140 mL of xylene and 1.96 g (8.33 mmol) of trans-4-(pyridin-2-yloxy)cyclohexane carboxylic acid hydrazide (WO 2010/060836 (3 Jun. 2010) F. HOFFMANN-LA ROCHE AG.) was refluxed for 20 hours under argon, then concentrated and the residue was purified by column chromatography using dichloromethane:methanol=9:1 as eluent. Thus, 2.76 g (78%) of the title product was obtained. MS (ESI) m/z 510.2 (M+H)$^+$.

Method B)

To a mixture of 3.75 g (11 mmol) of tert-butyl [7-chloro-2-(methylsulfanyl)-4,5-dihydro-3H-1-benzazepin-4-yl]carbamate (Intermediate 5), 110 mL of xylene and 2.87 g (12.2 mmol) of trans-4-(pyridin-2-yloxy)cyclohexane carboxylic acid hydrazide, 0.1 mL of concentrated hydrochloric acid was added under argon and the reaction mixture was refluxed for 18 hours, then concentrated and the residue was purified by column chromatography using dichloromethane:methanol=9:1 as eluent. Thus, 3.42 g (61%) of the title product was obtained. MS (ESI) m/z 510.2 (M+H)$^+$.

Example 6

8-chloro-1-[trans-4-(pyridin-2-yloxy)cyclohexyl]-5,6-dihydro-4H-[1,2,4]triazolo[4,3-a][1]benzazepine-5-amine

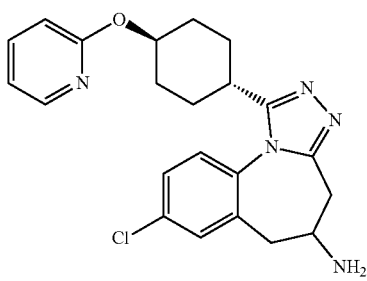 [SMILES: NC1Cc2cc(Cl)ccc2-n2c(nnc2[C@H]2CC[C@H](Oc3ccccn3)CC2)C1]

To a mixture of 2.76 g (5.41 mol) of tert-butyl {8-chloro-1-[trans-4-(pyridin-2-yloxy)cyclohexyl]-5,6-dihydro-4H-[1,2,4]triazolo[4,3-a][1]benzazepine-5-yl}carbamate (Example 5), 100 mL of ethyl acetate and 100 mL of ethanol, 50 mL of 2.5M hydrogen chloride solution in ethyl acetate was added and the reaction mixture was stirred at room temperature for 5 hours. Diethyl ether was added and the mixture was stirred at room temperature for 30 minutes. The precipitated product was filtered, washed with diethyl ether and dried. The product was dissolved in a mixture of dichloromethane and saturated NaHCO$_3$. After one hour of stirring, the phases were separated and the aqueous phase was extracted with dichloromethane, the combined organic phases were dried over anhydrous Na$_2$SO$_4$, filtered and concentrated. The residue was purified by column chromatography using dichloromethane:methanol=9:1 as eluent. Thus, 1.85 g (83%) of the title product was obtained. MS (ESI) m/z 410.2 (M+H)$^+$.

Example 7

(5S)-8-chloro-1[trans-4-(pyridin-2-yloxy)cyclohexyl]-5,6-dihydro-4H-[1,2,4]triazolo[4,3-a][1]benzazepine-5-amine

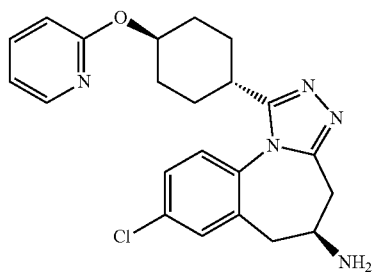 [SMILES: N[C@H]1Cc2cc(Cl)ccc2-n2c(nnc2[C@H]2CC[C@H](Oc3ccccn3)CC2)C1]

And

Example 8

(5R)-8-chloro-1-[trans-4-(pyridin-2-yloxy)cyclohexyl]-5,6-dihydro-4H-[1,2,4]triazolo[4,3-a][1]benzazepine-5-amine

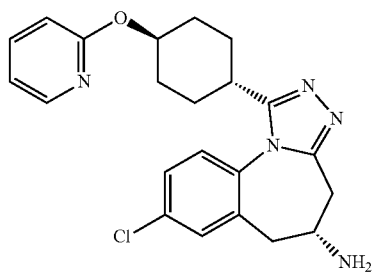 [SMILES: N[C@@H]1Cc2cc(Cl)ccc2-n2c(nnc2[C@H]2CC[C@H](Oc3ccccn3)CC2)C1]

The title products were prepared from the racemic 8-chloro-1-[trans-4-(pyridin-2-yloxy)cyclohexyl]-5,6-dihydro-4H-[1,2,4]triazolo[4,3-a][1]benzazepine-5-amine (Example 6) by chiral preparative HPLC (CHIRALPAK IA with preparative 20 µm stationary phase, 2.5×20 cm; F=15 mL/min, eluent: n-hexane:EtOH=8:2+0.3% diethylamine; isocratic, t=25° C.) to yield the (5S) enantiomer (T$_r$ 11.7 min; [α]$_D^{25}$=−21.1° (c=0.1; methanol); Example 7) and the (5R) enantiomer (T$_r$ 14.9 min; [α]$_D^{25}$=+14.5° (c=0.1; methanol); Example 8). The absolute configuration of the compounds was determined by VCD method and by $^1$H NMR spectroscopy of the diastereomeric pairs synthesized therefrom.

Example 9

N-{8-chloro-1-[trans-4-(pyridin-2-yloxy)cyclohexyl]-5,6-dihydro-4H-[1,2,4]triazolo[4,3-a][1]benzazepin-5-yl}acetamide

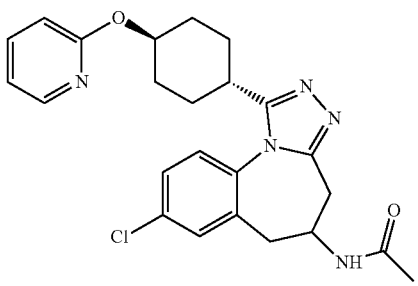 [SMILES: CC(=O)NC1Cc2cc(Cl)ccc2-n2c(nnc2[C@H]2CC[C@H](Oc3ccccn3)CC2)C1]

A mixture of 82 mg (0.2 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 2 mL of pyridine and 190 µL (2.0 mmol) of acetic anhydride was stirred at room temperature for 20 hours, then 5 mL of water was added to the reaction mixture and extracted three times with 20 mL of dichloromethane. The combined organic phases were dried over anhydrous Na$_2$SO$_4$, filtered and concentrated. Thus, 67 mg (74%) of the title product was obtained. MS (ESI) m/z 452.2 (M+H)$^+$.

Example 10

N-{8-chloro-1-[trans-4-(pyridin-2-yloxy)cyclohexyl]-5,6-dihydro-4H-[1,2,4]triazolo[4,3-a][1]benzazepin-5-yl}glycinamide

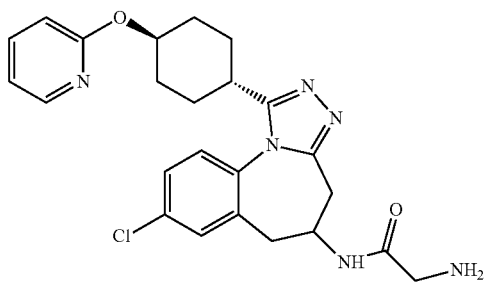 [SMILES: NCC(=O)NC1Cc2cc(Cl)ccc2-n2c(nnc2[C@H]2CC[C@H](Oc3ccccn3)CC2)C1]

a) Tert-butyl [2-({8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate A mixture of 87 mg (0.21 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 3 mL of DMF, 40 mg (0.23 mmol) of Boc-glycine, 95 mg (0.25 mmol) of HBTU and 44 µL (0.32 mmol) of TEA was stirred at room temperature for 20 hours, then the reaction mixture was concentrated and saturated NaHCO$_3$ solution was added to the residue. The precipitated product was filtered, washed with water, and dried. Thus, 91 mg (76%) of the title product was obtained. MS (ESI) m/z 567.3 (M+H)$^+$.

b) N-{8-chloro-1-[trans-4-(pyridin-2-yloxy)cyclohexyl]-5,6-dihydro-4H-[1,2,4]triazolo[4,3-a][1]benzazepin-5-yl}glycinamide To a mixture of 90 mg (0.16 mmol) of tert-butyl [2-({8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate (step a) of Example 10), 5 mL of ethyl acetate and 5 mL of ethanol, 2 mL of 2.5M hydrogen chloride solution in ethyl acetate was added and the reaction mixture was stirred at room temperature for 5 hours, then concentrated. The residue was dissolved in a mixture of dichloromethane and saturated NaHCO$_3$, after one hour of stirring, the phases were separated, the aqueous phase was extracted with dichloromethane, the combined organic phases were dried over anhydrous Na$_2$SO$_4$, filtered and concentrated. Thus, 49 mg (66%) of the title product was obtained. MS (ESI) m/z 467.2 (M+H)$^+$.

Example 11

N-{(5S)-8-chloro-1-[trans-4-(pyridin-2-yloxy)cyclohexyl]-5,6-dihydro-4H-[1,2,4]triazolo[4,3-a][1]benzazepin-5-yl}glycinamide

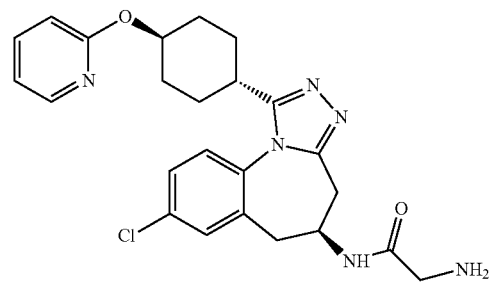 [SMILES: NCC(=O)N[C@H]1Cc2cc(Cl)ccc2-n2c(nnc2[C@H]2CC[C@H](Oc3ccccn3)CC2)C1]

a) Tert-butyl [2-({(5S)-8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate The title product was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) according to the method described in step a) of Example 10. MS (ESI) m/z 567.2 (M+H)$^+$.

b) N-{(5S)-8-chloro-1-[trans-4-(pyridin-2-yloxy)cyclohexyl]-5,6-dihydro-4H-[1,2,4]triazolo[4,3-a][1]benzazepin-5-yl}glycinamide The title product was prepared from tert-butyl [2-({(5S)-8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate (step a) of Example 11) according to the method described in step b) of Example 10. $[\alpha]_D^{25}=-33.2°$ (c=0.1; methanol); MS (ESI) m/z 467.2 (M+H)⁺.

Example 12

N-{(5R)-8-chloro-1-[trans-4-(pyridin-2-yloxy)cyclohexyl]-5,6-dihydro-4H-[1,2,4]triazolo[4,3-a][1]benzazepin-5-yl}glycinamide

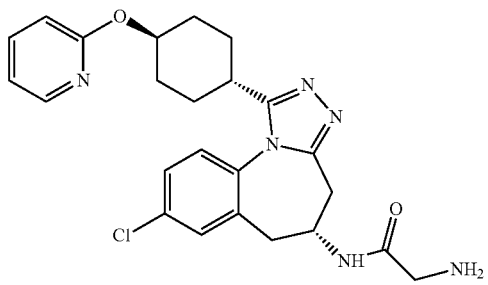 [SMILES: NCC(=O)N[C@@H]1Cc2cc(Cl)ccc2-n2c(nnc2[C@H]2CC[C@H](Oc3ccccn3)CC2)C1]

a) Tert-butyl [2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate The title product was prepared from (5R)-8-chloro-1-[trans-4-(pyridin-2-yloxy)cyclohexyl]-5,6-dihydro-4H-[1,2,4]triazolo[4,3-a][1]benzazepine-5-amine (Example 8) according to the method described in step a) of Example 10. MS (ESI) m/z 567.2 (M+H)

b) N-{(5R)-8-chloro-1-[trans-4-(pyridin-2-yloxy)cyclohexyl]-5,6-dihydro-4H-[1,2,4]triazolo[4,3-a][1]benzazepin-5-yl}glycinamide The title product was prepared from tert-butyl [2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxoethyl]carbamate (step a) of Example 12) according to the method described in step b) of Example 10. $[\alpha]_D^{25}=+18.4°$ (c=0.1; methanol); MS (ESI) m/z 467.2 (M+H)⁺.

Example 13

(2S)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide

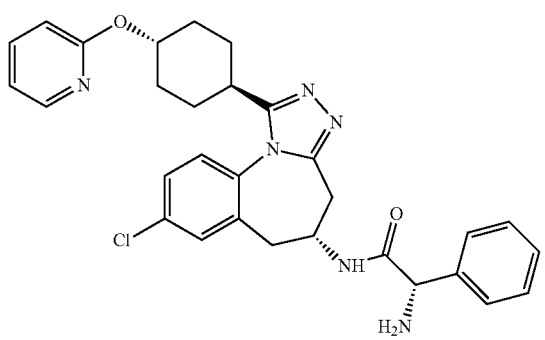 [SMILES: N[C@H](C(=O)N[C@@H]1Cc2cc(Cl)ccc2-n2c(nnc2[C@H]2CC[C@H](Oc3ccccn3)CC2)C1)c1ccccc1]

a) Tert-butyl [(1S)-2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxo-1-phenylethyl]carbamate The title product was prepared from (5R)-8-chloro-1-[trans-4-(pyridin-2-yloxy)cyclohexyl]-5,6-dihydro-4H-[1,2,4]triazolo[4,3-a][1]benzazepine-5-amine (Example 8) and Boc-Phg-OH according to the method described in step a) of Example 10. MS (ESI) m/z 643.2 (M+H)⁺.

b) (2S)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide The title product was prepared from tert-butyl [(1S)-2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxo-1-phenylethyl]carbamate (step a) of Example 13) according to the method described in step b) of Example 10. MS (ESI) m/z 543.2 (M+H)⁺.

Example 14

(2R)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide

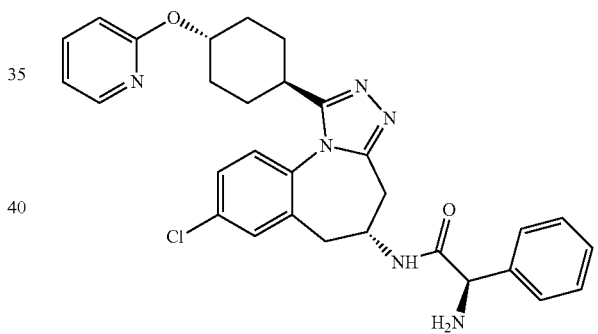

a) Tert-butyl [(1R)-2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxo-1-phenylethyl]carbamate The title product was prepared from (5R)-8-chloro-1-[trans-4-(pyridin-2-yloxy)cyclohexyl]-5,6-dihydro-4H-[1,2,4]triazolo[4,3-a][1]benzazepine-5-amine (Example 8) and Boc-D-Phg-OH according to the method described in step a) of Example 10. MS (ESI) m/z 643.2 (M+H)⁺.

b) (2R)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide The title product was prepared from tert-butyl [(1R)-2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-2-oxo-1-phenylethyl]carbamate (step a) of Example 14) according to the method described in step b) of Example 10. MS (ESI) m/z 543.2 (M+H)⁺.

Example 15

N-{8-chloro-1-[trans-4-(pyridin-2-yloxy)cyclohexyl]-5,6-dihydro-4H-[1,2,4]triazolo[4,3-a][1]benzazepin-5-yl}-2-hydroxyacetamide

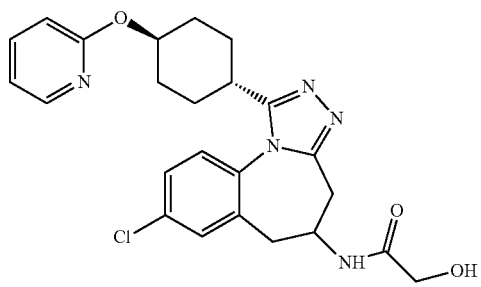 [SMILES: O=C(CO)NC1Cc2cc(Cl)ccc2-n2c(nnc2[C@H]2CC[C@H](Oc3ccccn3)CC2)C1]

0.10 g (0.24 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6) was dissolved in 5 mL of DMF, then 0.10 g (0.27 mmol) of HBTU, 0.17 mL (1.22 mmol) of triethylamine and 0.02 g (0.27 mmol) of hydroxyacetic acid were added. The reaction mixture was stirred for 16 hours at room temperature. The solution was concentrated, 20 mL of saturated NaHCO₃ solution was added to the residue, extracted twice with 20 mL of dichloromethane, the combined organic phases were dried over MgSO₄, filtered and concentrated. The residue was purified by column chromatography using dichloromethane:methanol=9:1 as eluent. The expected product was crystallized by trituration with diethyl ether to yield 0.07 g (62%) of the title product. LC-MS (ESI) m/z 468.2 (M+H)⁺.

Example 16

3-{8-chloro-1-[trans-4-(pyridin-2-yloxy)cyclohexyl]-5,6-dihydro-4H-[1,2,4]triazolo[4,3-a][1]benzazepin-5-yl}-1,1-dimethylurea

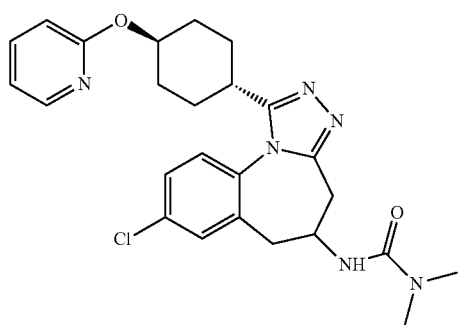 [SMILES: CN(C)C(=O)NC1Cc2cc(Cl)ccc2-n2c(nnc2[C@H]2CC[C@H](Oc3ccccn3)CC2)C1]

To a stirred solution of 37 mg (0.23 mmol) of 1,1-carbonyldiimidazole and 3 mL of dichloromethane a solution of 94 mg (0.23 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6) in 3 mL of DMF and 80 μL of DIPEA was added dropwise and the reaction mixture was stirred at room temperature for 1 hour. Then 1 mL of a 2M solution of dimethylamine in THF was added dropwise to the mixture and the mixture was stirred for further 2 hours at room temperature, then concentrated. The residue was dissolved in 20 mL of ethyl acetate and washed with saturated NaCl solution. The organic phase was dried over anhydrous Na₂SO₄, filtered and concentrated. The residue was purified by column chromatography using ammonium hydroxide:1,4-dioxane:ethanol=1:40:1 as eluent. Thus, 22 mg (20%) of the title product was obtained. MS (ESI) m/z 481.2 (M+H)⁺.

Example 17

N-{8-chloro-1-[trans-4-(pyridin-2-yloxy)cyclohexyl]-5,6-dihydro-4H-[1,2,4]triazolo[4,3-a][1]benzazepin-5-yl}-N²,N²-dimethylglycinamide

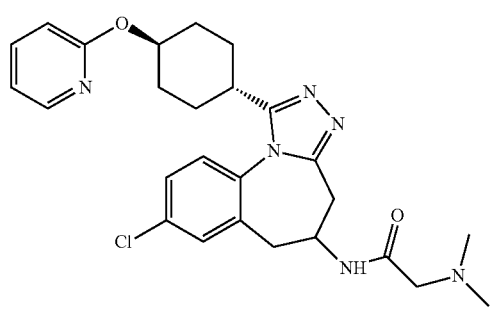 [SMILES: CN(C)CC(=O)NC1Cc2cc(Cl)ccc2-n2c(nnc2[C@H]2CC[C@H](Oc3ccccn3)CC2)C1]

The title product was prepared from 8-chloro-1-[trans-4-(pyridin-2-yloxy)cyclohexyl]-5,6-dihydro-4H-[1,2,4]triazolo[4,3-a][1]benzazepine-5-amine (Example 6) according to the method described in Example 16. LC-MS (ESI) m/z 495.2 (M+H)⁺.

Example 18

N-{8-chloro-1-[trans-4-(pyridin-2-yloxy)cyclohexyl]-5,6-dihydro-4H-[1,2,4]triazolo[4,3-a][1]benzazepin-5-yl}methanesulfonamide

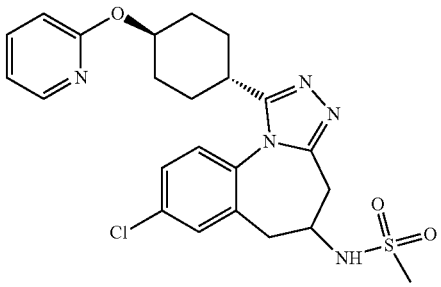 [SMILES: CS(=O)(=O)NC1Cc2cc(Cl)ccc2-n2c(nnc2[C@H]2CC[C@H](Oc3ccccn3)CC2)C1]

To a solution of 200 mg (0.49 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 10 mL of dichloromethane and 84 μL (0.6 mmol) of triethylamine, 46 μL (0.6 mmol) of methanesulfonylchloride was added and the reaction mixture was stirred at room temperature overnight. Then, additional 84 μL (0.6 mmol) of triethylamine and 46 μL (0.6 mmol) of methanesulfonylchloride were added to the reaction mixture and stirred at room temperature overnight. The reaction mixture was then diluted with dichloromethane, washed with saturated NaHCO$_3$ solution and saturated NaCl solution, the organic phase was dried over anhydrous Na$_2$SO$_4$, filtered and concentrated. The residue was purified by column chromatography using dichloromethane:methanol=9:1 as eluent. Thus 93 mg (39%) of the title product was obtained. MS (ESI) m/z 488.2 (M+H)$^+$.

Example 19

N-{8-chloro-1-[trans-4-pyridin-2-lox cyclohexyl]-5,6-dihydro-4H-[1,2,4]triazolo[4,3-a][1]benzazepin-5-yl}-N-methylmethanesulfonamide

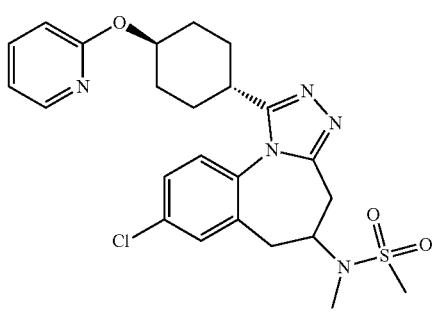 [SMILES: CN(C1Cc2cc(Cl)ccc2-n2c(nnc2[C@H]2CC[C@H](Oc3ccccn3)CC2)C1)S(C)(=O)=O]

To a solution of 50 mg (0.1 mmol) of N-{8-chloro-1-[trans-4-(pyridin-2-yloxy)cyclohexyl]-5,6-dihydro-4H-[1,2,4]triazolo[4,3-a][1]benzazepin-5-yl}methanesulfonamide (Example 18) in 10 mL of DMF 10 mg (0.25 mmol) of sodium hydride (60% dispersion in oil) was added and the reaction mixture was stirred at room temperature for 15 minutes. 15 μL (0.24 mmol) of iodomethane was then added and the reaction mixture was stirred at room temperature overnight. Then, additional 10 mg of sodium hydride (60% dispersion in oil) and 15 μL of iodomethane were added to the reaction mixture and stirred at room temperature overnight. The reaction mixture was then diluted with water and extracted with ethyl acetate. The combined organic phases were dried over anhydrous Na$_2$SO$_4$, filtered and concentrated. The residue was purified by column chromatography using dichloromethane:methanol=95:5 as eluent. Thus, 33 mg (65%) of the title product was obtained. MS (ESI) m/z 502.2 (M+H)$^+$.

Example 20

N'-{8-chloro-1-[trans-4-(pyridin-2-yloxy)cyclohexyl]-5,6-dihydro-4H-[1,2,4]triazolo[4,3-a][1]benzazepin-5-yl}-N,N-dimethylsulfamide

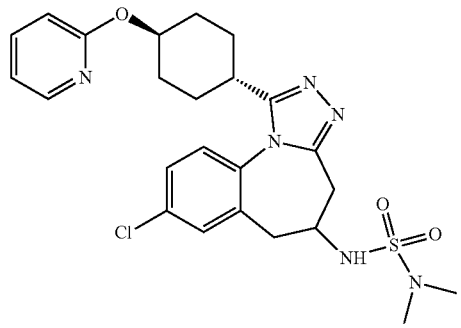 [SMILES: CN(C)S(=O)(=O)NC1Cc2cc(Cl)ccc2-n2c(nnc2[C@H]2CC[C@H](Oc3ccccn3)CC2)C1]

To a solution of 82 mg (0.2 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 5 mL of dichloromethane and 35 μL (0.25 mmol) of triethylamine, 25 μL (0.23 mmol) of N,N-dimethylsulfamoyl chloride was added and the reaction mixture was stirred at room temperature for 20 hours. Then, additional 35 μL of triethylamine and 25 μL of N,N-dimethylsulfamoyl chloride were added, and the mixture was stirred at 40° C. for 48 hours. The reaction mixture was diluted with dichloromethane, washed with saturated NaHCO$_3$ and saturated NaCl solution, the organic phase was dried over anhydrous Na$_2$SO$_4$, filtered and concentrated. The residue was purified by column chromatography using dichloromethane:methanol=9:1 as eluent. Thus 38 mg (37%) of the title product was obtained. MS (ESI) m/z 517.2 (M+H)$^+$.

Example 21

8-chloro-N-methyl-1-[trans-4-(pyridin-2-yloxy)cyclohexyl]-5,6-dihydro-4H-[1,2,4]triazolo[4,3a][1]benzazepine-5-amine

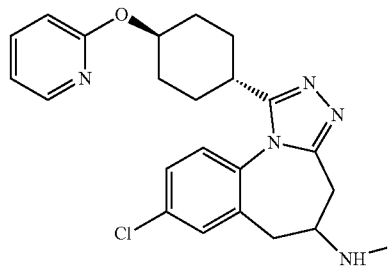

a) Tert-butyl {8-chloro-1-[trans-4-(pyridin-2-yloxy)cyclohexyl]-5,6-dihydro-4H-[1,2,4]triazolo[4,3-a][1]benzazepin-5-yl}methylcarbamate

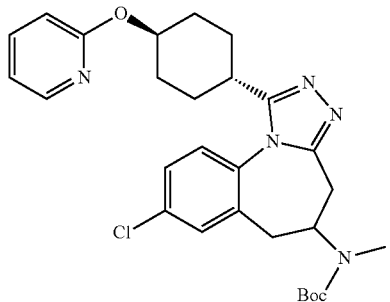 [SMILES: CN(C(=O)OC(C)(C)C)C1Cc2cc(Cl)ccc2-n2c(nnc2[C@H]2CC[C@H](Oc3ccccn3)CC2)C1]

To a solution of 98 mg (0.19 mol) of tert-butyl {8-chloro-1-[trans-4-(pyridin-2-yloxy)cyclohexyl]-5,6-dihydro-4H-[1,2,4]triazolo[4,3-a][1]benzazepin-5-yl}carbamate (Example 5) in 10 mL of DMF 20 mg (0.5 mmol) of sodium hydride (60% dispersion in oil) was added and the reaction mixture was stirred at room temperature for 15 minutes. Then, 30 μL (0.48 mmol) of iodomethane was added and the mixture was stirred at room temperature overnight. Then, additional 20 mg of sodium hydride (60% dispersion in oil) and 30 μL of iodomethane were added to the reaction mixture and stirred at room temperature overnight. The reaction mixture was then diluted with water and extracted with ethyl acetate. The combined organic phases were dried over anhydrous Na$_2$SO$_4$, filtered and concentrated. The residue was purified by column chromatography using dichloromethane:methanol=9:1 as eluent. Thus 58 mg (58%) of the title product was obtained. MS (ESI) m/z 524.3 (M+H)$^+$.

b) 8-chloro-N-methyl-1-[trans-4-(pyridin-2-yloxy)cyclohexyl]-5,6-dihydro-4H-[1,2,4]triazolo[4,3-a][1]benzazepine-5-amine The title product was prepared from tert-butyl {8-chloro-1-[trans-4-(pyridin-2-yloxy)cyclohexyl]-5,6-dihydro-4H-[1,2,4]triazolo[4,3-a][1]benzazepin-5-yl}methylcarbamate (step a) of Example 21) according to the method described in Example 6. MS (ESI) m/z 424.1 (M+H)$^+$.

Example 22

8-chloro-N,N-dimethyl-1-[trans-4-(pyridin-2-yloxy)cyclohexyl]-5,6-dihydro-4H-[1,2,4]triazolo[4,3-a][1]benzazepine-5-amine

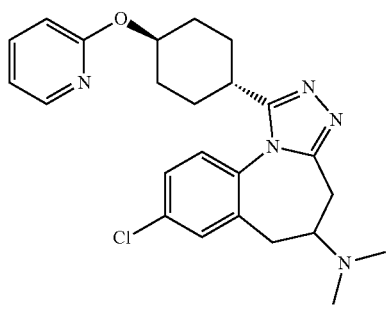 [SMILES: CN(C)C1Cc2cc(Cl)ccc2-n2c(nnc2[C@H]2CC[C@H](Oc3ccccn3)CC2)C1]

To a solution of 100 mg (0.24 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 15 mL of methanol, 182 μL (2.44 mmol) of 37% formaldehyde and 28 μL (0.488 mmol) acetic acid, 168 mg (0.79 mmol) of NaBH(OAc)$_3$ was added under ice-cooling, and the reaction mixture was stirred at room temperature for 20 hours. Then 10 mL of saturated NaHCO$_3$ solution was added to the reaction mixture and concentrated. 30 mL of water was added to the residue and extracted with dichloromethane. The combined organic phases were dried over Na$_2$SO$_4$, filtered and concentrated. The residue was purified by column chromatography using dichloromethane:methanol=9:1 as eluent. Thus, 68 mg (64%) of the title product was obtained. MS (ESI) m/z 438.2 (M+H)$^+$.

Example 23

8-chloro-N-ethyl-1-[trans-4-(pyridin-2-yloxy)cyclohexyl]-5,6-dihydro-4H-[1,2,4]triazolo[4,3-a][1]benzazepine-5-amine

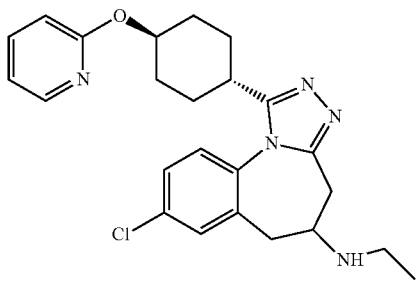 [SMILES: CCNC1Cc2cc(Cl)ccc2-n2c(nnc2[C@H]2CC[C@H](Oc3ccccn3)CC2)C1]

a) Tert-butyl {8-chloro-1-[trans-4-(pyridin-2-yloxy)cyclohexyl]-5,6-dihydro-4H-[1,2,4]triazolo[4,3-a][1]benzazepin-5-yl}ethylcarbamate

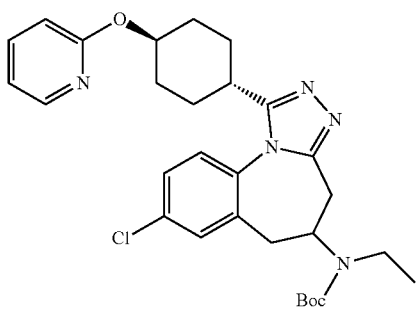 [SMILES: CCN(C(=O)OC(C)(C)C)C1Cc2cc(Cl)ccc2-n2c(nnc2[C@H]2CC[C@H](Oc3ccccn3)CC2)C1]

The title product was prepared from tert-butyl {8-chloro-1-[trans-4-(pyridin-2-yloxy)cyclohexyl]-5,6-dihydro-4H-[1,2,4]triazolo[4,3-a][1]benzazepin-5-yl}carbamate (Example 5) and ethyl iodide according to the method described in step a) of Example 21.

b) 8-chloro-N-ethyl-1-[trans-4-(pyridin-2-yloxy)cyclohexyl]-5,6-dihydro-4H-[1,2,4]triazolo[4,3-a][1]benzazepine-5-amine The title product was prepared from tert-butyl {8-chloro-1-[trans-4-(pyridin-2-yloxy)cyclohexyl]-5,6-dihydro-4H-[1, 2,4]triazolo[4,3-a][1]benzazepin-5-yl}ethylcarbamate (step a) of Example 23) according to the method described in Example 6. MS (ESI) m/z 438.2 (M+H)+.

Example 24

8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine

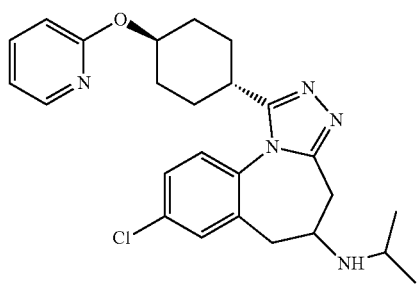 [SMILES: CC(C)NC1Cc2cc(Cl)ccc2-n2c(nnc2[C@H]2CC[C@H](Oc3ccccn3)CC2)C1]

To a mixture of 0.5 g (1.22 mmol) of 8-chloro-1-[trans-4-(pyridin-2-yloxy)cyclohexyl]-5,6-dihydro-4H-[1,2,4]triazolo[4,3-a][1]benzazepine-5-amine (Example 6), 50 mL of 1,2-dichloroethane, 0.45 mL (6.13 mmol) of acetone and 134 μL (2.34 mmol) of acetic acid, 0.8 g (3.77 mmol) of NaBH(OAc)$_3$ was added in small portions under ice-water cooling, and the reaction mixture was stirred at room temperature for 20 hours. Then, 50 mL of water was added to the reaction mixture, the pH was adjusted to 12 with 5% NaOH solution and extracted with dichloromethane. The combined organic phases were dried over Na$_2$SO$_4$, filtered and concentrated. The residue was purified by column chromatography using dichloromethane:methanol=95:5 as eluent. Thus, 0.434 g (79%) of the title product was obtained. MS (ESI) m/z 452.2 (M+H)+.

Example 25

(5S)-8-chloro-N-propan-2-yl)-1-[trans-4-pyridin-2-yloxy)cyclohexyl]-5,6-dihydro-4H-[1,2,4]triazolo[4,3-a][1]benzazepine-5-amine

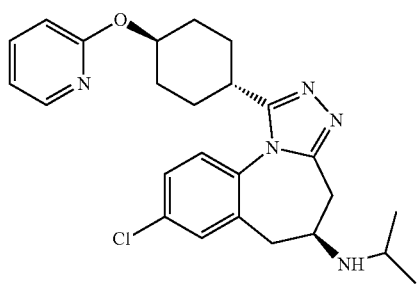 [SMILES: CC(C)N[C@H]1Cc2cc(Cl)ccc2-n2c(nnc2[C@H]2CC[C@H](Oc3ccccn3)CC2)C1]

The title product was prepared from (5S)-8-chloro-1-[trans-4-(pyridin-2-yloxy)cyclohexyl]-5,6-dihydro-4H-[1,2,4]triazolo[4,3-a][1]benzazepine-5-amine (Example 7) according to the method described in Example 24. $[\alpha]_D^{25}$=−29.3° (c=0.1; methanol); MS (ESI) m/z 452.3 (M+H)+.

Example 26

(5R)-8-chloro-N-(propan-2-yl-1-[trans-4-(pyridin-2-yloxy)cyclohexyl]-5,6-dihydro-4H-[1,2,4]triazolo[4,3-a][1]benzazepine-5-amine

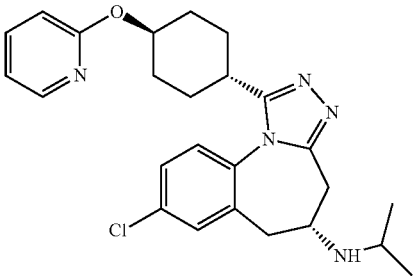 [SMILES: CC(C)N[C@@H]1Cc2cc(Cl)ccc2-n2c(nnc2[C@H]2CC[C@H](Oc3ccccn3)CC2)C1]

The title product was prepared from (5R)-8-chloro-1-[trans-4-(pyridin-2-yloxy)cyclohexyl]-5,6-dihydro-4H-[1,2,4]triazolo[4,3-a][1]benzazepine-5-amine (Example 8) according to the method described in Example 24. $[\alpha]_D^{25}$=+30.7° (c=0.1; methanol); MS (ESI) m/z 452.3 (M+H)+.

Example 27

8-chloro-N-cyclobutyl-1-[trans-4-(pyridin-2-yloxy)cyclohexyl]-5,6-dihydro-4H-[1,2,4]triazolo[4,3-a][1]benzazepine-5-amine

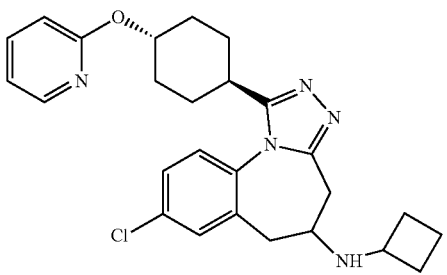 [SMILES: Clc1ccc2c(c1)CC(NC1CCC1)Cc1nnc([C@H]3CC[C@H](Oc4ccccn4)CC3)n1-2]

The title product was prepared from 8-chloro-1-[trans-4-(pyridin-2-yloxy)cyclohexyl]-5,6-dihydro-4H-[1,2,4]triazolo[4,3-a][1]benzazepine-5-amine (Example 6) and cyclobutanol according to the method described in Example 24. MS (ESI) m/z 464.2 (M+H)+.

171

Example 28

8-chloro-N-(oxetan-3-yl)-1[trans-4-(pyridin-2-yloxy)cyclohexyl]-5,6-dihydro-4H-[1,2,4]triazolo[4,3-a][1]benzazepine-5-amine

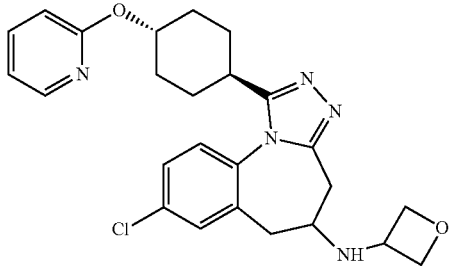 [SMILES: Clc1ccc2c(c1)CC(NC1COC1)Cc1nnc([C@H]3CC[C@H](Oc4ccccn4)CC3)n1-2]

The title product was prepared from 8-chloro-1-[trans-4-(pyridin-2-yloxy)cyclohexyl]-5,6-dihydro-4H-[1,2,4]triazolo[4,3-a][1]benzazepine-5-amine (Example 6) and oxetane-3-one according to the method described in Example 24. LC-MS (ESI) m/z 466.2 (M+H)+.

Example 29

8-chloro-1-[trans-4-(pyridin-2-yloxy)cyclohexyl]-N-(tetrahydro-2H-pyran-4-yl)-5,6-dihydro-4H-[1,2,4]triazolo[4,3-a][1]benzazepine-5-amine

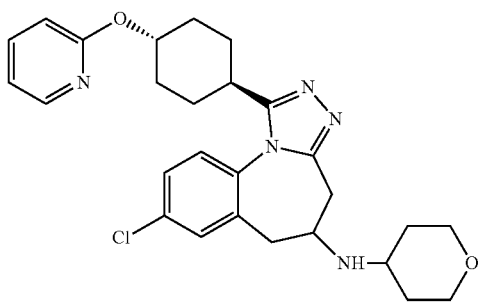 [SMILES: Clc1ccc2c(c1)CC(NC1CCOCC1)Cc1nnc([C@H]3CC[C@H](Oc4ccccn4)CC3)n1-2]

The title product was prepared from 8-chloro-1-[trans-4-(pyridin-2-yloxy)cyclohexyl]-5,6-dihydro-4H-[1,2,4]triazolo[4,3-a][1]benzazepine-5-amine (Example 6) and tetrahydro-4H-pyran-4-one according to the method described in Example 24. MS (ESI) m/z 494.2 (M+H)+.

172

Example 30

8-chloro-N-(4,4-difluorocyclohexyl)-1-[trans-4-(pyridin-2-yloxy)cyclohexyl]-5,6-dihydro-4H-[1,2,4]triazolo[4,3-a][1]benzazepine-5-amine

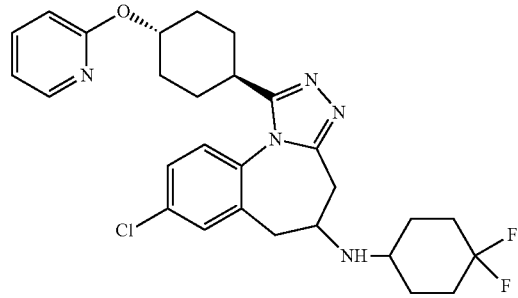 [SMILES: FC1(F)CCC(NC2Cc3cc(Cl)ccc3-n3c(nnc3[C@H]3CC[C@H](Oc4ccccn4)CC3)C2)CC1]

The title product was prepared from 8-chloro-1-[trans-4-(pyridin-2-yloxy)cyclohexyl]-5,6-dihydro-4H-[1,2,4]triazolo[4,3-a][1]benzazepine-5-amine (Example 6) and 4,4-difluorocyclohexanone according to the method described in Example 24. MS (ESI) m/z 528.2 (M+H)+.

Example 31

8-methoxy-1-[trans-4-(pyridin-2-yloxy)cyclohexyl]-5,6-dihydro-4H-[1,2,4]triazolo[4,3-a][1]benzazepine-5-amine hydrochloride

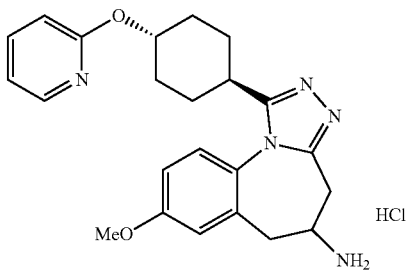 [SMILES: COc1ccc2c(c1)CC(N)Cc1nnc([C@H]3CC[C@H](Oc4ccccn4)CC3)n1-2 ; Cl]

a) Tert-butyl {8-methoxy-1-[trans-4-(pyridin-2-yloxy)cyclohexyl]-5,6-dihydro-4H-[1,2,4]triazolo[4,3-a][1]benzazepin-5-yl}carbamate

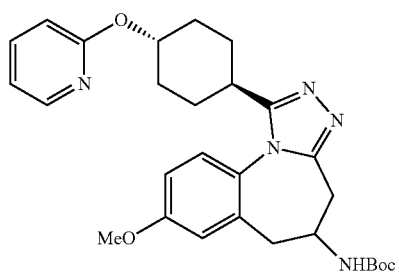 [SMILES: COc1ccc2c(c1)CC(NC(=O)OC(C)(C)C)Cc1nnc([C@H]3CC[C@H](Oc4ccccn4)CC3)n1-2]

A mixture of 113 mg (0.35 mmol) of tert-butyl (7-methoxy-2-thioxo-2,3,4,5-tetrahydro-1H-1-benzazepin- 4-yl)carbamate (Intermediate 15), 91 mg (0.39 mmol) of trans-4-(pyridin-2-yloxy)cyclohexane carboxylic acid hydrazide and 2 mL of 1,4-dioxane was stirred at 120° C. for 2 hours under microwave irradiation (200 W), then 80 mg (0.35 mmol) of silver benzoate was added and the reaction mixture was stirred under the same conditions for 2 more hours. The reaction mixture was filtered through Celite, washed with dichloromethane and concentrated. The residue was purified by column chromatography using dichloromethane:methanol=96:4 as eluent. Thus, 103 mg (58%) of the title product was obtained. MS (ESI) m/z 506.3 (M+H)$^+$.

b) 8-methoxy-1-[trans-4-(pyridin-2-yloxy)cyclohexyl]-5,6-dihydro-4H-[1,2,4]triazolo[4,3-a][1]benzazepine-5-amine hydrochloride A mixture of 103 mg (0.2 mmol) of tert-butyl {8-methoxy-1-[trans-4-(pyridin-2-yloxy)cyclohexyl]-5,6-dihydro-4H-[1,2,4]triazolo[4,3-a][1]benzazepin-5-yl}carbamate (step a) of Example 31) and 3 mL of 2.5M hydrogen chloride solution in ethyl acetate was stirred at room temperature for 2 hours. The precipitated crystals were filtered and washed with ethyl acetate. Thus, 65.4 mg (79%) of the title product was obtained. MS (ESI) m/z 406.2 (M+H)$^+$.

Example 32

8-methoxy-N-(propan-2-yl)-1-[trans-4-(pyridin-2-yloxy)cyclohexyl]-5,6-dihydro-4H-[1,2,4]triazolo[4,3-a][1]benzazepine-5-amine

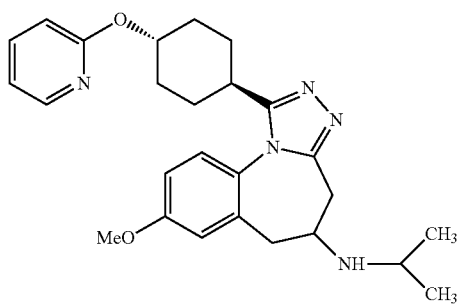 [SMILES: COc1ccc2c(c1)CC(NC(C)C)Cc1nnc([C@H]3CC[C@H](Oc4ccccn4)CC3)n1-2]

The title product was prepared from 8-methoxy-1-[trans-4-(pyridin-2-yloxy)cyclohexyl]-5,6-dihydro-4H-[1,2,4]triazolo[4,3-a][1]benzazepine-5-amine hydrochloride (Example 31) according to the method described in Example 24. MS (ESI) m/z 448.3 (M+H)$^+$.

Example 33

Tert-butyl {1-[trans-4-(pyridin-2-yloxy)cyclohexyl]-8-(trifluoromethyl)-5,6-dihydro-4H-[1,2,4]triazolo[4,3-a][1]benzazepin-5-yl}carbamate

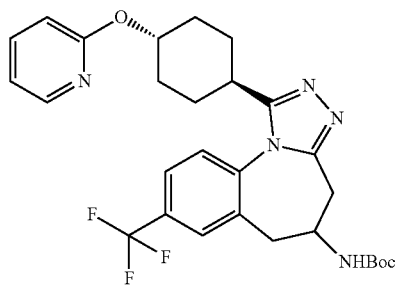 [SMILES: CC(C)(C)OC(=O)NC1Cc2cc(C(F)(F)F)ccc2-n2c(nnc2[C@H]2CC[C@H](Oc3ccccn3)CC2)C1]

0.46 g (1.22 mmol) tert-butyl[2-(methylsulfanyl)-7-(trifluoromethyl)-4,5-dihydro-3H-1-benzazepin-4-yl]carbamate (Intermediate 50) was dissolved in 30 mL of xylene and 0.45 g (1.83 mmol) of trans-4-(pyridin-2-yloxy)cyclohexane carboxylic acid hydrazide was added to the solution. A drop of concentrated hydrochloric acid was added to the reaction mixture and the mixture was refluxed for 2 hours. After cooling to room temperature, the solution was concentrated. The residue was purified by flash chromatography using dichloromethane:methanol=95:5 as eluent. Fractions containing the expected product were concentrated and the product crystallized by trituration with ether. Thus, 0.52 g (78%) of the title product was obtained. MS (ESI) m/z 544.2 (M+H)$^+$.

Example 34

1-[trans-4-(pyridin-2-yloxy)cyclohexyl]-8-(trifluoromethyl)-5,6-dihydro-4H-[1,2,4]triazolo[4,3-a][1]benzazepine-5-amine hydrochloride

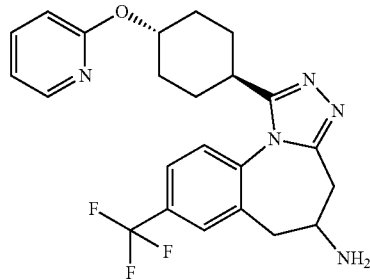 [SMILES: NC1Cc2cc(C(F)(F)F)ccc2-n2c(nnc2[C@H]2CC[C@H](Oc3ccccn3)CC2)C1]

0.52 g (0.95 mmol) of tert-butyl{1-[trans-4-(pyridin-2-yloxy)cyclohexyl]-8-(trifluoromethyl)-5,6-dihydro-4H-[1,2,4]triazolo[4,3-a][1]benzazepin-5-yl}carbamate (Example 33) was dissolved in 30 mL of ethyl acetate, and then 10 mL of 2.5M hydrogen chloride solution in ethyl acetate was added with ice-water cooling. The reaction mixture was stirred at room temperature for 4 hours, then 30 mL of diethyl ether was added and the mixture was cooled again in an ice-water bath. The precipitated product was filtered, washed with diethyl ether and dried. Thus, 0.39 g (86%) of the title product was obtained. MS (ESI) m/z 444.2 (M+H)$^+$. The product was used in the further reactions as a free base.

Example 35

N,N-dimethyl-1-[trans-4-(pyridin-2-yloxy)cyclohexyl]-8-(trifluoromethyl)-5,6-dihydro-4H-[1,2,4]triazolo[4,3-a][1]benzazepine-5-amine

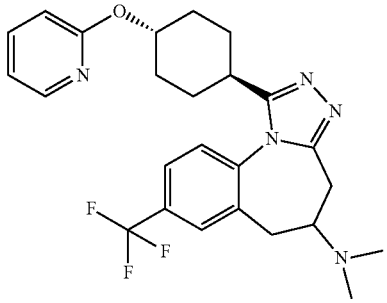 [SMILES: CN(C)C1Cc2cc(C(F)(F)F)ccc2-n2c(nnc2[C@H]2CC[C@H](Oc3ccccn3)CC2)C1]

The title product was prepared from 1-[trans-4-(pyridin-2-yloxy)cyclohexyl]-8-(trifluoromethyl)-5,6-dihydro-4H-[1,2,4]triazolo[4,3-a][1]benzazepine-5-amine (Example 34) according to the method described in Example 22. MS (ESI) m/z 472.2 (M+H)$^+$.

Example 36

N-(propan-2-yl)-1-[trans-4-(pyridin-2-yloxy)cyclohexyl]-8-(trifluoromethyl)-5,6-dihydro-4H-[1,2,4]triazolo[4,3-a][1]benzazepine-5-amine

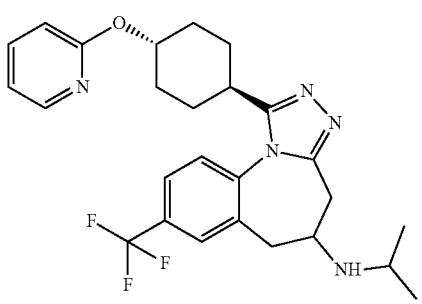 [SMILES: CC(C)NC1Cc2cc(C(F)(F)F)ccc2-n2c(nnc2[C@H]2CC[C@H](Oc3ccccn3)CC2)C1]

The title product was prepared from 1-[trans-4-(pyridin-2-yloxy)cyclohexyl]-8-(trifluoromethyl)-5,6-dihydro-4H-[1,2,4]triazolo[4,3-a][1]benzazepine-5-amine (Example 34) according to the method described in Example 24. MS (ESI) m/z 486.2 (M+H)$^+$.

Example 37

8-methyl-1-[trans-4-(pyridin-2-yloxy)cyclohexyl]-5,6-dihydro-4H-[1,2,4]triazolo[4,3-a][1]benzazepine-5-amine

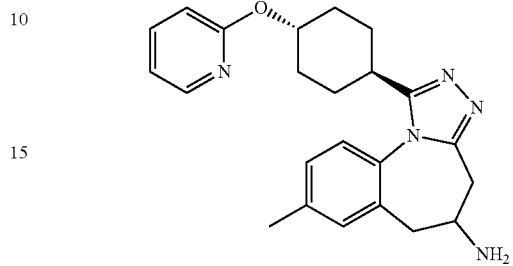

a) Tert-butyl {8-methyl-1-[trans-4-(pyridin-2-yloxy)cyclohexyl]-5,6-dihydro-4H-[1,2,4]triazolo[4,3-a][1]benzazepin-5-yl}carbamate A mixture of 30.6 mg (0.1 mmol) of tert-butyl (7-methyl-2-thioxo-2,3,4,5-tetrahydro-1H-1-benzazepin-4-yl)carbamate (Intermediate 23), 35.3 mg (0.15 mmol) of trans-4-(pyridin-2-yloxy)cyclohexane carboxylic acid hydrazide and 1 mL of n-butanol was refluxed for 48 hours, then concentrated. The residue was used without further purification. MS (ESI) m/z 490.3 (M+H)$^+$.

b) 8-methyl-1-[trans-4-(pyridin-2-yloxy)cyclohexyl]-5,6-dihydro-4H-[1,2,4]triazolo[4,3-a][1]benzazepine-5-amine A mixture of 91 mg (0.19 mmol) of tert-butyl {8-methyl-1-[trans-4-(pyridin-2-yloxy)cyclohexyl]-5,6-dihydro-4H-[1,2,4]triazolo[4,3-a][1]benzazepin-5-yl}carbamate (step a) of Example 37) and 4.8 mL of 2.5M hydrogen chloride solution in ethyl acetate was stirred at room temperature for 2.5 hours. The precipitated crystals were filtered and washed with ethyl acetate. Ethyl acetate and aqueous K$_2$CO$_3$ solution were added to the filtered hydrochloride salt and stirred for 10 minutes at room temperature. The phases were separated, the organic phase was dried over anhydrous Na$_2$SO$_4$, filtered and concentrated. The residue was purified by gradient chromatography using dichloromethane:methanol=93:7→90:10 as eluent. Thus, 35 mg (49%) of the title product was obtained. MS (ESI) m/z 390.2 (M+H)$^+$.

Example 38

8-methyl-N-(propan-2yl)-1-[trans-4-(pyridin-2-yloxy)cyclohexyl]-5,6-dihydro-4H-[1,2,4]triazolo[4,3-a][1]benzazepine-5-amine

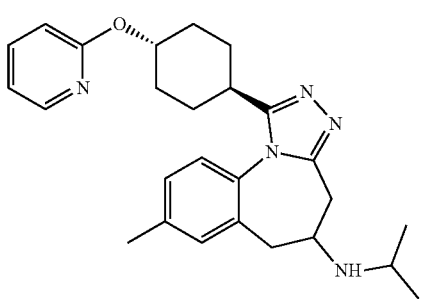

The title product was prepared from 8-methyl-1-[trans-4-(pyridin-2-yloxy)cyclohexyl]-5,6-dihydro-4H-[1,2,4]triazolo[4,3-a][1]benzazepine-5-amine (Example 37) according to the method described in Example 24. MS (ESI) m/z 432.3 (M+H)+.

Example 39

8-bromo-1-[trans-4-(pyridin-2-yloxy)cyclohexyl]-5,6-dihydro-4H-[1,2,4]triazolo[4,3-a][1]benzazepine-5-amine

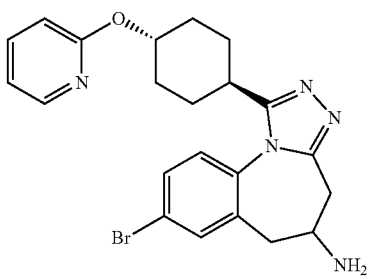 [SMILES: Cc1ccc2c(c1)CC(N)Cc1nnc([C@H]3CC[C@H](Oc4ccccn4)CC3)n1-2]

A mixture of 0.68 g (1.8 mmol) of tert-butyl{-[trans-4-(pyridin-2-yloxy)cyclohexyl]-8-(trifluoromethyl)-5,6-dihydro-4H-[1,2,4]triazolo[4,3-a][1]benzazepin-5-yl}carbamate (Example 33), 0.65 g (2.75 mmol) trans-4-(pyridin-2-yloxy)cyclohexane carboxylic acid hydrazide and 18 mL of n-butanol was refluxed for 29 hours, then concentrated. 25 mL of 2.5M hydrogen chloride solution in ethyl acetate was added to the residue and stirred at room temperature for 1.5 hours. The precipitated crystals were filtered and washed with ethyl acetate. Ethyl acetate and aqueous K₂CO₃ solution were added to the filtered hydrochloride salt and stirred for 10 minutes at room temperature. The phases were separated, the organic phase was dried over anhydrous Na₂SO₄, filtered and concentrated. The residue was purified by gradient chromatography using dichloromethane:methanol 95:5→85:15 as eluent. Thus, 0.64 g (78%) of the title product was obtained. MS (ESI) m/z 454.1 (M+H)+.

Example 40

8-bromo-N-(propan-2-yl)-1-[trans-4-(pyridin-2-yloxy)cyclohexyl]-5,6-dihydro-4H-[1,2,4]triazolo[4,3-a][1]benzazepine-5-amine

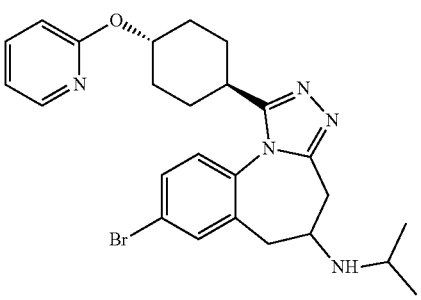 [SMILES: CC(C)NC1Cc2cc(Br)ccc2-n2c(nnc2[C@H]2CC[C@H](Oc3ccccn3)CC2)C1]

The title product was prepared from 8-bromo-1-[trans-4-(pyridin-2-yloxy)cyclohexyl]-5,6-dihydro-4H-[1,2,4]triazolo[4,3-a][1]benzazepine-5-amine (Example 39) according to the method described in Example 24. MS (ESI) m/z 498.1 (M+H)+.

Example 41

8-chloro-1-(3,3-difluorocyclobutyl)-N-(propan-2-yl)-5,6-dihydro-4H-[1,2,4]triazolo[4,3-a][1]benzazepine-5-amine

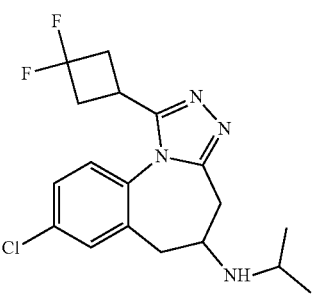 [SMILES: CC(C)NC1Cc2cc(Cl)ccc2-n2c(nnc2C2CC(F)(F)C2)C1]

a) Tert-butyl [8-chloro-1-(3,3-difluorocyclobutyl)-5,6-dihydro-4H-[1,2,4]triazolo[4,3-a][1]benzazepin-5-yl]carbamate

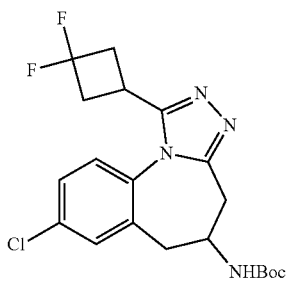 [SMILES: CC(C)(C)OC(=O)NC1Cc2cc(Cl)ccc2-n2c(nnc2C2CC(F)(F)C2)C1]

0.19 g (0.59 mmol) of tert-butyl (7-chloro-2-thioxo-2,3,4,5-tetrahydro-1H-1-benzazepin-4-yl)carbamate (Intermediate 4) was dissolved in 10 mL of xylene and 0.14 g (0.90 mmol) of 3,3-difluorocyclobutane carboxylic acid hydrazide (Intermediate 57) was added to the solution. The reaction mixture was refluxed under argon for 6 days and then concentrated. The product was purified by column chromatography using dichloromethane:methanol:25% ammonia solution=18:1:0.1 as eluent. The appropriate fractions were concentrated and the residue was crystallized by trituration with ether. Thus, 0.11 g (42%) of the title product was obtained. MS (ESI) m/z 425.2 (M+H)$^+$.

b) 8-chloro-1-(3,3-difluorocyclobutyl)-5,6-dihydro-4H-[1,2,4]triazolo[4,3-a][1]benzazepine-5-amine

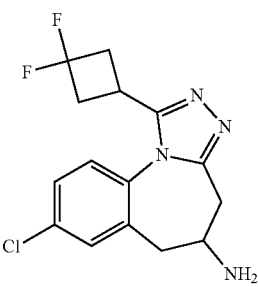 [SMILES: NC1Cc2cc(Cl)ccc2-n2c(nnc2C2CC(F)(F)C2)C1]

0.10 g (0.25 mmol) of tert-butyl [8-chloro-1-(3,3-difluorocyclobutyl)-5,6-dihydro-4H-[1,2,4]triazolo[4,3-a][1]benzazepin-5-yl]carbamate (step a) of Example 41) was dissolved in 10 mL of ethyl acetate, then 2 mL of 2.5M hydrogen chloride solution in ethyl acetate was added to the solution. The reaction mixture was stirred at room temperature for 5 hours, then diethyl ether was added and the product was extracted twice with 20 mL of water. The pH of the combined aqueous phases was basified with saturated Na$_2$CO$_3$ solution and the highly precipitated mixture was extracted twice with 20 mL of dichloromethane. The combined organic phases were dried over MgSO$_4$, filtered and concentrated. Thus, 0.05 g (66%) of the title product was obtained. MS (ESI) m/z 325.2 (M+H)$^+$.

c) 8-chloro-1-(3,3-difluorocyclobutyl)-N-(propan-2-yl)-5,6-dihydro-4H-[1,2,4]triazolo[4,3-a][1]benzazepine-5-amine The title product was prepared from 8-chloro-1-(3,3-difluorocyclobutyl)-5,6-dihydro-4H-[1,2,4]triazolo[4,3-a][1]benzazepine-5-amine (step b) of Example 41) according to the method described in Example 24. MS (ESI) m/z 367.2 (M+H)$^+$.

Example 42

8-chloro-1-(4,4-difluorocyclohexyl)-N-(propan-2-yl)-5,6-dihydro-4H-[1,2,4]triazolo[4,3-a][1]benzazepine-5-amine

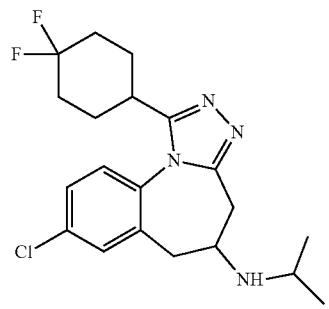 [SMILES: CC(C)NC1Cc2cc(Cl)ccc2-n2c(nnc2C2CCC(F)(F)CC2)C1]

a) Tert-butyl [8-chloro-1-(4,4-difluorocyclohexyl)-5,6-dihydro-4H-[1,2,4]triazolo[4,3-a][1]benzazepin-5-yl]carbamate

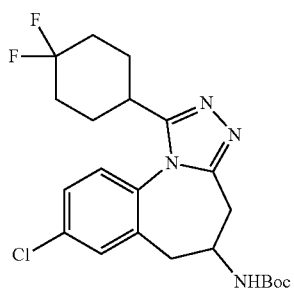 [SMILES: CC(C)(C)OC(=O)NC1Cc2cc(Cl)ccc2-n2c(nnc2C2CCC(F)(F)CC2)C1]

The title product was prepared from tert-butyl (7-chloro-2-thioxo-2,3,4,5-tetrahydro-1H-1-benzazepin-4-yl)carbamate (Intermediate 4) and 4,4-difluorocyclohexane carboxylic acid hydrazide (Intermediate 67) according to the method described in step a) of Example 41. MS (ESI) m/z 453.2 (M+H)$^+$.

b) 3-chloro-1-(4,4-difluorocyclohexyl)-5,6-dihydro-4H-[1,2,4]triazolo[4,3-a][1]benzazepine-5-amine

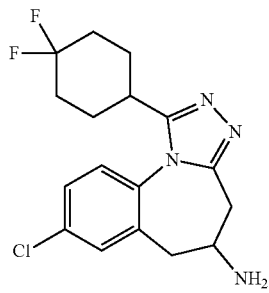 [SMILES: NC1Cc2cc(Cl)ccc2-n2c(nnc2C2CCC(F)(F)CC2)C1]

The title product was prepared from tert-butyl [8-chloro-1-(4,4-difluorocyclohexyl)-5,6-dihydro-4H-[1,2,4]triazolo[4,3-a][1]benzazepin-5-yl]carbamate (step a) of Example 42) according to the method described in step b) of Example 41. MS (ESI) m/z 353.1 (M+H)⁺.

c) 8-chloro-1-(4,4-difluorocyclohexyl)-N-(propan-2-yl)-5,6-dihydro-4H-[1,2,4]triazolo[4,3-a][1]benzazepine-5-amine The title product was prepared from 8-chloro-1-(4,4-difluorocyclohexyl)-5,6-dihydro-4H-[1,2,4]triazolo[4,3-a][1]benzazepine-5-amine (step b) of Example 42) according to the method described in Example 24. MS (ESI) m/z 395.1 (M+H)⁺.

Example 43

8-chloro-1-[trans-4-trifluoromethyl)cyclohexyl]-5,6-dihydro-4H-[1,2,4]triazolo[4,3-a][1]benzazepine-5-amine

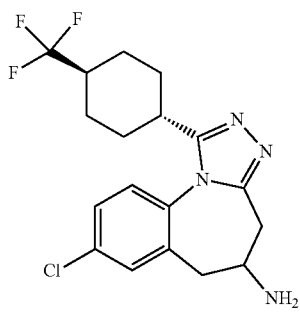 [SMILES: NC1Cc2cc(Cl)ccc2-n2c(nnc2[C@H]2CC[C@H](C(F)(F)F)CC2)C1]

a) Tert-butyl {8-chloro-1-[trans-4-(trifluoromethyl)cyclohexyl]-5,6-dihydro-4H-[1,2,4]triazolo[4,3-a][1]benzazepin-5-yl}carbamate

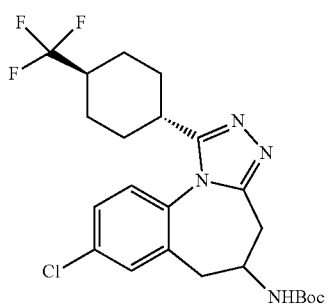 [SMILES: CC(C)(C)OC(=O)NC1Cc2cc(Cl)ccc2-n2c(nnc2[C@H]2CC[C@H](C(F)(F)F)CC2)C1]

The title product was prepared from tert-butyl [7-chloro-2-(methylsulfanyl)-4,5-dihydro-3H-1-benzazepin-4-yl]carbamate (Intermediate 5) and trans-4-(trifluoromethyl)cyclohexane carboxylic acid hydrazide (Intermediate 55) according to the method described in Method B) of Example 5. MS (ESI) m/z 485.2 (M+H)⁺.

b) 8-chloro-1-[trans-4-(trifluoromethyl)cyclohexyl]-5,6-dihydro-4H-[1,2,4]triazolo[4,3-a][1]benzazepine-5-amine The title product was prepared from tert-butyl {8-chloro-1-[trans-4-(trifluoromethyl)cyclohexyl]-5,6-dihydro-4H-[1,2,4]triazolo[4,3-a][1]benzazepin-5-yl}carbamate (step a) of Example 43) according to the method described in Example 6. MS (ESI) m/z 385.2 (M+H)⁺.

Example 44

8-chloro-N-(propan-2-yl)-1-[trans-4-(trifluoromethyl)cyclohexyl]-5,6-dihydro-4H-[1,2,4]triazolo[4,3-a][1]benzazepine-5-amine

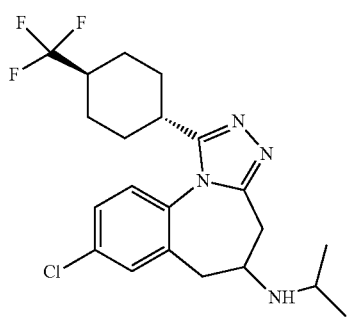 [SMILES: CC(C)NC1Cc2cc(Cl)ccc2-n2c(nnc2[C@H]2CC[C@H](C(F)(F)F)CC2)C1]

The title product was prepared from 8-chloro-1-[trans-4-(trifluoromethyl)cyclohexyl]-5,6-dihydro-4H-[1,2,4]triazolo[4,3-a][1]benzazepine-5-amine (Example 43) according to the method described in Example 24. MS (ESI) m/z 427.2 (M+H)⁺.

Example 45

8-bromo-1-[trans-4-(trifluoromethyl)cyclohexyl]-5,6-dihydro-4H-[1,2,4]triazolo[4,3-a][1]benzazepine-5-amine

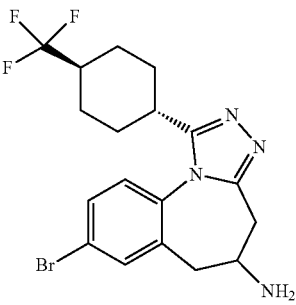 [SMILES: NC1Cc2cc(Br)ccc2-n2c(nnc2[C@H]2CC[C@H](C(F)(F)F)CC2)C1]

The title product was prepared from tert-butyl (7-bromo-2-thioxo-2,3,4,5-tetrahydro-1H-1-benzazepin-4-yl)carbamate (Intermediate 33) and trans-4-(trifluoromethyl)cyclohexane carboxylic acid hydrazide (Intermediate 55) according to the method described in Example 39. MS (ESI) m/z 431.1 (M+H)⁺.

Example 46

8-bromo-N-(propan-2-yl)-1-[trans-4-(trifluoromethyl)cyclohexyl]-5,6-dihydro-4H-[1,2,4]triazolo[4,3-a][1]benzazepine-5-amine

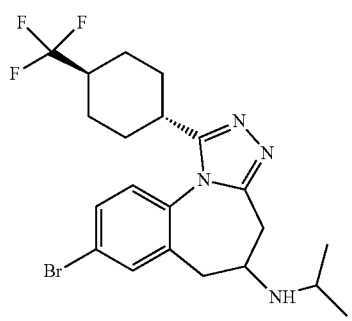 [SMILES: CC(C)NC1Cc2cc(Br)ccc2-n2c(nnc2[C@H]2CC[C@H](C(F)(F)F)CC2)C1]

The title product was prepared from 8-bromo-1-[trans-4-(trifluoromethyl)cyclohexyl]-5,6-dihydro-4H-[1,2,4]triazolo[4,3-a][1]benzazepine-5-amine (Example 45) according to the method described in Example 24. MS (ESI) m/z 471.1 (M+H)+.

Example 47

1'-[trans-4-pyridin-2-yloxy)cyclohexyl]-8'-trifluoromethyl 4'H,6'H-spiro[1,3-dioxolane-2,5'-[1,2,4]triazolo[4,3-a][1]benzazepine]

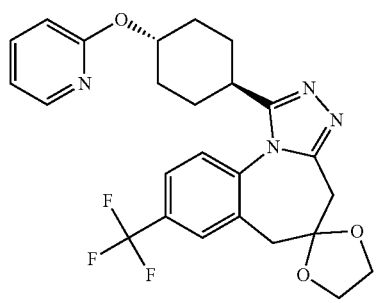 [SMILES: FC(F)(F)c1ccc2c(c1)CC1(Cc3nnc([C@H]4CC[C@H](Oc5ccccn5)CC4)n3-2)OCCO1]

0.80 g (2.79 mmol) of 7-(trifluoromethyl)-1,5-dihydrospiro[1-benzazepine-4,2'-[1,3]dioxolane]-2(3H)-one (Intermediate 43) was dissolved in 60 mL of dichloromethane, then 0.02 mL (0.28 mmol) of trifluoroacetic acid and 0.50 g (3.34 mml) of trimethyloxonium tetrafluoroborate were added to the solution under argon. The reaction mixture was stirred at room temperature for 24 hours and then 0.80 g (3.34 mmol) of trans-4-(pyridin-2-yloxy)cyclohexane carboxylic acid hydrazide was added to the solution. The reaction mixture was refluxed for 6 hours, then the solution was concentrated. The residue was purified by column chromatography using dichloromethane:methanol=95:5 as eluent. The fractions containing the product were concentrated to yield 0.53 g (39%) of the title product. MS (ESI) m/z 487.2 (M+H)+.

Example 48

1-[trans-4-(pyridin-2-yloxy)cyclohexyl]-8-(trifluoromethyl)-4H-[1,2,4]triazolo[4,3-a][1]benzazepin-5(6H)-one

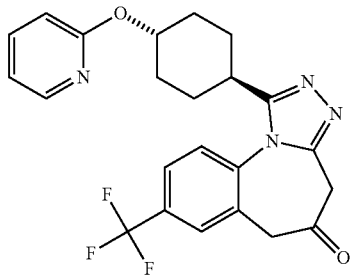 [SMILES: O=C1Cc2cc(C(F)(F)F)ccc2-n2c(nnc2[C@H]2CC[C@H](Oc3ccccn3)CC2)C1]

0.54 g (1.11 mmol) of 1'-[trans-4-(pyridin-2-yloxy)cyclohexyl]-8'-(trifluoromethyl)-4'H,6'H-spiro[1,3-dioxolane-2,5'-[1,2,4]triazolo[4,3-a][1]benzazepine] (Example 47) was dissolved in 20 mL of methanol and 25 mL of concentrated hydrochloric acid was added to the solution. The reaction mixture was refluxed for 2 hours and then, after cooling to room temperature, 50 mL of water was added and the pH was adjusted to 7-8 with 30% NaOH solution. The solution was extracted three times with 30 mL of ethyl acetate, and the combined organic phases were washed with water, then with saturated NaCl solution, dried over MgSO₄, filtered and concentrated. The residue was purified by column chromatography using ethyl acetate:ethanol=3:1 as eluent. The appropriate fractions were concentrated and the residue was crystallized by trituration with ether. Thus, 0.30 g (61%) of the title product was obtained. MS (ESI) m/z 443.2 (M+H)+.

Example 49

1-[trans-4-(pyridin-2-yloxy)cyclohexyl]-8-(trifluoromethyl)-5,6-dihydro-4H-[1,2,4]triazolo[4,3-a][1]benzazepin-5-ol

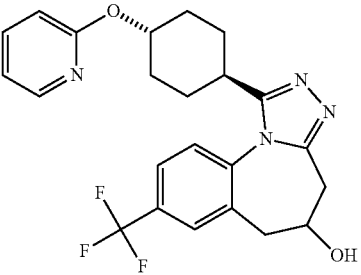 [SMILES: OC1Cc2cc(C(F)(F)F)ccc2-n2c(nnc2[C@H]2CC[C@H](Oc3ccccn3)CC2)C1]

0.32 g (0.72 mmol) of 1-[trans-4-(pyridin-2-yloxy)cyclohexyl]-8-(trifluoromethyl)-4H-[1,2,4]triazolo[4,3-a][1]benzazepine-5(6H)-one (Example 48) was dissolved in 20 mL of methanol and the solution was cooled to 0° C. Under stirring and cooling with ice-water, 0.03 g (0.87 mmol) of NaBH₄ was added to the reaction mixture. The solution was stirred at 0° C. for 10 min and then at room temperature for further 2 hours. The reaction mixture was concentrated, 10 mL of water was added to the residue and the pH of the solution was adjusted to about 7 with 5% hydrochloric acid solution. The aqueous phase was extracted twice with 20 mL of dichloromethane, the combined organic phases were dried over MgSO$_4$, filtered and concentrated. The residue was crystallized by trituration with ether. Thus, 0.32 g (99%) of the title product was obtained. MS (ESI) m/z 445.2 (M+H)$^+$.

Example 50

5-methoxy-1-[trans-4-(pyridin-2-yloxy)cyclohexyl]-8-(trifluoromethyl)-5,6-dihydro-4H-[1,2,4]triazolo[4,3-a][1]benzazepine

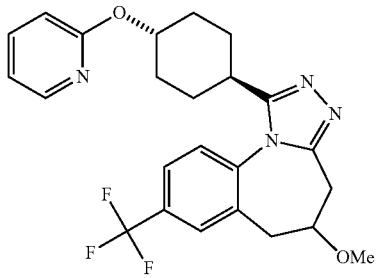 [SMILES: COC1Cc2cc(C(F)(F)F)ccc2-n2c(nnc2[C@H]2CC[C@H](Oc3ccccn3)CC2)C1]

0.10 g (0.23 mmol) of 1-[trans-4-(pyridin-2-yloxy)cyclohexyl]-8-(trifluoromethyl)-5,6-dihydro-4H-[1,2,4]triazolo[4,3-a][1]benzazepin-5-ol (Example 49) was dissolved in 10 mL of DMF and the solution was cooled to 0° C. 8.1 mg (0.34 mmol) of sodium hydride (60% dispersion in oil) was added to the solution and the mixture was stirred at 0° C. for 1 hour. 28.0 μL (0.45 mmol) of iodomethane was added to the reaction mixture and it was allowed to warm to room temperature and stirred for 16 hours. The reaction mixture was poured into water and extracted twice with 20 mL of ethyl acetate. The combined organic phases were washed with water and saturated NaCl solution, dried over anhydrous MgSO$_4$, filtered and concentrated. The residue was purified by column chromatography using dichloromethane:methanl=95:5 as eluent. The expected product was crystallized by trituration with n-hexane to yield 0.05 g (47%) of the title product. MS (ESI) m/z 459.2 (M+H)$^+$.

Example 51

5-(cyclopropylmethoxy)-1-[trans-4-(pyridin-2-yloxy)cyclohexyl]-8-(trifluoromethyl)-5,6-dihydro-4H-[1,2,4]triazolo[4,3-a][1]benzazepine

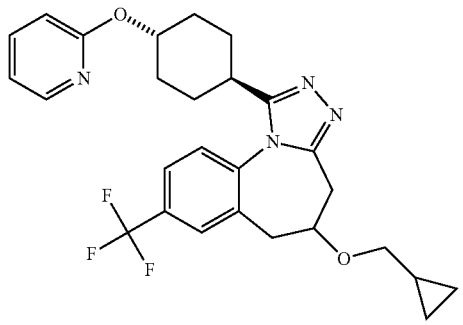 [SMILES: FC(F)(F)c1ccc2c(c1)CC(OCC1CC1)Cc1nnc([C@H]3CC[C@H](Oc4ccccn4)CC3)n1-2]

0.10 g (0.23 mmol) of 1-[trans-4-(pyridin-2-yloxy)cyclohexyl]-8-(trifluoromethyl)-5,6-dihydro-4H-[1,2,4]triazolo[4,3-a][1]benzazepin-5-o (Example 49) was dissolved in 10 mL of DMF and the solution was cooled to 0° C. 8.1 mg (0.34 mmol) of sodium hydride (60% dispersion in oil) was added to the solution and the mixture was stirred at 0° C. for 1 hour. 87.3 μL (0.90 mmol) of (bromomethyl)cyclopropane was added to the reaction mixture, and then it was allowed to warm to room temperature and stirred for 16 hours. Then the solution was cooled again and further 4.0 mg (0.17 mmol) of sodium hydride (60% dispersion in oil) and 43.7 μL (0.45 mmol) of (bromomethyl)cyclopropane were added to the reaction mixture. After stirring at room temperature for 6 hours, the reaction mixture was poured into water and extracted twice with 20 mL of dichloromethane. The combined organic phases were washed with water, dried over anhydrous MgSO$_4$, filtered and concentrated. The residue was purified by column chromatography using dichloromethane:methanol=95:5 as eluent. The appropriate fractions were concentrated and the residue was crystallized by trituration with n-hexane to yield 0.07 g (65%) of the title product. MS (ESI) m/z 499.3 (M+H)$^+$.

Example 52

5-{[tert-butyl(dimethyl)silyl]oxy}-8-chloro-1-[trans-4-(pyridin-2-yloxy)cyclohexyl]-5,6-dihydro-4H-[1,2,4]triazolo[4,3-a][1]benzazepine

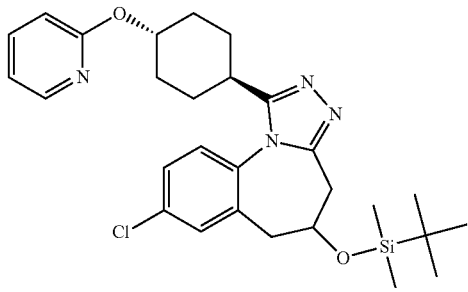 [SMILES: CC(C)(C)[Si](C)(C)OC1Cc2cc(Cl)ccc2-n2c(nnc2[C@H]2CC[C@H](Oc3ccccn3)CC2)C1]

0.36 g (1.06 mmol) of 4-{[tert-butyl(dimethyl)silyl]oxy}-7-chloro-1,3,4,5-tetrahydro-2H-1-benzazepine-2-thione (Intermediate 63) was dissolved in 20 mL of xylene and 0.42 g (180 mmol) of trans-4-(pyridin-2-yloxy)cyclohexane carboxylic acid hydrazide was added to the solution. The reaction mixture was refluxed for 96 hours, cooled to room temperature and concentrated. The residue was purified by column chromatography using dichloromethane:methanol=95:5 as eluent. The appropriate fractions were concentrated and the residue was crystallized by trituration with ether. Thus, 0.21 g (37%) of the title product was obtained. MS (ESI) m/z 525.2 (M+H)$^+$.

Example 53

8'-chloro-1'-[trans-4-(pyridin-2-yloxy)cyclohexyl]-4'H,6'H-spiro[1,3-dioxolane-2,5'-[1,2,4]triazolo[4,3-a][1]benzazepine]

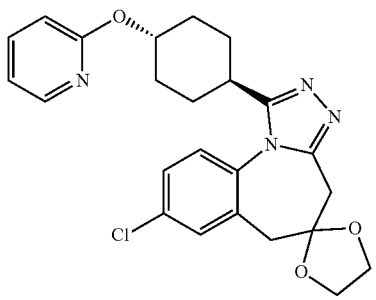 [SMILES: Clc1ccc2c(c1)CC1(Cc3nnc([C@H]4CC[C@H](Oc5ccccn5)CC4)n3-2)OCCO1]

The title product was prepared from 7-chloro-1,5-dihydrospiro[1-benzazepine-4,2'-[1,3]dioxolane]-2(3H-one (Intermediate 53) according to the method described in Example is 47. MS (ESI) m/z 453.2 (M+H)+.

Example 54

8-chloro-1-[trans-4-(pyrin-2-yloxy)cyclohexyl]-4H-[1,2,4]triazolo[4,3-a][1]benzazepin-5(6H)-one

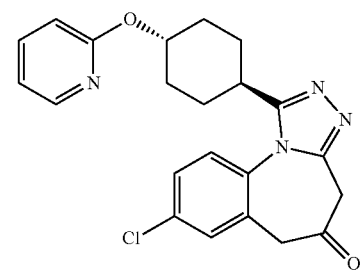 [SMILES: O=C1Cc2cc(Cl)ccc2-n2c(nnc2[C@H]2CC[C@H](Oc3ccccn3)CC2)C1]

The title product was prepared from 8'-chloro-1'-[trans-4-(pyridin-2-yloxy)cyclohexyl]-4'H,6'H-spiro[1,3-dioxolane-2,5'-[1,2,4]triazolo[4,3-a][1]benzazepine] (Example 53) according to the method described in Example 48. MS (ESI) m/z 409.2 (M+H)+.

Example 55

8-chloro-1-[trans-4-(pyridin-2-yloxy)cyclohexyl]-5,6-dihydro-4H-[1,2,4]triazolo[4,3-a][1]benzazepin-5-ol

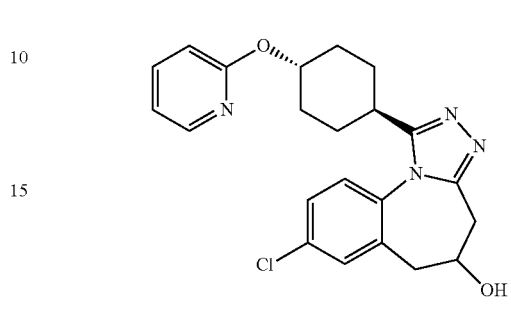

Method A)

0.28 g (0.53 mmol) of 5-{[tert-butyl(dimethyl)silyl]oxy}-8-chloro-1-[trans-4-(pyridin-2-yloxy)cyclohexyl]-5,6-dihydro-4H-[1,2,4]triazolo[4,3-a][1]benzazepine (Example 52) was dissolved in 20 mL of THF. 1.07 mL (1.07 mmol) of 1M tetrabutylammonium fluoride (TBAF) solution in THF was added dropwise to the above solution and the reaction mixture was stirred at room temperature for 5 hours. 50 mL of water was added to the reaction mixture and extracted twice with 50 mL of ethyl acetate. The combined organic phases were washed with saturated NaCl solution, dried over Na$_2$SO$_4$, filtered and concentrated. The residue was purified by column chromatography using dichloromethane:methanol=90:10 as eluent. The appropriate fractions were concentrated and the residue was crystallized by trituration with ether. Thus, 0.19 g (86%) of the title product was obtained. MS (ESI) m/z 411.1 (M+H)+.

Method B)

The title product was prepared from 8-chloro-1-[trans-4-(pyridin-2-yloxy)cyclohexyl]-4H-[1,2,4]triazolo[4,3-a][1]benzazepine-5(6H)-one (Example 54) according to the method described in Example 49. MS (ESI) m/z 411.2 (M+H)+.

Example 56

(5S)-8-chloro-1-[trans-4-(pyridin-2-yloxy)cyclohexyl]-5,6-dihydro-4H-[1,2,4]triazolo[4,3-a][1]benzazepin-5-ol

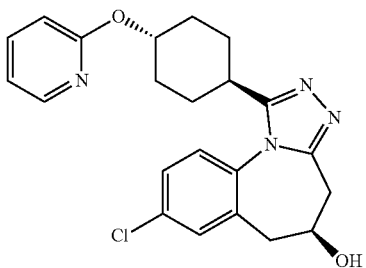 [SMILES: O[C@H]1Cc2cc(Cl)ccc2-n2c(nnc2[C@H]2CC[C@H](Oc3ccccn3)CC2)C1]

Example 57

(5R)-8-chloro-1-[trans-4-(pyridin-2-yloxy)cyclohexyl]-5,6-dihydro-4H-[1,2,4]triazolo[4,3-a][1]benzazepin-5-ol

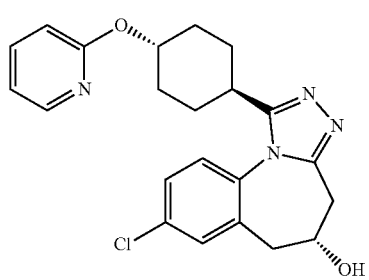 [SMILES: O[C@@H]1Cc2cc(Cl)ccc2-n2c(nnc2[C@H]2CC[C@H](Oc3ccccn3)CC2)C1]

The title products were prepared from the racem 8-chloro-1-[trans-4-(pyridin-2-yloxy)cyclohexyl]-5,6-dihydro-4H-[1,2,4]triazolo[4,3-a][1]benzazepin-5-ol (Example 55) by chiral preparative HPLC (CHIRALPAK IA with preparative 20 µm stationary phase, 2.5×20 cm; F=15 mL/min, eluent: tert-butyl methyl ether:dichloromethane:ethanol=85:10:5; isocratic, t=25° C.) to yield the (5S) enantiomer ($T_r$ 16.2 min; $[\alpha]_D^{25}$=–15.6° (c=0.1; chloroform); Example 56) and the (5R) enantiomer ($T_r$ 19.8 min: $[\alpha]_D^{25}$=+11.6° (c=0.1; chloroform); Example 57). The absolute configuration of the compounds was determined by VCD method and by $^1$H NMR spectroscopy of the diastereomeric pairs synthesized therefrom.

Example 58

8-chloro-5-methoxy-1-[trans-4-(pyridin-2-yloxy)cyclohexyl]-5,6-dihydro-4H-[1,2,4]triazolo[4,3-a][1]benzazepine

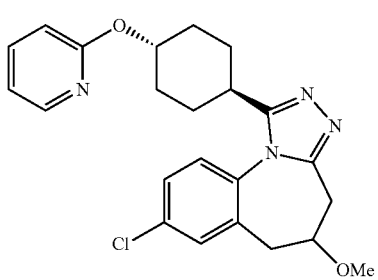 [SMILES: COC1Cc2cc(Cl)ccc2-n2c(nnc2[C@H]2CC[C@H](Oc3ccccn3)CC2)C1]

The title product was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) according to the method described in Example 50. MS (ESI) m/z 425.2 (M+H)+.

Example 59

5-(Cyclopropylmethoxy)-8-chloro-1-[trans-4-(pyridin-2-yloxy)cyclohexyl]-5,6-dihydro-4H-[1,2,4]triazolo[4,3-a][1]benzazepine

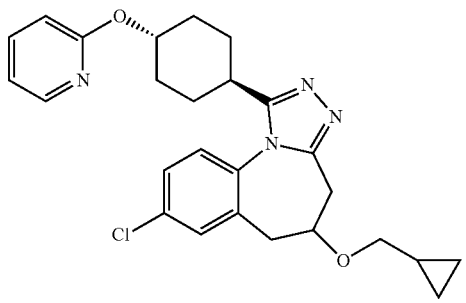 [SMILES: Clc1ccc2c(c1)CC(OCC1CC1)Cc1nnc([C@H]3CC[C@H](Oc4ccccn4)CC3)n1-2]

The title product was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) according to the method described in Example 51, MS (ESI) m/z 465.2 (M+H)+.

Example 60

2-({8-chloro-1-[trans-4-(pyridin-2-yloxy)cyclohexyl]-5,6-dihydro-4H-[1,2,4]triazolo[4,3-a][1]benzazepin-5-yl}oxy)-N,N-dimethylethanamine

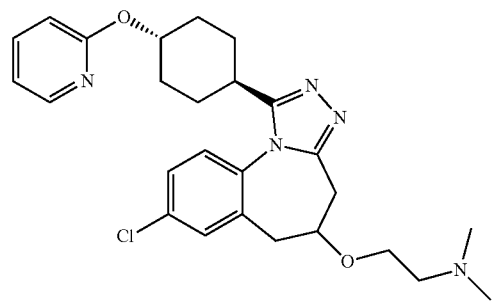 [SMILES: CN(C)CCOC1Cc2cc(Cl)ccc2-n2c(nnc2[C@H]2CC[C@H](Oc3ccccn3)CC2)C1]

0.08 g (0.19 mmol) of 8-chloro-1-[trans-4-(pyridin-2-yloxy)cyclohexyl]-5,6-dihydro-4H-[1,2,4]triazolo[4,3-a][1]benzazepin-5-ol (Example 55) was dissolved in 8 mL of DMF, the solution was cooled to 0° C. and 0.05 g (1.32 mmol) of sodium hydride (60% dispersion in oil) was added and the resulting mixture was stirred at 0° C. for half an hour. Then, 0.08 g (0.56 mmol) of 2-chloro-N,N-dimethylethanamine hydrochloride was added to the reaction mixture and it was stirred at room temperature for 16 hours. The reaction mixture was poured on ice and extracted twice with 20 mL of ethyl acetate. The combined organic phases were washed with water and saturated NaCl solution, dried over anhydrous MgSO4, filtered and concentrated. The residue was purified by column chromatography using dichloromethane:methanol:25% ammonia solution=18:1:0.1 as eluent. The appropriate fractions were concentrated and the residue was crystallized by trituration with diethyl ether to yield 0.04 g (47%) of the title product. MS (ESI) m/z 482.2 (M+H)+.

Example 61

8'-chloro-1'-[trans-4-(trifluoromethyl)cyclohexyl]-4'H,6'H-spiro[1,3-dioxolane-2,5'-[1,2,4]triazolo[4,3-a][1]benzazepine]

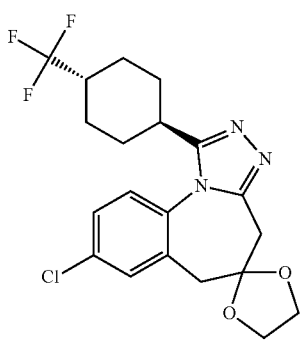 [SMILES: FC(F)(F)[C@H]1CC[C@H](c2nnc3n2-c2ccc(Cl)cc2CC2(C3)OCCO2)CC1]

The title product was prepared from 7-chloro-1,5-dihydrospiro[1-benzazepine-4,2'-[1,3]dioxolane]-2(3H)-one (Intermediate 53) and trans-4-(trifluoromethyl)cyclohexane carboxylic acid hydrazide (Intermediate 55) according to the method described in Example 47. MS (ESI) m/z 428.1 (M+H)$^+$.

Example 62

8'-bromo-1'-[trans-4-(pyridin-2-yloxy)cyclohexyl]-4'H,6'H-spiro[1,3-dioxolane-2,5' [1,2,4]triazolo[4,3-a][1]benzazepine]

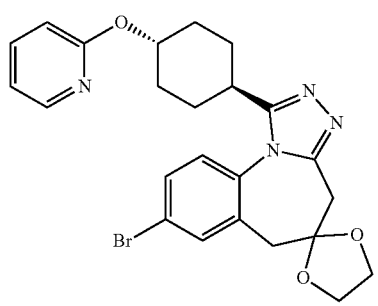 [SMILES: Brc1ccc2c(c1)CC1(Cc3nnc([C@H]4CC[C@H](Oc5ccccn5)CC4)n3-2)OCCO1]

To a solution of 121 mg (0.41 mmol) of 7-bromo-1,5-dihydrospiro[1-benzazepine-4,2'-[1,3]dioxolane]-2(3H)-one (Intermediate 36) and 8 mL of dry dichloromethane, 3.11 μL (0.04 mmol) of trifluoroacetic acid and 72 mg (0.49 mmol) of trimethyloxonium tetrafluoroborate were added under nitrogen atmosphere at room temperature. The reaction mixture was stirred at room temperature for 17 hours, then 107 mg (0.45 mmol) of trans-4-(pyridin-2-yloxy)cyclohexane carboxylic acid hydrazide was added and refluxed for 6.5 hours. The reaction mixture was concentrated, 10 mL of toluene and 1 drop of acetic acid was added to the residue and refluxed for 3 hours, then the reaction mixture was concentrated. The residue was purified by gradient chromatography using dichloromethane:methanol=97:3-+90:10 as eluent. Thus, 121 mg (60%) of the title product was obtained. MS (ESI) m/z 499.1 (M+H)$^+$.

Example 63

1'-[trans-4-(pyridin-2-yloxy)cyclohexyl]-4'H,6'H-spiro[1,3-dioxolane-2,5'-[1,2,4]triazolo[4,3-a][1]benzazepine]

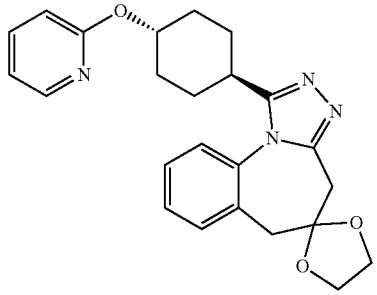 [SMILES: c1ccc(O[C@H]2CC[C@H](c3nnc4n3-c3ccccc3CC3(C4)OCCO3)CC2)nc1]

The title product was prepared from 1,5-dihydrospiro[1-benzazepine-4,2'-[1,3]dioxolane]-2(3H)-one (Intermediate 70) according to the method described in Example 47. MS (ESI) m/z 419.2 (M+H)$^+$.

Example 64

8-bromo-1-[trans-4-pyridin-2-yloxy)cyclohexyl]-4H-[1,2,4]triazolo[4,3-a][1]benzazepin-5(6H)-one

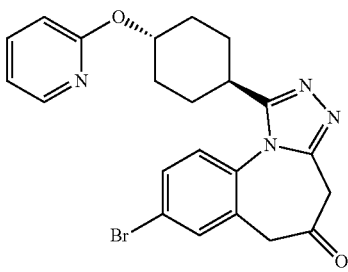 [SMILES: O=C1Cc2cc(Br)ccc2-n2c(nnc2[C@H]2CC[C@H](Oc3ccccn3)CC2)C1]

The title product was prepared from 8'-bromo-1-[trans-4-(pyridin-2-yloxy)cyclohexyl]-4'H,6'H-spiro[1,3-dioxolane-2,5'-[1,2,4]triazolo[4,3-a][1]benzazepine] (Example 62) according to the method described in Example 48. MS (ESI) m/z 453.0 (M+H)$^+$.

Example 65

8-bromo-1-[trans-4-(pyridin-2-yloxy)cyclohexyl]-5,6-dihydro-4H-[1,2,4]triazolo[4,3-a][1]benzazepin-5-ol

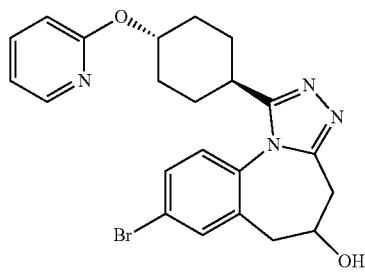

The title product was prepared from 8-bromo-1-[trans-4-(pyridin-2-yloxy)cyclohexyl]-4H-[1,2,4]triazolo[4,3-a][1]benzazepine-5(6H)-one (Example 64) according to the method described in Example 49. MS (ESI) m/z 457.1 (M+H)⁺.

Example 66

1'-[trans-4-(pyridin-2-yloxy)cyclohexyl]-4'H,6'H-spiro[1,3-dioxolane-2,5'-[1,2,4]triazolo[4,3-a][1]benzazepine]-8'-carbonitrile

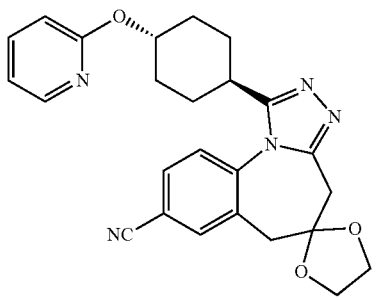 [SMILES: N#Cc1ccc2c(c1)CC1(Cc3nnc([C@H]4CC[C@H](Oc5ccccn5)CC4)n3-2)OCCO1]

A mixture of 49.7 mg (0.1 mmol) of 8'-bromo-1'-[trans-4-(pyridin-2-yloxy)cyclohexyl]-4'H,6'H-spiro[1,3-dioxolane-2,5'-[1,2,4]triazolo[4,3-a][1]benzazepine] (Example 62), 13.4 mg (0.15 mmol) of copper(I) cyanide and 0.6 mL of dry DMF under microwave irradiation conditions in a CEM Explorer microwave reactor was stirred at 220° C. for 30 minutes. The reaction mixture was diluted with dichloromethane, filtered through Celite, washed with dichloromethane. The filtrate was concentrated and ethyl acetate and aqueous ammonia solution were added to the residue. The phases were separated, the organic phase was washed once with aqueous ammonia, dried over anhydrous Na₂SO₄, filtered and concentrated. The residue was purified by reversed-phase chromatography using acetonitrile:water containing 1% trifluoroacetic acid=1:1 as eluent. Thus, 17.8 mg (40%) of the title product was obtained. MS (ESI) m/z 444.2 (M+H)⁺.

Example 67

(5S)-8-chloro-N,N-dimethyl-1-[trans-4-pyridin-2-yloxy)cyclohexyl]-5,6-dihydro-4H-[1,2,4]triazolo[4,3-a][1]benzazepine-5-amine

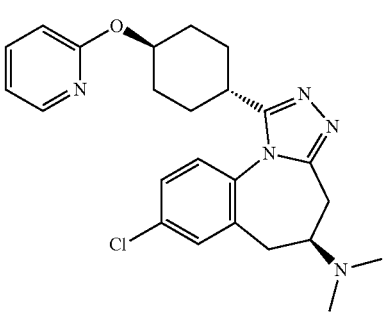 [SMILES: CN(C)[C@H]1Cc2cc(Cl)ccc2-n2c(nnc2[C@H]2CC[C@H](Oc3ccccn3)CC2)C1]

The title product was prepared from (5S)-8-chloro-1-[trans-4-(pyridin-2-yloxy)cyclohexyl]-5,6-dihydro-4H-[124]triazolo[4,3-a][1]benzazepine-5-amine (Example 7) according to the method described in Example 22. $[\alpha]_D^{25}$=−36.8° (c=0.1; methanol); MS (ESI) m/z 438.2 (M+H)⁺.

Example 68

(5S)—N-{8-chloro-1[trans-4-(pyridin-2-yloxy)cyclohexyl]-5,6-dihydro-4H-[1,2,4]triazolo[4,3-a][1]benzazepin-5-yl}acetamide

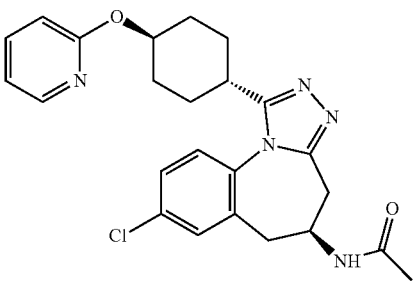 [SMILES: CC(=O)N[C@H]1Cc2cc(Cl)ccc2-n2c(nnc2[C@H]2CC[C@H](Oc3ccccn3)CC2)C1]

The title product was prepared from (5S)-8-chloro-1-[trans-4-(pyridin-2-yloxy)cyclohexyl]-5,6-dihydro-4H-[1,2,4]triazolo[4,3-a][1]benzazepine-5-amine (Example 7) according to the method described in Example 9. $[\alpha]_D^{25}$=−24.3° (c=0.1; methanol); MS (ESI) m/z 452.2 (M+H)⁺.

Example 69

8'-chloro-1'-[trans-4-(piperidin-1-ylmethyl)cyclohexyl]-4'H,6'H-spiro[1,3-dioxolane-2,5'-[1,2,4]triazolo[4,3-a][1]benzazepine]

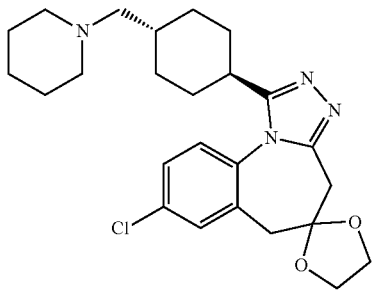 [SMILES: Clc1ccc2c(c1)CC1(Cc3nnc([C@H]4CC[C@H](CN5CCCCC5)CC4)n3-2)OCCO1]

The title product was prepared from 7-chloro-1,5-dihydrospiro[1-benzazepine-4,2'-[1,3]dioxolane]-2(3H)-one (Intermediate 53) and trans-4-(piperidin-1-ylmethyl)cyclohexane carboxylic acid hydrazide (Intermediate 65) according to the method described in Example 47. MS (ESI) m/z 457.2 (M+H)$^+$.

Example 70

[Trans-4-(8'-chloro-4'H,6'H-spiro[1,3-dioxolane-2,5'-[1,2,4]triazolo[4,3-a][1]benzazepine]-1'-yl)cyclohexyl](pyrrolidin-1-yl)methanone

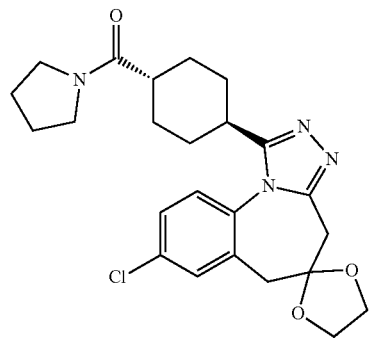 [SMILES: O=C([C@H]1CC[C@H](c2nnc3n2-c2ccc(Cl)cc2CC2(C3)OCCO2)CC1)N1CCCC1]

The title product was prepared from 7-chlor-1,5-dihydrospiro[1-benzazepine-4,2'-[1,3]dioxolane]-2(3H)-one (Intermediate 53) and trans-4-(pyrrolidin-1-ylcarbonyl)cyclohexane carboxylic acid hydrazide (Intermediate 78) according to the method described in Example 47. MS (ESI) m/z 457.2 (M+H)$^+$.

Example 71

8-chloro-1-[trans-4-(trifluoromethyl)cyclohexyl]-4H-[1,2,4]triazolo[4,3-a][1]benzazepin-5(6H)-one

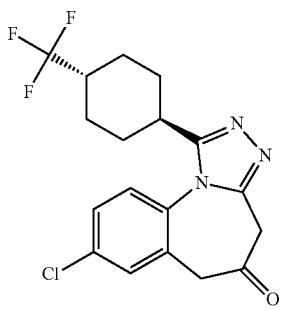 [SMILES: O=C1Cc2cc(Cl)ccc2-n2c(nnc2[C@H]2CC[C@H](C(F)(F)F)CC2)C1]

The title product was prepared from 8'-chloro-1'-[trans-4-(trifluoromethyl)cyclohexyl]-4'H,6'H-spiro[1,3-dioxolane-2,5'-[1,2,4]triazolo[4,3-a][1]benzazepine] (Example 61) according to the method described in Example 48. MS (ESI) m/z 384.1 (M+H)$^+$.

Example 72

8-chloro-1-[trans-4-(trifluoromethyl)cyclohexyl]-5,6-dihydro-4H-[1,2,4]triazolo[4,3-a][1]benzazepine-5-ol

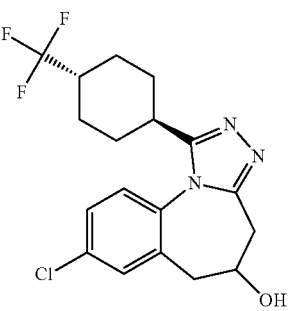 [SMILES: OC1Cc2cc(Cl)ccc2-n2c(nnc2[C@H]2CC[C@H](C(F)(F)F)CC2)C1]

The title product was prepared from 8-chloro-1-[trans-4-(trifluoroethyl)cyclohexyl]-4H-[1,2,4]triazolo[4,3-a][1]benzazepine-5(6H)-one (Example 71) according to the method described in Example 49. MS (ESI) m/z 386.1 (M+H)$^+$.

Example 73

(cis)-8-(8'-chloro-4'H,6'H-spiro[1,3-dioxolane-2,5'-[1,2,4]triazolo[4,3-a][1]benzazepine]-1'-il)-3-methyl-1-oxa-3-azaspiro[4.5]decan-2-one

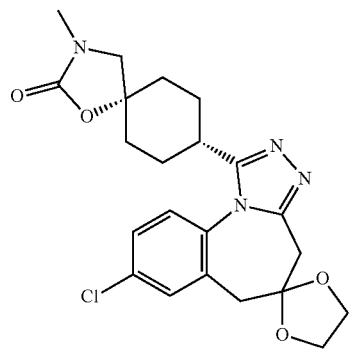 [SMILES: CN1C[C@]2(CC[C@H](c3nnc4n3-c3ccc(Cl)cc3CC3(C4)OCCO3)CC2)OC1=O]

The title product was prepared from 7-chloro-1,5-dihydrospiro[1-benzazepine-4,2'-[1,3]dioxolane]-2(3H)-one (Intermediate 53) and (cis)-3-methyl-2-oxo-1-oxa-3-azaspiro[4.5]decane-8-carboxylic acid hydrazide (Intermediate 87) according to the method described in Example 47. MS (ESI) m/z 445.2 (M+H)+.

Example 74

8-chloro-5-methoxy-1-[trans-4-(trifluoromethyl)cyclohexyl]-5,6-dihydro-4H-[1,2,4]triazolo[4,3-a][1]benzazepine

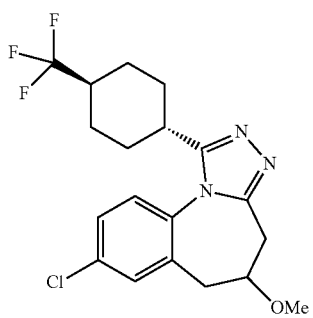 [SMILES: COC1Cc2cc(Cl)ccc2-n2c(nnc2[C@H]2CC[C@H](C(F)(F)F)CC2)C1]

The title product was prepared from 8-chloro-1-[trans-4-(trifluoromethyl)cyclohexyl]-5,6-dihydro-4H-[1,2,4]triazolo[4,3-a][1]benzazepin-5-ol (Intermediate 72) according to the method described in Example 50. MS (ESI) m/z 400.1 (M+H)+.

Example 75

(trans)-8-(8'-chloro-4'H, 6'H-spiro[1,3-dioxolane-2, 5'-[1,2,4]triazolo[4,3-a][1]benzazepin]-1'-yl)-3-methyl-1-oxa-3-azaspiro[4.5]decan-2-one

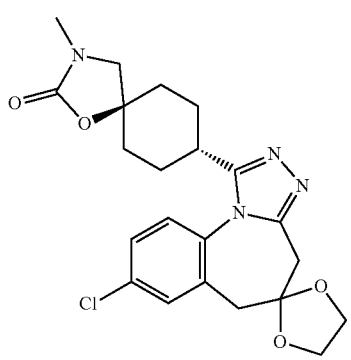 [SMILES: CN1C[C@]2(CC[C@@H](c3nnc4n3-c3ccc(Cl)cc3CC3(C4)OCCO3)CC2)OC1=O]

The title product was prepared from 7-chloro-1,5-dihydrospiro[1-benzazepine-4,2'-[1,3]dioxolane]-2(3H)-one (Intermediate 53) and (trans)-3-methyl-2-oxo-1-oxa-3-azaspiro[4.5]decane-8-carboxylic acid hydrazide (Intermediate 86) according to the method described in Example 47. MS (ESI) m/z 445.1 (M+H)+.

Example 76

N-{(5S)-8-chloro-1-[trans-4-(pyridin-2-yloxy)cyclohexyl]-5,6-dihydro-4H-[1,2,4]triazolo[4,3-a][1]benzazepin-5-yl}-N-methylmethanesulfonamide

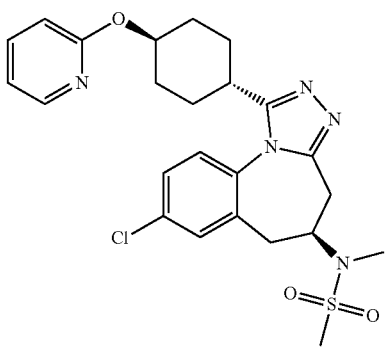 [SMILES: CN([C@H]1Cc2cc(Cl)ccc2-n2c(nnc2[C@H]2CC[C@H](Oc3ccccn3)CC2)C1)S(C)(=O)=O]

a) N-{(5S)-8-chloro-1-[trans-4-(pyridin-2-yloxy)cyclohexyl]-5,6-dihydro-4H-[1,2,4]triazolo[4,3-a][1]benzazepin-5-yl}methanesulfonamide

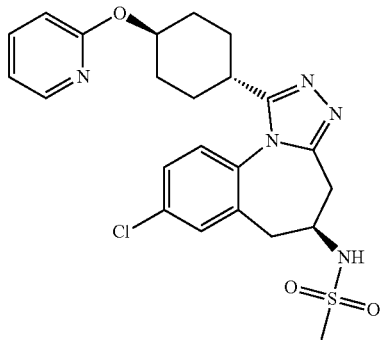 [SMILES: CS(=O)(=O)N[C@H]1Cc2cc(Cl)ccc2-n2c(nnc2[C@H]2CC[C@H](Oc3ccccn3)CC2)C1]

To a solution of 204 mg (0.5 mmol) of (5S)-8-chloro-1-[trans-4-(pyridin-2-yloxy)cyclohexyl]-5,6-dihydro-4H-[1,2,4]triazolo[4,3-a][1]benzazepine-5-amine (Example 7) and 5 mL of pyridine, 46 µL (70.6 mmol) of methanesulfonyl chloride was added and the reaction mixture was stirred at room temperature overnight. The reaction mixture was then diluted with dichloromethane, washed with saturated NaHCO₃ solution and saturated NaCl solution, the organic phase was dried over anhydrous Na₂SO₄, filtered and concentrated. The residue was purified by column chromatography using dichloromethane:methanol=9:1 as eluent. Thus, 90 mg (37%) of the title product was obtained. MS (ESI) m/z 488.3 (M+H)⁺.

b) N-{(5S)-8-chloro-1-[trans-4-pyridin-2-yloxy)cyclohexyl]-5,6-dihydro-4H-[1,2,4]triazolo[4,3-a][1]benzazepin-5-yl}-N-methylmethanesulfonamide The title product was prepared from N-{(5S)-8-chloro-1-[trans-4-(pyridin-2-yloxy)cyclohexyl]-5,6-dihydro-4H-[1,2,4]triazolo[4,3-a][1]benzazepin-5-yl}methanesulfonamide (step a) of Example 76) according to the method described in Example 19. MS (ESI) m/z 502.2 (M+H)⁺.

Example 77

(5S)-8-chloro-N-ethyl-1-[trans-4-(pyridin-2-yloxy)cyclohexyl]-5,6-dihydro-4H-[1,2,4]triazolo[4,3-a][1]benzazepine-5-amine

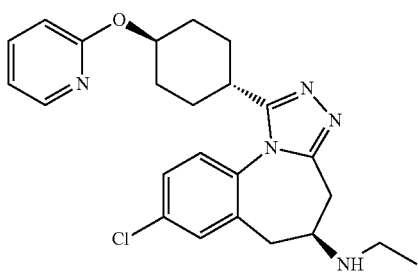 [SMILES: CCN[C@H]1Cc2cc(Cl)ccc2-n2c(nnc2[C@H]2CC[C@H](Oc3ccccn3)CC2)C1]

a) Tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}carbamate

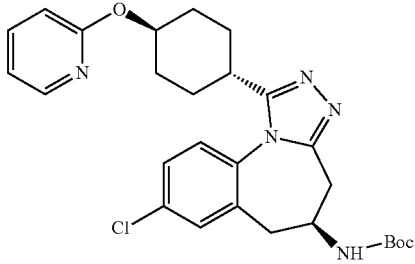 [SMILES: CC(C)(C)OC(=O)N[C@H]1Cc2cc(Cl)ccc2-n2c(nnc2[C@H]2CC[C@H](Oc3ccccn3)CC2)C1]

To a solution of 204 mg (0.5 mmol) of (5S)-8-chloro-1-[trans-4-(pyridin-2-yloxy)cyclohexyl]-5,6-dihydro-4H-[1,2,4]triazolo[4,3-a][1]benzazepine-5-amine (Example 7) and 10 mL of dichloromethane 275 µL (1.5 mmol) DIPEA and 130 mg (0.6 mmol) di-tert-butyl dicarbonate were added and the reaction mixture was stirred at room temperature overnight. The reaction mixture was diluted with dichloromethane, washed with saturated NaHCO₃ solution and with water, the organic phase was dried over anhydrous Na₂SO₄, filtered and concentrated. Thus, 246 mg (97%) of the title product was obtained. MS (ESI) m/z 510.2 (M+H)⁺.

b) Tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}ethylcarbamate

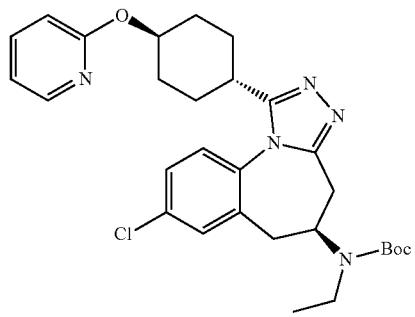 [SMILES: CCN(C(=O)OC(C)(C)C)[C@H]1Cc2cc(Cl)ccc2-n2c(nnc2[C@H]2CC[C@H](Oc3ccccn3)CC2)C1]

The title product was prepared from tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}carbamate (step a) of Example 77) according to the method described in step a) of Example 23. MS (ESI) m/z 538.2 (M+H)⁺.

c) (5)-8-chloro-N-ethyl-1-[trans-4-(pyridin-2-yloxy)cyclohexyl]-5,6-dihydro-4H-[1,2,4]triazolo[4,3-a][1]benzazepine-5-amine The title product was prepared from tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}ethylcarbamate (step b) of Example 77) according to the method described in Example 6. MS (ESI) m/z 438.3 (M+H)⁺.

Example 78

(5S)-8-chloro-N-methyl-1-[trans-4-(pyridin-2-yloxy)cyclohexyl]-5,6-dihydro-4H-[1,2,4]triazolo[4,3-a][1]benzazepine-5-amine

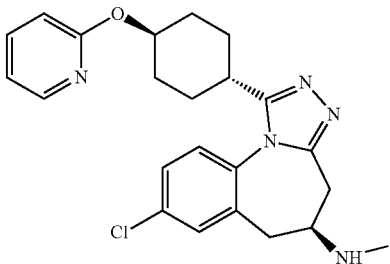 [SMILES: CN[C@H]1Cc2cc(Cl)ccc2-n2c(nnc2[C@H]2CC[C@H](Oc3ccccn3)CC2)C1]

a) Tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}methylcarbamate

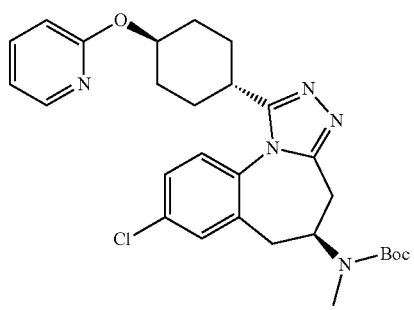 [SMILES: CN(C(=O)OC(C)(C)C)[C@H]1Cc2cc(Cl)ccc2-n2c(nnc2[C@H]2CC[C@H](Oc3ccccn3)CC2)C1]

The title product was prepared from tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}carbamate (step a) of Example 77) according to the method described in step a) of Example 21. MS (ESI) m/z 524.3 (M+H)$^+$.

b) (5S)-8-chloro-N-methyl-1-[trans-4-(pyridin-2-yloxy)cyclohexyl]-5,6-dihydro-4H-[1,2,4]triazolo[4,3-a][1]benzazepine-5-amine The title product was prepared from tert-butyl {(5S)-8-chloro-1-[trans-4-(pyridin-2-yloxy)cyclohexyl]-5,6-dihydro-4H-[1,2,4]triazolo[4,3-a][1]benzazepin-5-yl}methylcarbamate (step a) of Example 78) according to the method described in Example 6. MS (ESI) m/z 424.2 (M+H)$^+$.

Example 79

8'-chloro-1'-[1-(pyridin-2-yl)azetidin-3-yl]-4'H,6'H-spiro[1,3-dioxolane-2,5'-[1,2,4]triazolo[4,3-a][1]benzazepine]

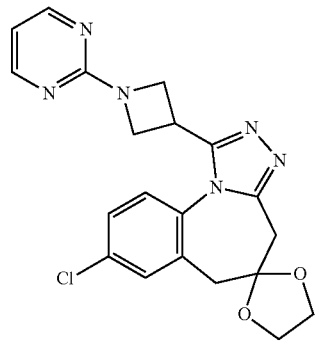 [SMILES: Clc1ccc2c(c1)CC1(Cc3nnc(C4CN(c5ncccn5)C4)n3-2)OCCO1]

The title product was prepared from 7-chloro-1,5-dihydrospiro[1-benzazepine-4,2'-[1,3]dioxolane]-2(3H)-one (intermediate 53) and 1-(pyrimidin-2-yl)azetidine-3-carboxylic acid hydrazide (Intermediate 82) according to the method described in Example 47. MS (ESI) m/z 411.1 (M+H)$^+$.

Example 80

N-{(5S)-8-chloro-1-[trans-4-(pyridin-2-cyclohexyl]-5,6-dihydro-4H-[1,2,4]triazolo[4,3-a][1]benzazepin-5-yl}-4-fluorobenzamide

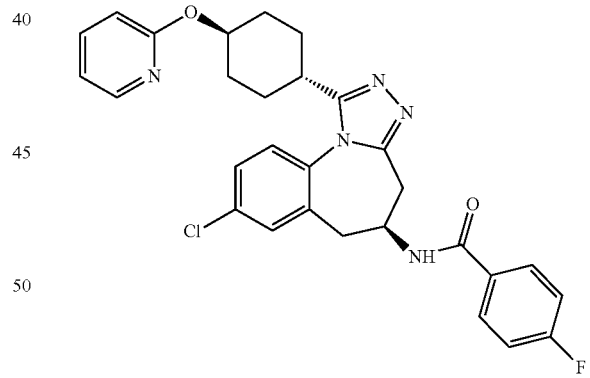

To a solution of 204 mg (0.5 mmol) of (5S)-8-chloro-1-[trans-4-(pyridin-2-yloxy)cyclohexyl]-5,6-dihydro-4H-[1,2,4]triazolo[4,3-a][1]benzazepine-5-amine (Example 7) and 3 mL of pyridine, 90 μL (0.76 mmol) 4-fluorobenzoyl-chloride was added and the reaction mixture was stirred at room temperature overnight. The reaction mixture was then diluted with ethyl acetate, washed with water, the organic phase was dried over anhydrous Na$_2$SO$_4$, filtered and concentrated. The residue was purified by column chromatography using dichloromethane:methanol=9:1 as eluent. Thus, 155 mg (58.5%) of the title product was obtained. [α]$_D^{25}$=−69.8° (c=0.1; methanol); MS (ESI) m/z 532.2 (M+H)$^+$.

Example 81

8'-bromo-1'-[trans-4-(trifluoromethyl)cyclohexyl]-4'H,6'H-spiro[1,3-dioxolane-2,5'-[1,2,4]triazolo[4,3-a][1]benzazepine]

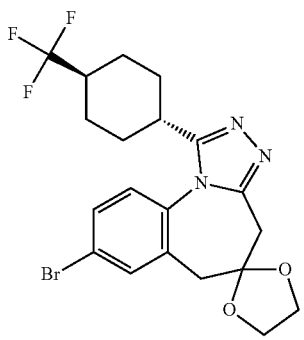 [SMILES: FC(F)(F)[C@H]1CC[C@H](c2nnc3n2-c2ccc(Br)cc2CC2(C3)OCCO2)CC1]

The title product was prepared from 7-bromo-1,5-dihydrospiro[1-benzazepine-4,2'-[1,3]dioxolane]-2(3H)-one (Intermediate 36) and trans-4-(trifluoromethyl)cyclohexane carboxylic acid hydrazide (intermediate 55) according to the method described in Example 47. MS (ESI) m/z 472.1 (M+H)$^+$.

Example 82

5-(propan-2-ylamino)-1-[trans-4-(pyridin-2-yloxy)cyclohexyl]-5,6-dihydro-4H-[1,2,4]triazolo[4,3-a][1]benzazepin-8-carbonitrile trifluoroacetate

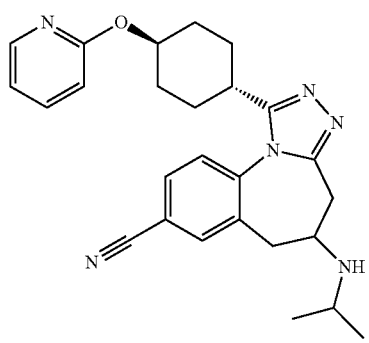 [SMILES: CC(C)NC1Cc2cc(C#N)ccc2-n2c(nnc2[C@H]2CC[C@H](Oc3ccccn3)CC2)C1]

The title product was prepared from 8-bromo-N-(propan-2-yl)-1-[trans-4-(pyridin-2-yloxy)cyclohexyl]-5,6-dihydro-4H-[1,2,4]triazolo[4,3-a][1]benzazepine-5-amine (Example 40) according to the method described in Example 66. MS (ESI) m/z 443.3 (M+H)$^+$.

Example 83

(S-8-chloro-N-4-fluorobenzyl)-1-[trans-4-pyridin-2-lox cyclohexyl]-5,6-dihydro-4H-[1,2,4]triazolo[4,3-a][1]benzazepine-5-amine

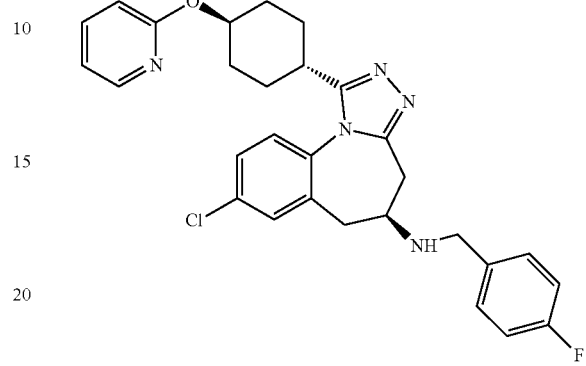

To a solution of 204 mg (0.5 mmol) of (5S)-8-chloro-1-[trans-4-(pyridin-2-yloxy)cyclohexyl]-5,6-dihydro-4H-[1,2,4]triazolo[4,3-a][1]benzazepine-5-amine (Example 7) and 5 mL of DMF, 30 mg (0.75 mmol) sodium-hydride (60% dispersion in oil) was added and the reaction mixture was stirred at room temperature for 15 minutes. Then 90 μL (0.75 mmol) of 4-fluorobenzyl chloride was added and it was stirred at room temperature overnight. At this time, the reaction mixture was diluted with ethyl acetate, washed with water, the organic phase was dried over anhydrous Na$_2$SO$_4$, filtered and concentrated. The residue was purified by column chromatography using dichloromethane:methanol=9:1 as eluent. Thus, 55 mg (21%) of the title product was obtained. [α]$_D^{25}$=−22.1° (c=0.1; methanol); MS (ESI) m/z 518.3 (M+H)$^+$.

Example 84

1'-[trans-4-(trifluoromethyl)cyclohexyl]-4'H,6'H-spiro[1,3-dioxolane-2,5'-[1,2,4]triazolo[4,3-a][1]benzazepine]-8'-carbonitrile

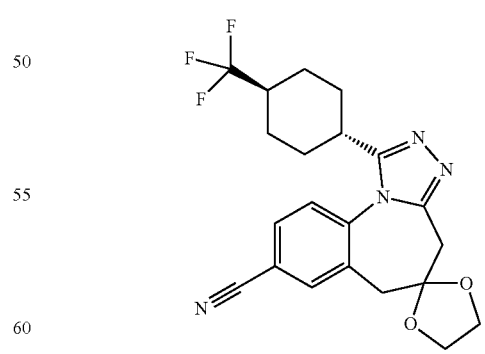

The title product was prepared from 8'-bromo-1'-[trans-4-(trifluoromethyl)cyclohexyl]-4'H,6'H-spiro[1,3-dioxolane-2,5'-[1,2,4]triazolo[4,3-a][1]benzazepine] (Example 81) according to the method described in Example 66. MS (ESI) m/z 419.2 (M+H)$^+$.

Example 85

[Trans-4-(8'-bromo-4'H,6'H-spiro[1,3-dioxolane-2,5'-[1,2,4]triazolo[4,3-a][1]benzazepin]-1'-yl)cyclohexyl](piperidin-1-yl)methanone

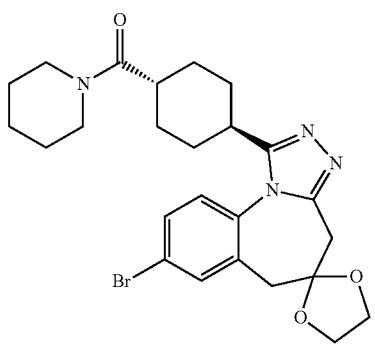 [SMILES: O=C([C@H]1CC[C@H](c2nnc3n2-c2ccc(Br)cc2CC2(C3)OCCO2)CC1)N1CCCCC1]

The title product was prepared from 7-bromo-1,5-dihydrospiro[1-benzazepine-4,2'-[1,3]dioxolane]-2(3H)-one (Intermediate 36) and trans-4-(piperidin-1-ylcarbonyl)cyclohexane carboxylic acid hydrazide (Intermediate 97) according to the method described in Example 62. MS (ESI) m/z 517.2 (M+H)+.

Example 86 methyl trans-4-(8-bromo-5-oxo-5,6-dihydro-4H-[1,2,4]triazolo[4,3-a][1]benzazepin-1-yl)cyclohexane carboxylate

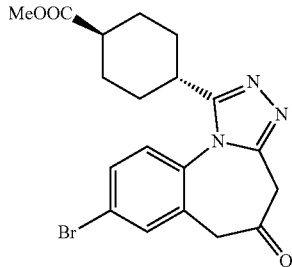

And

Example 87

8-bromo-1-[trans-4-(piperidin-1-ylcarbonyl)cyclohexyl]-4H-[1,2,4]triazolo[4,3-a][1]benzazepin-5(6H)-one

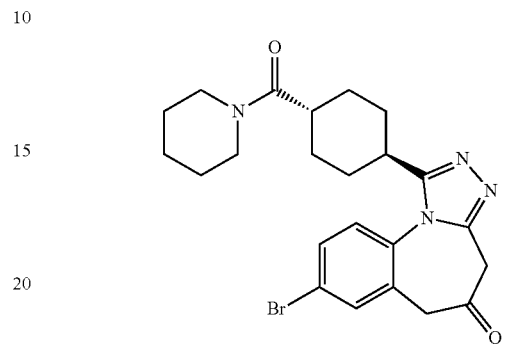

A mixture of 118 mg (0.23 mmol) of [trans-4-(8'-bromo-4'H,6'H-spiro[1,3-dioxolane-2,5'-[1,2,4]triazolo[4,3-a][1]benzazepin]-1'-yl)cyclohexyl](piperidin-1-yl)methanone (Example 85), 3.1 mL of methanol and 4.7 mL concentrated hydrochloric acid was refluxed for 2.5 hours, then cooled to room temperature. The pH of the reaction mixture was adjusted to basic with 10% $K_2CO_3$ solution and extracted with dichloromethane, the combined organic phases were dried over anhydrous $Na_2SO_4$, filtered and concentrated. The residue was purified by column chromatography using ethyl acetate:methanol=4:1 as eluent. Concentration of the first fraction yielded 17 mg (18%) of methyl trans-4-(8-bromo-5-oxo-5,6-dihydro-4H-[1,2,4]triazolo[4,3-a][1]benzazepin-1-yl)cyclohexane carboxylate (Example 86). MS (ESI) m/z 420.1 (M+H)+. Concentration of the second fraction yielded 35 mg (32%) of 8-bromo-1-[trans-4-(piperidin-1-ylcarbonyl)cyclohexyl]-4H-[1,2,4]triazolo[4,3-a][1]benzazepin-5(6H)-one (Example 87). MS (ESI) m/z 471.1 (M+H)+.

Example 88

8'-chloro-1'-[trans-4-(pyridin-2-yloxy)cyclohexyl]-4'H,6'H-spiro[1,3-dioxane-2,5'-[1,2,4]triazolo[4,3-a][1]benzazepine]

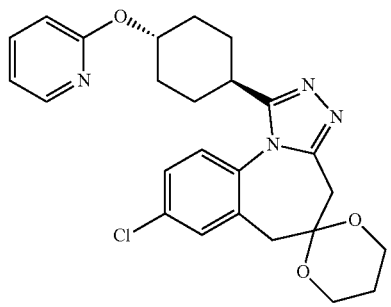 [SMILES: Clc1ccc2c(c1)CC1(Cc3nnc([C@H]4CC[C@H](Oc5ccccn5)CC4)n3-2)OCCCO1]

The title product was prepared from 7-chloro-1,5-dihydrospiro[1-benzazepine-4,2'-[1,3]dioxane]-2(3H)-one (in-

Example 89

8'-chloro-1'-[trans-4-(trifluoromethyl)cyclohexyl]-4'H,6'H-spiro[[1,3]dioxane-2,5'-[1,2,4]triazolo[4,3-a][1]benzazepine]

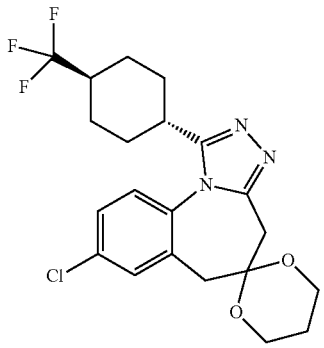 [SMILES: FC(F)(F)[C@H]1CC[C@H](c2nnc3n2-c2ccc(Cl)cc2CC2(C3)OCCCO2)CC1]

The title product was prepared from 7-chloro-1,5-dihydrospiro[1-benzazepine-4,2'-[1,3]dioxane]-2(3H)-one (Intermediate 98) and trans-4-(trifluoromethyl)cyclohexane carboxylic acid hydrazide (Intermediate 55) according to the method described in Example 47. MS (ESI) m/z 442.1 (M+H)⁺.

Example 90

1'-[trans-4-(piperidin-1-ylcarbonyl)cyclohexyl]-4'H,6'H-spiro[1,3-dioxolane-2,5'-[1,2,4]triazolo[4,3-a][1]benzazepin]-8'-carbonitrile

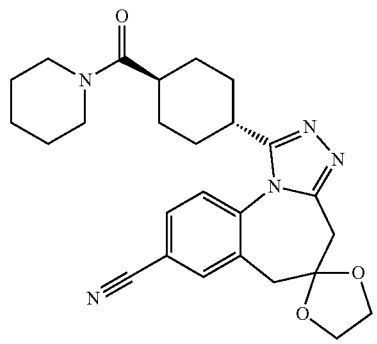 [SMILES: N#Cc1ccc2c(c1)CC1(Cc3nnc([C@H]4CC[C@H](C(=O)N5CCCCC5)CC4)n3-2)OCCO1]

The title product was prepared from [trans-4-(8'-bromo-4'H,6'H-spiro[1,3-dioxolane-2,5'-[1,2,4]triazolo[4,3-a][1]benzazepin]-1'-yl)cyclohexyl](piperidin-1-yl)methanone (Example 85) according to the method described in Example 66. MS (ESI) m/z 462.2 (M+H)⁺.

Example 91

8-bromo-1-[trans-4-(trifluoromethyl)cyclohexyl]-4H-[1,2,4]triazolo[4,3-a][1]benzazepin-5(6H)-one

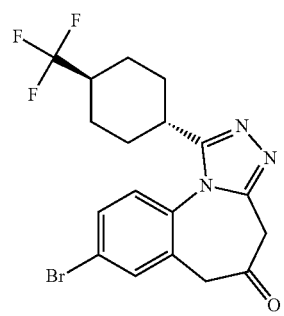 [SMILES: O=C1Cc2cc(Br)ccc2-n2c(nnc2[C@H]2CC[C@H](C(F)(F)F)CC2)C1]

The title product was prepared from 8'-bromo-1'-[trans-4-(trifluoromethyl)cyclohexyl]-4'H,6'H-spiro[1,3-dioxolane-2,5'-[1,2,4]triazolo[4,3-a][1]benzazepine] (Example 81) according to the method described in Example 48. MS (ESI) m/z 429.2 (M+H)⁺.

Example 92

[Trans-4-(8-bromo-5-hydroxy-5,6-dihydro-4H-[1,2,4]triazolo[4,3-a][1]benzazepin-1-yl)cyclohexyl](piperidin-1-yl)methanone

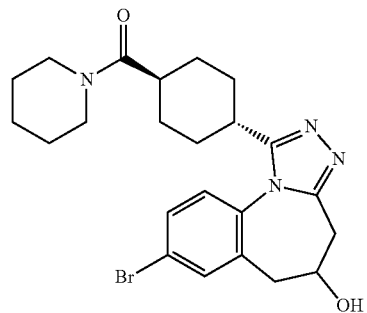 [SMILES: O=C([C@H]1CC[C@H](c2nnc3n2-c2ccc(Br)cc2CC(O)C3)CC1)N1CCCCC1]

The title product was prepared from 8-bromo-1-[trans-4-(piperidin-1-ylcarbonyl)cyclohexyl]-4H-[1,2,4]triazolo[4,3-a][1]benzazepine-5(6H)-one (Example 87) according to the method described in Example 49. MS (ESI) m/z 473.1 (M+H)⁺.

Example 93

8-bromo-1-[trans-4-trifluoromethyl)cyclohexyl]-5,6-dihydro-4H-[1,2,4]triazolo[4,3-a][1]benzazepin-5-ol

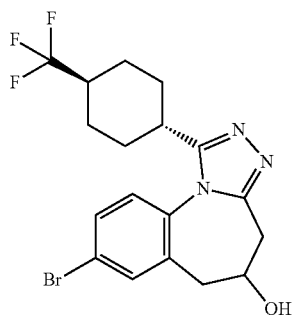 [SMILES: OC1Cc2cc(Br)ccc2-n2c(nnc2[C@H]2CC[C@H](C(F)(F)F)CC2)C1]

The title product was prepared from 8-bromo-1-[trans-4-(trifluromethyl)cyclohexyl]-4H-[1,2,4]triazolo[4,3-a][1]benzazepine-5(6H)-one (Example 91) according to the method described in Example 49. MS (ESI) m/z 432.0 (M+H)$^+$.

Example 94

1'-(1,4'-bipiperidin-1'-yl)-8'-chloro-4'H,6'H-spiro[1,3-dioxolane-2,5'-[1,2,4]triazolo[4,3-a][1]benzazepine]

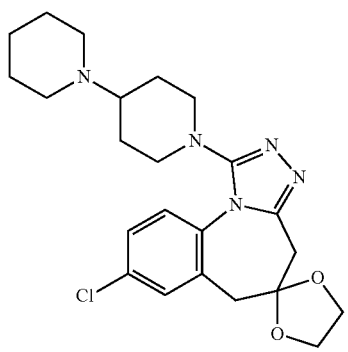 [SMILES: Clc1ccc2c(c1)CC1(Cc3nnc(N4CCC(N5CCCCC5)CC4)n3-2)OCCO1]

A mixture of 60 mg (0.168 mmol) of 1-bromo-8'-chlor-4'H,6'H-spiro[1,3-dioxolane-2,5'-[1,2,4]triazolo[4,3-][1]benzazepine] (Intermediate 96) and 255 mg (1.514 mmol) of 4-piperidinopiperidine was stirred at 130-140° C. for 3-4 hours under argon. After cooling to room temperature it was purified by column chromatography using dichloromethane:methanol:ammonium hydroxide=18:1:0.1 as eluent. The resulting crude product was further purified on a preparative TLC plate using dichloromethane:methanol:ammonium hydroxide=18:1:0.1 as eluent. Thus, 20.5 mg (27%) of the title product was obtained. MS (ESI) m/z 444.2 (M+H)$^+$.

Example 95

Tert-butyl [1-(1,4'-bipiperidin-1'-yl)-8-chloro-5,6-dihydro-4H-[1,2,4]triazolo[4,3-a][1]benzazepin-5-yl]carbaminate

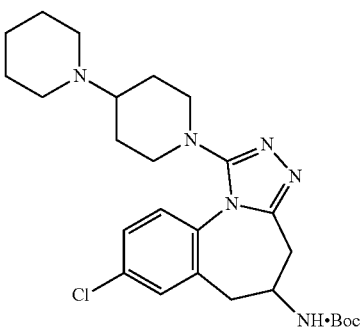

The title product was prepared from tert-butyl (1-bromo-8-chloro-5,6-dihydro-4H-[1,2,4]triazolo[4,3-a][1]benzazepin-5-yl)carbamate (Intermediate 94) according to the method described in Example 94. MS (ESI) m/z 501.3 (M+H)$^+$.

Example 96

8'-fluoro-1'-[trans-4-(pyridin-2-yloxy)cyclohexyl]-4'H,6'H-spiro[1,3-dioxolane-2,5'-[1,2,4]triazolo[4,3-a][1]benzazepine]

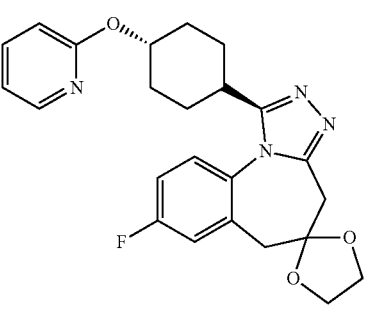

The title product was prepared from 7-fluoro-1,5-dihydrospiro[1-benzazepine-4,2-[1,3]dioxolane]-2(3H)-one (Intermediate 92) according to the method described in Example 47. MS (ESI) m/z 437.3 (M+H)$^+$.

Example 97

(5S)-8-chloro-N-(4-fluorobenzyl)-N-methyl-1-[trans-4-(pyridin-2-yloxy)cyclohexyl]-5,6-dihydro-4H-[1,2,4]triazolo[4,3-a][1]benzazepin-5-amine

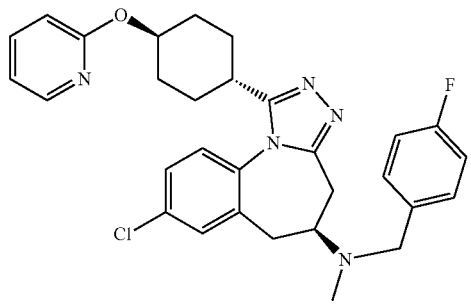 [SMILES: CN(Cc1ccc(F)cc1)[C@H]1Cc2cc(Cl)ccc2-n2c(nnc2[C@H]2CC[C@H](Oc3ccccn3)CC2)C1]

The title compound was prepared from (5S)-8-chlor-N-(4-fluorobenzyl)-1-[trans-4-(pyridin-2-yloxy)cyclohexyl]-5,6-dihydro-4H-[1,2,4]triazolo[4,3-a][1]benzazepin-5-amine (Example 83) and iodomethane according to the method described in Step a) of Example 21. $[\alpha]_D^{20}$=−68.7 (c=0.1; methanol); MS (ESI) m/z 532.3 (M+H)$^+$.

Example 98

N-{(5S)-8-chloro-1-[trans-4-(pyridin-2-yloxy)cyclohexyl]-5,6-dihydro-4H-[1,2,4]triazolo[4,3-a][1]benzazepin-5-yl}prop-2-enamide

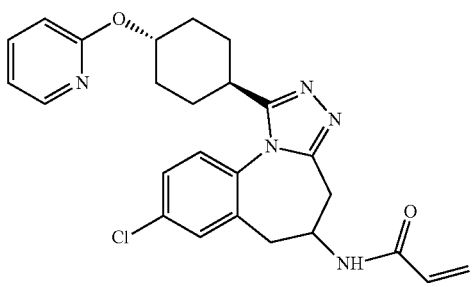 [SMILES: C=CC(=O)NC1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and acrylic acid according to the method described in Step a) of Example 10. $[\alpha]_D^{20}$=−24° (c=0.1; methanol); MS (ESI) m/z 464.2 (M+H)$^+$.

Example 99

(5R)-8-chloro-N-ethyl-1-[trans-4-(pyridin-2-yloxy)cyclohexyl]-5,6-dihydro-4H-[1,2,4]triazolo[4,3-a][1]benzazepin-5-amine

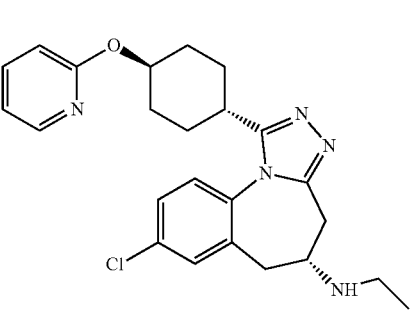 [SMILES: CCN[C@@H]1Cc2cc(Cl)ccc2-n2c(nnc2[C@H]2CC[C@H](Oc3ccccn3)CC2)C1]

a) Tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}carbamate

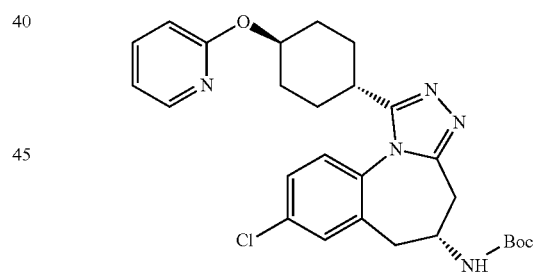

A mixture of 400 mg (0.976 mmol) of (5R)-8-chloro-1-[trans-4-(pyridin-2-yloxy)cyclohexyl]-5,6-dihydro-4H-[1,2,4]triazolo[4,3-][1]benzazepin-5-amine (Example 8), 20 mL of dichloromethane, 260 mg (1.19 mmol) of di-tert-butyl-dicarbonate and 0.55 mL (3.16 mmol) of N,N-diisopropyl-ethylamine was stirred at room temperature for 18 h, then diluted with dichloromethane and water, the organic layer was separated and the water phase was extracted with dichloromethane. The combined organic phases were dried over Na$_2$SO$_4$, filtered and concentrated to yield 500 mg (100%) of the title compound, which was used in the next step without further purification.

b) Tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}ethylcarbamate

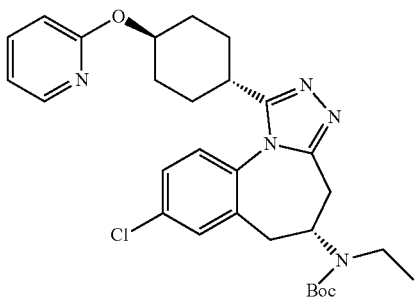 [SMILES: CCN(C(=O)OC(C)(C)C)[C@@H]1Cc2cc(Cl)ccc2-n2c(nnc2[C@H]2CC[C@H](Oc3ccccn3)CC2)C1]

The title compound was prepared from tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}carbamate (Step a) of Example 99) and ethyl iodide according to the method described in Step a) of Example 21. MS (ESI) m/z 538.3 (M+H)⁺.

c) (5R)-8-chloro-N-ethyl-1-[trans-4-(pyridin-2-yloxy)cyclohexyl]-5,6-dihydro-4H-[1,2,4]triazolo[4,3-a][1]benzazepin-5-amine The title compound was prepared from tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}ethylcarbamate (Step b) of Example 99) according to the method described in Example 6. $[\alpha]_D^{20}$=+23.1° (c=0.1; methanol); MS (ESI) m/z 438.1 (M+H)⁺.

Example 100

(5R)-8-chloro-N-methyl-1-[trans-4-(pyridin-2-yloxy)cyclohexyl]-5,6-dihydro-4H-[1,2,4]triazolo[4,3-a][1]benzazepin-5-amine

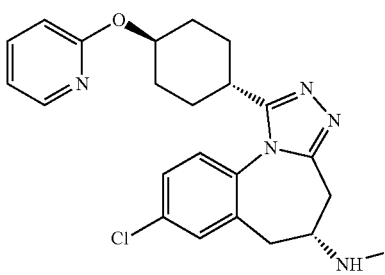 [SMILES: CN[C@@H]1Cc2cc(Cl)ccc2-n2c(nnc2[C@H]2CC[C@H](Oc3ccccn3)CC2)C1]

a) Tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}methylcarbamate

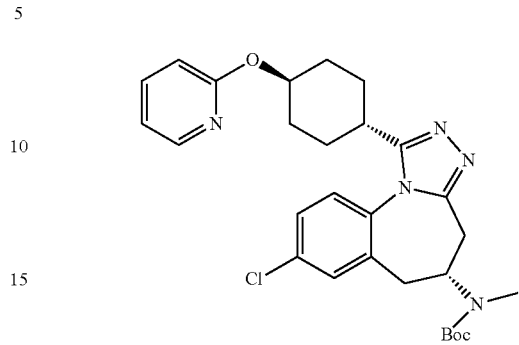

The title compound was prepared from tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}carbamate (Step a) of Example 99) and iodomethane according to the method described in Step a) of Example 21. MS (ESI) m/z 524.3 (M+H)⁺.

b) (5R)-8-chloro-N-methyl-1-[trans-4-(pyridin-2-yloxy)cyclohexyl]-5,6-dihydro-4H-[1,2,4]triazolo[4,3-a][1]benzazepin-5-amine The title compound was prepared from tert-butyl {(5R)-8-chloro-1-[trans-4-(pyridin-2-yloxy)cyclohexyl]-5,6-dihydro-4H-[1,2,4]triazolo[4,3-a][1]benzazepin-5-yl}methylcarbamate (Step a) of Example 100) according to the method described in Example 6. $[\alpha]_D^{20}$=+21.4° (c=0.1; methanol): MS (ESI) m/z 424.1 (M+H)⁺.

Example 101

(5R)-8-chloro-N,N-dimethyl-1-[trans-4-(pyridin-2-yloxy)cyclohexyl]-5,6-dihydro-4H-[1,2,4]triazolo[4,3-a][1]benzazepin-5-amine

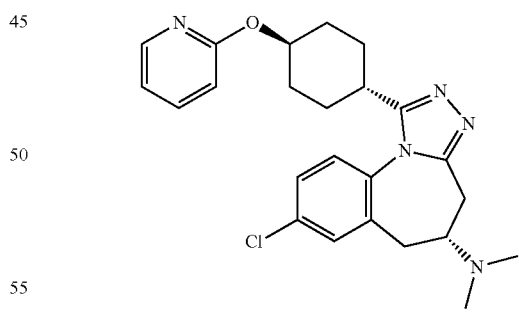

A mixture of 5.93 g (14.5 mmol) of (5R)-8-chloro-1-[trans-4-(pyridin-2-yloxy)cyclohexyl]-5,6-dihydro-4H-[1,2,4]triazolo[4,3a][1]benzazepin-5-amine (Example 8), 11 mL of 37% formaldehyde solution in water, 100 mL of methanol and 65 mL of dichloromethane was cooled to 5 and 15.9 g (75 mmol) of sodium triacetoxyborohydride was added to the reaction mixture at such a rate to keep the internal temperature below 5° C. After completion of the addition the reaction mixture was stirred at room temperature for 5 h, then concentrated. The residue was dissolved in water and the pH was adjusted to 8 by addition of 10% NaOH solution. The precipitated product was filtered off, washed with water and dried to yield 5.75 g (91%) of the title compound. [β]$_D^{20}$=+25.6° (c=0.1; methanol); MS (ESI) m/z 438.2 (M+H)$^+$.

Example 102

1-[trans-4-(pyridin-2-yloxy)cyclohexyl]-4H-[1,2,4]triazolo[4,3-a][1]benzazepin-5(6H)-one

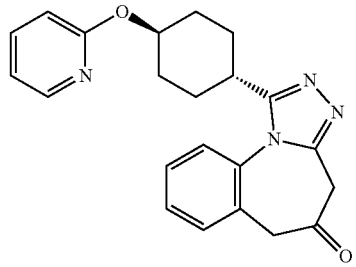 [SMILES: O=C1Cc2ccccc2-n2c(nnc2[C@H]2CC[C@H](Oc3ccccn3)CC2)C1]

The title compound was prepared from 1'-[trans-4-(pyridin-2-yloxy)cyclohexyl]-4'H,6'H-spiro[1,3-dioxolane-2,5'-[1,2,4]triazolo[4,3-a][1]benzazepine] (Example 63) according to the method described in Example 48. MS (ESI) m/z 375.1 (M+H)$^+$.

Example 103

(5S)-8-chloro-5-methoxy-1-[trans-4-pyridin-2-yloxy)cyclohexyl]-5,6-dihydro-4H-[1,2,4]triazolo[4,3-a][1]benzazepine

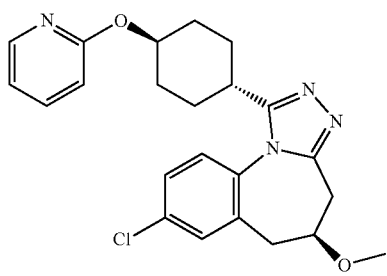 [SMILES: CO[C@H]1Cc2cc(Cl)ccc2-n2c(nnc2[C@H]2CC[C@H](Oc3ccccn3)CC2)C1]

And

Example 104

(5R)-8-chloro-5-methoxy-1-[trans-4-(pyridin-2-yloxy)cyclohexyl]-5,6-dihydro-4H-[1,2,4]triazolo[4,3-a][1]benzazepine

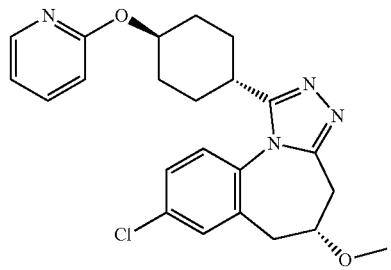 [SMILES: CO[C@@H]1Cc2cc(Cl)ccc2-n2c(nnc2[C@H]2CC[C@H](Oc3ccccn3)CC2)C1]

The title compounds were obtained from the racemic 8-chloro-5-methoxy-1-[trans-4-(pyridin-2-yloxy)cyclohexyl]-5,6-dihydro-4H-[1,2,4]triazolo[4,3-a][1]benzazepine (Example 58) by chiral preparative HPLC (CHIRALPAK IA preparative 20 μm stationary phase; 2.5×20 cm; F=18 mL/min; eluent: tert-butyl methyl ether:dichloromethane:ethanol=85:10:5; isocratic; t=25° C.). The first eluting compound was the (5S) enantiomer (T$_r$ 15.4 min; [α]$_D^{20}$=+11.8° (c=0.1; chloroform); Example 103) and the second eluting compound was the (5R) enantiomer (T$_r$ 21.5 min; [β]$_D^{20}$=−12.0° (c=0.1; chloroform); Example 104). The absolute configuration of the compounds was determined by VCD spectroscopy.

Example 105

8-chloro-5-(propan-2-yloxy)-1-[trans-4-(pyridin-2-yloxy)cyclohexyl]-5,6-dihydro-4H-[1,2,4]triazolo[4,3-a][1]benzazepine

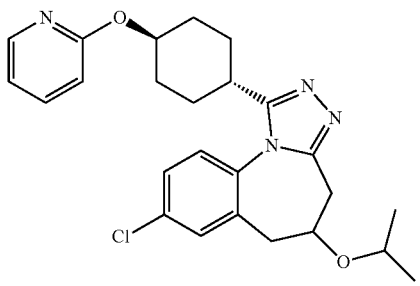 [SMILES: CC(C)OC1Cc2cc(Cl)ccc2-n2c(nnc2[C@H]2CC[C@H](Oc3ccccn3)CC2)C1]

A mixture of 100 mg (0.243 mmol) of 8-chloro-1-[trans-4-(pyridin-2-yloxy)cyclohexyl]-5,6-dihydro-4H-[1,2,4]triazolo[4,3-a][1]benzazepin-5-ol (Example 55), 5 mL of DMF and 12.7 mg (0.316 mmol) of 60% sodium hydride in mineral oil was stirred at 0° C. for 30 min, then 52.4 μL (0.316 mmol) of diisopropyl sulfate was added and the reaction mixture was stirred at room temperature for 18 h. The mixture was diluted with water, extracted with ethyl acetate, the combined organic layers were washed with brine, dried over Na$_2$SO$_4$, filtered and concentrated. The residue was purified by flash column chromatography using

Example 106

8'-chloro-1'-[trans-4-(pyridin-2-yloxy)cyclohexyl]-4°,6'-spiro[1,3-dioxepane-2,5'-[1,2,4]triazolo[4,3-a][1]benzazepine]

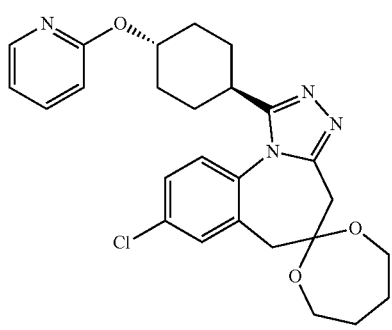 [SMILES: Clc1ccc2c(c1)CC1(Cc3nnc([C@H]4CC[C@H](Oc5ccccn5)CC4)n3-2)OCCCCO1]

The title compound was prepared from 7-chloro-1,5-dihydrospiro[1-benzazepine-4,2'-[1,3]dioxepan]-2(3H)-one (Step c) of Intermediate 104) according to the method described in Example 47. MS (ESI) m/z 481.2 (M+H)⁺.

Example 107

1-[trans-4-(pyridin-2-yloxy)cyclohexyl]-5,6-dihydro-4H-[1,2,4]triazolo[4,3-a][1]benzazepin-5-ol

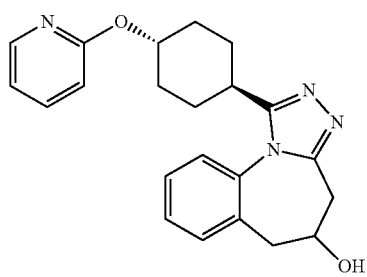 [SMILES: OC1Cc2ccccc2-n2c(nnc2[C@H]2CC[C@H](Oc3ccccn3)CC2)C1]

The title compound was prepared from 1-[trans-4-(pyridin-2-yloxy)cyclohexyl]-4H-[1,2,4]triazolo[4,3-a][1]benzazepin-5(6H)-one (Example 102) according to the method described in Example 49. MS (ESI) m/z 377.2 (M+H)⁺.

Example 108

Trans-4-(8'-chloro-4'H,6'H-spiro[1,3-dioxolane-2,5'-[1,2,4]triazolo[4,3-a][1]benzazepin]-1'-yl)cyclohexyl (morpholin-4-yl)methanone

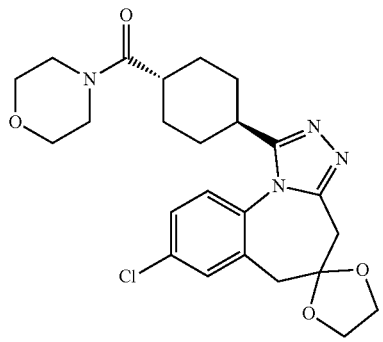 [SMILES: O=C([C@H]1CC[C@H](c2nnc3n2-c2ccc(Cl)cc2CC2(C3)OCCO2)CC1)N1CCOCC1]

Under argon to a mixture of 100 mg (0.39 mmol) of 7-chloro-1,5-dihydrospiro[1-benzazepine-4,2'-[1,3]dioxolan]-2(3H)-one (Intermediate 53) and 10 mL of dichloromethane 3 μL (0.04 mmol) of trifluoroacetic acid and 70 mg (0.47 mmol) of trimethyloxonium tetrafluoroborate were added. The reaction mixture was stirred at room temperature for 6 h, then 151 mg (0.59 mmol) of trans-4-(morpholin-4-ylcarbonyl)cyclohexane carbohydrazide (Intermediate 79) and 10 mL of acetonitrile were added and the mixture was refluxed for 8 h. After concentration the residue was purified by flash column chromatography using dichloromethane:methanol:ammonium hydroxide solution=180:10:1 as eluent to yield 72 mg (39%) of the title compound. MS (ESI) m/z 473.2 (M+H)⁺.

Example 109

5-methoxy-1-[trans-4-(pyridin-2-yloxy)cyclohexyl]-5,6-dihydro-4H-[1,2,4]triazolo[4,3-a][1]benzazepine

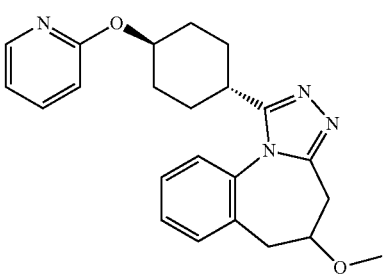 [SMILES: COC1Cc2ccccc2-n2c(nnc2[C@H]2CC[C@H](Oc3ccccn3)CC2)C1]

The title compound was prepared from 1-[trans-4-(pyridin-2-yloxy)cyclohexyl]-5,6-dihydro-4H-[1,2,4]triazolo[4,3-a][1]benzazepin-5-ol (Example 107) according to the method described in Example 50. MS (ESI) m/z 391.2 (M+H)⁺.

Example 110

8-fluoro-1-[trans-4-(pyridin-2-yloxy)cyclohexyl]-4H-[1,2,4]triazolo[4,3-a][1]benzazepin-5(6H)-one

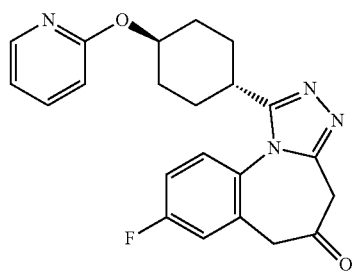 [SMILES: O=C1Cc2cc(F)ccc2-n2c(nnc2[C@H]2CC[C@H](Oc3ccccn3)CC2)C1]

The title compound was prepared from 8'-fluoro-1'-[trans-4-(pyridin-2-yloxy)cyclohexyl]-4'H,6'H-spiro[1,3-dioxolane-2,5'-[1,2,4]triazolo[4,3-a][1]benzazepine](Example 96) according to the method described in Example 48. MS (ESI) m/z 393.3 (M+H)⁺.

Example 111

8-fluoro-1-[trans-4-(pyridin-2-yloxy)cyclohexyl]-5,6-dihydro-4H-[1,2,4]triazolo[4,3-a][1]benzazepin-5-ol

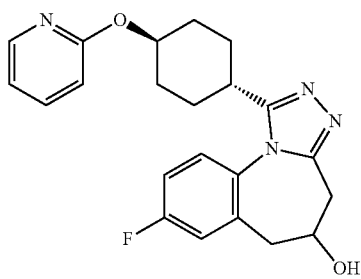 [SMILES: OC1Cc2cc(F)ccc2-n2c(nnc2[C@H]2CC[C@H](Oc3ccccn3)CC2)C1]

The title compound was prepared from 8-fluoro-1-[trans-4-(pyridin-2-yloxy)cyclohexyl]-4H-[1,2,4]triazolo[4,3-a][1]benzazepin-5(6H)-one (Example 110) according to the method described in Example 49. MS (ESI) m/z 395.2 (M+H)⁺.

Example 112

Tert-butyl {8-chloro-1-[trans-4-(morpholin-4-yl)cyclohexyl]-5,6-dihydro-4H-[1,2,4]triazolo[4,3-a][1]benzazepin-5-yl}carbamate

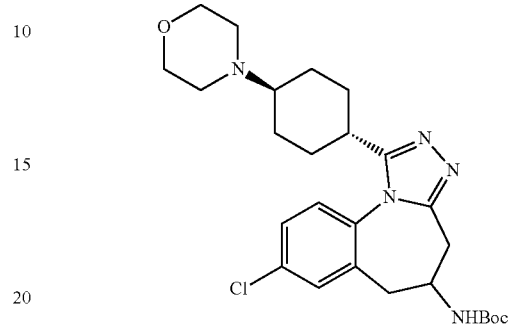

The title compound was prepared from tert-butyl (7-chloro-2-oxo-2,3,4,5-tetrahydro-1H-1-benzazepin-4-yl)carbamate (Intermediate 5) and trans-4-(morpholin-4-yl)cyclohexane carbohydrazide (Intermediate 81) according to the method described in Method B of Example 5. MS (ESI) m/z 502.2 (M+H)⁺.

Example 113

8-chloro-1-[trans-4-(morpholin-4-yl)cyclohexyl]-5,6-dihydro-4H-[1,2,4]triazolo[4,3-a][1]benzazepin-5-amine

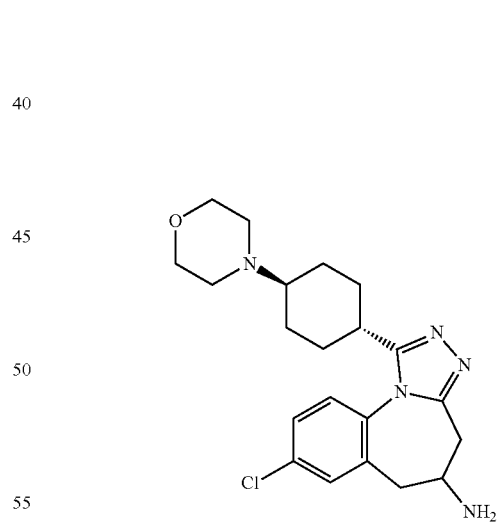

The title compound was prepared from ter-butyl {8-chloro-1-[trans-4-(morpholin-4-yl)cyclohexyl]-5,6-dihydro-4H-[1,2,4]triazolo[4,3-a][1]benzazepin-5-yl}carbamate (Example 112) according to the method described in Example 6. MS (ESI) m/z 402.1 (M+H)⁺.

Example 114

8-chloro-1-[trans-4-(morpholin-4-yl)cyclohexal]-N-propan-2-yl)-5,6-dihydro-4H-[1,2,4]triazolo[4,3-a][1]benzazepin-5-amine

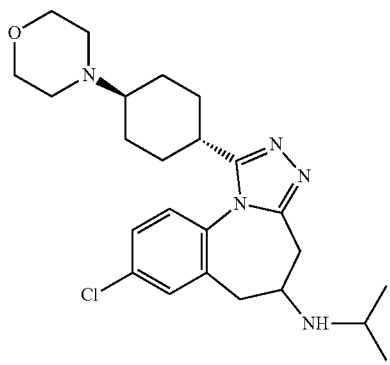 [SMILES: CC(C)NC1Cc2cc(Cl)ccc2-n2c(nnc2[C@H]2CC[C@H](N3CCOCC3)CC2)C1]

The title compound was prepared from tert-butyl 8-chloro-1-[trans-4-(morpholin-4-yl)cyclohexyl]-5,6-dihydro-4H-[1,2,4]triazolo[4,3-a][1]benzazepin-5-amine (Example 113) according to the method described in Example 24. MS (ESI) m/z 444.2 (M+H)$^+$.

Example 115

(5r,8r)-8-(8'-chloro-4'H,6'H-spiro[1,3-dioxolane-2,5-[1,2,4]triazolo[4,3-a][1]benzazepin]-1'-yl)-2-(propan-2-yl-2-azaspiro[4,5]decan-1-one

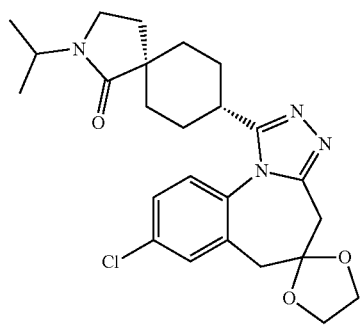 [SMILES: CC(C)N1CC[C@]2(CC[C@@H](c3nnc4n3-c3ccc(Cl)cc3CC3(C4)OCCO3)CC2)C1=O]

The title compound was prepared from 7-chloro-1,5-dihydrospiro[1-benzazepine-4,2'-[1,3]dioxolan]-2(3H)-one (Intermediate 53) and (5r,8r)-1-oxo-2-(propan-2-yl)-2-azaspiro[4.5]decane-8-carbohydrazide (Intermediate 102) according to the method described in Example 62. MS (ESI) m/z 471.2 (M+H)$^+$.

Example 116 (5r,8r)-8-(8-chloro-5-hydroxy-5,6-dihydro-4H-[1,2,4]triazolo[4,3-a][1]benzazepin-1-yl)-2-(propan-2-yl)-2-azaspiro[4,5]decan-1-one

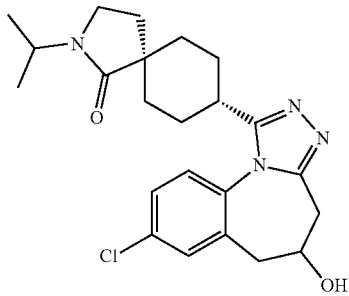 [SMILES: CC(C)N1CC[C@]2(CC[C@@H](c3nnc4n3-c3ccc(Cl)cc3CC(O)C4)CC2)C1=O]

a) 8-chloro-1-[(5r,8r)-1-oxo-2-(propan-2-yl-2-azaspiro[4,5]dec-8-yl]-4H-[1,2,4]triazolo[4,3-a][1]benzazepin-5(6H)-one

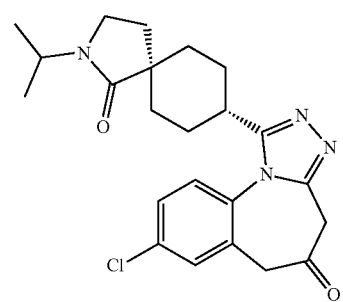 [SMILES: CC(C)N1CC[C@]2(CC[C@@H](c3nnc4n3-c3ccc(Cl)cc3CC(=O)C4)CC2)C1=O]

The title compound was prepared from (5r,8r)-8-(8'-chloro-4'H,6'H-spiro[1,3-dioxolane-2,5'-[1,2,4]triazolo[4,3-a][1]benzazepin]-1'-yl)-2-(propan-2-yl)-2-azaspiro[4.5]decan-1-one (Example 115) according to the method described in Example 48. MS (ESI) m/z 427.3 (M+H)$^+$.

b) (5r,8r)-8-(8-chloro-5-hydroxy-5,6-dihydro-4H-[1,2,4]triazolo[4,3-a][1]benzazepin-1-yl)-2-(propan-2-yl)-2-azaspiro[4,5]decan-1-one The title compound was prepared from 8-chloro-1-[(5r,8r)-1-oxo-2-(propan-2-yl)-2-azaspiro[4,5]dec-8-yl]-4H-[1,2,4]triazolo[4,3-a][1]benzazepin-5(6H)-one (Step a) of Example 116) according to the method described in Example 49. MS (ESI) m/z 429.1 (M+H)$^+$.

Example 117

(5S)-8-chloro-1-[trans-4-pyridin-2-lox cyclohexyl]-5-(pyrrolidin-1-yl)-5,6-dihydro-4H-[1,2,4]triazolo[4,3-a][1]benzazepine

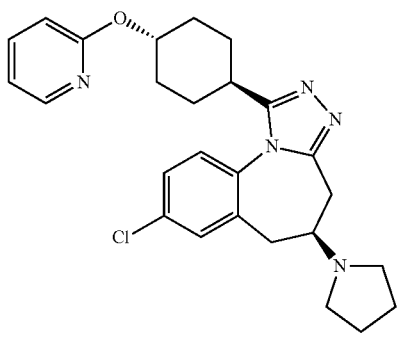 [SMILES: Clc1ccc2c(c1)C[C@H](N1CCCC1)Cc1nnc([C@H]3CC[C@H](Oc4ccccn4)CC3)n1-2]

A mixture of 400 mg (0.976 mmol) of (5S)-8-chloro-1-[trans-4-(pyridin-2-yloxy)cyclohexyl]-5,6-dihydro-4H-[1,2,4]triazolo[4,3-a][1]benzazepin-5-amine (Example 7), 20 mL of DMF, 117 µL (0.98 mmol) of 1,4-dibromobutane and 954 mg (2.93 mmol) of Cs$_2$CO$_3$ was stirred at 40° C. for 24 h, then concentrated. The residue was dissolved in water and extracted with ethyl acetate. The combined organic phases were dried over Na$_2$SO$_4$, filtered and concentrated. The residue was purified by flash column chromatography using dichloromethane:methanol=95:5 as eluent to yield 35 mg (8%) of the title compound. MS (ESI) m/z 464.3 (M+H)$^+$.

Example 118

N-{(5S)-8-chloro-1-[trans-4-pyridin-2-yloxy)cyclohexyl]-5,6-dihydro-4H-[1,2,4]triazolo[4,3-a][1]benzazepin-5-yl}-2,2-dimethylpropanamide

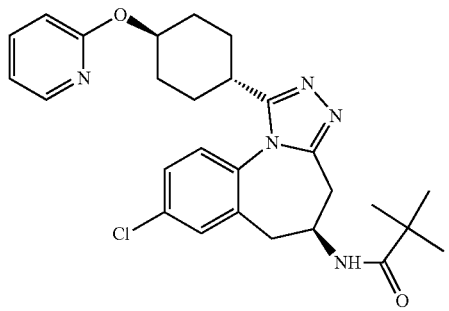 [SMILES: CC(C)(C)C(=O)N[C@H]1Cc2cc(Cl)ccc2-n2c(nnc2[C@H]2CC[C@H](Oc3ccccn3)CC2)C1]

A mixture of 82 mg (0.2 mmol) of (5S)-8-chloro-1-[trans-4-(pyridin-2-yloxy)cyclohexyl]-5,6-dihydro-4H-[1,2,4]triazolo[4,3-a][1]benzazepin-5-amine (Example 7), 5 mL of dichloromethane, 35 µL (0.25 mmol) of triethylamine and 30 µL (0.24 mmol) of trimethylacetyl chloride was stirred at room temperature for 3 h, then diluted with dichloromethane and successively washed with saturated NaHCO$_3$ solution and brine. The organic phase was dried over Na$_2$SO$_4$, filtered and concentrated to yield 93 mg (94%) of the title compound. [β]$_D^{25}$=−32.1° (c=0.1; methanol) MS (ESI) m/z 494.3 (M+H)$^+$.

Example 119

N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide

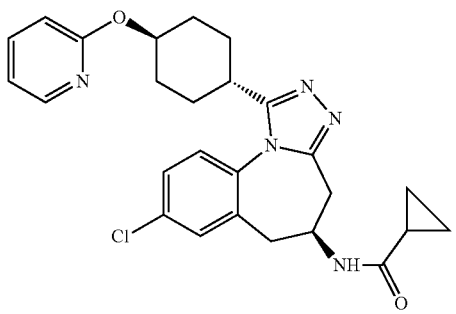 [SMILES: O=C(N[C@H]1Cc2cc(Cl)ccc2-n2c(nnc2[C@H]2CC[C@H](Oc3ccccn3)CC2)C1)C1CC1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and cyclo propanecarboxylic acid according to the method described in Step a) of Example 10. [α]$_D^{25}$=−45.3° (c=0.1; methanol); MS (ESI) m/z 478.3 (M+H)$^+$.

Example 120

N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide

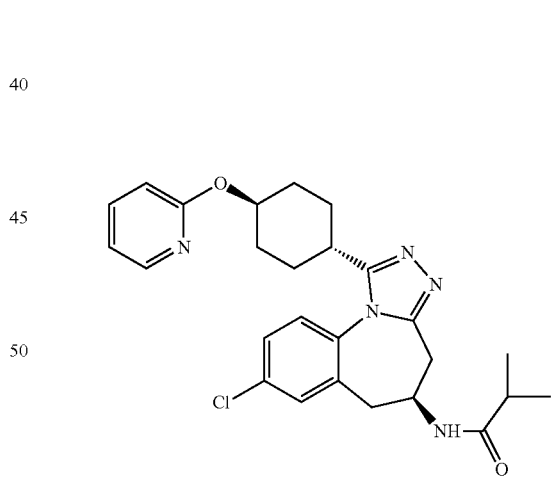

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and isobutyric acid according to the method described in Step a) of Example 10. [α]$_D^{25}$=−30.6° (c=0.1; methanol): MS (ESI) m/z 480.3 (M+H)$^+$.

Example 121

N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide

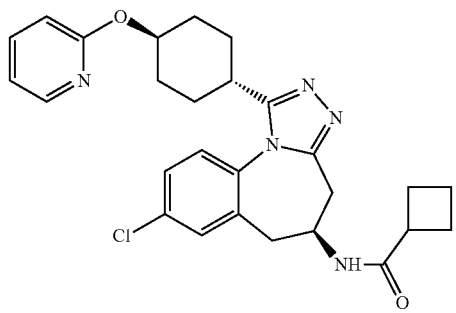 [SMILES: O=C(N[C@H]1Cc2cc(Cl)ccc2-n2c(nnc2[C@H]2CC[C@H](Oc3ccccn3)CC2)C1)C1CCC1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and cyclobutanecarboxylic acid according to the method described in Step a) of Example 10. $[\alpha]_D^{25}=-39.3°$ (c=0.1; methanol); MS (ESI) m/z 492.3 (M+H)$^+$.

Example 122

(5S)-8-chloro-5-(morpholin-4-yl)-1-[trans-4-(pyridin-2-yloxy)cyclohexyl]-5,6-dihydro-4H-[1,2,4]triazolo[4,3-a][1]benzazepine

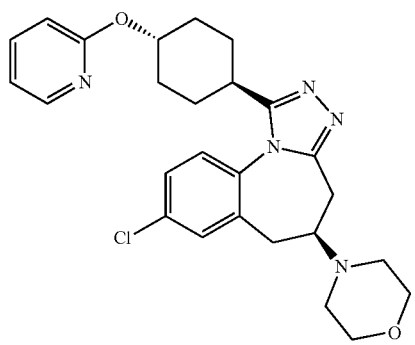 [SMILES: Clc1ccc2c(c1)C[C@H](N1CCOCC1)Cc1nnc([C@H]3CC[C@H](Oc4ccccn4)CC3)n1-2]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and bis(2-iodoethyl)ether according to the method described in Example 117. MS (ESI) m/z 480.2 (M+H)$^+$.

Example 123

N-{(5R)-8-chloro-1-[trans-4-(pyridin-2-yloxy)cyclohexyl]-5,6-dihydro-4H-[2,4]triazolo[4,3-a][1]benzazepin-5-yl}-2,2-dimethylpropanamide

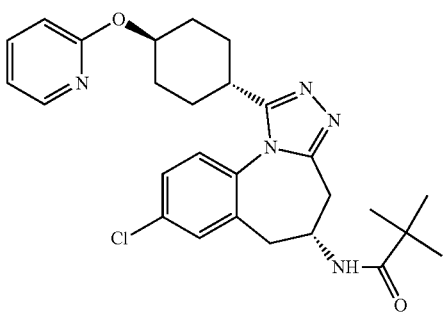 [SMILES: CC(C)(C)C(=O)N[C@@H]1Cc2cc(Cl)ccc2-n2c(nnc2[C@H]2CC[C@H](Oc3ccccn3)CC2)C1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) is according to the method described in Example 118. $[\alpha]_D^{20}=+21.6°$ (c=0.1; methanol); MS (ESI) m/z 494.2 (M+H)$^+$.

Example 124

N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide

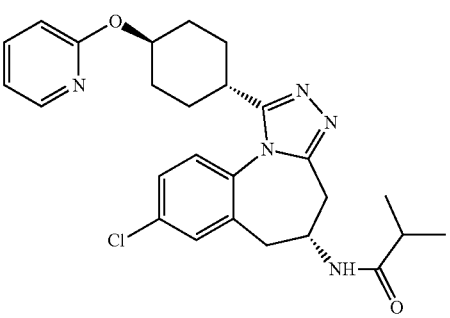 [SMILES: CC(C)C(=O)N[C@@H]1Cc2cc(Cl)ccc2-n2c(nnc2[C@H]2CC[C@H](Oc3ccccn3)CC2)C1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and isobutyric acid according to the method described in Step a) of Example 10. $[\alpha]_D^{20}=+29.4°$ (c=0.1; methanol); MS (ESI) m/z 480.2 (M+H)$^+$.

Example 125

N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide

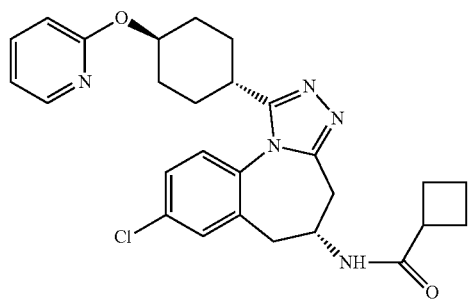 [SMILES: O=C(N[C@@H]1Cc2cc(Cl)ccc2-n2c(nnc2[C@H]2CC[C@H](Oc3ccccn3)CC2)C1)C1CCC1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and cyclobutanecarboxylic acid according to the method described in Step a) of Example 10. $[\alpha]_D^{20}$=+29.8° (c=0.1; methanol); MS (ESI) m/z 492.2 (M+H)$^+$.

Example 126

N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide

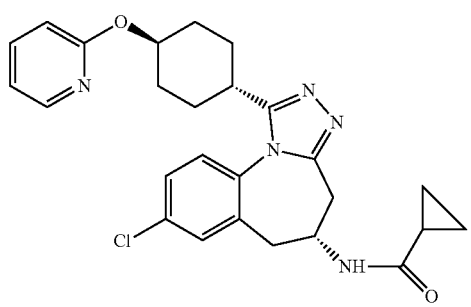 [SMILES: O=C(N[C@@H]1Cc2cc(Cl)ccc2-n2c(nnc2[C@H]2CC[C@H](Oc3ccccn3)CC2)C1)C1CC1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and cyclopropanecarboxylic acid according to the method described in Step a) of Example 10, $[\alpha]_D^{20}$=+30.5° (c=0.1; methanol); MS (ESI) m/z 478.2 (M+H)$^+$.

Example 127

(5S)-8-chloro-5-(piperidin-1-yl)-1-[trans-4-(pyridin-2-yloxy)cyclohexyl]-5,6-dihydro-4H-[1,2,4]triazolo[4,3-a][1]benzazepine

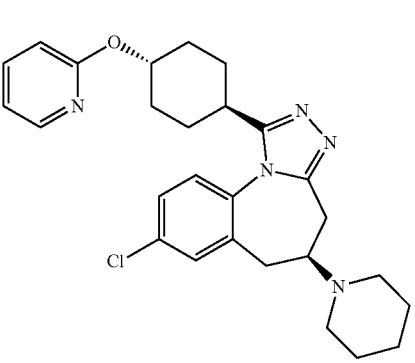 [SMILES: Clc1ccc2c(c1)C[C@H](N1CCCCC1)Cc1nnc([C@H]3CC[C@H](Oc4ccccn4)CC3)n1-2]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 1,5-dibromopentane according to the method described in Example 117. MS (ESI) m/z 478.4 (M+H)$^+$.

Example 128

5S)—N-(butan-2-yl)-8-chloro-1-[trans-4-pyridin-2-yloxy)cyclohexyl]-5,6-dihydro-4H-[1,2,4]triazolo[4,3-a][1]benzazepin-5-amine

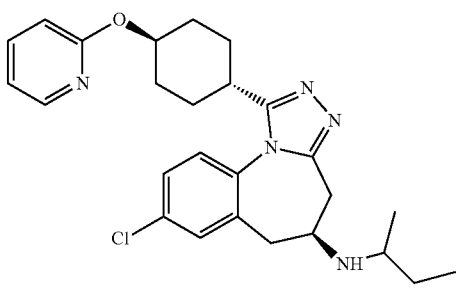 [SMILES: CCC(C)N[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 2-butanone according to the method described in Example 24. MS (ESI) m/z 466.4 (M+H)$^+$.

Example 129

(5s,8s)-8-(8'-chloro-4'H,6'H-spiro[1,3-dioxolane-2,5-[1,2,4]triazolo[4,3-a][1]benzazepin]-1'-yl)-2-(propan-2-yl)-2-azaspiro[4.5]decan-1-one

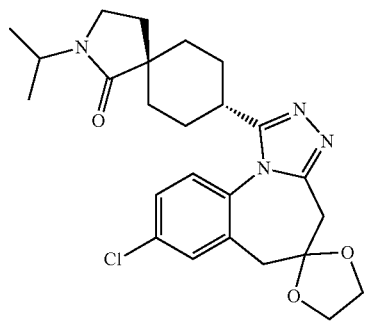 [SMILES: CC(C)N1CC[C@]2(CC[C@H](c3nnc4n3-c3ccc(Cl)cc3CC3(C4)OCCO3)CC2)C1=O]

The title compound was prepared from 7-chloro-1,5-dihydrospiro[1-benzazepine-4,2'-[1,3]dioxolan]-2(3H)-one (Intermediate 53) and (5s,8s)-1-oxo-2-(propan-2-yl)-2-azaspiro[4.5]decane-8-carbohydrazide (Intermediate 101) according to the method described in Example 62. MS (ESI) m/z 471.2 (M+H)$^+$.

Example 130

8-chloro-5-methoxy-1-[trans-4-(morpholin-4-yl)cyclohexyl]-5,6-dihydro-4H-[1,2,4]triazolo[4,3-a][1]benzazepine

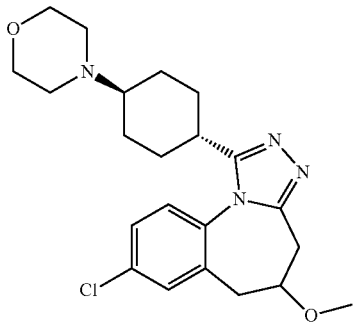 [SMILES: COC1Cc2cc(Cl)ccc2-n2c(nnc2[C@H]2CC[C@H](N3CCOCC3)CC2)C1]

The title compound was prepared from 7-chloro-4-methoxy-1,3,4,5-tetrahydro-2H-1-benzazepine-2-thione (Step e) of Intermediate 103) and trans-4-(morpholin-4-yl)cyclohexane carbohydrazide (Intermediate 81) according to the method described in Step a) of Example 37. MS (ESI) m/z 417.3 (M+H)$^+$.

Example 131

8-chloro-5-ethoxy-1-[trans-4-(pyridin-2-yloxy)cyclohexyl]-5,6-dihydro-4H-[1,2,4]triazolo[4,3-a][1]benzazepine

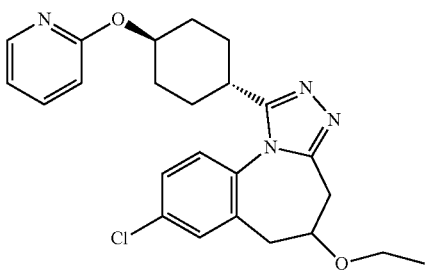 [SMILES: CCOC1Cc2cc(Cl)ccc2-n2c(nnc2[C@H]2CC[C@H](Oc3ccccn3)CC2)C1]

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and ethyl iodide according to the method described in Example 50. MS (ESI) m/z 439.3 (M+H)$^+$.

Example 132

(5R)-8-chloro-5-methoxy-1-[trans-4-(trifluoromethyl)cyclohexyl]-5,6-dihydro-4H-[1,2,4]triazolo[4,3-a][1]benzazepine

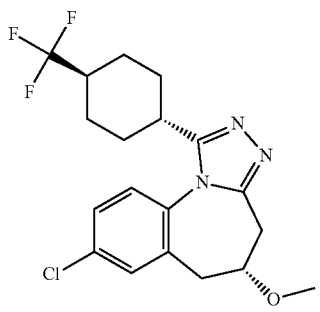 [SMILES: CO[C@@H]1Cc2cc(Cl)ccc2-n2c(nnc2[C@H]2CC[C@H](C(F)(F)F)CC2)C1]

Example 133

(5S)-8-chloro-5-methoxy-1-[trans-4-trifluoromethyl)cyclohexyl]-5,6-dihydro-4H-[1,2,4]triazolo[4,3-a][1]benzazepine

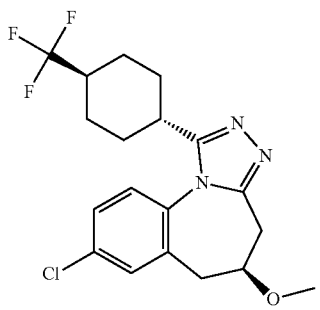 [SMILES: CO[C@H]1Cc2cc(Cl)ccc2-n2c(nnc2[C@H]2CC[C@H](C(F)(F)F)CC2)C1]

The title compounds were obtained from the racemic 8-chloro-5-methoxy-1-[trans-4-(trifluoromethyl)cyclohexyl]-5,6-dihydro-4H-[1,2,4]triazolo[4,3-a][1]benzazepine (Example 74) by chiral preparative HPLC (CHIRALPAK IG preparative 20 μm stationary phase; 1.6×25 cm; F=12 mL/min; eluent: tert-butyl methyl ether:dichloromethane:ethanol=90:8:2; isocratic; t=25° C.). The optical rotation of the first eluting compound ($T_r$ 18.0 min) was $[\alpha]_D^{20}$=+15.6° (c=0.1; chloroform); and that of the second eluting compound ($T_r$ 23.3 min) was $[\alpha]_D^{20}$=−13.5° (c=0.1; chloroform). The absolute configuration of the compounds was not determined.

Example 134

8-fluoro-5-methoxy-1-[trans-4-(pyridin-2-yloxy)cyclohexyl]-5,6-dihydro-4H-[1,2,4]triazolo[4,3-a][1]benzazepine

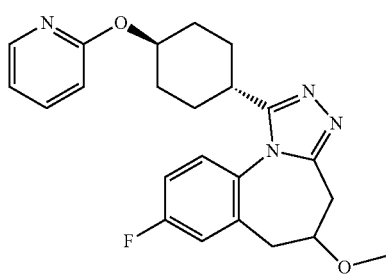 [SMILES: COC1Cc2cc(F)ccc2-n2c(nnc2[C@H]2CC[C@H](Oc3ccccn3)CC2)C1]

The title compound was prepared from 8-fluoro-1-[trans-4-(pyridin-2-yloxy)cyclohexyl]-5,6-dihydro-4H-[1,2,4]triazolo[4,3-a][1]benzazepin-5-o (Example 111) according to the method described in Example 50. MS (ESI) m/z 409.3 (M+H)⁺.

Example 135

8-chloro-N-(propan-2-yl)-1-[1-(pyridin-2-yl)piperidin-4-yl]-5,6-dihydro-4H-[1,2,4]triazolo[4,3-a][1]benzazepin-5-amine

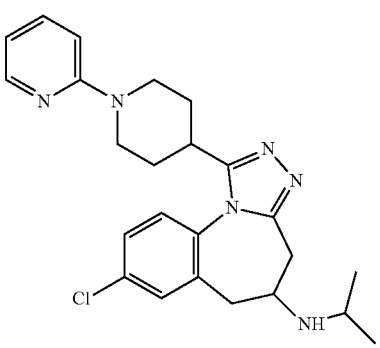 [SMILES: CC(C)NC1Cc2cc(Cl)ccc2-n2c(nnc2C2CCN(c3ccccn3)CC2)C1]

The title compound was prepared from 8-chloro-1-[1-(pyridin-2-yl)piperidin-4-yl]-5,6-dihydro-4H-[1,2,4]triazolo[4,3-a][1]benzazepin-5-amine (Example 2) according to the method described in Example 24. MS (ESI) m/z 437.4 (M+H)⁺.

Example 136

2-({8-chloro-1-[trans-4-(pyridin-2-yloxy)cyclohexyl]-5,6-dihydro-4H-[1,2,4]triazolo[4,3-a][1]benzazepin-5-yl}oxy)ethanol

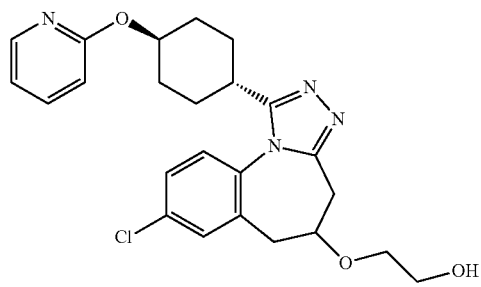 [SMILES: OCCOC1Cc2cc(Cl)ccc2-n2c(nnc2[C@H]2CC[C@H](Oc3ccccn3)CC2)C1]

a) 8-chloro-1-[trans-4-(pyridin-2-yloxy)cyclohexyl]-5-[2-(tetrahydro-2H-pyran-2-yloxy)ethoxy]-5,6-dihydro-4H-[1,2,4]triazolo[4,3-a][1]benzazepine

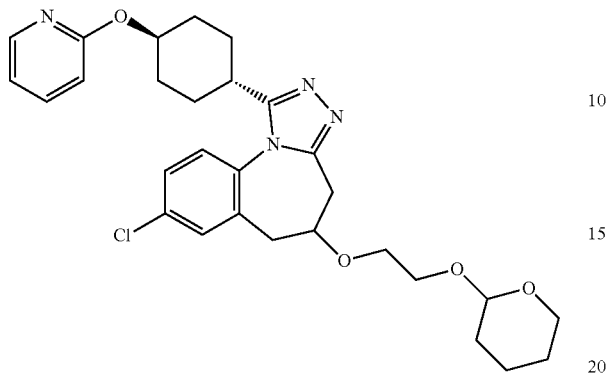

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and 2-(2-bromoethoxy)tetrahydro-2H-pyran according to the method described in Example 50. MS (ESI) m/z 539.1 (M+H)+.

b) 2-({8-chloro-1-[trans-4-(pyridin-2-yloxy)cyclohexyl]-5,6-dihydro-4H-[1,2,4]triazolo[4,3-a][1]benzazepin-5-yl}oxy)ethanol A mixture of 146 mg (0.27 mmol) of 8-chloro-1-[trans-4-(pyridin-2-yloxy)cyclohexyl]-5-[2-(tetrahydro-2H-pyran-2-yloxy)ethoxy]-5,6-dihydro-4H-[1,2,4]triazolo[4,3-a][1]benzazepine (Step a) of Example 136), 4 mL of acetic acid, 2 mL of THF and 1 mL of water was stirred at 45° C. for 20 h, then diluted with water. The so obtained mixture was alkalified with saturated NaHCO₃ solution, extracted with ethyl acetate, the combined organic layers were dried over MgSO₄, filtered and concentrated to yield 118 mg (96%) of the title compound. MS (ESI) m/z 455.4 (M+H)+.

Example 137

(5S)-8-chloro-N,N-diethyl-1-[trans-4-(pyridin-2-yloxy)cyclohexyl]-5,6-dihydro-4H-[1,2,4]triazolo[4,3-a][1]benzazepin-5-amine

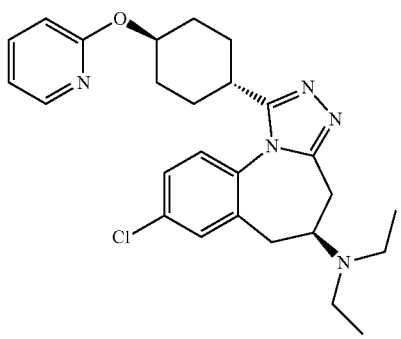 [SMILES: CCN(CC)[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and acetaldehyde according to the method described in Example 24. MS (ESI) m/z 466.4 (M+H)+.

Example 138

8-chloro-N-methyl-N-(propan-2-yl)-1-[trans-4-(pyridin-2-yloxy)cyclohexyl]-5,6-dihydro-4H-[1,2,4]triazolo[4,3-a][1]benzazepin-5-amine

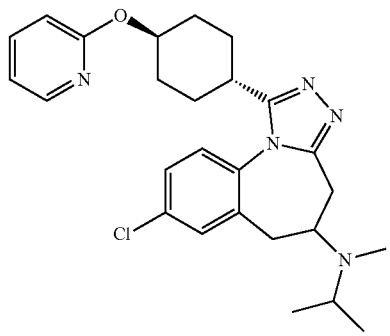 [SMILES: CC(C)N(C)C1Cc2cc(Cl)ccc2-n2c(nnc2[C@H]2CC[C@H](Oc3ccccn3)CC2)C1]

A mixture of 110 mg (0.24 mmol) of 8-chloro-N-(propan-2-yl)-1-[trans-4-(pyridin-2-yloxy)cyclohexyl]-5,6-dihydro-4H-[1,2,4]triazolo[4,3-a][1]benzazepin-5-amine (Example 24), 15 mL of methanol, 182 μL of 37% formaldehyde solution in water and 28 μL of acetic acid was cooled to 5° C. and 169 mg (0.8 mmol) of sodium triacetoxyborohydride was added to the reaction mixture at such a rate to keep the internal temperature below 5° C. After completion of the addition the reaction mixture was stirred at room temperature for 24 h, then concentrated. The residue was dissolved in water and the pH was adjusted to 8 by addition of saturated NaHCO₃ solution, then the mixture was extracted with ethyl acetate, the combined organic layers were dried over Na₂SO₄, filtered and concentrated to yield 107 g (94%) of the title compound. MS (ESI) m/z 466.2 (M+H)+.

Example 139

Tert-butyl {8-chloro-1-[4-(3-chloropyridin-2-yl)piperazin-1-yl]-5,6-dihydro-4H-[1,2,4]triazolo[4,3-a][1]benzazepin-5-yl}carbamate

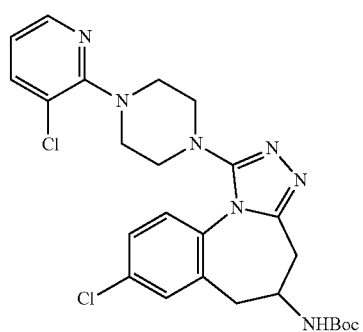 [SMILES: CC(C)(C)OC(=O)NC1Cc2cc(Cl)ccc2-n2c(nnc2N2CCN(c3ncccc3Cl)CC2)C1]

The title compound was prepared from tert-butyl (1-bromo-8-chloro-5,6-dihydro-4H-[1,2,4]triazolo[4,3-a][1]benzazepin-5-yl)carbamate (Intermediate 94) and 1-(3-chlo-

235 ropyridin-2-yl)piperazine according to the method described in Example 94. MS (ESI) m/z 530.4 (M+H)+.

Example 140

Tert-butyl 4-(8-chloro-5-methoxy-5,6-dihydro-4H-[1,2,4]triazolo[4,3-a][1]benzazepin-1-yl)piperidine-1-carboxylate

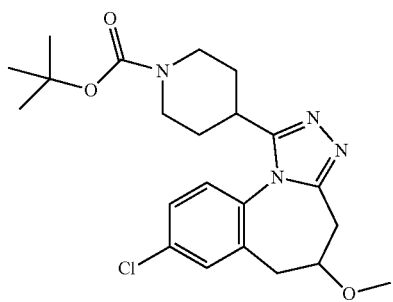 [SMILES: COC1Cc2cc(Cl)ccc2-n2c(nnc2C2CCN(C(=O)OC(C)(C)C)CC2)C1]

The title compound was prepared from 7-chloro-4-methoxy-1,3,4,5-tetrahydro-2H-1-benzazepin-2-one (Step d) of Intermediate 103) and tert-butyl 4-(hydrazinylcarbonyl)piperidine-1-carboxylate according to the method described in Example 47. MS (ESI) m/z 433.2 (M+H)+.

Example 141

N-{(5R)-8-chloro-1-[trans-4-(pyridin-2-yloxy)cyclohexyl]-5,6-dihydro-4H-[1,2,4]triazolo[4,3-a][1]benzazepin-5-yl}-D-valinamide

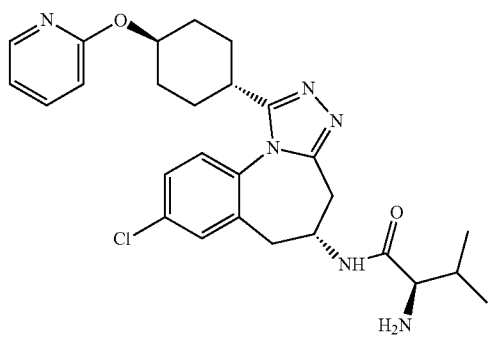 [SMILES: CC(C)[C@@H](N)C(=O)N[C@@H]1Cc2cc(Cl)ccc2-n2c(nnc2[C@H]2CC[C@H](Oc3ccccn3)CC2)C1]

236 a) Tert-butyl [(2R)-1-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-3-methyl-1-oxobutan-2-yl]carbamate

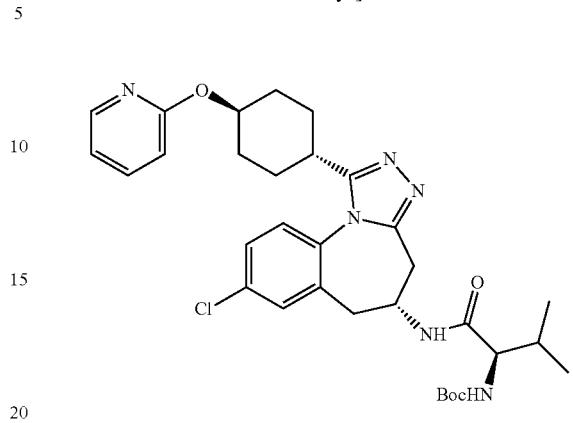

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and cyclobutanecarboxylic acid according to the method described in Step a) of Example 10 and it was used without further purification in the next step.

b) N-{(5R)-8-chloro-1-[trans-4-(pyridin-2-yloxy)cyclohexyl]-5,6-dihydro-4H-[1,2,4]triazolo[4,3-a][1]benzazepin-5-yl}-D-valinamide The title compound was prepared from tert-butyl [(2R)-1-({(5R)-8-chloro-1-[trans-4-(pyridin-2-yloxy)cyclohexyl]-5,6-dihydro-4H-[1,2,4]triazolo[4,3-a][1]benzazepin-5-yl}amino)-3-methyl-1-oxobutan-2-yl]carbamate (Step a) of Example 141) according to the method described in Example 6. $[\alpha]_D^{20}$=+7° (c=0.1; methanol); MS (ESI) m/z 509.2 (M+H)+.

Example 142

Tert-butyl {1-[trans-4-(pyridin-2-yloxy)cyclohexyl]-5,6-dihydro-4H-[1,2,4]triazolo[4,3-a][1]benzazepin-5-yl}carbamate

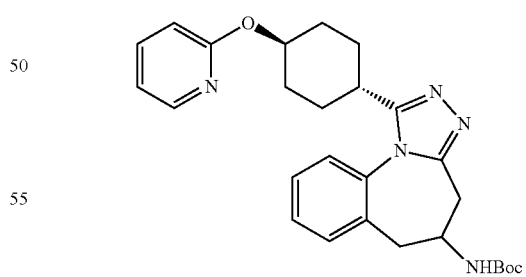

A mixture of 552 mg (1.8 mmol) of tert-butyl [2-(methylsulfanyl)-4,5-dihydro-3H-1-benzazepin-4-yl]carbamate (Intermediate 105), 27 mL of 1,4-dioxane, 464 mg (1.97 mmol) of trans-4-(pyridin-2-yloxy)cyclohexanecarbohydrazide (WO 2010/060836 (3 Jun. 2010) F. HOFFMANN-LA ROCHE AG.) and 10 µL of concentrated hydrochloric acid was refluxed under argon for 6.5 h, then concentrated. The residue was purified by column chromatography using

Example 143

Tert-butyl {8-fluoro-1-[trans-4-(pyridin-2-yloxy)cyclohexyl]-5,6-dihydro-4H-[1,2,4]triazolo[4,3-a][1]benzazepin-5-yl}carbamate

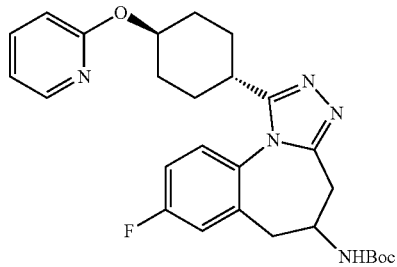 [SMILES: CC(C)(C)OC(=O)NC1Cc2cc(F)ccc2-n2c(nnc2[C@H]2CC[C@H](Oc3ccccn3)CC2)C1]

The title compound was prepared from tert-butyl [7-fluoro-2-(methylsulfanyl)-4,5-dihydro-3H-1-benzazepin-4-yl]carbamate (Step g) of Intermediate 106) according to the method described in Example 142. MS (ESI) m/z 494.2 (M+H)$^+$.

Example 144

1-[trans-4-(pyridin-2-yloxy)cyclohexyl]-5,6-dihydro-4H-[1,2,4]triazolo[4,3-a][1]benzazepin-5-amine

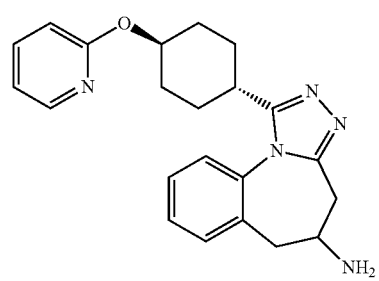 [SMILES: NC1Cc2ccccc2-n2c(nnc2[C@H]2CC[C@H](Oc3ccccn3)CC2)C1]

The title compound was prepared from tert-butyl {1-[trans-4-(pyridin-2-yloxy)cyclohexyl]-5,6-dihydro-4H-[1,2,4]triazolo[4,3-a][1]benzazepin-5-yl}carbamate (Example 142) according to the method described in Example 6. MS (ESI) m/z 376.2 (M+H)$^+$.

Example 145

8-fluoro-1-[trans-4-(pyridin-2-yloxy)cyclohexyl]-5,6-dihydro-4H-[1,2,4]triazolo[4,3-a][1]benzazepin-5-amine

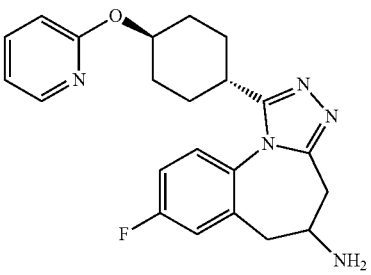 [SMILES: NC1Cc2cc(F)ccc2-n2c(nnc2[C@H]2CC[C@H](Oc3ccccn3)CC2)C1]

The title compound was prepared from tert-butyl {-fluoro-1-[trans-4-(pyridin-2-yloxy)cyclohexyl]-5,6-dihydro-4H-[1,2,4]triazolo[4,3-a][1]benzazepin-5-yl}carbamate (Example 143) according to the method described in Example 6. MS (ESI) m/z 394.2 (M+H)$^+$.

Example 146

8-fluoro-N-(propan-2-yl)-1-[trans-4-(pyridin-2-yloxy)cyclohexyl]-5,6-dihydro-4H-[1,2,4]triazolo[4,3-a][1]benzazepin-5-amine

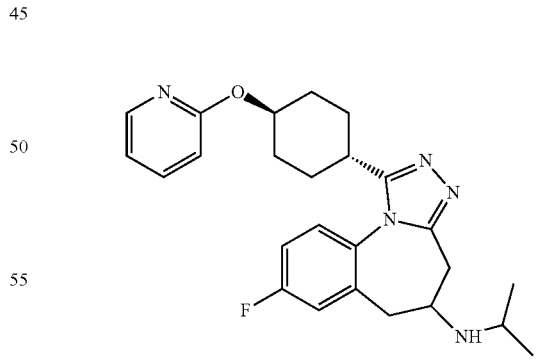

The title compound was prepared from 8-fluoro-1-[trans-4-(pyridin-2-yloxy)cyclohexyl]-5,6-dihydro-4H-[1,2,4]triazolo[4,3-a][1]benzazepin-5-amine (Example 145) according to the method described in Example 24. MS (ESI) m/z 436.2 (M+H)$^+$.

Example 147

8-fluoro-N,N-dimethyl-1-[trans-4-(pyridin-2-yloxy)cyclohexyl]-5,6-dihydro-4H-[1,2,4]triazolo[4,3-a][1]benzazepin-5-amine

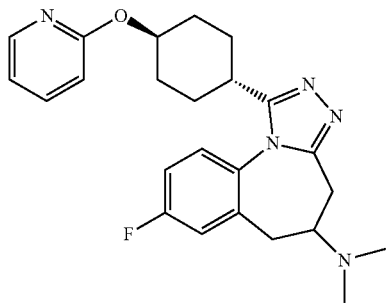 [SMILES: CN(C)C1Cc2cc(F)ccc2-n2c(nnc2[C@H]2CC[C@H](Oc3ccccn3)CC2)C1]

The title compound was prepared from 8-fluoro-1-[trans-4-(pyridin-2-yloxy)cyclohexyl]-5,6-dihydro-4H-[1,2,4]triazolo[4,3-a][1]benzazepin-5-amine (Example 145) according to the method described in Example 101. MS (ESI) m/z 436.2 (M+H)$^+$.

Example 148

N,N-dimethyl-1-[trans-4-pyridin-2-yloxy)cyclohexyl]-5,6-dihydro-4H-[1,2,4]triazolo[4,3-a][1]benzazepin-5-amine

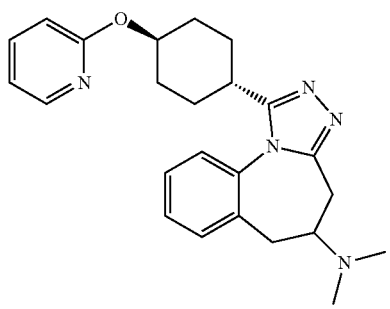 [SMILES: CN(C)C1Cc2ccccc2-n2c(nnc2[C@H]2CC[C@H](Oc3ccccn3)CC2)C1]

The title compound was prepared from 1-[trans-4-(pyridin-2-yloxy)cyclohexyl]-5,6-dihydro-4H-[1,2,4]triazolo[4,3-a][1]benzazepin-5-amine (Example 144) according to the method described in Example 101. MS (ESI) m/z 404.2 (M+H)$^+$.

Example 149

8'-fluoro-1'-[trans-4-(trifluoromethyl)cyclohexyl]-4'H,6'H-spiro[1,3-dioxolane-2,5'-[1,2,4]triazolo[4,3-a][1]benzazepine]

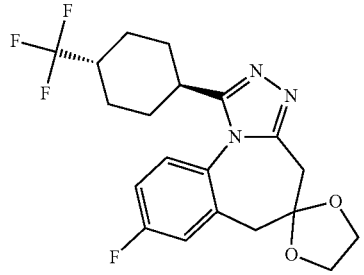 [SMILES: Fc1ccc2c(c1)CC1(Cc3nnc([C@H]4CC[C@H](C(F)(F)F)CC4)n3-2)OCCO1]

The title compound was prepared from 7-fluoro-1,5-dihydrospiro[1-benzazepine-4,2'-[1,3]dioxolan]-2(3H)-one (Intermediate 92) and trans-4-(trifluoromethyl)cyclohexane carbohydrazide (Intermediate 55) according to the method described in Example 47. MS (ESI) m/z 404.2 (M+H)$^+$.

Example 150

N-(propan-2-yl)-1-[trans-4-(pyridin-2-yloxy)cyclohexyl]-5,6-dihydro-4H-[1,2,4]triazolo[4,3-a][1]benzazepin-5-amine

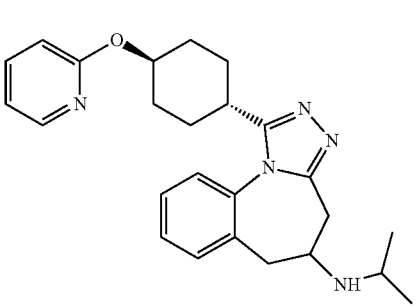 [SMILES: CC(C)NC1Cc2ccccc2-n2c(nnc2[C@H]2CC[C@H](Oc3ccccn3)CC2)C1]

The title compound was prepared from 1-[trans-4-(pyridin-2-yloxy)cyclohexyl]-5,6-dihydro-4H-[1,2,4]triazolo[4,3-a][1]benzazepin-5-amine (Example 144) according to the method described in Example 24. MS (ESI) m/z 418.2 (M+H)$^+$.

Example 151

N-{(5S)-8-chloro-1-[trans-4-pyridin-2-yloxy)cyclohexyl]-5,6-dihydro-4H-[1,2,4]triazolo[4,3-a][1]benzazepin-5-yl}tetrahydro-2H-pyran-4-carboxamide

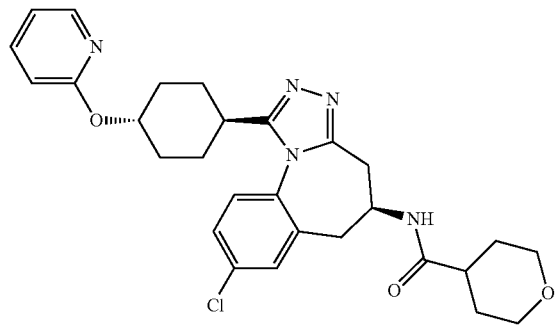 [SMILES: O=C(N[C@H]1Cc2cc(Cl)ccc2-n2c(nnc2[C@H]2CC[C@H](Oc3ccccn3)CC2)C1)C1CCOCC1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and tetrahydro-2H-pyran-4-carboxylic acid according to the method described in Step a) of Example 10. $[\alpha]_D^{20}=-41°$ (c=0.1; methanol); MS (ESI) m/z 522.2 (M+H)$^+$.

Example 152

N-{(5S)-8-chloro-1-[trans-4-pyridin-2-yloxy)cyclohexyl]-5,6-dihydro-4H-[1,2,4]triazolo[4,3-a][1]benzazepin-5-yl}-2-methylbutanamide

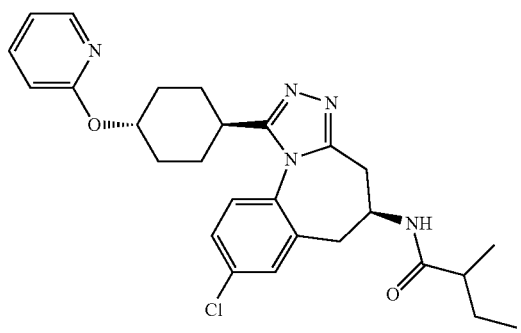 [SMILES: CCC(C)C(=O)N[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 2-methylbutyric acid according to the method described in Step a) of Example 10. MS (ESI) m/z 494.2 (M+H)$^+$.

Example 153

N-{(5S)-8-chloro-1-[trans-4-(pyridin-2-yloxy)cyclohexyl]-5,6-dihydro-4H-[1,2,4]triazolo[4,3-a][1]benzazepin-5-yl}-N$^3$,N$^3$-dimethyl-β-alaninamide

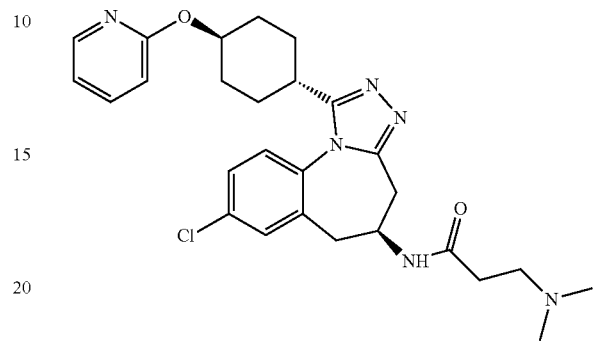

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 3-(dimethylamino)propanic acid according to the method described in Step a) of Example 10. $[\alpha]_D^{20}2=-15°$ (c=0.1; methanol); MS (ESI) m/z 509.2 (M+H)$^+$.

Example 154

(5S)-8-chloro-N-cyclopentyl-1-[trans-4-(pyridin-2-yloxy)cyclohexyl]-5,6-dihydro-4H-[1,2,4]triazolo[4,3-a][1]benzazepin-5-amine

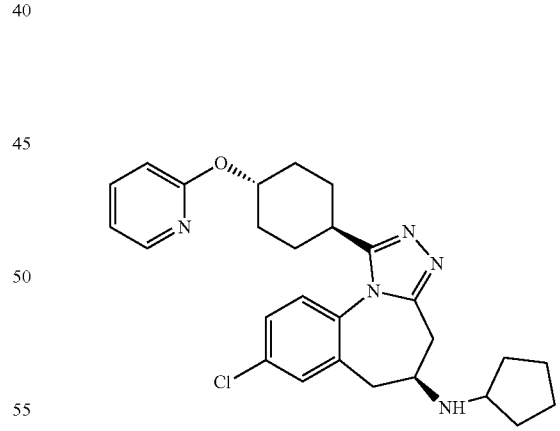

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and cyclopentanone according to the method described in Example 24. $[\alpha]_D^{20}=-19°$ (c=0.1; methanol); MS (ESI) m/z 478.2 (M+H)$^+$.

Example 155

8'-chloro-1'-(1'H,3H-spiro[2-benzofuran-1,4'-piperidin]-1'-yl)-4'H,6'H-spiro[1,3-dioxolane-2,5'-[1,2,4]triazolo[4,3-a][1]benzazepine]

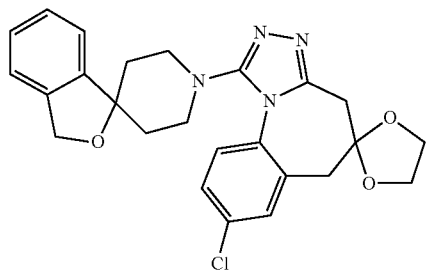 [SMILES: Clc1ccc2c(c1)CC1(Cc3nnc(N4CCC5(CC4)OCc4ccccc45)n3-2)OCCO1]

The title compound was prepared from 1'-bromo-8'-chloro-4'H,6'H-spiro[1,3-dioxolane-2,5'-[1,2,4]triazolo[4,3-a][1]benzazepine] (Intermediate 96) and 3H-spiro[2-benzofuran-1,4'-piperidine] (Combi-Blocks) according to the method described in Example 94. MS (ESI) m/z 465.2 (M+H)$^+$.

Example 156

8-chloro-1-(1'H,3H-spiro[2-benzofuran-1,4'-piperidin]-1'-yl)-4H-[1,2,4]triazolo[4,3-a][1]benzazepin-5(6H)-one

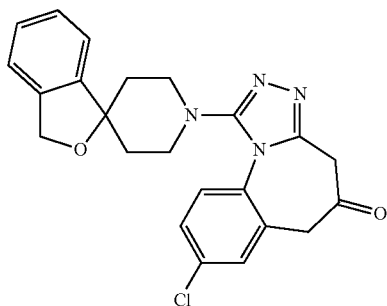 [SMILES: O=C1Cc2cc(Cl)ccc2-n2c(nnc2N2CCC3(CC2)OCc2ccccc23)C1]

The title compound was prepared from 8'-chloro-1'-(1'H,3H-spiro[2-benzofuran-1,4'-piperidin]-1'-yl)-4'H,6'H-spiro[1,3-dioxolane-2,5'-[1,2,4]triazolo[4,3-a][1]benzazepine] (Example 155) according to the method described in Example 48. MS (ESI) m/z 421.2 (M+H)$^+$.

Example 157

8'-chloro-1'-[4-(pyridin-2-yloxy)piperidin-1-yl]-4'H,6'H-spiro[1,3-dioxolane-2,5'-[1,2,4]triazolo[4,3-a][1]benzazepine]

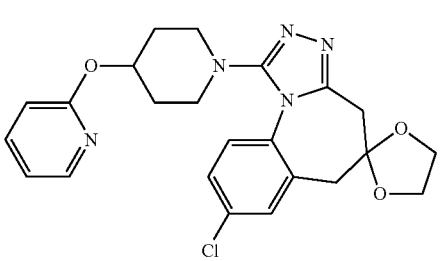 [SMILES: Clc1ccc2c(c1)CC1(Cc3nnc(N4CCC(Oc5ccccn5)CC4)n3-2)OCCO1]

The title compound was prepared from 1'-bromo-8'-chloro-4'H,6'H-spiro[1,3-dioxolane-2,5'-[1,2,4]triazolo[4,3-a][1]benzazepine] (Intermediate 96) and 2-(piperidin-4-yloxy)pyridine according to the method described in Example 94. MS (ESI) m/z 454.1 (M+H)$^+$.

Example 158

N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylbutanamide

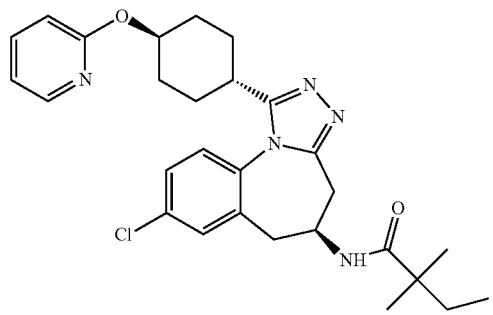 [SMILES: CCC(C)(C)C(=O)N[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 2,2-dimethylbutyric acid according to the method described in Step a) of Example 10. $[\alpha]_D^{20}=-16°$ (c=0.1; methanol); MS (ESI) m/z 508.2 (M+H)$^+$.

Example 159

N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-hydroxy-2-methylpropanamide

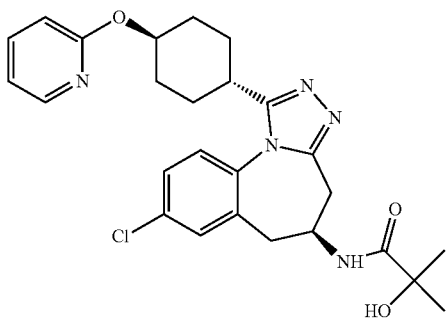 [SMILES: CC(C)(O)C(=O)N[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 2-hydroxy-2-methylpropanoic acid according to the method described in Step a) of Example 10. $[X]°=-30°$ (c=0.1; methanol); MS (ESI) m/z 496.2 (M+H)$^+$.

Example 160

(5S)-8-chloro-N-ethyl-N-methyl-1-[trans-4-pyridin-2-yloxy)cyclohexyl]-5,6-dihydro-4H-[1,2,4]triazolo[4,3-a][1]benzazepin-5-amine

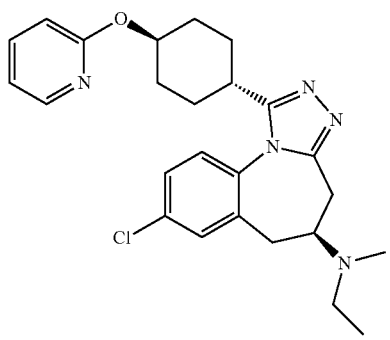 [SMILES: CCN(C)[C@H]1Cc2cc(Cl)ccc2-n2c(nnc2[C@H]2CC[C@H](Oc3ccccn3)CC2)C1]

The title compound was prepared from (5S)-8-chloro-N-methyl-1-[trans-4-(pyridin-2-yloxy)cyclohexyl]-5,6-dihydro-4H-[1,2,4]triazolo[4,3-a][1]benzazepin-5-amine (Example 78) and acetaldehyde according to the method described in Example 24. $[\alpha]_D^{20}=-37°$ (c=0.1; methanol); MS (ESI) m/z 452.2 (M+H)$^+$.

Example 161

(5S)-8-chloro-N-(2-methylpropyl-1-[trans-4-pyridin-2-yloxy)cyclohexyl]-5,6-dihydro-4H-[1,2,4]triazolo[4,3-a][1]benzazepin-5-amine

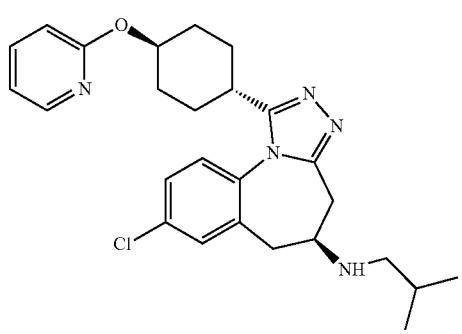 [SMILES: CC(C)CN[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and isobutyraldehyde according to the method described in Example 24. $[\alpha]_D^{20}=-22°$ (c=0.1; methanol); MS (ESI) m/z 466.2 (M+H)$^+$.

Example 162

8'-chloro-1'-[trans-4-(morpholin-4-yl)cyclohexyl]-4'H,6'H-spiro[1,3-dioxolane-2,5'-[1,2,4]triazolo[4,3-a][1]benzazepine]hydrochloride

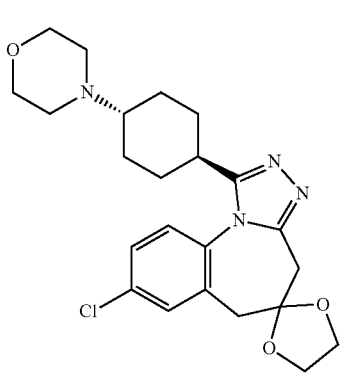 [SMILES: Clc1ccc2c(c1)CC1(Cc3nnc([C@H]4CC[C@H](N5CCOCC5)CC4)n3-2)OCCO1]

The title compound was prepared from 7-chloro-1,5-dihydrospiro[1-benzazepine-4,2'-[1,3]dioxolan]-2(3H)-one (Intermediate 53) and trans-4-(morpholin-4-yl)cyclohexane carbohydrazide (Intermediate 81) according to the method described in Example 47. MS (ESI) m/z 445.2 (M+H)$^+$.

Example 163

8-chloro-N,N-dimethyl-1-(1'H,3H-spiro[2-benzofuran-1,4'-piperidin]-1'-yl)-5,6-dihydro-4H-[1,2,4]triazolo[4,3-a][1]benzazepin-5-amine

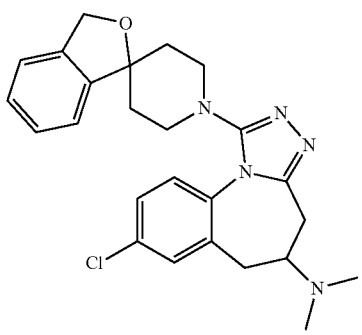 [SMILES: CN(C)C1Cc2cc(Cl)ccc2-n2c(nnc2N2CCC3(CC2)OCc2ccccc23)C1]

a) Tert-butyl [8-chloro-1-(1'H,3H-spiro[2-benzofuran-1,4'-piperidin]-1'-yl)-5,6-dihydro-4H-[1,2,4]triazolo[4,3-a][1]benzazepin-5-yl]carbamate

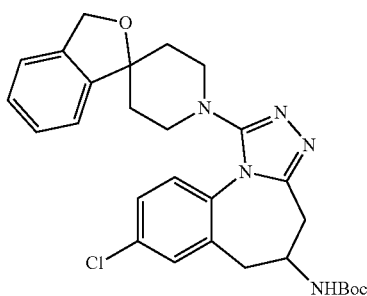 [SMILES: CC(C)(C)OC(=O)NC1Cc2cc(Cl)ccc2-n2c(nnc2N2CCC3(CC2)OCc2ccccc23)C1]

The title compound was prepared from tert-butyl (1-bromo-1-chloro-5,6-dihydro-4H-[1,2,4]triazolo[4,3-a][1]benzazepin-5-yl)carbamate (Intermediate 94) and 3H-spiro[2-benzofuran-1,4'-piperidine] (Combi-Blocks) according to the method described in Example 94. MS (ESI) m/z 522.4 (M+H)⁺.

b) 8-chloro-1-(1'H,3H-spiro[2-benzofuran-1,4'-piperidin]-1'-yl)-5,6-dihydro-4H-[1,2,4]triazolo[4,3-a][1]benzazepin-5-amine

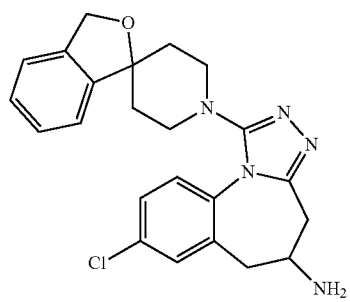 [SMILES: NC1Cc2cc(Cl)ccc2-n2c(nnc2N2CCC3(CC2)OCc2ccccc23)C1]

The title compound was prepared from tert-butyl [8-chloro-1-(1'H,3H-spiro[2-benzofuran-1,4'-piperidin]-1'-yl)-5,6-dihydro-4H-[1,2,4]triazolo[4,3-a][1]benzazepin-5-yl]carbamate (Step a) of Example 163) according to the method described Example 6 and it was used without further purification in the next step.

c) 8-chloro-N,N-dimethyl-1-(1'H,3H-spiro[2-benzofuran-1,4-piperidin]-1'-yl-5,6-dihydro-4H-[1,2,4]triazolo[4,3-a][1]benzazepin-5-amine The title compound was prepared from 8-chloro-1-(1'H,3H-spiro[2-benzofuran-1,4'-piperidin]-1'-yl)-5,6-dihydro-4H-[1,2,4]triazolo[4,3-a][1]benzazepin-5-amine (Step b) of Example 163) according to the method described in Example 101. MS (ESI) m/z 450.1 (M+H)⁺.

Example 164

8'-chloro-1-[4-(3-chloropyridin-2-yl)piperazin-1-yl]-4'H,6'H-spiro[1,3-dioxolane-2,5'-[1,2,4]triazolo[4,3-a][1]benzazepine]

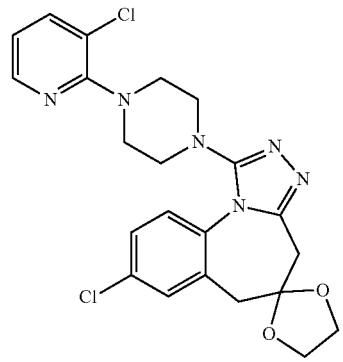 [SMILES: Clc1ccc2c(c1)CC1(Cc3nnc(N4CCN(c5ncccc5Cl)CC4)n3-2)OCCO1]

The title compound was prepared from 1'-bromo-8'-chloro-4'H,6'H-spiro[1,3-dioxolane-2,5'-[1,2,4]triazolo[4,3-a][1]benzazepine] (Intermediate 96) and 1-(3-chloropyridin-2-yl)piperazine according to the method described in Example 94. MS (ESI) m/z 473.1 (M+H)⁺.

Example 165

(5S)-8-chloro-N-(2,2-dimethylpropyl)-1-[trans-4-(pyridin-2-yloxy)cyclohexyl]-5,6-dihydro-4H-[1,2,4]triazolo[4,3-a][1]benzazepin-5-amine

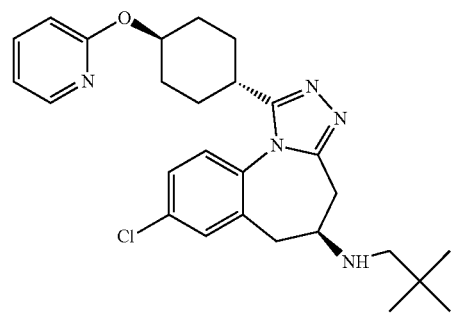 [SMILES: CC(C)(C)CN[C@H]1Cc2cc(Cl)ccc2-n2c(nnc2[C@H]2CC[C@H](Oc3ccccn3)CC2)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and trimethylacetaldehyde according to the method described in Example 24. $[\alpha]_D^{20}=-19°$ (c=0.1; methanol): MS (ESI) m/z 522.2 (M+H)$^+$.

Example 166

[Trans-4-(8-chloro-5-methoxy-5,6-dihydro-4H-[1,2,4]triazolo[4,3-a][1]benzazepin-1-yl)cyclohexyl](4-methylpiperazin-1-yl)methanone

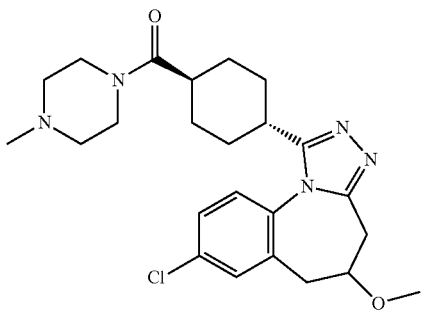

The title compound was prepared from 7-chlor-4-methoxy-1,3,4,5-tetrahydro-2H-1-benzazepin-2-one (Step d) of Intermediate 103) and trans-4-[(4-methylpiperazin-1-yl)carbonyl]cyclohexanecarbohydrazide (Step b) of Intermediate 107) according to the method described in Example 108. MS (ESI) m/z 458.3 (M+H)$^+$.

Example 167

(5R)-8-chloro-5-(morpholin-4-yl)-1-[trans-4-(pyridin-2-yloxy)cyclohexyl]-5,6-dihydro-4H-[1,2,4]triazolo[4,3-a][1]benzazepine

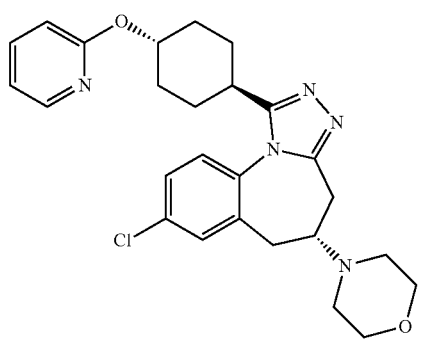 [SMILES: Clc1ccc2c(c1)C[C@@H](N1CCOCC1)Cc1nnc([C@H]3CC[C@H](Oc4ccccn4)CC3)n1-2]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and bis(2-iodoethyl)ether according to the method described in Example 117. MS (ESI) m/z 480.2 (M+H)$^+$.

Example 168

N-{(5R)-8-chloro-1-[trans-4-(pyridin-2-yloxy)cyclohexyl]-5,6-dihydro-4H-[1,2,4]triazolo[4,3-a][1]benzazepin-5-yl}acetamide

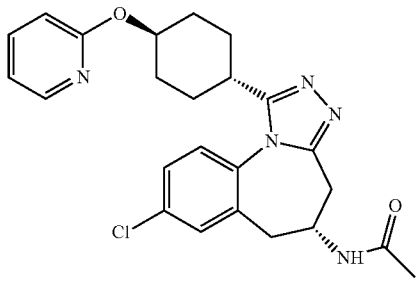

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) according to the method described in Example 9. $[\alpha]_D^{20}=+29°$ (c=0.1; methanol): MS (ESI) m/z 452.2 (M+H)$^+$.

Example 169

N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-hydroxy-2-methylpropanamide

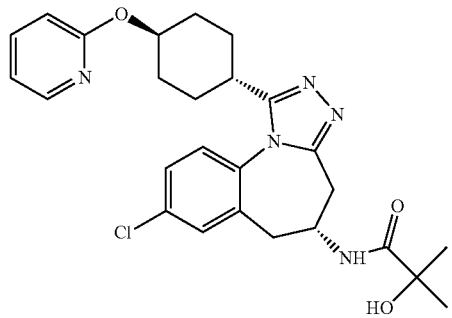 [SMILES: CC(C)(O)C(=O)N[C@@H]1Cc2cc(Cl)ccc2-n2c(nnc2[C@H]2CC[C@H](Oc3ccccn3)CC2)C1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 2-hydroxy-2-methylpropanoic acid according to the method described in Step a) of Example 10. $[\alpha]_D^{20}=+32°$ (c=0.1; methanol); MS (ESI) m/z 496.2 (M+H)$^+$.

Example 170

8-chloro-5-methoxy-1-[1-(tetrahydro-2H-pyran-4-yl)piperidin-4-yl]-5,6-dihydro-4H-[1,2,4]triazolo[4,3-a][1]benzazepine

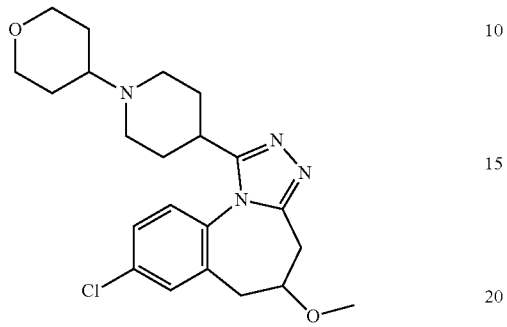

The title compound was prepared from 7-chlor-4-methoxy-1,3,4,5-tetrahydro-2H-1-benzazepin-2-one (Step d) of Intermediate 103) and 1-(tetrahydro-2H-pyran-4-yl)piperidine-4-carbohydrazide (Intermediate 108) according to the method described in Example 108. MS (ESI) m/z 417.2 (M+H)$^+$.

Example 171

8'-chloro-1'-4-(pyridin-2-yl)piperazin-z-vi-4'H,6'H-spiro[1,3-dioxolane-2,5'-[1,2,4]triazolo[4,3-a][1]benzazepine]

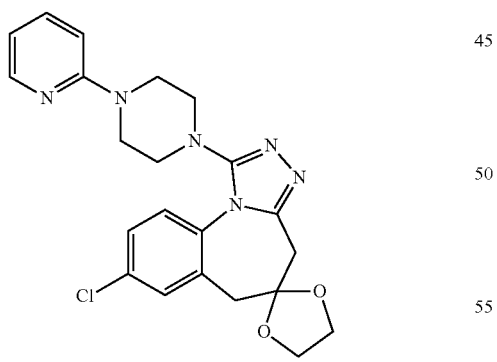

The title compound was prepared from 1'-bromo-8'-chloro-4'H,6'H-spiro[1,3-dioxolane-2,5'-[1,2,4]triazolo[4,3-a][1]benzazepine] (Intermediate 96) and 1-(pyridin-2-yl)piperazine according to the method described in Example 94. MS (ESI) m/z 439.2 (M+H)$^+$.

Example 172

8-chloro-1-(1'H,3H-spiro[2-benzofuran-1,4'-piperidin]-1'-yl)-5,6-dihydro-4H-[1,2,4]triazolo[4,3-a][1]benzazepin-5-ol

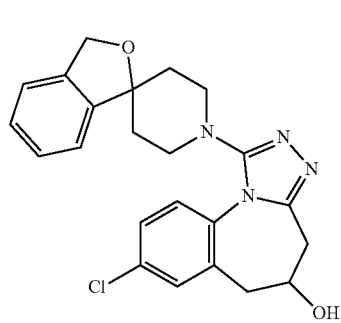 [SMILES: OC1Cc2cc(Cl)ccc2-n2c(nnc2N2CCC3(CC2)OCc2ccccc23)C1]

The title compound was prepared from 8-chloro-1-(1'H,3H-spiro[2-benzofuran-1,4'-piperidin]-1'-yl)-4H-[1,2,4]triazolo[4,3-a][1]benzazepin-5(6H-one (Example 156) according to the method described in Example 49. MS (ESI) m/z 423.2 (M+H)$^+$.

Example 173

8-chloro-1-[4-(3-chloropyridin-2-yl)piperidin-1-yl]-5,6-dihydro-4H-[1,2,4]triazolo[4,3-a][1]benzazepin-5-ol

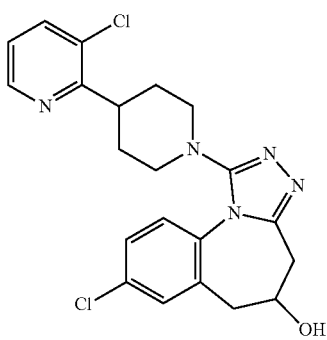 [SMILES: OC1Cc2cc(Cl)ccc2-n2c(nnc2N2CCC(c3ncccc3Cl)CC2)C1]

a) 8-chloro-1-[4-(3-chloropyridin-2-yl)piperidin-1-yl]-4H-[1,2,4]triazolo[4,3-a][1]benzazepin-5(6H)-one

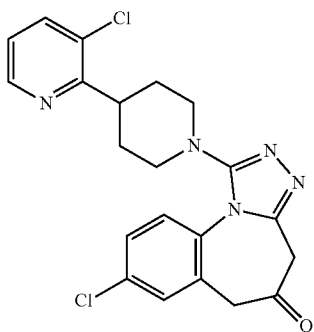 [SMILES: O=C1Cc2cc(Cl)ccc2-n2c(nnc2N2CCC(c3ncccc3Cl)CC2)C1]

The title compound was prepared from 8'-chloro-1'-[4-(3-chloropyridin-2-yl)piperazin-1-yl]-4'H,6'H-spiro[1,3-dioxolane-2,5'-[1,2,4]triazolo[4,3-a][1]benzazepine] (Example 164) according to the method described in Example 48. MS (ESI) m/z 429.0 (M+H)+.

b) 8-chloro-1-[4-(3-chloropyridin-2-yl)piperidin-1-yl]-5,6-dihydro-4H-[1,2,4]triazolo[4,3-a][1]benzazepin-5-ol The title compound was prepared from 8-chloro-1-[4-(3-chloropyridin-2-yl)piperidin-1-yl]-4H-[1,2,4]triazolo[4,3-a][1]benzazepin-5(6H)-one (Step a) of Example 173) according to the method described in Example 49. MS (ESI) m/z 431.1 (M+H)+.

Example 174

(5R)-8-chloro-1-[trans-4-pyridin-2-lox cyclohexyl]-5-(pyrrolidin-1-yl)-5,6-dihydro-4H-[1,2,4]triazolo[4,3-a][1]benzazepine

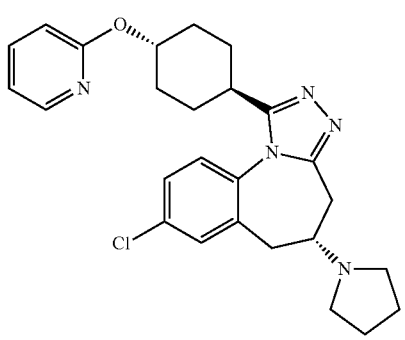 [SMILES: Clc1ccc2c(c1)C[C@@H](N1CCCC1)Cc1nnc([C@H]3CC[C@H](Oc4ccccn4)CC3)n1-2]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 1,4-dibromobutane according to the method described in Example 117. MS (ESI) m/z 464.2 (M+H)+.

Example 175

8-chloro-5-methoxy-1-{1-[(3S)-tetrahydrofuran-3-yl]piperidin-4-yl}-5,6-dihydro-4H-[1,2,4]triazolo[4,3-a][1]benzazepine

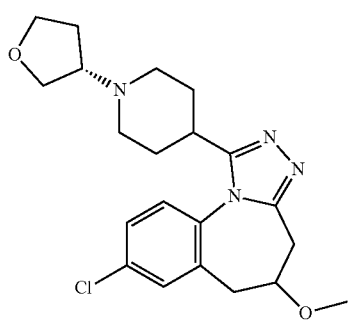 [SMILES: COC1Cc2cc(Cl)ccc2-n2c(nnc2C2CCN([C@H]3CCOC3)CC2)C1]

The title compound was prepared from 7-chloro-4-methoxy-1,3,4,5-tetrahydro-2H-1-benzazepin-2-one (Step d) of Intermediate 103) and 1-[(3S)-tetrahydrofuran-3-yl]piperidine-4-carbohydrazide (Step b) of Intermediate 109) according to the method described in Example 108. MS (ESI) m/z 403.2 (M+H)+.

Example 176

(5R)-8-fluoro-5-methoxy-1-[trans-4-(pyridin-2-yloxy)cyclohexyl]-5,6-dihydro-4H-[1,2,4]triazolo[4,3-a][1]benzazepine

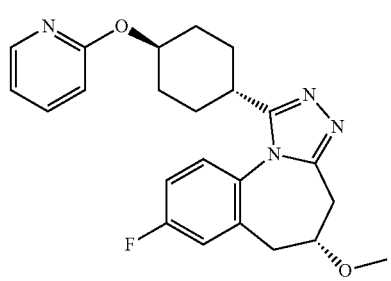 [SMILES: CO[C@@H]1Cc2cc(F)ccc2-n2c(nnc2[C@H]2CC[C@H](Oc3ccccn3)CC2)C1]

Example 177

(5S)-8-fluoro-5-methoxy-1-[trans-4-(pyridin-2-yloxy)cyclohexyl]-5,6-dihydro-4H-[1,2,4]triazolo[4,3-a][1]benzazepine

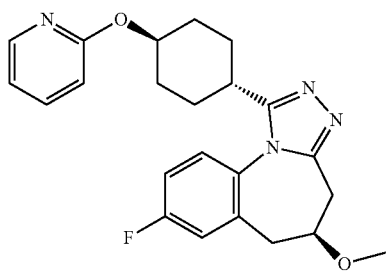 [SMILES: CO[C@H]1Cc2cc(F)ccc2-n2c(nnc2[C@H]2CC[C@H](Oc3ccccn3)CC2)C1]

The title compounds were obtained from the racemic 8-fluoro-5-methoxy-1-[trans-4-(pyridin-2-yloxy)cyclohexyl]-5,6-dihydro-4H-[1,2,4]triazolo[4,3-a][1]benzazepine (Example 134) by chiral preparative HPLC (CHIRALPAK IG preparative 20 μm stationary phase; 5×30 cm; F=50 mL/min; eluent: tert-butyl methyl ether:dichloromethane: ethanol=92:3:5; isocratic; t=25° C.). The optical rotation of the first eluting compound (T; 17.3 min) was $[\alpha]_D^{20}=-7°$ (c=0.1; methanol); and that of the second eluting compound (T$_r$ 21.7 min) was $[\alpha]_D^{20}=+12°$ (c=0.1; methanol). The absolute configuration of the compounds was not determined.

Example 178

8-chloro-5-methoxy-1-{1-[(3R)-tetrahydrofuran-3-yl]piperidin-4-yl}-5,6-dihydro-4H-[1,2,4]triazolo[4,3-a][1]benzazepine

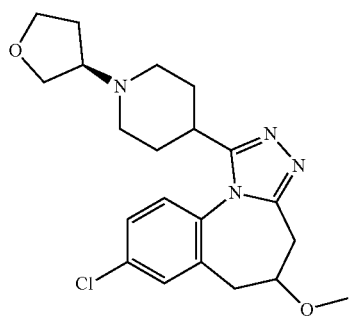 [SMILES: COC1Cc2cc(Cl)ccc2-n2c(nnc2C2CCN([C@@H]3CCOC3)CC2)C1]

The title compound was prepared from 7-chloro-4-methoxy-1,3,4,5-tetrahydro-2H-1-benzazepin-2-one (Step d) of Intermediate 103) and 1-[(3R)-tetrahydrofuran-3-yl]piperidine-4-carbohydrazide (Step b) of Intermediate 110) according to the method described in Example 108. MS (ESI) m/z 403.2 (M+H)$^+$.

Example 179

N-{(5R)-8-chloro-1-[trans-4-(pyridin-2-yloxy)cyclohexyl]-5,6-dihydro-4H-[1,2,4]triazolo[4,3-a][1]benzazepin-5-yl}-N$^3$,N$^3$-dimethyl-β-alaninamide

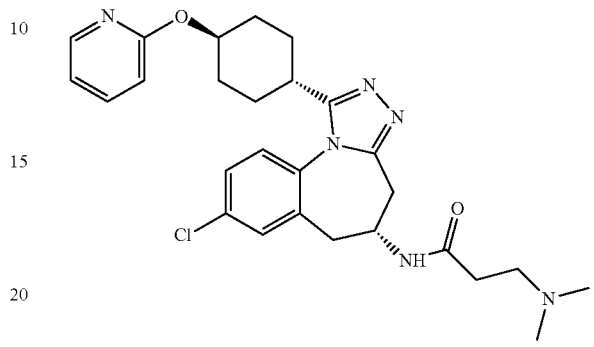

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 3-(dimethylamino)propanoic acid according to the method described in Step a) of Example 10. $[\alpha]_D^{20}=+20°$ (c=0.1; methanol); MS (ESI) m/z 509.2 (M+H)$^+$.

Example 180

N-{(5R)-8-chloro-1-[trans-4-(pyridin-2-yloxy)cyclohexyl]-5,6-dihydro-4H-[1,2,4]triazolo[4,3-a][1]benzazepin-5-yl}tetrahydro-2H-pyran-4-carboxamide

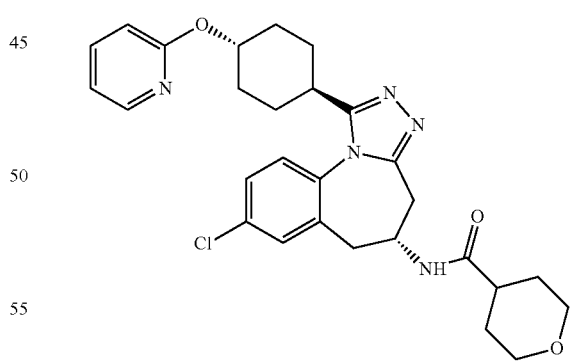

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and tetrahydro-2H-pyran-4-carboxylic acid according to the method described in Step a) of Example 10. $[\alpha]_D^{20}=+29°$ (c=0.1; methanol); MS (ESI) m/z 522.2 (M+H)$^+$.

Example 181

8-chloro-1-[4-(pyridin-2-yloxy)piperidin-1-yl]-5,6-dihydro-4H-[1,2,4]triazolo[4,3-a][1]benzazepin-5-ol

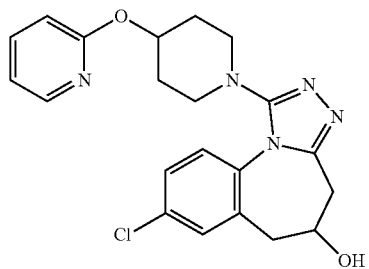 [SMILES: OC1Cc2cc(Cl)ccc2-n2c(nnc2N2CCC(Oc3ccccn3)CC2)C1]

a) 8-chloro-1-[4-(pyridin-2-yloxy piperidin-1-yl]-4H-[1,2,4]triazolo[4,3-a][1]benzazepin-5(6H)-one

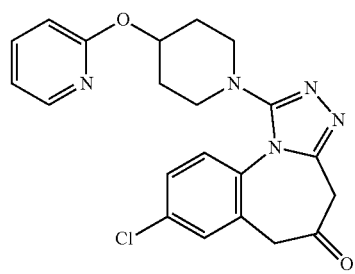 [SMILES: O=C1Cc2cc(Cl)ccc2-n2c(nnc2N2CCC(Oc3ccccn3)CC2)C1]

The title compound was prepared from 8'-chloro-1'-[4-(pyridin-2-yloxy)piperidin-1-yl]-4'H,6'H-spiro[1,3-dioxolane-2,5'-[1,2,4]triazolo[4,3-a][1]benzazepine] (Example 157) according to the method described in Example 48 and it was used without further purification in the next step.

b) 8-chloro-1-[4-(3-chloropyridin-2-yl)piperidin-1-yl]-5,6-dihydro-4H-[1,2,4]triazolo[4,3-a][1]benzazepin-5-ol The title compound was prepared from 8-chloro-1-[4-(3-chloropyridin-2-yl)piperidin-1-yl]-4H-[1,2,4]triazolo[4,3-a][1]benzazepin-5(6H)-one (Step a) of Example 181) according to the method described in Example 49. MS (ESI) m/z 412.2 (M+H)+.

Example 182

8-chloro-5-methoxy-1-[trans-4-(4-methylpiperazin-1-yl)cyclohexyl]-5,6-dihydro-4H-[1,2,4]triazolo[4,3-a][1]benzazepine

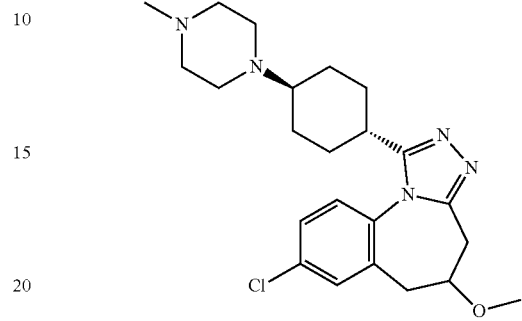

And

Example 183

8-chloro-5-methoxy-1-[cis-4-(4-methylpiperazin-1-yl)cyclohexyl]-5,6-dihydro-4H-[1,2,4]triazolo[4,3-a][1]benzazepine

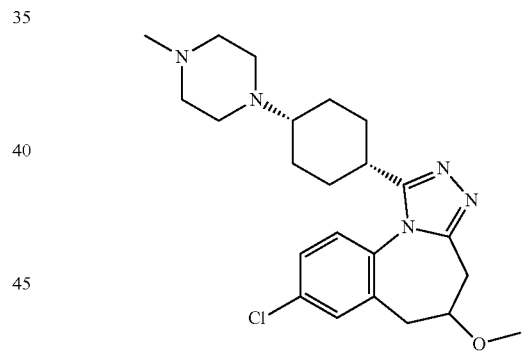

The title compounds were prepared from 7-chloro-4-methoxy-1,3,4,5-tetrahydro-2H-1-benzazepin-2-one (Step d) of Intermediate 103) and a mixture of cis-4-(4-methylpiperazin-1-yl)cyclohexanecarbohydrazide (Intermediate 113) and trans-4-(4-methylpiperazin-1-yl)cyclohexanecarbohydrazide (Intermediate 114) according to the method described in Example 108. The cis- and trans isomers were separated by preparative HPLC (Lux Amylose with 1.5 μm stationary phase; 150×21.2 mm; F=22 mL/min; eluent: A:water+0.1% TFA, B: acetonitrile+0.1% TFA, gradient: B % 10→90; t=40° C.) According to $^1$HNMR spectroscopy the first fraction (retention time: 6.6 min) was 8-chloro-5-methoxy-1-[trans-4-(4-methylpiperazin-1-yl)cyclohexyl]-5,6-dihydro-4H-[1,2,4]triazolo[4,3-a][1]benzazepine (Example 182), while the second fraction (retention time: 8.6 min) was 8-chloro-5-methoxy-1-[cis-4-(4-methylpiperazin-1-yl)cyclohexyl]-5,6-dihydro-4H-[1,2,4]triazolo[4,3-a][1]benzazepine (Example 183). MS (ESI) m/z 430.2 (M+H)+.

Example 184

8-chloro-5-methoxy-1-[1-(pyridin-3-ylmethyl)pyrrolidin-3-yl]-5,6-dihydro-4H-[1,2,4]triazolo[4,3-a][1]benzazepine

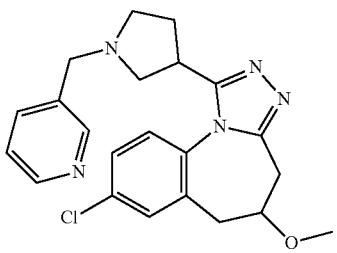 [SMILES: COC1Cc2cc(Cl)ccc2-n2c(nnc2C2CCN(Cc3cccnc3)C2)C1]

The title compound was prepared from 7-chloro-4-methoxy-1,3,4,5-tetrahydro-2H-1-benzazepin-2-one (Step d) of Intermediate 103) and 1-(pyridin-3-ylmethyl)pyrrolidine-3-carbohydrazide (Step b) of Intermediate 115) according to the method described in Example 108. MS (ESI) m/z 410.2 (M+H)$^+$.

Example 185

8-chloro-5-methoxy-1-[1-(pyridin-2-ylmethyl)pyrrolidin-3-yl]-5,6-dihydro-4H-[1,2,4]triazolo[4,3-a][1]benzazepine

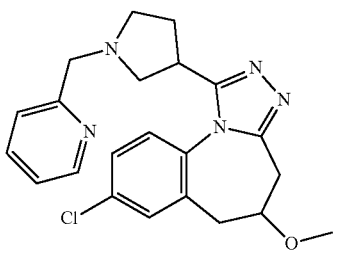 [SMILES: COC1Cc2cc(Cl)ccc2-n2c(nnc2C2CCN(Cc3ccccn3)C2)C1]

The title compound was prepared from 7-chloro-4-methoxy-1,3,4,5-tetrahydro-2H-1-benzazepin-2-one (Step d) of Intermediate 103) and 1-(pyridin-2-ylmethyl)pyrrolidine-3-carbohydrazide (Step b) of Intermediate 116) according to the method described in Example 108. MS (ESI) m/z 410.2 (M+H)$^+$.

Example 186

N-(5R)-8-chloro-1-[trans-4-(pyridin-2-yloxy)cyclohexyl]-5,6-dihydro-4H-[1,2,4]triazolo[4,3-a][1]benzazepin-5-yl-2-cyanoacetamide

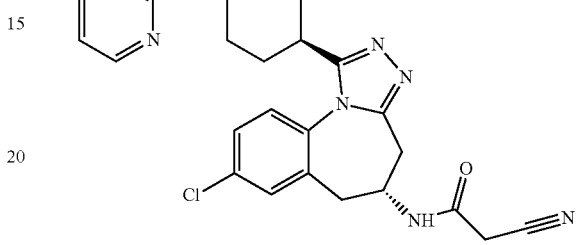

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and cyanoacetic acid according to the method described in Step a) of Example 10. [α]$_D^{20}$=+32° (c=0.1; methanol); MS (ESI) m/z 477.3 (M+H)$^+$.

Example 187

[3-(8-chloro-5-methoxy-5,6-dihydro-4H-[1,2,4]triazolo[4,3-a][1]benzazepin-1-yl)pyrrolidin-1-yl](pyridin-3-yl)methanone

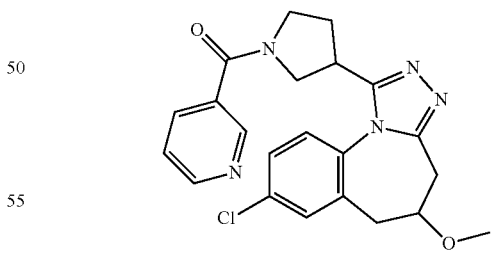

The title compound was prepared from 7-chloro-4-methoxy-1,3,4,5-tetrahydro-2H-1-benzazepin-2-one (Step d) of Intermediate 103) and 1-(pyridin-3-ylcarbonyl)pyrrolidine-3-carbohydrazide (Step b) of Intermediate 117) according to the method described in Example 108. MS (ESI) m/z 424.2 (M+H)$^+$.

Example 188

8'-chloro-1'-{1-[(3R)tetrahydrofuran-3-yl]piperidin-4-yl}-4'H,6'H-spiro[1,3-dioxolane-2,5'-[1,2,4]triazolo[4,3-a][1]benzazepine]

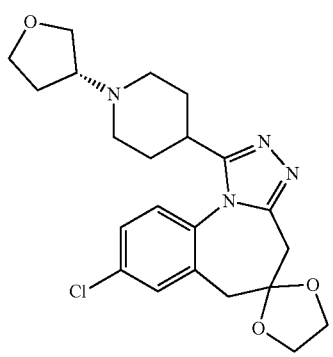 [SMILES: Clc1ccc2c(c1)CC1(Cc3nnc(C4CCN([C@@H]5CCOC5)CC4)n3-2)OCCO1]

The title compound was prepared from 7-chloro-1,5-dihydrospiro[1-benzazepine-4,2-[1,3]dioxolan]-2(3H)-ne (Intermediate 53) and 1-[(3R)-tetrahydrofuran-3-yl]piperidine-4-carbohydrazide (Step b) of Intermediate 110) according to the method described in Example 108. MS (ESI) m/z 431.2 (M+H)$^+$.

Example 189

[3-(8-chloro-5-methoxy-5,6-dihydro-4H-[1,2,4]triazolo[4,3-a][1]benzazepin-1-yl)pyrrolidin-1-yl](pyridin-2-yl)methanone

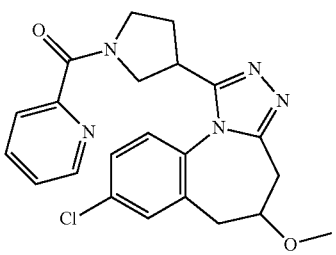 [SMILES: COC1Cc2cc(Cl)ccc2-n2c(nnc2C2CCN(C(=O)c3ccccn3)C2)C1]

The title compound was prepared from 7-chloro-4-methoxy-1,3,4,5-tetrahydro-2H-1-benzazepin-2-one (Step d) of Intermediate 103) and 1-(pyridin-2-ylcarbonyl)pyrrolidine-3-carbohydrazide (Step d) of Intermediate 118) according to the method described in Example 108. MS (ESI) m/z 424.2 (M+H)$^+$.

Example 190

Trans-4-(8'-chloro-4'H,6'H-spiro[1,3-dioxolane-2,5'-[1,2,4]triazolo[4,3-a][1]benzazepin]-1'-yl)-N,N-dimethylcyclohexanamine

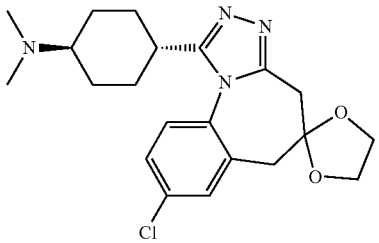 [SMILES: CN(C)[C@H]1CC[C@H](c2nnc3n2-c2ccc(Cl)cc2CC2(C3)OCCO2)CC1]

Under argon to a mixture of 100 mg (0.69 mmol) of 7-chloro-1,5-dihydrospiro[1-benzazepine-4,2'-[1,3]dioxolan]-2(3H)-one (Intermediate 53), 10 mL of dichloromethane and 218 mg (1.58 mmol) of K$_2$CO$_3$ 117 mg (0.788 mmol) of trimethyloxonium tetrafluoroborate was added. The reaction mixture was stirred at room temperature for 20 h, then filtered. The filtrate was concentrated and the residue was dissolved in 20 mL of acetonitrile. 39 µL (0.51 mmol) of trifluoroacetic acid and 87.6 mg (0.47 mmol) of trans-4-(dimethylamino)cyclohexanecarbohydrazide (Intermediate 80) were added and the reaction mixture was stirred at 70° C. for 3 h. After concentration the residue was dissolved in dichloromethane and washed with 5% HCl solution. The organic phase was discarded. The pH of the acidic water phase was adjusted to 8 by addition of saturated Na$_2$CO$_3$ solution and extracted with dichloromethane. The combined organic layers were dried over MgSO$_4$, filtered and concentrated. The residue was purified by flash column chromatography using dichloromethane:methanol:ammonium hydroxide solution=180:10:1 as eluent to yield 56 mg (35%) of the title compound. MS (ESI) m/z 403.2 (M+H)$^+$.

Example 191

8-chloro-5-methoxy-1-(1'H,3H-spiro[2-benzofuran-1,4'-piperidin]-1'-yl)-5,6-dihydro-4H-[1,2,4]triazolo[4,3-a][1]benzazepine

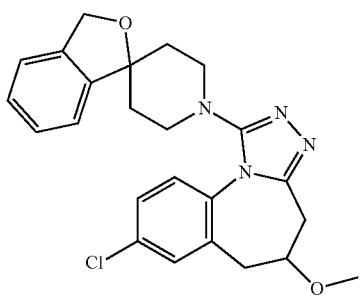

The title compound was prepared from 8-chloro-1-(1'H,3H-spiro[2-benzofuran-1,4'-piperidin]-1'-yl)-5,6-dihydro-4H-[1,2,4]triazolo[4,3-a][1]benzazepin-5-ol (Example 172) according to the method described in Example 50. MS (ESI) m/z 437.2 (M+H)$^+$.

Example 192

8-chloro-1-[4-(3-chloropyridin-2-yl)piperazin-1-yl]-5-methoxy-5,6-dihydro-4H-[1,2,4]triazolo[4,3-a][1]benzazepine

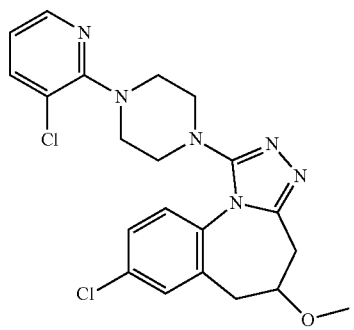 [SMILES: COC1Cc2cc(Cl)ccc2-n2c(nnc2N2CCN(c3ncccc3Cl)CC2)C1]

The title compound was prepared from 8-chloro-1-[4-(3-chloropyridin-2-yl)piperidin-1-yl]-5,6-dihydro-4H-[1,2,4]triazolo[4,3-a][1]benzazepin-5-ol (Example 173) according to the method described in Example 50. MS (ESI) m/z 445.2 (M+H)$^+$.

Example 193

N-[trans-4-(8'-chloro-4'H,6'H-spiro[1,3-dioxolane-2,5'-[1,2,4]triazolo[4,3-a][1]benzazepin]-1'-yl)cyclohexyl]pyridin-2-amine

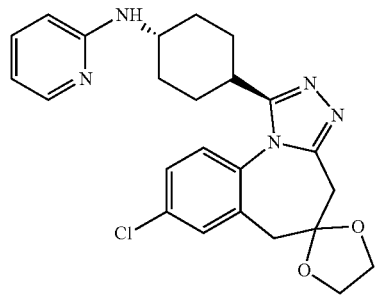

The title compound was prepared from 7-chloro-1,5-dihydrospiro[1-benzazepine-4,2'-[1,3]dioxolan]-2(3H)-one (Intermediate 53) and trans-4-(pyridin-2-ylamino)cyclohexanecarbohydrazide (Step b) of Intermediate 135) according to the method described in Example 190. MS (ESI) m/z 452.2 (M+H)$^+$.

Example 194

N'-{(5R)-8-chloro-1-[trans-4-(pyridin-2-yloxy)cyclohexyl]-5,6-dihydro-4H-[1,2,4]triazolo[4,3-a][1]benzazepin-5-yl}-N,N-dimethylethane-1,2-diamine

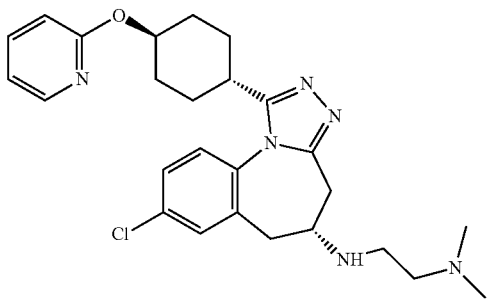 [SMILES: CN(C)CCN[C@@H]1Cc2cc(Cl)ccc2-n2c(nnc2[C@H]2CC[C@H](Oc3ccccn3)CC2)C1]

A mixture of 100 mg (0.24 mmol) of (5R)-8-chloro-1-[trans-4-(pyridin-2-yloxy)cyclohexyl]-5,6-dihydro-4H-[1,2,4]triazolo[4,3-a][1]benzazepin-5-amine (Example 8), 15 mL of ethanol, 14 µL (0.24 mmol) of acetic acid, 30 mg (0.24 mmol) of 2-(dimethylamino)acetaldehyde hydrochloride and 46 mg (0.73 mmol) of sodium cyanoborohydride was stirred at room temperature for 20 h, then concentrated. The residue was dissolved in saturated NaHCO$_3$ solution and extracted with ethyl acetate. The combined organic layers were dried over Na$_2$SO$_4$, filtered and concentrated. The residue was purified by flash column chromatography using dichloromethane:methanol:ammonium hydroxide solution=95:5:0.1 as eluent to yield 39 mg (33%) of the title compound. MS (ESI) m/z 481.3 (M+H)$^+$.

Example 195

8-chloro-1-[trans-4-(pyridin-2-yloxy)cyclohexyl]-5,6-dihydro-4H-[1,2,4]triazolo[4,3-a][1]benzazepin-5-yl acetate

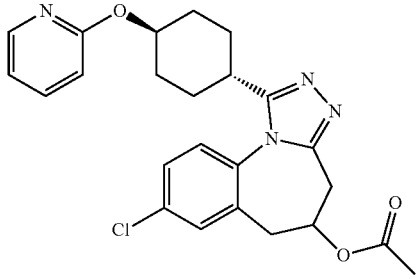 [SMILES: CC(=O)OC1Cc2cc(Cl)ccc2-n2c(nnc2[C@H]2CC[C@H](Oc3ccccn3)CC2)C1]

A mixture of 100 mg (0.24 mmol) of 8-chloro-1-[trans-4-(pyridin-2-yloxy)cyclohexyl]-5,6-dihydro-4H-[1,2,4]triazolo[4,3-a][1]benzazepin-5-ol (Example 55), 10 mL of dichloromethane, 23 µL (0.24 mmol) of acetic anhydride and 34 µL (0.24 mmol) of TEA was stirred at room temperature for 24 h, then 23 µL (0.24 mmol) of acetic anhydride and 34 µL (0.24 mmol) of TEA were added and stirring was continued at room temperature for further 24 h. Then 23 µL (0.24 mmol) of acetic anhydride and 34 µL (0.24 mmol) of TEA were added and stirring was continued at room temperature for further 24 h. The mixture was concentrated and

Example 196

2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethanol

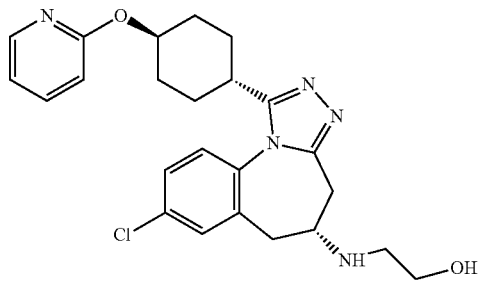 [SMILES: OCCN[C@@H]1Cc2cc(Cl)ccc2-n2c(nnc2[C@H]2CC[C@H](Oc3ccccn3)CC2)C1]

a) (5R)—N-[2-(benzyloxy)ethyl]-8-chloro-1-[trans-4-(pyridin-2-yloxy)cyclohexyl]-5,6-dihydro-4H-[1,2,4]triazolo[4,3-a][1]benzazepin-5-amine

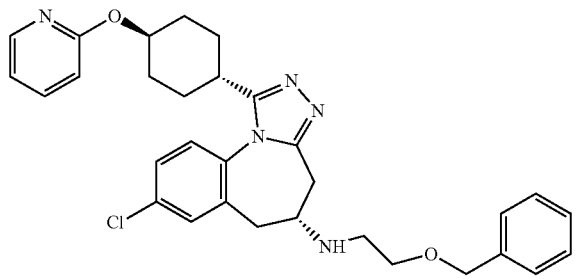 [SMILES: Clc1ccc2c(c1)C[C@@H](NCCOCc1ccccc1)Cc1nnc([C@H]3CC[C@H](Oc4ccccn4)CC3)n1-2]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and benzoyloxyacetaldehyde according to the method described in Example 194. MS (ESI) m/z 544.3 (M+H)$^+$.

b) 2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethanol A mixture of 144 mg (0.26 mmol) of (5R)—N-[2-(benzyloxy)ethyl]-8-chloro-1-[trans-4-(pyridin-2-yloxy)cyclohexyl]-5,6-dihydro-4H-[1,2,4]triazolo[4,3-a][1]benzazepin-5-amine (Step a) of Example 196) and 30 mL of 6N HCl solution was refluxed for 1 h, then cooled to room temperature and the pH of the mixture was adjusted to 7 by addition of saturated Na$_2$CO$_3$ solution. The so obtained mixture was extracted with ethyl acetate, the combined organic layers were dried over Na$_2$SO$_4$, filtered and concentrated. The residue was crystallized with chloroform to yield 53 mg (44%) of the title compound. The mother liquor was purified by flash column chromatography using dichloromethane:methanol:ammonium hydroxide solution=9:1:0.1 as eluent to yield 47 mg (43%) of the title compound. MS (ESI) m/z 453.2 (M+H)$^+$.

Example 197

8-chloro-5-methoxy-1-[4-(pyridin-2-yloxy)piperidin-1-yl]-5,6-dihydro-4H-[1,2,4]triazolo[4,3a][1]benzazepine

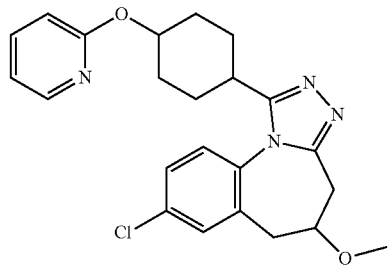 [SMILES: COC1Cc2cc(Cl)ccc2-n2c(nnc2C2CCC(Oc3ccccn3)CC2)C1]

The title compound was prepared from 8-chloro-1-[4-(3-chloropyridin-2-yl)piperidin-1-yl]-5,6-dihydro-4H-[1,2,4]triazolo[4,3-a][1]benzazepin-5-ol (Example 181) according to the method described in Example 50. MS (ESI) m/z 426.2 (M+H)$^+$.

Example 198

8'-chloro-1'-(trans-4-methoxy-4-methylcyclohexyl)-4'H,6'H-spiro[1,3-dioxolane-2,5'-[1,2,4]triazolo[4,3-a][1]benzazepine]

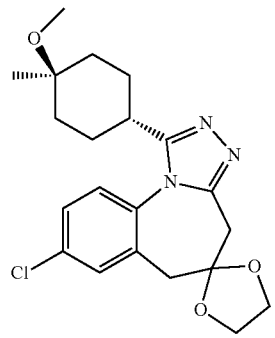 [SMILES: CO[C@]1(C)CC[C@@H](c2nnc3n2-c2ccc(Cl)cc2CC2(C3)OCCO2)CC1]

Under argon to a mixture of 100 mg (0.39 mmol) of 7-chloro-1,5-dihydrospiro[1-benzazepine-4,2'-[1,3]dioxolan]-2(3H)-one (Intermediate 53) and 10 mL of dichloromethane 3 μL (0.04 mmol) of trifluoroacetic acid and 70 mg (0.47 mmol) of trimethyloxonium tetrafluoroborate were added. The reaction mixture was stirred at room temperature for 20 h, then 147 mg (0.79 mmol) of a 21:79 mixture of cis-4-methoxy-4-methylcyclohexanecarbohydrazide and trans-4-methoxy-4-methylcyclohexanecarbohydrazide (Intermediate 119) was added and the reaction mixture was refluxed for 8 h. After concentration the residue was dissolved in 20 mL of 1,4-dioxane and the mixture was refluxed for 6 h, then concentrated. The residue was purified by flash column chromatography using dichloromethane:methanol: ammonium hydroxide solution=180:10:1 as eluent to yield 82 mg (52%) of the title compound. MS (ESI) m/z 404.1 (M+H)$^+$.

Example 199

(5S)-8-chloro-N-cyclopropylmethyl)-1-[trans-4-pyridin-2-yloxy)cyclohexyl]-5,6-dihydro-4H-[1,2,4]triazolo[4,3-a][1]benzazepin-5-amine

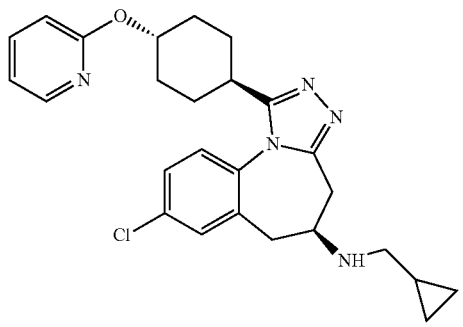 [SMILES: Clc1ccc2c(c1)C[C@H](NCC1CC1)Cc1nnc([C@H]3CC[C@H](Oc4ccccn4)CC3)n1-2]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and cyclopropanecarboxaldehyde according to the method described in Example 24. $[\alpha]_D^{20}=-28°$ (c=0.1; methanol); MS (ESI) m/z 464.2 (M+H)$^+$.

Example 200

N-{(5S-8-chloro-1-[trans-4-(pyridin-2-yloxy)cyclohexyl]-5,6-dihydro-4H-[1,2,4]triazolo[4,3-a][1]benzazepin-5-yl}-1-methylpiperidine-4-carboxamide

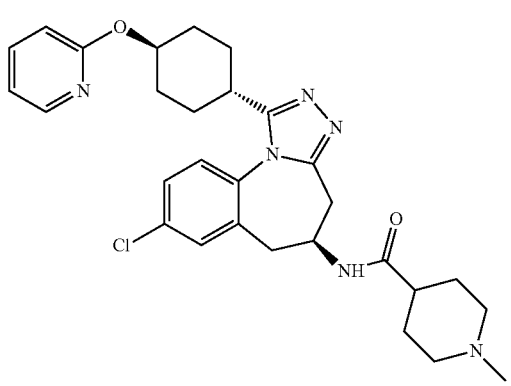 [SMILES: CN1CCC(C(=O)N[C@H]2Cc3cc(Cl)ccc3-n3c(nnc3[C@H]3CC[C@H](Oc4ccccn4)CC3)C2)CC1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 1-methylpiperidine 4-carboxylic acid according to the method described in Step a) of Example 10. $[\alpha]_D^{20}=-31°$ (c=0.1; methanol); MS (ESI) m/z 535.5 (M+H)$^+$.

Example 201

N-{(5S)-8-chloro-1-[trans-4-pyridin-2-yloxy)cyclohexyl]-5,6-dihydro-4H-[1,2,4]triazolo[4,3-a][1]benzazepin-5-yl}-2,2,2-trifluoroacetamide

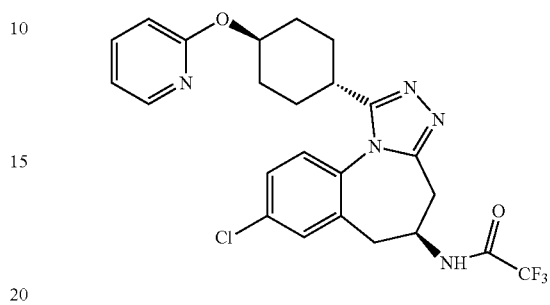

A mixture of 82 mg (0.2 mmol) of (5S)-8-chloro-1-[trans-4-(pyridin-2-yloxy)cyclohexyl]-5,6-dihydro-4H-[1,2,4]triazolo[4,3-a][1]benzazepin-5-amine (Example 7),5 is mL of dichloromethane, 73 µL (0.4 mmol) of DIPEA and 55 µL (0.4 mmol) of trifluoroacetic anhydride was stirred at room temperature for 20 h, then 73 µL (0.4 mmol) of DIPEA and 55 µL (0.4 mmol) of trifluoroacetic anhydride were added and stirring was continued for 3 h. The mixture was diluted with dichloromethane, washed with saturated NaHCO$_3$ solution, dried over Na$_2$SO$_4$, filtered and concentrated to yield 100 mg (99%) of the title compound. $[\alpha]_D^{20}=-13°$ (c=0.1; methanol); MS (ESI) m/z 506.2 (M+H)$^+$.

Example 202

8-chloro-5-(2-methoxyethoxy)-1-[trans-4-(pyridin-2-yloxy)cyclohexyl]-5,6-dihydro-4H-[1,2,4]triazolo[4,3-a][1]benzazepine

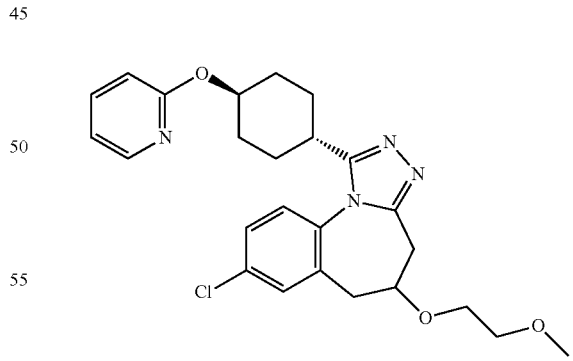

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and 2-bromoethyl methyl ether according to the method described in Example 50. MS (ESI) m/z 469.4 (M+H)$^+$.

Example 203

8-chloro-1-(4-methoxy-4-methylcyclohexyl)-N-(propan-2-yl)-5,6-dihydro-4H-[1,2,4]triazolo[4,3-a][1]benzazepin-5-amine

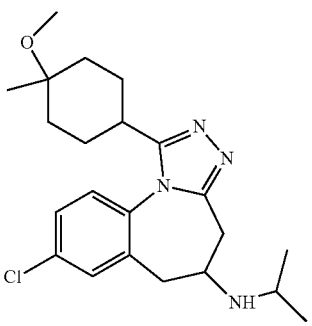 [SMILES: COC1(C)CCC(c2nnc3n2-c2ccc(Cl)cc2CC(NC(C)C)C3)CC1]

a) Tert-butyl [8-chloro-1-(4-methoxy-4-methylcyclohexyl)-5,6-dihydro-4H-[1,2,4]triazolo[4,3-a][1]benzazepin-5-yl]carbamate

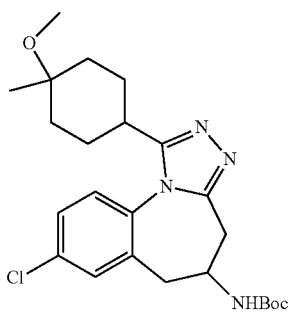 [SMILES: COC1(C)CCC(c2nnc3n2-c2ccc(Cl)cc2CC(NC(=O)OC(C)(C)C)C3)CC1]

The title compound was prepared from tert-butyl (7-chloro-2-thioxo-2,3,4,5-tetrahydro-1H-1-benzazepin-4-yl)carbamate (Intermediate 4) and a 21:79 mixture of cis-4-methoxy-4-methylcyclohexanecarbohydrazide and trans-4-methoxy-4-methylcyclohexanecarbohydrazide (Intermediate 119) according to the method described in Example 1. MS (ESI) m/z 461.4 (M+H)$^+$.

b) 8-chloro-1-(4-methoxy-4-methylcyclohexyl)-5,6-dihydro-4H-[1,2,4]triazolo[4,3-a][1]benzazepin-5-amine

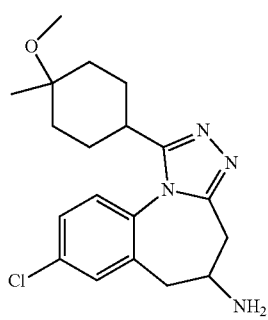 [SMILES: COC1(C)CCC(c2nnc3n2-c2ccc(Cl)cc2CC(N)C3)CC1]

The title compound was prepared from tert-butyl [8-chloro-1-(4-methoxy-4-methylcyclohexyl)-5,6-dihydro-4H-[1,2,4]triazolo[4,3-a][1]benzazepin-5-yl]carbamate (Step a) of Example 203) according to the method described in Example 2 and it was used without further purification in the next step.

c) 8-chloro-1-(4-methoxy-4-methylcyclohexyl)-N-(propan-2-yl)-5,6-dihydro-4H-[1,2,4]triazolo[4,3-a][1]benzazepin-5-amine The title compound was prepared from 8-chloro-1-(4-methoxy-4-methylcyclohexyl)-5,6-dihydro-4H-[1,2,4]triazolo[4,3-a][1]benzazepin-5-amine (Step b) of Example 203) according to the method described in Example 24, it was a 8:92 mixture of cis- and trans-isomers. MS (ESI) m/z 403.2 (M+H)$^+$.

Example 204

8'-chloro-1'-(trans-4-methoxy-4-methylcyclohexyl)-4'H,6'H-spiro[1,3-dioxane-2,5'-[1,2,4]triazolo[4,3-a][1]benzazepine]

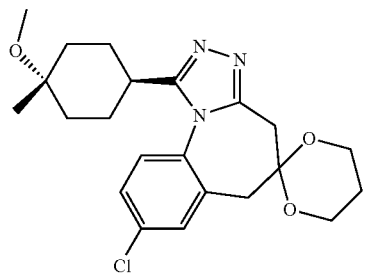 [SMILES: CO[C@]1(C)CC[C@@H](c2nnc3n2-c2ccc(Cl)cc2CC2(C3)OCCCO2)CC1]

And

Example 205

8'-chloro-1'-(cis-4-methoxy-4-methylcyclohexyl)-4',6'H-spiro[1,3-dioxane-2,5'-[1,2,4]triazolo[4,3-a][1]benzazepine]

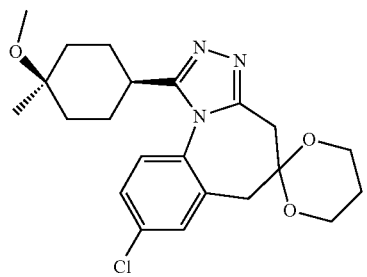 [SMILES: CO[C@]1(C)CC[C@H](c2nnc3n2-c2ccc(Cl)cc2CC2(C3)OCCCO2)CC1]

The title compounds were prepared from 7-chloro-1,5-dihydrospiro[1-benzazepine-4,2'-[1.3]dioxan]-2(3H)-ne (Intermediate 98) and a 21:79 mixture of cis-4-methoxy-4-methylcyclohexanecarbohydrazide and trans-4-methoxy-4-methylcyclohexanecarbohydrazide (Intermediate 119) according to the method described in Example 198. The cis- and trans-isomers were separated by flash column chromatography using dichloromethane:methanol:ammonium hydroxide solution=180:10:1 as eluent. According to ¹HNMR spectroscopy the first fraction was 8'-chloro-1'-(trans-4-methoxy-4-methylcyclohexyl)-4'H,6'H-spiro[1,3-dioxane-2,5'-[1,2,4]triazolo[4,3-a][1]benzazepine](Example 204), while the second fraction was 8'-chloro-1'-(cis-4-methoxy-4-methylcyclohexyl)-4'H,6'H-spiro[1,3-dioxane-2,5'-[1,2,4]triazolo[4,3-a][1]benzazepine](Example 205). MS (ESI) m/z 418.2 (M+H)⁺.

Example 206

8-chloro-5-fluoro-1-[trans-4-(pyridin-2-yloxy)cyclohexyl]-5,6-dihydro-4H-[1,2,4]triazolo[4,3-a][1]benzazepine

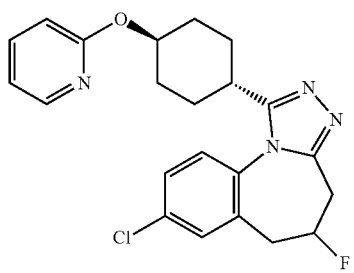 [SMILES: FC1Cc2cc(Cl)ccc2-n2c(nnc2[C@H]2CC[C@H](Oc3ccccn3)CC2)C1]

Under argon a stirred solution of 170 mg (0.41 mmol) of 8-chloro-1-[trans-4-(pyridin-2-yloxy)cyclohexyl]-5,6-dihydro-4H-[1,2,4]triazolo[4,3-a][1]benzazepin-5-ol (Example 55) in 10 mL of dichloromethane was cooled to −78° C. and a solution of 147 mg (0.91 mmol) of (diethylamino) sulfur trifluoride in 5 mL of dichloromethane was added. The reaction mixture was allowed to warm to room temperature over 5 h, then diluted with saturated NaHCO₃ solution, the phases were separated and water phase was extracted with dichloromethane. The combined organic phases were dried over MgSO₄, filtered and concentrated. The residue was purified by reversed phase flash column chromatography using acetonitrile and 0.1% TFA containing water=35:65 as eluent to yield 15 mg (9%) of the title compound. MS (ESI) m/z 413.1 (M+H)⁺.

Example 207

8-chloro-5-[2-(methylsulfonyl)ethoxy]-1-[trans-4-(pyridin-2-yloxy)cyclohexyl]-5,6-dihydro-4H-[1,2,4]triazolo[4,3-a][1]benzazepine

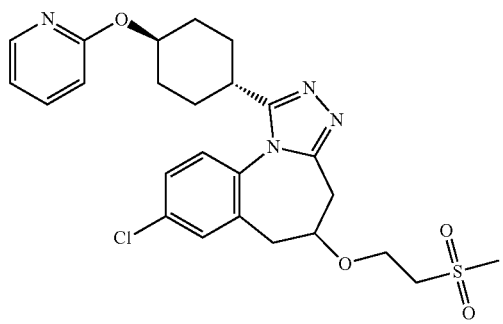 [SMILES: CS(=O)(=O)CCOC1Cc2cc(Cl)ccc2-n2c(nnc2[C@H]2CC[C@H](Oc3ccccn3)CC2)C1]

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and 1-bromo-2-(methylsulfonyl)ethane according to the method described in Example 50. MS (ESI) m/z 517.1 (M+H)⁺.

Example 208

8-chloro-N-hydroxy-1-[trans-4-(pyridin-2-yloxy)cyclohexyl]-4H-[1,2,4]triazolo[4,3-a][1]benzazepin-5(6H)-imine

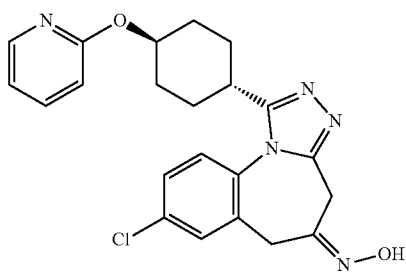 [SMILES: O/N=C1/Cc2cc(Cl)ccc2-n2c(nnc2[C@H]2CC[C@H](Oc3ccccn3)CC2)C1]

A mixture of 100 mg (0.245 mmol) of 8-chloro-1-[trans-4-(pyridin-2-yloxy)cyclohexyl]-4H-[1,2,4]triazolo[4,3-a][1]benzazepin-5(6H)-one (Example 54), 5 mL of pyridine, 5 mL of methanol and 17 mg (0.245 mmol) of hydroxylamine hydrochloride was refluxed for 3 h, then concentrated. The residue was dissolved in dichloromethane, washed with 5% citric acid solution and water, the organic phase was dried over MgSO₄, filtered and concentrated. The residue was purified by flash column chromatography using dichloromethane:methanol:ammonium hydroxide solution=180:10:1 as eluent to yield 34 mg (33%) of the title compound. MS (ESI) m/z 424.1 (M+H)⁺.

Example 209

(5S)-8-chloro-N-methyl-N-(prop-2-yn-1-yl)-1-[trans-4-(pyridin-2-yloxy)cyclohexyl]-5,6-dihydro-4H-[1,2,4]triazolo[4,3-a][1]benzazepin-5-amine

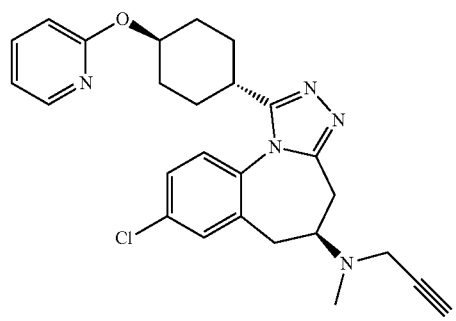 [SMILES: C#CCN(C)[C@H]1Cc2cc(Cl)ccc2-n2c(nnc2[C@H]2CC[C@H](Oc3ccccn3)CC2)C1]

A mixture of 43 mg (0.1 mmol) of (5S)-8-chloro-N-methyl-1-[trans-4-(pyridin-2-yloxy)cyclohexyl]-5,6-dihydro-4H-[1,2,4]triazolo[4,3-a][1]benzazepin-5-amine (Example 78), 5 mL of acetone, 20 μL (0.13 mmol) of 80% propargyl bromide solution in toluene and 42 mg (0.13 mmol) of cesium carbonate was stirred at room temperature for 20 h, then 20 μL (0.13 mmol) of 80% propargyl bromide solution in toluene and 42 mg (0.13 mmol) of cesium carbonate were added and stirring was continued for 20 h. The reaction mixture was filtered, the filtrate was concentrated and the residue was purified by column chromatography using dichloromethane:methanol=9:1 as eluent to yield 30 mg (64%) of the title compound. $[\alpha]_D^{20}=-22°$ (c=0.1; methanol); MS (ESI) m/z 462.1 (M+H)$^+$.

Example 210

N-{(5S)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide

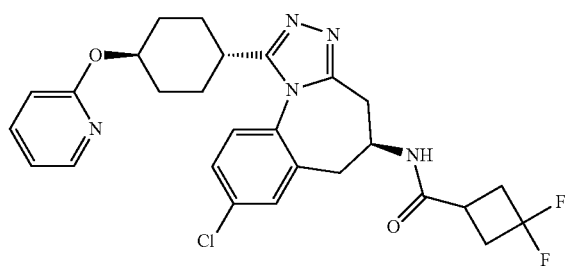 [SMILES: O=C(N[C@H]1Cc2cc(Cl)ccc2-n2c(nnc2[C@H]2CC[C@H](Oc3ccccn3)CC2)C1)C1CC(F)(F)C1]

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 3,3-difluorocyclobutanecarboxylic acid according to the method described in Step a) of Example 10. $[\alpha]_D^{20}=-37°$ (c=0.1; methanol); MS (ESI) m/z 528.2 (M+H)$^+$.

Example 211

8-chloro-5-(prop-2-yn-1-yloxy)-1-[trans-4-(pyridin-2-yloxy)cyclohexyl]-5,6-dihydro-4H-[1,2,4]triazolo[4,3-a][1]benzazepine

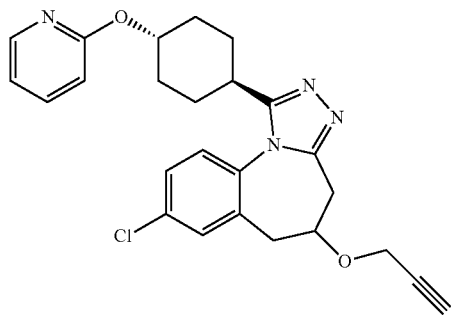 [SMILES: C#CCOC1Cc2cc(Cl)ccc2-n2c(nnc2[C@H]2CC[C@H](Oc3ccccn3)CC2)C1]

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and 80% propargyl bromide solution in toluene according to the method described in Example 50. MS (ESI) m/z 449.2 (M+H)$^+$.

Example 212

8-chloro-1-[trans-4-(pyridin-2-yloxy)cyclohexyl]-5,6-dihydro-4H-[1,2,4]triazolo[4,3-a][1]benzazepin-5-yl 4,4-difluorocyclohexanecarboxylate

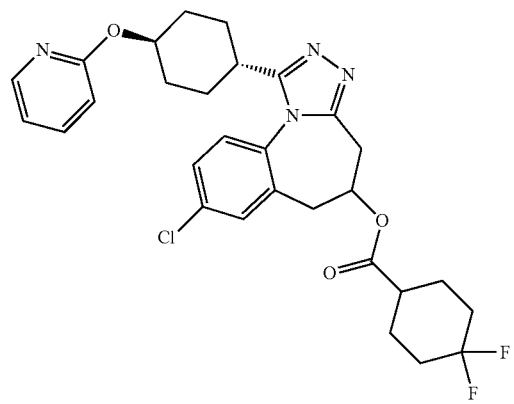 [SMILES: O=C(OC1Cc2cc(Cl)ccc2-n2c(nnc2[C@H]2CC[C@H](Oc3ccccn3)CC2)C1)C1CCC(F)(F)CC1]

Under argon a mixture of 80 mg (0.19 mmol) of 8-chloro-1-[trans-4-(pyridin-2-yloxy)cyclohexyl]-5,6-dihydro-4H-[1,2,4]triazolo[4,3-a][1]benzazepin-5-ol (Example 55), 15 mL of dichloromethane, 35 mg (0.21 mmol) of 4,4-difluorocyclohexanecarboxylic acid, 44 mg (0.21 mmol) of N,N'-dicyclohexylcarbodiimide and 2.4 mg (0.02 mmol) of 4-(dimethylamino)pyridine was stirred at room temperature for 20 h. After completion of the reaction the mixture was diluted with water, 10% NaHCO$_3$ solution and dichloromethane. The phases were separated, the organic phase was dried over MgSO$_4$, filtered and concentrated. The residue was purified by flash column chromatography using dichloromethane:methanol=95:5 as eluent to yield 66 mg (61%) of the title compound. MS (ESI) m/z 557.2 (M+H)$^+$.

Example 213

8-chloro-1-[trans-4-(pyridin-2-yloxy)cyclohexyl]-5,6-dihydro-4H-[1,2,4]triazolo[4,3-a][1]benzazepin-5-yl 3,3-difluorocyclobutanecarboxylate

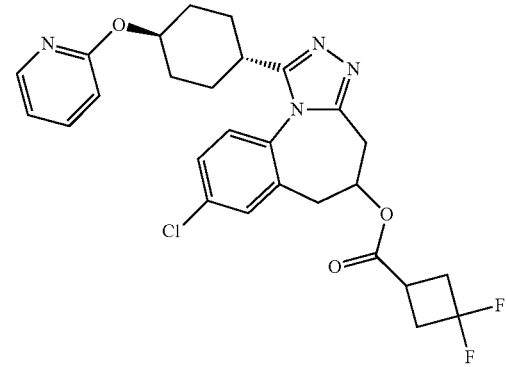 [SMILES: O=C(OC1Cc2cc(Cl)ccc2-n2c(nnc2[C@H]2CC[C@H](Oc3ccccn3)CC2)C1)C1CC(F)(F)C1]

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and 3,3-dif-

Example 214

N-{(5S)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide

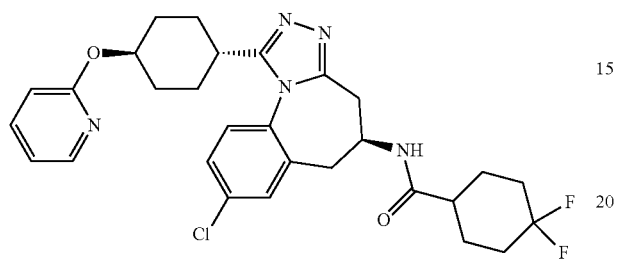

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 4,4-difluorocyclohexanecarboxylic acid according to the method described in Step a) of Example 10. $[\alpha]_D^{20}=-34°$ (c=0.1; methanol); MS (ESI) m/z 556.2 (M+H)+.

Example 215

8-chloro-1-[trans-4-pyridin-2-yloxy)cyclohexyl]-5,6-dihydro-4H-[1,2,4]triazolo[4,3-a][1]benzazepin-5-yl cyanoacetate

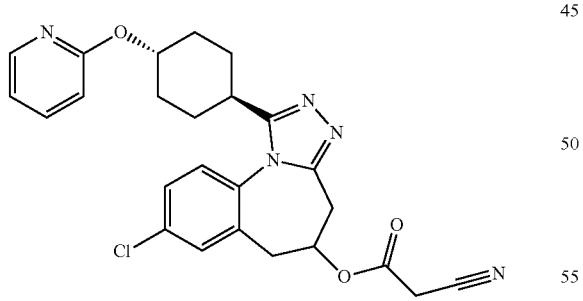

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and cyanoacetic acid according to the method described in Example 212. MS (ESI) m/z 478.1 (M+H)+.

Example 216

8-chloro-1-[trans-4-(pyridin-2-yloxy)cyclohexyl]-5,6-dihydro-4H-[1,2,4]triazolo[4,3-a][1]benzazepin-5-yl N,N-dimethylglycinate

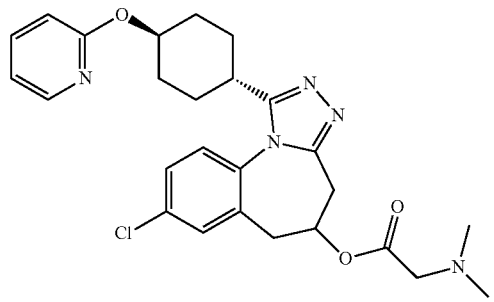 [SMILES: CN(C)CC(=O)OC1Cc2cc(Cl)ccc2-n2c(nnc2[C@H]2CC[C@H](Oc3ccccn3)CC2)C1]

The title compound was prepared from 8-chloro-1-[trans-4-(pyridin-2-yloxy)cyclohexyl]-5,6-dihydro-4H-[1,2,4]triazolo[4,3-a][1]benzazepin-5-ol (Example 55) and N,N-dimethylglycine according to the method described in Example 212. MS (ESI) m/z 496.2 (M+H)+.

Example 217

N-{(5R)-8-chloro-1-[trans-4-(pyridin-2-yloxy)cyclohexyl]-5,6-dihydro-4H-[1,2,4]triazolo[4,3-a][1]benzazepin-5-yl}-2,2,2-trifluoroacetamide

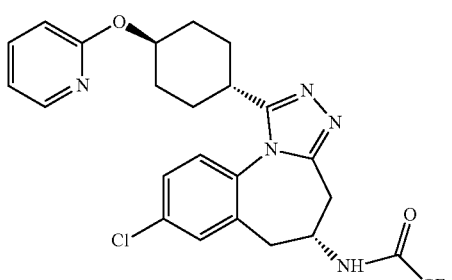

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) according to the method described in Example 201. $[\alpha]_D^{20}=+21°$ (c=0.1; methanol); MS (ESI) m/z 506.1 (M+H)+.

Example 218

1-[cis-4-(8-chloro-5-methoxy-5,6-dihydro-H-[1,2,4]triazolo[4,3-a][1]benzazepin-1-yl)cyclohexyl]pyrrolidin-2-one

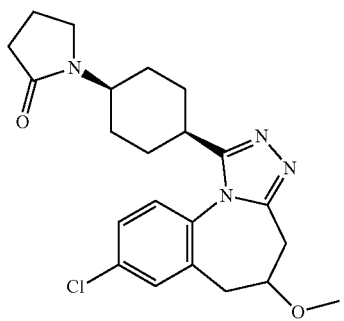 [SMILES: COC1Cc2cc(Cl)ccc2-n2c(nnc2[C@H]2CC[C@@H](N3CCCC3=O)CC2)C1]

And

Example 219

1-[trans-4-(8-chloro-5-methoxy-5,6-dihydro-4H-[1,2,4]triazolo[4,3-a][1]benzazepin-1-yl)cyclohexyl]pyrrolidin-2-one

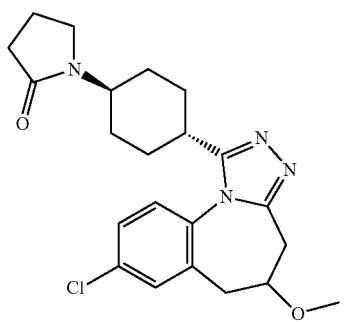 [SMILES: COC1Cc2cc(Cl)ccc2-n2c(nnc2[C@H]2CC[C@H](N3CCCC3=O)CC2)C1]

The title compounds were prepared from 7-chloro-4-methoxy-1,3,4,5-tetrahydro-2H-1-benzazepin-2-one (Step d) of Intermediate 103) and 4-(2-oxopyrrolidin-1-yl)cyclohexanecarbohydrazide (Intermediate 120) according to the method described in Example 108. The cis- and trans isomers were separated by preparative HPLC (Kinetex EVO C18 with 5 μm stationary phase; 150×21.2 mm; F=20 mL/min; eluent: A:water+0.1% TFA, B: acetonitrile+0.1% TFA, gradient: B % 0.6→35; t=40° C.) According to $^1$HNMR spectroscopy the first fraction (retention time: 18.5 min) was 1-[cis-4-(8-chloro-5-methoxy-5,6-dihydro-4H-[1,2,4]triazolo[4,3-a][1]benzazepin-1-yl)cyclohexyl]pyrrolidin-2-one (Example 218), while the second fraction (retention time: 19.2 min) was 1-[trans-4-(8-chloro-5-methoxy-5,6-dihydro-4H-[1,2,4]triazolo[4,3-a][1]benzazepin-1-yl)cyclohexyl]pyrrolidin-2-one (Example 219). MS (ESI) m/z 415.2 (M+H)$^+$.

Example 220

N-{(5R)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide

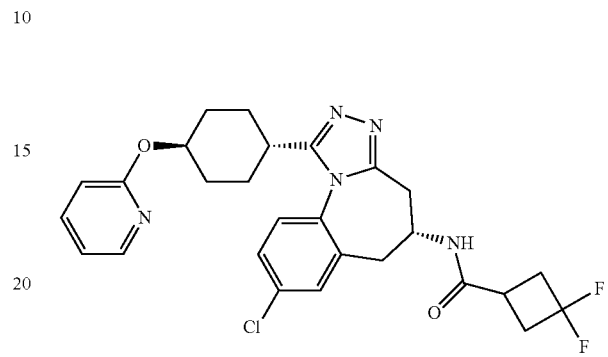

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 3,3-difluorocyclobutanecarboxylic acid according to the method described in Step a) of Example 10. $[\alpha]_D^{20}$=+48° (c=0.1; methanol); MS (ESI) m/z 528.2 (M+H)$^+$.

Example 221

N-{(5R)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide

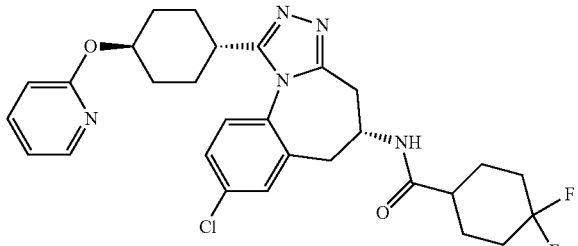

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 4,4-difluorocyclohexanecarboxylic acid according to the method described in Step a) of Example 10. $[\alpha]_D^{20}$=+38° (c=01; methanol); MS (ESI) m/z 556.2 (M+H)$^+$.

Example 222

8-chloro-5-methoxy-1-[cis-4-methoxy-4-(trifluoromethyl)cyclohexyl]-5,6-dihydro-4H-[1,2,4]triazolo[4,3-a][1]benzazepine

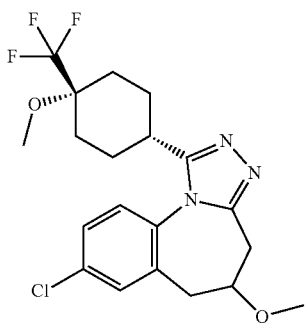 [SMILES: COC1Cc2cc(Cl)ccc2-n2c(nnc2[C@H]2CC[C@](OC)(C(F)(F)F)CC2)C1]

The title compound was prepared from 7-chloro-4-methoxy-1,3,4,5-tetrahydr-2H-1-benzazepin-2-one (Step d) of Intermediate 103) and cis-4-methoxy-4-(trifluoromethyl)cyclohexanecarbohydrazide (Intermediate 123) according to the method described in Example 108. MS (ESI) m/z 430.2 (M+H)$^+$.

Example 223

8-chloro-5-methoxy-1-[trans-4-methoxy-4-(trifluoromethyl)cyclohexyl]-5,6-dihydro-4H-[1,2,4]triazolo[4,3-a][1]benzazepine

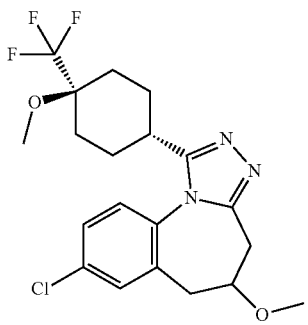 [SMILES: COC1Cc2cc(Cl)ccc2-n2c(nnc2[C@H]2CC[C@@](OC)(C(F)(F)F)CC2)C1]

The title compound was prepared from 7-chloro-4-methoxy-1,3,4,5-tetrahydr-2H-1-benzazepin-2-one (Step d) of Intermediate 103) and trans-4-methoxy-4-(trifluoromethyl)cyclohexanecarbohydrazide (Intermediate 124) according to the method described in Example 108. MS (ESI) m/z 430.2 (M+H)$^+$.

Example 224

(5S)-8-chloro-1-[trans-4-(pyridin-2-yloxy)cyclohexyl]-N-(2,2,2-trifluoroethyl)-5,6-dihydro-4H-[1,2,4]triazolo[4,3-a][1]benzazepin-5-amine

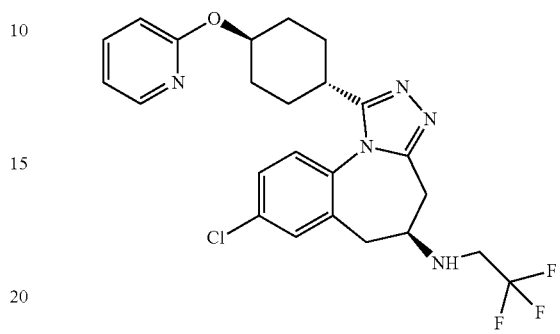

A mixture of 82 mg (0.2 mmol) of (5S)-8-chloro-1-[trans-4-(pyridin-2-yloxy)cyclohexyl]-5,6-dihydro-4H-[1,2,4]triazolo[4,3a][1]benzazepin-5-amine (Example 7), mL of dichloromethane, 190 µL (1.32 mmol) of 2,2,2-trifluoroethyl trifluoromethanesulfonate and 230 µL (1.32 mmol) of DIPEA was stirred at room temperature for 20 h, then 190 µL (1.32 mmol) of 2,2,2-trifluoroethyl trifluoromethanesulfonate and 230 µL (1.32 mmol) of DIPEA were added and stirring was continued at 40° C. for 90 h. The reaction mixture was concentrated and water was added to the residue. The precipitated solid material was filtered off, washed with water and purified by column chromatography using dichloromethane:methanol=9:1 as eluent to yield 8 mg (8%) of the title compound. MS (ESI) m/z 492.2 (M+H)$^+$.

Example 225

N-{(5S)-8-chloro-1-[trans-4-pyridin-2-yloxy)cyclohexyl]-5,6-dihydro-4H-[1,2,4]triazolo[4,3-a][1]benzazepin-5-yl}-3-methyloxetane-3-carboxamide

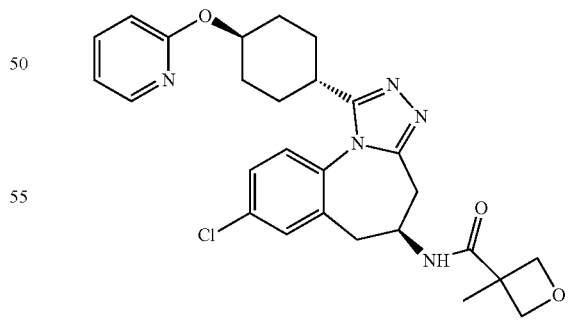

The title compound was prepared from (5S)-8-chloro-1-[trans-4-(pyridin-2-yloxy)cyclohexyl]-5,6-dihydro-4H-[1,2,4]triazolo[4,3-a][1]benzazepin-5-amine (Example 7) and 3-methyloxetane-3-carboxylic acid according to the method described in Step a) of Example 10. [α]$_D^{20}$=−28° (c=0.1; methanol); MS (ESI) m/z 508.3 (M+H)$^+$.

Example 226

N-{(5R)-8-chloro-1-[trans-4-(pyridin-2-yloxy)cyclohexyl]-5,6-dihydro-4H-[1,2,4]triazolo[4,3-a][1]benzazepin-5-yl}-3-methyloxetan-3-carboxamide

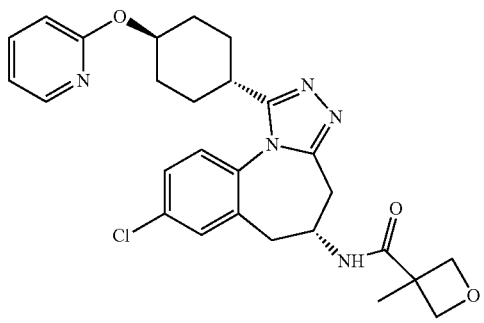 [SMILES: CC1(C(=O)N[C@@H]2Cc3cc(Cl)ccc3-n3c(nnc3[C@H]3CC[C@H](Oc4ccccn4)CC3)C2)COC1]

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and 3-methyloxetane-3-carboxylic acid according to the method described in Step a) of Example 10. $[\alpha]_D^{20}$=+26° (c=0.1; methanol); MS (ESI) m/z 508.2 (M+H)$^+$.

Example 227

Trans-4-(8'-chloro-4'H,6'H-spiro[1,3-dioxolane-2,5'-[1,2,4]triazolo[4,3-a][1]benzazepin]-1'-yl)-N-(4-methoxybenzyl)cyclohexanamine

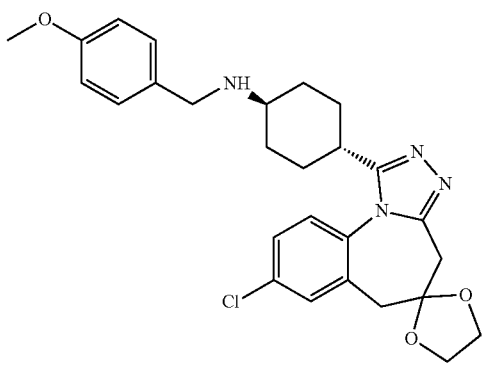 [SMILES: COc1ccc(CN[C@H]2CC[C@H](c3nnc4n3-c3ccc(Cl)cc3CC3(C4)OCCO3)CC2)cc1]

The title compound was prepared from 7-chloro-1,5-dihydrospiro[1-benzazepine-4,2'-[1,3]dioxolan]-2(3H)-one (Intermediate 53) and trans-4-[(4-methoxybenzyl)amino]cyclohexanecarbohydrazide (Intermediate 125) according to the method described in Example 108. MS (ESI) m/z 495.2 (M+H)$^+$.

Example 228

Tert-butyl [2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethyl]carbamate

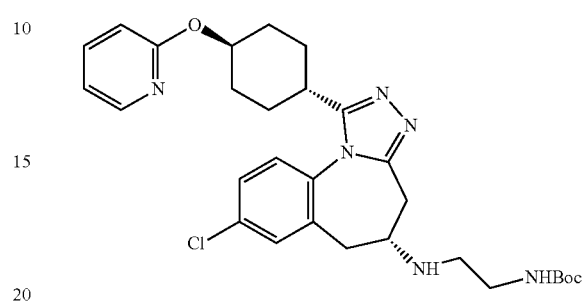

The title compound was prepared from (5R)-8-chloro-1-[trans-4-(pyridin-2-yloxy)cyclohexyl]-5,6-dihydro-4H-[1,2,4]triazolo[4,3-a][1]benzazepin-5-amine (Example 8) and tert-butyl (2-oxoethyl)carbamate according to the method described in Example 190. MS (ESI) m/z 432.2 (M+H)$^+$.

Example 229

8'-chloro-1'-(trans-4-ethoxy-4-ethylcyclohexyl)-4'H,6'H-spiro[1,3-dioxolane-2,5'-[1,2,4]triazolo[4,3-a][1]benzazepine]

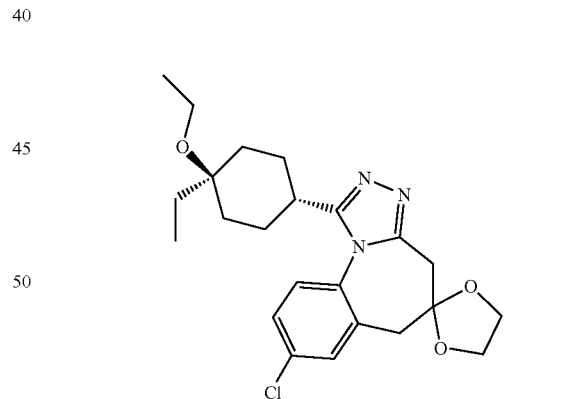

The title compound was prepared from 7-chloro-1,5-dihydrospiro[1-benzazepine-4,2'-[1,3]dioxolan]-2(3H)-one (Intermediate 53) and trans-4-ethoxy-4-ethylcyclohexanecarbohydrazide (Step c) of Intermediate 126) according to the method described in Example 190. MS (ESI) m/z 432.2 (M+H)$^+$.

Example 230

Trans-4-(8'-chloro-4'H,6'H-spiro[1,3-dioxolane-2,5'-[1,2,4]triazolo[4,3-a][1]benzazepin]-1'-yl)-N-(4-methoxybenzyl)-N-methylcyclohexanamine

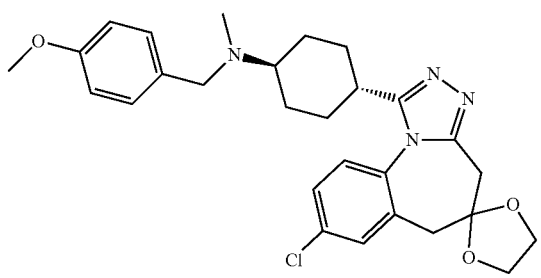 [SMILES: COc1ccc(CN(C)[C@H]2CC[C@H](c3nnc4n3-c3ccc(Cl)cc3CC3(C4)OCCO3)CC2)cc1]

The title compound was prepared from trans-4-(8'-chloro-4'H,6'H-spiro[1,3-dioxolane-2,5'-[1,2,4]triazolo[4,3-a][1]benzazepin]-1'-yl)-N-(4-methoxybenzyl)-cyclohexanamine (Example 227) according to the method described in Example 101. MS (ESI) m/z 509.2 (M+H)$^+$.

Example 231

8'-chloro-1'-[1-(pyridin-3-ylmethyl)pyrrolidin-3-yl]-4'H,6'H-spiro[1,3-dioxolane-2,5'-[1,2,4]triazolo[4,3-a][1]benzazepine]

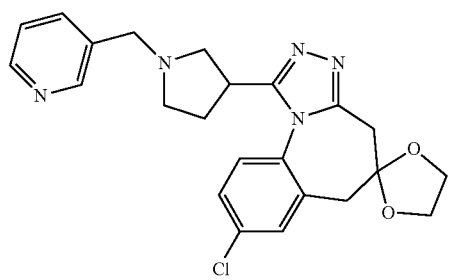 [SMILES: Clc1ccc2c(c1)CC1(Cc3nnc(C4CCN(Cc5cccnc5)C4)n3-2)OCCO1]

The title compound was prepared from 7-chloro-1,5-dihydrospiro[1-benzazepine-4,2'-[1,3]dioxolan]-2(3H)-one (Intermediate 53) and 1-(pyridin-3-ylmethyl)pyrrolidine-3-carbohydrazide (Step b) of Intermediate 115) according to the method described in Example 108. MS (ESI) m/z 438.2 (M+H)$^+$.

Example 232

8-chloro-5-methoxy-1-[4-pyridin-2yl) piperazin-1-yl]-5,6-dihydro-4H-[1,2,4]triazolo[4,3-a][1]benzazepine

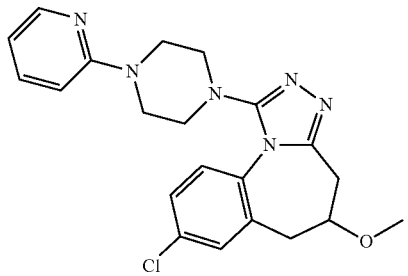 [SMILES: COC1Cc2cc(Cl)ccc2-n2c(nnc2N2CCN(c3ccccn3)CC2)C1]

a) 8-chloro-1-[4-(pyridin-2-yl)piperazin-1-yl]-4H-[1,2,4]triazolo[4,3-a][1]benzazepin-5(6H)-one

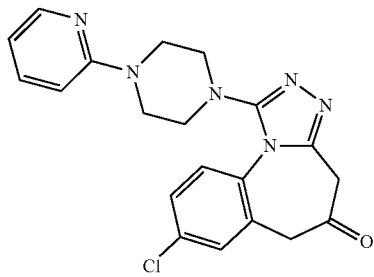 [SMILES: O=C1Cc2cc(Cl)ccc2-n2c(nnc2N2CCN(c3ccccn3)CC2)C1]

The title compound was prepared from 8'-chloro-1'-[4-(pyridin-2-yl)piperazin-1-yl]-4'H,6'H-spiro[1,3-dioxolane-2,5'-[1,2,4]triazolo[4,3-a][1]benzazepine] (Example 171) according to the method described in Example 48. MS (ESI) m/z 395.1 (M+H)$^+$.

b) 8-chloro-1-[4-(pyridin-2-yl)piperazin-1-yl]-5,6-dihydro-4H-[1,2,4]triazolo[4,3-a][1]benzazepin-5-ol

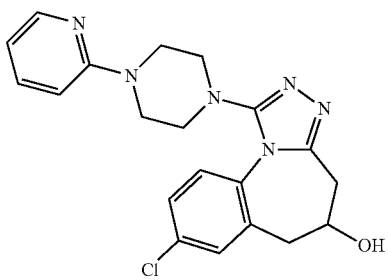 [SMILES: OC1Cc2cc(Cl)ccc2-n2c(nnc2N2CCN(c3ccccn3)CC2)C1]

The title compound was prepared from 8-chloro-1-[4-(pyridin-2-yl)piperazin-1-yl]-4H-[1,2,4]triazolo[4,3-a][1]benzazepin-5(6H-one (Step a) of Example 232) according to the is method described in Example 49. MS (ESI) m/z 397.2 (M+H)$^+$.

c) 8-chloro-5-methoxy-1-[4-(pyridin-2-yl)piperazin-1-yl]-5,6-dihydro-4H-[1,2,4]triazolo[4,3-a][1]benzazepine The title compound was prepared from 8-chloro-1-[4-(pyridin-2-yl)piperazin-1-yl]-5,6-dihydro-4H-[1,2,4]triazolo[4,3-a][1]benzazepin-5-ol (Step b) of Example 232) according to the method described in Example 50. MS (ESI) m/z 411.3 (M+H)$^+$.

Example 233

8-chloro-1-(trans-4-ethyl-4-methoxycyclohexyl)-N,N-dimethyl-5,6-dihydro-4H-[1,2,4]triazolo[4,3-a][1]benzazepin-5-amine

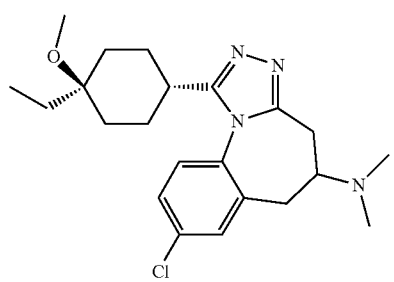 [SMILES: CC[C@]1(OC)CC[C@H](c2nnc3n2-c2ccc(Cl)cc2CC(N(C)C)C3)CC1]

a) Tert-butyl [8-chloro-1-(trans-4-ethyl-4-methoxycyclohex)-5,6-dihydro-4H-[1,2,4]triazolo[4,3-a][1]benzazepin-5-yl]carbamate

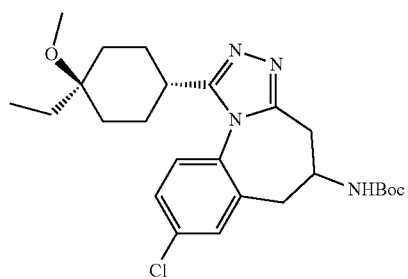 [SMILES: CC[C@]1(OC)CC[C@H](c2nnc3n2-c2ccc(Cl)cc2CC(NC(=O)OC(C)(C)C)C3)CC1]

The title compound was prepared from tert-butyl (7-chloro-2-oxo-2,3,4,5-tetrahydro-1H-1-benzazepin-4-yl)carbamate (Intermediate 5) and 4-ethyl-4-methoxycyclohexane-carbohydrazide (Step b) of Intermediate 127) according to the method described in Method B of Example 5. MS (ESI) m/z 475.3 (M+H)$^+$.

b) 8-chloro-1-(trans-4-ethyl-4-methoxycyclohexyl)-5,6-dihydro-4H-[1,2,4]triazolo[4,3-a][1]benzazepin-5-amine

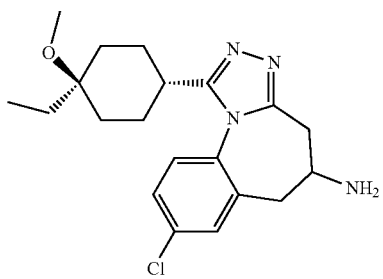 [SMILES: CC[C@]1(OC)CC[C@H](c2nnc3n2-c2ccc(Cl)cc2CC(N)C3)CC1]

The title compound was prepared from tert-butyl [8-chloro-1-(trans-4-ethyl-4-methoxycyclohexyl)-5,6-dihydro-4H-[1,2,4]triazolo[4,3-a][1]benzazepin-5-yl]carbamate (Step a) of Example 233) according to the method described in Example 2. MS (ESI) m/z 375.1 (M+H)$^+$.

c) 8-chloro-1-(trans-4-ethyl-4-methoxycyclohexyl)-N,N-dimethyl-5,6-dihydro-4H-[1,2,4]triazolo[4,3-a][1]benzazepin-5-amine The title compound was prepared from 8-chloro-1-(trans-4-ethyl-4-methoxycyclohexyl)-5,6-dihydro-4H-[1,2,4]triazolo[4,3-a][1]benzazepin-5-amine (Step b) of Example 233) according to the method described in Example 101. MS (ESI) m/z 403.3 (M+H)$^+$.

Example 234

8-chloro-1-(trans-4-ethoxy-4-methylcyclohexyl)-N,N-dimethyl-5,6-dihydro-4H-[1,2,4]triazolo[4,3-a][1]benzazepin-5-amine

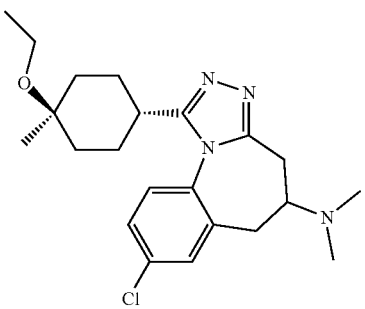 [SMILES: CCO[C@]1(C)CC[C@@H](c2nnc3n2-c2ccc(Cl)cc2CC(N(C)C)C3)CC1]

a) Tert-butyl [8-chloro-1-(trans-4-ethoxy-4-methyl-cyclohexyl)-5,6-dihydro-4H-[1,2,4]triazolo[4,3-a][1]benzazepin-5-yl]carbamate

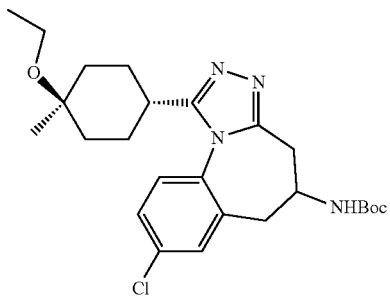 [SMILES: CCO[C@]1(C)CC[C@@H](c2nnc3n2-c2ccc(Cl)cc2CC(NC(=O)OC(C)(C)C)C3)CC1]

The title compound was prepared from tert-butyl (7-chlor-2-oxo-2,3,4,5-tetrahydro-1H-1-benzazepin-4-yl)carbamate (Intermediate 5) and trans-4-ethoxy-4-methylcyclohexanecarbohydrazide (Step b) of Intermediate 128) according to the method described in Method B of Example 5. MS (ESI) m/z 475.3 (M+H)+.

b) 8-chloro-1-(trans-4-ethoxy-4-methylcyclohexyl)-5,6-dihydro-4H-[1,2,4]triazolo[4,3-a][1]benzazepin-5-amine

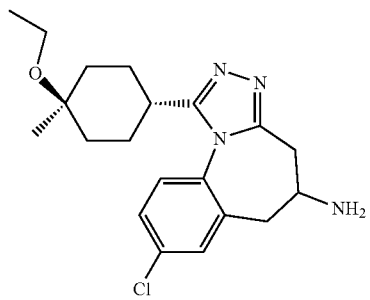 [SMILES: CCO[C@]1(C)CC[C@@H](c2nnc3n2-c2ccc(Cl)cc2CC(N)C3)CC1]

The title compound was prepare from tert-buty [8-chloro-1-(trans-4-ethoxy-4-methylcyclohexyl)-5,6-dihydro-4H-[1,2,4]triazolo[4,3-a][1]benzazepin-5-yl]carbamate (Step a) of Example 234) according to the method described in Example 2. MS (ESI) m/z 375.2 (M+H)+.

c) 8-chloro-1-(trans-4-ethoxy-4-methylcyclohexyl)-N,N-dimethyl-5,6-dihydro-4H-[1,2,4]triazolo[4,3-a][1]benzazepin-5-amine The title compound was prepared from 8-chloro-1-(trans-4-ethoxy-4-methylcyclohexyl)-5,6-dihydro-4H-[1,2,4]triazolo[4,3-a][1]benzazepin-5-amine (Step b) of Example 234) according to the method described in Example 101. MS (ESI) m/z 403.3 (M+H)+.

Example 235

8'-chloro-1'-[trans-4-methoxy-4-(trifluoromethyl)cyclohexyl]-4'H,6'H-spiro[1,3-dioxolane-2,5'-[1,2,4]triazolo[4,3-a][1]benzazepine]

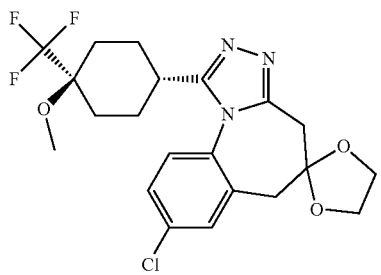 [SMILES: CO[C@]1(C(F)(F)F)CC[C@@H](c2nnc3n2-c2ccc(Cl)cc2CC2(C3)OCCO2)CC1]

The title compound was prepared from 7-chloro-1,5-dihydrospiro[1-benzazepine-4,2'-[1,3]dioxolan]-2(3H)-one (Intermediate 53) and trans-4-methoxy-4-(trifluoromethyl)cyclohexanecarbohydrazide (Intermediate 124) according to the method described in Example 108. MS (ESI) m/z 458.2 (M+H)+.

Example 236

8'-chloro-1'-[cis-4-methoxy-4-(trifluoromethyl)cyclohexyl]-4'H,6'H-spiro[1,3-dioxolane-2,5'-[1,2,4]triazolo[4,3-a][1]benzazepine]

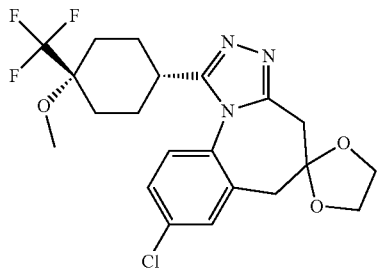 [SMILES: CO[C@]1(C(F)(F)F)CC[C@H](c2nnc3n2-c2ccc(Cl)cc2CC2(C3)OCCO2)CC1]

The title compound was prepared from 7-chloro-1,5-dihydrospiro[1-benzazepine-4,2'-[1,3]dioxolan]-2(3H)-one (Intermediate 53) and cis-4-methoxy-4-(trifluoromethyl)cyclohexanecarbohydrazide (Intermediate 123) according to the method described in Example 108. MS (ESI) m/z 458.2 (M+H)+.

Example 237

8'-chloro-1'-(trans-4-ethoxy-4-methylcyclohexyl)-4'H,6'H-spiro[1,3-dioxolane-2,5-[1,2,4]triazolo[4,3-a][1]benzazepine]

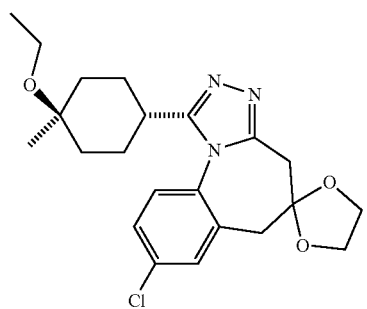

The title compound was prepared from 7-chloro-1,5-dihydrospiro[1-benzazepine-4,2'-[1,3]dioxolan]-2(3H)-one (Intermediate 53) and trans-4-ethoxy-4-methylcyclohexanecarbohydrazide (Step b) of Intermediate 128) according to the method described in Example 190. MS (ESI) m/z 418.2 (M+H)+.

Example 238

8'-chloro-1'-(trans-4-ethoxy-4-propylcyclohexyl)-4'H,6'-spiro[1,3-dioxolane-2,5'-[1,2,4]triazolo[4,3-a][1]benzazepine]

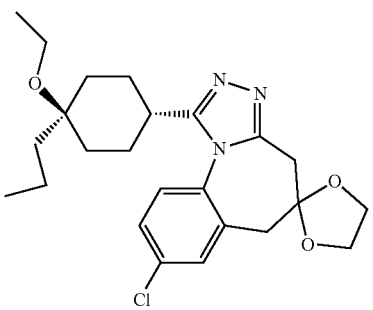 [SMILES: CCC[C@]1(OCC)CC[C@H](c2nnc3n2-c2ccc(Cl)cc2CC2(C3)OCCO2)CC1]

The title compound was prepared from 7-chloro-1,5-dihydrospiro[1-benzazepine-4,2'-[1,3]dioxolan]-2(3H)-one (Intermediate 53) and 4-ethoxy-4-propylcyclohexanecarbohydrazide (Step d) of Intermediate 129) according to the method described in Example 190. MS (ESI) m/z 446.3 (M+H)+.

Example 239

8'-chloro-1'-[1-(pyridin-2-ylmethyl)pyrrolidin-3-yl]-4'H,6'H-spiro[1,3-dioxolane-2,5'-[1,2,4]triazolo[4,3-a][1]benzazepine]

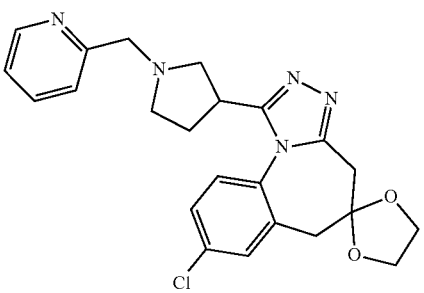 [SMILES: Clc1ccc2c(c1)CC1(Cc3nnc(C4CCN(Cc5ccccn5)C4)n3-2)OCCO1]

The title compound was prepared from 7-chloro-1,5-dihydrospiro[1-benzazepine-4,2'-[1,3]dioxolan]-2(3H)-one (Intermediate 53) and 1-(pyridin-2-ylmethyl)pyrrolidine-3-carbohydrazide (Step b) of Intermediate 116) according to the method described in Example 190. MS (ESI) m/z 438.3 (M+H)+.

Example 240

8'-chloro-1'-(cis-4-ethyl-4-methoxycyclohexyl)-4'H,6'H-spiro[1,3-dioxolane-2,5'-[1,2,4]triazolo[4,3-a][1]benzazepine]

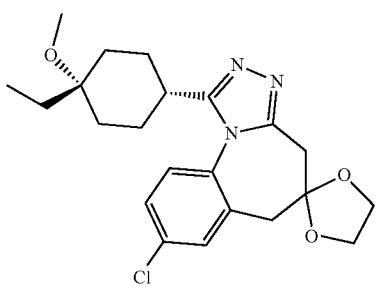 [SMILES: CC[C@]1(OC)CC[C@@H](c2nnc3n2-c2ccc(Cl)cc2CC2(C3)OCCO2)CC1]

291

And

Example 241

8'-chloro-1'-(trans-4-ethyl-4-methoxycyclohexyl)-4'H,6'H-spiro[1,3-dioxolane-2,5'-[1,2,4]triazolo[4,3-a][1]benzazepine]

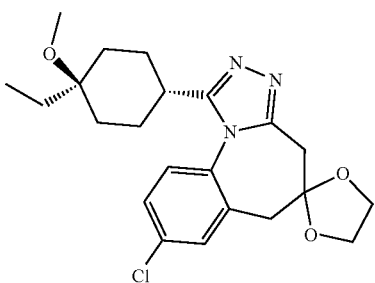 [SMILES: CC[C@]1(OC)CC[C@H](c2nnc3n2-c2ccc(Cl)cc2CC2(C3)OCCO2)CC1]

The title compounds were prepared from 7-chloro-1,5-dihydrospiro[1-benzazepine-4,2'-[1,3]dioxolan]-2(3H)-one (Intermediate 53) and 4-ethyl-4-methoxycyclohexane-carbohydrazide (Step b) of Intermediate 127) according to the method described in Example 190. The cis and trans isomers were separated by flash column chromatography using dichloromethane:methanol=9:1 as eluent. MS (ESI) m/z 418.2 (M+H)$^+$.

Example 242

8'-chloro-1'-(trans-4-methoxy-4-propylcyclohexyl)-4'H,6'H-spiro[1,3-dioxolane-2,5'-[1,2,4]triazolo 4,3a][1]benzoepin

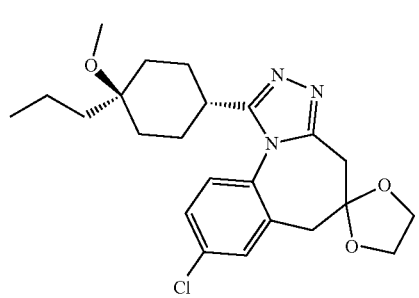 [SMILES: CCC[C@]1(OC)CC[C@H](c2nnc3n2-c2ccc(Cl)cc2CC2(C3)OCCO2)CC1]

292

And

Example 243

8'-chloro-1'-(cis-4-methoxy-4-propylcyclohexyl)-4'H,6'H-spiro[1,3-dioxolane-2,5-[1,2,4]triazolo[4,3-a][1]benzazepine]

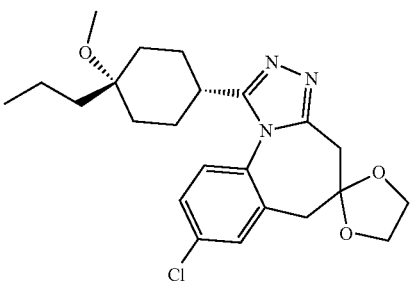 [SMILES: CCC[C@]1(OC)CC[C@@H](c2nnc3n2-c2ccc(Cl)cc2CC2(C3)OCCO2)CC1]

The title compounds were prepared from 7-chlor-1,5-dihydrospiro[1-benzazepine-4,2'-[1,3]dioxolan]-2(3H)-one (Intermediate 53) and 4-methoxy-4-propylcyclohexanecarbohydrazide (Step b) of Intermediate 130) according to method described in Example 190. The cis and trans isomers were separated by flash column chromatography using dichloromethane:methanol=95:5 as eluent. MS (ESI) m/z 432.2 (M+H)$^+$.

Example 244

8-chloro-1-(trans-4-ethoxy-4-ethylcyclohexyl)-N-(propan-2-yl)-5,6-dihydro-4H-[1,2,4]triazolo[4,3-a][1]benzazepin-5-amine

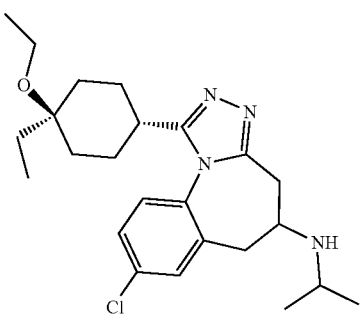 [SMILES: CCO[C@]1(CC)CC[C@@H](c2nnc3n2-c2ccc(Cl)cc2CC(NC(C)C)C3)CC1]

293 a) Tert-butyl [8-chloro-1-(trans-4-ethoxy-4-ethylcyclohexyl)-5,6-dihydro-4H-[1,2,4]triazolo[4,3-a][1]benzazepin-5-yl]carbamate

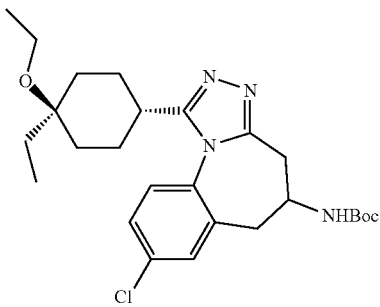 [SMILES: CCO[C@]1(CC)CC[C@@H](c2nnc3n2-c2ccc(Cl)cc2CC(NC(=O)OC(C)(C)C)C3)CC1]

The title compound was prepared from tert-butyl (7-chloro-2-oxo-2,3,4,5-tetrahydro-1H-1-benzazepin-4-yl)carbamate (Intermediate 5) and trans-4-ethoxy-4-ethylcyclohexanecarbohydrazide (Step c) of Intermediate 126) according to the method described in Method B of Example 5. MS (ESI) m/z 489.3 (M+H)$^+$.

b) 8-chloro-1-(trans-4-ethoxy-4-ethylcyclohexyl)-5,6-dihydro-4H-[1,2,4]triazolo[4,3-a][1]benzazepin-5-amine

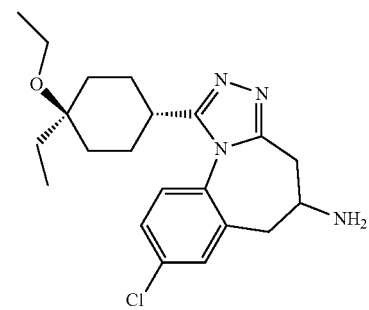 [SMILES: CCO[C@]1(CC)CC[C@@H](c2nnc3n2-c2ccc(Cl)cc2CC(N)C3)CC1]

The title compound was prepared from tert-butyl [8-chloro-1-(trans-4-ethoxy-4-ethylcyclohexyl)-5,6-dihydro-4H-[1,2,4]triazolo[4,3-a][1]benzazepin-5-yl]carbamate (Step a) of Example 244) according to the method described in Example 2. MS (ESI) m/z 389.3 (M+H)$^+$.

c) 8-chloro-1-(trans-4-ethoxy-4-ethylcyclohexyl)-N-(propan-2-yl)-5,6-dihydro-4H-[1,2,4]triazolo[4,3-a][1]benzazepin-5-amine The title compound was prepared from 8-chloro-1-(trans-4-ethoxy-4-ethylcyclohexyl)-5,6-dihydro-4H-[1,2,4]triazolo[4,3-a][1]benzazepin-5-amine (Step b) of Example 244) according to the method described in Example 24. MS (ESI) m/z 431.3 (M+H)$^+$.

Example 245

8-chloro-1-(trans-4-ethoxy-4-ethylcyclohexyl)-N,N-dimethyl-5,6-dihydro-4H-[1,2,4]triazolo[4,3-a][1]benzazepin-5-amine

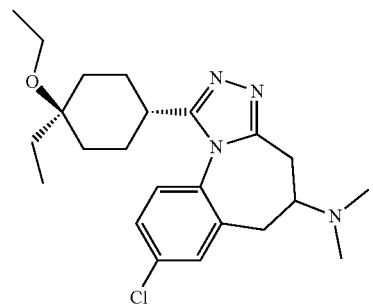 [SMILES: CCO[C@]1(CC)CC[C@@H](c2nnc3n2-c2ccc(Cl)cc2CC(N(C)C)C3)CC1]

The title compound was prepared from 8-chloro-1-(trans-4-ethoxy-4-ethylcyclohexyl)-5,6-dihydro-4H-[1,2,4]triazolo[4,3-a][1]benzazepin-5-amine (Step b) of Example 244) according to the method described in Example 101. MS (ESI) m/z 417.3 (M+H)$^+$.

Example 246

8'-chloro-1'-[(3R)-1-(pyridin-2-ylmethyl)pyrrolidin-3-yl]-4'H,6'H-spiro[1,3-dioxolane-2,5'-[1,2,4]triazolo[4,3-a][1]benzazepine]

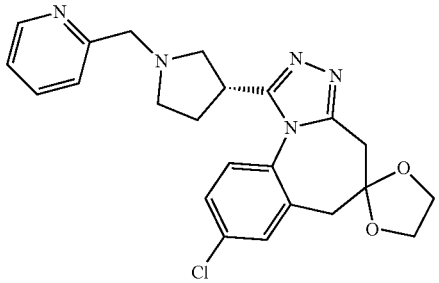 [SMILES: Clc1ccc2c(c1)CC1(Cc3nnc([C@@H]4CCN(Cc5ccccn5)C4)n3-2)OCCO1]

The title compound was prepared from 7-chloro-1,5-dihydrospiro[1-benzazepine-4,2'-[1,3]dioxolan]-2(3H)-one (Intermediate 53) and (3R)-1-(pyridin-2-ylmethyl)pyrrolidine-3-carbohydrazide (Step b) of Intermediate 131) according to the method described in Example 190. MS (ESI) m/z 438.1 (M+H)$^+$.

Example 247

8-chloro-5-methoxy-1-[(3R)-1-pyridin-3-ylmethyl)pyrrolidin-3-yl]-5,6-dihydro-4H-[1,2,4]triazolo[4,3-a][1]benzazepine

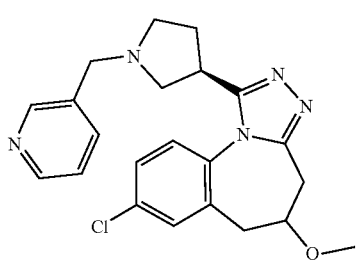 [SMILES: COC1Cc2cc(Cl)ccc2-n2c(nnc2[C@@H]2CCN(Cc3cccnc3)C2)C1]

The title compound was prepared from 7-chloro-4-methoxy-1,3,4,5-tetrahydro-2H-1-benzazepin-2-one (Step d) of Intermediate 103) and (3R)-1-(pyridin-3-ylmethyl) pyrrolidine-3-carbohydrazide (Step b) of Intermediate 133) according to the method described in Example 108. MS (ESI) m/z 410.1 (M+H)+.

Example 248

8-chloro-5-methoxy-1-[(3R)-1-(pyridin-2-ylmethyl)pyrrolidin-3-yl]-5,6-dihydro-4H-[1,2,4]triazolo[4,3-a][1]benzazepine

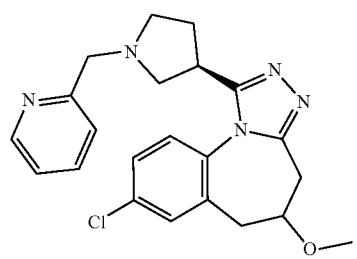 [SMILES: COC1Cc2cc(Cl)ccc2-n2c(nnc2[C@@H]2CCN(Cc3ccccn3)C2)C1]

The title compound was prepared from 7-chloro-4-methoxy-1,3,4,5-tetrahydro-2H-1-benzazepin-2-one (Step d) of Intermediate 103) and (3R)-1-(pyridin-2-ylmethyl)pyrrolidine-3-carbohydrazide (Step b) of Intermediate 131) according to the method described in Example 108. MS (ESI) m/z 410.2 (M+H)+.

Example 249

8'-chloro-1-[(3S)-1-(pyridin-3-ylmethyl)pyrrolidin-3-yl]-4'H,6'H-spiro[1,3-dioxolane-2,5'-[1,2,4]triazolo[4,3-a][1]benzazepine]

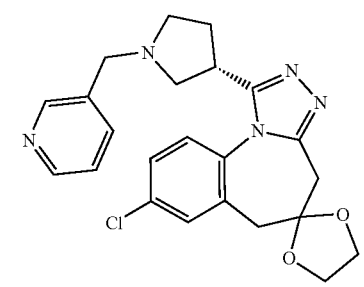 [SMILES: Clc1ccc2c(c1)CC1(Cc3nnc([C@H]4CCN(Cc5cccnc5)C4)n3-2)OCCO1]

The title compound was prepared from 7-chloro-1,5-dihydrospiro[1-benzazepine-4,2'-[1,3]dioxolan]-2(3H)-one (Intermediate 53) and (3S)-1-(pyridin-3-ylmethyl)pyrrolidine-3-carbohydrazide (Step b) of Intermediate 134) according to the method described in Example 190. MS (ESI) m/z 438.1 (M+H)+.

Example 250

8'-chloro-1'-[(3R)-1-(pyridin-3-ylmethyl)pyrrolidin-3-yl]-4'H, 6'H-spiro[1,3-dioxolane-2,5'-[1,2,4]triazolo[4,3-a][1]benzazepine]

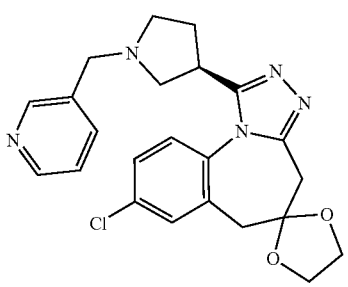 [SMILES: Clc1ccc2c(c1)CC1(Cc3nnc([C@@H]4CCN(Cc5cccnc5)C4)n3-2)OCCO1]

The title compound was prepared from 7-chloro-1,5-dihydrospiro[1-benzazepine-4,2'-[1,3]dioxolan]-2(3H)-one (Intermediate 53) and (3R)-1-(pyridin-3-ylmethyl)pyrrolidine-3-carbohydrazide (Step b) of Intermediate 133) according to the method described in Example 190. MS (ESI) m/z 438.1 (M+H)+.

Example 251

8-chloro-5-methoxy-1-[(3S)-1-(pyridin-3-ylmethyl)pyrrolidin-3-yl]-5,6-dihydro-4H-[1,2,4]triazolo[4,3-a][1]benzazepine

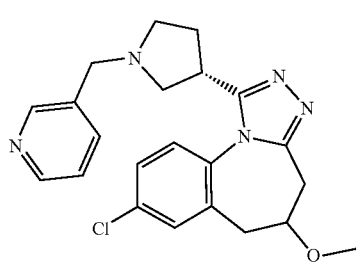 [SMILES: COC1Cc2cc(Cl)ccc2-n2c(nnc2[C@H]2CCN(Cc3cccnc3)C2)C1]

The title compound was prepared from 7-chloro-4-methoxy-1,3,4,5-tetrahydro-2H-1-benzazepin-2-one (Step d) of Intermediate 103) and (3S)-1-(pyridin-3-ylmethyl)pyrrolidine-3-carbohydrazide (Step b) of Intermediate 134) according to the method described in Example 108. MS (ESI) m/z 410.1 (M+H)$^+$.

Example 252

8'-chloro-1'-[(3S)-1-(pyridin-2-ylmethyl)pyrrolidin-3-yl]-4'H,6'H-spiro[1,3-dioxolane-2,5'-[1,2,4]triazolo[4,3-a][1]benzazepine]

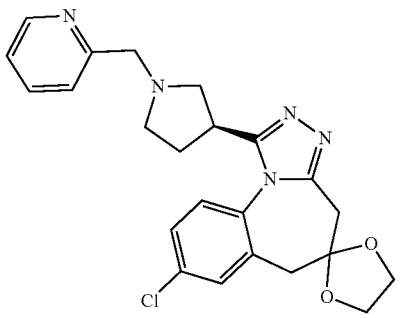 [SMILES: Clc1ccc2c(c1)CC1(Cc3nnc([C@H]4CCN(Cc5ccccn5)C4)n3-2)OCCO1]

The title compound was prepared from 7-chlor-1,5-dihydrospiro[1-benzazepine-4,2'-[1,3]dioxolan]-2(3H)-one (Intermediate 53) and (3S)-1-(pyridin-2-ylmethyl)pyrrolidine-3-carbohydrazide (Step b) of Intermediate 132) according to the method described in Example 190. MS (ESI) m/z 438.1 (M+H)$^+$.

Example 253

8-chloro-5-methoxy-1-[(3S)-1-(pyridin-2-ylmethyl)pyrrolidin-3-yl]-5,6-dihydro-4H-[1,2,4]triazolo[4,3-a][1]benzazepine

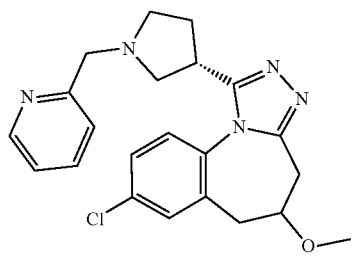 [SMILES: COC1Cc2cc(Cl)ccc2-n2c(nnc2[C@H]2CCN(Cc3ccccn3)C2)C1]

The title compound was prepared from 7-chlor-4-methoxy-1,3,4,5-tetrahydr-2H-1-benzazepin-2-one (Step d) of Intermediate 103) and (3S)-1-(pyridin-2-ylmethyl)pyrrolidine-3-carbohydrazide (Step b) of Intermediate 132) according to the method described in Example 108. MS (ESI) m/z 410.1 (M+H)$^+$.

The following formulation examples illustrate representative pharmaceutical compositions of this invention. The present invention however is not limited to the following pharmaceutical compositions.

A) Solid Oral Dosage Forms
  I. Tablets

| | |
|---|---|
| Active substance(s) | 0.01-90% |
| Filler | 1-99.9% |
| Binder | 0-20% |
| Disintegrant | 0-20% |
| Lubricant | 0-10% |
| Other specific excipient(s) | 0-50% |

II. Orodispersible Films

| | |
|---|---|
| Active substance(s) | 0.01-90% |
| Film forming agent | 1-99.9% |
| Plasticiser | 0-40% |
| Other specific excipient(s) | 0-50% |

B) Liquid Oral Dosage Forms
  III. Oral Suspensions

| | |
|---|---|
| Active substances(s) | 0.01-50% |
| Liquid vehicle | 10-99.9% |
| Wetting agent | 0-50% |
| Thickener | 0-50% |
| Buffering agent | q.s. |
| Osmotic agent | 0-50% |
| Preservatives | q.s. |

IV. Syrups

| | |
|---|---|
| Active substance(s) | 0.01-50% |
| Solvent | 10-99.9% |
| Sugar component | 1-20% |
| Flavouring agents | 0-10% |

C) Parenteral Dosage Forms
V. Intravenous injections

| Active substance(s) | 0.01-50% |
|---|---|
| Solvent | 10-99.9% |
| Co-solvent | 0-99.9% |
| Osmotic agent | 0-50% |
| Buffering agent | q.s. |

D) Other Dosage Forms
VI. Suppositories

| Active substance(s) | 0.01-50% |
|---|---|
| Suppository base | 1-99.9% |
| Surface-active agents | 0-20% |
| Lubricant | 0-20% |
| Preservatives | q.s. |

VII. Eye Drops

| Active substance(s) | 0.01-50% |
|---|---|
| Water | 0-99.9% |
| Solvent | 0-99.9% |
| Osmotic agent | 0-20% |
| Viscosity enhancer | 0-20% |
| Bufferin agent | q.s. |
| Preservatives | q.s. |

The invention claimed is:

1. A compound of general formula (I)

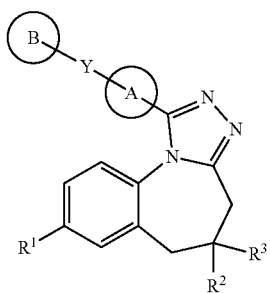

wherein
ring A is a cycloalkyl or heterocyclyl group;
Y is —O—, —C(O)—, —CH$_2$—, —NH—, —C$_{1-4}$alkyl-N(R$^{18}$)— or bond if ring B is present; or —N(C$_{1-4}$alkyl)$_2$, C(O)OC$_{1-4}$alkyl, C$_{1-4}$alkyl optionally substituted with halogen, C$_{1-4}$alkoxy group or halogen if ring B is absent;
ring B is absent or is an optionally substituted heteroaryl, aryl or heterocyclyl group;
or B—Y—A- jointly represents a 3H-spiro[2-benzofuran-1,4'-piperidin-1'-yl]; or

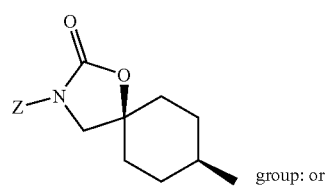
group: or

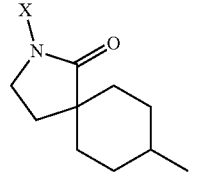
group: or

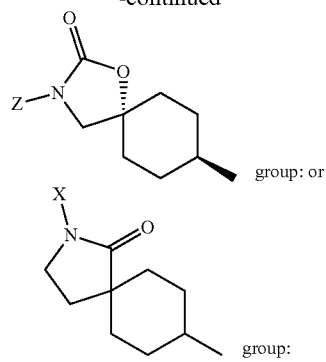
group:

R$^1$ is a hydrogen, halogen, C$_{1-4}$alky, C$_{1-4}$alkoxy, CF$_3$ or CN;
R$^2$ is a hydrogen or C$_{1-4}$alkyl group;
R$^3$ is a NR$^4$R$^5$, OR$^6$ group or halogen;
or R$^2$ and R$^3$ jointly represent —O—(CH$_2$)$_m$—O—, oxo or =N—OH group;
R$^4$ and R$^5$ is independently a hydrogen; C$_{1-4}$alkyl optionally substituted with OH, halogen, cycloalkyl, optionally substituted aryl or NR$^8$R$^9$ group; Cy$^1$; C(O)R$^7$; —S(O$_2$)R$^{10}$ or C$_{2-4}$alkynyl group;
or R$^4$ and R$^5$ taken together with the N to which they are attached form a heterocycle;
R$^6$ is a hydrogen; C$_{1-4}$alkyl optionally substituted with OH, halogen, Cy$^2$, C$_{1-4}$alkoxy, —S(O)$_2$-C$_{1-4}$alkyl or NR$^{11}$R$^{12}$ group; C(O)R$^{13}$; Si(CH$_3$)$_2$-t-butyl or C$_{2-4}$alkynyl group;
R$^7$ is a C$_{1-4}$alkyl optionally substituted with OH, CN, halogen, Cy$^3$ or NR$^{11}$R$^{12}$ group; C$_{1-4}$alkoxy, C$_{2-4}$alkenyl, Cy$^3$ or N(C$_{1-4}$alkyl)$_2$ group;
R$^8$ and R$^9$ is independently a hydrogen, C$_{1-4}$alkyl or C(O)OR$^{21}$ group;
R$^{10}$ is a C$_{1-4}$alkyl, OH or NR$^{14}$R$^{15}$ group;
R$^{11}$ and R$^{12}$ is independently a hydrogen or C$_{1-4}$alkyl group;
or R$^{11}$ and R$^{12}$ taken together with the N to which they are attached form an optionally substituted heterocycle;
R$^{13}$ is a C$_{1-4}$alkyl optionally substituted with CN or NR$^{19}$R$^{20}$ group; Cy$^3$ or NR$^{16}$R$^{17}$ group;
R$^{14}$ and R$^{15}$ is independently a hydrogen or C$_{1-4}$alkyl group;
R$^{16}$ and R$^{17}$ is independently a hydrogen, C$_{1-4}$alkyl, or optionally substituted aryl group;
or R$^{16}$ and R$^{17}$ taken together with the N to which they are attached form a heterocycle;
R$^{18}$ and R$^{21}$ is a hydrogen or C$_{1-4}$alkyl group;
R$^{19}$ and R$^{20}$ is independently a hydrogen or C$_{1-4}$alkyl group;
Cy$^1$ is an optionally substituted cycloalkyl, heterocyclyl or heteroaryl group;
Cy$^2$ is an optionally substituted aryl or cycloalkyl group;
Cy$^3$ is an optionally substituted aryl, cycloalkyl, heterocyclyl or heteroaryl group;
X is a C$_{1-4}$alkyl, aryl or heteroaryl group;
Z is a C$_{1-4}$alkyl group;
m is 2, 3, 4 or 5
and/or salts thereof and/or geometric isomers thereof and/or stereoisomers thereof and/or enantiomers thereof and/or racemates thereof and/or diastereomers thereof and/or biologically active metabolites thereof and/or prodrugs thereof and/or solvates thereof and/or hydrates thereof and/or polymorphs thereof.

2. The compound according to claim 1, wherein $R^1$ is a hydrogen, fluorine, chlorine, bromine, methyl, methoxy, $CF_3$ or CN.

3. The compound according to claim 1, wherein
ring A is a 3- to 6-membered saturated carbocyclic group or a 4- to 7-membered saturated heterocycle containing 1 or 2 N;
ring B is absent or is an optionally substituted 6- or 5-membered mono-heteroaryl group, 6- to 10-membered aromatic carbocycle, or 4- to 7-membered saturated, monocyclic, bicyclic, fused and/or bridged heterocycle containing 1, 2 or 3 heteroatoms selected from O, S or N; or B—Y-A- jointly represents a 3H-spiro [2-benzofuran-1,4'-piperidin-1'-yl]; or

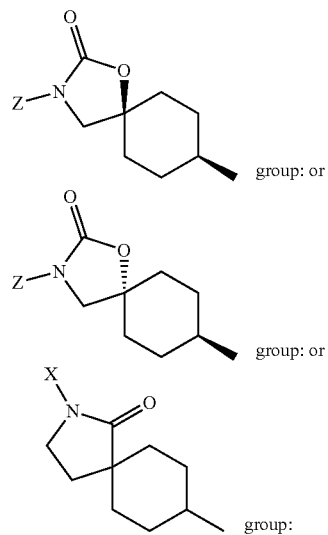

X is an isopropyl group
Z is a methyl group.

4. The compound according to claim 1, wherein ring A is a 4- to 6-membered saturated carbocyclic group or a 4- to 7-membered saturated heterocycle containing 1 or 2 N attached via a ring nitrogen to Y or to the triazole ring of the 5,6-dihydro-4H-[1,2,4]triazolo[4,3-a][1]benzazepine core.

5. The compound according to claim 1, wherein ring A is cyclohexyl, Y is —O—, ring B is pyridin-2-yl and $R^1$ is chlorine.

6. The compound according to claim 1, wherein
$R^2$ is a hydrogen or $C_{1-4}$alkyl group;
$R^3$ is a $NR^4R^5$ group;
$R^4$ and $R^5$ is independently a hydrogen; $C_{1-4}$alkyl optionally substituted with OH, halogen, cycloalkyl, optionally substituted aryl or $NR^8R^9$ group; $Cy^1$; $C(O)R^7$; —$S(O_2)R^{10}$ or $C_{2-4}$alkynyl group,
or $R^4$ and $R^5$ taken together with the N to which they are attached form a heterocycle;
$R^7$ is a $C_{1-4}$alkyl optionally substituted with OH, CN, halogen, $Cy^3$ or $NR^{11}R^{12}$ group; $C_{1-4}$alkoxy, $C_{2-4}$alkenyl, $Cy^3$ or $N(C_{1-4}alkyl)_2$ group;
$R^8$ and $R^9$ is independently hydrogen, $C_{1-4}$alkyl or $C(O)OR^{21}$ group;
$R^{10}$ is a $C_{1-4}$alkyl, OH or $NR^{14}R^{15}$ group;
$R^{11}$ and $R^{12}$ is independently a hydrogen or $C_{1-4}$alkyl group;
or $R^{11}$ and $R^{12}$ taken together with the N to which they are attached form an optionally substituted heterocycle;
$R^{14}$ and $R^{15}$ is independently a hydrogen or $C_{1-4}$alkyl group;
$R^{21}$ is a hydrogen or $C_{1-4}$alkyl group;
$Cy^1$ is an optionally substituted cycloalkyl, heterocyclyl or heteroaryl group;
$Cy^3$ is an optionally substituted aryl, cycloalkyl, heterocyclyl or heteroaryl group.

7. The compound according to claim 6, wherein $R^2$ is a hydrogen and $R^4$ and $R^5$ are independently a hydrogen, or a $C_{1-4}$alkyl group.

8. The compound according to claim 1, wherein
$R^2$ is a hydrogen or $C_{1-4}$alkyl group;
$R^3$ is an $OR^6$ group;
$R^6$ is a hydrogen; $C_{1-4}$alkyl group optionally substituted with OH, halogen, $Cy^2$, $C_{1-4}$alkoxy, —$S(O)_2$—$C_{1-4}$alkyl or $NR^{11}R^{12}$ group; $C(O)R^{13}$, $Si(CH_3)_2$-t-butyl or $C_{2-4}$alkynyl group;
$R^{11}$ and $R^{12}$ is independently a hydrogen or $C_{1-4}$alkyl group;
or $R^{11}$ and $R^{12}$ taken together with the N to which they are attached form an optionally substituted heterocycle;
$R^{13}$ is a $C_{1-4}$alkyl group optionally substituted with CN or $NR^{19}R^{20}$ group; $Cy^3$ or $NR^{16}R^{17}$ group;
$R^{16}$ and $R^{17}$ is independently a hydrogen, $C_{1-4}$alkyl or optionally substituted aryl group;
or $R^{16}$ and $R^{17}$ taken together with the N to which they are attached form a heterocycle;
$R^{19}$ and $R^{20}$ is independently a hydrogen or $C_{1-4}$alkyl group;
$Cy^2$ is an optionally substituted aryl or cycloalkyl group.

9. The compound according to claim 8, wherein $R^2$ is a hydrogen and $R^6$ is a hydrogen, or a $C_{1-4}$alkyl group.

10. The compound according to claim 6, wherein the absolute configuration of the carbon at position 5 in the 5,6-dihydro-4H-[1,2,4]triazolo[4,3-a][1]benzazepine core is (S) or (R).

11. The compound according to claim 1, wherein $R^2$ and $R^3$ jointly represent —O—$(CH_2)_m$—O—, oxo or =N—OH group, m is 2, 3, 4 or 5.

12. The compound according to claim 11, wherein $R^2$ and $R^3$ jointly represent —O—$(CH_2)_m$—O— and m is 2.

13. A compound selected from the group consisting of:
tert-butyl [8-chloro-1-[1-(pyridin-2-yl)piperidin-4-yl]-5,6-dihydro-4H-[1,2,4]triazolo[4,3-a][1]benzazepin-5-yl] carbamate,
8-chloro-1-[1-(pyridin-2-yl)piperidin-4-yl]-5,6-dihydro-4H-[1,2,4]triazolo[4,3-a][1]benzazepine-5-amine,
N-[8-chloro-[1-(pyridin-2-yl)piperidin-4-yl]-5,6-dihydro-4H-[1,2,4]triazolo[4,3-a][1]benzazepin-5-yl]acetamide,
N-(8-chloro-[1-(pyridin-2-yl)piperidin-4-yl]-5,6-dihydro-4H-[1,2,4]triazolo[4,3-a][1]benzazepin-5-yl)-2-methylpropanamide,
tert-butyl {8-chloro-1-[trans-4-(pyridin-2-yloxy)cyclohexyl]-5,6-dihydro-4H-[1,2,4]triazolo[4,3-a]benzazepine-5-yl}carbamate,
8-chloro-1-[trans-4-(pyridin-2-yloxy)cyclohexyl]-5,6-dihydro-4H-[1,2,4]triazolo[4,3-a][1]benzazepine-5-amine,
(5S)-8-chloro-1-[trans-4-(pyridin-2-yloxy)cyclohexyl]-5,6-dihydro-4H-[1,2,4]triazolo[4,3-a][1]benzazepine-5-amine,
(5R)-8-chloro-1-[trans-4-(pyridin-2-yloxy)cyclohexyl]-5,6-dihydro-4H-[1,2,4]triazolo[4,3-a][1]benzazepine-5-amine, N-{8-chloro-1-[trans-4-(pyridin-2-yloxy)cyclohexyl]-5,6-dihydro-4H-[1,2,4]triazolo[4,3-a][1]benzazepin-5-yl}acetamide, N-{8-chloro-1-[trans-4-(pyridin-2-yloxy)cyclohexyl]-5,6-dihydro-4H-[1,2,4]triazolo[4,3-a][1]benzazepin-5-yl}glycinamide, N-{(5S)-8-chloro-1-[trans-4-(pyridin-2-yloxy)cyclohexyl]-5,6-dihydro-4H-[1,2,4]triazolo[4,3-a][1]benzazepin-5-yl}glycinamide, N-{(5R)-8-chloro-1-[trans-4-(pyridin-2-yloxy)cyclohexyl]-5,6-dihydro-4H-[1,2,4]triazolo[4,3-a][1]benzazepin-5-yl}glycinamide, (2S)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide, (2R)-2-amino-N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-phenylacetamide, N-{8-chloro-1-[trans-4-(pyridin-2-yloxy)cyclohexyl]-5,6-dihydro-4H-[1,2,4]triazolo[4,3-a][1]benzazepin-5-yl}-2-hydroxyacetamide, 3-{8-chloro-1-[trans-4-(pyridin-2-yloxy)cyclohexyl]-5,6-dihydro-4H-[1,2,4]triazolo[4,3-a][1]benzazepin-5-yl}-1,1-dimethylurea, N-{8-chloro-1-[trans-4-(pyridin-2-yloxy)cyclohexyl]-5,6-dihydro-4H-[1,2,4]triazolo[4,3-a][1]benzazepin-5-yl}-$N^2,N^2$-dimethylglycinamide, N-{8-chloro-1-[trans-4-(pyridin-2-yloxy)cyclohexyl]-5,6-dihydro-4H-[1,2,4]triazolo[4,3-a][1]benzazepin-5-yl}methanesulfonamide, N-{8-chloro-1-[trans-4-(pyridin-2-yloxy)cyclohexyl]-5,6-dihydro-4H-[1,2,4]triazolo[4,3-a][1]benzazepin-5-yl}-N-methylmethanensulfonamide, N-{8-chloro-1-[trans-4-(pyridin-2-yloxy)cyclohexyl]-5,6-dihydro-4H-[1,2,4]triazolo[4,3-a][1]benzazepin-5-yl}-N,N-dimethylsulfamide, 8-chloro-N-methyl-1-[trans-4-(pyridin-2-yloxy)cyclohexyl]-5,6-dihydro-4H-[1,2,4]triazolo[4,3-a][1]benzazepine-5-amine, 8-chloro-N,N-dimethyl-1-[trans-4-(pyridin-2-yloxy)cyclohexyl]-5,6-dihydro-4H-[1,2,4]triazolo[4,3-a][1]benzazepine-5-amine, 8-chloro-N-ethyl-1-[trans-4-(pyridin-2-yloxy)cyclohexyl]-5,6-dihydro-4H-[1,2,4]triazolo[4,3-a][1]benzazepine-5-amine, 8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine, (5S)-8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine, (5R)-8-chloro-N-(propan-2-yl)-1-[trans-4-(pyridin-2-yloxy)cyclohexyl]-5,6-dihydro-4H-[1,2,4]triazolo[4,3-a][1]benzazepine-5-amine, 8-chloro-N-cyclobutyl-1-[trans-4-(pyridin-2-yloxy)cyclohexyl]-5,6-dihydro-4H-[1,2,4]triazolo[4,3-a][1]benzazepine-5-amine, 8-chloro-N-(oxetan-3-yl)-1-[trans-4-(pyridin-2-yloxy)cyclohexyl]-5,6-dihydro-4H-[1,2,4]triazolo[4,3-a][1]benzazepine-5-amine, 8-chloro-1-[trans-4-(pyridin-2-yloxy)cyclohexyl]-N-(tetrahydro-2H-pyran-4-yl)-5,6-dihydro 4H-[1,2,4]triazolo[4,3-a][1]benzazepine-5-amine, 8-chloro-N-(4,4-difluorocyclohexyl)-1-[trans-4-(pyridin-2-yloxy)cyclohexyl]-5,6-dihydro-4H-[1,2,4]triazolo[4,3-a][1]benzazepine-5-amine, 8-methoxy-1-[trans-4-(pyridin-2-yloxy)cyclohexyl]-5,6-dihydro-4H-[1,2,4]triazolo[4,3-a][1]benzazepine-5-amine hydrochloride, 8-methoxy-N-(propan-2-yl)-1-[trans-4-(pyridin-2-yloxy)cyclohexyl]-5,6-dihydro-4H-[1,2,4]triazolo[4,3-a][1]benzazepine-5-amine, tert-butyl {1-[trans-4-(pyridin-2-yloxy)cyclohexyl]-8-(trifluoromethyl)-5,6-dihydro-4H-[1,2,4]triazolo[4,3-a][1]benzazepin-5-yl}carbamate, 1-[trans-4-(pyridin-2-yloxy)cyclohexyl]-8-(trifluoromethyl)-5,6-dihydro-4H-[1,2,4]triazolo[4,3-a][1]benzazepine-5-amine hydrochloride, N,N-dimethyl-1-[trans-4-(pyridin-2-yloxy)cyclohexyl]-8-(trifluoromethyl)-5,6-dihydro-4H-[1,2,4]triazolo[4,3-a][1]benzazepine-5-amine, N-(propan-2-yl)-1-[trans-4-(pyridin-2-yloxy)cyclohexyl]-8-(trifluoromethyl)-5,6-dihydro-4H-[1,2,4]triazolo[4,3-a][1]benzazepine-5-amine, 8-methyl-1-[trans-4-(pyridin-2-yloxy)cyclohexyl]-5,6-dihydro-4H-[1,2,4]triazolo[4,3-a][1]benzazepine-5-amine, 8-methyl-N-(propan-2-yl)-1-[trans-4-(pyridin-2-yloxy)cyclohexyl]-5,6-dihydro-4H-[1,2,4]triazolo[4,3-a][1]benzazepine-5-amine, 8-bromo-1-[trans-4-(pyridin-2-yloxy)cyclohexyl]-5,6-dihydro-4H-[1,2,4]triazolo[4,3-a][1]benzazepine-5-amine, 8-bromo-N-(propan-2-yl)-1-[trans-4-(pyridin-2-yloxy)cyclohexyl]-5,6-dihydro-4H-[1,2,4]triazolo[4,3-a][1]benzazepine-5-amine, 8-chloro-1-(3,3-difluorocyclobutyl)-N-(propan-2-yl)-5,6-dihydro-4H-[1,2,4]triazolo[4,3-a][1]benzazepine-5-amine, 8-chloro-1-(4,4-difluorocyclohexyl)-N-(propan-2-yl)-5,6-dihydro-4H-[1,2,4]triazolo[4,3-a][1]benzazepine-5-amine, 8-chloro-1-[trans-4-(trifluoromethyl)cyclohexyl]-5,6-dihydro-4H-[1,2,4]triazolo[4,3-a][1]benzazepine-5-amine, 8-chloro-N-(propan-2-yl)-1-[trans-4-(trifluoromethyl)cyclohexyl]-5,6-dihydro-4H-[1,2,4]triazolo[4,3-a][1]benzazepine-5-amine, 8-bromo-1-[trans-4-(trifluoromethyl)cyclohexyl]-5,6-dihydro-4H-[1,2,4]triazolo[4,3-a][1]benzazepine-5-amine, 8-bromo-N-(propan-2-yl)-1-[trans-4-(trifluoromethyl)cyclohexyl]-5,6-dihydro-4H-[1,2,4]triazolo[4,3-a][1]benzazepine-5-amine, 1'-[trans-4-(pyridin-2-yloxy)cyclohexyl]-8'-(trifluoromethyl)-4'H,6'H-spiro[1,3-dioxolane-2,5'-[1,2,4]triazolo[4,3-a][1]benzazepine], 1-[trans-4-(pyridin-2-yloxy)cyclohexyl]-8-(trifluoromethyl)-4H-[1,2,4]triazolo[4,3-a][1]benzazepin-5(6H)-one, 1-[trans-4-(pyridin-2-yloxy)cyclohexyl]-8-(trifluoromethyl)-5,6-dihydro-4H-[1,2,4]triazolo[4,3-a][1]benzazepin-5-ol, 5-methoxy-1-[trans-4-(pyridin-2-yloxy)cyclohexyl]-8-(trifluoromethyl)-5,6-dihydro-4H-[1,2,4]triazolo[4,3-a][1]benzazepine, 5-(cyclopropylmethoxy)-1-[trans-4-(pyridin-2-yloxy)cyclohexyl]-8-(trifluoromethyl)-5,6-dihydro-4H-[1,2,4]triazolo[4,3-a][1]benzazepine, 5-{[tert-butyl(dimethyl)silyl]oxy}-8-chloro-1-[trans-4-(pyridin-2-yloxy)cyclohexyl]-5,6-dihydro-4H-[1,2,4]triazolo[4,3-a][1]benzazepine, 8'-chloro-1'-[trans-4-(pyridin-2-yloxy)cyclohexyl]-4'H,6'H-spiro[1,3-dioxolane-2,5'-[1,2,4]triazolo[4,3-a][1]benzazepine],
8-chloro-1-[trans-4-(pyridin-2-yloxy)cyclohexyl]-4H-[1,2,4]triazolo[4,3-a][1]benzazepin-5(6H)-one,
8-chloro-1-[trans-4-(pyridin-2-yloxy)cyclohexyl]-5,6-dihydro-4H-[1,2,4]triazolo[4,3-a][1]benzazepin-5-ol,
(5S)-8-chloro-1-[trans-4-(pyridin-2-yloxy)cyclohexyl]-5,6-dihydro-4H-[1,2,4]triazolo[4,3-a][1]benzazepin-5-ol,
(5R)-8-chloro-1-[trans-4-(pyridin-2-yloxy)cyclohexyl]-5,6-dihydro-4H-[1,2,4]triazolo[4,3-a][1]benzazepin-5-ol,
8-chloro-5-methoxy-1-[trans-4-(pyridin-2-yloxy)cyclohexyl]-5,6-dihydro-4H-[1,2,4]triazolo[4,3-a][1]benzazepine,
5-(cyclopropylmethoxy)-8-chloro-1-[trans-4-(pyridin-2-yloxy)cyclohexyl]-5,6-dihydro-4H-[1,2,4]triazolo[4,3-a][1]benzazepine,
2-({8-chloro-1-[trans-4-(pyridin-2-yloxy)cyclohexyl]-5,6-dihydro-4H-[1,2,4]triazolo[4,3-a][1]benzazepin-5-yl}oxy)-N,N-dimethylethanamine,
8'-chloro-1'-[trans-4-(trifluoromethyl)cyclohexyl]-4'H,6'H-spiro[1,3-dioxolane-2,5'-[1,2,4]triazolo[4,3-a][1]benzazepine],
8'-bromo-1'-[trans-4-(pyridin-2-yloxy)cyclohexyl]-4'H,6'H-spiro[1,3-dioxolane-2,5'-[1,2,4]triazolo[4,3-a][1]benzazepine],
1'-[trans-4-(pyridin-2-yloxy)cyclohexyl]-4'H,6'H-spiro[1,3-dioxolane-2,5'-[1,2,4]triazolo[4,3-a][1]benzazepine],
8-bromo-1-[trans-4-(pyridin-2-yloxy)cyclohexyl]-4H-[1,2,4]triazolo[4,3-a][1]benzazepin-5(6H)-one,
8-bromo-1-[trans-4-(pyridin-2-yloxy)cyclohexyl]-5,6-dihydro-4H-[1,2,4]triazolo[4,3-a][1]benzazepin-5-ol,
1'-[trans-4-(pyridin-2-yloxy)cyclohexyl]-4'H,6'H-spiro[1,3-dioxolane-2,5'-[1,2,4]triazolo[4,3-a][1]benzazepin]-8'-carbonitrile,
(5S)-8-chloro-N,N-dimethyl-1-[trans-4-(pyridin-2-yloxy)cyclohexyl]-5,6-dihydro-4H-[1,2,4]triazolo[4,3-a][1]benzazepine-5-amine,
(5S)—N-{8-chloro-1-[trans-4-(pyridin-2-yloxy)cyclohexyl]-5,6-dihydro-4H-[1,2,4]triazolo[4,3-a][1]benzazepin-5-yl}acetamide,
8'-chloro-1'-[trans-4-(pyridin-2-ylmethyl)cyclohexyl]-4'H,6'H-spiro[1,3-dioxolane-2,5'-[1,2,4]triazolo[4,3-a][1]benzazepine],
[trans-4-(8'-chloro-4'H,6'H-spiro[1,3-dioxolane-2,5'-[1,2,4]triazolo[4,3-a][1]benzazepine]-1'-yl)cyclohexyl](pyrrolidin-1-yl)methanone,
8-chloro-1-[trans-4-(trifluoromethyl)cyclohexyl]-4H-[1,2,4]triazolo[4,3-a][1]benzazepin-5(6H)-one,
8-chloro-1-[trans-4-(trifluoromethyl)cyclohexyl]-5,6-dihydro-4H-[1,2,4]triazolo[4,3-a][1]benzazepin-5-ol,
(cis)-8-(8'-chloro-4'H,6'H-spiro[1,3-dioxolane-2,5'-[1,2,4]triazolo[4,3-a][1]benzazepin]-1'-yl)-3-methyl-1-oxa-3-azaspiro[4.5]decan-2-one,
8-chloro-5-methoxy-1-[trans-4-(trifluoromethyl)cyclohexyl]-5,6-dihydro-4H-[1,2,4]triazolo[4,3-a][1]benzazepine,
(trans)-8-(8'-chloro-4'H,6'H-spiro[1,3-dioxolane-2,5'-[1,2,4]triazolo[4,3-a][1]benzazepin]-1'-yl)-3-methyl-1-oxa-3-azaspiro[4.5]decan-2-one,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-N-methylmethanesulfonamide,
(5S)-8-chloro-N-ethyl-1-[trans-4-(pyridin-2-yloxy)cyclohexyl]-5,6-dihydro-4H-[1,2,4]triazolo[4,3-a][1]benzazepine-5-amine,
(5S)-8-chloro-N-methyl-1-[trans-4-(pyridin-2-yloxy)cyclohexyl]-5,6-dihydro-4H-[1,2,4]triazolo[4,3-a][1]benzazepine-5-amine,
8'-chloro-1'-[1-(pyrimidin-2-yl)azetidin-3-yl]-4'H,6'H-spiro[1,3-dioxolane-2,5'-[1,2,4]triazolo[4,3-a][1]benzazepine],
N-{(5S)-8-chloro-1-[trans-4-(pyridin-2-yloxy)cyclohexyl]-5,6-dihydro-4H-[1,2,4]triazolo[4,3-a][1]benzazepin-5-yl}-4-fluorobenzamide,
8'-bromo-1'-[trans-4-(trifluoromethyl)cyclohexyl]-4'H,6'H-spiro[1,3-dioxolane-2,5'-[1,2,4]triazolo[4,3-a][1]benzazepine],
5-(propan-2-ylamino)-1-[trans-4-(pyridin-2-yloxy)cyclohexyl]-5,6-dihydro-4H-[1,2,4]triazolo[4,3-a][1]benzazepin-8-carbonitrile trifluoroacetate,
(5S)-8-chloro-N-(4-fluorobenzyl)-1-[trans-4-(pyridin-2-yloxy)cyclohexyl]-5,6-dihydro-4H-[1,2,4]triazolo[4,3-a][1]benzazepine-5-amine,
1'-[trans-4-(trifluoromethyl)cyclohexyl]-4'H,6'H-spiro[1,3-dioxolane-2,5'-[1,2,4]triazolo[4,3-a][1]benzazepine]-8'-carbonitrile,
[trans-4-(8'-bromo-4'H,6'H-spiro[1,3-dioxolane-2,5'-[1,2,4]triazolo[4,3-a][1]benzazepin]-1'-yl)cyclohexyl](piperidin-1-yl)methanone,
methyl trans-4-(8-bromo-5-oxo-5,6-dihydro-4H-[1,2,4]triazolo[4,3-a][1]benzazepin-1-yl)cyclohexane carboxylate,
8-bromo-1-[trans-4-(piperidin-1-ylcarbonyl)cyclohexyl]-4H-[1,2,4]triazolo[4,3-a][1]benzazepin-5(6H)-one,
8'-chloro-1'-[trans-4-(trifluoromethyl)cyclohexyl]-4'H,6'H-spiro[1,3-dioxane-2,5'-[1,2,4]triazolo[4,3-a][1]benzazepine],
1'-[trans-4-(piperidin-1-ylcarbonyl)cyclohexyl]-4'H,6'H-spiro[1,3-dioxolane-2,5'-[1,2,4]triazolo[4,3-a][1]benzazepin]-8'-carbonitrile,
8'-chloro-1'-[trans-4-(pyridin-2-yloxy)cyclohexyl]-4'H,6'H-spiro[1,3-dioxane-2,5'-[1,2,4]triazolo[4,3-a][1]benzazepine],
8-bromo-1-[trans-4-(trifluoromethyl)cyclohexyl]-4H-[1,2,4]triazolo[4,3-a][1]benzazepin-5(6H)-one,
[trans-4-(8-bromo-5-hydroxy-5,6-dihydro-4H-[1,2,4]triazolo[4,3-a][1]benzazepin-1-yl)cyclohexyl](piperidin-1-yl)methanone,
8-bromo-1-[trans-4-(trifluoromethyl)cyclohexyl]-5,6-dihydro-4H-[1,2,4]triazolo[4,3-a][1]benzazepin-5-ol,
1'-(1,4'-bipiperidin-1'-yl)-8'-chloro-4'H,6'H-spiro[1,3-dioxolane-2,5'-[1,2,4]triazolo[4,3-a][1]benzazepine],
tert-butyl [1-(1,4'-bipiperidin-1'-yl)-8-chloro-5,6-dihydro-4H-[1,2,4]triazolo[4,3-a][1]benzazepin-5-yl]carbamate,
8'-fluoro-1'-[trans-4-(pyridin-2-yloxy)cyclohexyl]-4'H,6'H-spiro[1,3-dioxolane-2,5'-[1,2,4]triazolo[4,3-a][1]benzazepine],
(5S)-8-chloro-N-(4-fluorobenzyl)-N-methyl-1-[trans-4-(pyridin-2-yloxy)cyclohexyl]-5,6-dihydro-4H-[1,2,4]triazolo[4,3-a][1]benzazepine-5-amine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}prop-2-enamide,
(5R)-8-chloro-N-ethyl-1-[trans-4-(pyridin-2-yloxy)cyclohexyl]-5,6-dihydro-4H-[1,2,4]triazolo[4,3-a][1]benzazepin-5-amine, (5R)-8-chloro-N-methyl-1-[trans-4-(pyridin-2-yloxy)cyclohexyl]-5,6-dihydro-4H-[1,2,4]triazolo[4,3-a][1]benzazepin-5-amine,
(5R)-8-chloro-N,N-dimethyl-1-[trans-4-(pyridin-2-yloxy)cyclohexyl]-5,6-dihydro-4H-[1,2,4]triazolo[4,3-a][1]benzazepin-5-amine,
1-[trans-4-(pyridin-2-yloxy)cyclohexyl]-4H-[1,2,4]triazolo[4,3-a][1]benzazepin-5(6H)-one,
(5S)-8-chloro-5-methoxy-1-[trans-4-(pyridin-2-yloxy)cyclohexyl]-5,6-dihydro-4H-[1,2,4]triazolo[4,3-a][1]benzazepine,
(5R)-8-chloro-5-methoxy-1-[trans-4-(pyridin-2-yloxy)cyclohexyl]-5,6-dihydro-4H-[1,2,4]triazolo[4,3-a][1]benzazepine,
8-chloro-5-(propan-2-yloxy)-1-[trans-4-(pyridin-2-yloxy)cyclohexyl]-5,6-dihydro-4H-[1,2,4]triazolo[4,3-a][1]benzazepine,
8'-chloro-1'-[trans-4-(pyridin-2-yloxy)cyclohexyl]-4'H,6'H-spiro[1,3-dioxepane-2,5'-[1,2,4]triazolo[4,3-a][1]benzazepine],
1-[trans-4-(pyridin-2-yloxy)cyclohexyl]-5,6-dihydro-4H-[1,2,4]triazolo[4,3-a][1]benzazepin-5-ol,
[trans-4-(8'-chloro-4'H,6'H-spiro[1,3-dioxolane-2,5'-[1,2,4]triazolo[4,3-a][1]benzazepin]-1'-yl)cyclohexyl](morpholin-4-yl)methanone
5-methoxy-1-[trans-4-(pyridin-2-yloxy)cyclohexyl]-5,6-dihydro-4H-[1,2,4]triazolo[4,3-a][1]benzazepine,
8-fluoro-1-[trans-4-(pyridin-2-yloxy)cyclohexyl]-4H-[1,2,4]triazolo[4,3-a][1]benzazepin-5(6H)-one,
8-fluoro-1-[trans-4-(pyridin-2-yloxy)cyclohexyl]-5,6-dihydro-4H-[1,2,4]triazolo[4,3-a][1]benzazepin-5-ol,
tert-butyl {8-chloro-1-[trans-4-(morpholin-4-yl)cyclohexyl]-5,6-dihydro-4H-[1,2,4]triazolo[4,3-a][1]benzazepin-5-yl}carbamate,
8-chloro-1-[trans-4-(morpholin-4-yl)cyclohexyl]-5,6-dihydro-4H-[1,2,4]triazolo[4,3-a][1]benzazepin-5-amine,
8-chloro-1-[trans-4-(morpholin-4-yl)cyclohexyl]-N-(propan-2-yl)-5,6-dihydro-4H-[1,2,4]triazolo[4,3-a][1]benzazepin-5-amine,
(5r,8r)-8-(8'-chloro-4'H,6'H-spiro[1,3-dioxolane-2,5'-[1,2,4]triazolo[4,3-a][1]benzazepin]-1'-yl)-2-(propan-2-yl)-2-azaspiro[4.5]decan-1-one,
(5r,8r)-8-(8-chloro-5-hydroxy-5,6-dihydro-4H-[1,2,4]triazolo[4,3-a][1]benzazepin-1-yl)-2-(propan-2-yl)-2-azaspiro[4.5]decan-1-one,
(5S)-8-chloro-1-[trans-4-(pyridin-2-yloxy)cyclohexyl]-5-(pyrrolidin-1-yl)-5,6-dihydro-4H-[1,2,4]triazolo[4,3-a][1]benzazepine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylpropanamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide,
(5S)-8-chloro-5-(morpholin-4-yl)-1-[trans-4-(pyridin-2-yloxy)cyclohexyl]-5,6-dihydro-4H-[1,2,4]triazolo[4,3-a][1]benzazepine,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylpropanamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-methylpropanamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclobutanecarboxamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}cyclopropanecarboxamide,
(5S)-8-chloro-5-(piperidin-1-yl)-1-[trans-4-(pyridin-2-yloxy)cyclohexyl]-5,6-dihydro-4H-[1,2,4]triazolo[4,3-a][1]benzazepine,
(5S)—N-(butan-2-yl)-8-chloro-1-[trans-4-(pyridin-2-yloxy)cyclohexyl]-5,6-dihydro-4H-[1,2,4]triazolo[4,3-a][1]benzazepin-5-amine,
(5s,8s)-8-(8'-chloro-4'H,6'H-spiro[1,3-dioxolane-2,5'-[1,2,4]triazolo[4,3-a][1]benzazepin]-1'-yl)-2-(propan-2-yl)-2-azaspiro[4.5]decan-1-one,
8-chloro-5-methoxy-1-[trans-4-(morpholin-4-yl)cyclohexyl]-5,6-dihydro-4H-[1,2,4]triazolo[4,3-a][1]benzazepine,
8-chloro-5-ethoxy-1-[trans-4-(pyridin-2-yloxy)cyclohexyl]-5,6-dihydro-4H-[1,2,4]triazolo[4,3-a][1]benzazepine,
(5R)-8-chloro-5-methoxy-1-[trans-4-(trifluoromethyl)cyclohexyl]-5,6-dihydro-4H-[1,2,4]triazolo[4,3-a][1]benzazepine,
(5S)-8-chloro-5-methoxy-1-[trans-4-(trifluoromethyl)cyclohexyl]-5,6-dihydro-4H-[1,2,4]triazolo[4,3-a][1]benzazepine,
8-fluoro-5-methoxy-1-[trans-4-(pyridin-2-yloxy)cyclohexyl]-5,6-dihydro-4H-[1,2,4]triazolo[4,3-a][1]benzazepine,
8-chloro-N-(propan-2-yl)-1-[1-(pyridin-2-yl)piperidin-4-yl]-5,6-dihydro-4H-[1,2,4]triazolo[4,3-a][1]benzazepin-5-amine,
2-({8-chloro-1-[trans-4-(pyridin-2-yloxy)cyclohexyl]-5,6-dihydro-4H-[1,2,4]triazolo[4,3-a][1]benzazepin-5-yl}oxy)ethanol,
(5S)-8-chloro-N,N-diethyl-1-[trans-4-(pyridin-2-yloxy)cyclohexyl]-5,6-dihydro-4H-[1,2,4]triazolo[4,3-a][1]benzazepin-5-amine,
8-chloro-N-methyl-N-(propan-2-yl)-1-[trans-4-(pyridin-2-yloxy)cyclohexyl]-5,6-dihydro-4H-[1,2,4]triazolo[4,3-a][1]benzazepin-5-amine,
tert-butyl {8-chloro-1-[4-(3-chloropyridin-2-yl)piperazin-1-yl]-5,6-dihydro-4H-[1,2,4]triazolo[4,3-a][1]benzazepin-5-yl}carbamate,
tert-butyl 4-(8-chloro-5-methoxy-5,6-dihydro-4H-[1,2,4]triazolo[4,3-a][1]benzazepin-1-yl)piperidine-1-carboxylate,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-D-valinamide,
tert-butyl {1-[trans-4-(pyridin-2-yloxy)cyclohexyl]-5,6-dihydro-4H-[1,2,4]triazolo[4,3-a][1]benzazepin-5-yl}carbamate,
tert-butyl {8-fluoro-1-[trans-4-(pyridin-2-yloxy)cyclohexyl]-5,6-dihydro-4H-[1,2,4]triazolo[4,3-a][1]benzazepin-5-yl}carbamate,
1-[trans-4-(pyridin-2-yloxy)cyclohexyl]-5,6-dihydro-4H-[1,2,4]triazolo[4,3-a][1]benzazepin-5-amine,
8-fluoro-1-[trans-4-(pyridin-2-yloxy)cyclohexyl]-5,6-dihydro-4H-[1,2,4]triazolo[4,3-a][1]benzazepin-5-amine, 8-fluoro-N-(propan-2-yl)-1-[trans-4-(pyridin-2-yloxy)cyclohexyl]-5,6-dihydro-4H-[1,2,4]triazolo[4,3-a][1]benzazepin-5-amine,
8-fluoro-N,N-dimethyl-1-[trans-4-(pyridin-2-yloxy)cyclohexyl]-5,6-dihydro-4H-[1,2,4]triazolo[4,3-a][1]benzazepin-5-amine,
N,N-dimethyl-1-[trans-4-(pyridin-2-yloxy)cyclohexyl]-5,6-dihydro-4H-[1,2,4]triazolo[4,3-a][1]benzazepin-5-amine,
8'-fluoro-1'-[trans-4-(trifluoromethyl)cyclohexyl]-4'H,6'H-spiro[1,3-dioxolane-2,5'-[1,2,4]triazolo[4,3-a][1]benzazepine],
N-(propan-2-yl)-1-[trans-4-(pyridin-2-yloxy)cyclohexyl]-5,6-dihydro-4H-[1,2,4]triazolo[4,3-a][1]benzazepin-5-amine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}tetrahydro-2H-pyran-4-carboxamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-methylbutanamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-$N^3,N^3$-dimethyl-β-alaninamide,
(5S)-8-chloro-N-cyclopentyl-1-[trans-4-(pyridin-2-yloxy)cyclohexyl]-5,6-dihydro-4H-[1,2,4]triazolo[4,3-a][1]benzazepin-5-amine,
8'-chloro-1'-(1'H,3H-spiro[2-benzofuran-1,4'-piperidin]-1'-yl)-4'H,6'H-spiro[1,3-dioxolane-2,5'-[1,2,4]triazolo[4,3-a][1]benzazepine],
8-chloro-1-(1'H,3H-spiro[2-benzofuran-1,4'-piperidin]-1'-yl)-4H-[1,2,4]triazolo[4,3-a][1]benzazepin-5(6H)-one,
8'-chloro-1'-[4-(pyridin-2-yloxy)piperidin-1-yl]-4'H,6'H-spiro[1,3-dioxolane-2,5'-[1,2,4]triazolo[4,3-a][1]benzazepine],
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2-dimethylbutanamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2-hydroxy-2-methylpropanamide,
(5S)-8-chloro-N-ethyl-N-methyl-1-[trans-4-(pyridin-2-yloxy)cyclohexyl]-5,6-dihydro-4H-[1,2,4]triazolo[4,3-a][1]benzazepin-5-amine,
(5S)-8-chloro-N-(2-methylpropyl)-1-[trans-4-(pyridin-2-yloxy)cyclohexyl]-5,6-dihydro-4H-[1,2,4]triazolo[4,3-a][1]benzazepin-5-amine,
8'-chloro-1'-[trans-4-(morpholin-4-yl)cyclohexyl]-4'H,6'H-spiro[1,3-dioxolane-2,5'-[1,2,4]triazolo[4,3-a][1]benzazepine] hydrochloride,
8-chloro-N,N-dimethyl-1-(1'H,3H-spiro[2-benzofuran-1,4'-piperidin]-1'-yl)-5,6-dihydro-4H-[1,2,4]triazolo[4,3-a][1]benzazepin-5-amine,
8'-chloro-1'-[4-(3-chloropyridin-2-yl)piperazin-1-yl]-4'H,6'H-spiro[1,3-dioxolane-2,5'-[1,2,4]triazolo[4,3-a][1]benzazepine],
(5S)-8-chloro-N-(2,2-dimethylpropyl)-1-[trans-4-(pyridin-2-yloxy)cyclohexyl]-5,6-dihydro-4H-[1,2,4]triazolo[4,3-a][1]benzazepin-5-amine,
[trans-4-(8-chloro-5-methoxy-5,6-dihydro-4H-[1,2,4]triazolo[4,3-a][1]benzazepin-1-yl)cyclohexyl](4-methylpiperazin-1-yl)methanone,
(5R)-8-chloro-5-(morpholin-4-yl)-1-[trans-4-(pyridin-2-yloxy)cyclohexyl]-5,6-dihydro-4H-[1,2,4]triazolo[4,3-a][1]benzazepine,
N-{(5R)-8-chloro-1-[trans-4-(pyridin-2-yloxy)cyclohexyl]-5,6-dihydro-4H-[1,2,4]triazolo[4,3-a][1]benzazepin-5-yl}acetamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-hydroxy-2-methylpropanamide,
8-chloro-5-methoxy-1-[1-(tetrahydro-2H-pyran-4-yl)piperidin-4-yl]-5,6-dihydro-4H-[1,2,4]triazolo[4,3-a][1]benzazepine,
8'-chloro-1'-[4-(pyridin-2-yl)piperazin-1-yl]-4'H,6'H-spiro[1,3-dioxolane-2,5'-[1,2,4]triazolo[4,3-a][1]benzazepine],
8-chloro-1-(1'H,3H-spiro[2-benzofuran-1,4'-piperidin]-1'-yl)-5,6-dihydro-4H-[1,2,4]triazolo[4,3-a][1]benzazepin-5-ol,
8-chloro-1-[4-(3-chloropyridin-2-yl)piperidin-1-yl]-5,6-dihydro-4H-[1,2,4]triazolo[4,3-a][1]benzazepin-5-ol,
(5R)-8-chloro-1-[trans-4-(pyridin-2-yloxy)cyclohexyl]-5-(pyrrolidin-1-yl)-5,6-dihydro-4H-[1,2,4]triazolo[4,3-a][1]benzazepine,
8-chloro-5-methoxy-1-{1-[(3S)-tetrahydrofuran-3-yl]piperidin-4-yl}-5,6-dihydro-4H-[1,2,4]triazolo[4,3-a][1]benzazepine,
(5R)-8-fluoro-5-methoxy-1-[trans-4-(pyridin-2-yloxy)cyclohexyl]-5,6-dihydro-4H-[1,2,4]triazolo[4,3-a][1]benzazepine,
(5S)-8-fluoro-5-methoxy-1-[trans-4-(pyridin-2-yloxy)cyclohexyl]-5,6-dihydro-4H-[1,2,4]triazolo[4,3-a][1]benzazepine,
8-chloro-5-methoxy-1-{1-[(3R)-tetrahydrofuran-3-yl]piperidin-4-yl}-5,6-dihydro-4H-[1,2,4]triazolo[4,3-a][1]benzazepine,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-$N^3,N^3$-dimethyl-β-alaninamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}tetrahydro-2H-pyran-4-carboxamide,
8-chloro-1-[4-(pyridin-2-yloxy)piperidin-1-yl]-5,6-dihydro-4H-[1,2,4]triazolo[4,3-a][1]benzazepin-5-ol,
8-chloro-5-methoxy-1-[trans-4-(4-methylpiperazin-1-yl)cyclohexyl]-5,6-dihydro-4H-[1,2,4]triazolo[4,3-a][1]benzazepine,
8-chloro-5-methoxy-1-[cis-4-(4-methylpiperazin-1-yl)cyclohexyl]-5,6-dihydro-4H-[1,2,4]triazolo[4,3-a][1]benzazepine,
8-chloro-5-methoxy-1-[1-(pyridin-3-ylmethyl)pyrrolidin-3-yl]-5,6-dihydro-4H-[1,2,4]triazolo[4,3-a][1]benzazepine,
8-chloro-5-methoxy-1-[1-(pyridin-2-ylmethyl)pyrrolidin-3-yl]-5,6-dihydro-4H-[1,2,4]triazolo[4,3-a][1]benzazepine,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-2-cyanoacetamide,
[3-(8-chloro-5-methoxy-5,6-dihydro-4H-[1,2,4]triazolo[4,3-a][1]benzazepin-1-yl)pyrrolidin-1-yl](pyridin-3-yl)methanone,
8'-chloro-1'-{1-[(3R)-tetrahydrofuran-3-yl]piperidin-4-yl}-4'H,6'H-spiro[1,3-dioxolane-2,5'-[1,2,4]triazolo[4,3-a][1]benzazepine],
[3-(8-chloro-5-methoxy-5,6-dihydro-4H-[1,2,4]triazolo[4,3-a][1]benzazepin-1-yl)pyrrolidin-1-yl](pyridin-2-yl)methanone,
trans-4-(8'-chloro-4'H,6'H-spiro[1,3-dioxolane-2,5'-[1,2,4]triazolo[4,3-a][1]benzazepin]-1'-yl)-N,N-dimethylcyclohexanamine, 8-chloro-5-methoxy-1-(1'H,3H-spiro[2-benzofuran-1,4'-piperidin]-1'-yl)-5,6-dihydro-4H-[1,2,4]triazolo[4,3-a][1]benzazepine,
8-chloro-1-[4-(3-chloropyridin-2-yl)piperazin-1-yl]-5-methoxy-5,6-dihydro-4H-[1,2,4]triazolo[4,3-a][1]benzazepine,
N-[trans-4-(8'-chloro-4'H,6'H-spiro[1,3-dioxolane-2,5'-[1,2,4]triazolo[4,3-a][1]benzazepin]-1'-yl)cyclohexyl]pyridin-2-amine,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-N,N-dimethylethane-1,2-diamine,
8-chloro-1-[trans-4-(pyridin-2-yloxy)cyclohexyl]-5,6-dihydro-4H-[1,2,4]triazolo[4,3-a][1]benzazepin-5-yl acetate,
2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethanol,
8-chloro-5-methoxy-1-[4-(pyridin-2-yloxy)piperidin-1-yl]-5,6-dihydro-4H-[1,2,4]triazolo[4,3-a][1]benzazepine,
8'-chloro-1'-(trans-4-methoxy-4-methylcyclohexyl)-4'H,6'H-spiro[1,3-dioxolane-2,5'-[1,2,4]triazolo[4,3-a][1]benzazepine],
(5S)-8-chloro-N-(cyclopropylmethyl)-1-[trans-4-(pyridin-2-yloxy)cyclohexyl]-5,6-dihydro-4H-[1,2,4]triazolo[4,3-a][1]benzazepin-5-amine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-1-methylpiperidine-4-carboxamide,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-2,2,2-trifluoroacetamide,
8-chloro-5-(2-methoxyethoxy)-1-[trans-4-(pyridin-2-yloxy)cyclohexyl]-5,6-dihydro-4H-[1,2,4]triazolo[4,3-a][1]benzazepine,
8-chloro-1-(4-methoxy-4-methylcyclohexyl)-N-(propan-2-yl)-5,6-dihydro-4H-[1,2,4]triazolo[4,3-a][1]benzazepin-5-amine,
8'-chloro-1'-(trans-4-methoxy-4-methylcyclohexyl)-4'H,6'H-spiro[1,3-dioxane-2,5'-[1,2,4]triazolo[4,3-a][1]benzazepine],
8'-chloro-1'-(cis-4-methoxy-4-methylcyclohexyl)-4'H,6'H-spiro[1,3-dioxane-2,5'-[1,2,4]triazolo[4,3-a][1]benzazepine],
8-chloro-5-fluoro-1-[trans-4-(pyridin-2-yloxy)cyclohexyl]-5,6-dihydro-4H-[1,2,4]triazolo[4,3-a][1]benzazepine,
8-chloro-5-[2-(methylsulfonyl)ethoxy]-1-[trans-4-(pyridin-2-yloxy)cyclohexyl]-5,6-dihydro-4H-[1,2,4]triazolo[4,3-a][1]benzazepine,
8-chloro-N-hydroxy-1-[trans-4-(pyridin-2-yloxy)cyclohexyl]-4H-[1,2,4]triazolo[4,3-a][1]benzazepin-5(6H)-imine,
(5S)-8-chloro-N-methyl-N-(prop-2-yn-1-yl)-1-[trans-4-(pyridin-2-yloxy)cyclohexyl]-5,6-dihydro-4H-[1,2,4]triazolo[4,3-a][1]benzazepin-5-amine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide,
8-chloro-5-(prop-2-yn-1-yloxy)-1-[trans-4-(pyridin-2-yloxy)cyclohexyl]-5,6-dihydro-4H-[1,2,4]triazolo[4,3-a][1]benzazepine,
8-chloro-1-[trans-4-(pyridin-2-yloxy)cyclohexyl]-5,6-dihydro-4H-[1,2,4]triazolo[4,3-a][1]benzazepin-5-yl 4,4-difluorocyclohexanecarboxylate,
8-chloro-1-[trans-4-(pyridin-2-yloxy)cyclohexyl]-5,6-dihydro-4H-[1,2,4]triazolo[4,3-a][1]benzazepin-5-yl 3,3-difluorocyclobutanecarboxylate,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide,
8-chloro-1-[trans-4-(pyridin-2-yloxy)cyclohexyl]-5,6-dihydro-4H-[1,2,4]triazolo[4,3-a][1]benzazepin-5-yl cyanoacetate,
8-chloro-1-[trans-4-(pyridin-2-yloxy)cyclohexyl]-5,6-dihydro-4H-[1,2,4]triazolo[4,3-a][1]benzazepin-5-yl N,N-dimethylglycinate,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-2,2,2-trifluoroacetamide,
1-[cis-4-(8-chloro-5-methoxy-5,6-dihydro-4H-[1,2,4]triazolo[4,3-a][1]benzazepin-1-yl)cyclohexyl]pyrrolidin-2-one,
1-[trans-4-(8-chloro-5-methoxy-5,6-dihydro-4H-[1,2,4]triazolo[4,3-a][1]benzazepin-1-yl)cyclohexyl]pyrrolidin-2-one,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-3,3-difluorocyclobutanecarboxamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-4,4-difluorocyclohexanecarboxamide,
8-chloro-5-methoxy-1-[cis-4-methoxy-4-(trifluoromethyl)cyclohexyl]-5,6-dihydro-4H-[1,2,4]triazolo[4,3-a][1]benzazepine,
8-chloro-5-methoxy-1-[trans-4-methoxy-4-(trifluoromethyl)cyclohexyl]-5,6-dihydro-4H-[1,2,4]triazolo[4,3-a][1]benzazepine,
(5S)-8-chloro-1-[trans-4-(pyridin-2-yloxy)cyclohexyl]-N-(2,2,2-trifluoroethyl)-5,6-dihydro-4H-[1,2,4]triazolo[4,3-a][1]benzazepin-5-amine,
N-{(5S)-8-chloro-1-[trans-4-(pyridin-2-yloxy)cyclohexyl]-5,6-dihydro-4H-[1,2,4]triazolo[4,3-a][1]benzazepin-5-yl}-3-methyloxetane-3-carboxamide,
N-{(5R)-8-chloro-1-[trans-4-(pyridin-2-yloxy)cyclohexyl]-5,6-dihydro-4H-[1,2,4]triazolo[4,3-a][1]benzazepin-5-yl}-3-methyloxetane-3-carboxamide,
trans-4-(8'-chloro-4'H,6'H-spiro[1,3-dioxolane-2,5'-[1,2,4]triazolo[4,3-a][1]benzazepin]-1'-yl)-N-(4-methoxybenzyl)cyclohexanamine,
tert-butyl [2-({(5R)-8-chloro-1-[trans-4-(pyridin-2-yloxy)cyclohexyl]-5,6-dihydro-4H-[1,2,4]triazolo[4,3-a][1]benzazepin-5-yl}amino)ethyl]carbamate,
8'-chloro-1'-(trans-4-ethoxy-4-ethylcyclohexyl)-4'H,6'H-spiro[1,3-dioxolane-2,5'-[1,2,4]triazolo[4,3-a][1]benzazepine],
trans-4-(8'-chloro-4'H,6'H-spiro[1,3-dioxolane-2,5'-[1,2,4]triazolo[4,3-a][1]benzazepin]-1'-yl)-N-(4-methoxybenzyl)-N-methylcyclohexanamine,
8'-chloro-1'-[1-(pyridin-3-ylmethyl)pyrrolidin-3-yl]-4'H,6'H-spiro[1,3-dioxolane-2,5'-[1,2,4]triazolo[4,3-a][1]benzazepine],
8-chloro-5-methoxy-1-[4-(pyridin-2-yl)piperazin-1-yl]-5,6-dihydro-4H-[1,2,4]triazolo[4,3-a][1]benzazepine,
8-chloro-1-(trans-4-ethyl-4-methoxycyclohexyl)-N,N-dimethyl-5,6-dihydro-4H-[1,2,4]triazolo[4,3-a][1]benzazepin-5-amine,
8-chloro-1-(trans-4-ethoxy-4-methylcyclohexyl)-N,N-dimethyl-5,6-dihydro-4H-[1,2,4]triazolo[4,3-a][1]benzazepin-5-amine, 8'-chloro-1'-[trans-4-methoxy-4-(trifluoromethyl)cyclohexyl]-4'H,6'H-spiro[1,3-dioxolane-2,5'-[1,2,4]triazolo[4,3-a][1]benzazepine],
8'-chloro-1'-[cis-4-methoxy-4-(trifluoromethyl)cyclohexyl]-4'H,6'H-spiro[1,3-dioxolane-2,5'-[1,2,4]triazolo[4,3-a][1]benzazepine],
8'-chloro-1'-(trans-4-ethoxy-4-methylcyclohexyl)-4'H,6'H-spiro[1,3-dioxolane-2,5'-[1,2,4]triazolo[4,3-a][1]benzazepine],
8'-chloro-1'-(trans-4-ethoxy-4-propylcyclohexyl)-4'H,6'H-spiro[1,3-dioxolane-2,5'-[1,2,4]triazolo[4,3-a][1]benzazepine],
8'-chloro-1'-[1-(pyridin-2-ylmethyl)pyrrolidin-3-yl]-4'H,6'H-spiro[1,3-dioxolane-2,5'-[1,2,4]triazolo[4,3-a][1]benzazepine],
8'-chloro-1'-(cis-4-ethyl-4-methoxycyclohexyl)-4'H,6'H-spiro[1,3-dioxolane-2,5'-[1,2,4]triazolo[4,3-a][1]benzazepine],
8'-chloro-1'-(trans-4-ethyl-4-methoxycyclohexyl)-4'H,6'H-spiro[1,3-dioxolane-2,5'-[1,2,4]triazolo[4,3-a][1]benzazepine],
8'-chloro-1'-(trans-4-methoxy-4-propylcyclohexyl)-4'H,6'H-spiro[1,3-dioxolane-2,5'-[1,2,4]triazolo[4,3-a][1]benzazepine],
8'-chloro-1'-(cis-4-methoxy-4-propylcyclohexyl)-4'H,6'H-spiro[1,3-dioxolane-2,5'-[1,2,4]triazolo[4,3-a][1]benzazepine],
8-chloro-1-(trans-4-ethoxy-4-ethylcyclohexyl)-N-(propan-2-yl)-5,6-dihydro-4H-[1,2,4]triazolo[4,3-a][1]benzazepin-5-amine,
8-chloro-1-(trans-4-ethoxy-4-ethylcyclohexyl)-N,N-dimethyl-5,6-dihydro-4H-[1,2,4]triazolo[4,3-a][1]benzazepin-5-amine,
8'-chloro-1'-[(3R)-1-(pyridin-2-ylmethyl)pyrrolidin-3-yl]-4'H,6'H-spiro[1,3-dioxolane-2,5'-[1,2,4]triazolo[4,3-a][1]benzazepine],
8-chloro-5-methoxy-1-[(3R)-1-(pyridin-3-ylmethyl)pyrrolidin-3-yl]-5,6-dihydro-4H-[1,2,4]triazolo[4,3-a][1]benzazepine,
8-chloro-5-methoxy-1-[(3R)-1-(pyridin-2-ylmethyl)pyrrolidin-3-yl]-5,6-dihydro-4H-[1,2,4]triazolo[4,3-a][1]benzazepine,
8'-chloro-1'-[(3S)-1-(pyridin-3-ylmethyl)pyrrolidin-3-yl]-4'H,6'H-spiro[1,3-dioxolane-2,5'-[1,2,4]triazolo[4,3-a][1]benzazepine],
8'-chloro-1'-[(3R)-1-(pyridin-3-ylmethyl)pyrrolidin-3-yl]-4'H,6'H-spiro[1,3-dioxolane-2,5'-[1,2,4]triazolo[4,3-a][1]benzazepine],
8-chloro-5-methoxy-1-[(3S)-1-(pyridin-3-ylmethyl)pyrrolidin-3-yl]-5,6-dihydro-4H-[1,2,4]triazolo[4,3-a][1]benzazepine,
8'-chloro-1'-[(3S)-1-(pyridin-2-ylmethyl)pyrrolidin-3-yl]-4'H,6'H-spiro[1,3-dioxolane-2,5'-[1,2,4]triazolo[4,3-a][1]benzazepine] and
8-chloro-5-methoxy-1-[(3S)-1-(pyridin-2-ylmethyl)pyrrolidin-3-yl]-5,6-dihydro-4H-[1,2,4]triazolo[4,3-a][1]benzazepine.

14. A pharmaceutical composition comprising therapeutically effective amount of a compound of general formula (I) and/or salt thereof and/or geometric isomer thereof and/or stereoisomer thereof and/or enantiomer thereof and/or racemate thereof and/or diastereomer thereof and/or biologically active metabolite thereof and/or prodrug thereof and/or solvate thereof and/or hydrate thereof and/or polymorph thereof according to claim 1 as active substance and a pharmaceutically acceptable excipient.

15. A combinational composition comprising therapeutically effective amount of a compound of general formula (I) and/or salt thereof and/or geometric isomer thereof and/or stereoisomer thereof and/or enantiomer thereof and/or racemate thereof and/or diastereomer thereof and/or biologically active metabolite thereof and/or prodrug thereof and/or solvate thereof and/or hydrate thereof and/or polymorph thereof according to claim 1 and one or more other active substances.

16. A method for treating and/or preventing a disease or condition associated with V1a receptor function comprising administering to a mammal in need of said treating and/or prophylaxis, the pharmaceutical composition of claim 14.

17. A process for the preparation of a pharmaceutical composition having V1a receptor antagonist activity comprising combining a therapeutically effective amount of a compound of general formula (I) and/or salt thereof and/or geometric isomer thereof and/or stereoisomer thereof and/or enantiomer thereof and/or racemate thereof and/or diastereomer thereof and/or biologically active metabolite thereof and/or prodrug thereof and/or solvate thereof and/or hydrate thereof and/or polymorph thereof according to claim 1 as active substance with pharmaceutically acceptable excipients.

18. A method for treating and/or preventing a disease or condition associated with V1a receptor function comprising administering to a mammal in need of said treating and/or prophylaxis, a therapeutically effective amount of a compound of general formula (I) and/or salt thereof and/or geometric isomer thereof and/or stereoisomer thereof and/or enantiomer thereof and/or racemate thereof and/or diastereomer thereof and/or biologically active metabolite thereof and/or prodrug thereof and/or solvate thereof and/or hydrate thereof and/or polymorph thereof according to claim 1 alone or with pharmaceutically acceptable excipients.

19. The method according to claim 18, wherein the disease or condition associated with V1a receptor function is selected from the group consisting of various pathological conditions of the female sex organs, long-standing conditions in blood pressure control, conditions resulting from inappropriate secretion of vasopressin, anxiety, depression, aggression, disorders of the central nervous system where one of the symptoms and/or syndromes of the disease may be related to anxiety, depression, aggression or show comorbidity with them, aggressive behavioural disorders and/or irritability, behavioural hyperactivity disorders, cognitive disorders or other neuropsychiatric disorders.

20. A compound selected from the group consisting of:
1 tert-butyl (7-chloro-2-oxo-2,3,4,5-tetrahydro-1H-1-benzazepin-4-yl)carbamate,
tert-butyl-(7-bromo-2-oxo-2,3,4,5-tetrahydro-1H-1-benzazepin-4-yl)carbamate,
tert-butyl-(7-chloro-2-thioxo-2,3,4,5-tetrahydro-11H-1-benzazepin-4-yl)carbamate,
tert-butyl-(7-bromo-2-thioxo-2,3,4,5-tetrahydro-1H-1-benzazepin-4-yl)carbamate,
tert-butyl-(7-chloro-2-(methylsulfanyl)-4,5-dihydro-3H-1-benzazepin-4-yl)carbamate,
7-chloro-1,5-dihydrospiro[1-benzazepine-4,2'-[1,3]dioxolane]-2(3H)-one,
7-bromo-1,5-dihydrospiro[1-benzazepine-4,2'-[1,3]dioxolane]-2(3H)-one,
4-{[tert-butyl(dimethyl)silyl]oxy}-7-chloro-1,3,4,5-tetrahydro-2H-1-benzazepin-2-one,
4-{[tert-butyl(dimethyl)silyl]oxy}-7-chloro-1,3,4,5-tetrahydro-2H-1-benzazepin-2-thione, 7-chloro-4-methoxy-1,3,4,5-tetrahydro-2H-1-benzazepin-2-one, and 7-chloro-4-methoxy-1,3,4,5-tetrahydro-2H-1-benzazepine-2-thione.

21. The method according to claim 18, further comprising administering one or more additional active substances.

* * * * *

UNITED STATES PATENT AND TRADEMARK OFFICE
CERTIFICATE OF CORRECTION

PATENT NO. : 11,298,363 B2
APPLICATION NO. : 16/954085
DATED : April 12, 2022
INVENTOR(S) : Baska et al.

It is certified that error appears in the above-identified patent and that said Letters Patent is hereby corrected as shown below:

In the Claims

In Column 299, Claim 1, Line 66, delete "group:" and insert -- group; --, therefor.

In Column 300, Claim 1, Line 7, delete "group:" and insert -- group; --, therefor.

In Column 300, Claim 1, Line 15, delete "group:" and insert -- group; --, therefor.

In Column 301, Claim 3, Line 23, delete "group:" and insert -- group; --, therefor.

In Column 301, Claim 3, Line 30, delete "group:" and insert -- group; --, therefor.

Signed and Sealed this
Seventh Day of June, 2022

Katherine Kelly Vidal
*Director of the United States Patent and Trademark Office*